US012758559B2

(12) United States Patent
Shaw et al.

(10) Patent No.: US 12,758,559 B2
(45) Date of Patent: Oct. 13, 2026

(54) RXFP1 AGONISTS

(71) Applicant: BRISTOL-MYERS SQUIBB COMPANY, Princeton, NJ (US)

(72) Inventors: Scott A. Shaw, Lawrence Township, NJ (US); Adam James Clarke, Crosswicks, NJ (US); Todd J. Friends, Chesterfield, NJ (US); Arvind Mathur, Bridgewater, NJ (US); Michael C. Myers, Newtown, PA (US); Jianqing Li, Guilford, CT (US); Kumar Balashanmuga Pabbisetty, Piscataway, NJ (US); Shun Su, San Diego, CA (US); George O. Tora, Langhorne, PA (US); Benjamin P. Vokits, New York City, NY (US); Laxman Pasunoori, Warangal (IN); Nicholas R. Wurtz, Pennington, NJ (US); Donald J.P. Pinto, Churchville, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 228 days.

(21) Appl. No.: 18/701,276

(22) PCT Filed: Oct. 28, 2022

(86) PCT No.: PCT/US2022/078835

§ 371 (c)(1),
(2) Date: Apr. 15, 2024

(87) PCT Pub. No.: WO2023/077040

PCT Pub. Date: May 4, 2023

(65) Prior Publication Data

US 2025/0268903 A1 Aug. 28, 2025

Related U.S. Application Data

(60) Provisional application No. 63/273,370, filed on Oct. 29, 2021.

(51) Int. Cl.

| | |
|---|---|
| ***C07D 233/72*** | (2006.01) |
| ***A61K 31/167*** | (2006.01) |
| ***A61K 31/27*** | (2006.01) |
| ***A61K 31/337*** | (2006.01) |
| ***A61K 31/341*** | (2006.01) |
| ***A61K 31/351*** | (2006.01) |
| ***A61K 31/41*** | (2006.01) |
| ***A61K 31/4174*** | (2006.01) |
| ***A61K 31/4184*** | (2006.01) |
| ***A61K 31/445*** | (2006.01) |
| ***A61K 31/5375*** | (2006.01) |
| ***C07C 237/24*** | (2006.01) |

(Continued)

(52) U.S. Cl.

CPC ........ *A61K 31/5375* (2013.01); *A61K 31/167* (2013.01); *A61K 31/27* (2013.01); *A61K 31/337* (2013.01); *A61K 31/341* (2013.01); *A61K 31/351* (2013.01); *A61K 31/41* (2013.01); *A61K 31/4174* (2013.01); *A61K 31/4184* (2013.01); *A61K 31/445* (2013.01); *C07C 237/24* (2013.01); *C07C 271/54* (2013.01); *C07C 317/50* (2013.01); *C07D 233/72* (2013.01); *C07D 235/26* (2013.01); *C07D 257/06* (2013.01); *C07D 295/155* (2013.01); *C07D 305/06* (2013.01); *C07D 307/20* (2013.01); *C07D 309/08* (2013.01)

(58) Field of Classification Search

CPC ............................ C07D 233/72; C07C 237/24

See application file for complete search history.

(56) References Cited

FOREIGN PATENT DOCUMENTS

| | | | |
|---|---|---|---|
| WO | 2011163502 | A1 | 12/2011 |
| WO | 2013165606 | A1 | 11/2013 |

(Continued)

OTHER PUBLICATIONS

Garber_2001, "Relaxin decreases renal interstitial fibrosis and slowsprogression of renal disease", Kidney International, vol. 59 (2001), pp. 876-882.

(Continued)

*Primary Examiner* — Shawquia Jackson
(74) *Attorney, Agent, or Firm* — Hong Liu

(57) ABSTRACT

The disclosure relates to compounds of Formula (I), which are RXFP1 receptor agonists, compositions containing them, and methods of using them, for example, in the treatment of heart failure, fibrotic diseases, and related diseases such as lung disease (e.g., idiopathic pulmonary fibrosis), kidney disease (e.g., chronic kidney disease), or hepatic disease (e.g., non-alcoholic steatohepatitis and portal hypertension).

(I)

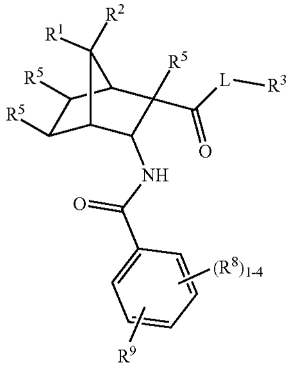

24 Claims, No Drawings

(51) Int. Cl.

| | |
|---|---|
| ***C07C 271/54*** | (2006.01) |
| ***C07C 317/50*** | (2006.01) |
| ***C07D 235/26*** | (2006.01) |
| ***C07D 257/06*** | (2006.01) |
| ***C07D 295/155*** | (2006.01) |
| ***C07D 305/06*** | (2006.01) |
| ***C07D 307/20*** | (2006.01) |
| ***C07D 309/08*** | (2006.01) |

(56) References Cited

FOREIGN PATENT DOCUMENTS

| | | | |
|---|---|---|---|
| WO | 2022122773 | A1 | 6/2022 |
| WO | 2023/076626 | A1 | 5/2023 |
| WO | 2023077041 | A1 | 5/2023 |
| WO | 2023077070 | A1 | 5/2023 |

OTHER PUBLICATIONS

Ludwig_2004, "Convenient Synthesis of Pyrrole- and Indolecarboxylic Acid tert-Butylesters", Synthetic Communications, 34:20, 3691-3695.
Mohammed et al., "Coronary Microvascular Rarefaction and MyocardialFibrosis in Heart Failure With Preserved Ejection Fraction", Circulation, vol. 131, pp. 550-559 (2015).
Roger et al., "Heart Disease and Stroke Statistics—2012 Update", Circulation, vol. 125, e2-220 (2012).
Teerlink_2013, "Serelaxin, recombinant human relaxin-2, for treatment ofacute heart failure (RELAX-AHF): a randomised, placebo-controlled trial", The Lancet, vol. 381, Issue 9860 p. 29-39 Jan. 5, 2013.
Allen, Jr., Loyd V., "Remington: The Science and Practice of Pharmacy, vol. I and vol. II. Twenty-second edition", Pharmaceutical Press, 2012, p. 2724.
Bennett_2014 "Relaxin decreases the severity of established hepatic fibrosis in mice", Liver International 34: 416-426.
Borlaug, et al. "Heart failure with preserved ejection fraction: pathophysiology, diagnosis, and treatment", European Heart Journal (2011) 32, 670-679.
Borlaug_2011 "Diastolic and Systolic Heart Failure Are Distinct Phenotypes Within the Heart Failure Spectrum", vol. 123, Issue 18, May 10, 2011; pp. 2006-2014.
Chen_2018, "Pd-Catalyzed, ortho C—H Methylation and Fluorination of Benzaldehydes Using Orthanilic Acids as Transient Directing Groups"; J. Am. Chem. Soc. 2018, 140, 2789-2792.
Clapp et al., "Cardiovascular Function Before, During, and After the First and Subsequent Pregnancies", Am J Cardiol, vol. 80, pp. 1469-1473 (1997).
Conrad et al., "Maternal vasodilation in pregnancy: the emerging role of relaxin", Regul. Integr. Comp. Physiol., vol. 301, pp. R267-R275 (2011).
Damman et al., "The Cardiorenal Syndrome in Heart Failure", Progress in Cardiovascular Diseases, vol. 54, pp. 144-154 (2011).
De Keulenaer_2011_"Systolic and Diastolic Heart Failure Are Overlapping Phenotypes Within the Heart Failure Spectrum"; vol. 123, Issue 18, May 10, 2011; pp. 1996-2005.
Greene, T.W. et al., Protecting Groups in Organic Synthesis, 4th Edition, Wiley (2007).
Halls et al., "Relaxin Family Peptide Receptors—former orphans reunite with their parent ligands to activate multiple signalling pathways", British J of Pharmacology, vol. 150, pp. 677-691 (2007).
Halls ML., et al. "Relaxin Activates Multiple cAMP Signaling Pathway Profiles in Different Target Cells", Ann. N Y Acad. Sci., vol. 1160, 108-111 (2009).
Halls, et al., "Relaxin Family Peptide Receptors RXFP1 and RXFP2 ModulatecAMP Signaling by Distinct Mechanisms", vol. 70, pp. 214-226 (2006).
Halls_2009, "RXFP1 Couples to the Gαi3-Gβγ-PI3K-PKCζ Pathway via the Final 10 Amino Acids of the Receptor C-terminal Tail", Annals of the New York Academy of Sciences, 1160, 117-120.
Heidenreich et al., "Forecasting the Future of Cardiovascular Disease in the United States", Circulation, vol. 123, pp. 933-944 (2011).
Hisaw_1926 , "Experimental relaxation of the pubic ligament of the guinea pig", Proc Soc Exp Biol Med 23:661-663.
Hsu et al., "Activation of Orphan Receptors by the Hormone Relaxin", Science, vol. 295, pp. 671-674 (2002).
Jessup et al., "Medical Progress. Heart Failure", The New England Journal of Medicine, vol. 348, pp. 3007-3018 (2003).
Jeyabalan_2010, "Renal Physiology and Pathophysiology in Pregnancy", Renal and Electrolyte Disorders, 2010, pp. 462-518.
Kemp et al., "The pathophysiology of heart failure", Cardiovascular Pathology, vol. 21, pp. 365-371 (2012).
MacMillan_2016, "Silyl Radical Activation of Alkyl Halides in Metallaphotoredox Catalysis: A Unique Pathway for Cross-Electrophile Coupling", J. Am. Chem. Soc. 2016, 138, 8084-8087.
Matsushita, et al.,"The Association of Hemoglobin A1c With Incident Heart Failure Among People Without Diabetes: The Atherosclerosis Risk in Communities Study", Diabetes, vol. 59, pp. 2020-2026 (2010).
Millane et al., "ABC of heart failure. Acute and chronic management strategies", BMJ, vol. 320 pp. 559-562 (2000).
Ponikowski_2014, "A randomized, double-blind, placebo-controlled, multicentre study to assess haemodynamic effects of serelaxin in patients with acute heart failure", European Heart Journal (2014) 35, 431-441.
Poppas et al., "Serial Assessment of the Cardiovascular System in Normal Pregnancy" Circulation, vol. 95(10) pp. 2407-2415 (1997).
Roger V. et al., "Trends in Heart Failure Incidence and Survival in a Community-Based Population", JAMA, vol. 292, pp. 344-350 (2004).
Roger, V.L., "Epidemiology of Heart Failure", Circulation Research , vol. 113(6), pp. 646-659 (2013).
Safety and Tolerability of Serelaxin, aDahlke_2015 "Recombinant Human Relaxin-2 in Developmentfor the Treatment of Acute Heart Failure, inHealthy Japanese Volunteers and a Comparisonof Pharmacokinetics and Pharmacodynamics inHealthy Japanese and Caucasian Populations", The Journal of Clinical Pharmacology2015, 55(4) 415-422.
Sherwood et al., "Relaxin's Physiological Roles and Other Diverse Actions", Endocr. Rev. vol. 25, pp. 205-234 (2004).
Smith_2006 "Influence of Recombinant Human Relaxin on RenalHemodynamics in Healthy Volunteers", J Am Soc Nephrol 17: 3192-3197, 2006.
Teichman et al., "Relaxin, a pleiotropic vasodilator for the treatment of heart failure", Heart Fail. Rev., vol. 14, pp. 321-329 (2009).
Unemori_1996, "Relaxin Induces an Extracellular Matrix-degrading Phenotype in Human Lung Fibroblasts In Vitro and Inhibits Lung Fibrosis in a Murine Model In Vivo", J. Clin. Invest, vol. 98, No. 12, Dec. 1996, 2739-2745.
Voors_2014, "Renal Hemodynamic Effects of Serelaxin in Patients With Chronic Heart Failure", vol. 7, Issue 6, Nov. 2014; pp. 994-1002.
Wohlfahrt et al., "Impact of chronic changes in arterial compliance and resistance on left ventricular ageing in humans", Eur. J. Heart Fail., vol. 17, pp. 27-34 (2015).

RXFP1 AGONISTS

CROSS-REFERENCE TO RELATED APPLICATIONS

This application is a 371 application of PCT/US2022/078835, filed Oct. 28, 2022, which claims the benefit of U.S. Provisional Application No. 63/273,370, filed Oct. 29, 2021, the disclosure of which is incorporated herein by reference in its entirety.

BACKGROUND OF THE INVENTION

The present disclosure relates to novel compounds which are relaxin family peptide receptor 1 (RXFP1) agonists, compositions containing them, and methods of using them, for example in the treatment of heart failure, fibrotic diseases, and related diseases such as lung disease (e.g., idiopathic pulmonary fibrosis), kidney disease (e.g., chronic kidney disease), and hepatic disease (e.g., non-alcoholic steatohepatitis and portal hypertension).

The human relaxin hormone (also called relaxin or H2 relaxin) is a 6-kDa peptide composed of 53 amino acids whose activity was initially discovered when Frederick Hisaw in 1926 injected crude extracts from swine corpus luteum into virgin guinea pigs and observed a relaxation of the fibrocartilaginous pubic symphysis joint (Hisaw F L., *Proc. Soc. Exp. Biol. Med.,* 1926, 23, 661-663). The relaxin receptor was previously known as Lgr7 but is now officially termed the relaxin family peptide receptor 1 (RXFP1) and was deorphanized as a receptor for relaxin in 2002 (Hsu S Y., et al., *Science,* 2002, 295, 671-674). RXFP1 is reasonably well conserved between mouse and human with 85% amino acid identity and is essentially ubiquitously expressed in humans and in other species (Halls M L., et al., *Br. J. Pharmacol.,* 2007, 150, 677-691). The cell signaling pathways for relaxin and RXFP1 are cell type dependent and quite complex (Halls M L., et al., *Br. J. Pharmacol.,* 2007, 150, 677-691; Halls M L., et al. *Ann. N Y Acad. Sci.,* 2009, 1160, 108-111; Halls M L., *Ann N Y Acad. Sci.,* 2007, 1160, 117-120). The best studied pathway is the relaxin-dependent increase in cellular levels of cAMP in which relaxin functions as an RXFP1 agonist to promote GαS coupling and activation of adenylate cyclase (Halls M L., et al., *Mol. Pharmacol.,* 2006, 70, 214-226).

Since the initial discovery of relaxin much experimental work has focused on delineating the role relaxin has played in female reproductive biology and the physiological changes that occur during mammalian pregnancy (Sherwood O D., *Endocr. Rev.,* 2004, 25, 205-234). During human gestation, in order to meet the nutritional demands imposed upon it by the fetus, the female body undergoes a significant ~30% decrease in systemic vascular resistance (SVR) and a concomitant ~50% increase in cardiac output (Jeyabalan A C., K. P., *Renal and Electolyte Disorders.* 2010, 462-518), (Clapp J F. & Capeless E., *Am. J. Cardio.,* 1997, 80, 1469-1473). Additional vascular adaptations include an ~30% increase in global arterial compliance that is important for maintaining efficient ventricular-arterial coupling, as well as an ~50% increase in both renal blood flow (RBF) and glomerular filtration rate (GFR), important for metabolic waste elimination (Jeyabalan A C., K. P., *Renal and Electolyte Disorders.??* 2010, 462-518), (Poppas A., et al., *Circ.,* 1997, 95, 2407-2415). Both pre-clinical studies in rodents as well as clinical studies performed in a variety of patient settings, provide evidence that relaxin is involved, at least to some extent, in mediating these adaptive physiological changes (Conrad K P., *Regul. Integr. Comp. Physiol.,* 2011, 301, R267-275), (Teichman S L., et al., *Heart Fail. Rev.,* 2009, 14, 321-329). Importantly, many of these adaptive responses would likely be of benefit to HF patients in that excessive fibrosis, poor arterial compliance, and poor renal function are all characteristics common to heart failure patients (Mohammed S F., et al., *Circ.,* 2015, 131, 550-559), (Wohlfahrt P., et al., *Eur. J. Heart Fail.,* 2015, 17, 27-34), (Damman K., et al., *Prog. Cardiovasc. Dis.,* 2011, 54, 144-153).

Heart failure (HF), defined hemodynamically as "systemic perfusion inadequate to meet the body's metabolic demands as a result of impaired cardiac pump function", represents a tremendous burden on today's health care system with an estimated United States prevalence of 5.8 million and greater than 23 million worldwide (Roger V L., et al., *Circ. Res.,* 2013, 113, 646-659). It is estimated that by 2030, an additional 3 million people in the United States alone will have HF, a 25% increase from 2010. The estimated direct costs (2008 dollars) associated with HF for 2010 was $25 billion, projected to grow to $78 B by 2030 (Heidenreich P A., et al., *Circ.,* 2011, 123, 933-944). Astoundingly, in the United States, 1 in 9 deaths has HF mentioned on the death certificate (Roger V L., et al., Circ., 2012, 125, e2-220) and, while survival after HF diagnosis has improved over time (Matsushita K., et al., *Diabetes,* 2010, 59, 2020-2026), (Roger V L., et al., *JAMA,* 2004, 292, 344-350), the death rate remains high with ~50% of people with HF dying within 5 years of diagnosis (Roger V L., et al., *Circ.,* 2012, 125, e2-220), (Roger V L., et al., *JAMA,* 2004, 292, 344-350).

The symptoms of HF are the result of inadequate cardiac output and can be quite debilitating depending upon the advanced stage of the disease. Major symptoms and signs of HF include: 1) dyspnea (difficulty in breathing) resulting from pulmonary edema due to ineffective forward flow from the left ventricle and increased pressure in the pulmonary capillary bed; 2) lower extremity edema occurs when the right ventricle is unable to accommodate systemic venous return; and 3) fatigue due to the failing heart's inability to sustain sufficient cardiac output (CO) to meet the body's metabolic needs (Kemp C D., & Conte J V., *Cardiovasc. Pathol.,* 2011, 21, 365-371). Also, related to the severity of symptoms, HF patients are often described as "compensated" or "decompensated". In compensated heart failure, symptoms are stable, and many overt features of fluid retention and pulmonary edema are absent. Decompensated heart failure refers to a deterioration, which may present as an acute episode of pulmonary edema, a reduction in exercise tolerance, and increasing breathlessness upon exertion (Millane T., et al., *BMJ,* 2000, 320, 559-562).

In contrast to the simplistic definition of poor cardiac performance not being able to meet metabolic demands, the large number of contributory diseases, multitude of risk factors, and the many pathological changes that ultimately lead to heart failure make this disease exceedingly complex (Jessup M. & Brozena S., *N. Engl. J. Med.,* 2003, 348, 3007-2018). Injurious events thought to be involved in the pathophysiology of HF range from the very acute such as myocardial infarction to a more chronic insult such as life-long hypertension. Historically, HF was primarily described as "systolic HF" in which decreased left-ventricular (LV) contractile function limits the expulsion of blood and hence results in a reduced ejection fraction (EF is stroke volume/end diastolic volume), or "diastolic HF" in which active relaxation is decreased and passive stiffness is increased limiting LV filling during diastole, however overall EF is maintained (Borlaug B A. & Paulus W J., *Eur Heart J.,* 2011, 32, 670-679). More recently, as it became understood that diastolic and systolic LV dysfunction was not uniquely specific to these two groups, new terminology was employed: "heart failure with reduced ejection fraction" (HFrEF), and "heart failure with preserved ejection fraction" (HFpEF) (Borlaug B A. & Paulus W J., *Eur Heart J.,* 2011, 32, 670-679). Although these two patient populations have very similar signs and symptoms, whether HFrEF and HFpEF represent two distinct forms of HF or two extremes of a single spectrum sharing a common pathogenesis is currently under debate within the cardiovascular community (Borlaug B A, & Redfield M M., *Circ.,* 2011, 123, 2006-2013), (De Keulenaer G W., & Brutsaert D L., *Circ.,* 2011, 123, 1996-2004).

Serelaxin, an intravenous (IV) formulation of the recombinant human relaxin peptide with a relatively short first-phase pharmacokinetic half-life of 0.09 hours, is currently being developed for the treatment of HF (Novartis, 2014). Serelaxin has been given to normal healthy volunteers (NHV) and demonstrated to increase RBF (Smith M C., et al., *J. Am. Soc. Nephrol.* 2006, 17, 3192-3197) and estimated GFR (Dahlke M., et al., *J. Clin. Pharmacol.,* 2015, 55, 415-422). Increases in RBF were also observed in stable compensated HF patients (Voors A A., et al., *Cir. Heart Fail.,* 2014, 7, 994-1002). In large clinical studies, favorable changes in worsening renal function, worsening HF, as well as fewer deaths, were observed in acute decompensated HF (ADHF) patients in response to an in-hospital 48 hour IV infusion of serelaxin (Teerlink J R., et al., *Lancet,* 2013, 381, 29-39), (Ponikowski P., et al., *Eur. Heart,* 2014, 35, 431-441). Suggesting that chronic dosing of serelaxin could provide sustained benefit to HF patients, improvement in renal function based on serum creatinine levels was observed in scleroderma patients given serelaxin continuously for 6 months using a subcutaneous pump (Teichman S L., et al., *Heart Fail. Rev.,* 2009, 14, 321-329). In addition to its potential as a therapeutic agent for the treatment of HF, continuous subcutaneous administration of relaxin has also been demonstrated to be efficacious in a variety of animal models of lung (Unemori E N., et al., *J. Clin. Invet.,* 1996, 98, 2739-2745), kidney (Garber S L., et al., *Kidney Int.,* 2001, 59, 876-882), and liver injury (Bennett R G., Liver Int., 2014, 34, 416-426).

In summary, a large body of evidence supports a role for relaxin-dependent agonism of RXFP1 mediating the adaptive changes that occur during mammalian pregnancy, and that these changes translate into favorable physiological effects and outcomes when relaxin is given to HF patients. Additional preclinical animal studies in various disease models of lung, kidney, and liver injury provide evidence that relaxin, when chronically administered, has the potential to provide therapeutic benefit for multiple indications in addition to HF. More specifically, chronic relaxin administration could be of benefit to patients suffering from lung disease (e.g., idiopathic pulmonary fibrosis), kidney disease (e.g., chronic kidney disease), or hepatic disease (e.g., non-alcoholic steatohepatitis and portal hypertension).

SUMMARY OF THE INVENTION

The present invention provides novel substituted norbornyl compounds, their analogues, including stereoisomers, tautomers, pharmaceutically acceptable salts, or solvates thereof, which are useful as RXFP1 receptor agonists.

The present invention also provides processes and intermediates for making the compounds of the present invention.

The present invention also provides pharmaceutical compositions comprising a pharmaceutically acceptable carrier and at least one of the compounds of the present invention or stereoisomers, tautomers, pharmaceutically acceptable salts, or solvates thereof.

The compounds of the invention may be used, for example, in the treatment and/or prophylaxis of heart failure, fibrotic diseases, and related diseases, such as; lung disease (e.g., idiopathic pulmonary fibrosis), kidney disease (e.g., chronic kidney disease), or hepatic disease (e.g., non-alcoholic steatohepatitis and portal hypertension).

The compounds of the present invention may be used in therapy.

The compounds of the present invention may be used for the manufacture of a medicament for the treatment and/or prophylaxis of heart failure.

The compounds of the invention can be used alone, in combination with other compounds of the present invention, or in combination with one or more, preferably one to two other agent(s).

These and other features of the invention will be set forth in expanded form as the disclosure continues.

DESCRIPTION OF THE INVENTION

The invention encompasses compounds of Formula (I), which are RXFP1 receptor agonists, compositions containing them, and methods of using them.

In a first aspect, the present invention provides, inter alia, compounds of Formula (I):

(I)

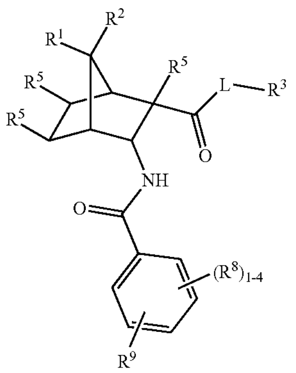

or pharmaceutically acceptable salts thereof, wherein;

L is —O— or —NH—;

$R^1$ is $C_{1-3}$ alkyl substituted with 1 aryl or $C_3$-6 cycloalkyl substituent;

$R^2$ is H;

or $R^1$ and $R^2$ are taken together to be $=CR^6R^7$, wherein "=" is a double bond;

or $R^1$ and $R^2$ together with the carbon atom to which they are both attached form a dioxolanyl substituted with 0-1 aryl substituent;

$R^3$ is $C_{1-8}$ alkyl substituted with 0-5 halo, CN, —OH, or $—OC_{1-3}$ alkyl substituents, $—(CR^dR^d)_n—C_{3-10}$-carbocyclyl substituted with 0-5 $R^4$ or $—(CR^dR^d)_n$-3 to 12-membered heterocyclyl comprising 1-4 heteroatoms selected from O, $S(=O)_p$, N, $NR^{4a}$, and substituted with 0-5 $R^4$;

$R^4$ is halo, CN, —OH, —$SF_5$, —S(═O)$_p$R$^c$, $C_{1-4}$ alkyl substituted with 0-5 halo, —OH, or —O$C_{1-4}$ alkyl substituents, —O$C_{1-4}$ alkyl substituted with 0-5 halo substituents, —(CR$^d$R$^d$)$_n$—$C_{3-10}$ carbocyclyl substituted with 0-5 R$^e$, or —(CR$^d$R$^d$)$_n$-4- to 6-membered heterocyclyl comprising 1-4 heteroatoms selected from O, S(═O)$_p$, N, and NR$^{4a}$; R$^{4a}$ is H, $C_{1-4}$ alkyl, or —S(═O)$_2$CF$_3$;

$R^5$ is H, halo, —OH, $C_{1-4}$ alkyl substituted with 0-5 halo substituents, or —O$C_{1-4}$ alkyl substituted with 0-5 halo substituents;

$R^6$ is H, halo, CN, $C_{1-7}$ alkyl substituted with 0-3 R$^{6a}$, $C_{2-7}$ alkenyl substituted with 0-3 R$^{6a}$, $C_{2-7}$ alkynyl substituted with 0-3 R$^{6a}$, —C(═O)OR$^{6b}$, —CONR$^{6b}$R$^{6b}$, —(CH$_2$)$_n$—$C_{3-10}$ carbocyclyl substituted with 0-5 R$^{14}$, or 3- to 12-membered heterocyclyl comprising 1-4 heteroatoms selected from O, S(═O)$_p$, N, or NR$^{13}$, and substituted with 0-5 R$^{14}$;

$R^{6a}$ is halo, —OH, —O$C_{1-4}$ alkyl, $C_{1-4}$ alkyl, aryl, or $C_{3-6}$ cycloalkyl substituted with 0-4 halo substituents;

$R^{6b}$ is H, $C_{1-4}$ alkyl substituted with 0-1 aryl substituent, or $C_{3-6}$ cycloalkyl substituted with 0-4 halo substituents;

$R^7$ is H or $C_{1-4}$ alkyl;

$R^8$ is H, halo, CN, —NR$^7$R$^7$ or —O$C_{1-4}$ alkyl substituted with 0-5 halo, OH, —O$C_{1-4}$ alkyl, $C_{3-6}$ cycloalkyl, aryl, or 4- to 9-membered heterocyclyl comprising 1-4 heteroatoms selected from O, S(═O)$_p$, and N substituents;

$R^9$ is —C(═O)OR$^{15}$, —C(═O)NR$^{15}$R$^{15}$, —S(═O)$_p$NR$^{15}$R$^{15}$, —S(═O)$_p$R$^c$, —NR$^{17}$R$^{17}$, $C_{1-8}$ alkyl substituted with 0-4 R$^{10}$ and 0-2 R$^{11}$, $C_{2-8}$ alkenyl substituted with 0-2 R$^{10}$ and 0-2 R$^{11}$, $C_{2-8}$ alkynyl substituted with 0-2 R$^{10}$ and 0-2 R$^{11}$, $C_{3-9}$ cycloalkyl substituted with 0-2 R$^{10}$ and 0-2 R$^{11}$, $C_{3-9}$ cycloalkenyl substituted with 0-2 R$^{10}$ and 0-2 R$^{11}$, fused $C_{3-6}$ cycloalkyl substituted with 0-2 R$^{10}$ and 0-2 R$^{11}$, $C_{6-9}$ spirocycloalkyl substituted with 0-2 R$^{10}$ and 0-2 R$^{11}$, A-$C_{3-6}$ carbocyclyl substituted with 0-2 R$^{10}$ and 0-2 R$^{11}$, or A-4- to 9-membered heterocyclyl comprising 1-4 heteroatoms selected from O, S(═O)$_p$, N and NR$^{18}$, and substituted with 0-2 R$^{10}$ and 0-2 R$^{11}$;

A is —O—, —S—, —CH$_2$O—, or —OCH$_2$—;

$R^{10}$ is halo, CN, or $C_{1-6}$ alkyl substituted with 0-4 R$^{11}$;

$R^{11}$ is halo, —OR$^b$, —NR$^a$R$^a$, —NR$^a$C(═O)R$^b$, —NR$^a$C(═O)OR$^b$, —NR$^a$C(═O)NR$^a$R$^a$, —NR$^a$S(═O)$_p$R$^c$, —NR$^a$S(═O)$_p$NR$^a$R$^a$, —C(═O)R$^b$, —C(═O)OR$^b$, —C(═O)NR$^a$R$^a$, —C(═O)NR$^a$S(═O)$_p$R$^c$, —OC(═O)R$^b$, —OC(═O)OR$^b$, —OC(═O)NR$^a$R$^a$, —OC(═O)NR$^a$OR$^b$, —S(═O)$_p$R$^c$, —S(═O)$_p$NR$^a$R$^a$, $C_{3-9}$ carbocyclyl substituted with 0-5 R$^e$, or 3- to 12-membered heterocyclyl comprising 1-4 heteroatoms selected from O, S(═O)$_p$, N, and NR$^{12}$, and substituted with 0-5 R$^e$;

$R^{12}$ is H, $C_{1-4}$ alkyl substituted with 0-4 halo or ORD substituents, or aryl;

$R^{13}$ is H, C(═O)$C_{1-4}$ alkyl, $C_{1-3}$ alkyl substituted with 0-3 Si($C_{1-3}$ alkyl) 3, or aryl substituted with 0-2 halo substituents;

$R^{14}$ is halo, CN, $C_{1-4}$ alkyl substituted with 0-3 halo substituents, —O$C_{1-4}$ alkyl substituted with 0-3 halo substituents, —(CH$_2$)$_n$—NR$^a$R$^a$, —(CH$_2$)$_n$-aryl substituted with 0-3 R$^e$, —O-aryl substituted with 0-3 R$^e$, or —(CH$_2$)$_n$-3- to 12-membered heterocyclyl comprising 1-4 heteroatoms selected from O, S(═O)$_p$, and N, and substituted with 0-3 R$^e$;

$R^{15}$ is H, $C_{1-6}$ alkyl substituted with 0-5 R$^e$, $C_{2-6}$ alkenyl substituted with 0-5 R$^e$, $C_{2-6}$ alkynyl substituted with 0-5 R$^e$, —(CH$_2$)$_n$—$C_{3-10}$ carbocyclyl substituted with 0-5 R$^e$, or —(CH$_2$)$_n$-3- to 12-membered heterocyclyl comprising 1-4 heteroatoms selected from O, S(═O)$_p$, N and NR$^{16}$, and substituted with 0-5 R$^e$; or R$^{15}$ and R$^{15}$ together with the nitrogen atom to which they are both attached form a 3- to 12-membered heterocyclyl comprising 1-4 heteroatoms selected from O, S(═O)$_p$, N, and NR$^{16}$, and substituted with 0-5 R$^e$;

$R^{16}$ is H, $C_{1-6}$ alkyl substituted with 0-5 R$^e$, —C(═O)R$^f$, —C(═O)OR$^f$, —C(═O)NR$^f$R$^f$, —S(═O)$_p$R, or —S(═O)$_p$NR$^f$R$^f$, $R^{17}$ is H, $C_{1-6}$ alkyl substituted with 0-5 R$^e$, $C_{2-6}$ alkenyl substituted with 0-5 R$^e$, $C_{2-6}$ alkynyl substituted with 0-5 R$^e$, —(CH$_2$)$_n$—$C_{3-10}$ carbocyclyl substituted with 0-5 R$^e$, or —(CH$_2$)$_n$-4- to 12-membered heterocyclyl comprising 1-4 heteroatoms selected from O, S(═O)$_p$, N, and NR$^{18}$, and substituted with 0-5 R$^e$;

$R^{18}$ is H, $C_{1-4}$ alkyl substituted with 0-4 halo or —OH substituents, —C(═O)R$^b$, —C(═O)OR$^b$, —C(═O)NR$^a$R$^a$, —S(═O)$_p$R$^c$, —S(═O)$_p$NR$^a$R$^a$, aryl substituted with 0-5 R$^e$, $C_{3-6}$ cycloalkyl substituted with 0-5 R$^e$, or 4- to 6-membered heterocyclyl comprising 1-4 heteroatoms selected from O, S(═O)$_p$, and N, and substituted with 0-5 R$^e$;

$R^a$ is H, $C_{1-6}$ alkyl substituted with 0-8 R$^e$, $C_{2-6}$ alkenyl substituted with 0-5 R$^e$, $C_{2-6}$ alkynyl substituted with 0-5 R$^e$, —(CH$_2$)$_n$—$C_{3-10}$ carbocyclyl substituted with 0-5 R$^e$, or —(CH$_2$)$_n$-3- to 12-membered heterocyclyl comprising 1-5 heteroatoms selected from O, S(═O)$_p$, and N, and substituted with 0-5 R$^e$; or R$^a$ and R$^a$ together with the nitrogen atom to which they are both attached form a 3- to 12-membered heterocyclyl comprising 1-4 heteroatoms selected from O, S(═O)$_p$, and N, and substituted with 0-5 R$^e$;

$R^b$ is H, $C_{1-6}$ alkyl substituted with 0-5 R$^e$, $C_{2-6}$ alkenyl substituted with 0-5 R$^e$, $C_{2-6}$ alkynyl substituted with 0-5 R$^e$, —(CH$_2$)$_n$—$C_{3-10}$carbocyclyl substituted with 0-5 R$^e$, or —(CH$_2$)$_n$-3- to 12-membered heterocyclyl comprising 1-5 heteroatoms selected from O, S(═O)$_p$, and N, and substituted with 0-5 R$^e$;

$R^c$ is $C_{1-6}$ alkyl substituted with 0-5 R$^e$, $C_{2-6}$ alkenyl substituted with 0-5 R$^e$, $C_{2-6}$ alkynyl substituted with 0-5 R$^e$, $C_{3-6}$ carbocyclyl substituted with 0-5 R$^e$, or 3- to 12-membered heterocyclyl comprising 1-5 heteroatoms selected from O, S(═O)$_p$, and N, and substituted with 0-5 R$^e$;

$R^d$ is H, $C_{1-4}$ alkyl, or $C_{3-6}$ cycloalkyl;

$R^e$ is halo, CN, NO$_2$, ═O, $C_{1-6}$ alkyl substituted with 0-5 R$^8$, $C_{2-6}$ alkenyl substituted with 0-5 R$^g$, $C_{2-6}$ alkynyl substituted with 0-5 R$^g$, —(CH$_2$)$_n$—$C_{3-10}$ carbocyclyl substituted with 0-5 R$^g$, —(CH$_2$)$_n$-3- to 12-membered heterocyclyl comprising 1-5 heteroatoms selected from O, S(═O)$_p$, and N, and substituted with 0-5 R$^g$, —(CH$_2$)$_n$OR$^f$, —C(═O)R$^f$, —C(═O)OR$^f$, —C(═O)NR$^f$R$^f$, —NR$^f$C(═O)R$^f$, —S(═O)$_p$R$^f$, —S(═O)$_p$NR$^f$R$^f$, —NR$^f$S(═O)$_p$R$^f$, —NR$^f$C(═O)OR$^f$, —OC(═O)NR$^f$R$^f$, or —(CH$_2$)$_n$NR$^f$R$^f$;

$R^f$ is H, $C_{1-6}$ alkyl, $C_{3-6}$ cycloalkyl, aryl, or 3- to 12-membered heterocyclyl comprising 1-4 heteroatoms selected from O, S(═O)$_p$, and N; or R$^f$ and R$^f$ together with the nitrogen atom to which they are both attached form a 3- to 12-membered heterocyclyl comprising 1-4 heteroatoms selected from O, S(═O)$_p$, and N;

$R^g$ is halo, CN, OH, O$C_{1-6}$ alkyl, $C_{1-6}$ alkyl, $C_{3-6}$ cycloalkyl, or aryl;

n is zero, 1, 2, or 3; and p is zero, 1, or 2.

In a second aspect within the scope of the first aspect, the present invention provides compounds of Formula (II):

(II)

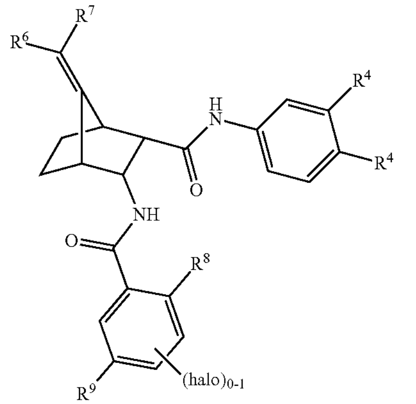

or pharmaceutically acceptable salts thereof, wherein:

$R^4$ is halo, $C_{1-4}$ alkyl substituted with 0-3 halo substituents, or $—OC_{1-4}$ alkyl substituted with 0-3 halo substituents;

$R^6$ is halo, CN, $C_{1-6}$ alkyl substituted with 0-3 $R^{6a}$, $C_{2-6}$ alkenyl substituted with 0-3 $R^{6a}$, $C_{2-6}$ alkynyl substituted with 0-3 $R^{6a}$, $C_{3-6}$ cycloalkyl substituted with 0-3 $R^{14}$, $C_{3-6}$ cycloalkenyl substituted with 0-3 $R^{14}$, phenyl substituted with 0-3 $R^{14}$, or 5- to 6-membered heterocyclyl comprising 1-3 heteroatoms selected from O, $S(═O)_p$, N, and $NR^{13}$, and substituted with 0-3 $R^{14}$;

$R^7$ is H or $C_{1-2}$ alkyl;

$R^{6a}$ is halo, $—OC_{1-4}$ alkyl, $C_{3-6}$ cycloalkyl, or phenyl;

$R^8$ is H, halo, CN, or $—OC_{1-4}$ alkyl substituted with 0-4 halo, OH, or $—OC_{1-4}$ alkyl;

$R^9$ is $C_{1-7}$ alkyl substituted with 0-3 $R^{10}$ and 0-2 $R^{11}$, $C_{2-7}$ alkenyl substituted with 0-2 $R^{10}$ and 0-2 $R^{11}$, $C_{2-7}$ alkynyl substituted with 0-2 $R^{10}$ and 0-2 $R^{11}$, $C_{3-9}$ cycloalkyl substituted with 0-2 $R^{10}$ and 0-2 $R^{11}$, or $C_{6-9}$ spirocycloalkyl substituted with 0-2 $R^{10}$ and 0-2 $R^{11}$, $—CH_2—O—C_6$ carbocyclyl substituted with 0-2 $R^{10}$ and 0-2 $R^{11}$, or $—O—C_{3-6}$ cycloalkyl substituted with 0-2 $R^{10}$ and 0-2 $R^{11}$;

$R^{10}$ is halo, CN, or $C_{1-5}$ alkyl substituted with 0-4 halo or —OH substituents;

$R^{11}$ is $—OR^b$, $—NR^aR^a$, $—NR^aC(═O)R^b$, $—NR^aC(═O)OR^b$, $—NR^aC(═O)NR^aR^a$, $—NR^aS(═O)_pR^c$, $—NR^aS(═O)_pNR^aR^a$, $—C(═O)R^b$, $—C(═O)OR^b$, $—C(═O)NR^aR^a$, $—C(═O)NR^aS(═O)_pR^c$, $—OC(═O)R^b$, $—OC(═O)NR^aR^a$, $—S(═O)_pR^c$,qj $—S(═O)_pNR^aR^a$, aryl substituted with 0-4 $R^e$, $C_{3-6}$ cycloalkyl substituted with 0-4 $R^e$, or 4- to 6-membered heterocyclyl comprising 1-4 heteroatoms selected from O, $S(═O)_p$, N and $NR^{12}$, and substituted with 0-4 $R^e$;

$R^{12}$ is H, $C_{1-2}$ alkyl, or phenyl;

$R^{13}$ is H, $C(═O)C_{1-3}$ alkyl, or $C_{1-3}$ alkyl substituted with 0-2 aryl substituted with 0-2 halo substituents;

$R^{14}$ is halo, CN, $C_{1-4}$ alkyl substituted with 0-3 halo substituents, $—OC_{1-4}$ alkyl substituted with 0-3 halo substituents, $—(CH_2)_{0-2}—NR^aR^a$, $—(CH_2)_{0-2}$-aryl substituted with 0-3 $R^e$, —O-aryl substituted with 0-3 $R^e$, or $—(CH_2)_{0-2}$-4- to 9-membered heterocyclyl comprising 1-4 heteroatoms selected from O, $S(═O)_p$, and N, and substituted with 0-3 $R^e$;

$R^a$ is H, $C_{1-5}$ alkyl substituted with 0-4 $R^e$, $C_{2-5}$ alkenyl substituted with 0-4 $R^e$, $C_{2-5}$ alkynyl substituted with 0-4 $R^e$, $—(CH_2)—C_{3-10}$ carbocyclyl substituted with 0-4 $R^e$, or $—(CH_2)_n$-4- to 9-membered heterocyclyl comprising 1-4 heteroatoms selected from O, $S(═O)_p$, and N, and substituted with 0-4 $R^e$; or $R^a$ and $R^a$ together with the nitrogen atom to which they are both attached form a 4- to 9-membered heterocyclyl comprising 1-4 heteroatoms selected from O, $S(═O)_p$, and N, and substituted with 0-4 $R^e$;

$R^b$ is H, $C_{1-5}$ alkyl substituted with 0-4 $R^e$, $C_{2-5}$ alkenyl substituted with 0-4 $R^e$, $C_{2-5}$ alkynyl substituted with 0-4 $R^e$, $—(CH_2)_n—C_{3-10}$ carbocyclyl substituted with 0-4 $R^e$, or $—(CH_2)_n$-4- to 9-membered heterocyclyl comprising 1-4 heteroatoms selected from O, $S(═O)_p$, and N, and substituted with 0-4 $R^e$;

$R^c$ is $C_{1-5}$ alkyl substituted with 0-4 $R^e$, $C_{2-5}$ alkenyl substituted with 0-4 $R^e$, $C_{2-5}$ alkynyl substituted with 0-4 $R^e$, $C_{3-6}$ carbocyclyl substituted with 0-4 $R^e$, or 4- to 9-membered heterocyclyl comprising 1-4 heteroatoms selected from O, $S(═O)_p$, and N, and substituted with 0-4 $R^e$;

$R^e$ is halo, CN, ═O, $C_{1-6}$ alkyl substituted with 0-5 $R^g$, $C_{2-6}$ alkenyl substituted with 0-5 $R^g$, $C_{2-6}$ alkynyl substituted with 0-5 $R^g$, $—(CH_2)_n—C_{3-6}$ carbocyclyl substituted with 0-5 $R^g$, $—(CH_2)_n—$ 4- to 9-membered heterocyclyl comprising 1-4 heteroatoms selected from O, $S(═O)_p$, and N, and substituted with 0-5 $R^g$, $—(CH_2)_nOR^f$, $—C(═O)OR^f$, $S(═O)_pR^f$, $C(═O)NR^fR^f$, $NR^fC(═O)R^f$, $S(═O)_pNR^fR^f$, $NR^fS(═O)_pR^f$, $NR^fC(═O)OR^f$, or $—(CH_2)_nNR^fR^f$;

$R^f$ is H, $C_{1-6}$ alkyl, $C_{3-6}$ cycloalkyl, or aryl; or $R^f$ and $R^f$ together with the nitrogen atom to which they are both attached form a 4- to 9-membered heterocyclyl comprising 1-4 heteroatoms selected from O, $S(═O)_p$, and N;

$R^g$ is halo, CN, OH, $C_{1-4}$ alkyl, $C_{3-6}$ cycloalkyl, or aryl.

n is zero, 1, 2, or 3; and p is zero, 1, or 2.

In a third aspect within the scope of the second aspect, the present invention provides compounds of Formula (II), or pharmaceutically acceptable salts thereof, wherein:

$R^4$ is halo or $C_{1-3}$ alkyl substituted with 0-3 halo substituents;

$R^6$ is $C_{1-5}$ alkyl substituted with 0-3 $R^{6a}$, $C_{3-6}$ cycloalkyl substituted with 0-3 $R^{14}$, or 5- to 6-membered heterocyclyl comprising 1-3 heteroatoms selected from O, $S(═O)_p$, N, and substituted with 0-3 $R^{14}$;

$R^{6a}$ is halo, $—OC_{1-4}$ alkyl, or $C_{3-6}$ cycloalkyl;

$R^7$ is H;

$R^8$ is $—OC_{1-3}$ alkyl substituted with 0-2 halo or —OH substituents;

$R^9$ is $C_{1-7}$ alkyl substituted with 0-3 $R^{10}$ and 0-2 $R^{11}$;

$R^{10}$ is halo, CN or $C_{1-4}$ alkyl substituted with 0-4 halo substituents;

$R^{11}$ is $—OR^b$, $—NR^aR^a$, $—NR^aC(═O)R^b$, $—NR^bC(═O)OR^b$, $—C(═O)R^b$, $—C(═O)OR^b$, $—C(═O)NR^aR^a$, $—OC(═O)NR^aR^a$, aryl substituted with 0-3 $R^e$, $C_{3-6}$ cycloalkyl substituted with 0-3 $R^e$, or 4- to 6-membered heterocyclyl comprising 1-4 heteroatoms selected from O, $S(═O)_p$, N and $NR^{12}$, and substituted with 0-3 $R^e$, $R^{12}$ is H, $C_{1-2}$ alkyl, or phenyl;

$R^{14}$ is halo, CN, $C_{1-4}$ alkyl substituted with 0-3 halo substituents, $—OC_{1-4}$ alkyl substituted with 0-3 halo substituents, $—(CH_2)_{0-2}—NR^aR^a$, $—(CH_2)_{0-2}$-aryl substituted with 0-3 $R^e$, —O-aryl substituted with 0-3

$R^e$, or $-(CH_2)_{0-2}$-4- to 9-membered heterocyclyl comprising 1-4 heteroatoms selected from O, $S(=O)_p$, and N, and substituted with 0-3 $R^e$;

$R^a$ is H, $C_{1-5}$ alkyl substituted with 0-4 $R^e$, $C_{2-5}$ alkenyl substituted with 0-4 $R^e$, $C_{2-5}$ alkynyl substituted with 0-4 $R^e$, $-(CH_2)_n-C_{3-10}$ carbocyclyl substituted with 0-4 $R^e$, or $-(CH_2)_n$-4- to 9-membered heterocyclyl comprising 1-4 heteroatoms selected from O, $S(=O)_p$, and N, and substituted with 0-4 $R^e$; or $R^a$ and $R^a$ together with the nitrogen atom to which they are both attached form a 4- to 9-membered heterocyclyl comprising 1-4 heteroatoms selected from O, $S(=O)_p$, and N, and substituted with 0-4 $R^e$;

$R^b$ is H, $C_{1-4}$ alkyl substituted with 0-4 $R^e$, $C_{2-4}$ alkenyl substituted with 0-4 $R^e$, $C_{2-5}$ alkynyl substituted with 0-4 $R^e$, $-(CH_2)_n-C_{3-10}$ carbocyclyl substituted with 0-4 $R^e$, or $-(CH_2)_n$-4- to 9-membered heterocyclyl comprising 1-4 heteroatoms selected from O, $S(=O)_p$, and N, and substituted with 0-4 $R^e$;

$R^e$ is halo, CN, =O, $C_{1-5}$ alkyl substituted with 0-5 $R^g$, $C_{2-5}$ alkenyl substituted with 0-4 $R^g$, $C_{2-5}$ alkynyl substituted with 0-4 $R^g$, $-(CH_2)_n-C_{3-6}$ cycloalkyl substituted with 0-4 $R^g$, $-(CH_2)_n$-aryl substituted with 0-4 $R^g$, $-(CH_2)_n$-4- to 9-membered heterocyclyl comprising 1-4 heteroatoms selected from O, $S(=O)_p$, and N, and substituted with 0-4 $R^g$, $-(CH_2)_nOR^f$, $-C(=O)OR^f$, $S(=O)_pR^f$, $C(=O)NR^fR^f$, $NR^fC(=O)R^f$, or $-(CH_2)_nNR^fR^f$;

$R^f$ is H, $C_{1-5}$ alkyl substituted with 0-3 $R^g$, $C_{3-6}$ cycloalkyl, or aryl; or $R^f$ and $R^f$ together with the nitrogen atom to which they are both attached form a 4- to 6-membered heterocyclyl comprising 1-4 heteroatoms selected from O, $S(=O)_p$, and N;

$R^g$ is halo, CN, OH, $OC_{1-4}$ alkyl, $C_{1-6}$ alkyl, $C_{3-6}$ cycloalkyl, or aryl;

n is zero, 1, 2, or 3; and p is zero, 1, or 2.

In a fourth aspect within the scope of the third aspect, the present invention provides compounds of Formula (II), or pharmaceutically acceptable salts thereof, wherein:

$R^4$ is halo or $CF_3$;

$R^6$ is $C_{1-3}$ alkyl substituted with 0-3 halo or $-OC_{1-3}$ alkyl substituents, $C_{3-6}$ cycloalkyl substituted with 0-2 halo substituents, or heterocyclyl selected from

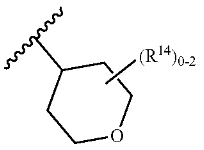 and 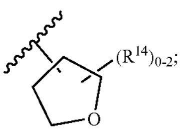

$R^8$ is $-OC_{1-3}$ alkyl substituted with 0-1-OH substituent;

$R^9$ is $C_{1-7}$ alkyl substituted with 0-3 halo, —OH, or CN substituents; and $R^{14}$ is halo, CN, or $C_{1-3}$ alkyl substituted with 0-3 halo substituents.

In a fifth aspect within the scope of the third aspect, the present invention provides compounds of Formula (II), or pharmaceutically acceptable salts thereof, wherein:

$R^4$ is halo or $CF_3$;

$R^6$ is $C_{1-3}$ alkyl substituted with 0-3 halo or $C_{3-6}$ cycloalkyl;

$R^9$ is $C_{1-3}$ alkyl substituted with 0-1 $R^{10}$ and 0-1 $R^{11}$;

$R^{10}$ is halo or $C_{1-4}$ alkyl substituted with 0-4 halo substituents;

$R^{11}$ is $-OR^b$;

$R^b$ is $C_{1-4}$ alkyl substituted with 0-3 $R^e$, $-(CH_2)_{0-1}-C_{3-6}$ cycloalkyl substituted with 0-4 $R^e$, $-(CH_2)_{0-1}$-phenyl substituted with 0-3 $R^e$, or $-(CH_2)_{0-1}$-heterocyclyl, wherein the heterocyclyl is

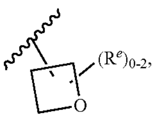 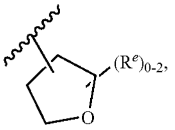 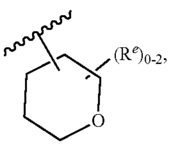

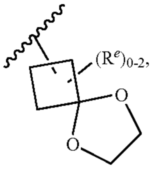 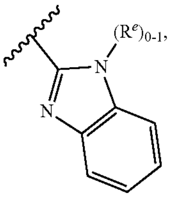

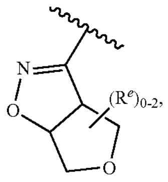 or 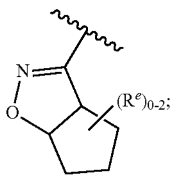

$R^e$ is halo, CN, $C_{1-5}$ alkyl substituted with 0-5 $R^g$, $-(CH_2)_nOR^f$, $-C(=O)OR^f$, or $C(=O)NR^fR^f$;

$R^f$ is H, $C_{1-4}$ alkyl substituted with 0-3 $R^g$;

$R^g$ is halo, CN, OH, $C_{1-6}$ alkyl, $C_{3-6}$ cycloalkyl, or aryl; and n is zero or 1.

In a sixth aspect within the scope of the third aspect, the present invention provides compounds of Formula (II), or pharmaceutically acceptable salts thereof, wherein:

$R^4$ is halo or $CF_3$;

$R^6$ is $C_{1-3}$ alkyl substituted with 0-3 halo substituents or $C_{3-6}$ cycloalkyl;

$R^9$ is $C_{1-3}$ alkyl substituted with 0-1 $R^{10}$ and 0-1 $R^{11}$;

$R^{10}$ is halo or $C_{1-4}$ alkyl substituted with 0-4 halo substituents;

$R^{11}$ is $-NR^aR^a$;

$R^a$ is H or $C_{1-4}$ alkyl substituted with 0-4 $R^e$, $C_{3-6}$ cycloalkyl substituted with 0-4 $R^e$; or $R^a$ and $R^a$ together with the nitrogen atom to which they are both attached form a heterocyclyl selected from

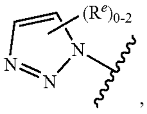, 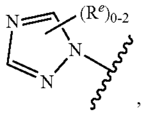, 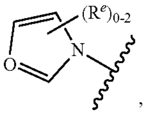,

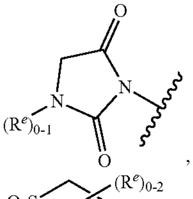, 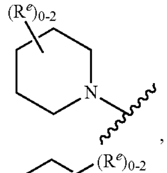, 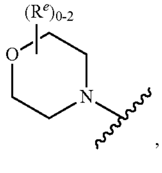,

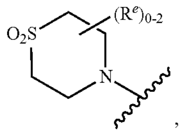, 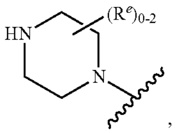, 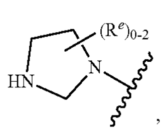,

-continued

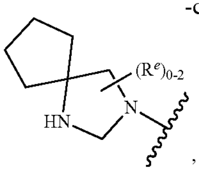

,

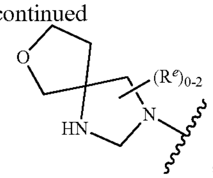

, and

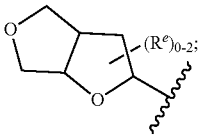

$R^e$ is halo, CN, —O, $C_{1-4}$ alkyl substituted with 0-4 $R^g$, —$(CH_2)_n$—$C_{3-6}$ cycloalkyl, —$(CH_2)_n$-4- to 6-membered heterocyclyl comprising 1-4 heteroatoms selected from O, $S(=O)_p$, and N, —$(CH_2)_n$-aryl, —$(CH_2)_nOR^f$, —$C(=O)OR^f$, $S(=O)_pR^f$, $C(=O)NR^fR^f$, or —$(CH_2)_nNR^fR^f$;

$R^f$ is H or $C_{1-4}$ alkyl; and $R^g$ is halo, CN, OH, $OC_{1-4}$ alkyl, $C_{1-4}$ alkyl, $C_{3-6}$ cycloalkyl, or aryl.

In a seventh aspect within the scope of the third aspect, the present invention provides compounds of Formula (II) or pharmaceutically acceptable salts thereof, wherein:

$R^4$ is halo or $CF_3$;

$R^6$ is $C_{1-3}$ alkyl substituted with 0-3 halo substituents or $C_{3-6}$ cycloalkyl;

$R^9$ is $C_{1-3}$ alkyl substituted with 0-1 $R^{10}$ and 0-1 $R^{11}$;

$R^{10}$ is halo or $C_{1-4}$ alkyl substituted with 0-4 halo substituents;

$R^{11}$ is —$OC(=O)NR^aR^a$;

$R^a$ is H, $C_{1-4}$ alkyl substituted with 0-4 $R^e$, $C_{3-6}$ cycloalkyl substituted with 0-4 $R^e$, or phenyl substituted with 0-4 $R^e$; or $R^a$ and $R^a$ together with the nitrogen atom to which they are both attached form a heterocyclyl selected from

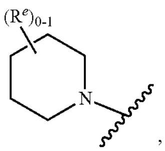

,

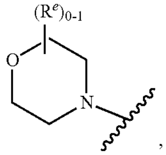

,

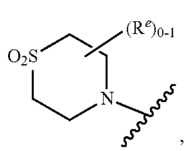

,

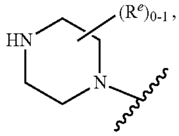

,

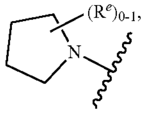

and

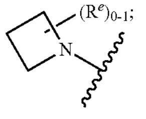

$R^e$ is halo, CN, =O, $C_{1-4}$ alkyl substituted with 0-3 $R^g$, —$(CH_2)_nOR^f$, —$C(=O)OR^f$, $S(=O)_pR^f$, $C(=O)NR^fR^f$, $NR^fC(=O)R^f$, or —$(CH_2)_nNR^fR^f$, $R^f$ is H or $C_{1-4}$ alkyl;

$R^g$ is halo, CN, OH, $C_{1-4}$ alkyl, $C_{3-6}$ cycloalkyl, or aryl;

n is zero or 1; and p is 2.

In an eighth aspect within the scope of the third aspect, the present invention provides compounds of Formula (II), or pharmaceutically acceptable salts thereof, wherein:

$R^4$ is halo or $CF_3$;

$R^6$ is $C_{1-3}$ alkyl substituted with 0-3 halo substituents or $C_{3-6}$ cycloalkyl;

$R^9$ is $C_{1-3}$ alkyl substituted with 0-1 $R^{10}$ and 0-1 $R^1$;

$R^{10}$ is halo or $C_{1-4}$ alkyl substituted with 0-4 halo substituents;

$R^{11}$ is —$NHC(=O)R^b$ or —$NR^aC(=O)OR^b$;

$R^a$ is H or $C_{1-3}$ alkyl;

$R^b$ is $C_{1-4}$ alkyl substituted with 0-3 $R^e$, $C_{3-6}$ cycloalkyl substituted with 0-3 $R^e$, phenyl substituted with 0-3 $R^e$, heterocyclyl selected from

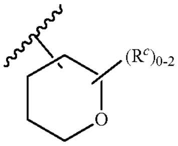

and

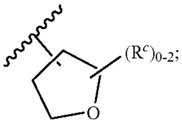

$R^e$ is halo, CN, $C_{1-4}$ alkyl substituted with 0-4 $R^8$, —$OR^f$, —C(=O)ORI, $C(=O)NR^fR^f$, $R^f$ is H or $C_{1-4}$ alkyl; and $R^g$ is halo, CN, OH, $C_{1-4}$ alkyl, $C_{3-6}$ cycloalkyl, or aryl.

In a ninth aspect within the scope of the second aspect, the present invention provides compounds of Formula (II) or pharmaceutically acceptable salts thereof, wherein:

$R^4$ is halo or $C_{1-4}$ alkyl substituted with 0-3 halo substituents;

$R^6$ is $C_{1-3}$ alkyl substituted with 0-3 halo substituents or $C_{3-6}$ cycloalkyl;

$R^8$ is —$OC_{1-3}$ alkyl;

$R^9$ is $C_{2-4}$ alkenyl substituted with 0-2 $R^{10}$ or 0-2 $R^{11}$;

$R^{10}$ is $C_{1-2}$ alkyl substituted with 0-4 halo or —OH substituents;

$R^{11}$ is —C(=O) R', —C(=O)OR', or —$C(=O)NR^aR^a$;

$R^a$ is H, $C_{1-4}$ alkyl substituted with 0-4 $R^e$, $C_{3-6}$ cycloalkyl substituted with 0-4 $R^e$, or phenyl substituted with 0-4 $R^e$; or $R^a$ and $R^a$ together with the nitrogen atom to which they are both attached form a 4- to 9-membered heterocyclyl comprising 1-4 heteroatoms selected from O, $S(=O)_p$, and N, and substituted with 0-4 $R^e$;

$R^b$ is H or $C_{1-4}$ alkyl;

$R^e$ is halo, $C_{1-6}$ alkyl substituted with 0-5 $R^8$, —$(CH_2)_{0-1}OR^f$, or —$C(=O)OR^f$, $R^f$ is H or $C_{1-4}$ alkyl; and $R^g$ is $C_{1-4}$ alkyl.

In a tenth aspect within the scope of the ninth aspect, the present invention provides compounds of Formula (II), or pharmaceutically acceptable salts thereof, wherein:

$R^4$ is halo or $CF_3$;

$R^6$ is $CF_3$ or cyclopropyl;

$R^8$ is —$OC_{1-3}$ alkyl;

$R^9$ is $C_{2-3}$ alkenyl substituted with 0-1 $R^{11}$;

$R^{11}$ is —$C(=O)NR^aR^a$, $R^a$ is H or $C_{1-4}$ alkyl substituted with 0-4 $R^e$, $C_{3-6}$ cycloalkyl substituted with 0-4 $R^e$; or $R^a$ and $R^a$ together with the nitrogen atom to which they are both attached form a heterocyclyl selected from

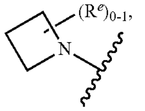

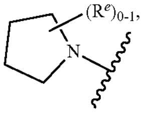

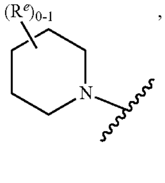

,

-continued

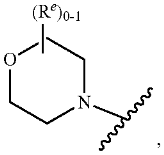
,
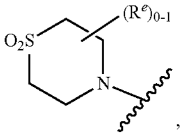
,
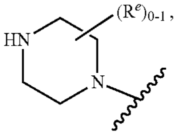
,
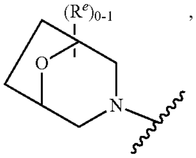
, and
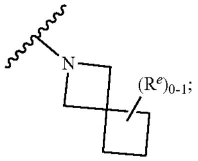

$R^e$ is halo, CN, $C_{1-4}$ alkyl substituted with 0-4 $R^8$, $—(CH_2)_{0-1}OR^f$, $—C(═O)OR^f$, and $R^f$ is H or $C_{1-4}$ alkyl; and $R^g$ is $C_{1-3}$ alkyl.

In an eleventh aspect within the scope of the second aspect, the present invention provides compounds of Formula (II) or pharmaceutically acceptable salts, thereof, wherein:

$R^4$ is halo or $C_{1-4}$ alkyl substituted with 0-3 halo substituents;

$R^6$ is $C_{1-3}$ alkyl substituted with 0-3 halo substituents or $C_{3-6}$ cycloalkyl;

$R^8$ is $—OC_{1-3}$ alkyl substituted with 0-2 halo or OH;

$R^9$ is $C_{2-6}$ alkynyl substituted with 0-2 $R^{11}$;

$R^{11}$ is $—OR^b$ or $—OC(═O)NR^aR^a$;

$R^a$ is H, $C_{1-4}$ alkyl substituted with 0-4 $R^e$, $C_{3-6}$ cycloalkyl substituted with 0-4 $R^e$, or phenyl substituted with 0-4 $R^e$;

$R^b$ is H or $C_{1-4}$ alkyl; and $R^e$ is halo or $C_{1-4}$ alkyl.

In a twelfth aspect within the scope of the second aspect, the present invention provides compounds of Formula (II) or pharmaceutically acceptable salts thereof, wherein:

$R^4$ is halo or $C_{1-4}$ alkyl substituted with 0-3 halo substituents;

$R^6$ is $C_{1-2}$ alkyl substituted with 0-3 F substituents or $C_{3-6}$ cycloalkyl;

$R^8$ is $—OC_{1-3}$ alkyl;

$R^9$ is $C_{3-9}$ cycloalkyl, $—O—C_{3-9}$ cycloalkyl, or fused $C_{3-6}$ cycloalkyl, each substituted with 0-2 $R^{10}$ and 0-2 $R^{11}$, $R^{10}$ is halo, CN, or $C_{1-4}$ alkyl substituted with 0-4 halo or —OH substituents;

$R^{11}$ is $—OR^b$, $—NR^aR^a$, $—NR^aC(═O)R^b$, $—C(═O)OR'$, $—C(═O)NR^aR^a$, or $—OC(═O)NR^aR^a$;

$R^a$ is H, $C_{1-4}$ alkyl substituted with 0-4 $R^e$, $C_{3-6}$ cycloalkyl substituted with 0-4 $R^e$, or phenyl substituted with 0-4 $R^e$; or $R^a$ and $R^a$ together with the nitrogen atom to which they are both attached form a 4- to 6-membered heterocyclyl comprising 1-4 heteroatoms selected from O, $S(═O)_p$, and N, and substituted with 0-4 $R^e$; and $R^b$ is H, $C_{1-4}$ alkyl, or 4- to 6-membered heterocyclyl comprising 1-4 heteroatoms selected from O, $S(═O)_p$, and N;

$R^e$ is halo, $—(CH_2)_nOR^f$ for $—C(═O)OR^f$; and $R^f$ is H or $C_{1-3}$ alkyl.

In a thirteenth aspect within the scope of the twelfth aspect, the present invention provides compounds of Formula (II) or pharmaceutically acceptable salts thereof, wherein:

$R^4$ is F or $CF_3$;

$R^6$ is $CF_3$, cyclopropyl, cyclobutyl, or cyclopentyl;

$R^8$ is $—OC_{1-3}$ alkyl;

$R^9$ is cyclobutyl, cyclopentyl, or cyclohexyl, bicycle[2,2,2]octanyl, each substituted with 0-2 $R^{10}$ and 0-2 $R^{11}$;

$R^{10}$ is F, CN, $CH_2OH$, $C(CH_3)_2OH$, or $CHC(CH_3)_2OH$;

$R^{11}$ is —OH, $—NHC(═O)R^b$, $—C(═O)OR^6$, or $—OC(═O)NR^aR^a$;

$R^a$ is H, $C_{1-4}$ alkyl substituted with 0-3$R^e$, $C_{3-6}$ cycloalkyl substituted with 0-3 $R^e$, or phenyl substituted with 0-3 $R^e$; and $R^b$ is H, $C_{1-4}$ alkyl, or

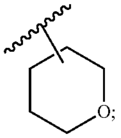

$R^e$ is halo, $—(CH_2)_{0-1}OR^f$ or $—C(═O)OR^f$; and $R^f$ is H or $C_{1-3}$ alkyl.

In a fourteenth aspect within the scope of the second aspect, the present invention provides compounds of Formula (II) or pharmaceutically acceptable salts thereof, wherein:

$R^4$ is halo or $C_{1-4}$ alkyl substituted with 0-3 halo;

$R^6$ is $C_{1-2}$ alkyl substituted with 0-3 F substituents or $C_{3-6}$ cycloalkyl;

$R^8$ is $—OC_{1-3}$ alkyl;

$R^9$ is $C_{6-9}$ spirocycloalkyl substituted with 0-2 $R^{11}$;

$R^{11}$ is $—OR^b$, $—NR^aR^a$, or $C(═O)OR^b$;

$R^a$ is H or $C_{1-4}$ alkyl; and $R^b$ is H or $C_{1-4}$ alkyl.

In a fifteenth aspect within the scope of the first aspect, the present invention provides compounds of Formula (I), or pharmaceutically acceptable salts thereof, wherein:

L is —NH;

$R^4$ is halo or $C_{1-4}$ alkyl substituted with 0-4 halo substituents;

$R^6$ is $C_{1-4}$ alkyl substituted with 0-3 halo substituents or $C_{3-6}$ cycloalkyl;

$R^7$ is H;

$R^8$ is halo or $—OC_{1-4}$ alkyl substituted with 0-5 halo substituents;

$R^9$ is $—S(═O)_pR^c$, or $—S(═O)_pNR^{15}R^{15}$.

$R^{15}$ is H, $C_{1-5}$ alkyl substituted with 0-5 $R^e$, $C_{3-10}$ carbocyclyl substituted with 0-5 $R^e$, or 4- to 9-membered heterocyclyl comprising 1-4 heteroatoms selected from O, $S(═O)_p$, N and $NR^{16}$, and substituted with 0-S $R^e$; or $R^{15}$ and $R^{15}$ together with the nitrogen atom to which they are both attached form a 4- to 9-membered heterocyclyl comprising 1-4 heteroatoms selected from O, $S(═O)_p$, N and $NR^{16}$, and substituted with 0-4 $R^e$;

$R^{16}$ is H, $C_{1-4}$ alkyl substituted with 0-5 $R^e$, $—C(═O)R^f$, $—C(═O)OR^f$, $—C(═O)NR^fR^f$, $—NR^fC(═O)R^f$, $—S(═O)_pR^f$, or $—S(═O)_pNR^fR^f$; $R^c$ is $C_{1-5}$ alkyl substituted with 0-5 $R^e$;

$R^c$ is $C_{1-3}$ alkyl substituted with 0-3 $R^e$;

$R^e$ is halo, $—(CH_2)\ OR^f$, $C(═O)OR^f$, or $C_{1-6}$ alkyl;

$R^f$ is H or $C_{1-3}$ alkyl; and n is zero, 1 or 2.

In a sixteenth aspect within the scope of the fifteenth aspect, the present invention provides compounds of Formula (I) or pharmaceutically acceptable salts thereof, wherein:

$R^4$ is F or $CF_3$;

$R^6$ is $CF_3$ or $C_{3-6}$ cycloalkyl;

$R^8$ is F or —$OC_{1-2}$ alkyl;

$R^9$ is —S(═O)$_2$NR$^{15}$R$^{15}$;

$R^{15}$ is H, $C_{1-8}$ alkyl substituted with 0-5 $R^e$, phenyl substituted with 0-5 $R^e$, or heterocyclyl selected from

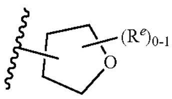 and 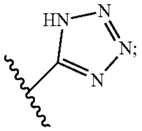

or $R^{15}$ and $R^{15}$ together with the nitrogen atom to which they are both attached form a heterocyclyl selected from

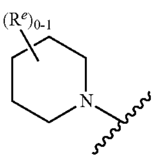, 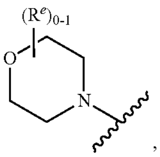, 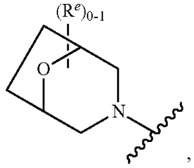,

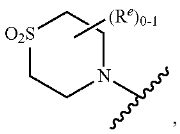, 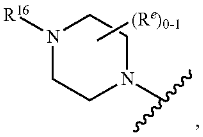, 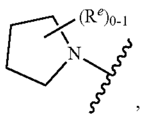,

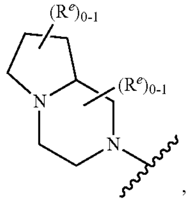, 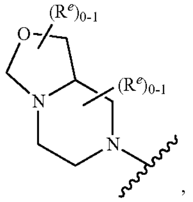,

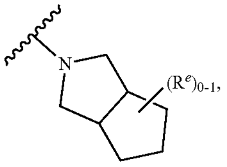 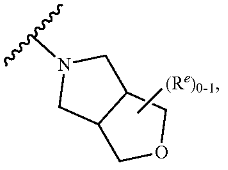

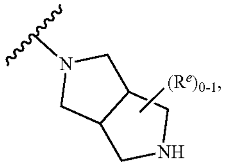 and 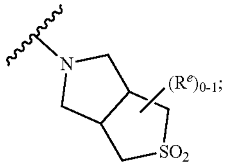

$R^{16}$ is H, $C_{1-3}$ alkyl substituted with 0-5 $R^e$, —C(═O)$R^f$, —C(═O)O$R^f$, —C(═O)N$R^f$$R^f$, —S(═O)$_p$$R^f$, or —S(═O)$_p$N$R^f$$R^f$.

$R^e$ is halo, —O, —(CH$_2$)$_{0-1}$O$R^f$, or $C_{15}$ alkyl; and $R^f$ is H or $C_{1-3}$ alkyl.

In a seventeenth aspect within the scope of the first aspect, the present invention provides compounds of Formula (I) or pharmaceutically acceptable salts thereof, wherein;

L is —NH;

$R^3$ is phenyl substituted with 2 $R^4$;

$R^4$ is F or $CF_3$;

$R^5$ is H;

$R^6$ is $CF_3$ or $C_{3-6}$ cycloalkyl;

$R^7$ is H;

$R^8$ is —$OC_{1-2}$ alkyl;

$R^9$ is —NR$^{17}$R$^{17}$;

$R^{17}$ is H or —(CH$_2$)-phenyl substituted with 0-4 $R^e$;

$R^e$ is halo, —OH, or $C_{1-6}$ alkyl; and n is zero or 1.

In an eighteenth aspect within the scope of the first aspect, the present invention provides compounds of Formula (I) or pharmaceutically acceptable salts thereof, wherein:

L is —NH;

$R^4$ is halo or $C_{1-4}$ alkyl substituted with 0-4 halo substituents;

$R^6$ is $C_{1-4}$ alkyl substituted with 0-3 halo substituents or $C_{3-6}$ cycloalkyl;

$R^7$ is H;

$R^8$ is halo or —$OC_{1-4}$ alkyl substituted with 0-5 halo substituents;

$R^9$ is —C(═O)OR$^{15}$ or —C(═O)NR$^{15}$R$^{15}$;

$R^{15}$ is H, $C_{1-5}$ alkyl substituted with 0-5 $R^e$, —(CH$_2$)$_n$—$C_{3-6}$ cycloalkyl substituted with 0-5 $R^e$, phenyl substituted with 0-5 $R^e$, or 4- to 9-membered heterocyclyl comprising 1-4 heteroatoms selected from O, S(═O)$_p$, N and NR$^{16}$, and substituted with 0-5 $R^e$; or $R^{15}$ and $R^{15}$ together with the nitrogen atom to which they are both attached form a 4- to 9-membered heterocyclyl comprising 1-4 heteroatoms selected from O, S(═O)$_p$, N and NR$^{16}$, and substituted with 0-5 $R^e$, $R^{16}$ is H, $C_{1-6}$ alkyl substituted with 0-5 $R^e$, —C(═O)$R^f$, —C(═O)O$R^f$, —C(═O)N$R^f$$R^f$, —S(═O)$_p$$R^f$, or —S(═O)$_p$N$R^f$$R^f$;

$R^e$ is halo, ═O, $C_{1-6}$ alkyl substituted with 0-2-OH substituents, —(CH$_2$)$_n$O$R^f$, —C(═O)$R^f$, —C(═O)O$R^f$, —C(═O)N$R^f$$R^f$, —N$R^f$C(═O)$R^f$, —S(═O)$_p$$R^f$, or —S(═O)$_p$N$R^f$$R^f$;

$R^f$ is H or $C_{1-3}$ alkyl; and n is zero, 1 or 2.

In a nineteenth aspect within the scope of the eighteenth aspect, the present invention provides compounds of Formula (I) or pharmaceutically acceptable salts thereof, $R^4$ is F or $CF_3$;

$R^6$ is $CF_3$ or $C_{3-6}$ cycloalkyl;

$R^8$ is halo or —$OC_{1-2}$ alkyl;

$R^9$ is —C(═O)NR$^{15}$R$^{15}$;

$R^{15}$ is H, $C_{1-5}$ alkyl substituted with 0-5 $R^e$, —CH$_2$—$C_{3-6}$ cycloalkyl substituted with 0-5 $R^e$, phenyl substituted with 0-5 $R^e$, or heterocyclyl selected from

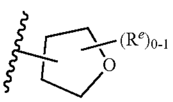 and 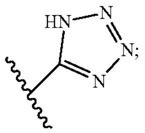

or $R^{15}$ and $R^{15}$ together with the nitrogen atom to which they are both attached form a heterocyclyl selected from

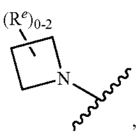, 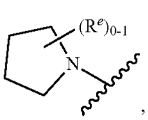, 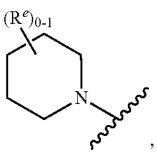,

-continued

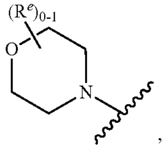, 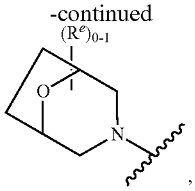, 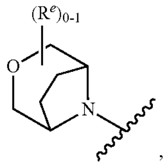,

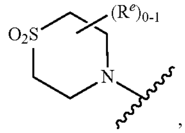, 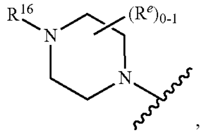,

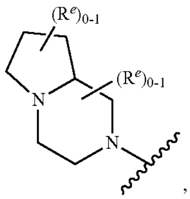, 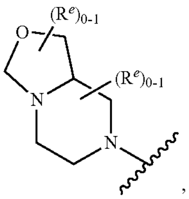,

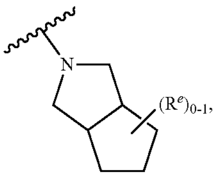

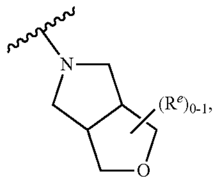

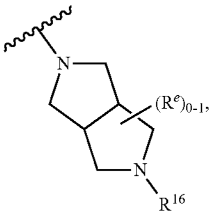

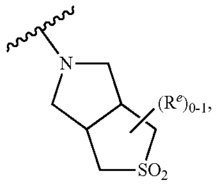

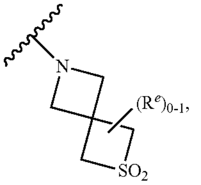 and 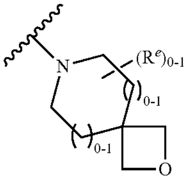;

$R^{16}$ is H or $C_{1-5}$ alkyl substituted with 0-5 $R^e$;

$R^e$ is halo, =O, $C_{1-6}$ alkyl substituted with 0-1 OH, $-(CH_2)_{0-1}OR^f$, $-C(=O)R^f$, $-C(=O)OR^f$, $-C(=O)NR^fR^f$, $-NR^fC(=O)R^f$, $-S(=O)_pR^f$, or $-S(=O)_pNR^fR^f$, and $R^f$ is H or $C_{1-3}$ alkyl.

In a twentieth aspect within the scope of the first aspect, the present invention provides compounds of Formula (III) or pharmaceutically acceptable salts thereof, wherein:

(III)

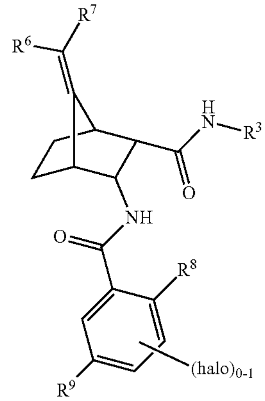

or a pharmaceutically acceptable salt thereof, wherein:

$R^3$ is $-CHR_d-C_{3-6}$-cycloalkyl substituted with 0-5 $R^4$ or phenyl substituted with 0-5 $R^4$;

$R^4$ is halo, CN, or $C_{1-4}$ alkyl substituted with 0-5 halo;

$R^5$ is H;

$R^6$ is $C_{1-3}$ alkyl substituted with 0-3 $R^{6a}$, $C_{3-6}$ cycloalkyl substituted with 0-5 $R^{14}$, or 3- to 6-membered heterocyclyl comprising 1-4 heteroatoms selected from O, $S(=O)_p$, N, and substituted with 0-5 $R^{14}$;

$R^{6a}$ is halo;

$R^7$ is H;

$R^8$ is $-OC_{1-3}$ alkyl;

$R^9$ is $-C(=O)NR^{15}R^{15}$, $-CH_2-O$-phenyl substituted with 0-2 $R^{10}$ and 0-2 $R^{11}$, $C_{3-9}$ cycloalkyl substituted with 0-2 $R^{10}$ and 0-2 $R^{11}$, or $-O-C_{3-6}$ cycloalkyl substituted with 0-2 $R^{10}$ and 0-2 $R^{11}$;

$R^{10}$ is halo, CN, or $C_{1-4}$ alkyl substituted with 0-4 halo or $-OH$ substituents;

$R^{11}$ is $-OR^b$, $-OC(=O)NR^aR^a$, or $-C(=O)OR^b$;

$R^{14}$ is halo, CN, or $C_{1-4}$ alkyl substituted with 0-3 halo substituents;

$R^{15}$ is H, $C_{1-5}$ alkyl substituted with 0-3 $R^e$, $-(CH_2)_n-C_{3-10}$ carbocyclyl substituted with 0-3 $R^e$; or $R^{15}$ and $R^{15}$ together with the nitrogen atom to which they are both attached form a 4- to 9-membered heterocyclyl comprising 1-4 heteroatoms selected from O, $S(=O)_p$, N and $NR^{16}$, and substituted with 0-3 $R^e$;

$R^{16}$ is H or $C_{1-4}$ alkyl substituted with 0-5 $R^e$;

$R^a$ is H, $C_{1-4}$ alkyl substituted with 0-5 $R^e$, $C_{3-6}$ carbocyclyl, or $-(CH_2)_n$-4- to 9-membered heterocyclyl comprising 1-4 heteroatoms selected from O, $S(=O)_p$, and N, and substituted with 0-5 $R^e$;

$R^b$ is H or $C_{1-4}$ alkyl;

$R^d$ is H or $C_{1-3}$ alkyl;

$R^e$ is halo, $C_{1-4}$ alkyl substituted with 0-3 $R^f$, ORE, or $-S(=O)_2C_{1-4}$ alkyl;

$R^f$ is H or $C_{1-4}$ alkyl;

$R^g$ is halo or $-OH$;

n is zero, 1, 2, or 3; and p is zero, 1, or 2.

In one embodiment of Formula (I), $R^1$ and $R^2$ combined are $=CR^6R^7$, $R^6$ and $R^7$ are both methyl.

In another embodiment of Formula (I), $R^1$ and $R^2$ combined are $=CR^6R^7$; $R^6$ is $CF_3$; $R^7$ is H.

In another embodiment of Formula (I), $R^1$ and $R^2$ combined are $=CR^6R^7$; $R^6$ is halo; $R^7$ is H.

In another embodiment of Formula (I), $R^1$ and $R^2$ combined are $=CR^6R^7$; $R^6$ is phenyl substituted with 0-1 $R^{14}$; $R^7$ is H; $R^{14}$ is halo, $-OC_{1-4}$ alkyl, or phenyl.

In another embodiment of Formula (I), $R^1$ and $R^2$ combined are $=CR^6R^7$; $R^6$ is 5-membered heterocyclyl comprising 1-3 heteroatoms selected from O and N; $R^7$ is H.

In another embodiment of Formula (I), $R^1$ and $R^2$ combined are $=CR^6R^7$; $R^6$ is $C_{3-6}$ cycloalkyl; $R^7$ is H.

In another embodiment of Formula (I), $R^1$ and $R^2$ combined are $=CR^6R^7$; $R^6$ is $-CH_2-C_{3-6}$ cycloalkyl substituted with halo; $R^7$ is H.

In another embodiment of Formula (I), $R^1$ and $R^2$ combined are $=CR^6R^7$; $R^6$ is cyclopropyl; $R^7$ is H.

In another embodiment of Formula (I), $R^3$ is $C_{1-6}$ alkyl.

In another embodiment of Formula (I), $R^3$ is

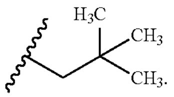

In another embodiment of Formula (I), $R^3$ is $C_{3-6}$ cycloalkyl substituted with 0-2 $R^4$.

In another embodiment of Formula (I), $R^3$ is $C_{3-6}$ cycloalkenyl substituted with 0-2 $R^4$.

In another embodiment of Formula (I), $R^3$ is

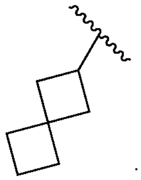 [SMILES: *C1CC2(CCC2)C1]

In another embodiment of Formula (I), $R^3$ is $-(CR^dR^d)_{1-2}$-phenyl substituted with 0-2 $R^4$; $R^4$ is halo, $CF_3$ or $OCF_3$; $R^d$ is H or methyl.

In another embodiment of Formula (I), $R^3$ is $-(CHR^d)-C_{3-6}$ cycloalkyl substituted with 0-2 $R^4$; $R^4$ is halo or $C_{1-2}$ alkyl; $R^a$ is H or $C_{1-2}$ alkyl.

In another embodiment of Formula (I), $R^3$ is

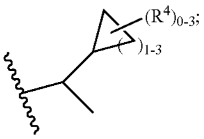

$R^4$ is halo or $C_{1-3}$ alkyl.

In another embodiment of Formula (I), $R^3$ is

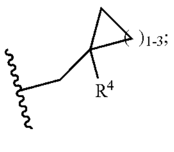

$R^4$ is $C_{1-2}$ alkyl.

In another embodiment of Formula (I), $R^3$ is

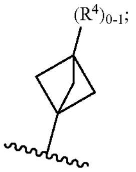

$R^4$ is halo or CN.

In another embodiment of Formula (I), $R^3$ is $-(CR^dR^d)_{1-2}$-5-membered heterocyclyl comprising 1-2 heteroatoms selected from O and N; $R^d$ is H or methyl.

In another embodiment of Formula (I), $R^4$ is halo, CN, $C_{1-2}$ alkyl substituted with 0-3 halo.

In another embodiment of Formula (I), $R^3$ is cyclopropyl, cyclobutyl, cyclopentyl substituted with 0-1 $R^4$, or cyclohexyl; $R^4$ is CN or $C_{1-2}$ alkyl.

In one embodiment of Formula (I), $R^5$ is H, halo, or OH.

In one embodiment of Formula (I), $R^6$ is $CH_3$ or $CF_3$

In another embodiment of Formula (I), $R^6$ is $C_{3-6}$ cycloalkyl substituted with 0-3 halo.

In another embodiment of Formula (I), $R^6$ is 5- to 6-membered heterocyclyl comprising 1-3 heteroatoms selected from O, $S(=O)_p$, N, and $NR^{13}$, and substituted with 0-3 $R^{14}$; $R^{14}$ is $C_{1-3}$ alkyl substituted with 0-3 halo.

In one embodiment of Formula (I), $R^7$ is H or $CH_3$.

In one embodiment of Formula (I), $R^8$ is halo or $-OCH_3$.

In one embodiment of Formula (I), $R^9$ is $C_{3-9}$ cycloalkyl or fused $C_{3-6}$ cycloalkyl, each substituted with 0-2 $R^{10}$ and 0-2 $R^{11}$.

In another embodiment of Formula (I), $R^9$ is $C_{6-9}$ spirocycloalkyl substituted with 0-2 $R^{11}$.

In one embodiment of Formula (I), $R^9$ is $-CH_2-O$-phenyl substituted with 0-2 $R^{10}$ and 0-2 $R^{11}$; $R^{10}$ is $C_{1-3}$ alkyl substituted with 0-4 halo; $R^{11}$ is $-OC(=O)NR^aR^a$; $R^a$ is H or phenyl.

In another embodiment of Formula (I), $R^9$ is $-O-C_{3-6}$ cycloalkyl substituted with 0-2 $R^{10}$ and 0-2 $R^{11}$.

In another embodiment of Formula (I), $R^9$ is

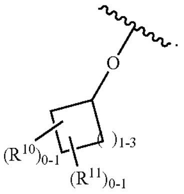

In another embodiment of Formula (I), $R^9$ is

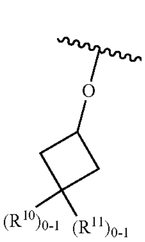

or

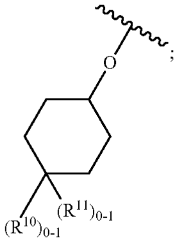

$R^{10}$ is $C_{1-4}$ alkyl; $R^{11}$ is $-C(=O)OR^b$; $R^b$ is H or $C_{1-3}$ alkyl.

For a compound of Formula (I), the scope of any instance of a variable substituent, including $R^1$, $R^2$, $R^3$, $R^4$, $R^{4a}$, $R^3$, $R^5$, $R^{6a}$, $R^{6b}$, $R^7$, $R^8$, $R^9$, $R^{10}$, $R^{11}$, $R^{12}$, $R^{13}$, $R^{14}$, $R^{15}$, $R^{16}$, $R^{17}$, $R^a$, $R^b$, $R^c$, $R^d$, $R^e$, $R^f$, and $R^g$ can be used independently with the scope of any other instance of a variable substituent. As such, the invention includes combinations of the different aspects.

Unless specified otherwise, these terms have the following meanings.

"Halo" includes fluoro, chloro, bromo, and iodo.

"Alkyl" or "alkylene" is intended to include both branched and straight-chain saturated aliphatic hydrocarbon groups having the specified number of carbon atoms. For example, "$C_1$ to $C_{10}$ alkyl" or "$C_{1-10}$ alkyl" (or alkylene), is intended to include $C_1$, $C_2$, $C_3$, $C_4$, $C_5$, $C_6$, $C_7$, $C_8$, $C_9$, and $C_{10}$ alkyl groups. Additionally, for example, "$C_1$ to $C_6$ alkyl" or "$C_1$-$C_6$ alkyl" denotes alkyl having 1 to 6 carbon atoms. Alkyl group can be unsubstituted or substituted with at least one hydrogen being replaced by another chemical group. Example alkyl groups include, but are not limited to, methyl (Me), ethyl (Et), propyl (e.g., n-propyl and isopropyl), butyl (e.g., n-butyl, isobutyl, t-butyl), and pentyl (e.g., n-pentyl, isopentyl, neopentyl). When "$C_0$ alkyl" or "$C_0$ alkylene" is used, it is intended to denote a direct bond. "Alkyl" also includes deuteroalkyl such as $CD_3$.

"Alkenyl" or "alkenylene" is intended to include hydrocarbon chains of either straight or branched configuration having one or more, preferably one to three, carbon-carbon double bonds that may occur in any stable point along the chain. For example, "$C_2$ to $C_6$ alkenyl" or "$C_{2-6}$ alkenyl" (or alkenylene), is intended to include $C_2$, $C_3$, $C_4$, $C_5$, and $C_6$ alkenyl groups; such as ethenyl, propenyl, butenyl, pentenyl, and hexenyl.

"Alkynyl" or "alkynylene" is intended to include hydrocarbon chains of either straight or branched configuration having one or more, preferably one to three, carbon-carbon triple bonds that may occur in any stable point along the chain. For example, "$C_2$ to $C_6$ alkynyl" or "$C_{2-6}$ alkynyl" (or alkynylene), is intended to include $C_2$, $C_3$, $C_4$, $C_5$, and $C_6$ alkynyl groups; such as ethynyl, propynyl, butynyl, pentynyl, and hexynyl.

"Fused" refers to any ring structure described herein which is fused to an existing ring structure in the compounds of the invention.

"Carbocycle", "carbocyclyl", or "carbocyclic residue" is intended to mean any stable 3-, 4-, 5-, 6-, 7-, or 8-membered monocyclic or bicyclic or 7-, 8-, 9-, 10-, 11-, 12-, or 13-membered bicyclic or tricyclic hydrocarbon ring, any of which may be saturated, partially unsaturated, unsaturated or aromatic. Examples of such carbocyclyls include, but are not limited to, cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane (decalin), [2.2.2]bicyclooctane, fluorenyl, phenyl, naphthyl, indanyl, adamantyl, anthracenyl, and tetrahydronaphthyl (tetralin). As shown above, bridged rings are also included in the definition of carbocyclyl (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a tricyclic ring. When a ring is bridged, the substituents recited for the ring may also be present on the bridge. When the term "carbocyclyl" is used, it is intended to include "aryl," "cycloalkyl," "spirocycloalkyl," and "cycloalkenyl." Preferred carbocyclyls, unless otherwise specified, are cyclopropyl, cyclobutyl, cyclopentyl, cyclohexyl, phenyl, and indanyl.

"Cycloalkyl" is intended to mean cyclized alkyl groups, including mono-, bi- or multicyclic ring systems. "$C_3$ to $C_7$ cycloalkyl" or "$C_{3-7}$ cycloalkyl" is intended to include $C_3$, $C_4$, $C_5$, $C_6$, and $C_7$ cycloalkyl groups. Non-limiting examples of monocyclic cycloalkyls include cyclopropyl, cyclobutyl, cyclopentyl, cyclohexyl, cycloheptyl and cyclooctyl. Non-limiting examples of multicyclic cycloalkyls include 1-decalinyl, norbornyl and adamantyl.

"Cycloalkenyl" is intended to mean cyclized alkenyl groups, including mono- or multi-cyclic ring systems that contain one or more double bonds in at least one ring; although, if there is more than one, the double bonds cannot form a fully delocalized pi-electron system throughout all the rings (otherwise the group would be "aryl," as defined herein). A cycloalkenyl can contain 3 to 10 atoms in the ring(s) or 3 to 8 atoms in the ring(s).

"Spirocycloalkyl" is intended to mean hydrocarbon bicyclic ring systems with both rings connected through a single atom. The ring can be different in size and nature, or identical in size and nature. Examples include spiropentane, spriohexane, spiroheptane, spirooctane, spirononane, or spirodecane.

"Bicyclic carbocyclyl" or "bicyclic carbocyclic group" is intended to mean a stable 9- or 10-membered carbocyclic ring system that contains two fused rings and consists of carbon atoms. Of the two fused rings, one ring is a benzo ring fused to a second ring; and the second ring is a 5- or 6-membered carbon ring which is saturated, partially unsaturated, or unsaturated. The bicyclic carbocyclic group may be attached to its pendant group at any carbon atom which results in a stable structure. The bicyclic carbocyclic group described herein may be substituted on any carbon if the resulting compound is stable. Examples of a bicyclic carbocyclic group are, but not limited to, naphthyl, 1,2-dihydronaphthyl, 1,2,3,4-tetrahydronaphthyl, and indanyl.

"Aryl" groups refer to monocyclic or polycyclic aromatic hydrocarbons, including, for example, phenyl, naphthyl, and phenanthranyl. Aryl moieties are well known and described, for example, in Lewis, R. J., ed., *Hawley's Condensed Chemical Dictionary,* 16th Edition, John Wiley & Sons, Inc., New York (2016).

"Benzyl" is intended to mean a methyl group on which one of the hydrogen atoms is replaced by a phenyl group, wherein said phenyl group may optionally be substituted with 1 to 5 groups, preferably 1 to 3 groups.

"Heterocycle", "heterocyclyl" or "heterocyclic ring" is intended to mean a stable 3-, 4-, 5-, 6-, or 7-membered monocyclic or bicyclic or 7-, 8-, 9-, 10-, 11-, 12-, 13-, or 14-membered polycyclic heterocyclic ring that is saturated, partially unsaturated, or fully unsaturated, and that contains carbon atoms and 1, 2, 3 or 4 heteroatoms independently selected from the group consisting of N, O and S; and including any polycyclic group in which any of the above-defined heterocyclic rings is fused to a benzene ring. The nitrogen and sulfur heteroatoms may optionally be oxidized (i.e., N→O and $S(O)_p$, wherein p is 0, 1 or 2). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocyclyl may optionally be quaternized. It is preferred that when the total number of S and O atoms in the heterocyclyl exceeds 1, then these heteroatoms are not adjacent to one another. It is preferred that the total number of S and O atoms in the heterocyclyl is not more than 1. Bridged rings are also included in the definition of heterocyclyl. When the term "heterocyclyl" is used, it is intended to include heteroaryl.

Examples of heterocyclyls include, but are not limited to, acridinyl, azetidinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, imidazolopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinylperimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridinyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocyclyls.

"Bicyclic heterocyclyl" "bicyclic heterocyclyl" or "bicyclic heterocyclic group" is intended to mean a stable 9- or 10-membered heterocyclic ring system which contains two fused rings and consists of carbon atoms and 1, 2, 3, or 4 heteroatoms independently selected from the group consisting of N, O and S. Of the two fused rings, one ring is a 5- or 6-membered monocyclic aromatic ring comprising a 5-membered heteroaryl ring, a 6-membered heteroaryl ring or a benzo ring, each fused to a second ring. The second ring is a 5- or 6-membered monocyclic ring which is saturated, partially unsaturated, or unsaturated, and comprises a 5-membered heterocyclyl, a 6-membered heterocyclyl or a carbocyclyl (provided the first ring is not benzo when the second ring is a carbocyclyl).

The bicyclic heterocyclic group may be attached to its pendant group at any heteroatom or carbon atom which results in a stable structure. The bicyclic heterocyclic group described herein may be substituted on carbon or on a nitrogen atom if the resulting compound is stable. It is preferred that when the total number of S and O atoms in the heterocyclyl exceeds 1, then these heteroatoms are not adjacent to one another. It is preferred that the total number of S and O atoms in the heterocyclyl is not more than 1.

Examples of a bicyclic heterocyclic group are, but not limited to, quinolinyl, isoquinolinyl, phthalazinyl, quinazolinyl, indolyl, isoindolyl, indolinyl, 1H-indazolyl, benzimidazolyl, 1,2,3,4-tetrahydroquinolinyl, 1,2,3,4-tetrahydroisoquinolinyl, 5,6,7,8-tetrahydroquinolinyl, 2,3-dihydrobenzofuranyl, chromanyl, 1,2,3,4-tetrahydroquinoxalinyl, and 1,2,3,4-tetrahydroquinazolinyl.

"Heteroaryl" is intended to mean stable monocyclic and polycyclic aromatic hydrocarbons that include at least one heteroatom ring member such as sulfur, oxygen, or nitrogen. Heteroaryl groups include, without limitation, pyridyl, pyrimidinyl, pyrazinyl, pyridazinyl, triazinyl, furyl, quinolyl, isoquinolyl, thienyl, imidazolyl, thiazolyl, indolyl, pyrroyl, oxazolyl, benzofuryl, benzothienyl, benzthiazolyl, isoxazolyl, pyrazolyl, triazolyl, tetrazolyl, indazolyl, 1,2,4-thiadiazolyl, isothiazolyl, purinyl, carbazolyl, benzimidazolyl, indolinyl, benzodioxolanyl, and benzodioxane. Heteroaryl groups are substituted or unsubstituted. The nitrogen atom is substituted or unsubstituted (i.e., Nor NR wherein R is H or another substituent, if defined). The nitrogen and sulfur heteroatoms may optionally be oxidized (i.e., N→O and $S(O)_p$, wherein p is 0, 1 or 2).

As referred to herein, the term "substituted" means that at least one hydrogen atom is replaced with a non-hydrogen group, provided that normal valencies are maintained and that the substitution results in a stable compound. When a substituent is keto (i.e., =O), then 2 hydrogens on the atom are replaced. Keto substituents are not present on aromatic moieties. When a ring system (e.g., carbocyclic or heterocyclic) is said to be substituted with a carbonyl group or a double bond, it is intended that the carbonyl group or double bond be part (i.e., within) of the ring. Ring double bonds, as used herein, are double bonds that are formed between two adjacent ring atoms (e.g., C=C, C=N, or N=N).

In cases wherein there are nitrogen atoms (e.g., amines) on compounds of the present invention, these may be converted to N-oxides by treatment with an oxidizing agent (e.g., mCPBA and/or hydrogen peroxides) to afford other compounds of this invention. Thus, shown and claimed nitrogen atoms are considered to cover both the shown nitrogen and its N-oxide (N→0) derivative.

When any variable occurs more than one time in any constituent or formula for a compound, its definition at each occurrence is independent of its definition at every other occurrence. Thus, for example, if a group is shown to be substituted with 0-3 R groups, then said group may optionally be substituted with up to three R groups, and at each occurrence R is selected independently from the definition of R. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom in which such substituent is bonded to the rest of the compound of a given formula, then such substituent may be bonded via any atom in such substituent. Combinations of substituents and/or variables are permissible only if such combinations result in stable compounds.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, malcate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Enantiomers and diastereomers are examples of stereoisomers. The term “enantiomer” refers to one of a pair of molecular species that are mirror images of each other and are not superimposable. The term “diastereomer” refers to stereoisomers that are not mirror images. The term “racemate” or “racemic mixture” refers to a composition composed of equimolar quantities of two enantiomeric species, wherein the composition is devoid of optical activity.

The term “counterion” is used to represent a negatively charged species such as chloride, bromide, hydroxide, acetate, and sulfate.

The invention includes all tautomeric forms of the compounds, atropisomers and rotational isomers.

All processes used to prepare compounds of the present invention and intermediates made therein are considered to be part of the present invention.

The symbols “R” and “S” represent the configuration of substituents around a chiral carbon atom(s). The isomeric descriptors “R” and “S” are used as described herein for indicating atom configuration(s) relative to a core molecule and are intended to be used as defined in the literature (IUPAC Recommendations 1996, *Pure and Applied Chemistry,* 68:2193-2222 (1996)).

The term “chiral” refers to the structural characteristic of a molecule that makes it impossible to superimpose it on its mirror image. The term “homochiral” refers to a state of enantiomeric purity. The term “optical activity” refers to the degree to which a homochiral molecule or nonracemic mixture of chiral molecules rotates a plane of polarized light.

The invention is intended to include all isotopes of atoms occurring in the compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

RXFP1 Cyclic Adenosine Monophosphate (cAMP) Assays. Human embryonic kidney cells 293 (HEK293) cells and HEK293 cells stably expressing human RXFP1, were cultured in MEM medium supplemented with 10% qualified FBS, and 300 ng/ml hygromycin (Life Technologies). Cells were dissociated and suspended in assay buffer. The assay buffer was HBSS buffer (with calcium and magnesium) containing 20 mM HEPES, 0.05% BSA, and 0.5 mM IBMX. Cells (3000 cells per well, except 1500 cell per well for HEK293 cells stably expressing human RXFP1) were added to 384-well Proxiplates (Perkin-Elmer). Cells were immediately treated with test compounds in DMSO (2% final) at final concentrations in the range of 0.010 nM to 50 μM. Cells were incubated for 30 min at room temperature. The level of intracellular cAMP was determined using the HTRF HiRange cAMP assay reagent kit (Cisbio) according to manufacturer’s instructions. Solutions of cryptate conjugated anti-cAMP and d2 fluorophore-labelled cAMP were made in a supplied lysis buffer separately. Upon completion of the reaction, the cells were lysed with equal volume of the d2-cAMP solution and anti-cAMP solution. After a 1 h room temperature incubation, time-resolved fluorescence intensity was measured using the Envision (Perkin-Elmer) at 400 nm excitation and dual emission at 590 nm and 665 nm. A calibration curve was constructed with an external cAMP standard at concentrations ranging from 2.7 μM to 0.1 pM by plotting the fluorescent intensity ratio from 665 nm emission to the intensity from the 590 om emission against cAMP concentrations. The potency and activity of a compound to inhibit cAMP production was then determined by fitting to a 4-parametric logistic equation from a plot of cAMP level versus compound concentrations.

The examples disclosed below were tested in the human RXFP1 (hRXFP1) HEK293 cAMP assay described above and found to have agonist activity. Table 1 lists $EC_{50}$ values in the hRXFP1 HEK293 cAMP assay measured for the examples.

TABLE 1

| Example | cAMP hRXFP1 HEK293 Assay $EC_{50}$ (nM) |
|---|---|
| 1 | 675 |
| 2 | 280 |
| 3 | 560 |
| 4 | 337 |
| 5 | 1010 |
| 6 | 1245 |
| 7 | 386 |
| 8 | 309 |
| 9 | 255 |
| 10 | 962 |
| 11 | 4706 |
| 12 | 10 |
| 13 | 625 |
| 14 | 13 |
| 15 | 36 |
| 16 | 94 |
| 17 | 121 |
| 18 | 124 |
| 19 | 125 |
| 20 | 142 |
| 21 | 330 |
| 22 | 417 |
| 23 | 993 |
| 24 | 1809 |
| 25 | 2039 |
| 26 | 1376 |
| 27 | 4676 |
| 28 | 56 |
| 29 | 400 |
| 30 | 710 |
| 31 | 180 |
| 32 | 740 |
| 33 | 580 |
| 34 | 470 |
| 35 | 667 |
| 36 | 442 |
| 37 | 780 |
| 38 | 250 |
| 39 | 611 |
| 40 | 19 |
| 41 | 201 |
| 42 | 214 |

TABLE 1-continued

| Example | cAMP hRXFP1 HEK293 Assay $EC_{50}$ (nM) |
|---|---|
| 43 | 157 |
| 44 | 186 |
| 45 | 3030 |
| 46 | 447 |
| 47 | 926 |
| 48 | 833 |
| 49 | 833 |
| 50 | 2347 |
| 51 | 2347 |
| 52 | 276 |
| 53 | 396 |
| 54 | 158 |
| 55 | 781 |
| 56 | 447 |
| 57 | 1436 |
| 58 | 1196 |
| 59 | 1275 |
| 60 | 648 |
| 61 | 603 |
| 62 | 172 |
| 63 | 4419 |
| 64 | 252 |
| 65 | 250 |
| 66 | 142 |
| 67 | 193 |
| 68 | 144 |
| 69 | 95 |
| 70 | 309 |
| 71 | 118 |
| 72 | 134 |
| 73 | 88 |
| 74 | 3546 |
| 75 | 91 |
| 76 | 66 |
| 77 | 62 |
| 78 | 229 |
| 79 | 104 |
| 80 | 303 |
| 81 | 373 |
| 82 | 125 |
| 83 | 1710 |
| 84 | 67 |
| 85 | 2995 |
| 86 | 45 |
| 87 | 9 |
| 88 | 28 |
| 89 | 45 |
| 90 | 14 |
| 91 | 70 |
| 92 | 172 |
| 93 | 248 |
| 94 | 62 |
| 95 | 50 |
| 96 | 46 |
| 97 | 82 |
| 98 | 111 |
| 99 | 268 |
| 100 | 372 |
| 101 | 194 |
| 102 | 439 |
| 103 | 725 |
| 104 | 988 |
| 105 | 1643 |
| 106 | 377 |
| 107 | 815 |
| 108 | 2270 |
| 109 | 2077 |
| 110 | 2520 |
| 111 | 106 |
| 112 | 324 |
| 113 | 341 |
| 114 | 457 |
| 115 | 536 |
| 116 | 940 |
| 117 | 1242 |
| 118 | 1783 |

TABLE 1-continued

| Example | cAMP hRXFP1 HEK293 Assay $EC_{50}$ (nM) |
|---|---|
| 119 | 1801 |
| 120 | 304 |
| 121 | 1074 |
| 122 | 2808 |
| 123 | 1268 |
| 124 | 1 |
| 125 | 13 |
| 126 | 35 |
| 127 | 74 |
| 128 | 96 |
| 129 | 111 |
| 130 | 114 |
| 131 | 264 |
| 132 | 380 |
| 133 | 384 |
| 134 | 561 |
| 135 | 644 |
| 136 | 776 |
| 137 | 400 |
| 138 | 428 |
| 139 | 694 |
| 140 | 736 |
| 141 | 829 |
| 142 | 167 |
| 143 | 202 |
| 144 | 134 |
| 145 | 84 |
| 146 | 234 |
| 147 | 21 |
| 148 | 6 |
| 149 | 857 |
| 150 | 715 |
| 151 | 1235 |
| 152 | 74 |
| 153 | 1625 |
| 154 | 1049 |
| 155 | 427 |
| 156 | 464 |
| 157 | 54 |
| 158 | 9 |
| 159 | 43 |
| 160 | 51 |
| 161 | 1157 |
| 162 | 1242 |
| 163 | 278 |
| 164 | 67 |
| 165 | 218 |
| 166 | 129 |
| 167 | 11 |
| 168 | 8 |
| 169 | 102 |
| 170 | 51 |
| 171 | 397 |
| 172 | 39 |
| 173 | 186 |
| 174 | 66 |
| 175 | 311 |
| 176 | 738 |
| 177 | 298 |
| 178 | 355 |
| 179 | 267 |
| 180 | 168 |
| 181 | 103 |
| 182 | 139 |
| 183 | 850 |
| 184 | 252 |
| 185 | 603 |
| 186 | 280 |
| 187 | 385 |
| 188 | 56 |
| 189 | 494 |
| 190 | 23 |
| 191 | 40 |
| 192 | 33 |
| 193 | 55 |
| 194 | 76 |

TABLE 1-continued

| Example | cAMP hRXFP1 HEK293 Assay $EC_{50}$ (nM) |
|---|---|
| 195 | 59 |
| 196 | 32 |
| 197 | 918 |
| 198 | 1917 |
| 199 | 719 |
| 200 | 203 |
| 201 | 14 |
| 202 | 186 |
| 203 | 858 |
| 204 | 341 |
| 205 | 611 |
| 206 | 3050 |
| 207 | 890 |
| 208 | 2,600 |
| 209 | 603 |
| 210 | 237 |
| 211 | 551 |
| 212 | 589 |
| 213 | 331 |
| 214 | 272 |
| 215 | 761 |
| 216 | 281 |
| 217 | 221 |
| 218 | 714 |
| 219 | 317 |
| 220 | 459 |
| 221 | 44.9 |
| 222 | 84.9 |
| 223 | 145 |
| 224 | 80.3 |
| 225 | 4,270 |
| 226 | 1,730 |
| 227 | 77.2 |
| 228 | 64.2 |
| 229 | 183 |
| 230 | 26.0 |
| 231 | 32.0 |
| 232 | 0.95 |
| 233 | 65.7 |
| 234 | 64.8 |
| 235 | 130 |
| 236 | 234 |
| 237 | 41.3 |
| 238 | 14.0 |
| 239 | 27.8 |
| 240 | 53.1 |
| 241 | 69.8 |
| 242 | 261 |
| 243 | 11.9 |
| 244 | 11.0 |
| 245 | 37.8 |
| 246 | 13.7 |
| 247 | 27.2 |
| 248 | 128 |
| 249 | 432 |
| 250 | 34.9 |
| 251 | 44.0 |
| 252 | 4.16 |
| 253 | 11.9 |
| 254 | 54.0 |
| 255 | 73.4 |
| 256 | 12.6 |
| 257 | 90.8 |
| 258 | 32.9 |
| 259 | 367 |
| 260 | 324 |
| 261 | 147 |
| 262 | 197 |
| 263 | 318 |
| 264 | 459 |
| 265 | 66.2 |
| 266 | 186 |
| 267 | 246 |
| 268 | 29.6 |
| 269 | 244 |
| 270 | 685 |

TABLE 1-continued

| Example | cAMP hRXFP1 HEK293 Assay $EC_{50}$ (nM) |
|---|---|
| 271 | 264 |
| 272 | 422 |
| 273 | 3,440 |
| 274 | 99.8 |
| 275 | 41.8 |
| 276 | 2,600 |
| 277 | 7.25 |
| 278 | 32.0 |
| 279 | 18.3 |
| 280 | 247 |
| 281 | 130 |
| 282 | 281 |
| 283 | 110 |
| 284 | 161 |
| 285 | 226 |
| 286 | 121 |
| 287 | 1,290 |
| 288 | 58.7 |
| 289 | 14.5 |
| 290 | 76.6 |
| 291 | 2.22 |
| 292 | 28.4 |
| 293 | 67.1 |
| 294 | 117 |
| 295 | 70.4 |
| 296 | 107 |
| 297 | 8.30 |
| 298 | 163 |
| 299 | 116 |
| 300 | 206 |
| 301 | 21.6 |
| 302 | 16.3 |
| 303 | 77.9 |
| 304 | 597 |
| 305 | 744 |
| 306 | 5.26 |
| 307 | 18.5 |
| 308 | 13.7 |
| 309 | 17.1 |
| 310 | 87.0 |
| 311 | 90.9 |
| 312 | 31.4 |
| 313 | 32.9 |
| 314 | 66.2 |
| 315 | 91.2 |
| 316 | 96.7 |
| 317 | 140 |
| 318 | 2,230 |
| 319 | 1,120 |
| 320 | 81.2 |
| 321 | 28.5 |
| 322 | 331 |
| 323 | 21.5 |
| 324 | 4.95 |
| 325 | 2,940 |
| 326 | 4,010 |
| 327 | 26.1 |
| 328 | 21.3 |
| 329 | 210 |
| 330 | 79.0 |
| 331 | 551 |
| 332 | 112 |
| 333 | 62.3 |
| 340 | 78.5 |
| 341 | 126 |
| 342 | 27.8 |
| 343 | 75.2 |
| 348 | 34.0 |
| 349 | 60.9 |
| 350 | 17.7 |
| 351 | 27.7 |
| 352 | 49.9 |
| 353 | 181 |
| 354 | 4,990 |
| 355 | 4,960 |
| 356 | 4,020 |

TABLE 1-continued

| Example | cAMP hRXFP1 HEK293 Assay $EC_{50}$ (nM) |
|---|---|
| 357 | 1,290 |
| 358 | 890 |
| 359 | 1,500 |
| 360 | 2,000 |
| 361 | 2,600 |
| 362 | 3.0 |
| 363 | 3.9 |
| 364 | 1.1 |
| 365 | 2.8 |
| 366 | 3.1 |
| 367 | 2.3 |
| 368 | 9.1 |
| 369 | 3.0 |
| 370 | 9.7 |
| 371 | 2.8 |
| 372 | 5.9 |
| 373 | 3.6 |
| 374 | 6.9 |
| 375 | 1.3 |
| 376 | 120 |
| 377 | 59 |

Pharmaceutical Compositions and Methods of Use

The compounds of Formula (I) are RXFP1 receptor agonists and may find use in the treatment of medical indications such as heart failure (e.g., HFREF and HFpEF), fibrotic diseases, and related diseases such as lung disease (e.g., idiopathic pulmonary fibrosis or pulmonary hypertesion), kidney disease (e.g., chronic kidney disease), or hepatic disease (e.g., non-alcoholic steatohepatitis and portal hypertension). The compounds of Formular (I) can also be used to treat disorders that are a result of or a cause of arterial stiffness, reduced arterial elasticity, reduced arterial compliance and distensibility including hypertension, kidney disease, peripheral arterial disease, carotid and cerebrovascular disease (i.e stroke and dementia), diabetes, microvascular disease resulting in end organ damage, coronary artery disease, and heart failure. The compounds described herein may also be used in the treatment of pre-eclampsia.

Another aspect of the invention is a pharmaceutical composition comprising a compound of Formula (I) and a pharmaceutically acceptable carrier.

Another aspect of the invention is a pharmaceutical composition comprising a compound of Formula (I) for the treatment of a relaxin-associated disorder and a pharmaceutically acceptable carrier.

Another aspect of the invention is a method of treating a disease associated with relaxin comprising administering an effective amount of a compound of Formula (I).

Another aspect of the invention is a method of treating a cardiovascular disease comprising administering an effective amount of a compound of Formula (I) to a patient in need thereof.

Another aspect of the invention is a method of treating heart failure comprising administering an effective amount of a compound of Formula (I) to a patient in need thereof.

Another aspect of the invention is a method of treating fibrosis comprising administering a therapeutically effective amount of a compound of Formula (I) to a patient in need thereof.

Another aspect of the invention is a method of treating a disease associated with fibrosis comprising administering a therapeutically effective amount of a compound of Formula (I) to a patient in need thereof.

Another aspect of the invention is a method of treating idiopathic pulmonary fibrosis comprising administering a therapeutically effective amount of a compound of Formula (I) to a patient in need thereof.

Another aspect of the invention is a method of treating a kidney disease (e.g., chronic kidney disease), comprising administering a therapeutically effective amount of a compound of Formula (I) to a patient in need thereof.

Another aspect of the invention is a method of treating or preventing kidney failure, comprising administering a therapeutically effective amount of a compound of Formula (I) to a patient in need thereof.

Another aspect of the invention is a method of improving, stabilizing or restoring renal function in a patient in need thereof, comprising administering a therapeutically effective amount of a compound of Formula (I) to the patient.

Another aspect of the invention is a method of treating a hepatic disease comprising administering a therapeutically effective amount of a compound of Formula (I) to a patient in need thereof.

Another aspect of the invention is a method of treating non-alcoholic steatohepatitis and portal hypertension comprising administering a therapeutically effective amount of a compound of Formula (I) to a patient in need thereof.

Another aspect of the invention is use of a compound of Formula (I) for prophylaxis and/or treatment of a relaxin-associated disorder.

Another aspect of the invention is a compound of Formula (I) for use in the prophylaxis and/or treatment of a relaxin-associated disorder.

Unless otherwise specified, the following terms have the stated meanings.

The term "patient" or "subject" refers to any human or non-human organism that could potentially benefit from treatment with a RXFP1 agonist as understood by practioners in this field. Exemplary subjects include human beings of any age with risk factors for cardiovascular disease. Common risk factors include, but are not limited to, age, sex, weight, family history, sleep apnea, alcohol or tobacco use, physical inactivity, arrhythmia, or signs of insulin resistance such as acanthosis nigricans, hypertension, dyslipidemia, or polycystic ovary syndrome (PCOS).

"Treating" or "treatment" cover the treatment of a disease-state as understood by practitioners in this field and include the following: (a) inhibiting the disease-state, i.e., arresting it development; (b) relieving the disease-state, i.e., causing regression of the disease state; and/or (c) preventing the disease-state from occurring in a mammal, in particular, when such mammal is predisposed to the disease-state but has not yet been diagnosed as having it.

"Preventing" or "prevention" cover the preventive treatment (i.e., prophylaxis and/or risk reduction) of a subclinical disease-state aimed at reducing the probability of the occurrence of a clinical disease-state as understood by practitioners in this field. Patients are selected for preventative therapy based on factors that are known to increase risk of suffering a clinical disease state compared to the general population. "Prophylaxis" therapies can be divided into (a) primary prevention and (b) secondary prevention. Primary prevention is defined as treatment in a subject that has not yet presented with a clinical disease state, whereas secondary prevention is defined as preventing a second occurrence of the same or similar clinical disease state. "Risk reduction" or "reducing risk" covers therapies that lower the incidence of development of a clinical disease state. As such, primary and secondary prevention therapies are examples of risk reduction.

"Therapeutically effective amount" is intended to include an amount of a compound of the present invention that is effective when administered alone or in combination with other agents to treat disorders as understood by practitioners in this field. When applied to a combination, the term refers to combined amounts of the active ingredients that result in the preventive or therapeutic effect, whether administered in combination, serially, or simultaneously.

"Disorders of the cardiovascular system" or "cardiovascular disorders" include for example the following disorders: hypertension (high blood pressure), peripheral and cardiac vascular disorders, coronary heart disease, stable and unstable angina pectoris, heart attack, myocardial insufficiency, abnormal heart rhythms (or arrhythmias), persistent ischemic dysfunction ("hibernating myocardium"), temporary postischemic dysfunction ("stunned myocardium"), heart failure, disturbances of peripheral blood flow, acute coronary syndrome, heart failure, heart muscle disease (cardiomyopathy), myocardial infarction and vascular disease (blood vessel disease).

"Heart failure" includes both acute and chronic manifestations of heart failure, as well as more specific or related types of disease, such as advanced heart failure, post-acute heart failure, cardio-renal syndrome, heart failure with impaired kidney function, chronic heart failure, chronic heart failure with mid-range ejection fraction (HFmEF), compensated heart failure, decompensated heart failure, right heart failure, left heart failure, global failure, ischemic cardiomyopathy, dilated cardiomyopathy, heart failure associated with congenital heart defects, heart valve defects, heart failure associated with heart valve defects, mitral stenosis, mitral insufficiency, aortic stenosis, aortic insufficiency, tricuspid stenosis, tricuspid insufficiency, pulmonary stenosis, pulmonary valve insufficiency, heart failure associated with combined heart valve defects, myocardial inflammation (myocarditis), chronic myocarditis, acute myocarditis, viral myocarditis, diabetic heart failure, alcoholic cardiomyopathy, heart failure associated with cardiac storage disorders, diastolic heart failure, systolic heart failure, acute phases of worsening heart failure, heart failure with preserved ejection fraction (HFpEF), heart failure with reduced ejection fraction (HFrEF), chronic heart failure with reduced ejection fraction (HFrEF), chronic heart failure with preserved ejection fraction (HFpEF), post myocardial remodeling, angina, hypertension, pulmonary hypertension and pulmonary artery hypertension.

"Fibrotic disorders" encompasses diseases and disorders characterized by fibrosis, including among others the following diseases and disorders: hepatic fibrosis, cirrhosis of the liver, NASH, pulmonary fibrosis or lung fibrosis, cardiac fibrosis, endomyocardial fibrosis, nephropathy, glomerulonephritis, interstitial renal fibrosis, fibrotic damage resulting from diabetes, bone marrow fibrosis and similar fibrotic disorders, scleroderma, morphea, keloids, hypertrophic scarring (also following surgical procedures), naevi, diabetic retinopathy, proliferative vitreoretinopathy and disorders of the connective tissue (for example sarcoidosis).

Relaxin-associated disorders include but are not limited to disorders of the cardiovascular system and fibrotic disorders.

The compounds of this invention can be administered by any suitable means, for example, orally, such as tablets, capsules (each of which includes sustained release or timed release formulations), pills, powders, granules, elixirs, tinctures, suspensions (including nanosuspensions, microsuspensions, spray-dried dispersions), syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

"Pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, Allen, L. V., Jr. et al., *Remington: The Science and Practice of Pharmacy* (2 Volumes), 22nd Edition, Pharmaceutical Press (2012).

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.1 to about 1000 mg per day, and most preferably between about 0.1 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition. A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule. A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The compounds may be employed in combination with other suitable therapeutic agents useful in the treatment of diseases or disorders including: anti-atherosclerotic agents, anti-dyslipidemic agents, anti-diabetic agents, anti-hyperglycemic agents, anti-hyperinsulinemic agents, anti-thrombotic agents, anti-retinopathic agents, anti-neuropathic agents, anti-nephropathic agents, anti-ischemic agents, anti-hypertensive agents, anti-obesity agents, anti-hyperlipidemic agents, anti-hypertriglyceridemic agents, anti-hypercholesterolemic agents, anti-restenotic agents, anti-pancreatic agents, lipid lowering agents, anorectic agents, memory enhancing agents, anti-dementia agents, cognition promoting agents, appetite suppressants, agents for treating heart failure, agents for treating peripheral arterial disease, agents for treating malignant tumors, and anti-inflammatory agents.

The additional therapeutic agents may include ACE inhibitors, β-blockers, diuretics, mineralocorticoid receptor antagonists, ryanodine receptor modulators, SERCA2a activators, renin inhibitors, calcium channel blockers, adenosine A1 receptor agonists, partial adenosine A1 receptor, dopamine β-hydroxylase inhibitors, angiotensin II receptor antagonists, angiotensin II receptor antagonists with biased agonism for select cell signaling pathways, combinations of angiotensin II receptor antagonists and neprilysin enzyme inhibitors, neprilysin enzyme inhibitors, soluble guanylate cyclase activators, myosin ATPase activators, rho-kinase 1 inhibitors, rho-kinase 2 inhibitors, apelin receptor agonists, nitroxyl donating compounds, calcium-dependent kinase II inhibitors, antifibrotic agents, galectin-3 inhibitors, vasopressin receptor antagonists, FPR2 receptor modulators, natriuretic peptide receptor agonists, transient receptor potential vanilloid-4 channel blockers, anti-arrhythmic agents, $I_f$ "funny current" channel blockers, nitrates, digitalis compounds, inotropic agents and β-receptor agonists, cell membrane rescaling agents for example Poloxamer 188, anti-hyperlipidemic agents, plasma HDL-raising agents, anti-hypercholesterolemic agents, cholesterol biosynthesis inhibitors (such as HMG CoA reductase inhibitors), LXR agonist, FXR agonist, probucol, raloxifene, nicotinic acid, niacinamide, cholesterol absorption inhibitors, bile acid sequestrants, anion exchange resins, quaternary amines, cholestyramine, colestipol, low density lipoprotein receptor inducers, clofibrate, fenofibrate, bezafibrate, ciprofibrate, gemfibrizol, vitamin B6, vitamin B12, anti-oxidant vitamins, anti-diabetes agents, platelet aggregation inhibitors, fibrinogen receptor antagonists, aspirin and fibric acid derivatives, PCSK9 inhibitors, aspirin, and P2Y12 Inhibitors such as Clopidogrel.

The additional therapeutic agents may also include nintedanib, Pirfenidone, LPA1 antagonists, LPA1 receptor antagonists, GLP1 analogs, tralokinumab (IL-13, AstraZeneca), vismodegib (hedgehog antagonist, Roche), PRM-151 (pentraxin-2, TGF beta-1, Promedior), SAR-156597 (bispecific Mab IL-4&IL-13, Sanofi), simtuzumab ((anti-lysyl oxidase-like 2 (anti-LOXL2) antibody, Gilead), CKD-942, PTL-202 (PDE inh./pentoxifylline/NAC oral control. release, Pacific Ther.), omipalisib (oral PI3K/mTOR inhibitor, GSK), IW-001 (oral sol. bovine type V collagen mod., Immune Works), STX-100 (integrin alpha V/beta-6 ant, Stromedix/Biogen), Actimmune (IFN gamma), PC-SOD (midismase; inhaled, LTT Bio-Pharma/CKD Pharm), lebrikizumab (anti-IL-13 SC humanized mAb, Roche), AQX-1125 (SHIP1 activator, Aquinox), CC-539 (JNK inhibitor, Celgene), FG-3019 (FibroGen), SAR-100842 (Sanofi), and obeticholic acid (OCA or INT-747, Intercept).

The above other therapeutic agents, when employed in combination with the compounds of the present invention may be used, for example, in those amounts indicated in the *Physicians' Desk Reference*, as in the patents set out above, or as otherwise determined by practitioners in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

The compounds of the present invention are also useful as standard or reference compounds, for example as a quality standard or control, in tests or assays involving RXFP1. Such compounds may be provided in a commercial kit, for example, for use in pharmaceutical research involving RXFP1. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness. The compounds of the present invention may also be used in diagnostic assays involving RXFP1.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of dyslipidemias and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Chemical Methods

Throughout the specification and the appended claims, a given chemical formula or name shall encompass all stereo and optical isomers and racemates thereof where such isomers exist. Unless otherwise indicated, all chiral (enantiomeric and diastereomeric) and racemic forms are within the scope of the invention. Many geometric isomers of C═C double bonds, C═N double bonds, ring systems, and the like can also be present in the compounds, and all such stable isomers are contemplated in the present invention. Cis- and trans-(or E- and Z-) geometric isomers of the compounds of the present invention are described and may be isolated as a mixture of isomers or as separated isomeric forms. The present compounds can be isolated in optically active or racemic forms. Optically active forms may be prepared by resolution of racemic forms or by synthesis from optically active starting materials. All processes used to prepare compounds of the present invention and intermediates made therein are considered to be part of the present invention. When enantiomeric or diastereomeric products are prepared, they may be separated by conventional methods, for example, by chromatography or fractional crystallization. Depending on the process conditions the end products of the present invention are obtained cither in free (neutral) or salt form. Both the free form and the salts of these end products are within the scope of the invention. If so desired, one form of a compound may be converted into another form. A free base or acid may be converted into a salt; a salt may be converted into the free compound or another salt; a mixture of isomeric compounds of the present invention may be separated into the individual isomers. Compounds of the present invention, free form and salts thereof, may exist in multiple tautomeric forms, in which hydrogen atoms are transposed to other parts of the molecules and the chemical bonds between the atoms of the molecules are consequently rearranged. It should be understood that all tautomeric forms, insofar as they may exist, are included within the invention.

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention.

The disclosure is not limited to the foregoing illustrative examples and the examples should be considered in all respects as illustrative and not restrictive, and all changes which come within the meaning and range of equivalency of the claims are therefore intended to be embraced.

It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene, T. W. et al., *Protecting Groups in Organic Synthesis,* 4th Edition, Wiley (2007)).

Abbreviations are defined as follows: "1×" for once, "2×" for twice, "3×" for thrice, "C" for degrees Celsius, "aq" for aqueous, "eq" or "equiv." for equivalent or equivalents, "g" for gram or grams, "mg" for milligram or milligrams, "L" for liter or liters, "mL" for milliliter or milliliters, "μL" for microliter or microliters, "N" for normal, "M" for molar, "nM" for nanomolar, "pM" for picomolar, "mol" for mole or moles, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "aq" for "aqueous", "sat." for saturated, "MW" for molecular weight, "MS" or "Mass Spec" for mass spectrometry, "ESI" for electrospray ionization mass spectroscopy, "LC-MS" for liquid chromatography mass spectrometry, "HPLC" for high pressure liquid chromatography, "RP HPLC" for reverse phase HPLC, "NMR" for nuclear magnetic resonance spectroscopy, "SFC" for super critical fluid chromatography, "[1]H" for proton, "δ" for delta, "s" for singlet, "d" for doublet, "t" for triplet, "q" for quartet, "m" for multiplet, "br" for broad, "Hz" for hertz, "MHz" for megahertz, and "α", "β", "R", "S", "E", and "Z" are stereochemical designations familiar to one skilled in the art.

AcCl acetyl chloride
AcOH acetic acid
AIBN Azobisisobutyronitrile
BHFFT bis(tetramethylene)fluoroformadmidinium hexafluorophosphate
Boc tert-butyloxycarbonyl
BuLi butyl lithium
DAST Diethylaminosulfur trifluoroide
DCE Dichloroethane
DCM Dichloromethane
DIEA diispropyl ethylamine
DMAP 4-dimethylamino pyridine
DMF Dimethylformamide
DPPA Diphenyl phosphorylazide
$Et_2O$ diethyl ether
EtOAc Ethylacetate
EtOH Ethanol
HATU (1-[Bis(dimethylamino)methylene]-1H-1,2,3-triazolo[4,5-b]pyridinium 3-oxid hexafluorophosphate)
HMPA hexamethylphosphoramide
IPA isopropanol
i-Pr Isopropyl
KHMDS potassium bis(trimethylsilyl)amide\
LDA lithium diisopropyl amide
MeCN Acetonitrile
MeOH Methanol
Me Methyl
NBS N-bromosuccinimide
Pd/C palladium on carbon
pTsOH p-toluenesulfonic acid
PyBroP Bromotripyrrolidinophosphonium hexafluorophosphate
T3P 2,4,6-Tripropyl-1,3,5,2,4,6-trioxatriphosphorinane-2,4,6-trioxide
TBAF tetra-n-butyl ammonium fluoride
t-Bu tert-butyl
Teoc 2-(trimethylsilyl)ethyl carboxylate
TFA trifluoro acetic acid
TFAA trifluoro acetic anhydride
THF Tetrahydrofuran
TsOH Tolulenesulfonic acid
XPhos-Pd-G2 2nd generation XPhos precatalyst CAS no. 1310584-14-5

The following methods were used in the exemplified examples, except where noted otherwise. Purification of intermediates and final products was carried out via either normal or reverse phase chromatography. Normal phase chromatography was carried out using prepacked $SiO_2$ cartridges eluting with either gradients of hexanes and ethyl acetate or DCM and MeOH unless otherwise indicated. Reverse phase preparative HPLC was carried out using C18 columns with UV 220 nm or prep LCMS detection eluting with gradients of Solvent A (90% water, 10% MeOH, 0.1% TFA) and Solvent B (10% water, 90% MeOH, 0.1% TFA) or with gradients of Solvent A (95% water, 5% ACN, 0.1% TFA) and Solvent B (5% water, 95% ACN, 0.1% TFA) or with gradients of Solvent A (95% water, 2% ACN, 0.1% HCOOH) and Solvent B (98% ACN, 2% water, 0.1% HCOOH) or with gradients of Solvent A (95% water, 5% ACN, 10 mM $NH_4OAc$) and Solvent B (98% ACN, 2% water, 10 mM $NH_4OAc$) or with gradients of Solvent A (98% water, 2% ACN, 0.1% $NH_4OH$) and Solvent B (98% ACN, 2% water, 0.1% $NH_4OH$).

LC/MS methods employed in characterization of examples are listed below.

Method A:

Instrument: Waters Acquity coupled with a Waters MICROMASS® ZQ Mass
Spectrometer
Linear gradient of 2 to 98% B over 1 min, with 0.5 min hold time at 98% B
UV visualization at 220 nm
Column: Waters BEH C18, 2.1×50 mm
Flow rate: 0.8 mL/min (Method A)
Mobile Phase A: 0.05% TFA, 100% water
Mobile Phase B: 0.05% TFA, 100% acetonitrile Method B:

Instrument: Shimadzu Prominence HPLC coupled with a Shimadzu LCMS-2020
Mass Spectrometer
Linear gradient of 0 to 100% B over 3 min, with 0.75 min hold time at 100% B
UV visualization at 220 nm
Column: Waters Xbridge C18, 2.1×50 mm, 1.7 μm particles
Flow rate: 1 mL/min
Mobile Phase A: 10 mM ammonium acetate, 95:5 water: acetonitrile
Mobile Phase B: 10 mM ammonium acetate, 5:95 water: acetonitrile Method C:

Instrument: Shimadzu Prominence HPLC coupled with a Shimadzu LCMS-2020
Mass Spectrometer
Linear gradient of 0 to 100% B over 3 min, with 0.75 min hold time at 100% B
UV visualization at 220 nm
Column: Waters Xbridge C18, 2.1×50 mm, 1.7 μm particles
Flow rate: 1 mL/min
Mobile Phase A: 0.1% TFA, 95:5 water:acetonitrile
Mobile Phase B: 0.1% TFA, 5:95 water:acetonitrile Method D:

Instrument: Waters Acquity coupled with a Waters MICROMASS® ZQ Mass
Spectrometer
Linear gradient of 10% B to 98% B over 1 min, with 0.5 min hold time at 98% B
UV visualization at 220 nm
Column: Waters Acquity GEN C18, 2.1×50 mm, 1.7 μm particles
Flow rate: 1 mL/min
Mobile Phase A: 0.05% TFA, 100% water
Mobile Phase B: 0.05% TFA, 100% acetonitrile NMR Employed in Characterization of Examples. $^1$H NMR spectra were obtained with Bruker or JEOL® Fourier transform spectrometers operating at frequencies as follows: $^1$H NMR: 400 MHz (Bruker or JEOL®) or 500 MHz (Bruker or JEOL®). Spectra data are reported in the format: chemical shift (multiplicity, coupling constants, number of hydrogens). Chemical shifts are specified in ppm downfield of a tetramethylsilane internal standard (δ units, tetramethylsilane=0 ppm) and/or referenced to solvent peaks, which in $^1H$ NMR spectra appear at 2.51 ppm for DMSO-$d_6$, 3.30 ppm for $CD_3OD$, 1.94 ppm for $CD_3CN$, and 7.24 ppm for $CDCl_3$.

Syntheses of key norbornyl intermediates are outlined in Schemes I-V. Norbornyl intermediates can be made with isopropylidene bridgehead substitution as described in Scheme I, starting from I-1. Diels-Alder cyclization with maleic anhydride furnished compound I-2, which was reduced and deprotected to yield 1-3. Curtius reaction with DPPA on the free acid in the presence of trimethylsilylethanol produced I-4. The trimethylsilylcarbamate was cleaved with TFA and the amine reprotected as the trifluoroacetamide I-5. The methyl ester was converted to the amide via treatment with 4-fluoro-3-trifluoromethylaniline and trimethyl aluminum to furnish I-6. Deprotection of the trifluoroacetamide using $K_2CO_3$ and MeOH produced amine I-7.

Scheme I

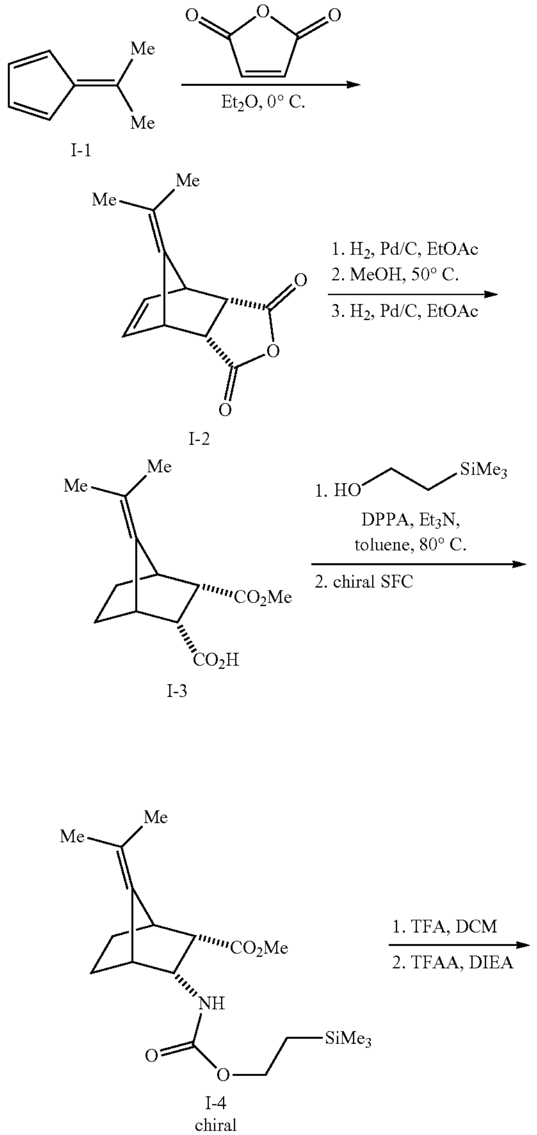

I-1

I-2

I-3

I-4
chiral

-continued

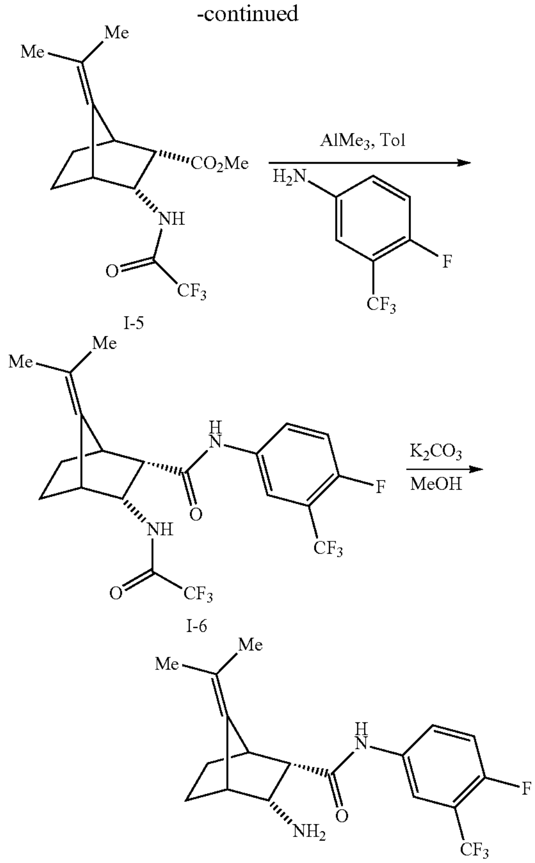

I-5

I-6

I-7

Intermediate I-2: At 0° C., into the reaction vessel was added $Et_2O$ (100 mL), 5-(propan-2-ylidene)cyclopenta-1,3-diene (10 g, 94 mmol), and furan-2,5-dione (10 g, 100 mmol).

The reaction mixture was stirred at 0° C. for 18 h, concentrated under reduced pressure and purified via silica gel chromatography to provide I-2 (3.74 g, 18.3 mmol, 19.0% yield). Intermediate I-2 is a known compound; please see: PCT Int. Appl., 2011163502, 29 Dec. 2011.

Intermediate I-3: Into the reaction vessel was added I-2 (2.74 g, 13.4 mmol), EtOAc (100 mL), pyridine (0.540 mL, 6.71 mmol), and Pd/C (70 mg, 0.070 mmol). The reaction mixture was stirred at 23° C. under 1 atm H2 ($H_2$ balloon) for 60 min filtered through Celite, and concentrated under reduced pressure. The residue was dissolved in MeOH (50 mL) and heated at 50° C. for 12 h. The solution was concentrated under reduced pressure (azeotroped with toluene 3x15 mL) to produce I-3 (3.21 g, 13.5 mmol, 100% yield) that was used without further purification.

Intermediate I-4: Into the reaction vessel was added I-3 (3.21 g, 13.5 mmol), $Et_3N$ (3.38 mL, 24.2 mmol), toluene (75 mL), and diphenylphosphoryl azide (4.35 mL, 20.2 mmol). The reaction mixture was stirred at 23° C. for 1 h and subsequently heated at 85° C. for 30 min. 2-(trimethylsilyl) ethanol (4.83 mL, 33.7 mmol) was added to the reaction mixture and, after stirring at 85° C. for 66 h, the reaction mixture was allowed to cool to 23° C. and purified via silica gel chromatography to provide racemic I-4 (3.71 g, 10.5 mmol, 78% yield) LC-MS RT=1.25 min; (M+H)=354.1. Method A. Racemic 1-4 was separated into individual enantiomers using chiral SFC. Preparative chromatographic conditions: Instrument: Thar 350 SFC; Column: Whelko-RR, 5x50 cm, 10 micron; Mobile phase: 13% IPA/87% $CO_2$; Flow conditions: 300 mL/min, 100 Bar, 35° C.; Detector wavelength: 220 nm; Injections details: 4 injections of 3.5 mL of 59 g/490 mL MeOH:DCM (4:1) 120 mg/mL in IPA. Analytical chromatographic conditions: Instrument: Thar analytical SFC; Column: Whelko-RR (0.46x25 cm, 5 micron; Mobile phase: 5% IPA/95% $CO_2$; Flow conditions: 3 mL/min, 140 Bar, 40° C.; Detector wavelength: 200-400 nm UV; RT=3.50 Peak #1, 4.42 Peak #2. Intermediate I-4 product Peak #1 was collected and carried forward to produce chiral I-5.

Intermediate I-5: Peak #1 of intermediate I-4 (2.87 g, 8.12 mmol) was dissolved in 10:1 DCM/TFA and stirred at rt for 72 h. The reaction mixture was concentrated under reduced pressure to generate (1R,2S,3R,4R)-methyl 3-amino-7-(propan-2-ylidene) bicyclo[2.2.1]heptane-2-carboxylate (1.699 g, 8.120 mmol, 100% yield) which was used without further purification. To (1R,2S,3R,4R)-methyl 3-amino-7-(propan-2-ylidene) bicyclo[2.2.1]heptane-2-carboxylate (1.7 g, 8.1 mmol) was added DCM (41 mL) and the flask was cooled to 0° C. via an ice bath. TFAA (1.26 mL, 8.90 mmol) and DIEA (5.7 mL, 33 mmol) were added. The reaction mixture was allowed to warm to 23° C. and stirred for 30 min. Saturated $NaHCO_3$ (50 mL) was added to the reaction mixture and the solution extracted with EtOAc (3x50 mL). The combined organic portions were dried over $Na_2SO_4$ filtered and concentrated under reduced pressure to afford I-5 (2.48 g, 8.12 mmol, 100% yield) that was used without further purification. LC-MS RT=1.11 min; MS (ESI) m/z=306.1 $(M+H)^+$; Method A.

Intermediate I-6: To a solution of intermediate I-5 (2.7 g, 8.8 mmol) in toluene (88 ml) was added trimethylaluminum (26.5 mmol) premixed with 4-fluoro-3 (trifluoromethyl) aniline (29.2 mmol) as a solution in toluene (0.275 M in amine, 0.25 M in trimethylaluminum). The reaction mixture was stirred at 60° C. for 30 min. On cooling to rt, the reaction mixture was diluted with EtOAc (100 mL) and sat. Rochelle's salt (100 mL) added. The aqueous portion was extracted with EtOAc (3x75 mL). The combined organic portion was dried over $Na_2SO_4$, filtered, concentrated under reduced pressure, and subjected to silica gel chromatography purification and the residue further purified by preparative reverse phase HPLC to yield (1R,2S,3R,4R)—N-(4-fluoro-3-(trifluoromethyl)phenyl)-7-(propan-2-ylidene)-3-(2,2,2-trifluoroacetamido) bicyclo[2.2.1]heptane-2-carboxamide I-6 (2.5 g, 5.5 mmol, 63% yield) as a yellow foam. LC-MS RT=1.20 min; MS (ESI) m/z=453.0 $(M+H)^+$; Method A.

Intermediate I-7: Intermediate I-6 (133 mg, 0.290 mmol) was dissolved in water (2.9 mL) and MeOH (2.9 mL), then $K_2CO_3$ (2.03 g, 1.47 mmol) was added. The reaction mixture was stirred at 40° C. for 4 h, then partitioned between water (5 mL) and extracted with EtOAc (3x10 mL). The combined organic extracts were dried over $Na_2SO_4$ filtered and concentrated under reduced pressure to afford I-7 (105 mg, 0.290 mmol, 100% yield) that was used without further purification. LC-MS RT=0.82 min; MS (ESI) m/z=357.1 $(M+H)^+$; Method A.

Scheme Ia

The norbornyl intermediate IIa-8 could also be prepared by the general route shown in Scheme Ia from furan-2,5-dione and ferrocenium hexafluorophosphate. Diels Alder condensation, followed by hydrolysis to IIa-2, Curtius rearrangement to the intermediate amine which was reduced under hydrogenation conditions and subsequently protected to generate intermediate IIa-3. Cleavage of the benzyl ester and cross coupling to $NHR_1R_2$ generated intermediates with the general structure IIa-5. Conversion of the $C_7$ hydroxy group to the ketone followed by Wittig olefination generated major isomer intermediate IIa-8. The major isomer was separated from the minor isomer by chromatography and the racemate separated into enantiopure IIa-8 (-).

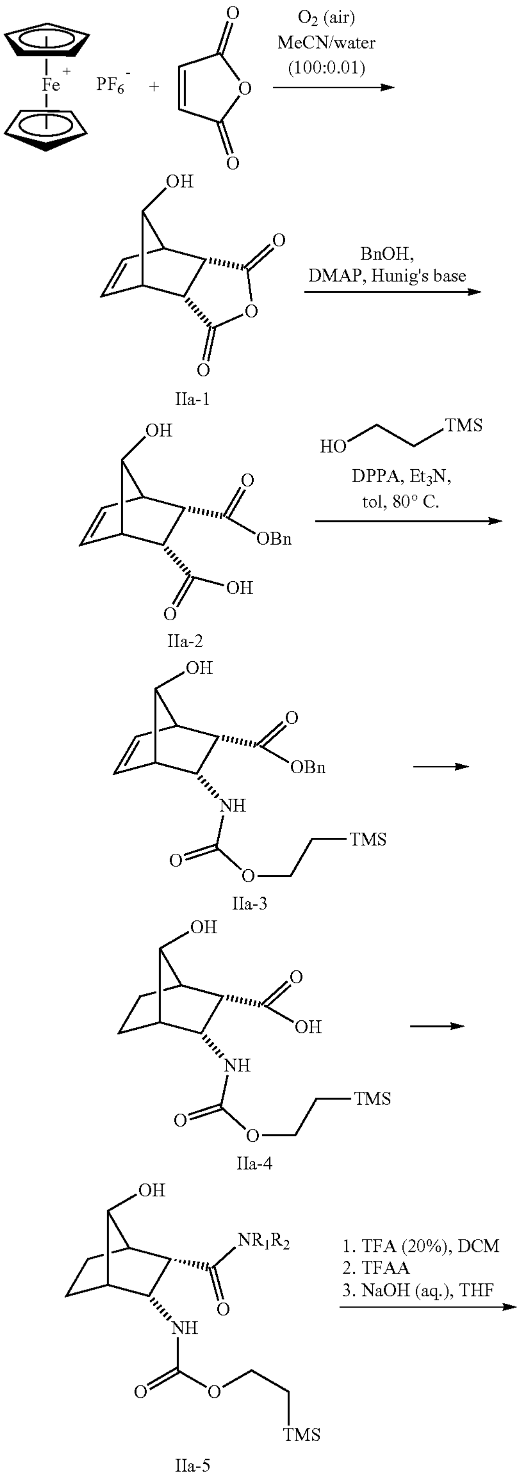

IIa-1

IIa-2

IIa-3

IIa-4

IIa-5

-continued
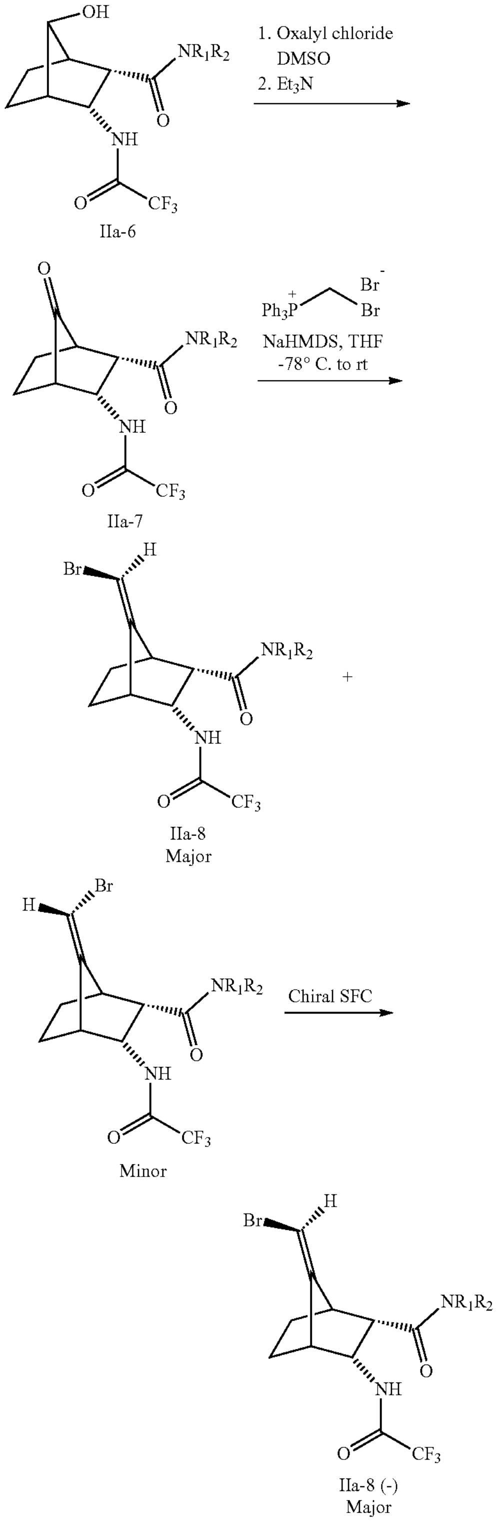
IIa-6
IIa-7
IIa-8
Major
Minor
IIa-8 (-)
Major
Scheme II
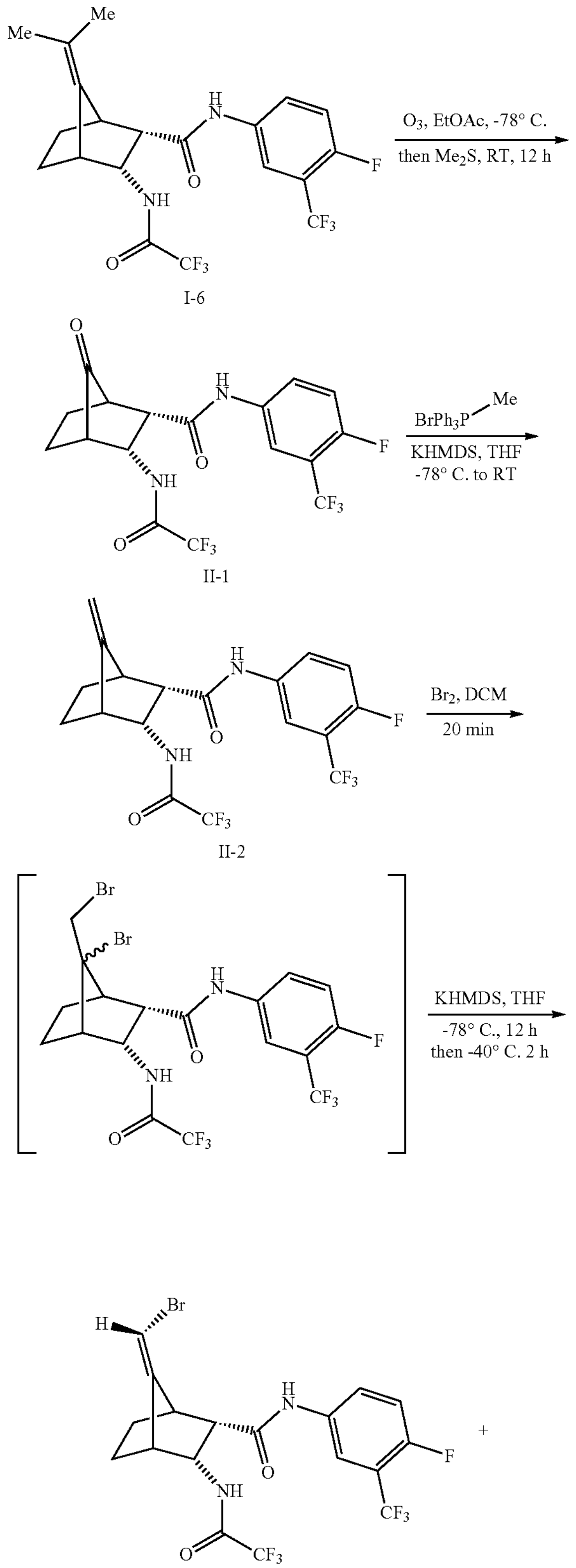
I-6
II-1
II-2
II-3
(peak 1, silica gel chrom.)
Scheme II shows how intermediate I-6 was converted to an olefinic bromide intermediate that allows for cross-coupling reactions at the C-7 methylidene.

-continued

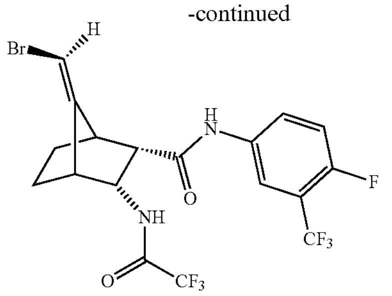

II-4
(peak 2, silica gel chrom.)

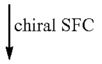

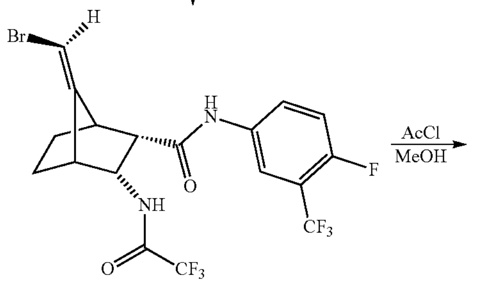

II-4
chiral
peak 1

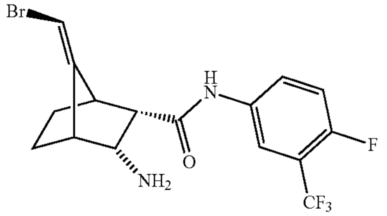

II-5

Intermediate II-1 Into the reaction vessel was added intermediate I-6 (110 mg, 0.243 mmol) and EtOAc (2 mL). The reaction mixture was cooled to −78° C. and $O_3$ was bubbled through the solution until the solution became pale purple/blue. $N_2$ was subsequently bubbled through the solution at −78° C. to remove excess $O_3$ (solution became colorless). Dimethyl sulfide (0.43 mL, 4.8 mmol) was subsequently added at −78° C. and the reaction mixture was allowed to warm to rt and stirred at rt for 12 h. After concentrating under reduced pressure, the residue was dissolved in EtOAc and filtered through silica gel to generate (1R,2S,3R,4S)—N-(4-fluoro-3-(trifluoromethyl)phenyl)-7-oxo-3-(2,2,2-trifluoroacetamido) bicyclo[2.2.1]heptane-2-carboxamide after removal of solvent under reduced pressure, (II-1, 101 mg, 0.237 mmol, 97.0% yield). 1H NMR (500 MHz, $CDCl_3$) δ 9.61 (br d, J=6.3 Hz, 1H), 7.76 (dd, J=5.9, 2.6 Hz, 1H), 7.71 (dt, J=8.9, 3.4 Hz, 1H), 7.66 (s, 1H), 7.23 (t, J=9.4 Hz, 1H), 4.70 (dt, J=10.3, 5.3 Hz, 1H), 3.33 (dd, J=10.5, 4.4 Hz, 1H), 2.54 (t, J=4.3 Hz, 1H), 2.42 (t, J=4.1 Hz, 1H), 2.20-2.10 (m, 1H), 2.06-1.99 (m, 1H), 1.96-1.81 (m, 2H).

Intermediate II-2: Into the reaction vessel was added bromo(methyl)triphenylphosphorane (419 mg, 1.17 mmol) (fine powder by grinding the commercial material) and THF (7 mL). The reaction mixture was cooled to −78° C. and KHMDS (1.2 mL, 1.2 mmol) was added. The reaction mixture was allowed to stir vigorously at −78° C. for 30 min and II-1 (100 mg, 0.24 mmol) was added at −78° C. After stirring at −78° C. for a further 10 min, the reaction mixture was allowed to warm to 23° C. and stirred for a further 1.5 h. The reaction mixture was cooled to −40° C. and quenched by the addition of sat. $NaHCO_3$. The resulting solution was extracted with EtOAc. The combined organic portion was dried over $Na_2SO_4$, filtered, concentrated under reduced pressure, and purified via silica gel chromatography to produce II-2 (71 mg, 0.17 mmol, 71% yield). LCMS RT=1.16 min; (M+H)=425.0; Method A.

Intermediates II-3 and II-4: Into the reaction vessel was added II-2 (71 mg, 0.17 mmol), DCM (3 mL), and $Br_2$ (0.03 mL, 0.6 mmol). The reaction mixture was stirred at 23° C. for 20 min and concentrated under reduced pressure utilizing a trap with sat. $Na_2S_2O_3$ to quench excess $Br_2$. The resulting dibromide was dissolved in THF (3 mL). After cooling to −78° C., KHMDS (1.0 mL, 1.0 mmol) was added. The reaction mixture was kept at −78° C. for 12 h and −40° C. for 2 h, quenched by the addition of sat. $NaHCO_3$ at −40° C., and the resulting solution extracted with EtOAc. The organic phase was collected, dried over $Na_2SO_4$, filtered, concentrated under reduced pressure, and purified via silica gel chromatography to produce II-4 (27 mg, 0.050 mmol, 32% yield) (peak2). LCMS RT=1.19 min; (M+H)=504.9; Method A. and the corresponding E-isomer II-3 (28 mg, 0.06 mmol, 33% yield) (peak 1).

Racemic II-4 (4 grams) was produced as outlined above and separated into individual enantiomers using chiral SFC. Preparative chromatographic conditions: Instrument: Thar 350 SFC; Column: Chiralcel OD-H, 5×50 cm, 5 micron; Mobile phase: 20% MeOH/80% $CO_2$; Flow conditions: 340 mL/min, 100 Bar, 35° C.; Detector wavelength: 220 nm; Injections details: 3.75 mL of 30 mg/mL in MeOH. Peak #1 RT=7.81 min, Peak #2 RT=10.97 min. Peak #1 of II-4 (1.9 grams) was collected and carried forward to produce chiral II-5.

Intermediate II-5: Into the reaction was added MeOH (3 mL) and AcCl (0.3 mL, 4.2 mmol). After stirring for 5 min, chiral Peak #1 II-4 (75 mg, 0.15 mmol) was added and the reaction mixture was stirred at 40° C. for 48 h. The reaction mixture was concentrated under reduced pressure produced II-5 (67 mg, 0.16 mmol, 100%) that was used without further purification. LC-MS RT=0.78 min; (M+H)=408.9; Method A.

Scheme III

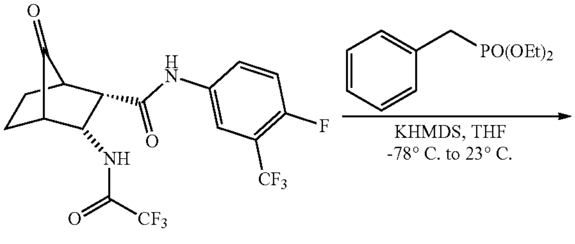

II-1

-continued

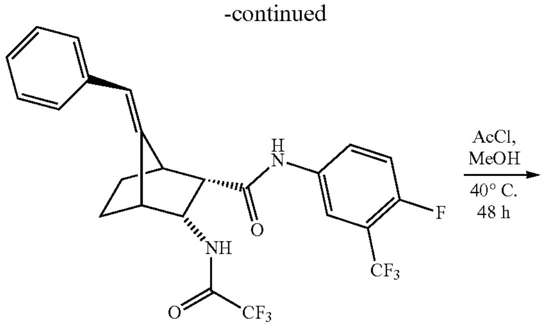

III-1
separate olefin isomers
silica gel chrom.

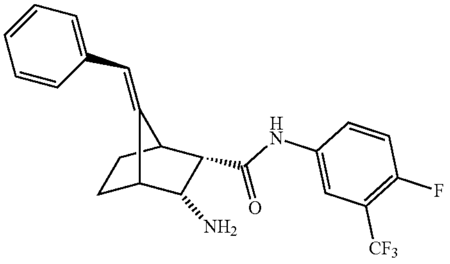

III-2

Intermediate III-1: In to the reaction vessel was added diethyl benzylphosphonate (375 mg, 1.64 mmol) and THF (10 mL). The reaction mixture was cooled to −78° C. and KHMDS (1.6 mL, 1.6 mmol) was added. This reaction mixture was stirred at −78° C. for 10 min and intermediate II-1 (140 mg, 0.328 mmol) was added. After 20 min, the reaction mixture was allowed to warm to rt and stirred at rt for 2 h. The reaction mixture was quenched by the addition of sat $NaHCO_3$ and the solution extracted with EtOAc. The combined organic portion was dried over $Na_2SO_4$, filtered, concentrated, and subjected to silica gel chromatography purification to the E-isomer byproduct (111 mg, 0.222 mmol, 67.5% yield) and (1R,2S,3R,4R,Z)-7-benzylidene-N-(4-fluoro-3-(trifluoromethyl)phenyl)-3-(2,2,2-trifluoroacetamido) bicyclo[2.2.1]heptane-2-carboxamide (III-1, 49 mg, 0.098 mmol, 30% yield). RT=1.23 min; MS (ESI) m/z=501.1 $(M+H)^+$; Method A.

Intermediate III-2: To a vial containing MeOH (3 mL) cooled to 0° C. (ice/water bath) was added acetyl chloride (0.3 mL, 4 mmol) dropwise. The resulting solution was stirred at rt for 10 min, then was added to III-1 (94 mg, 0.19 mmol). The reaction mixture was stirred at 40° C. for 48 h and concentration under reduced pressure afforded (1R,2S,3R,4R)-3-amino-7-((Z)-benzylidene)-N-(4-fluoro-3-(trifluoromethyl)phenyl) bicyclo[2.2.1]heptane-2-carboxamide (III-2, 73 mg, 0.18 mmol, 96% yield). RT=0.87 min; MS (ESI) m/z=405.1 $(M+H)^+$; Method A which was used without further purification.

Scheme IV demonstrates a general route to install C7 bridgehead functionality in similar manner as Scheme II, for example, but not limited to, cyclopropyl, cyclobutyl, and nBu.

Scheme IV

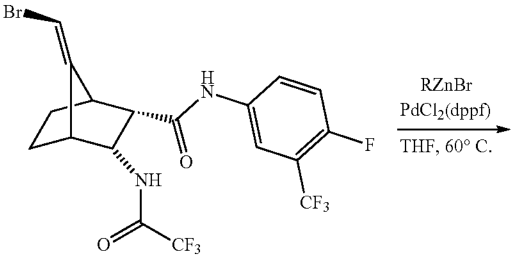

II-4

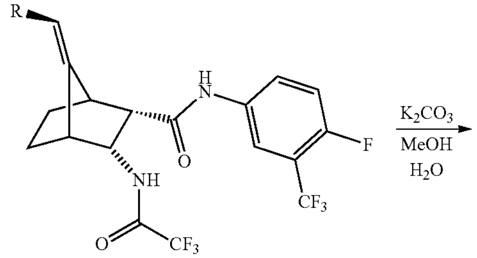

IV-1a, R = $^{cy}$Pr
IV-1b, R = $^{cy}$Bu
IV-1c, R = nBu

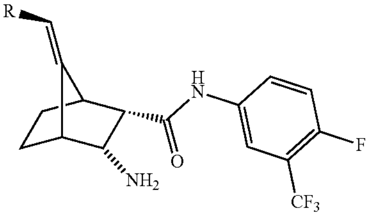

IV-2a, R = $^{cy}$Pr
IV-2b, R = $^{cy}$Bu
IV-2c, R = nBu

Intermediate IV-1a: A solution of II-4 (1.00 g, 1.98 mmol) in THF (9.9 mL) was treated with $PdCl_2$(dppf) (0.073 g, 0.099 mmol), under $N_2$, then cyclopropylzinc (II) bromide (15.9 mL, 7.95 mmol) was added and the reaction mixture heated to 60° C. for 2 h. The cooled reaction mixture was extracted from brine with EtOAc, and the combined organic portion concentrated under reduced pressure. The residue was purified by silica gel chromatograph to furnish (1R,2S,3R,4R,Z)-7-(cyclopropylmethylene)-N-(4-fluoro-3-(trifluoromethyl)phenyl)-3-(2,2,2-trifluoroacetamido) bicyclo[2.2.1]heptane-2-carboxamide (IV-1a, 646 mg, 1.39 mmol, 70.0% yield). LC-MS RT=1.07 min; MS (ESI) m/z=492.1 $(M+H)^+$; Method A.

Intermediate IV-2: A solution of IV-1a (646 mg, 1.39 mmol) in MeOH (9.3 mL) was treated with $K_2CO_3$ (961 mg, 6.96 mmol) in water (4.6 mL) and the reaction mixture was stirred for 18 h. The reaction mixture was extracted from phosphate buffer with EtOAc. The organic layer was concentrated to furnish (1R,2S,3R,4R,Z)-3-amino-7-(cyclopropylmethylene)-N-(4-fluoro-3-(trifluoromethyl)phenyl) bicyclo[2.2.1]heptane-2-carboxamide which was used without further purification (IV-2a, 512 mg, 1.39 mmol, 100% yield). RT=0.84 min; MS (ESI) m/z=369.1 $(M+H)^+$; Method A.

Intermediates IV-1b,c and IV-2b,c were prepared analagously from commercially available organozinc reagents.

Scheme V

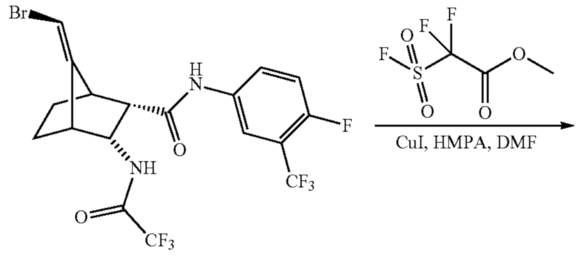

II-4

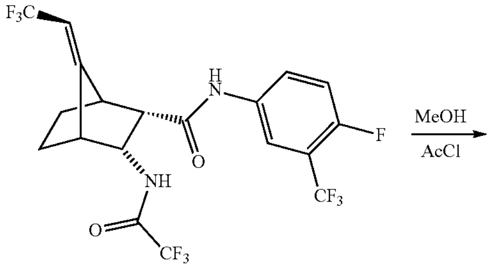

V-1

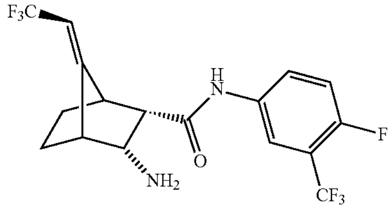

V-2

Intermediate V-1: Intermediate V-1 was prepared from II-4. To a 250 mL round bottom flask charged with methyl 2,2-difluoro-2-(fluorosulfonyl)acetate (2.5 mL, 20 mmol) in anhydrous DMF (50 mL) was added dropwise via dropping funnel to a suspension of II-4 and CuI (2.3 g, 12 mmol) in anhydrous DMF (100 mL) and HMPA (8.0 mL, 19 mmol) and the reaction mixture heated at 75° C. under an inert nitrogen atmosphere for 16 h. The cooled reaction mixture was filtered and purified by silica gel chromatography to produce V-1 (3.0 g, 6.1 mmol, 77% yield). 1H NMR (500 MHZ, $CDCl_3$) δ 9.38 (br d, J=6.1 Hz, 1H), 7.77-7.69 (m, 2H), 7.46 (s, 1H), 7.24 (t, J=9.1 Hz, 1H), 5.62 (q, J=7.2 Hz, 1H), 4.50 (dt, J==10.5, 5.3 Hz, 1H), 3.50-3.42 (m, 1H), 3.13-3.04 (m, 1H), 2.89 (t, J=4.0 Hz, 1H), 2.02-1.90 (m, 2H), 1.76-1.60 (m, 2H).

Intermediate V-2: Intermediate V-2 was prepared from V-1. MeOH (1.5 mL) and acetyl chloride (2.1 mmol) were charged into a 2 dram vial and stirred at 23° C. for 5 min. V-1 was added to the reaction vial and the contents heated at 40° C. for 24 h. Concentration with a stream of nitrogen gave V-2 as the HCl salt which was used without further purification. LC-MS RT=0.75 min; MS (ESI) m/z=397.1 $(M+H)^+$; Method A.

Scheme VI

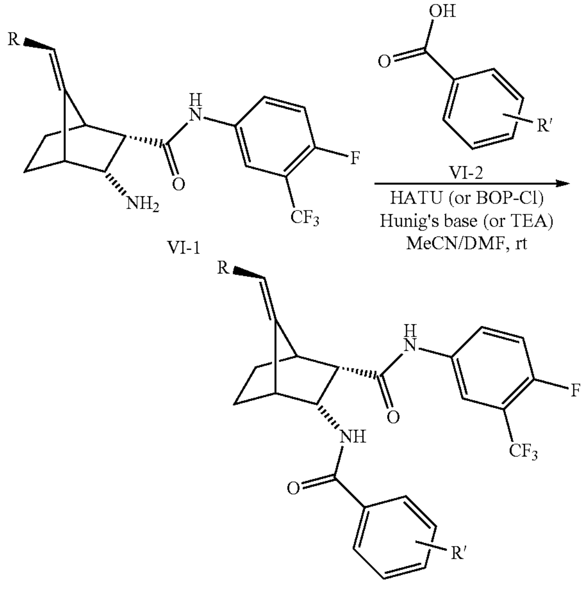

VI-1

Examples

Scheme VI outlines the methods for coupling the norbornyl amine cores of the general structures VI-1 to benzoic acids (VI-2) to form the respective amides. Amide formation could be accomplished under a variety of amide coupling conditions described, but not limited to HATU and BOP-Cl.

Scheme VII

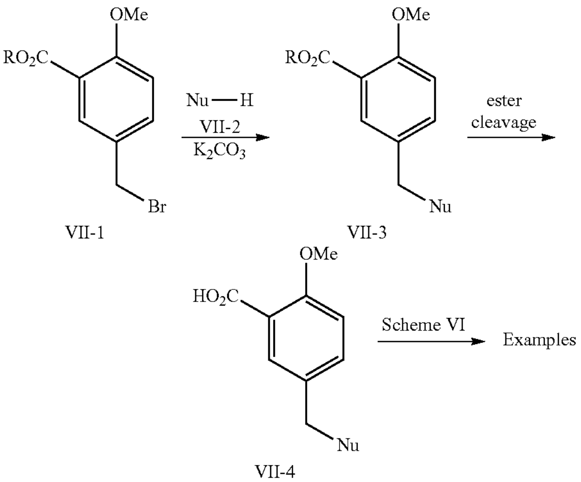

VII-1 VII-3 VII-4

Scheme VII illustrates an example method for the further functionalization of benzoic acids VI-1 for incorporation onto the norbornyl scaffold according to Scheme VI. Starting from benzyl bromide VII-1, a nucleophilic substitution using $K_2CO_3$ and a variety of nucleophiles VII-2 (NuH=alcohols, primary and secondary amines, etc.) led to formation of benzoate VII-3. Conversion of this ester to the benzoic acid of the general structure VII-4 was accomplished using standard conditions depending on the nature of R (e.g., R=Me, Et, saponification with LiOH/water; R=tBu, TFA mediated ester cleavage, R=—$CH_2CCl_3$, treatment with Zn/AcOH, etc.).

Scheme VIII

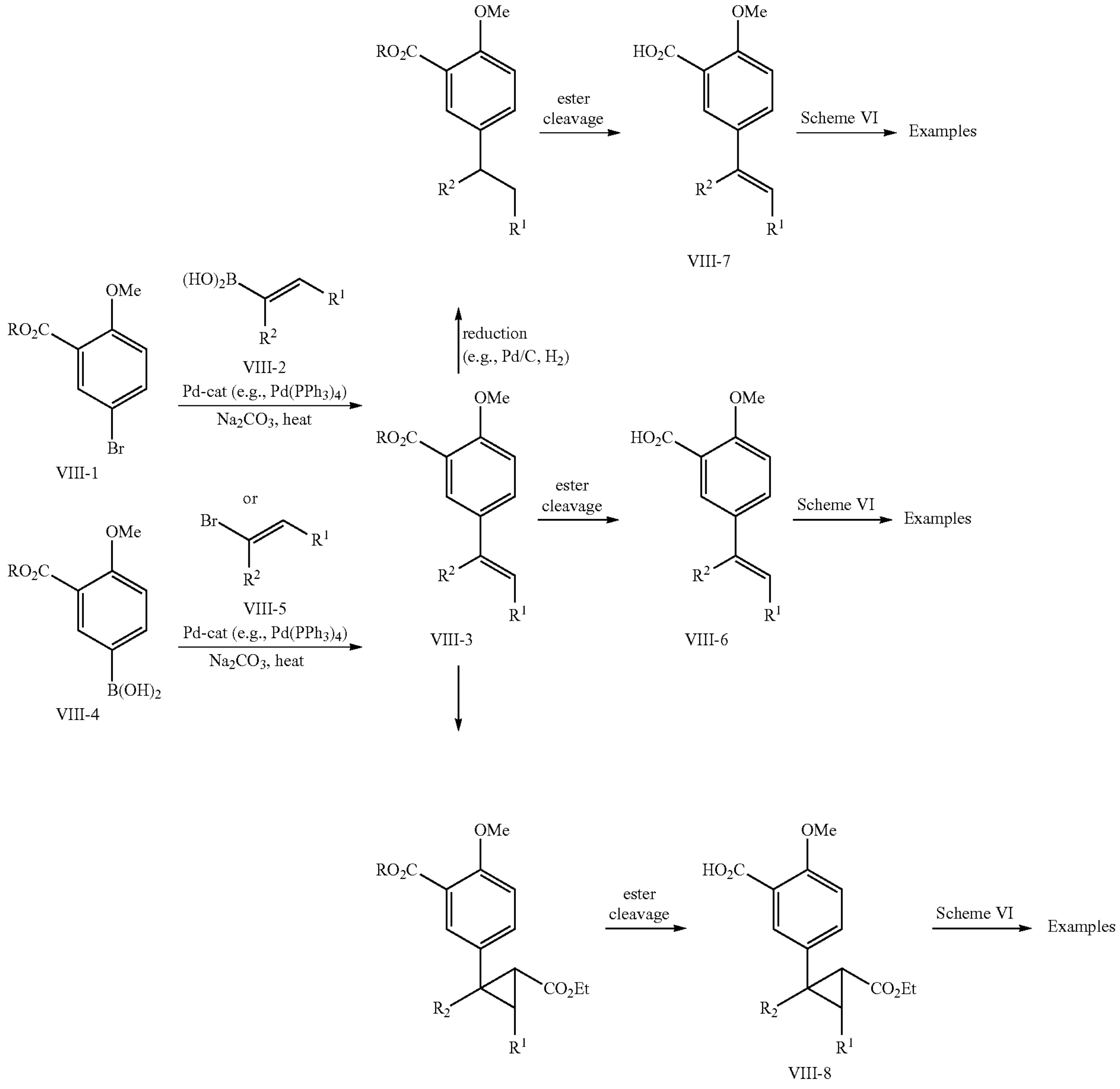

Scheme VIII outlines another method for the further functionalization of benzoic acids VI-1 for incorporation onto the norbornyl scaffold according to Scheme 6. Starting from bromobenzene VIII-1, performing a Suzuki reaction with a vinyl boronate VIII-2, Pd-catalyst, and base led to formation of benzoate VIII-3. Alternatively, VIII-3 could be prepared by reversing the components in the Suzuki reaction by using boronic acids of the general structure VIII-4 and vinyl halides of the general structure VIII-5. The resulting benzoate VIII-3 could be cleaved to the benzoic acid VIII-6. Alternatively, the olefin VIII-3 could be further manipulated (e.g., reduction with Pd/C, $H_2$; or cyclopropanoated with a diazoester and $Rh_2(OAc)_4$, etc.), followed by ester hydrolysis to furnish benzoic acids (e.g, VIII-7 or VIII-8 among others).

Scheme IX
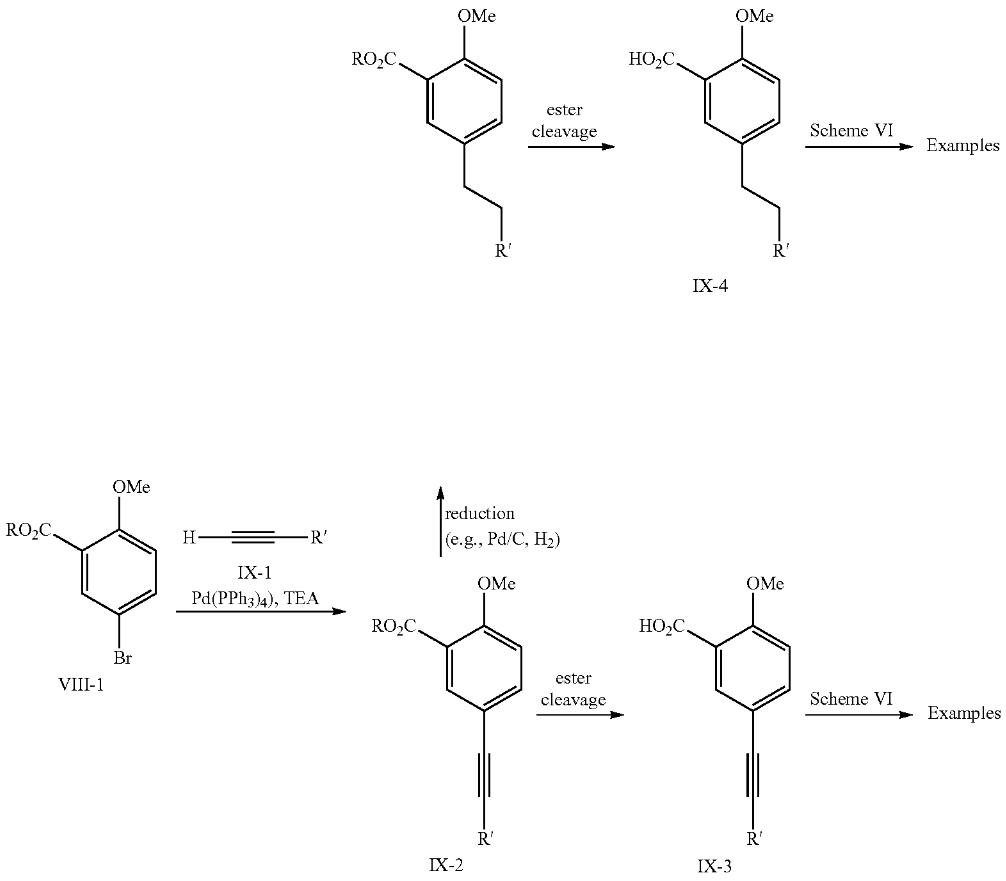
Alternatively, Scheme IX shows a strategy for the Pd-mediated coupling of intermediate VIII-1 to a variety of alkynes IX-1. The resulting esters IX-2 could be leaved directly to benzoic acids IX-3, or further elaborated for instance by reduction of the alkyne followed by ester cleavage to benzoic acids IX-4 (among other elaboration strategies).
Scheme X
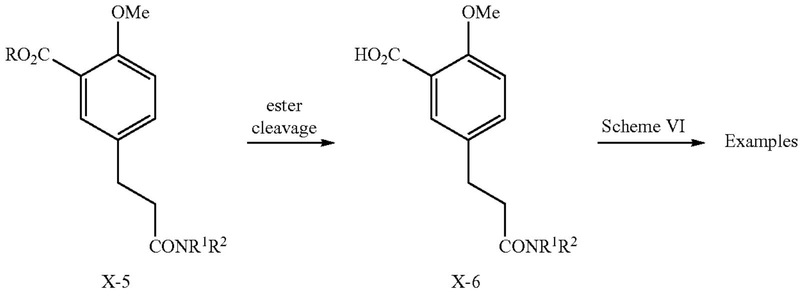

-continued

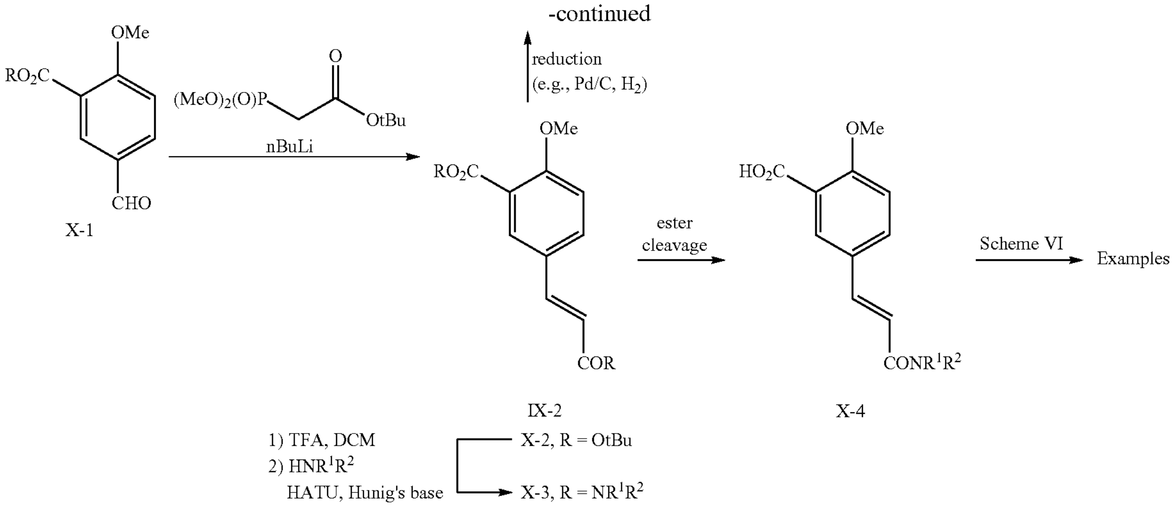

X-1

IX-2

X-4

Scheme X illustrates a method for the production of benzoic acids VI-1 for incorporation onto the norbornyl scaffold according to Scheme VI. Aldehyde X-1 was subjected to a Homer-Wadsworth-Emmons olefination to furnish enoate X-2. Deprotection of the t-butyl ester (TFA/DCM), followed by amide formation (e.g., HATU, Hunig's base) furnished enamides X-3 which could be saponified to acids X-4. Alternatively, X-3 could be reduced (e.g., Pd/C, $H_2$) to furnish X-5, which upon saponification yielded benzoic acids X-6.

Scheme XI

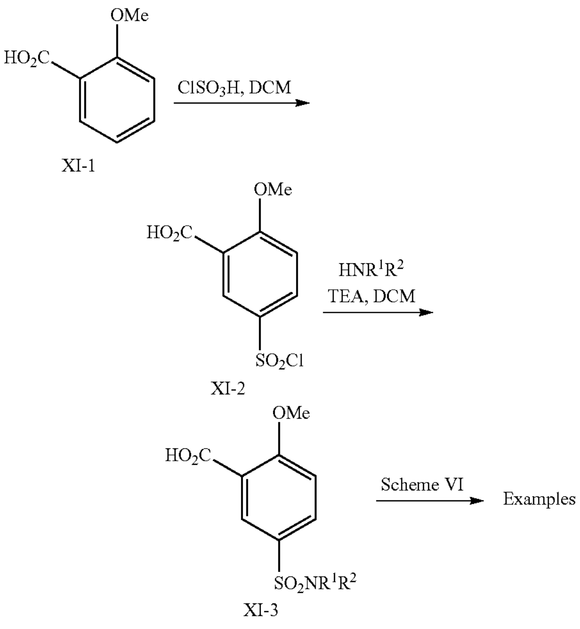

XI-1

XI-2

XI-3

Scheme XI demonstrates a route to the preparation of benzoic acids VI-1 bearing sulfonamides for incorporation onto the norbornyl scaffold according to Scheme VI. Treatment of benzoic acid XI-1 with chlorosulfonic acid furnished sulfonyl chloride XI-2. Treatment of XI-2 with amines in the presence of TEA formed benzoic acids XI-3.

Scheme XII

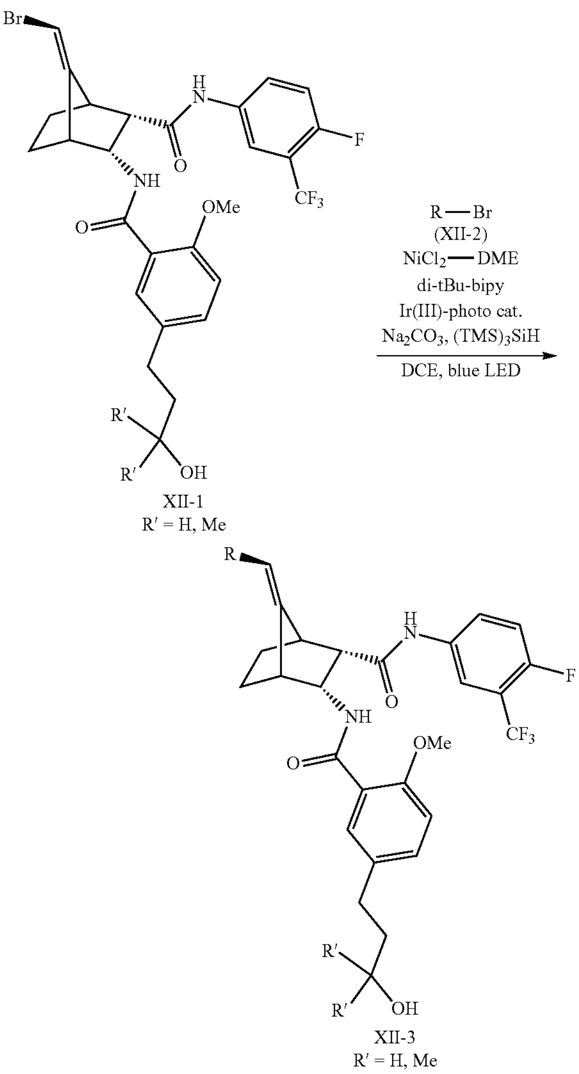

XII-1
R' = H, Me

XII-3
R' = H, Me

Scheme XII outlines a method for the late stage functionalization at C-7. Vinylbromides XII-1 (prepared from II-4 with benzoic acids of the general structure IX-4 prepared according to Scheme IX) were treated according to the procedure described by MacMillan et. al. (*J. Am. Chem. Soc.* 2016, 138, 8084-8087) and employing diverse alkyl halides XII-2 to furnish Examples of the general structure XII-3.

Scheme XIII

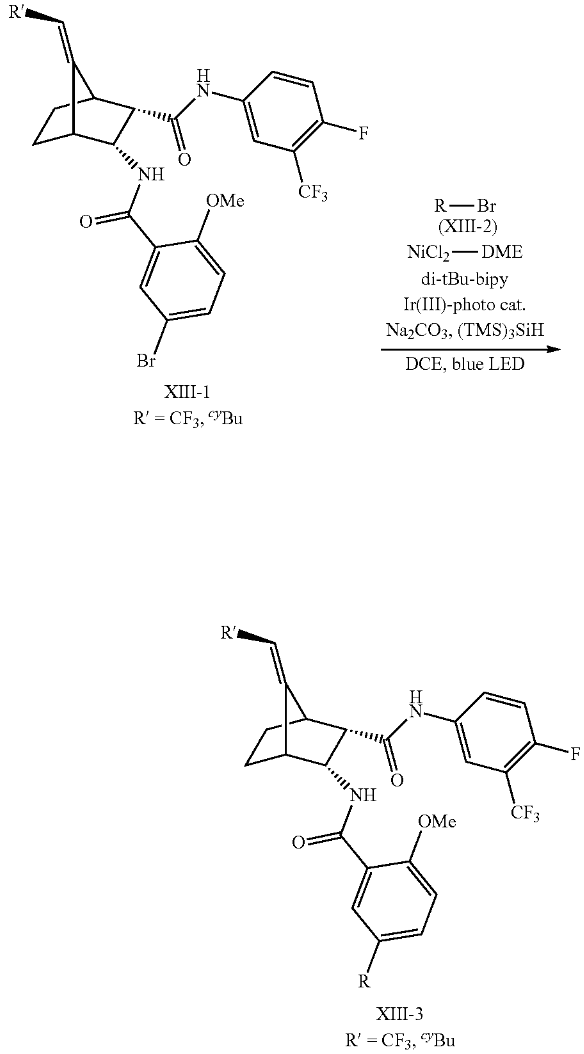

XIII-1
R′ = $CF_3$, $^{cy}$Bu

XIII-3
R′ = $CF_3$, $^{cy}$Bu

Alternatively, Scheme XIII outlines a method for the production of diverse aryl substitution on the salicylate. Arylbromides XIII-1 (prepared from IV-2b or V-2 and the commercially available 5-bromo-2-methoxybenzoic acid according to Scheme VI) were treated according to the procedure described by MacMillan et. al. (*J. Am. Chem. Soc.* 2016, 138, 8084-8087) and employing diverse alkyl halides XIII-2 to furnish Examples of the general structure XIII-3.

EXAMPLES

Example 1

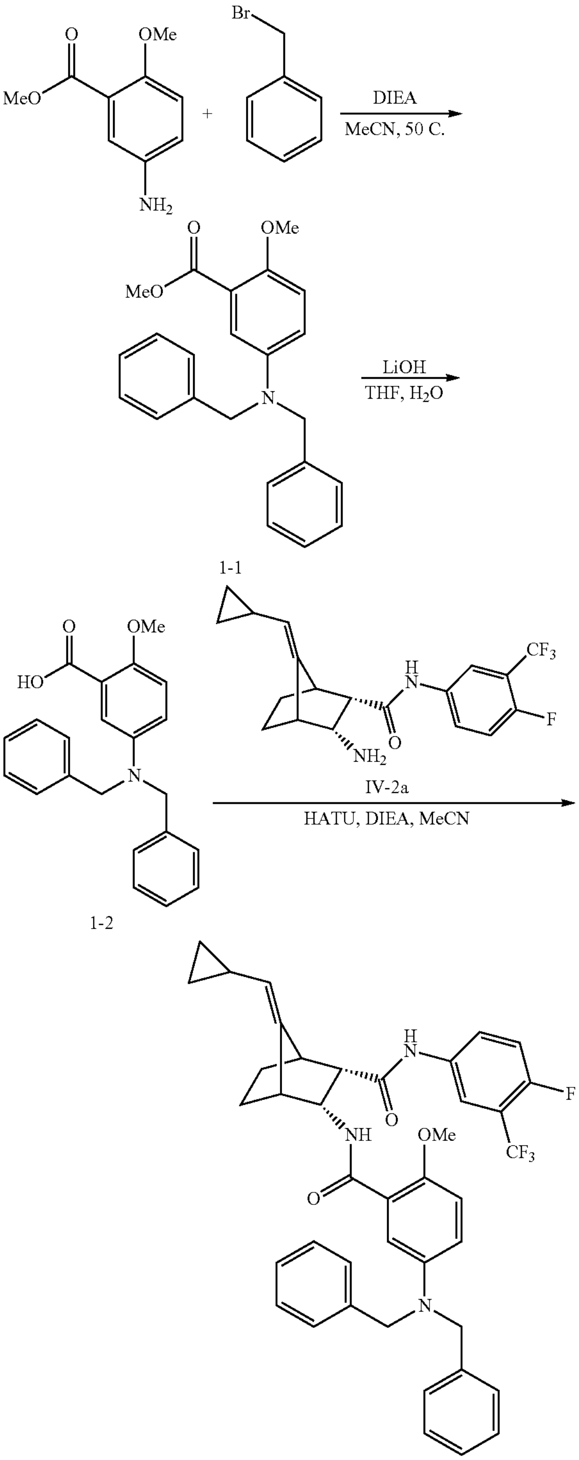

1-1

1-2

IV-2a

Example 1

Intermediate 1-1: To a vial containing methyl 5-amino-2-methoxybenzoate (100 mg, 0.55 mmol) and (bromomethyl)benzene (94 mg, 0.55 mmol) in MeCN (1.1 mL) was added (bromomethyl)benzene (94 mg, 0.55 mmol) and the reaction mixture was heated at 50° C. for 5 h. The reaction mixture was partitioned between water (10 mL) and extracted with EtOAc. The combined organic portions were dried over $Na_2SO_4$ and filtered, concentrated, then purified by silica gel chromatography to afford methyl 5-(dibenzylamino)-2-methoxybenzoate (1-1, 50 mg, 0.14 mmol, 25% yield), LC-MS RT: 1.05 min; MS (ESI) m/z 272 $(M+H)^+$; Method D.

Intermediate 1-2: To a vial containing 1-1 (50 mg, 0.14 mmol) in THF (1.4 mL) was added 1N LiOH (450 µl, 0.45 mmol). After stirring for 36 h, the reaction mixture was acidified with 1N HCl (2 mL), then partitioned between water (5 mL) and extracted with EtOAc. Combined organic portions were dried over $Na_2SO_4$ filtered and concentrated under reduced pressure. The residue was purified by reverse phase ISCO to afford 5-(dibenzylamino)-2-methoxybenzoic acid (1-2, 44 mg, 0.13 mmol, 92% yield). LC-MS RT: 0.98 min; MS (ESI) m/z 348 $(M+H)^+$; Method D.

Example 1: To a vial containing IV-2a (16 mg, 0.043 mmol) in MeCN (430 µl) was added 1-2 (18 mg, 0.052 mmol), HATU (20 mg, 0.052 mmol), and DIEA (23 µl, 0.130 mmol). The reaction mixture was stirred for 18 h at room temperature, then concentrated under reduced pressure, dissolved in DMSO and purified by HPLC to afford (1R,2S,3R,4R,Z)-7-(cyclopropylmethylene)-3-(5-(dibenzylamino)-2-methoxybenzamido)-N-(4-fluoro-3-(trifluoromethyl)phenyl) bicyclo[2.2.1]heptane-2-carboxamide (18 mg, 0.026 mmol, 60% yield). 1H-NMR (500 MHz, DMSO-d6) δ 10.24 (s, 1H), 9.57 (d, J=7.4 Hz, 1H), 8.00-7.95 (m, 1H), 7.50 (br d, J=12.9 Hz, 1H), 7.23 (t, J=9.7 Hz, 1H), 7.11 (d, J=2.9 Hz, 1H), 7.09-7.04 (m, 5H), 7.02-6.94 (m, 7H), 6.72 (d, J=9.0 Hz, 1H), 6.56 (dd, J=8.7, 3.1 Hz, 1H), 4.39 (s, 4H), 4.17-4.08 (m, 1H), 3.62 (S, 3H), 2.85 (dd, J=10.8, 4.1 Hz, 1H), 2.80-2.73 (m, 1H), 2.47-2.40 (m, 1H), 1.64-1.57 (m, 1H), 1.55-1.45 (m, 1H), 1.28-1.19 (m, 1H), 1.19-1.07 (m, 2H), 0.54-0.40 (m, 2H), 0.14-0.03 (m, 2H). LC-MS RT: 2.97 min; MS (ESI) m/z 698 $(M+H)^+$; Method A.

Example 2

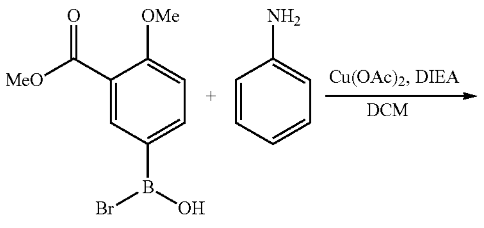

-continued

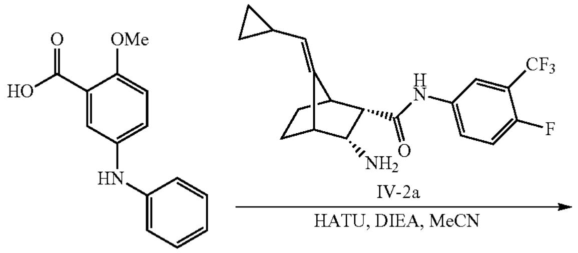

2-1

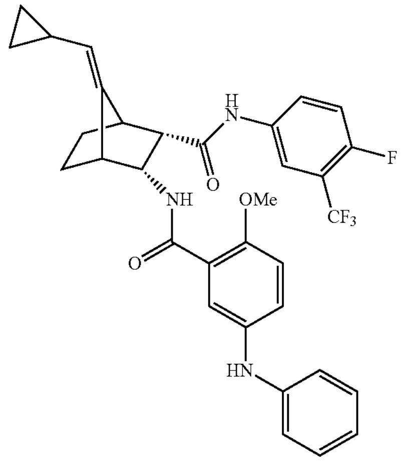

Example 2

Intermediate 2-1: To a vial was added 5-borono-2-methoxybenzoic acid (158 mg, 0.810 mmol), aniline (50 mg, 0.54 mmol), copper (II) acetate (195 mg, 1.10 mmol), DCM (1.1 mL), and DIEA (281 µl, 1.6 mmol). The reaction mixture was stirred at room temperature for 3 days, then partitioned between 1N HCl and extracted with EtOAc (3×10 ml). Combined organic portions were dried over $Na_2SO_4$, filtered, concentrated, then purified by reverse phase ISCO to afford 2-methoxy-5-(phenylamino)benzoic acid (2-1, 21 mg, 0.086 mmol, 16% yield) as a brown solid. LC-MS RT: 0.80 min; MS (ESI) m/z 244 $(M+H)^+$; Method D.

Example 2: Prepared from intermediate 2-1 and IV-2a according to the procedure for Example 1 to afford (1R,2S,3R,4R,Z)-7-(cyclopropylmethylene)-N-(4-fluoro-3-(trifluoromethyl)phenyl)-3-(2-methoxy-5-(phenylamino)benzamido) bicyclo[2.2.1]heptane-2-carboxamide (8.5 mg, 0.014 mmol, 65% yield). 1H-NMR (500 MHz, DMSO-d6) δ 10.52 (s, 1H), 9.89 (d, J=7.2 Hz, 1H), 8.23 (dd, J=6.1, 2.5 Hz, 1H), 8.01 (s, 1H), 7.80-7.75 (m, 1H), 7.75-7.71 (m, 1H), 7.53-7.44 (m, 1H), 7.25-7.16 (m, 3H), 7.11 (d, J=9.0 Hz, 1H), 6.94 (d, J=7.8 Hz, 2H), 6.76 (t, J=7.3 Hz, 1H), 4.68 (d, J=9.7 Hz, 1H), 4.48-4.38 (m, 1H), 3.96 (s, 3H), 3.19-3.11 (m, 1H), 3.11-3.04 (m, 1H), 2.76-2.67 (m, 1H), 1.92-1.84 (m, 1H), 1.83-1.75 (m, 1H), 1.55-1.47 (m, 1H), 1.46-1.34 (m, 2H), 0.81-0.66 (m, 2H), 0.41-0.28 (m, 2H). LC-MS RT: 2.77 min; MS (ESI) m/z 594 (M+H)+; Method B.

Example 4

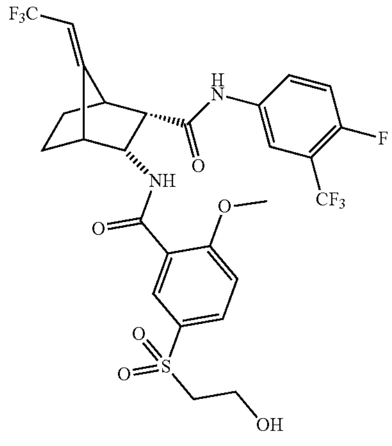

Intermediate 4-1

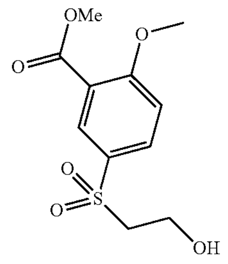 [SMILES: COC(=O)c1cc(S(=O)(=O)CCO)ccc1OC]

Preparation of methyl 5-((2-hydroxyethyl) sulfonyl)-2-methoxybenzoate; To a mixture of methyl 5-iodo-2-methoxybenzoate (175 mg, 0.599 mmol), potassium meta-bisulfite (266 mg, 1.19 mmol), sodium formate (90 mg, 1.3 mmol), tetrabutylammonium bromide (212 mg, 0.659 mmol), 1,10-phenanthroline (32.4 mg, 0.180 mmol), triphenylphosphine (47.1 mg, 0.180 mmol), palladium acetate (13.4 mg, 0.0600 mmol) was added DMSO (6 mL) and the reaction mixture stirred at 70° C. for 3 hours. The reaction mixture was allowed to cool to room temperature and 2-bromoethan-1-ol (210 μL, 2.9 mmol) was added and the resulting reaction mixture stirred for 18 h. The reaction mixture was diluted with ethyl acetate and the organic portion washed with brine. The organic portion was concentrated under reduced pressure and the residue purified using silica gel chromatography to yield Intermediate 4-1 (28 mg, 17% yield), MS (ESI) m/z: 275.1 (M+H).

Intermediate 4-2

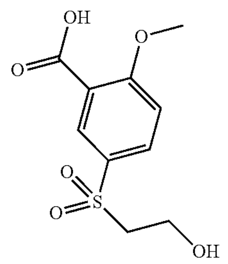 [SMILES: COc1ccc(S(=O)(=O)CCO)cc1C(=O)O]

Preparation of 5-((2-hydroxyethyl) sulfonyl)-2-methoxybenzoic acid: To a solution of Intermediate 4-1 (28 mg, 0.10 mmol) in THF (1 mL) and water (0.33 mL) was added LiOH (0.15 mL, 0.30 mmol). The resulting solution was stirred at room temperature for 1 h, acidified by the addition of 1N HCl and the solution extracted with ethyl acetate. The combined organic portions were concentrated under reduced pressure to yield 4-2 which was used without further purification (22 mg, 79% yield). MS (ESI) m/z: 261.1 (M+H), RT=0.70 min, Method A.

Example 4 was prepared by the methods described for Example 1 by starting from V-2 and 4-2 to furnish (1R,2S,3R,4R,Z)—N-(4-fluoro-3-(trifluoromethyl)phenyl)-3-(5-((2-hydroxyethyl) sulfonyl)-2-methoxybenzamido)-7-(2,2,2-trifluoroethylidene) bicyclo[2.2.1]heptane-2-carboxamide (4.4 mg; 12%). 1H NMR (500 MHz, DMSO-$d_6$) δ 10.67 (s, 1H), 10.03 (d, J=6.4 Hz, 1H), 8.39 (d, J=2.1 Hz, 1H), 8.21 (d, J=4.9 Hz, 1H), 8.04-7.96 (m, 1H), 7.79 (d, J=8.5 Hz, 1H), 7.49 (t, J=9.9 Hz, 1H), 7.43 (d, J=8.8 Hz, 1H), 5.93 (m, 1H), 4.51 (br. s., 1H), 4.10 (s, 3H), 3.66 (d, J=4.9 Hz, 1H), 3.51-3.36 (m, 1H), 3.31-3.21 (m, 2H), 2.99 (br. s., 1H), 1.98-1.82 (m, 2H), 1.49 (d, J=5.5 Hz, 2H); LC-MS (M+H) =639.08; HPLC RT=2.24 min; Method B.

Examples 5 & 6

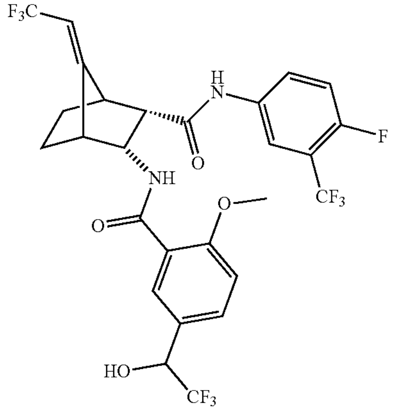

Intermediate 5-1

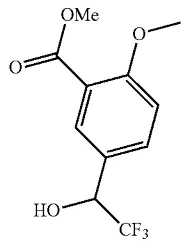 [SMILES: COC(=O)c1cc(C(O)C(F)(F)F)ccc1OC]

A solution of methyl 5-formyl-2-methoxybenzoate (0.500 g, 2.57 mmol), (trifluoromethyl)trimethylsilane (0.62 mL, 3.86 mmol) in THF (7.8 mL) was treated with TBAF (7 mg, 0.03 mmol) at 0° C. The solution was allowed to warm to rt over 18 h. The reaction mixture was concentrated under reduced pressure and purified by silica gel chromatography to furnish methyl 2-methoxy-5-(2,2,2-trifluoro-1-hydroxyethyl)benzoate (5-1, 650 mg, 2.46 mmol, 96.0% yield). 1H NMR (400 MHZ, $CDCl_3$) δ 7.94 (d, J=2.2 Hz, 1H), 7.64 (dd, J=8.8, 2.4 Hz, 1H), 7.06 (d, J=8.6 Hz, 1H), 5.04 (d, J=6.6 Hz, 1H), 3.97 (s, 3H), 3.94 (s, 3H), 2.67 (br s, 1H)

Intermediate 5-2

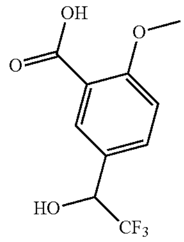 [SMILES: COc1ccc(C(O)C(F)(F)F)cc1C(=O)O]

Intermediate 5-2 was prepared from 5-1 procedure used for Intermediate 4-2. LC-MS (M+H)=251.0; HPLC RT=0.64 min; Method A.

Examples 5 & 6 were prepared by the method described for Example 1 by starting from V-2 furnish (2S,3R,7Z)—N-[4-fluoro-3-(trifluoromethyl)phenyl]-3-[2-methoxy-5-(2,2,2-trifluoro-1-hydroxyethyl)benzamido]-7-(2,2,2-trifluoroethylidene) bicyclo[2.2.1]heptane-2-carboxamide as a racemate. The enantiomers were separated according to the following conditions: Column: Chiral AD, 30×250 mm, 5 micron, Flow Rate: 100 mL/min, Oven Temperature: 40 C, BPR Setting: 120 bar, UV wavelength: 220 nm, Mobile Phase: 85% $CO_2$/15% IPA w/0.1% DEA (isocratic).

Example 5, Peak 1 (>95% de, 4.8 mg, 48% yield), RT=6.2 min. 1H NMR (500 MHZ, DMSO-d6) δ 10.69 (s, 1H), 9.95 (d, J=7.1 Hz, 1H), 8.24 (dd, J=6.4, 2.5 Hz, 1H), 8.10 (d, J=1.9 Hz, 1H), 7.84-7.77 (m, 1H), 7.61 (dd, J=8.6, 2.1 Hz, 1H), 7.51 (t, J=9.7 Hz, 1H), 7.23 (d, J=8.7 Hz, 1H), 5.94 (q, J=7.9 Hz, 1H), 5.24-5.12 (m, 1H), 4.57-4.50 (m, 1H), 4.02 (s, 3H), 3.58-3.41 (m, 1H), 3.33-3.20 (m, 2H), 2.99 (br s, 1H), 2.01-1.82 (m, 2H), 1.57-1.43 (m, 2H). LC-MS (M+H)=629.31; HPLC RT=2.48 min; Method C Example 6, Peak 2 (>95% de, 5.2 mg, 52% yield), RT=11.8 min. 1H NMR (500 MHZ, DMSO-d6) δ 10.67 (s, 1H), 9.93 (d, J=7.0 Hz, 1H), 8.24 (dd, J=6.3, 2.3 Hz, 1H), 8.09 (d, J=1.8 Hz, 1H), 7.84-7.76 (m, 1H), 7.62 (dd, J=8.7, 2.0 Hz, 1H), 7.50 (t, J=9.8 Hz, 1H), 7.23 (d, J=8.5 Hz, 1H), 6.02-5.88 (m, 1H), 5.25-5.13 (m, 1H), 4.61-4.50 (m, 1H), 4.02 (s, 3H), 3.24 (br s, 1H), 2.99 (br s, 1H), 2.90 (s, 1H), 2.74 (s, 1H), 1.98 (br t, J=9.6 Hz, 1H), 1.92-1.83 (m, 1H), 1.50 (br d, J=6.7 Hz, 2H). LC-MS (M+H)=629.31; HPLC RT=2.49 min; Method C Example 7

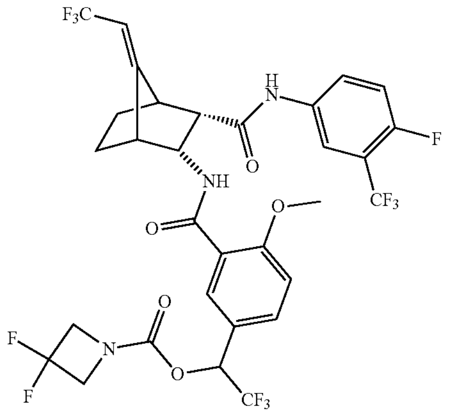

A mixture of 5 & 6 (40 mg, 0.064 mmol), DCM (1 mL), pyridine (0.05 mL, 0.6 mmol), 4-nitrophenyl carbonochloridate (64 mg, 0.31 mmol), and DMAP (7 mg, 0.06 mmol) were added to a flask and allowed to stir for 18 h. The reaction mixture was concentrated under reduced pressure and the residue purified by preparative reverse phase HPLC. The diastereomers were separated according to the following conditions: Column: Chiral AD, 30×250 mm, 5 micron, Flow Rate: 100 mL/min, Oven Temperature: 40° C., BPR Setting: 120 bar, UV wavelength: 220 nm, Mobile Phase: 90% $CO_2$/10% IPA w/0.1% DEA (isocratic)

Peak 1, RT=8.4 min (2.7 mg, 5.3% yield, >95% de) Example 7, Peak 2, RT=11.4 min (1.2 mg, 2.4% yield, >95% de). $^1$H NMR (500 MHz, DMSO-d6) δ 10.73-10.62 (m, 1H), 9.97 (d, J=7.0 Hz, 1H), 8.37 (d, J=6.7 Hz, 1H), 8.24 (dd, J=6.3, 2.3 Hz, 1H), 8.13 (d, J=1.5 Hz, 1H), 7.83-7.78 (m, 1H), 7.72-7.62 (m, 1H), 7.51 (t, J=9.8 Hz, 1H), 7.29 (d, J=8.9 Hz, 1H), 6.34-6.25 (m, 1H), 5.95 (q, J=7.8 Hz, 1H), 4.58-4.49 (m, 1H), 4.04 (s, 3H), 3.91 (s, 2H), 3.00 (br d, J=2.7 Hz, 1H), 2.86 (td, J=14.0, 8.2 Hz, 2H), 2.68-2.57 (m, 2H), 2.01-1.86 (m, 3H), 1.58-1.42 (m, 2H). LC-MS (M+H)=762.3; HPLC RT=2.61 min; Method C.

Example 8

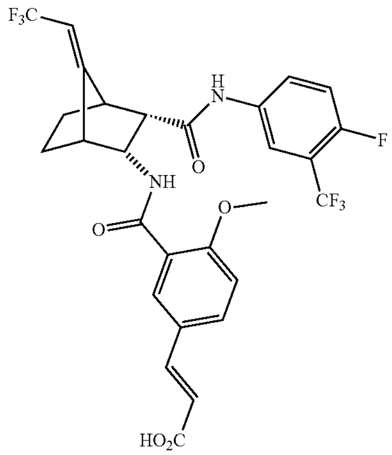

Intermediate 8-1

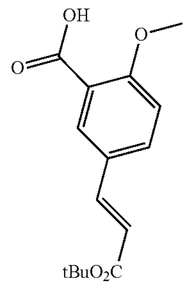 [SMILES: COc1ccc(/C=C/C(=O)OC(C)(C)C)cc1C(=O)O]

Intermediate 8-1 was prepared from the corresponding known methyl ester in quantitative yield (material used without purification) according to the procedure used for 4-2. LC-MS (M+H)=279.2; HPLC RT=0.86 min; Method A.

Intermediate 8-2

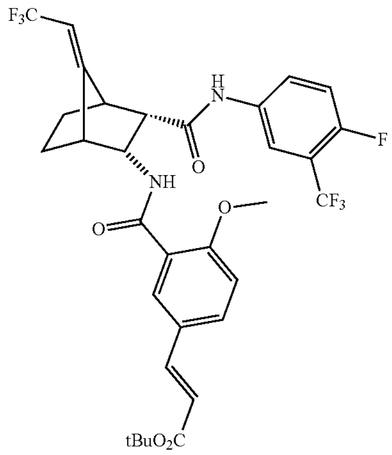

Intermediate 8-2 was prepared from 8-1 and V-2 according to the procedure used for Example 1 LC-MS (M+H)=657.36; HPLC RT=2.88 min; Method C.

A solution of 8-2 (20 mg, 0,030 mmol) in DCM (0.3 mL) was treated with TFA (0.3 mL). After 30 min, the reaction mixture was concentrated under reduced pressure and the residue purified by reverse phase HPLC to furnish (E)-3-(3-(((1R,2R,3S,4R,Z)-3-((4-fluoro-3-(trifluoromethyl)phenyl) carbamoyl)-7-(2,2,2-trifluoroethylidene) bicyclo[2.2.1] heptan-2-yl) carbamoyl)-4-methoxyphenyl) acrylic acid (17 mg, 0.028 mmol, 92% yield). $^{1}H$ NMR (500 MHz, DMSO-d6) δ 10.67 (s, 1H), 9.91 (d, J=7.0 Hz, 1H), 8.22 (dd, J=6.1, 2.1 Hz, 1H), 8.14 (br s, 1H), 7.86 (br d, J=8.9 Hz, 1H), 7.82-7.77 (m, 1H), 7.61-7.46 (m, 2H), 7.24 (d, J=8.9 Hz, 1H), 6.40 (br d, J=16.5 Hz, 1H), 5.99-5.90 (m, 1H), 4.58-4.47 (m, 1H), 4.04 (s, 3H), 3.60-3.43 (m, 1H), 3.35-3.22 (m, 1H), 3.00 (br s, 1H), 2.02-1.85 (m, 2H), 1.50 (br d, J=7.0 Hz, 2H). LC-MS (M+H)=601.05; HPLC RT=1.94 min; Method C.

Example 9

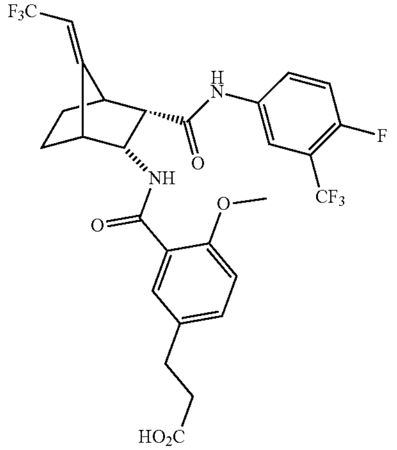

Intermediate 9-1

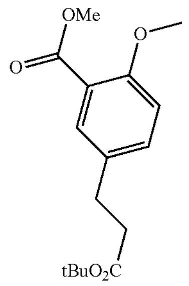 [SMILES: COC(=O)c1cc(CCC(=O)OC(C)(C)C)ccc1OC]

A solution of methyl (E)-5-(3-(tert-butoxy)-3-oxoprop-1-en-1-yl)-2-methoxybenzoate (0.108 g, 0.369 mmol) in ethanol (1.23 mL) was treated with Pd—C(10 wt %, 0.039 g, 0.37 mmol). The slurry was put under an atmosphere of $H_2$ (balloon pressure) and stirred for 18 h. The reaction mixture was filtered through celite and concentrated under reduced pressure to furnish methyl 5-(3-(tert-butoxy)-3-oxopropyl)-

2-methoxybenzoate (0.109 g, 0.369 mmol, 100% yield) which was used without further purification. LC-MS (M+H−(tBu)=233.9; HPLC RT=0.95 min; Method A.

Example 9 was prepared according the method used for example 8 by employing 9-1 as to furnish 3-(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl) propanoic acid (39 mg, 65%). $^1$H NMR (500 MHz, DMSO-d6) δ 10.63 (s, 1H), 9.95-9.82 (m, 1H), 8.23 (br d, J=4.0 Hz, 1H), 7.79 (br s, 2H), 7.54-7.45 (m, 1H), 7.36 (br d, J=7.9 Hz, 1H), 7.10 (br d, J=8.5 Hz, 1H), 5.93 (br d, J=7.9 Hz, 1H), 4.52 (br s, 1H), 3.97 (s, 3H), 3.39-3.17 (m, 1H), 2.98 (br s, 1H), 2.79 (br s, 2H), 2.51 (br s, 3H), 2.10-1.84 (m, 2H), 1.49 (br d, J=6.4 Hz, 2H). LC-MS (M+H)=603.13; HPLC RT=1.97 min; Method C.

Example 10

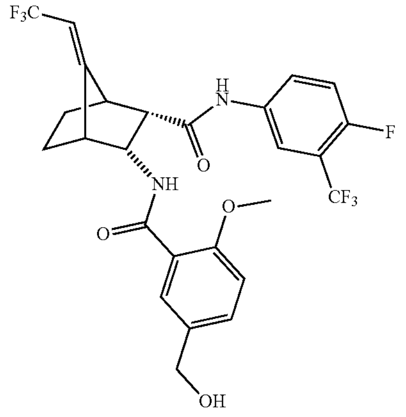 [SMILES: COc1ccc(CO)cc1C(=O)N[C@@H]1C2CCC(/C2=C/C(F)(F)F)[C@@H]1C(=O)Nc1ccc(F)c(C(F)(F)F)c1]

Example 10 was prepared by employing the procedure for Example 1 with V-2 and 5-formyl-2-methoxybenzoic acid. Upon completion of the amide forming reaction, the solution was diluted with MeOH and treated with an excess of $NaBH_4$. After, 18 h, the reaction mixture was extracted from water with EtOAc. The organic layer was concentrated under reduced pressure and the residue purified by preparative reverse phase HPLC to furnish (1R,2S,3R,4R,Z)—N-(4-fluoro-3-(trifluoromethyl)phenyl)-3-(5-(hydroxymethyl)-2-methoxybenzamido)-7-(2,2,2-trifluoroethylidene) bicyclo[2.2.1]heptane-2-carboxamide (1.7 mg, 3.1%). 1H NMR (500 MHz, DMSO-d6) δ 10.67 (s, 1H), 9.90 (d, J=6.9 Hz, 1H), 8.25 (dd, J=6.2, 2.1 Hz, 1H), 7.91 (d, J=1.9 Hz, 1H), 7.81-7.75 (m, 1H), 7.51 (t, J=9.8 Hz, 1H), 7.44 (dd, J=8.4, 2.0 Hz, 1H), 7.14 (d, J=8.5 Hz, 1H), 5.95 (d, J=7.8 Hz, 1H), 4.53 (br t, J=4.0 Hz, 1H), 4.45 (br d, J=4.7 Hz, 1H), 3.99 (s, 3H), 3.51-3.37 (m, 2H), 3.23 (br s, 1H), 3.00 (s, 2H), 2.05-1.82 (m, 2H), 1.49 (br d, J=6.0 Hz, 2H). LC-MS (M+H)=560.99; HPLC RT=2.26 min; Method C.

Example 11

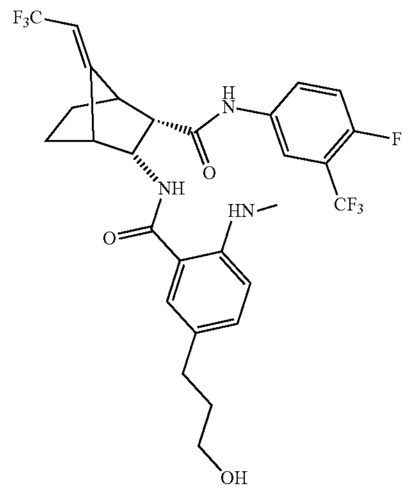 [SMILES: CNc1ccc(CCCO)cc1C(=O)N[C@@H]1C2CCC(/C2=C/C(F)(F)F)[C@@H]1C(=O)Nc1ccc(F)c(C(F)(F)F)c1]

Intermediate 11-1

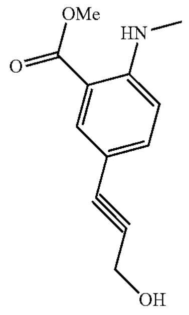 [SMILES: CNc1ccc(C#CCO)cc1C(=O)OC]

A slurry of methyl 4-bromo-2-(methylamino)benzoate (250 mg, 1.02 mmol), propargyl alcohol (80 μL, 1.3 mmol), palladium tetrakis (23 mg, 0.020 mmol) and copper (I) iodide (1.9 mg, 10 μmol) in TEA (3 mL) was degassed, and under $N_2$ atmosphere heated to 80° C. for 18 h. The reaction mixture was quenched by the addition of water and the solution extracted with ethyl acetate.

The organic layer was concentrated under reduced pressure and the residue purified by silica gel chromatography to furnish 11-1 (82 mg, 0.35 mmol, 34% yield). MS (ESI) m/z: 220.2 (M+H).

Intermediate 11-2

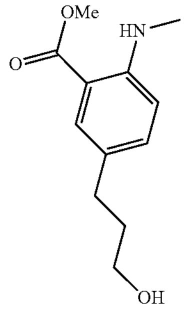 [SMILES: CNc1ccc(CCCO)cc1C(=O)OC]

A solution of 11-1 (80 mg, 0.36 mmol) in EtOH (1.2 mL) was treated with Pd—C(38 mg, 0.036 mmol) and hydrogenated at 55 PSI for 18 h. The reaction mixture was filtered through celite and concentrated under reduced pressure to furnish 11-2 (81 mg, 0.36 mmol, 100% yield) MS (ESI) m/z: 220.2 (M+H).

Intermediate 11-3

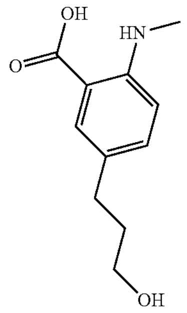

To a solution of 11-2 (13 mg, 0,060 mmol) in THF (1 mL) and water (0.33 mL) was added LiOH (0.091 mL, 0.18 mmol). The solution was stirred at room temperature for 1 hour, acidified using 1N HCl followed by extraction with EtOAc. The organic layers were concentrated under reduced pressure and taken onto the next step without further purification as 11-3: (12.6 mg, 0.06 mmol, 100% yield). MS (ESI) m/z: 210.3 (M+H).

Example 11 was prepared in a similar way as Example 1 by employing Intermediate 11-3 to furnish (1R,2S,3R,4R,Z)—N-(4-fluoro-3-(trifluoromethyl)phenyl)-3-(5-(3-hydroxypropyl)-2-(methylamino)benzamido)-7-(2,2,2-trifluoroethylidene) bicyclo[2.2.1]heptane-2-carboxamide, Example 11: (2.8 mg, 4.5 mmol, 4.6% yield). $^1$H NMR (500 MHz, DMSO-$d_6$) δ 10.68 (s, 1H), 9.04 (br. s., 1H), 8.12 (d, J=3.7 Hz, 1H), 7.77 (d, J=8.9 Hz, 1H), 7.46 (t, J=9.8 Hz, 1H), 7.20 (s, 1H), 7.15 (d, J=8.5 Hz, 1H), 6.57 (d, J=8.5 Hz, 1H), 5.89 (q, J=7.8 Hz, 1H), 4.38 (br. s., 1H), 3.64 (br. s., 2H), 3.41-3.33 (m, 2H), 3.24 (dd, J=10.8, 3.8 Hz, 1H), 3.16 (br. s., 1H), 2.97 (br. s., 1H), 2.70 (d, J=4.3 Hz, 3H), 2.48-2.41 (m, 2H), 1.88 (d, J=7.9 Hz, 2H), 1.67-1.58 (m, 2H), 1.48 (d, J=7.9 Hz, 2H); LC-MS (M+H)=588.17; HPLC RT=2.39 min; Method B.

Example 12

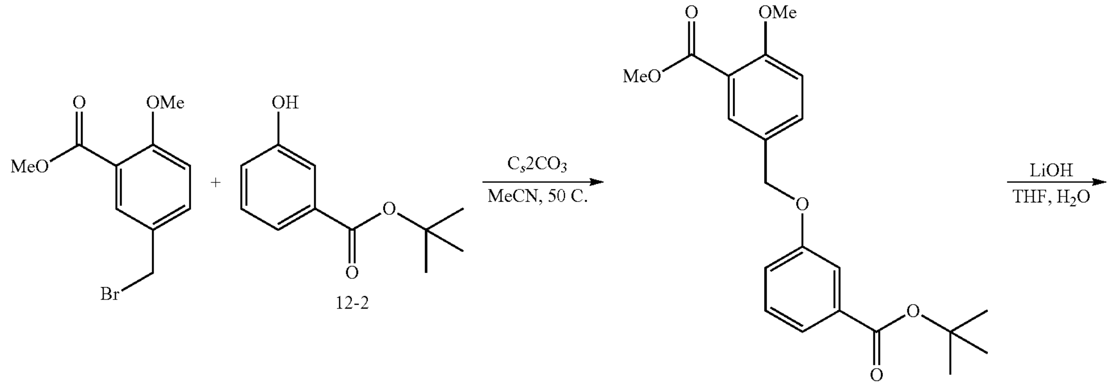

12-2

12-1

-continued

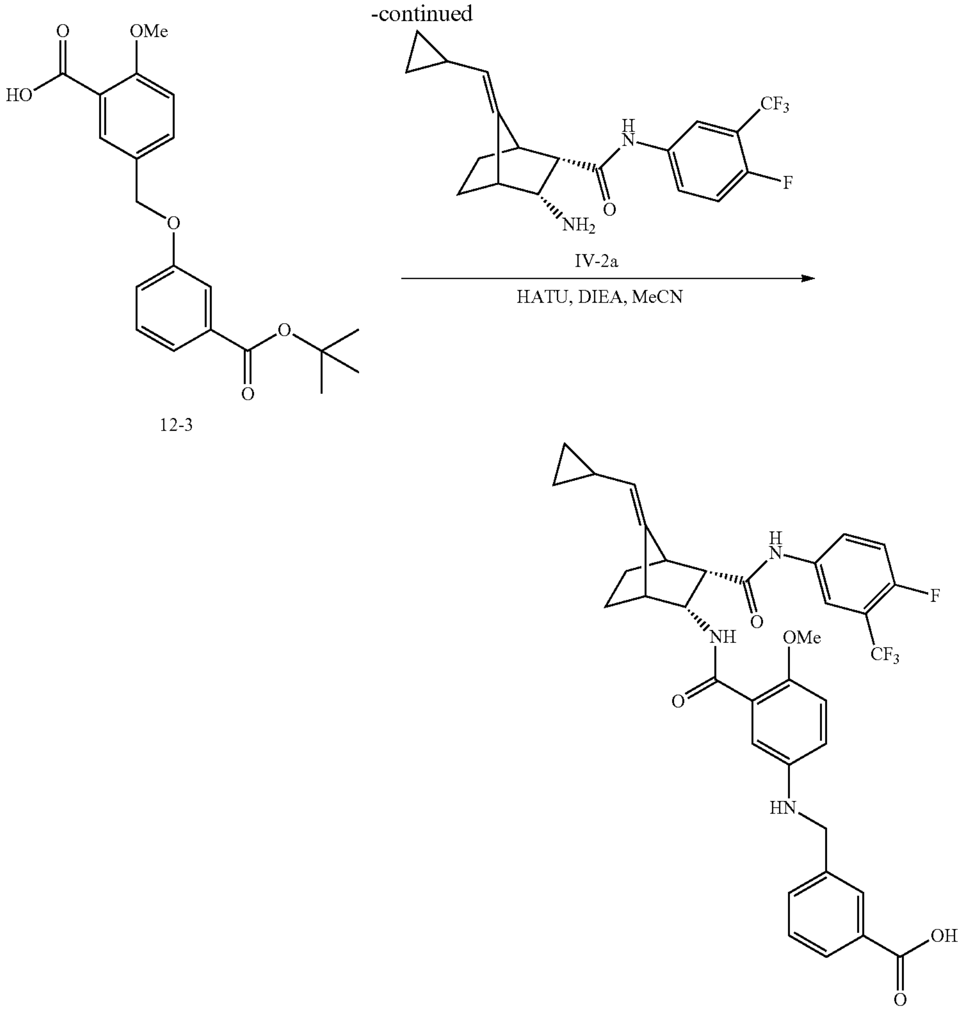

12-3

Example 12

Intermediate 12-1: To a vial containing methyl 5-(bromomethyl)-2-methoxybenzoate (100 mg, 0.39 mmol) and tert-butyl 3-hydroxybenzoate (12-2, 90 mg, 0.46 mmol) in MeCN (0.77 mL) was added $Cs_2CO_3$ (377 mg, 1.20 mmol) and the reaction mixture was heated at 50° C. for Sh. The reaction mixture was partitioned between water and extracted with EtOAc. The combined organic portions were dried over $Na_2SO_4$ filtered and concentrated under reduced pressure, then purified by silica gel chromatography to afford methyl 5-((3-(tert-butoxycarbonyl) phenoxy)methyl)-2-methoxybenzoate (12-1, 120 mg, 0.31 mmol, 80% yield) as a clear oil. 1H NMR (500 MHz, $CDCl_3$) δ 7.90 (d, J=2.3 Hz, 1H), 7.62-7.59 (m, 2H), 7.56 (dd, J=8.5, 2.4 Hz, 1H), 7.37-7.30 (m, 1H), 7.13 (ddd, J=8.3, 2.6, 1.1 Hz, 1H), 7.01 (d, J=8.5 Hz, 1H), 5.04 (s, 2H), 3.93 (s, 3H), 3.91 (s, 3H), 1.61-1.58 (m, 9H). LC-MS RT; Method D.

Intermediate 12-3: To a vial containing 12-1 (55 mg, 0.15 mmol) in THF was added 1 N LiOH (480 μl, 0.16 mmol). After stirring for 36 h at room temperature, the reaction mixture was acidified by the addition of 1N HCl (2 mL), partitioned between water and the resulting solution extracted with EtOAc. The combined organic portions were dried over $Na_2SO_4$ filtered and concentrated to afford 5-((3-(tert-butoxycarbonyl) phenoxy)methyl)-2-methoxybenzoic acid (12-3, 53 mg, 0.15 mmol, 100% yield) which was used without further purification. LC-MS RT: 0.98 min; MS (ESD) m/z; Method D.

Example 12: To a vial containing IV-2a (8.0 mg, 0.022 mmol) in MeCN (0.22 mL) was added 12-3 (9.3 mg, 0.026 mmol), HATU (9.9 mg, 0.026 mmol), and DIEA (11 μl, 0.065 mmol). The reaction mixture was stirred for 18 h at room temperature, concentrated under reduced pressure, and the residue dissolved in 1:1 TFA/DCM. After stirring for 18 hr at room temperature, the reaction mixture was concentrated under reduced pressure and the residue was dissolved in DMSO and purified by HPLC to afford 3-((3-(((1R,2R,3S,4R,Z)-7-(cyclopropylmethylene)-3-((4-fluoro-3-(trifluoromethyl)phenyl) carbamoyl) bicyclo[2.2.1]heptan-2-yl) carbamoyl)-4-methoxybenzyl)oxy)benzoic acid (7.2 mg, 10 μmol, 48% yield). 1H NMR (500 MHZ, DMSO-d6) δ 10.52 (s, 1H), 9.88 (br d, J=7.0 Hz, 1H), 8.20 (dd, J=6.3, 1.7 Hz, 1H), 8.01 (d, J=1.5 Hz, 1H), 7.81-7.74 (m, 1H), 7.58 (dd, J=8.7, 1.4 Hz, 1H), 7.53 (d, J=7.9 Hz, 1H), 7.51-7.43 (m, 2H), 7.41 (t, J=7.9 Hz, 1H), 7.24 (dd, J=7.9, 1.5 Hz, 1H), 7.20 (d, J=8.5 Hz, 1H), 5.12 (s, 2H), 4.68 (d, J=9.5 Hz, 1H), 4.47-4.39 (m, 1H), 3.99 (s, 2H), 3.14 (dd, J=10.7, 4.0 Hz, 1H), 3.11-3.05 (m, 1H), 2.74-2.67 (m, 1H), 1.88-1.81 (m, 1H), 1.80-1.74 (m, 1H), 1.54-1.45 (m, 1H), 1.45-1.32 (m, 2H), 0.80-0.63 (m, 2H), 0.41-0.25 (m, 2H). LC-MS RT: 2.58 min; MS (ESI) m/z 653 $(M+H)^+$; Method A.

Examples 13, & 15-30 (Table 2) were prepared according to the procedures above for Example 12 with appropriate nucleophiles replacing 12-2 and the appropriate norbornyl amines replacing IV-2a.

Example 14

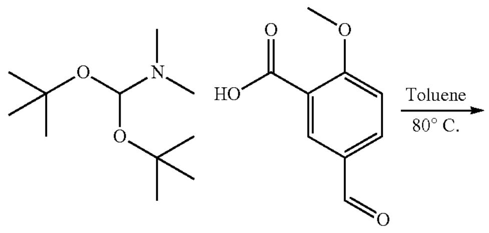

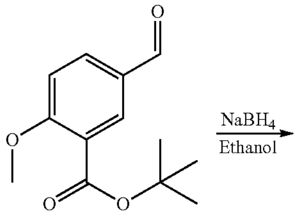

14-1

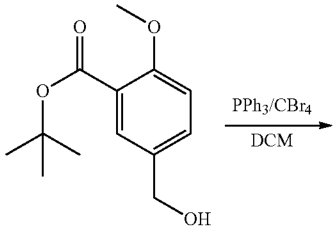

14-2

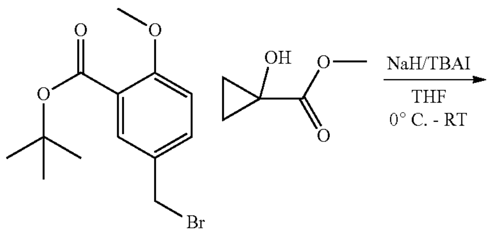

14-3

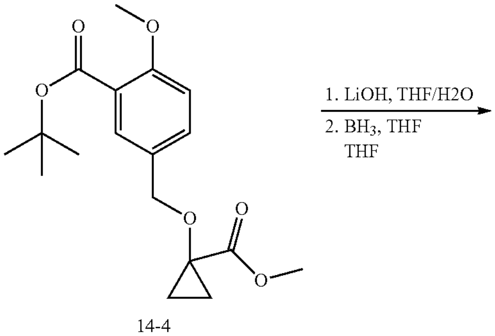

14-4

-continued

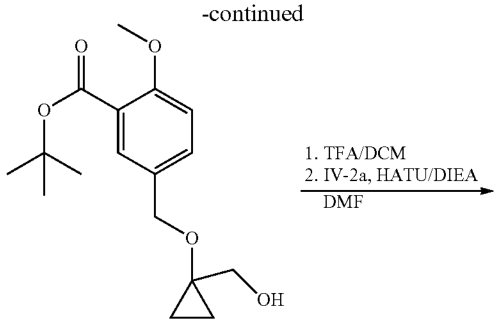

14-5

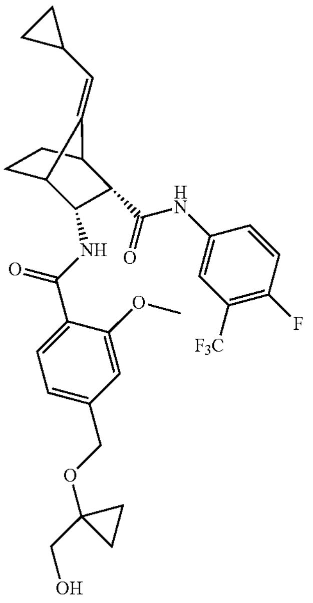

Example 14

Intermediate 14-1: tert-Butyl 5-formyl-2-methoxybenzoate

N,N-Dimethylformamide-di-tert-butyl acetate (500 mg, 2.46 mmol) was added dropwise to a solution of 5-formyl-2-methoxybenzoic acid (1.57 mL, 7.38 mmol) in toluene (7.5 mL) at 80° C. The reaction mixture was heated at 80° C. for 16 h, then diluted with water (10 mL) and extracted with $Et_2O$ (3×10 mL). The combined organic phases were washed with brine (30 mL), dried over $MgSO_4$, filtered and concentrated in vacuo to afford 14-1 (513 mg, 88%) as a pale yellow solid. The material was used in the next step without further purification. 1H NMR (500 MHZ, $CDCl_3$) δ 9.94 (s, 1H), 8.25 (d, J=2.2 Hz, 1H), 8.00 (dd, J=8.8, 2.2 Hz, 1H), 7.10 (d, J=8.8 Hz, 1H), 4.01 (s, 3H), 1.63 (s, 9H)

Intermediate 14-2: tert-Butyl 5-(hydroxymethyl)-2-methoxybenzoate Intermediate 14-1 (513 mg, 2.171 mmol) was dissolved in EtOH (13 mL) and treated $NaBH_4$ (82 mg, 2.17 mmol). The reaction mixture was stirred at rt for 1 hour, treated with water (10 mL) and concentrated under reduced pressure. The residue was purified on ISCO (0-100% EtOA/Hex) to afford Intermediate 14-2 (470 mg, 91%) as a clear oil. MS m/z=239.08 (M+H). $^1H$ NMR (500 MHZ, $CDCl_3$) δ 7.74 (d, J=2.2 Hz, 1H), 7.47 (dd, J=8.5, 2.5 Hz, 1H), 6.98 (d, J=8.5 Hz, 1H), 4.67 (d, J=5.8 Hz, 2H), 3.92 (s, 3H), 1.62 (s, 9H)

Intermediate 14-3: tert-Butyl 5-(bromomethyl)-2-methoxybenzoate

To a solution of Intermediate 14-2 (470 mg, 1.97 mmol) in DCM (10 mL) was added triphenylphosphane (776 mg, 2.96 mmol) and $CBr_4$ (981 mg, 2.96 mmol). After 2 h, the reaction mixture was concentrated in vacuo and purified by silica gel chromatography to afford Intermediate 14-3 (370 mg, 62%) as a white solid. MS m/z=304.3 (M+H). 1H NMR (500 MHz, $CDCl_3$) δ 7.80-7.70 (m, 1H), 7.49 (dd, J=8.7, 2.3 Hz, 1H), 6.95 (d, J=8.8 Hz, 1H), 4.51 (s, 2H), 3.92 (s, 3H), 1.62 (s, 9H)

Intermediate 14-4: tert-Butyl 2-methoxy-5-((1-(methoxycarbonyl)cyclopropoxy)methyl)benzoate To a solution of methyl 1-hydroxycyclopropane-1-carboxylate (100 mg, 0.86 mmol) and tetrabutylammonium iodide (31 mg, 0.086 mmol) in dry THF (16 mL), was added NaH (60 wt %, 37 mg, 0.94 mmol) in portions at 0° C. The reaction mixture was allowed to warm to rt, stirred for another 15 min then treated with Intermediate 14-3. After 3 h, the solvent was removed in vacuo, the residue was dissolved in 25 mL ether and the solution washed with water. The organic phase was dried over $MgSO_4$, filtered and the solvent was removed in vacuum. The residue was purified by silica gel chromatography to afford Intermediate 14-4 (96 mg, 33%) as an oil. MS m/z=337.08 (M+H).

Intermediate 14-5: tert-Butyl 5-((1-(hydroxymethyl) cyclopropoxy)methyl)-2-methoxybenzoate A solution of Intermediate 14-4 (95 mg, 0.282 mmol) in THF (2.0 mL) and water (0.667 mL) was treated with LiOH (0.282 mL, 0.282 mmol). The clear colorless solution was stirred at rt for 24 h. The reaction mixture was acidified by the addition of HCl (1.0 M) to pH 1 then the solution extracted with EtOAc. The organic layer was dried over $Na_2SO_4$ filtered and concentrated under reduced pressure to afford a clear oil which was dissolved in THF (1.0 ml) and treated with borane (1 M in THF, 0.25 ml, 0.25 mmol). After 16 h, the reaction mixture was diluted with EtOAc, quenched by the addition of HCl (1.0 M, 10 mL) and stirred at room temperature for an additional 1 h. The layers were separated, and the organic layer was dried over $MgSO_4$, filtered and concentrated in vacuo to afford a colorless oil which was purified by silica gel chromatography to afford Intermediate 14-5 (38 mg, 42%) as a clear oil. MS m/z=309.08 (M+H). 1H NMR (500 MHZ, CHLOROFORM-d) δ 7.71-7.62 (m, 1H), 7.41 (dd, J=8.5, 2.2 Hz, 1H), 6.95 (d, J=8.5 Hz, 1H), 4.57 (s, 2H), 3.90 (s, 3H), 3.74 (s, 2H), 1.61 (s, 9H), 1.02-0.92 (m, 2H), 0.71-0.61 (m, 2H)

Example 14: (1R,2S,3R,4R,Z)-7-(cyclopropylmethylene)-N-(4-fluoro-3-(trifluoromethyl) phenyl)-3-(4-((1-(hydroxymethyl)cyclopropoxy)methyl)-2-methoxybenzamido) bicyclo[2.2.1]heptane-2-carboxamide Intermediate 14-5 (25 mg, 0.081 mmol) was combined with DCM (1 mL) and treated with TFA (0.3 mL). After 30 min, the reaction mixture was concentrated under reduced pressure, dissolved in EtOAc and the solution washed with brine. The organic layer was dried over sodium sulfate, filtered and concentrated to afford a white powder which was dissolved in DMF (1.0 mL) and treated with Intermediate IV-2a (29 mg, 0.080 mmol), HATU (36.0 mg, 0.100 mmol) and DIEA 42.5 μl, 0.240 mmol). After 18 h, The reaction mixture was concentrated under reduced pressure then purified by prep HPLC to give example 14 (13 mg, 26%) as a clear oil. LCMS RT=2.5 min, Method B, m/z=603.9 (M+H).

Example 31

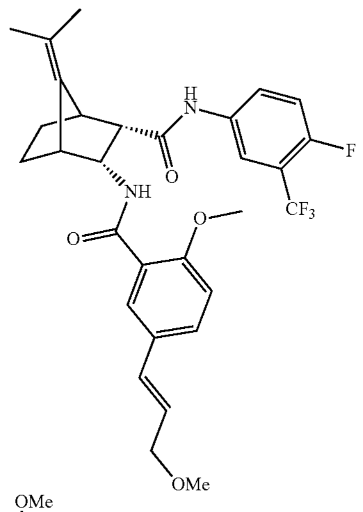

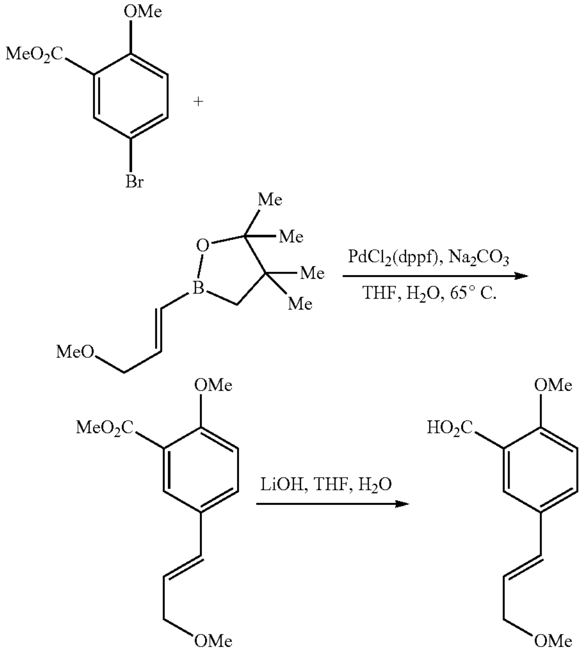

31-1 31-2

Intermediate 31-1: Into the reaction vessel containing methyl 5-bromo-2-methoxybenzoate (148 mg, 0.606 mmol) was added (E)-2-(3-methoxyprop-1-en-1-yl)-4,4,5,5-tetramethyl-1,3,2-dioxaborolane (100 mg, 0.51 mmol), $PdCl_2$ (dppf)-$CH_2Cl$ adduct (82 mg, 0.10 mmol), and $Na_2CO_3$ (1.0 mL, 2.0 mmol). The reaction mixture was degassed by bubbling nitrogen for 2 min, sealed, and stirred at 65° C. for 2 h. After cooling to 23° C., the reaction mixture was extracted with EtOAc. The organic phase was dried over $Na_2SO_4$, filtered, concentrated under reduced pressure and purified via silica gel chromatography to produce 31-1 (83 mg, 0.35 mmol, 70% yield). LC-MS RT=0.84 min; MS (ESI) m/z=237.0 $(M+H)^+$; Method A.

Intermediate 31-2: Into the reaction vessel was added 31-1 (40 mg, 0.17 mmol), THF (1 mL), water (0.5 mL), and LiOH monohydrate (35 mg, 0.85 mmol). The reaction mixture was stirred at 23° C. for 1 h, diluted with EtOAc (10 mL), and washed with sat. $NH_4Cl$ containing 1.5 mmol HCl. The organic phase was dried over $Na_2SO_4$ filtered and concentrated to provide 31-2 (37 mg, 0.17 mmol, 98% yield) that was used without further purification. LC-MS RT=0.69 min; MS (ESI) m/z=220.9 $(M+H)^+$; Method D.

Example 31 was prepared from 31-1 and I-7 according to the general procedure used for Example 1. (2S,3R)—N-[4-fluoro-3-(trifluoromethyl)phenyl]-3-{2-methoxy-5-[(1E)-3-methoxyprop-1-en-1-yl]benzamido}-7-(propan-2-ylidene) bicyclo[2.2.1]heptane-2-carboxamide (9.8 mg, 62%). $^1H$ NMR (500 MHZ, $CDCl_3$) δ 9.23 (br d, J=7.9 Hz, 1H), 8.20 (d, J=2.4 Hz, 1H), 8.11 (s, 1H), 7.85 (dd, J=6.3, 2.6 Hz, 1H), 7.57 (dt, J=8.7, 3.5 Hz, 1H), 7.47 (dd, J=8.5, 2.4 Hz, 1H), 7.05 (t, J=9.4 Hz, 1H), 6.91 (d, J=8.6 Hz, 1H), 6.57 (d, J=15.9 Hz, 1H), 6.23 (dt, J=15.9, 6.0 Hz, 1H), 4.73 (td, J=9.2, 4.3 Hz, 1H), 4.09 (dd, J=6.1, 1.2 Hz, 2H), 3.97 (s, 3H), 3.39 (s, 3H), 3.08-2.98 (m, 3H), 2.22-2.12 (m, 1H), 1.81-1.74 (m, 1H), 1.73 (s, 3H), 1.72 (s, 3H), 1.64-1.53 (m, 2H). LC-MS RT=1.23 min; MS (ESI) m/z=651.2 $(M+H)^+$; Method B.

Example 32

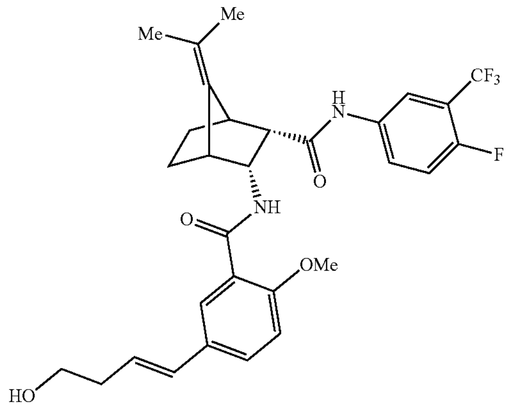

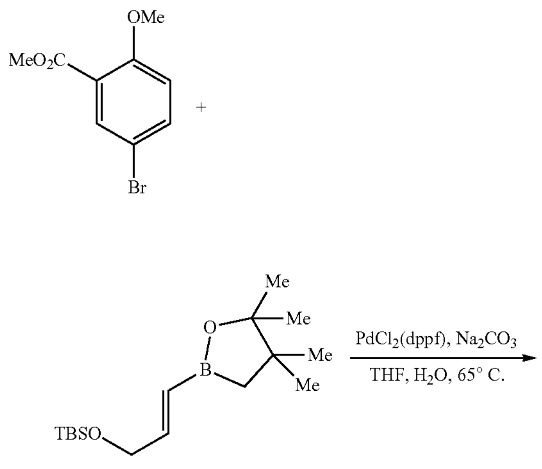

-continued

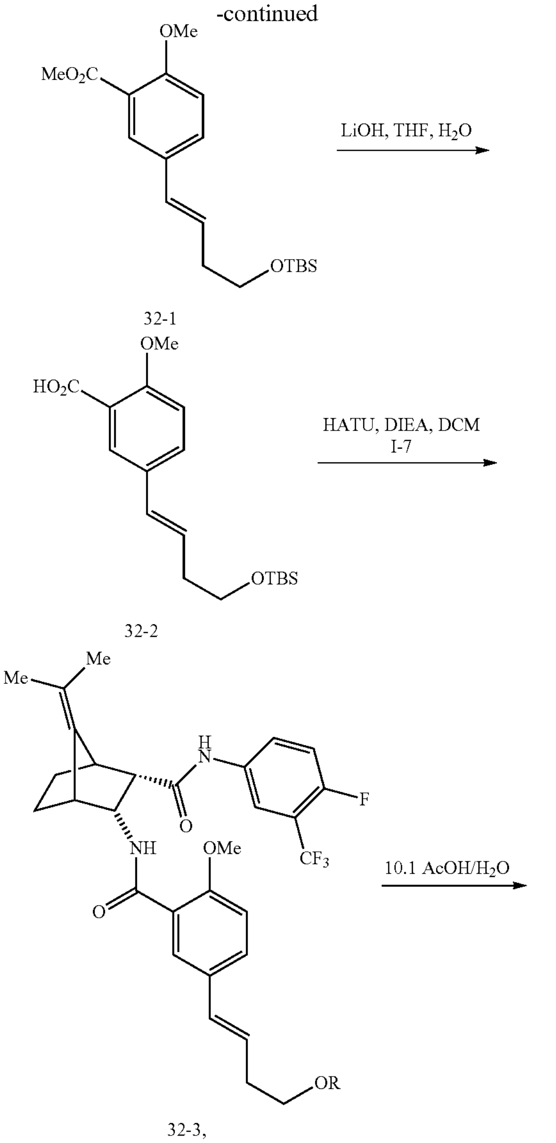

32-1

32-2

32-3,
R = TBS example 32
R = H

Intermediate 32-1 was prepared from methyl 5-bromo-2-methoxybenzoate and (E)-tert-butyldimethyl ((4-(4,4,5,5-tetramethyl-1,3,2-dioxaborolan-2-yl) but-3-en-1-yl)oxy) silane in the same manner as intermediate 31-1. (132 mg, 0.380 mmol, 98% yield). LC-MS RT=1.28 min; MS (ESI) m/z=351.1 $(M+H)^+$; Method A.

Intermediate 32-2 was prepared from 32-1 in the same manner as intermediate 31-2 (56 mg, 0.17 mmol, 97% yield). LC-MS RT=1.18 min; MS (ESI) m/z=337.0 $(M+H)^+$; Method A.

Intermediate 32-3: Intermediate 32-3 was prepared from 32-2 in the same manner as Example 31 (8.8 mg, 0.01 mmol, 47% yield). LC-MS RT=1.43 min; MS (ESI) m/z=675.1 $(M+H)^+$; Method A.

Procedure for example 32: Into the reaction vessel was added 32-3 (8.8 mg, 0.010 mmol), AcOH (1 mL), and $H_2O$ (0.1 mL). After stirring at 23° C. for 12 h, the reaction mixture was concentrated under reduced pressure and purified via preparative RP-HPLC to produce example 32 (1.9 mg, 3.25 μmol, 25% yield). $^1$H NMR (500 MHz, $CDCl_3$) δ 9.23 (br d, J=7.6 Hz, 1H), 8.19 (d, J=2.2 Hz, 1H), 8.12 (br s, 1H), 7.83 (dd, J=6.1, 2.4 Hz, 1H), 7.66-7.56 (m, 1H), 7.41 (dd, J=8.5, 2.3 Hz, 1H), 7.05 (t, J=9.4 Hz, 1H), 6.89 (d, J=8.5 Hz, 1H), 6.46 (d, J=15.9 Hz, 1H), 6.21-6.08 (m, 1H), 4.77-4.68 (m, 1H), 3.97 (s, 3H), 3.80-3.69 (m, 2H), 3.09-2.97 (m, 3H), 2.49 (q, J=6.6 Hz, 2H), 2.22-2.12 (m, 1H), 1.81-1.74 (m, 1H), 1.73 (s, 3H), 1.71 (s, 3H), 1.62-1.58 (m, 2H), LC-MS RT: 1.17 min; MS (ESI) m/z=561.3 (M+H)+; Method B.

Example 33

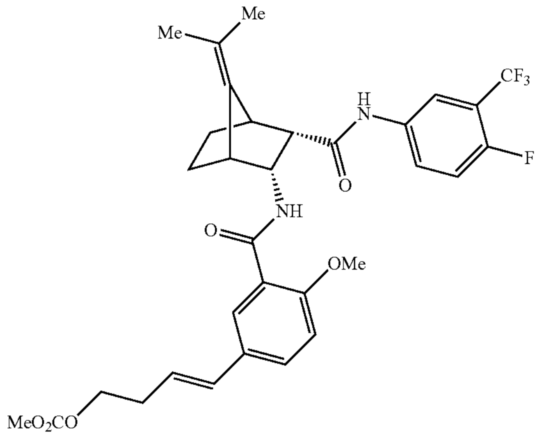

Into the reaction vessel was added Example 32 (5 mg, 8.92 μmol), DCM (1 mL), DIEA (0.05 mL, 0.27 mmol), and methyl chloroformate (0.014 mL, 0.18 mmol). After stirring at rt for 30 min, the reaction mixture was concentrated under reduced pressure and the residue purified by prep-HPLC purification to produce (E)-4-(3-(((1R,2R,3S,4R)-3-((4-fluoro-3-(trifluoromethyl)phenyl) carbamoyl)-7-(propan-2-ylidene) bicyclo[2.2.1]heptan-2-yl) carbamoyl)-4-methoxy-phenyl) but-3-en-1-yl methyl carbonate (2.4 mg, 3.6 μmol, 41% yield). $^1$H NMR (500 MHZ, $CDCl_3$) δ 9.21 (br d, J=7.6 Hz, 1H), 8.17 (d, J=2.3 Hz, 1H), 8.11 (s, 1H), 7.84 (dd, J=6.3, 2.6 Hz, 1H), 7.58 (dt, J=8.9, 3.4 Hz, 1H), 7.41 (dd, J=8.6, 2.3 Hz, 1H), 7.05 (t, J=9.4 Hz, 1H), 6.88 (d, J=8.5 Hz, 1H), 6.44 (d, J=15.9 Hz, 1H), 6.21-6.07 (m, 1H), 4.80-4.68 (m, 1H), 4.25 (t, J=6.7 Hz, 2H), 3.97 (s, 3H), 3.78 (s, 3H), 3.11-2.96 (m, 3H), 2.61-2.55 (m, 2H), 2.22-2.14 (m, 1H), 1.81-1.74 (m, 1H), 1.73 (s, 3H), 1.72 (s, 3H), 1.64-1.59 (m, 2H). LC-MS RT: 1.24 min; MS (ESI) m/z=619.3 (M+H)+; Method B.

Example 34

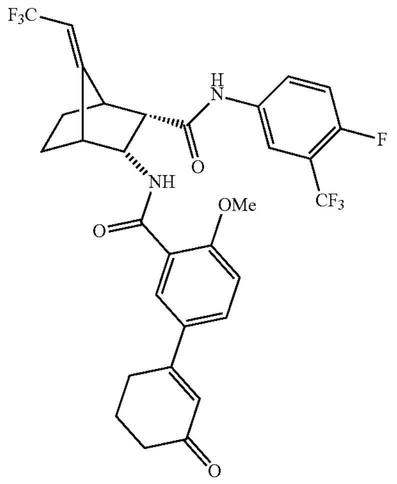 [SMILES: COc1ccc(C2=CC(=O)CCC2)cc1C(=O)N[C@@H]1C2CCC(/C2=C/C(F)(F)F)[C@@H]1C(=O)Nc1ccc(F)c(C(F)(F)F)c1]

Intermediate 34-1

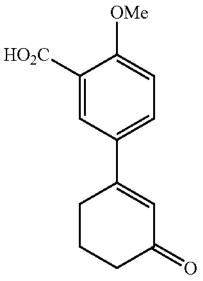 [SMILES: COc1ccc(C2=CC(=O)CCC2)cc1C(=O)O]

A solution of 5-borono-2-methoxybenzoic acid (1.00 g, 5.10 mmol), 3-chlorocyclohex-2-en-1-one (0.666 g, 5.10 mmol) and $Pd(Ph_3P)_4$ (0.295 g, 0.255 mmol) in dioxane (25 mL) was degassed and treated with $Na_2CO_3$ (15.31 mL, 15.31 mmol) as a 1 M aq. solution. The reaction mixture was heated at 100° C. for 18 h, allowed to cool and extracted from water with EtOAc. The organic layer was concentrated under reduced pressure and the residue purified by silica gel chromatography to furnish 4-methoxy-5'-oxo-2',3',4',5'-tetrahydro-[1,1'-biphenyl]-3-carboxylic acid (701 mg, 2.85 mmol, 55.0% yield). LC-MS RT: 0.90 min; MS (ESI) m/z=246.8 (M+H)+; Method A.

Example 34 was prepared from V-2 and 34-1 according to the general procedure employed in Example 1 (7.2 mg, 72% yield). 1H NMR (500 MHz, DMSO-d6) δ 10.68 (s, 1H), 9.95 (d, J=6.8 Hz, 1H), 8.27-8.17 (m, 2H), 7.87 (dd, J=8.7, 2.5 Hz, 1H), 7.82-7.73 (m, 1H), 7.50 (t, J=9.7 Hz, 1H), 7.26 (d, J=8.8 Hz, 1H), 6.32 (s, 1H), 5.94 (d, J=7.7 Hz, 1H), 4.58-4.46 (m, 1H), 4.05 (s, 3H), 3.24 (br s, 1H), 2.99 (br s, 1H), 2.89 (s, 1H), 2.81-2.71 (m, 2H), 2.37 (t, J=6.6 Hz, 2H), 2.11-1.81 (m, 4H), 1.49 (br d, J=7.0 Hz, 2H). LC-MS RT: 2.47 min; MS (ESI) m/z=625.3 (M+H)+; Method C.

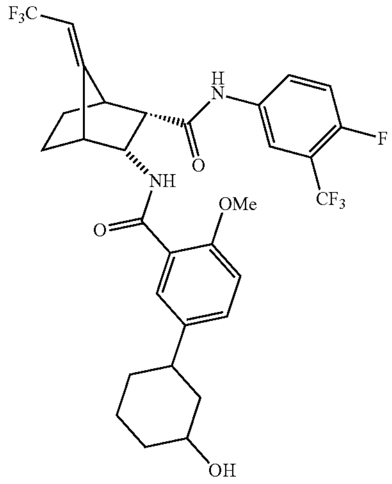 [SMILES: COc1ccc(C2CCCC(O)C2)cc1C(=O)N[C@@H]1C2CCC(/C2=C/C(F)(F)F)[C@@H]1C(=O)Nc1ccc(F)c(C(F)(F)F)c1]

Examples 35-38

Intermediate 35-1

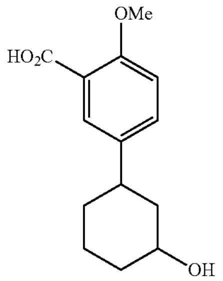 [SMILES: COc1ccc(C2CCCC(O)C2)cc1C(=O)O]

A solution of 34-1 (100 mg, 0.406 mmol) in EtOH (4 mL) was treated with $PtO_2$ (9.2 mg, 0.041 mmol) and the reaction mixture hydrogenated (50 psi) for 18 h at rt. The reaction mixture was filtered through celite and concentrated under reduced pressure to furnish 2-methoxy-5-(3-oxocyclohexyl) benzoic acid (35-1, 101 mg, 0.406 mmol, 100% yield) LC-MS RT: 0.99 min; MS (ESI) m/z=250.9 (M+H)+; Method A.

Example 35 was prepared from V-2 and 35-1 according to the general procedure employed in Example 1 to furnish (2S,3R,7Z)—N-[4-fluoro-3-(trifluoromethyl)phenyl]-3-[5-(3-hydroxycyclohexyl)-2-methoxybenzamido]-7-(2,2,2-trifluoroethylidene) bicyclo[2.2.1]heptane-2-carboxamide as a mixture of 4 isomers. The isomers were separated under the following conditions: Instrument: Agilent analytical LC, Column: IG SFC 30×250 mm ID, 5 μm, Flow rate: 85 mL/min, Mobile Phase: 85/15 $CO_2$/(IPA), Detector Wavelength: 220 nm to generate Examples 35-38.

Example 35, Peak 1, RT=25 min (>95% de, 23 mg, 20% yield). 1H NMR (400 MHZ, CD3OD) δ 10.22 (br d, J=7.0 Hz, 1H), 8.17 (dd, J=6.3, 2.3 Hz, 1H), 7.90 (d, J=2.2 Hz, 1H), 7.77 (dt, J=8.5, 3.4 Hz, 1H), 7.39 (dd, J=8.5, 2.3 Hz, 1H), 7.32-7.24 (m, 1H), 7.10 (d, J=8.6 Hz, 1H), 5.77 (q, J=7.6 Hz, 1H), 4.73-4.60 (m, 1H), 4.06 (s, 3H), 3.75-3.58 (m, 1H), 3.41 (br s, 1H), 3.26 (dd, J=10.8, 4.2 Hz, 1H), 2.95 (br s, 1H), 2.64-2.50 (m, 1H), 2.26-2.19 (m, 1H), 2.13-1.97 (m, 3H), 1.94-1.75 (m, 2H), 1.68-1.57 (m, 2H), 1.54-1.24 (m, 6H). LC-MS RT: 1.41 min; MS (ESI) m/z=629.4 (M+H)+; Method A. Example 36, Peak 2, RT=31 min (>95% de, 19 mg, 17% yield). 1H NMR (400 MHZ, $CD_3OD$) δ 10.31-10.15 (m, 1H), 8.17 (dd, J=6.3, 2.5 Hz, 1H), 7.91 (d, J=2.4 Hz, 1H), 7.77 (dt, J=8.6, 3.5 Hz, 1H), 7.46-7.25 (m, 2H), 7.10 (d, J=8.6 Hz, 1H), 5.78 (q, J=7.7 Hz, 1H), 4.71-4.58 (m, 1H), 4.20-4.14 (m, 1H), 4.06 (s, 3H), 3.41 (br s, 1H), 3.26 (dd, J=10.8, 4.2 Hz, 1H), 3.11-2.90 (m, 2H), 2.28-2.01 (m, 2H), 1.97-1.75 (m, 5H), 1.73-1.40 (m, 7H). LC-MS RT: 1.40 min; MS (ESI) m/z=629.4 (M+H)+; Method A.

Example 37, Peak 3, RT=46.5 min (>95% de, 20 mg, 18% yield). $^1$H NMR (400 MHZ, $CD_3OD$) & 10.22 (br d, J=7.3 Hz, 1H), 8.17 (dd, J=6.3, 2.5 Hz, 1H), 7.91 (d, J=2.4 Hz, 1H), 7.77 (dt, J=8.5, 3.5 Hz, 1H), 7.40 (dd, J=8.6, 2.4 Hz, 1H), 7.31 (t, J=9.6 Hz, 1H), 7.10 (d, J=8.6 Hz, 1H), 5.83-5.72 (m, 1H), 4.68 (td, J=7.2, 3.5 Hz, 1H), 4.21-4.12 (m, 1H), 4.06 (s, 3H), 3.41 (br s, 1H), 3.26 (dd, J=10.8, 4.2 Hz, 1H), 3.15-2.90 (m, 3H), 2.33-2.15 (m, 2H), 2.11-1.99 (m, 2H), 1.96-1.83 (m, 4H), 1.75-1.63 (m, 4H), 1.49 (br d, J=8.6 Hz, 1H). LC-MS RT: 1.40 min; MS (ESI) m/z 629.4 (M+H)+; Method A.

Example 38, Peak 4, RT=51 min (>95% de, 20 mg, 18% yield). $^1$H NMR (400 MHZ, $CD_3OD$) δ 10.23 (br d, J=7.0 Hz, 1H), 8.17 (dd, J=6.4, 2.4 Hz, 1H), 7.90 (d, J=2.2 Hz, 1H), 7.77 (dt, J=8.5, 3.6 Hz, 1H), 7.39 (dd, J=8.6, 2.4 Hz, 1H), 7.31 (t, J=9.6 Hz, 1H), 7.10 (d, J=8.6 Hz, 1H), 5.77 (q, J=7.7 Hz, 1H), 4.67 (dt, J=7.2, 3.5 Hz, 1H), 4.07 (s, 3H), 3.67 (brt, J=4.2 Hz, 1H), 3.41 (br s, 1H), 3.25 (dd, J=10.8, 4.2 Hz, 1H), 2.95 (br s, 1H), 2.69-2.54 (m, 1H), 2.28-2.18 (m, 1H), 2.13-1.98 (m, 3H), 1.94-1.87 (m, 1H), 1.78 (br d, J=12.5 Hz, 1H), 1.66-1.55 (m, 2H), 1.52-1.25 (m, 6H). LC-MS RT: 1.39 min; MS (ESI) m/z=629.4 (M+H)+; Method A.

Example 39

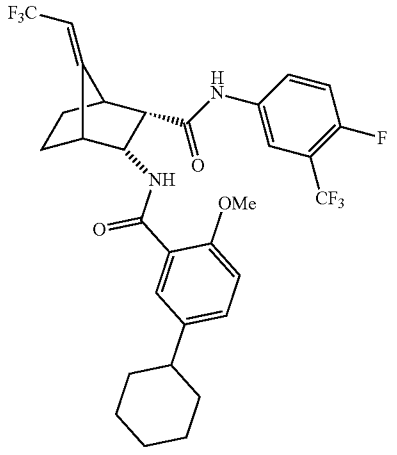 [SMILES: COc1ccc(C2CCCCC2)cc1C(=O)N[C@@H]1C2CCC(/C2=C/C(F)(F)F)[C@@H]1C(=O)Nc1ccc(F)c(C(F)(F)F)c1]

(2S,3R,7Z)-3-(5-cyclohexyl-2-methoxybenzamido)-N-[4-fluoro-3-(trifluoromethyl)phenyl]-7-(2,2,2-trifluoroethylidene) bicyclo[2.2.1]heptane-2-carboxamide, Example 39 (20 mg, 18%) was isolated as an over reduced by product of the synthesis of Examples 35-38. $^1$H NMR (500 MHz, DMSO-d6) δ 10.62 (s, 1H), 9.84 (d, J=7.0 Hz, 1H), 8.23 (dd, J=6.4, 2.4 Hz, 1H), 7.85-7.70 (m, 2H), 7.50 (t, J=9.6 Hz, 1H), 7.34 (dd, J=8.5, 2.1 Hz, 1H), 7.09 (d, J=8.5 Hz, 1H), 5.94 (q, J=7.7 Hz, 1H), 4.52 (br d, J=4.3 Hz, 1H), 3.96 (s, 3H), 3.22 (br s, 1H), 2.98 (br s, 1H), 2.51-2.39 (m, 2H), 2.06-1.84 (m, 2H), 1.81-1.65 (m, 5H), 1.49 (br d, J=7.3 Hz, 2H), 1.40-1.29 (m, 4H), 1.26-1.16 (m, 1H). LC-MS RT: 3.00 min; MS (ESI) m/z=613.07 (M+H)+; Method C.

Examples 40-43

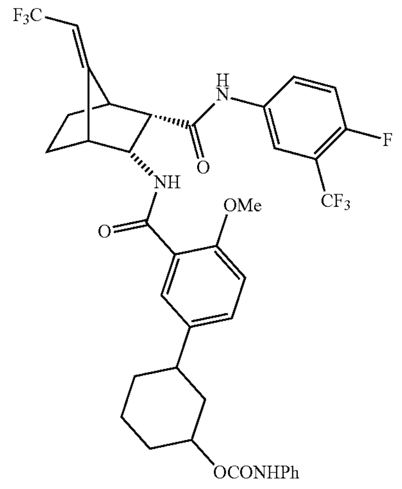

A solution of Example 35 prior to resolution (153 mg, 0.243 mmol) in DCM (4.8 mL) was treated with phenyl isocyanate (0.05, 0.4 mmol) and the reaction mixture allowed to stir for 18 h. The reaction mixture was then concentrated under reduced pressure and the residue purified by reverse phase HPLC. The resulting isomeric mixture was resolved according to the following conditions. Instrument: Waters 100 Prep SFC Column: Chiral OD 30×250 mm. 5 micron, Mobile Phase: 80% $CO_2$/20% MeOH w/0.1% DEA, Flow Conditions: 100 mL/min, Detector Wavelength: 220 nm Example 40, Peak 1, RT=15.2 min (>95% de, 9.2 mg, 5.0% yield). 1H NMR (500 MHz, DMSO-d6) δ 10.69-10.57 (m, 1H), 9.89 (br d, J=7.0 Hz, 1H), 9.57 (br s, 1H), 8.31-8.19 (m, 1H), 7.92-7.73 (m, 2H), 7.54-7.45 (m, 3H), 7.38 (dd, J=8.5, 2.1 Hz, 1H), 7.28 (t, J=7.9 Hz, 2H), 7.13 (d, J=8.5 Hz, 1H), 6.99 (t, J=7.3 Hz, 1H), 5.94 (q, J=7.9 Hz, 1H), 5.05 (br s, 1H), 4.62-4.46 (m, 1H), 3.98 (s, 3H), 3.32-3.21 (m, 1H), 3.01 (s, 1H), 3.00-2.87 (m, 2H), 2.07-1.86 (m, 4H), 1.86-1.69 (m, 3H), 1.65 (br dd, J=11.1, 3.2 Hz, 1H), 1.62-1.36 (m, 4H). LC-MS RT: 2.88 min; MS (ESI) m/z=748.11 (M+H)+; Method C.

Example 41, Peak 2, RT=18.1 min (>95% de, 26 mg, 14% yield). 1H NMR (500 MHz, DMSO-d6) δ 10.63 (s, 1H), 9.88 (d, J=7.0 Hz, 1H), 9.56 (br s, 1H), 8.23 (dd, J=6.6, 2.3 Hz, 1H), 7.85-7.74 (m, 2H), 7.56-7.47 (m, 3H), 7.38 (dd, J=8.5, 2.1 Hz, 1H), 7.28 (t, J=7.8 Hz, 2H), 7.13 (d, J=8.5 Hz, 1H), 6.99 (t, J=7.3 Hz, 1H), 5.94 (q, J=8.1 Hz, 1H), 5.05 (br s, 1H), 4.55-4.46 (m, 1H), 3.98 (s, 3H), 3.23 (br d, J=1.2 Hz, 1H), 3.04-2.88 (m, 2H), 2.07-1.86 (m, 4H), 1.85-1.54 (m, 6H), 1.55-1.38 (m, 3H). LC-MS RT: 2.88 min; MS (ESI) m/z=747.89 (M+H)+; Method C.

Example 42, Peak 3, RT=24.5 min (>95% de, 26 mg, 14% yield). 1H NMR (500 MHz, DMSO-d6) δ 10.64 (s, 1H), 9.87 (d, J=7.1 Hz, 1H), 9.62-9.48 (m, 1H), 8.21 (br d, J=6.1 Hz, 1H), 7.81 (s, 2H), 7.53-7.39 (m, 4H), 7.26 (t, J=7.9 Hz, 2H), 7.11 (d, J=8.7 Hz, 1H), 6.97 (s, 1H), 5.92 (q, J=7.8 Hz, 1H), 4.78-4.67 (m, 1H), 4.52 (br d, J=3.0 Hz, 1H), 3.96 (s, 3H), 3.34-3.13 (m, 2H), 2.97 (br s, 1H), 2.75-2.63 (m, 1H), 2.16-2.04 (m, 2H), 2.02-1.95 (m, 1H), 1.91-1.80 (m, 2H), 1.77-1.69 (m, 1H), 1.54-1.44 (m, 4H), 1.41-1.27 (m, 2H). LC-MS RT: 2.87 min; MS (ESI) m/z 748.29 (M+H)+; Method C.

Example 43, Peak 4, RT=32.1 min (>95% de, 24 mg, 13% yield). 1H NMR (500 MHz, DMSO-d6) δ 10.70-10.61 (m, 1H), 9.87 (br d, J=7.2 Hz, 1H), 9.55 (br s, 1H), 8.28-8.17 (m, 1H), 7.85-7.66 (m, 2H), 7.52-7.33 (m, 5H), 7.25 (t, J=7.9 Hz, 2H), 7.11 (d, J=8.8 Hz, 1H), 7.01-6.91 (m, 1H), 5.95-5.84 (m, 1H), 4.81-4.69 (m, 1H), 4.58-4.47 (m, 1H), 3.96 (s, 3H), 3.30-3.15 (m, 2H), 2.97 (br s, 1H), 2.75-2.63 (m, 1H), 2.13-2.03 (m, 2H), 1.89-1.82 (m, 2H), 1.77-1.64 (m, 1H), 1.55-1.44 (m, 4H), 1.41-1.24 (m, 2H). LC-MS RT: 2.87 min; MS (ESI) m/z=748.10 (M+H)+; Method C.

Examples 44-46

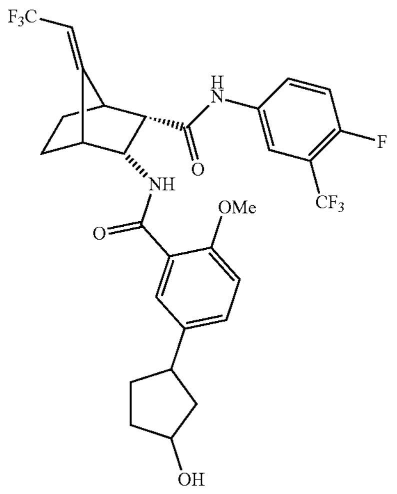 [SMILES: COc1ccc(C2CCC(O)C2)cc1C(=O)N[C@@H]1C2CCC(/C2=C/C(F)(F)F)[C@@H]1C(=O)Nc1ccc(F)c(C(F)(F)F)c1]

Examples 44-46 were prepared as a mixture of four diastereomers according to the same method employed for the production of Examples 35-38 by substituting 3-chloro-cyclopent-2-en-3-one as the starting material. The isomers were resolved as follows. Agilent analytical LC, IG SFC 30×250 mm, 5 micron, 85 mL/min, 90/10 $CO_2$/EtOH, Detectro wavelength: 220 nm.

Example 44, Peak 1, RT=11.0 min (>95% de, 5.0 mg, 5.0% yield). 1H NMR (400 MHz, CD3OD) δ 8.17 (dd, J=6.3, 2.8 Hz, 1H), 7.93 (d, J=2.6 Hz, 1H), 7.77 (dt, J=8.9, 3.5 Hz, 1H), 7.49-7.41 (m, 1H), 7.31 (t, J=9.6 Hz, 1H), 7.11 (d, J=8.6 Hz, 1H), 5.78 (q, J=7.5 Hz, 1H), 4.70-4.62 (m, 1H), 4.07 (s, 2H), 3.41 (br s, 1H), 3.29-3.22 (m, 6H), 2.95 (br s, 1H), 2.34-2.19 (m, 2H), 2.16-2.01 (m, 3H), 1.97-1.88 (m, 1H), 1.86-1.69 (m, 2H), 1.66-1.58 (m, 2H), 1.23 (td, J=6.5, 1.2 Hz, 1H). LC-MS RT: 1.11 min; MS (ESI) m/z=613.0 (M+H)+; Method A.

Peak 2, RT=15.8 min (5.0 mg, 5.0% yield). Material was not fully resolved with a close eluting impurity Example 45, Peak 3, RT=24.0 min (>95% de, 8.0 mg, 8.0% yield). 1H NMR (400 MHz, $CD_3OD$) δ 8.31-8.27 (m, 1H), 8.18 (dd, J=6.4, 2.9 Hz, 1H), 7.98 (d, J=2.4 Hz, 1H), 7.84-7.75 (m, 1H), 7.49 (dd, J=8.6, 2.2 Hz, 1H), 7.32 (t, J=9.7 Hz, 1H), 7.16 (d, J=8.6 Hz, 1H), 5.78 (d, J=7.7 Hz, 1H), 4.72-4.62 (m, 1H), 4.08 (s, 2H), 3.41 (br d, J=2.4 Hz, 2H), 3.32-3.22 (m, 2H), 2.96 (br d, J=3.1 Hz, 1H), 2.63 (dd, J=18.0, 7.7 Hz, 1H), 2.49-2.29 (m, 4H), 2.27-2.19 (m, 1H), 2.12-1.94 (m, 3H), 1.65-1.54 (m, 3H). LC-MS RT: 1.11 min; MS (ESI) m/z 613.0 (M+H)+; Method A.

Example 46, Peak 4, RT=27.9 min (>95% de, 11.0 mg, 11.0% yield). $^1$H NMR (400 MHz, CD3OD) δ 8.32-8.27 (m, 1H), 8.18 (dd, J=6.2, 2.9 Hz, 1H), 7.98 (d, J=2.4 Hz, 1H), 7.83-7.73 (m, 2H), 7.49 (dd, J=8.7, 2.3 Hz, 1H), 7.35-7.25 (m, 2H), 7.16 (d, J=8.6 Hz, 1H), 5.78 (d, J=7.7 Hz, 1H), 4.72-4.63 (m, 1H), 4.14 (s, 1H), 4.11-4.06 (m, 3H), 3.52-3.39 (m, 2H), 3.30-3.23 (m, 2H), 2.96 (br d, J=3.1 Hz, 1H), 2.63 (dd, J=18.0, 7.7 Hz, 1H), 2.49-2.28 (m, 4H), 2.26-2.18 (m, 1H), 2.10-1.93 (m, 3H). LC-MS RT: 1.11 min; MS (ESI) m/z 613.0 (M+H)+; Method A.

Examples 48-51

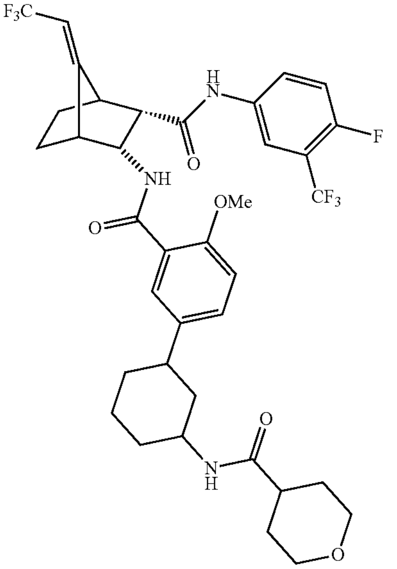 [SMILES: COc1ccc(C2CCCC(NC(=O)C3CCOCC3)C2)cc1C(=O)N[C@@H]1C2CCC(/C2=C/C(F)(F)F)[C@@H]1C(=O)Nc1ccc(F)c(C(F)(F)F)c1]

Intermediate 48-1

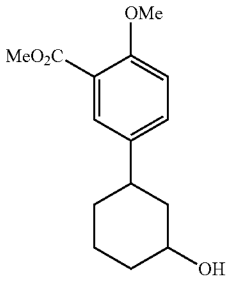 [SMILES: COC(=O)c1cc(C2CCCC(O)C2)ccc1OC]

Intermediate 48-1 was prepared according to the procedure for Intermediate 35-1 by employing the known methyl benzoate boronic acid as the starting material.

Intermediate 48-2

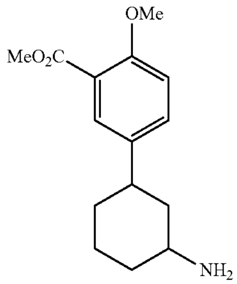 [SMILES: COC(=O)c1cc(C2CCCC(N)C2)ccc1OC]

A solution of 48-1 (376 mg, 1.42 mmol) in DCM (5.7 mL) was treated with $Ms_2O$ (273 mg, 1.56 mmol) followed by dropwise addition of TEA (0.30 mL, 2.1 mmol) and stirred for 18 h. The reaction mixture was extracted from 0.1 N HCL with DCM. The organic layer was concentrated under reduced pressure and used as is as methyl 2-methoxy-5-(3-((methylsulfonyl)oxy)cyclohexyl)benzoate (487 mg, 1.42 mmol, 100% yield) which was used without further purification.

A solution of methyl 2-methoxy-5-(3-((methylsulfonyl)oxy)cyclohexyl)benzoate (0.487 g, 1.42 mmol) in DMF (14 mL) was treated with sodium azide (0.139 g, 2.13 mmol) and heated to 50° C. for 18 h. The reaction mixture was extracted from water with EtOAc. The organic layer was concentrated under reduced pressure and methyl 5-(3-azidocyclohexyl)-2-methoxybenzoate (0.412 g, 1.42 mmol, 100% yield) was used without further purification.

A solution of methyl 5-(3-azidocyclohexyl)-2-methoxybenzoate (412 mg, 1.42 mmol) in EtOAc (14 mL) was treated with Pd—C(152 mg, 0.142 mmol) and under $H_2$ introduced under balloon pressure. The reaction mixture was stirred for 18 h, filtered through celite and concentrated under reduced pressure to furnish methyl 5-(3-aminocyclohexyl)-2-methoxybenzoate (48-2, 375 mg, 1.42 mmol, 100% yield). LC-MS RT: 0.57 min; MS (ESI) m/z=264.1 (M+H)+; Method A which was used without further purification Intermediate 48-3

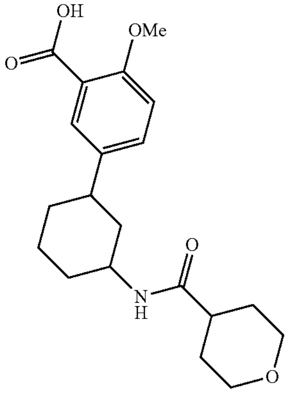 [SMILES: COc1ccc(C2CCCC(NC(=O)C3CCOCC3)C2)cc1C(=O)O]

A solution of 48-2 (120 mg, 0.456 mmol) in DCM (2.2 mL) was treated with Hunig's base (0.08 mL, 0.5 mmol) and tetrahydro-2H-pyran-4-carbonyl chloride (68 mg, 0.45 mmol) and the reaction mixture stirred for 18 h. The reaction mixture was extracted from 0.1 N HCl with DCM. The organic layer was concentrated under reduced pressure and methyl 2-methoxy-5-(3-(tetrahydro-2H-pyran-4-carboxamido)cyclohexyl)benzoate (174 mg, 0.463 mmol, 102% yield) used without further purification.

A solution of methyl 2-methoxy-5-(3-(tetrahydro-2H-pyran-4-carboxamido)cyclohexyl)benzoate (171 mg, 0.455 mmol) in dioxane (1.7 mL)/water (0.35 mL)/MeOH (0.18 mL) was treated with LiOH (96 mg, 2.2 mmol) and the solution heated to 40° C. for 18 h. The reaction mixture was adjusted to pH-1 by the addition of HCl the solution extracted with EtOAc. The organic layer was concentrated under reduced pressure to furnish 2-methoxy-5-(3-(tetrahydro-2H-pyran-4-carboxamido)cyclohexyl)benzoic acid (48-3, 165 mg, 0.455 mmol, 100% yield) which was used without further purification. LC-MS RT: 0.70 min; MS (ESI) m/z=362.1 (M+H)+; Method A.

Examples 48-51 Combining V-2 and 48-3 according to the general procedure used in Example 1 led to 4 diastereomers that were separated according to the following conditions. Instrument: Waters 100 Prep SFC Column: Chiral IC 21×250 mm. 5 micron Mobile Phase: 80% $CO_2$/20% MeOH w/0.1% DEA Flow Conditions: 60 mL/min Detector Wavelength: 220 nm.

Example 48, Peak 1, RT=5.75 min (>95% de, 9.9 mg, 2.9% yield). 1H NMR (500 MHz, DMSO-d6) δ 10.63 (s, 1H), 9.87 (br d, J=7.0 Hz, 1H), 8.30-8.15 (m, 1H), 7.88-7.75 (m, 3H), 7.49 (t, J=9.7 Hz, 1H), 7.35 (dd, J=8.6, 2.1 Hz, 1H), 7.11 (d, J=8.6 Hz, 1H), 5.93 (q, J=7.9 Hz, 1H), 4.51 (br d, J=4.4 Hz, 1H), 4.04-3.94 (m, 4H), 3.87 (br d, J=11.2 Hz, 2H), 3.49-3.45 (m, 1H), 3.37-3.21 (m, 3H), 2.98 (br s, 1H), 2.93-2.84 (m, 1H), 2.05-1.83 (m, 2H), 1.79-1.53 (m, 11H), 1.50-1.34 (m, 4H). LC-MS RT: 2.47 min; MS (ESI) m/z=739.9 (M+H)+; Method C.

Example 49, Peak 2, RT=9.3 min (>95% de, 5.2 mg, 1.5% yield). $^1$H NMR (500 MHZ, DMSO-d6) δ 10.63 (s, 1H), 9.88 (br d, J=7.2 Hz, 1H), 8.23 (br d, J=5.8 Hz, 1H), 7.79 (br d, J=18.3 Hz, 3H), 7.50 (t, J=9.7 Hz, 1H), 7.42-7.32 (m, 1H), 7.11 (d, J=8.6 Hz, 1H), 5.94 (br d, J=7.4 Hz, 1H), 4.64-4.45 (m, 1H), 3.97 (s, 4H), 3.88 (br d, J=10.7 Hz, 2H), 3.47-3.41 (m, 2H), 3.36-3.14 (m, 3H), 2.98 (br s, 1H), 2.87 (br s, 1H), 2.05-1.82 (m, 2H), 1.74-1.52 (m, 11H), 1.49-1.34 (m, 3H). LC-MS RT: 2.44 min; MS (ESI) m/z=740.3 (M+H)+; Method C.

Example 50, Peak 3, RT=11.8 min (>95% de, 13.1 mg, 4.0% yield). 1H NMR (500 MHz, DMSO-d6) δ 10.64 (s, 1H), 9.88 (br d, J=6.5 Hz, 1H), 8.30-8.19 (m, 1H), 7.84-7.74 (m, 3H), 7.50 (br t, J=9.6 Hz, 1H), 7.35 (br d, J=8.3 Hz, 1H), 7.19-7.07 (m, 1H), 5.93 (br d, J=7.9 Hz, 1H), 4.60-4.47 (m, 1H), 4.07-3.95 (m, 4H), 3.87 (br d, J=11.0 Hz, 2H), 3.56-3.42 (m, 3H), 3.37-3.14 (m, 3H), 2.98 (br s, 1H), 2.02-1.80 (m, 3H), 1.75-1.37 (m, 13H). LC-MS RT: 2.44 min; MS (ESI) m/z=740.34 (M+H)+; Method C.

Example 51, Peak 2, RT=12.6 min (>95% de, 3.5 mg, 1.0% yield). 1H NMR (500 MHz, DMSO-d6) δ 10.64 (s, 1H), 9.88 (br d, J=6.9 Hz, 1H), 8.33-8.19 (m, 1H), 7.89-7.70 (m, 3H), 7.50 (br t, J=9.7 Hz, 1H), 7.36 (dd, J=8.5, 2.3 Hz, 1H), 7.11 (d, J=8.5 Hz, 1H), 5.94 (q, J=8.2 Hz, 1H), 4.59-4.39 (m, 1H), 4.05-3.93 (m, 4H), 3.87 (br d, J=10.7 Hz, 2H), 3.56-3.49 (m, 1H), 3.38-3.15 (m, 3H), 3.05-2.83 (m, 2H), 2.04-1.84 (m, 2H), 1.78-1.54 (m, 10H), 1.52-1.32 (m, 5H). LC-MS RT: 2.58 min; MS (ESI) m/z=740.1 (M+H)+; Method C.

Examples 52 & 53

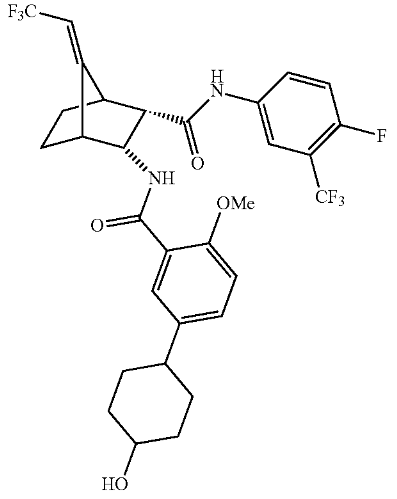

Intermediate 52-1

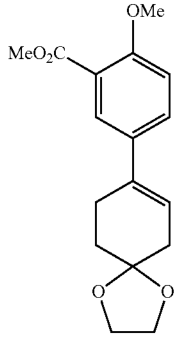

A solution of methyl 5-bromo-2-methoxybenzoate (0.500 g, 2.04 mmol), 4,4,5,5-tetramethyl-2-(1,4-dioxaspiro[4.5]dec-7-en-8-yl)-1,3,2-dioxaborolane (0.543 g, 2.04 mmol) and $PdCl_2$(dppf) (0.030 g, 0.041 mmol) in dioxane (10 mL) was degassed and treated with $Na_2CO_3$ (6.1 mL, 6.1 mmol) solution. The reaction mixture was heated to 80° C. for 18 h. The reaction mixture was extracted from water with EtOAc. The organic layer was concentrated under reduced pressure and the residue purified by silica gel chromatography to furnish methyl 2-methoxy-5-(1,4-dioxaspiro[4.5]dec-7-en-8-yl)benzoate which was used without further purification, (52-1, 374 mg, 1.22 mmol, 60.2% yield). LC-MS RT: 1.11 min; MS (ESI) m/z=305.0 (M+H)+; Method A.

Intermediate 52-2

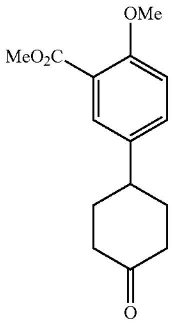 [SMILES: COC(=O)c1cc(C2CCC(=O)CC2)ccc1OC]

A solution of 52-1 (285 mg, 0.936 mmol) in EtOAc (9.4 mL) was treated with Pd—C(100 mg, 0.0940 mmol) and under balloon pressure of Hz. The reaction mixture was filtered through celite and concentrated under reduced pressure to furnish methyl 2-methoxy-5-(1,4-dioxaspiro[4.5]decan-8-yl)benzoate (287 mg, 0.936 mmol, 100% yield) which was used without further purification.

A solution of methyl 2-methoxy-5-(1,4-dioxaspiro[4.5]decan-8-yl)benzoate (287 mg, 0.936 mmol) in MeOH (9.4 mL) was treated with HCl (9.4 mL, 9.4 mmol) and stirred for 18 h. The reaction mixture was concentrated under reduced pressure and purified by silica gel chromatography to furnish methyl 2-methoxy-5-(4-oxocyclohexyl)benzoate which was used without further purification, (52-2, 145 mg, 0.553 mmol, 59.1% yield). LC-MS RT: 0.76 min; MS (ESI) m/z=285.0 (M+H+MeOH)+; Method A.

Intermediate 52-3

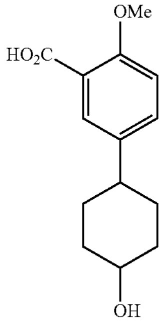 [SMILES: COc1ccc(C2CCC(O)CC2)cc1C(=O)O]

A solution of 52-2 (145 mg, 0.553 mmol) in MeOH (5.5 mL) was treated with sodium borohydride (105 mg, 2.76 mmol) and stirred for 18 h. The reaction mixture was extracted from water with EtOAc. The organic layer was concentrated under reduced pressure and methyl 5-(4-hydroxycyclohexyl)-2-methoxybenzoate used without further purification, (146 mg, 0.553 mmol, 100% yield)

A solution of methyl 5-(4-hydroxycyclohexyl)-2-methoxybenzoate (0.146 g, 0.553 mmol) in THE (2.1 mL)/water (0.42 mL)/MeOH (0.21 mL) was treated with LIOH (0.116 g, 2.77 mmol) and the solution heated to 40° C. for 18 h. The reaction mixture was adjusted to pH −1 by the addition of HCl then the solution extracted with EtOAc. The organic layer was concentrated under reduced pressure and 5-(4-hydroxycyclohexyl)-2-methoxybenzoic acid used without further purification, (0.138 g, 0.553 mmol, 100% yield). LC-MS RT: 0.62 min; MS (ESI) m/z=251.1 (M+H)+; Method A.

Examples 52 & 53 Combining V-2 and 52-3 according to the general procedure used in Example 1 generated 2 diastereomers that were separated via the following method. Instrument: Waters 100 Prep SFC Column: Chiral AD 30×250 mm. 5 micron Mobile Phase: 80% $CO_2$/20% IPA w/0.1% DEA Flow Conditions: 100 mL/min Detector Wavelength: 220.

Example 52, Peak 1, RT=4.95 min (>95% de, 20.2 mg, 11% yield). 1H NMR (500 MHz, DMSO-d6) δ 10.62 (s, 1H), 9.85 (d, J=7.0 Hz, 1H), 8.24 (dd, J=6.4, 2.1 Hz, 1H), 7.78 (br d, J=2.1 Hz, 2H), 7.51 (t, J=9.8 Hz, 1H), 7.36 (dd, J=8.4, 2.3 Hz, 1H), 7.09 (d, J=8.5 Hz, 1H), 5.95 (q, J=7.6 Hz, 1H), 4.61-4.48 (m, 2H), 3.97 (s, 3H), 3.45 (br dd, J=10.2, 6.0 Hz, 1H), 3.30-3.20 (m, 1H), 2.99 (br s, 1H), 2.43 (td, J=11.7, 2.7 Hz, 1H), 2.01 (br t, J=9.3 Hz, 1H), 1.94-1.85 (m, 3H), 1.74 (br d, J=12.5 Hz, 2H), 1.56-1.37 (m, 5H), 1.33-1.22 (m, 2H). LC-MS RT: 2.47 min; MS (ESI) m/z=629.1 (M+H)+; Method C.

Example 53, Peak 2, RT=8.51 min (>95% de, 1.1 mg, 0.5% yield). 1H NMR (500 MHz, DMSO-d6) δ 10.64 (s, 1H), 9.87 (d, J=7.0 Hz, 1H), 8.24 (dd, J=6.1, 1.5 Hz, 1H), 7.90-7.75 (m, 2H), 7.51 (t, J=9.6 Hz, 1H), 7.36 (dd, J=8.5, 2.4 Hz, 1H), 7.10 (d, J=8.5 Hz, 1H), 5.95 (d, J=7.6 Hz, 2H), 4.53 (br dd, J=10.8, 6.6 Hz, 1H), 4.04-3.95 (m, 3H), 3.89 (br s, 1H), 3.23 (br s, 1H), 2.99 (br s, 1H), 2.50-2.44 (m, 1H), 2.07-1.86 (m, 3H), 1.84-1.68 (m, 4H), 1.61-1.42 (m, 6H). LC-MS RT: 2.58 min; MS (ESI) m/z=629.1 (M+H)+; Method C.

Example 55

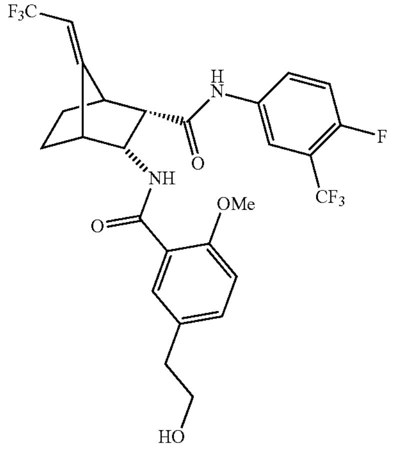

Intermediate 55-1

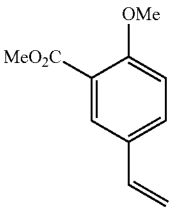

Intermediate 55-1 was prepared according to the same general method employed in 31-1 but substituting vinyl boronic acid and bromobenzoate. (514 mg, 65.5% yield)

Intermediate 55-2

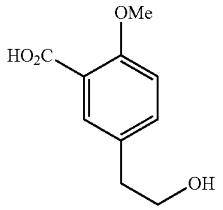 [SMILES: COc1ccc(CCO)cc1C(=O)O]

A solution of 55-1 (150 mg, 0.780 mmol) in THF (3.9 mL) at 0° C. was treated with 9-BBN (1.7 mL, 0.858 mmol) and allowed to warm to rt over 18 h. The reaction mixture was treated with NaOH (31 mg, 0.78 mmol) in MeOH (1 mL) and to this solution was added hydrogen peroxide (0.03 mL, 0.8 mmol). After 1 h, the reaction mixture was extracted from water with EtOAc. The organic layer was concentrated under reduced pressure and the residue purified by silica gel chromatography to furnish methyl 5-(2-hydroxyethyl)-2-methoxybenzoate (60 mg, 0.28 mmol, 36% yield).

A solution of methyl 5-(2-hydroxyethyl)-2-methoxybenzoate (60 mg, 0.28 mmol) in dioxane (1 mL)/water (0.22 mL)/MeOH (0.1 mL) was treated with LiOH (60.0 mg, 1.42 mmol) and the solution heated to 40° C. for 18 h. The reaction mixture was adjusted to pH ~1 by the addition of HCl then the solution extracted with EtOAc. The organic layer was concentrated under reduced pressure to furnish 5-(2-hydroxyethyl)-2-methoxybenzoic acid (55-2, 56.0 mg, 0.285 mmol, 100% yield) which was used without further purification.

Example 55 was prepared from V-2 and 55-2 according to the general procedure used in Example 1 (9.0 mg, 7.0% yield). 1H NMR (500 MHZ, DMSO-d6) δ 10.63 (s, 1H), 9.87 (d, J=7.0 Hz, 1H), 8.28-8.17 (m, 1H), 7.87-7.70 (m, 2H), 7.50 (s, 1H), 7.35 (dd, J=8.4, 1.7 Hz, 1H), 7.09 (d, J=8.5 Hz, 1H), 5.94 (q, J=7.9 Hz, 1H), 4.64 (s, 1H), 4.54-4.48 (m, 1H), 3.97 (s, 3H), 3.62-3.52 (m, 1H), 3.34-3.18 (m, 1H), 2.99 (br s, 1H), 2.69 (t, J=6.9 Hz, 2H), 2.52-2.49 (m, 2H), 2.04-1.80 (m, 2H), 1.49 (br d, J=6.1 Hz, 2H). LC-MS RT: 2.40 min; MS (ESI) m/z=575.3 (M+H)+; Method C.

Examples 57 & 58 (Trans-Isomers)

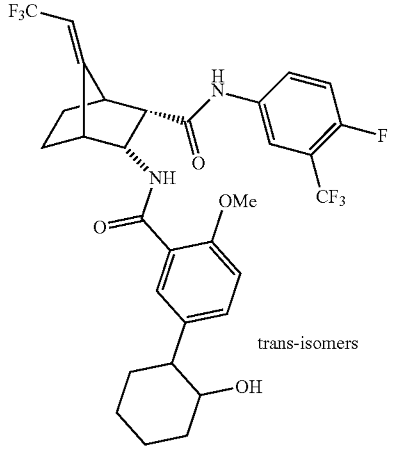 [SMILES: COc1ccc(C2CCCCC2O)cc1C(=O)N[C@@H]1C2CCC(/C2=C/C(F)(F)F)[C@@H]1C(=O)Nc1ccc(F)c(C(F)(F)F)c1]

trans-isomers

Intermediate 57-1

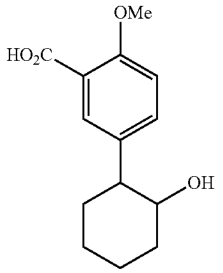 [SMILES: COc1ccc(C2CCCCC2O)cc1C(=O)O]

Intermediate 57-1 was prepared as a racemic mixture of trans-diastereomers according to the procedure outlined for Intermediate 55-2 except substituting the appropriate vinyl boronic acid in the Suzuki reaction. LC-MS RT: 0.71 min; MS (ESI) m/z=251.1 (M+H)+; Method A.

Examples 57 & 58 was prepared from V-2 and 57-1 accoding to the procedure used in Example 1. The diastereomers were separated according to the following conditions: Column: XBridge C18, 200 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 50% B, 50-95% B over 22 minutes, then a 4-minute hold at 100% B; Flow Rate: 20 mL/min; Column Temperature: 25° C.

Example 57, Peak 1 (>95% de, 23 mg, 11% yield). 1H NMR (500 MHz, DMSO-d6) δ 10.63 (s, 1H), 9.85 (dd, J=6.7, 3.4 Hz, 1H), 8.22 (br d, J=6.4 Hz, 1H), 7.83-7.74 (m, 2H), 7.49 (t, J=9.6 Hz, 1H), 7.33 (br d, J=8.2 Hz, 1H), 7.07 (d, J=8.5 Hz, 1H), 5.92 (q, J=7.8 Hz, 1H), 4.52 (br d, J=4.0 Hz, 1H), 4.33 (t, J=6.6 Hz, 1H), 3.96 (s, 3H), 3.58-3.37 (m, 2H), 3.31-3.18 (m, 1H), 2.98 (br s, 1H), 2.31 (br t, J=11.1 Hz, 1H), 2.12-1.84 (m, 3H), 1.79-1.58 (m, 3H), 1.49 (br d, J=6.7 Hz, 2H), 1.40-1.16 (m, 4H). LC-MS RT: 2.59 min; MS (ESI) m/z=629.4 (M+H)+; Method C.

Example 58, Peak 2 (>95% de, 5.6 mg, 2.5% yield), 1H NMR (500 MHz, DMSO-d6) δ 10.71-10.61 (m, 1H), 9.90-9.79 (m, 1H), 8.23 (br d, J=5.4 Hz, 1H), 8.06 (s, 1H), 7.84-7.74 (m, 2H), 7.59 (br d, J=8.9 Hz, 1H), 7.50 (br t, J=9.7 Hz, 1H), 7.11 (br d, J=8.7 Hz, 1H), 5.97-5.83 (m, 1H), 4.57-4.46 (m, 1H), 3.99-3.87 (m, 3H), 3.63-3.46 (m, 2H), 3.31-3.19 (m, 1H), 2.98 (br s, 1H), 2.07-1.83 (m, 3H), 1.78-1.54 (m, 6H), 1.53-1.40 (m, 4H). LC-MS RT: 2.56 min; MS (ESI) m/z=629.3 (M+H)+; Method C.

Example 59 (Cis-Isomers)

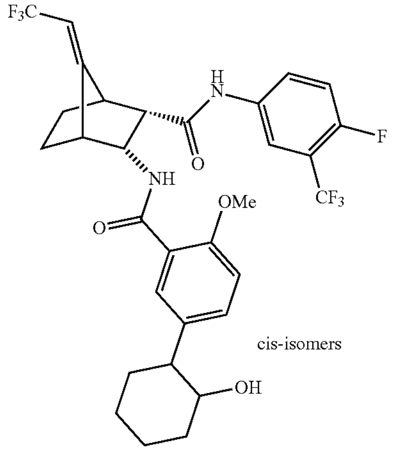 [SMILES: COc1ccc(C2CCCCC2O)cc1C(=O)N[C@@H]1C2CCC(/C2=C/C(F)(F)F)[C@@H]1C(=O)Nc1ccc(F)c(C(F)(F)F)c1]

cis-isomers

A mixture of Example 57 & 58 prior to resolution (110 mg, 0.175 mmol), 4-nitrobenzoic acid (29.2 mg, 0.175 mmol), and $PPh_3$ (55 mg, 0.21 mmol) in THF (1.7 mL) at 0° C. was treated with DIAD (0.04 mL, 0.2 mmol) and allowed to warm to rt overnight. The reaction mixture was extracted from phosphate buffer with EtOAc. The organic layer was concentrated and the residue purified by silica gel chromatography to furnish 2-(3-(((1R,2R,3S,4R,Z)-3-((4-fluoro-3-(trifluoromethyl)phenyl) carbamoyl)-7-(2,2,2-trifluoroethylidene) bicyclo[2.2.1]heptan-2-yl) carbamoyl)-4-methoxyphenyl)cyclohexyl 4-nitrobenzoate which was used without further purification.

A solution of 2-(3-(((1R,2R,3S,4R,Z)-3-((4-fluoro-3-(trifluoromethyl)phenyl) carbamoyl)-7-(2,2,2-trifluoroethylidene) bicyclo[2.2.1]heptan-2-yl) carbamoyl)-4-methoxyphenyl)cyclohexyl 4-nitrobenzoate (170 mg, 0.219 mmol) in MeOH (1.8 mL) was treated with $K_2CO_3$ (30.2 mg, 0.219 mmol) After 1 h, the reaction mixture was extreted from phosphate buffer with EtOAc. The organic layer was concentrated and the residue purified by reverse phase HPLC to furnish (1R,2S,3R,4R,Z)-7-(bromomethylene)-N-(4-fluoro-3-(trifluoromethyl)phenyl)-3-(5-(2-hydroxycyclohexyl)-2-methoxybenzamido) bicyclo[2.2.1]heptane-2-carboxamide as a mixture of cis-isomers (6.5 mg, 5%). $^1$H NMR (500 MHz, DMSO-d6) δ 10.71-10.59 (m, 1H), 9.84 (brt, J=7.3 Hz, 1H), 8.22 (br d, J=4.0 Hz, 1H), 7.85-7.70 (m, 2H), 7.49 (br t, J=9.5 Hz, 1H), 7.37 (br d, J=8.2 Hz, 1H), 7.06 (br d, J=8.6 Hz, 1H), 5.92 (br d, J=8.0 Hz, 1H), 4.57-4.46 (m, 1H), 4.27-4.13 (m, 1H), 3.95 (d, J=2.5 Hz, 3H), 3.80 (br s, 1H), 3.31-3.18 (m, 2H), 3.07-2.94 (m, 2H), 2.03-1.86 (m, 3H), 1.74 (br d, J=11.1 Hz, 2H), 1.67-1.59 (m, 1H), 1.57-1.25 (m, 6H). LC-MS RT: 2.71 min; MS (ESI) m/z=629.0 (M+H)+; Method C.

Examples 62 & 63

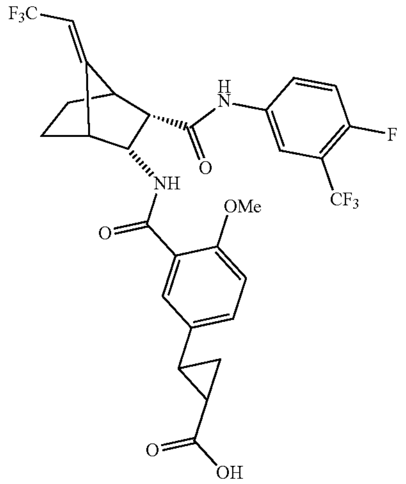 [SMILES: COc1ccc(C2CC2C(=O)O)cc1C(=O)N[C@@H]1C2CCC(/C2=C/C(F)(F)F)[C@@H]1C(=O)Nc1ccc(F)c(C(F)(F)F)c1]

Intermediate 62-1

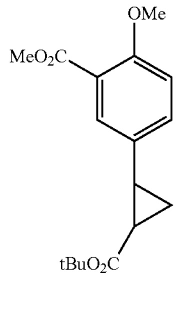 [SMILES: COC(=O)c1cc(C2CC2C(=O)OC(C)(C)C)ccc1OC]

A solution of 55-1 (150 mg, 0.780 mmol) in DCM (3.9 mL) was treated with rhodium (II) acetate dimer (6.9 mg, 0.016 mmol) followed by slow addition of t-Bu-diazoacetate (0.11 mL, 0.78 mmol). The reaction mixture was stirred for 18 h. The reaction mixture was concentrated under reduced pressure and the residue purified by silica gel chrommatography to furnish methyl 5-(2-(tert-butoxycarbonyl)cyclopropyl)-2-methoxybenzoate (61-1, 180 mg, 0.588 mmol, 75% yield). LC-MS RT: 0.85 min; MS (ESI) m/z=250.1 (M+H-tBu)+; Method A.

Intermediate 62-2

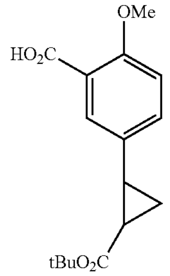 [SMILES: COc1ccc(C2CC2C(=O)OC(C)(C)C)cc1C(=O)O]

Intermediate 62-1 was treated according to the general procedure for 35-1 to furnish acid 62-2. (quantitative) LC-MS RT: 0.85 min; MS (ESI) m/z=237.1 (M+H-tBu)+; Method A.

Examples 62 & 63 was prepared from V-2 and 62-2 according to the general procedure used in Example 1 followed by treatment with TFA/DCM according to the general procedure for Example 9. The diastereomers were separated as follows. Column: XBridge C18, 200 mm×19 mm, 5-μm particles; Mobile Phase A: 5:95 acetonitrile:water with ammonium acetate; Mobile Phase B: 95:5 acetonitrile: water with ammonium acetate; Gradient: a 0-minute hold at 40% B, 40-80% B over 20 minutes, then a 0-minute hold at 100% B; Flow Rate: 20 mL/min; Column Temperature: 25 C.

Example 62, Peak 1 (3.8 mg, 5.2% yield). 1H NMR (500 MHz, DMSO-d6) δ 10.64 (s, 1H), 9.91-9.85 (m, 1H), 8.24-8.18 (m, 1H), 7.83-7.76 (m, 1H), 7.68 (s, 1H), 7.54-7.45 (m, 1H), 7.31 (br d, J=1.8 Hz, 1H), 7.10 (d, J=8.5 Hz, 1H), 5.92 (q, J=8.1 Hz, 1H), 4.57-4.41 (m, 1H), 3.96 (s, 3H), 3.30-3.21 (m, 2H), 3.00-2.96 (m, 1H), 2.42-2.33 (m, 1H), 2.02-1.81 (m, 2H), 1.74-1.67 (m, 1H), 1.53-1.45 (m, 2H), 1.40 (dt, J=9.2, 4.7 Hz, 1H), 1.31-1.24 (m, 1H). LC-MS RT: 2.03 min; MS (ESI) m/z=615.1 (M+H)+; Method C.

Example 63, Peak 2 (2.8 mg, 3.9% yield). 1H NMR (500 MHz, DMSO-d6) δ 10.77-10.65 (m, 1H), 9.88 (dd, J=6.9, 3.8 Hz, 1H), 8.27-8.20 (m, 1H), 7.86-7.71 (m, 2H), 7.48 (t, J=9.6 Hz, 1H), 7.35 (br d, J=8.2 Hz, 1H), 7.05 (d, J=8.9 Hz, 1H), 5.92 (q, J=7.6 Hz, 1H), 4.55-4.43 (m, 1H), 3.96 (s, 3H), 3.31-3.20 (m, 2H), 2.98 (br s, 1H), 2.50-2.44 (m, 1H), 2.06-1.93 (m, 2H), 1.54-1.37 (m, 4H), 1.31-1.15 (m, 1H). LC-MS RT: 2.14 min; MS (ESI) m/z=615.2 (M+H)+; Method C.

Examples 64 & 65

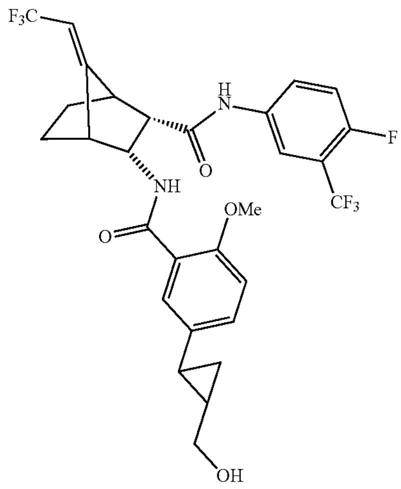 [SMILES: COc1ccc(C2CC2CO)cc1C(=O)N[C@@H]1C2CCC(/C2=C/C(F)(F)F)[C@@H]1C(=O)Nc1ccc(F)c(C(F)(F)F)c1]

Intermediate 64-1

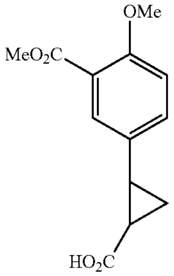 [SMILES: COC(=O)c1cc(C2CC2C(=O)O)ccc1OC]

Intermediate 64-1 was prepared from 62-1 by treatment with TFA/DCM as described by the general method for Example 9. (quantitative yield) LC-MS RT: 0.68 min; MS (ESI) m/z=251.1 (M+H-tBu)+; Method A.

Intermediate 64-2

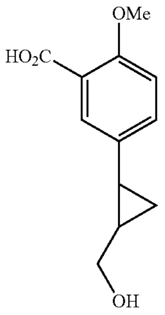 [SMILES: COc1ccc(C2CC2CO)cc1C(=O)O]

A solution of 64-1 (549 mg, 2.19 mmol) in THF (11 mL) was treated with BH3. THF (2.2 mL, 2.2 mmol) and the reaction mixture was allowed to stir for 18 h. The reaction mixture was extracted from 1 M HCl with EtOAc concentrated under reduced pressure and purified by silica gel chromamtography to furnish methyl 5-(2-(hydroxymethyl) cyclopropyl)-2-methoxybenzoate (120 mg, 0.508 mmol, 23.2% yield). A solution of methyl 5-(2-(hydroxymethyl) cyclopropyl)-2-methoxybenzoate (507 mg, 2.14 mmol) in THF (7 mL)/water (1.4 mL) was treated with LiOH (451 mg, 10.7 mmol) and heated at 40° C. for 18 h. The reaction mixture was adjusted to pH 1 by the addition of HCl, and the solution extracted with EtOAc. The organic layer was concentrated under reduced pressure to furnish 5-(2-(hydroxymethyl)cyclopropyl)-2-methoxybenzoic acid (64-2, 477 mg, 2.14 mmol, 100% yield) which was used without further purification.

Examples 64 & 65

Combining V-2 and 64-2 according to the general procedure used in Example 1 yielded diastereomers that were separated according to the following conditions. Waters 100 Prep SFC Chiral AS 30×250 mm. 5 micron, 90% $CO_2$/10% MeOH w/0.1% DEA, 100 mL/min Example 64, Peak 1, RT=3.9 min (6.3 mg, 5.0% yield). $^1$H NMR (500 MHz, DMSO-d6) δ 10.64 (s, 1H), 9.88 (s, 1H), 8.22 (br d, J=6.1 Hz, 1H), 7.82-7.72 (m, 2H), 7.49 (t, J=9.6 Hz, 1H), 7.36 (td, J=8.4, 2.1 Hz, 1H), 7.08 (d, J=8.2 Hz, 1H), 5.93 (d, J=7.9 Hz, 1H), 4.51 (br d, J=3.7 Hz, 1H), 3.97 (d, J=0.9 Hz, 3H), 3.31-3.20 (m, 2H), 3.09-2.91 (m, 3H), 2.15 (br d, J=7.3 Hz, 1H), 2.04-1.81 (m, 3H), 1.49 (br d, J=6.1 Hz, 2H), 1.29 (br d, J=7.0 Hz, 1H), 0.95 (br d, J=4.9 Hz, 1H), 0.71 (q, J=5.4 Hz, 1H). LC-MS RT: 2.26 min; MS (ESI) m/z=601.1 (M+H)+; Method C.

Example 65, Peak 2, RT=6.6 min (10.0 mg, 7.9% yield). 1H NMR (500 MHz, DMSO-d6) δ 10.63 (s, 1H), 9.86 (br d, J=6.7 Hz, 1H), 8.23 (br d, J=4.0 Hz, 1H), 7.84-7.73 (m, 1H), 7.64 (d, J=1.8 Hz, 1H), 7.50 (t, J=9.8 Hz, 1H), 7.29-7.18 (m, 1H), 7.07 (d, J=8.5 Hz, 1H), 6.00-5.90 (m, 1H), 4.60-4.42 (m, 1H), 3.95 (s, 3H), 3.34 (br d, J=5.5 Hz, 1H), 3.30-3.18 (m, 2H), 2.99 (br s, 1H), 2.04-1.82 (m, 3H), 1.82-1.73 (m, 1H), 1.49 (br d, J=7.0 Hz, 2H), 1.19 (br d, J=4.3 Hz, 2H), 0.89-0.75 (m, 2H). LC-MS RT: 2.25 min; MS (ESI) m/z=601.4 (M+H)+; Method C.

Examples 66 & 67

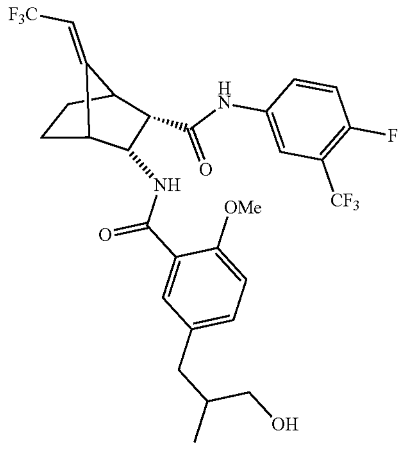 [SMILES: COc1ccc(CC(C)CO)cc1C(=O)N[C@@H]1C2CCC(/C2=C/C(F)(F)F)[C@@H]1C(=O)Nc1ccc(F)c(C(F)(F)F)c1]

Intermediate 66-1

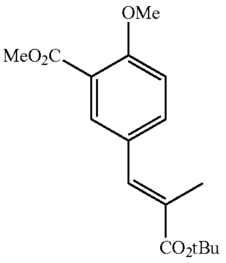 [SMILES: COC(=O)c1cc(/C=C(\C)C(=O)OC(C)(C)C)ccc1OC]

A slurry of methyl 5-bromo-2-methoxybenzoate (0.5 g, 2 mmol), tert-butyl methacrylate (0.435 g, 3.06 mmol), $Pd_2(dba)_3$ (0.047 g, 0.051 mmol), $PtBu_3$ (0.021 g, 0.12 mmol) and TEA (0.43 mL, 3.0 mmol) in dioxane (10.2 mL) was degassed and heated to 100° C. in a sealed vessel. The cooled reaction mixture was extracted from water with EtOAc. The organic layer was concentrated under reduced pressure and the residue purified by silica gel chromatography to furnish methyl (Z)-5-(3-(tert-butoxy)-2-methyl-3-oxoprop-1-en-1-yl)-2-methoxybenzoate (66-1, 0.625 g, 2.040 mmol, 100% yield) LC-MS RT: 1.04 min; MS (ESI) m/z=307.2 (M+H)+; Method A.

Intermediate 66-2

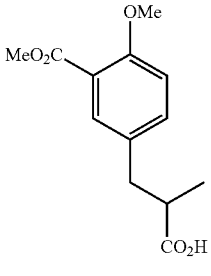

Intermediate 66-1 was converted to 66-2 by employing the same hydrogenation procedure as in 60-1 followed by the same TFA/DCM procedure employed in Example 9. (quantitative yield) LC-MS RT: 0.87 min; Method A.

Intermediate 66-3

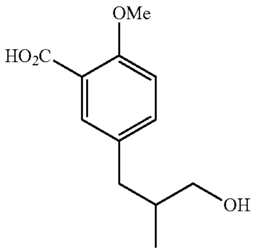 [SMILES: COc1ccc(CC(C)CO)cc1C(=O)O]

Intermediate 66-2 was converted to 66-3 by employing the same reduction and saponification procedures as in 64-1. (quantitative yield) LC-MS RT: 0.64 min; MS (ESI) m/z=225.1 (M+H)+; Method A.

Examples 66 & 67

Combining V-2 and 66-3 according to the general procedure used in Example 1 yielded diastereomers that were separated according to the following conditions. Waters 100 Prep SFC Chiral AD, 30×250 mm. 5 micron, 85% $CO_2$/15% IPA w/0.1% DEA, 100 mL/min. Example 66, Peak 1, RT=7.0 min (7.4 mg, 11% yield). $^1H$ NMR (500 MHz, DMSO-d6) δ 10.66-10.59 (m, 1H), 9.87 (d, J=7.0 Hz, 1H), 8.22 (dd, J=6.4, 2.1 Hz, 1H), 7.83-7.76 (m, 1H), 7.73 (d, J=2.1 Hz, 1H), 7.50 (t. J=9.6 Hz, 1H), 7.30 (dd, J=8.5, 2.1 Hz, 1H), 7.10 (d, J=8.5 Hz, 1H), 5.93 (d, J=7.9 Hz, 1H), 4.57 (t, J=5.2 Hz, 1H), 4.54-4.48 (m, 1H), 3.97 (s, 3H), 3.47 (br s, 1H), 3.24 (dt, J=17.0, 5.4 Hz, 3H), 2.99 (br s, 1H), 2.68 (br dd, J=13.4, 5.8 Hz, 1H), 2.26 (dd, J=13.3, 8.4 Hz, 1H), 2.05-1.85 (m, 2H), 1.73 (br dd, J=13.9, 6.3 Hz, 1H), 1.50 (br d, J=6.4 Hz, 2H), 0.76 (d, J=6.7 Hz, 3H). LC-MS RT: 2.47 min; MS (ESI) m/z=602.9 (M+H)+; Method C.

Example 67, Peak 2, RT=14.4 min (7.8 mg, 12% yield). $^1H$ NMR (500 MHz, DMSO-d6) δ 10.63 (s, 1H), 9.88 (d, J=6.7 Hz, 1H), 8.23 (dd, J=6.1, 2.1 Hz, 1H), 7.81-7.72 (m, 2H), 7.50 (t. J=9.8 Hz, 1H), 7.30 (dd, J=8.4, 2.0 Hz, 1H), 7.10 (d, J=8.2 Hz, 1H), 5.94 (q, J=8.0 Hz, 1H), 4.61-4.48 (m, 2H), 3.97 (s, 3H), 3.46 (br s, 1H), 3.31-3.18 (m, 3H), 2.99 (br s, 1H), 2.69 (dd, J=13.6, 5.6 Hz, 1H), 2.26 (dd, J=13.4, 8.2 Hz, 1H), 2.07-1.85 (m, 2H), 1.80-1.68 (m, 1H), 1.50 (br d, J=6.7 Hz, 2H), 0.76 (d, J=6.7 Hz, 3H). LC-MS RT: 2.47 min; MS (ESI) m/z=603.1 (M+H)+; Method C.

Example 68

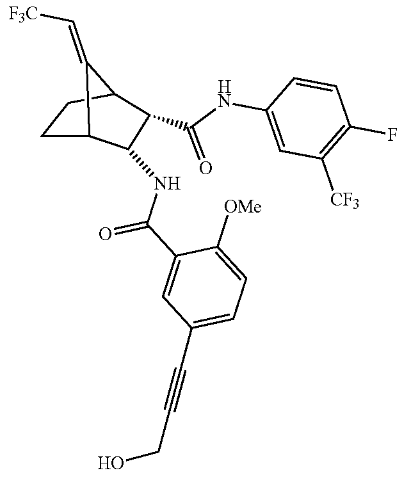 [SMILES: COc1ccc(C#CCO)cc1C(=O)N[C@@H]1C2CCC(/C2=C/C(F)(F)F)[C@@H]1C(=O)Nc1ccc(F)c(C(F)(F)F)c1]

Intermediate 68-1

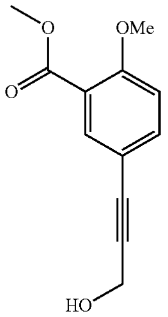 [SMILES: COC(=O)c1cc(C#CCO)ccc1OC]

To methyl 5-bromo-2-methoxybenzoate (3.0 g, 12 mmol) and propargyl alcohol (1.5 mL, 25 mmol) slurried in TEA (31 mL) was added $Pd(PPb_3)_4$ (0.28 g, 0.25 mmol) and CuI (0.023 g, 0.12 mmol). The vessel was sparged with $N_2$ and heated at 80° C. for 16 h. The reaction mixture was partitioned between water with EtOAc and the organic layer was separated and dried over $Na_2SO_4$. The organic layer was decanted and concentrated under vacuum and the residue purified by flash chromatography to furnish methyl 5-(3-hydroxyprop-1-yn-1-yl)-2-methoxybenzoate (68-1, 1.3 g, 6.1 mmol, 50% yield). $^1$H NMR (500 MHz, $CDCl_3$) δ 7.92 (d, J=2.1 Hz, 1H), 7.56 (dd, J=8.7, 2.3 Hz, 1H), 6.95 (d, J=8.7 Hz, 1H), 4.50 (d, J=6.1 Hz, 2H), 3.94 (s, 3H), 3.91 (s, 3H), 1.64 (t, J=6.1 Hz, 1H). MS (ESI) m/z 221.1 (M+H).

Intermediate 68-2

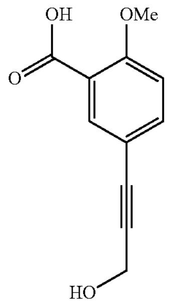 [SMILES: COc1ccc(C#CCO)cc1C(=O)O]

Intermediate 68-2 was prepared from 68-1 according to the saponification procedure employed for 32-2. (quantitative) LC-MS RT: 0.76 min; MS (ESI) m/z=206.8 (M+H)+; Method A.

Example 68 was prepared from V-2 and 68-2 according to the procedure used in Example 1. (27.5 mg, 48% yield) 1H NMR (500 MHz, DMSO-d6) δ 10.64 (s, 1H), 9.93 (d, J=7.0 Hz, 2H), 8.23 (dd, J=6.6, 2.3 Hz, 1H), 7.95 (d, J=2.1 Hz, 1H), 7.82-7.77 (m, 1H), 7.58-7.48 (m, 3H), 7.21 (d, J=8.5 Hz, 1H), 5.31 (t, J=6.0 Hz, 1H), 4.57-4.47 (m, 1H), 4.29 (d, J=5.8 Hz, 2H), 4.03 (s, 3H), 3.24 (br s, 1H), 2.99 (br s, 1H), 2.01-1.87 (m, 2H), 1.59-1.39 (m, 2H). LC-MS RT: 2.33 min; MS (ESI) m/z=585.2 (M+H)+; Method C.

Examples 70-81 (Table 2) were prepared according to the methods described for Examples 68 & 69 substituting the appropriate acetylene, bromobenzoate, isocyanate, and/or norbonryl core as substitution dictates.

Example 82

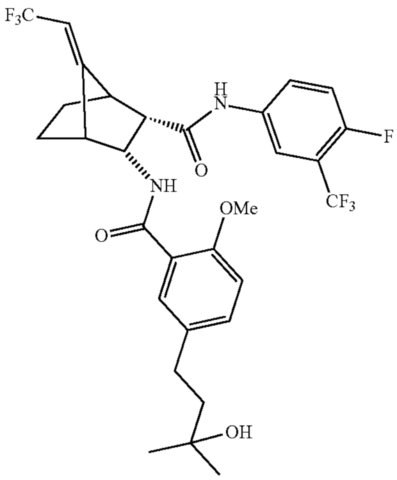 [SMILES: COc1ccc(CCC(C)(C)O)cc1C(=O)N[C@@H]1C2CCC(/C2=C/C(F)(F)F)[C@@H]1C(=O)Nc1ccc(F)c(C(F)(F)F)c1]

Intermediate 82-1

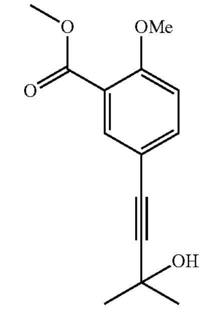 [SMILES: COC(=O)c1cc(C#CC(C)(C)O)ccc1OC]

Intermediate 82-1 was prepared according to the general procedure for 68-1 by substituting propargyl alcohol with gem-dimethyl substituted propargyl alcohol.

Intermediate 82-2

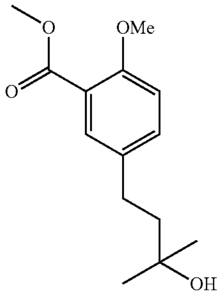 [SMILES: COC(=O)c1cc(CCC(C)(C)O)ccc1OC]

A solution of 82-1 (150 mg, 0.604 mmol) in EtOH (2 mL) was treated with Pd(OH) 2/C (8.5 mg, 0.060 mmol). The slurry under a balloon pressure of $H_2$ was stirred for 18 h. The reaction mixture was filtered through celite and concentrated under reduced pressure to furnish methyl 5-(3-hydroxy-3-methylbutyl)-2-methoxybenzoate (82-2, 152 mg, 0.604 mmol, 100% yield) contaminated with some des-hydroxy material. LC-MS RT: 1.12 min; MS (ESI) m/z=253.0 (M+H)+; Method A.

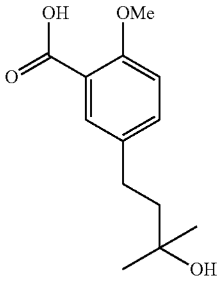 [SMILES: COc1ccc(CCC(C)(C)O)cc1C(=O)O]

Intermediate 82-3

Intermediate 82-3 was prepared from 82-2 according to the saponification procedure employed for 32-2. (quantitative yield) LC-MS RT: 1.12 min; MS (ESI) m/z=220.9 (M+H+$H_2$O)+; Method A.

Example 82 was prepared from V-2 and 82-3 according to the general procedure used in Example 1. (52 mg, 48% yield) $^1$H NMR (500 MHz, DMSO-d6) δ 10.64 (s, 1H), 9.92-9.83 (m, 1H), 8.29-8.20 (m, 1H), 7.83-7.74 (m, 2H), 7.50 (t, J=9.8 Hz, 1H), 7.32 (dd, J=8.5, 2.3 Hz, 1H), 7.08 (d, J=8.5 Hz, 1H), 5.98-5.90 (m, 1H), 4.58-4.46 (m, 1H), 4.28 (s, 1H), 3.96 (s, 3H), 3.22 (br s, 1H), 2.98 (br s, 1H), 2.62-2.56 (m, 3H), 2.04-1.86 (m, 2H), 1.64-1.57 (m, 2H), 1.49 (br d, J=6.0 Hz, 2H), 1.13 (s, 6H). LC-MS RT: 2.54 min; MS (ESI) m/z=616.89 (M+H)+; Method C.

Example 83

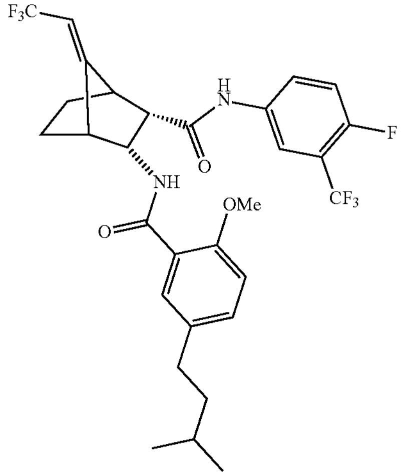 [SMILES: COc1ccc(CCC(C)C)cc1C(=O)N[C@@H]1C2CCC(/C2=C/C(F)(F)F)[C@@H]1C(=O)Nc1ccc(F)c(C(F)(F)F)c1]

Example 83 was isolated as a byproduct in the production of Example 82 owing to over-reduction in the hydrogenation step. (12 mg, 11% yield) 1H NMR (500 MHz, DMSO-d6) δ 10.41 (s, 1H), 9.64 (d, J=7.1 Hz, 1H), 8.01 (br d, J=4.5 Hz, 1H), 7.63-7.48 (m, 2H), 7.27 (t, J=9.7 Hz, 1H), 7.10 (dd, J=8.5, 2.0 Hz, 1H), 6.86 (d, J=8.5 Hz, 1H), 5.71 (q, J=7.9 Hz, 1H), 4.33-4.22 (m, 1H), 3.74 (s, 3H), 3.27-3.15 (m, 3H), 2.99 (br s, 1H), 2.75 (br s, 1H), 1.86-1.58 (m, 2H), 1.33-1.13 (m, 5H), 0.66 (d, J=6.6 Hz, 6H). LC-MS RT: 3.03 min; MS (ESI) m/z=601.1 (M+H)+; Method C.

Examples 84-103 (Table 2) were prepared according to the methods outlined above for Examples 82 & 83 by substituting the appropriate acetylene, bromobenzoate, isocyanate, and/or norbornyl core.

Example 104

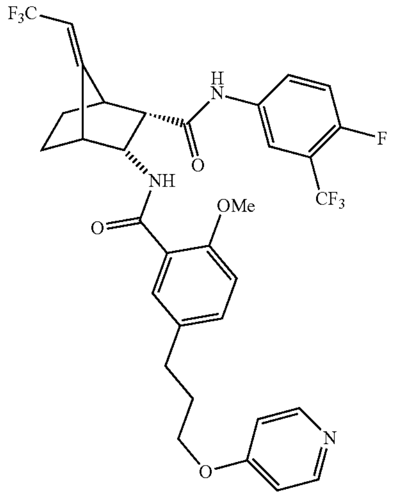

Intermediate 104-1

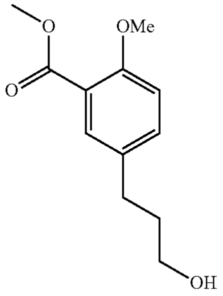 [SMILES: COC(=O)c1cc(CCCO)ccc1OC]

To a solution of 68-1 (1.3 g, 5.9 mmol) dissolved in EtOH (60 mL) was added Pd/C (0.63 g, 5.9 mmol) and submitted to hydrogen at balloon pressure. The reaction mixture was stirred 16 h, filtered over celite and concentrated under vacuum to furnish methyl 5-(3-hydroxypropyl)-2-methoxybenzoate (104-1, 470 mg, 2.1 mmol, 35% yield). MS (ESI) m/z 225.3 (M+H).

Intermediate 104-2

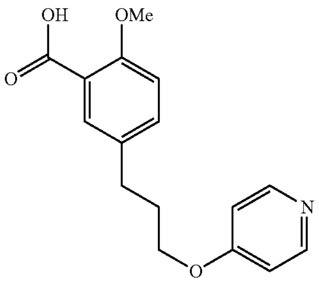 [SMILES: COc1ccc(CCCOc2ccncc2)cc1C(=O)O]

A solution of 104-1 (60 mg, 0.26 mmol) in DMSO (1.3 μl) was treated with NaH (60%, 32 mg, 0.80 mmol) and stirred 30 min. To this solution was added 4-chloropyridine (30 mg, 0.26 mmol) and the reaction mixture was stirred for 18 h then treated with water and LiOH and stirred for an additional 24 h. The reaction mixture was adsorbed on celite and purified by reverse phase chromatography to furnish 2-methoxy-5-(3-(pyridin-4-yloxy) propyl)benzoic acid 104-2 (28 mg, 0.097 mmol, 36. % yield). LC-MS RT: 0.54 min; MS (ESI) m/z=288.0 (M+H)+; Method A.

Example 104 was prepared from V-2 and 104-2 according to the general procedure used in Example 1 (33.8 mg, 40% yield). 1H NMR (500 MHZ, DMSO-d6) δ 10.64 (s, 1H), 9.88 (d, J=6.7 Hz, 1H), 8.24 (dd, J=6.1, 2.4 Hz, 1H), 8.14 (dd, J=4.9, 1.2 Hz, 1H), 7.84-7.76 (m, 2H), 7.74-7.66 (m, 1H), 7.51 (t, J=9.8 Hz, 1H), 7.38 (dd, J=8.5, 2.1 Hz, 1H), 7.12 (d, J=8.5 Hz, 1H), 6.96 (dd, J=6.7, 5.5 Hz, 1H), 6.82 (d, J=8.2 Hz, 1H), 5.95 (d, J=7.6 Hz, 1H), 4.60-4.47 (m, 1H), 4.29-4.17 (m, 2H), 3.98 (s, 3H), 3.24 (br s, 1H), 3.00 (br s, 1H), 2.71 (br t, J=7.6 Hz, 2H), 2.00 (quin, J=7.2 Hz, 4H), 1.90 (br s, 1H), 1.50 (br d, J=7.0 Hz, 2H). LC-MS RT: 2.49 min; MS (ESI) m/z=665.9 (M+H)+; Method C.

Example 105 (Table 2) was prepared according to the procedures described for Example 104 by substituting the appropriate chloroarene in the SNAr step.

Example 106

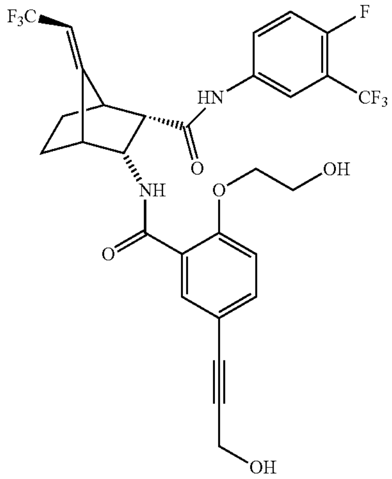

Intermediate 106-1

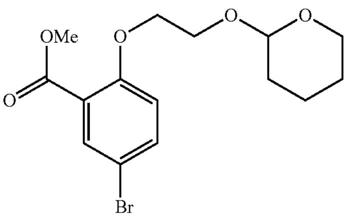 [SMILES: COC(=O)c1cc(Br)ccc1OCCOC1CCCCO1]

To a solution of 2-(2-bromoethoxy)tetrahydro-2H-pyran (1.1 g, 5.2 mmol) dissolved in DMF (14 mL) was added $K_2CO_3$ (0.72 g, 5.2 mmol), methyl 5-bromo-2-hydroxybenzoate (1.0 g, 4.3 mmol), and sodium iodide (0.065 g, 0.43 mmol) and stirred 72 h. The reaction was partitioned between water and EtOAc and the organic layer was separated, dried over $Na_2SO_4$, and the fluid was decanted and concentrated under vacuum. The residue was purified via flash chromatography to furnish methyl 5-bromo-2-(2-((tetrahydro-2H-pyran-2-yl)oxy) ethoxy)benzoate (1.0 g, 2.8 mmol, 64% yield): $^1$H NMR (500 MHz, $CDCl_3$) δ 7.91 (d, J=2.6 Hz, 1H), 7.55 (dd, J=8.9, 2.6 Hz, 1H), 6.94 (d, J=8.9 Hz, 1H), 4.76 (t, J=3.6 Hz, 1H), 4.32-4.18 (m, 2H), 4.08 (dt, J=11.4, 4.7 Hz, 1H), 3.95-3.82 (m, 5H), 3.60-3.49 (m, 1H), 1.92-1.79 (m, 1H), 1.78-1.70 (m, 1H), 1.68-1.49 (m, 4H). MS (ESI) m/z 382.7 (M+Na).

Intermediate 106-2

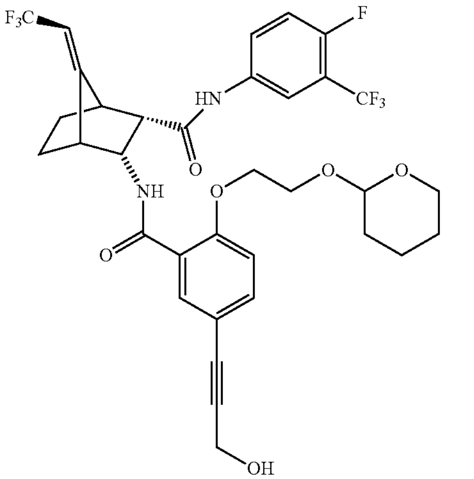

Intermediate 106-2 was prepared from 106-1 using the general procedures described for to Example 68 utilizing propargyl alcohol for the Sonagashira cross coupling to yield (1R,2S,3R,4R,Z)—N-(4-fluoro-3-(trifluoromethyl) phenyl)-3-(5-(3-hydroxyprop-1-yn-1-yl)-2-(2-((tetrahydro-2H-pyran-2-yl)oxy) ethoxy)benzamido)-7-(2,2,2-trifluoroethylidene) bicyclo[2.2.1]heptane-2-carboxamide. (quantitative yield) MS (ESI) m/z 699.3 (M+H).

To a solution 106-2 (75 mg, 0.11 mmol) dissolved in THF (0.6 mL) was added water (0.2 mL) and TFA (0.3 mL). After 1 hour, the reaction mixture was concentrated under reduced pressure and the residue purified via preparative HPLC to furnish (1R,2S,3R,4R,Z)—N-(4-fluoro-3-(trifluoromethyl) phenyl)-3-(2-(2-hydroxyethoxy)-5-(3-hydroxyprop-1-yn-1-yl)benzamido)-7-(2,2,2-trifluoroethylidene) bicyclo[2.2.1] heptane-2-carboxamide, 106 (11 mg, 0.019 mmol, 17% yield): $^{1}$H NMR (500 MHZ, DMSO-$d_6$) δ 10.60 (s, 1H), 9.60 (d, J=7.3 Hz, 1H), 8.07 (dd, J=6.3, 2.3 Hz, 1H), 7.89 (d, J=2.1 Hz, 1H), 7.75 (br dd, J=8.2, 3.4 Hz, 1H), 7.53 (dd, J=8.7, 2.3 Hz, 1H), 7.47 (t, J=9.8 Hz, 1H), 7.24 (d, J=8.9 Hz, 1H), 5.93 (q, J=7.9 Hz, 1H), 5.36 (t, J=6.0 Hz, 1H), 4.90 (t, J=5.6 Hz, 1H), 4.65-4.53 (m, 1H), 4.02-3.81 (m, 2H), 3.25 (dd, J=10.8, 4.1 Hz, 1H), 3.19 (br s, 1H), 2.99 (br s, 1H), 2.11-1.97 (m, 2H), 1.52 (br d, J=8.9 Hz, 2H).

Analytical LC-MS: 1.11 min; MS (ESI) m/z 615.2 (M+H); Method C.

Example 109

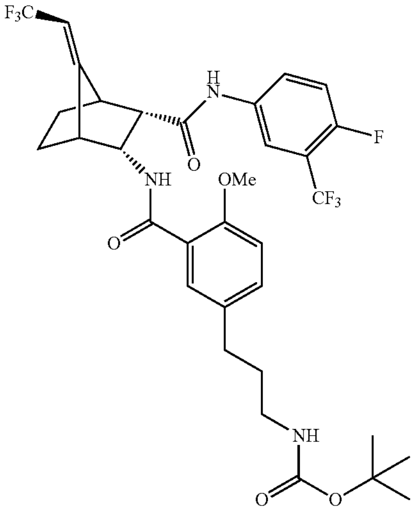

Intermediate 109

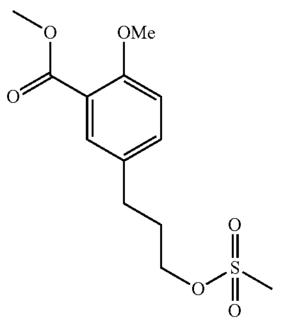 [SMILES: COC(=O)c1cc(CCCOS(C)(=O)=O)ccc1OC]

To a solution of 104-1 (1.0 g, 4.5 mmol) and DIEA (0.94 mL, 5.4 mmol) dissolved in DCM (9 mL) and cooled to 0° C. was added $Ms_2O$ (0.93 g, 5.4 mmol). After 30 min the reaction mixture was diluted with $Et_2O$ and the solution washed with 1 M HCl. The ether layer was washed with water, dried over $Na_2SO_4$, decanted and concentrated under vacuum to furnish methyl 2-methoxy-5-(3-((methylsulfonyl)oxy) propyl)benzoate (109-1, 0.99 g, 3.3 mmol, 73% yield). 1H NMR (500 MHz, $CDCl_3$) δ 7.64 (d, J=2.3 Hz, 1H), 7.36-7.31 (m, 1H), 6.95 (d, J=8.5 Hz, 1H), 4.24 (t, J=6.3 Hz, 2H), 3.96-3.87 (m, 6H), 3.05-3.00 (m, 3H), 2.78-2.68 (m, 2H), 2.15-2.04 (m, 2H). MS (ESI) m/z 303.2 (M+H).

Intermediate 109-2

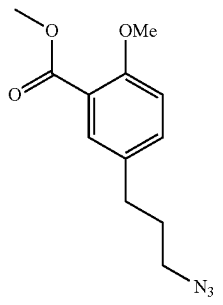 [SMILES: COC(=O)c1cc(CCCN=[N+]=[N-])ccc1OC]

To a solution of 109-1 (0.25 g, 0.66 mmol) dissolved in DMSO (2.2 mL) was added sodium azide (0.13 g, 2.0 mmol) and stirred 16 h at 50° C. The reaction solution was partitioned between EtOAc and water, and the organic phase was separated, washed with water, brine, and dried over $Na_2SO_4$. The flui was decanted and concentrated under vacuum and residue was purified via flash chromatography to furnish methyl 5-(3-azidopropyl)-2-methoxybenzoate (109-2, 0.055 g, 0.22 mmol, 33% yield). 1H NMR (500 MHz, $CDCl_3$) δ 7.64 (d, J=2.4 Hz, 1H), 7.31 (dd, J=8.5, 2.4 Hz, 1H), 6.94 (d, J=8.5 Hz, 1H), 3.92 (s, 3H), 3.91 (s, 3H), 3.31 (t, J=6.8 Hz, 2H), 2.75-2.66 (m, 2H), 1.96-1.88 (m, 2H). MS (ESI) m/z 250.1 (M+H).

Intermediate 109-3

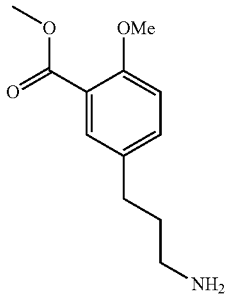 [SMILES: COC(=O)c1cc(CCCN)ccc1OC]

To a solution of 109-2 (0.30 g, 1.2 mmol) dissolved in EtOH (12 mL) was added Pd/C (0.13 g, 1.2 mmol) and the atmosphere was evacuated and replaced with hydrogen at balloon pressure. The reaction solution was filtered and concentrated under vacuum to furnish methyl 5-(3-aminopropyl)-2-methoxybenzoate (109-3, 0.27 g, 1.2 mmol, quantitative yield). $^1$H NMR (500 MHz, $CDCl_3$) δ 7.64 (d, J=2.4 Hz, 1H), 7.31 (dd, J=8.5, 2.4 Hz, 1H), 6.94 (d, J=8.5 Hz, 1H), 3.92 (s, 3H), 3.91 (s, 3H), 3.31 (t, J=6.8 Hz, 2H), 2.75-2.66 (m, 2H), 1.96-1.88 (m, 2H). MS (ESI) m/z 250.1 (M+H).

Intermediate 109-4

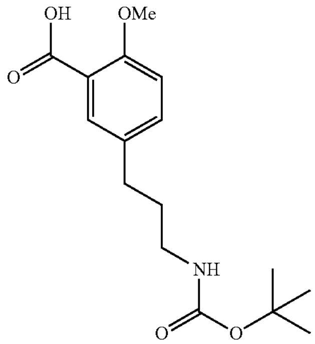 [SMILES: COc1ccc(CCCNC(=O)OC(C)(C)C)cc1C(=O)O]

To a solution of 109-3 (0.20 g, 0.90 mmol) dissolved in 1,4-dioxane (4.5 mL) was added water (4.4 mL), Boc-anhydride (0.21 mL, 0.90 mmol), and NaOH (0.072 g, 1.8 mmol) and stirred 16 h. The reaction mixture was neutralized by the addition of 0.1 M HCl, and the solution extracted with EtOAc. The organic phase was separated, dried over $Na_2SO_4$, decanted and concentrated under vacuum to furnish 5-(3-((tert-butoxycarbonyl) amino) propyl)-2-methoxybenzoic acid (109-4, 0.28 g, 0.90 mmol, 100% yield) as a residue which was used without further purification. MS (ESI) m/z 254.2 (M+H-fBu).

Example 109 was prepared from V-2 and 109-3 according to the general procedure for Example 1. (7.3 mg, 2.4% yield) $^1$H NMR (500 MHz, DMSO-$d_6$) δ 10.64 (s, 1H), 9.85 (br d, J=7.0 Hz, 1H), 8.20 (dd, J=6.6, 2.3 Hz, 1H), 7.84-7.67 (m, 2H), 7.48 (t, J=9.8 Hz, 1H), 7.33 (dd, J=8.5, 2.1 Hz, 1H), 7.09 (d, J=8.5 Hz, 1H), 6.86-6.74 (m, 1H), 5.91 (q, J=7.8 Hz, 1H), 4.58-4.45 (m, 1H), 3.96 (s, 3H), 3.30-3.16 (m, 2H), 2.97 (br s, 1H), 2.94-2.86 (m, 2H), 2.00 (br t, J=9.2 Hz, 1H), 1.90-1.84 (m, 1H), 1.70-1.58 (m, 2H), 1.49 (br d, J=6.7 Hz, 2H), 1.36 (s, 9H). Analytical LC-MS: 2.74 min; MS (ESI) m/z 688.6 (M+H); Method C.

Example 110

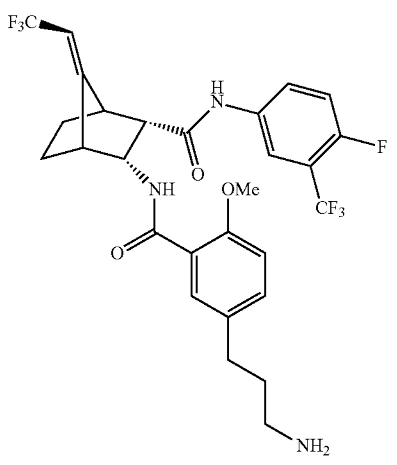

To a solution of Example 109 (0.17 g, 0.24 mmol) dissolved in methanol (2.4 mL) was added 4 N HCl in 1,4-dioxane (0.30 mL, 1.2 mmol) and the reaction mixture stirred for 16 h. The reaction mixture was concentrated under reduced pressure and purified via preparative HPLC to furnish (1R,2S,3R,4R,Z)-3-(5-(3-aminopropyl)-2-methoxybenzamido)-N-(4-fluoro-3-(trifluoromethyl)phenyl)-7-(2,2,2-trifluoroethylidene) bicyclo[2.2.1]heptane-2-carboxamide (0.16 g, 0.25 mmol, 100% yield): $^1H$ NMR (500 MHz, DMSO-$d_6$) δ 9.89 (br d, J=7.0 Hz, 1H), 8.33-8.20 (m, 1H), 7.87-7.72 (m, 2H), 7.51 (t, J=9.6 Hz, 1H), 7.34 (dd, J=8.4, 2.0 Hz, 1H), 7.11 (d, J=8.5 Hz, 1H), 5.94 (q, J=7.6 Hz, 1H), 4.59-4.46 (m, 1H), 3.98 (s, 3H), 3.30 (br dd, J=11.0, 4.3 Hz, 1H), 3.23 (br d, J=0.6 Hz, 1H), 3.00 (br s, 1H), 2.00 (br t, J=9.2 Hz, 1H), 1.89 (br t, J=8.5 Hz, 1H), 1.83 (s, 3H), 1.74-1.61 (m, 2H), 1.57-1.40 (m, 2H). Analytical LC-MS: 1.98 min; MS (ESI) m/z 587.91 (M+H); Method C.

Example 111

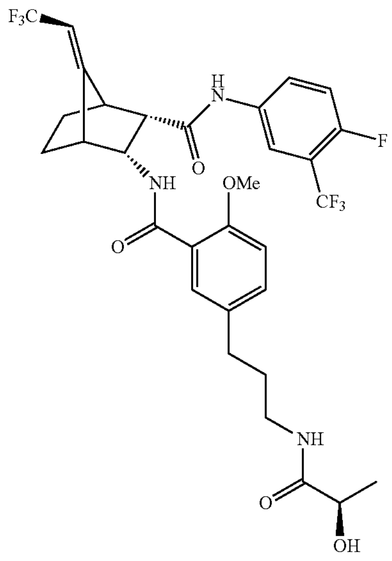

To a mixture of Example 110 (0.020 g, 0.032 mmol), DIEA (0.022 mL, 0.13 mmol), and (R)-2-hydroxypropanoic acid (3 mg, 0.03 mmol) slurried in MeCN (0.3 mL) was added HATU (0.012 g, 0.032 mmol) and the reaction mixture stirred 2 h. The reaction solution was partitioned between EtOAc and pH 7.4 phosphate buffer, and the organic layer was separated, concentrated under vacuum and purified via preparative HPLC to furnish (1R,2S,3R,4R,Z)—N-(4-fluoro-3-(trifluoromethyl)phenyl)-3-(5-(3-((R)-2-hydroxypropanamido) propyl)-2-methoxybenzamido)-7-(2,2,2-trifluoroethylidene) bicyclo[2.2.1]heptane-2-carboxamide (5.0 mg, 24% yield). 1H NMR (500 MHz, DMSO-$d_6$) δ 10.65 (s, 1H), 9.87 (d, J=7.0 Hz, 1H), 8.22 (dd, J=6.6, 2.3 Hz, 1H), 7.85-7.67 (m, 3H), 7.50 (t, J=9.8 Hz, 1H), 7.34 (dd, J=8.5, 2.1 Hz, 1H), 7.10 (d, J=8.5 Hz, 1H), 5.93 (q, J=7.8 Hz, 1H), 4.59-4.45 (m, 1H), 3.97 (s, 3H), 3.32-3.26 (m, 1H), 3.22 (br s, 1H), 3.08 (q, J=6.7 Hz, 2H), 2.98 (br s, 1H), 2.00 (br t, J=9.2 Hz, 1H), 1.92-1.78 (m, 1H), 1.69 (quin, J=7.2 Hz, 2H), 1.56-1.42 (m, 2H), 1.21 (d, J=6.7 Hz, 3H). Analytical LC-MS: 2.41 min; MS (ESI) m/z 660.0 (M+H); Method C.

Examples 112-116 (Table 2) were prepared using the general methods described above for Example 111 using the corresponding commercially available carboxylic acids.

Example 117

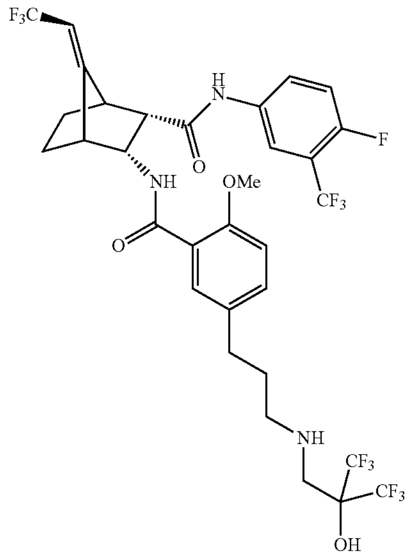

To a mixture of Example 110 (0.020 g, 0.032 mmol) and DIEA (0.017 mL, 0,096 mmol), slurried in MeCN (0.321 mL) was added 2,2-bis(trifluoromethyl) oxirane (4 μL, 0.03 mmol) and stirred 2 h. The reaction solution was concentrated under reduced pressure and purified via preparative HPLC to (1R,2S,3R,4R,Z)—N-(4-fluoro-3-(trifluoromethyl)phenyl)-3-(2-methoxy-5-(3-((3,3,3-trifluoro-2-hydroxy-2-(trifluoromethyl) propyl)amino) propyl)benzamido)-7-(2,2,2-trifluoroethylidene) bicyclo[2.2.1] heptane-2-carboxamide (10 mg, 41% yield). 1H NMR (500 MHz, DMSO-$d_6$) δ 10.64 (s, 1H), 9.85 (d, J=7.3 Hz, 1H), 8.21 (dd, J=6.4, 2.4 Hz, 1H), 7.82-7.72 (m, 2H), 7.49 (t, J=9.8 Hz, 1H), 7.33 (dd, J=8.5, 2.1 Hz, 1H), 7.09 (d, J=8.5 Hz, 1H), 5.92 (q, J=7.8 Hz, 1H), 4.58-4.45 (m, 1H), 3.96 (s, 3H), 3.25 (br dd, J=10.8, 4.1 Hz, 1H), 3.21 (br s, 1H), 2.99 (s, 3H), 2.00 (br t, J=9.5 Hz, 1H), 1.94-1.81 (m, 2H), 1.67 (quin, J=7.3 Hz, 2H), 1.55-1.41 (m, 2H). Analytical LC-MS: 2.06 min; MS (ESI) m/z 786.2 (M+H); Method C.

Examples 118 & 119 were prepared using the general methods described above for Example 117 using the corresponding commercially available expoxides.

Example 120

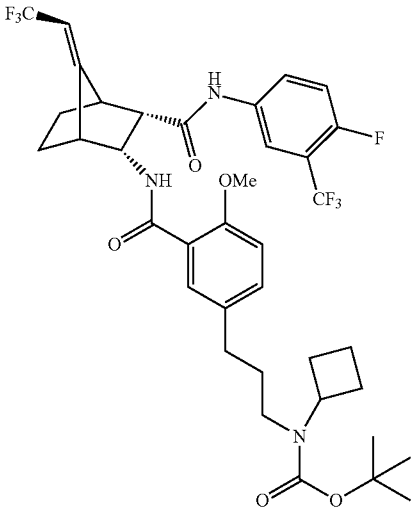

Intermediate 120-1

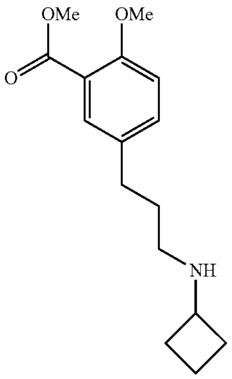 [SMILES: COC(=O)c1cc(CCCNC2CCC2)ccc1OC]

To a solution of 109-1 (0.10 g, 0.33 mmol) dissolved in DMF (1.1 mL) was added cyclobutanamine (0.085 mL, 0.99 mmol) and the reaction mixture stirred at 50° C. for 16 h. The reaction solution was partitioned between EtOAc and water, and the organic layer was separated and concentrated under vacuum to furnish methyl 5-(3-(cyclobutylamino) propyl)-2-methoxybenzoate (120-1, 0.092 g, 0.33 mmol, 100% yield), used directly. MS (ESI) m/z 278.2 (M+H).

Intermediate 120-2

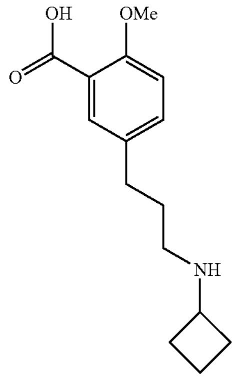 [SMILES: COc1ccc(CCCNC2CCC2)cc1C(=O)O]

To a solution of 120-1 (0.092 g, 0.33 mmol) dissolved in THF (2.7 mL) was added lithium hydroxide monohydrate (0.028 g, 0.66 mmol) and water (0.7 mL) and the reaction mixture stirred for 16 h. The reaction mixture was diluted with water, and neutralized to pH 6 and extracted into EtOAc. The organic layer was dried over $Na_2SO_4$, filtered and concentrated, and 5-(3-(cyclobutylamino) propyl)-2-methoxybenzoic acid (120-2, 0.087 g, 0.33 mmol, 100% yield) was used without further purification. MS (ESI) m/z 264.2 (M+H).

Intermediate 120-3

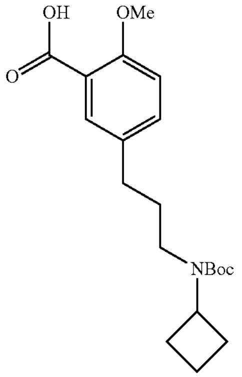 [SMILES: COc1ccc(CCCN(C(=O)OC(C)(C)C)C2CCC2)cc1C(=O)O]

To a solution of 120-2 (0.087 g, 0.33 mmol) dissolved in a mixture of 1,4-dioxane (1.7 mL) and water (1.7 mL) was added sodium hydroxide (0.026 g, 0.66 mmol) followed by Boc-anhydride (0.15 mL, 0.66 mmol) and the reaction mixture stirred for 1 h. The reaction mixture was neutralized with 1M HCl, diluted with EtOAc. The organic layer separated, dried over $Na_2SO_4$, filtered and concentrated under reduced pressure to furnish 5-(3-((tert-butoxycarbonyl) (cyclobutyl)amino) propyl)-2-methoxybenzoic acid (120-3, 60 mg, 0.17 mmol, 50% yield), used directly MS (ESI) m/z 264.1 (M+H-Boc).

Example 120 was prepared from 120-3 according to the general procedures outlined for Example 109 (17.4 mg, 16.4% yield). 1H NMR (500 MHz, DMSO-d6) δ 10.64 (s, 1H), 9.84 (br d, J=6.7 Hz, 1H), 8.28-8.16 (m, 1H), 7.85-7.72 (m, 2H), 7.49 (t, J=9.6 Hz, 1H), 7.34 (dd, J=8.5, 1.8 Hz, 1H), 7.10 (d, J=8.2 Hz, 1H), 5.93 (q, J=7.8 Hz, 1H), 4.59-4.45 (m, 1H), 3.26 (br dd, J=11.0, 4.3 Hz, 1H), 3.22 (br s, 1H), 3.18-3.07 (m, 2H), 2.98 (br s, 1H), 2.08-1.95 (m, 5H), 1.93-1.81 (m, 1H), 1.66 (dt, J=14.8, 7.2 Hz, 2H), 1.60-1.41 (m, 5H), 1.33 (br s, 9H). Analytical LC-MS: 3.07 min; MS (ESI) m/z 742.2 (M+H); Method C.

Example 121 (Table 2) was prepared analogous to Example 120 substituting morpholine in step 120-1. Example 122 was prepared from Example 120 under conditions similar to Example 110.

Example 123

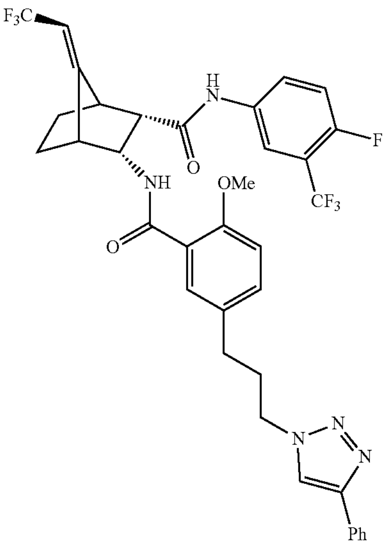

Intermediate 123-1

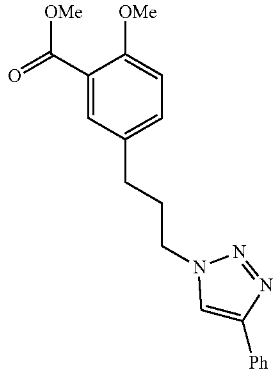 [SMILES: COC(=O)c1cc(CCCn2cc(-c3ccccc3)nn2)ccc1OC]

To a solution of 109-2 (0.050 g, 0.20 mmol), ethynylbenzene (0.041 g, 0.40 mmol) dissolved in DMF (1.5 mL) and water (0.5 ml) was added copper (II) sulfate pentahydrate (0.035 g, 0.14 mmol) and sodium ascorbate (0.040 g, 0.21 mmol) and the reaction mixture stirred for 3 h. The reaction suspension was partitioned between EtOAc and water, and the aqueous layer was washed 2× with EtOAc. The combined organic layers were dried over $Na_2SO_4$. The fluid was decanted and concentrated under vacuum and the residue purified via flash chromatography to furnish methyl 2-methoxy-5-(3-(4-phenyl-1H-1,2,3-triazol-1-yl) propyl) benzoate (52 mg, 0.15 mmol, 74% yield). MS (ESI) m/z 352.3 (M+H).

Example 123 was prepared from 123-1 according to the general procedures employed in Example 109 (27.4 mg, 41.4% yield). 1H NMR (500 MHz, DMSO-d6) δ 10.64 (s, 1H), 9.89 (d, J=7.0 Hz, 1H), 8.58 (s, 1H), 8.24 (dd, J=6.3, 2.3 Hz, 1H), 7.88-7.73 (m, 4H), 7.50 (t, J=9.8 Hz, 1H), 7.45 (t, J=7.6 Hz, 2H), 7.40-7.28 (m, 2H), 7.12 (d, J=8.5 Hz, 1H), 5.94 (q, J=7.8 Hz, 1H), 4.58-4.49 (m, 1H), 4.41 (t, J=7.0 Hz, 2H), 3.97 (s, 3H), 3.28 (br dd, J=11.4, 4.1 Hz, 1H), 3.24 (br s, 1H), 3.04-2.95 (m, 1H), 2.61 (brt, J=7.6 Hz, 2H), 2.23-2.13 (m, 2H), 2.05-1.95 (m, 1H), 1.93-1.84 (m, 1H), 1.57-1.42 (m, 2H). Analytical LC-MS: 2.64 min; MS (ESI) m/z 716.2 (M+H); Method C.

Example 124

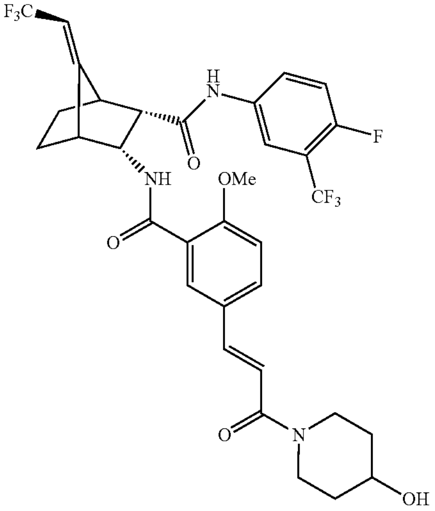

Intermediate 124-1

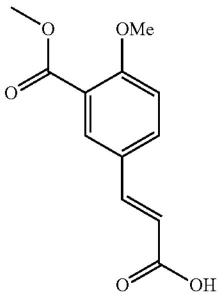 [SMILES: COC(=O)c1cc(/C=C/C(=O)O)ccc1OC]

To a solution of methyl (E)-5-(3-(tert-butoxy)-3-oxoprop-1-en-1-yl)-2-methoxybenzoate (1.2 g, 4.0 mmol) dissolved in DCM (32 mL) was added TFA (8 mL) and the reaction mixture stirred for 16 h. The reaction solution was concentrated under reduced pressure and residual TFA was azeotroped with toluene under vacuum to furnish (E)-3-(4-methoxy-3-(methoxycarbonyl)phenyl) acrylic acid (124-1, 0.99 g, 4.0 mmol, 100% yield). 1H NMR (500 MHz, $CDCl_3$) δ 8.04 (d, J=2.4 Hz, 1H), 7.75 (d, J=16.0 Hz, 1H), 7.68 (dd, J=8.9, 2.3 Hz, 1H), 7.04 (d, J=8.7 Hz, 1H), 6.40 (d, J=16.0 Hz, 1H), 3.98 (s, 3H), 3.94 (s, 3H). MS (ESI) m/z 237.2 (M+H).

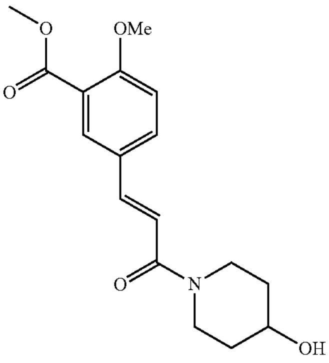 [SMILES: COC(=O)c1cc(/C=C/C(=O)N2CCC(O)CC2)ccc1OC]

Intermediate 124-2

To a solution of 124-1 (0.094 g, 0.40 mmol) dissolved in MeCN (4 mL) was added DIEA (0.21 mL, 1.2 mmol) and piperidin-4-ol (0.041 mg, 0.40 mmol) and HATU (0.15 g, 0.40 mmol) and the reaction mixture stirred for 16 h. The reaction mixture was partitioned between EtOAc and water, and the organic phase was separated and dried over $Na_2SO_4$. The organic layer was decanted, concentrated under vacuum and purified via flash chromatography to furnish methyl (E)-5-(3-(4-hydroxypiperidin-1-yl)-3-oxoprop-1-en-1-yl)-2-methoxybenzoate (124-2, 0.13 g, 0.40 mmol, 100% yield). MS (ESI) m/z 320.4 (M+H).

Intermediate 124-3

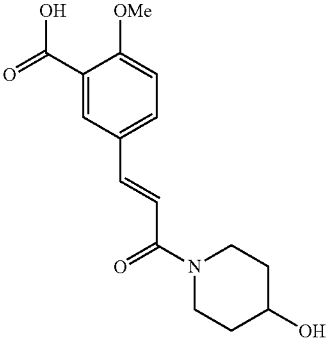 [SMILES: COc1ccc(/C=C/C(=O)N2CCC(O)CC2)cc1C(=O)O]

To a solution of 124-2 (0.060 g, 0.19 mmol) dissolved in THF (0.8 mL) was added Water (0.2 mL) and lithium hydroxide monohydrate (8 mg, 0.2 mmol) and the reaction mixture stirred for 16 h. The reaction solution was diluted with water and carefully neutralized to pH 5 by the addition of 1N HCl and subsequently saturated with NaCl and the solution extracted with EtOAc. The organic layer was separated, dried over $Na_2SO_4$, decanted and concentrated under vacuum to furnish (E)-5-(3-(4-hydroxypiperidin-1-yl)-3-oxoprop-1-en-1-yl)-2-methoxybenzoic acid (124-3, 35 mg, 0.12 mmol, 62% yield). MS (ESI) m/z 306.3 (M+H).

Example 124 was prepared from V-2 and 124-3 according to the general procedures employed in Example 1 (5.1 mg, 11% yield). 1H NMR (500 MHZ, DMSO-d6) δ 10.55 (s, 1H), 9.87 (br d, J=6.7 Hz, 1H), 8.21 (br d, J=4.0 Hz, 1H), 8.16 (s, 1H), 7.87 (br d, J=7.3 Hz, 1H), 7.82-7.72 (m, 1H), 7.54-7.37 (m, 2H), 7.22 (br d, J=8.5 Hz, 1H), 7.14 (br d, J=15.6 Hz, 1H), 4.93 (br d, J=3.7 Hz, 1H), 4.70 (br d, J=9.8 Hz, 1H), 4.51-4.36 (m, 1H), 4.10-3.91 (m, 4H), 3.74 (br d, J=3.7 Hz, 1H), 3.60 (br s, 1H), 3.41-3.26 (m, 1H), 3.16 (br dd, J=10.8, 3.5 Hz, 1H), 3.10 (br s, 2H), 2.72 (br s, 1H), 1.88-1.65 (m. 4H), 1.55-1.20 (m, 5H), 0.81-0.64 (m, 2H), 0.35 (br s, 2H). Analytical LC-MS: 2.27 min; MS (ESI) m/z 656.2 (M+H); Method C.

Examples 125-141 were prepared according to the methods described for example 124, substituting the appropriate, amine and norbornyl core. Hydrogenation of the olefin for examples where relevant was conducted according to the procedure for Example 9.

Example 142

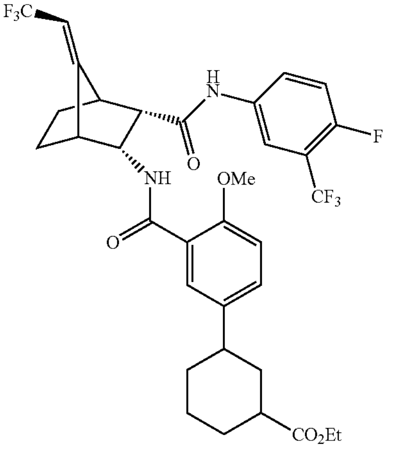

Intermediate 142-1

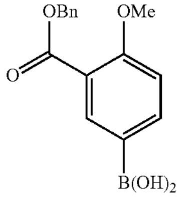 [SMILES: COc1ccc(B(O)O)cc1C(=O)OCc1ccccc1]

A solution of 5-borono-2-methoxybenzoic acid (1.0 g, 5.10 mmol) in DMF (20 mL) was treated with benzyl bromide (0.61 mL, 5.1 mmol) and $K_2CO_3$ (0.705 g, 5.10 mmol) and stirred at rt for 18 h. The reaction mixture was extracted from water with EtOAc. The organic layer was washed with water and brine, concentrated under reduced pressure and the residue purified by silica gel chromatography (DCM/MeOH). Fractions containing product were concentrated under reduced pressure, taken up in EtOAc and the solution washed with 1N HCl. The organic layer was concentrated under reduced pressure to furnish (3-((benzyloxy)carbonyl)-4-methoxyphenyl) boronic acid (142-1, 1104 mg, 3.86 mmol, 76% yield). Analytical LC-MS: 0.94 min; MS (ESI) m/z 243.2 (M+H-$B(OH)_2$); Method A.

Intermediate 142-2

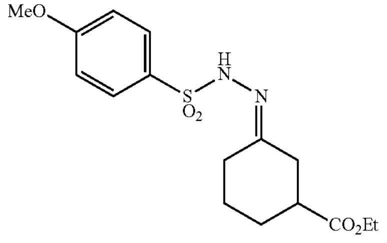 [SMILES: CCOC(=O)C1CCC/C(=N\NS(=O)(=O)c2ccc(OC)cc2)C1]

A slurry of 4-methoxybenzenesulfonohydrazide (594 mg, 2.94 mmol), ethyl 3-oxocyclohexane-1-carboxylate (500 mg, 2.94 mmol) in dioxane (14 mL) was heated at 80° C. and stirred for 18 h. The reaction mixture was concentrated under reduced pressure and the residue purified by silica gel chromatography to furnish ethyl (Z)-3-(2-((4-methoxyphenyl) sulfonyl) hydrazineylidene)cyclohexane-1-carboxylate (142-2, 704 mg, 1.98 mmol, 67.6% yield). Analytical LC-MS: 0.89 min; MS (ESI) m/z 355.1 (M+H); Method A.

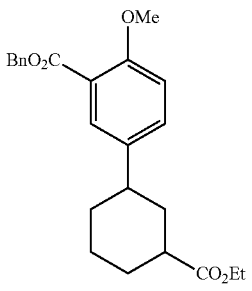

Intermediate 142-3

A slurry of 142-1 (0.424 g, 1.481 mmol), 142-2 (0.350 g, 0.988 mmol), $Cs_2CO_3$ (0.804 g, 2.469 mmol) in dioxane (4.9 mL) was heated at 110° C. for 18 h. The reaction mixture was partitioned between water and EtOAc. The organic layer was concentrated under reduced pressure and the residue purified by silica gel chromatography to furnish benzyl 5-(3-(ethoxycarbonyl)cyclohexyl)-2-methoxybenzoate (142-3, 298 mg, 0.752 mmol, 76% yield). Analytical LC-MS: 1.32 min; MS (ESI) m/z 397.3 (M+H); Method A.

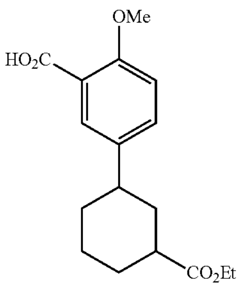 [SMILES: CCOC(=O)C1CCCC(c2ccc(OC)c(C(=O)O)c2)C1]

Intermediate 142-4

A solution of 142-3 (200 mg, 0.504 mmol) in EtOAc (5 mL) was treated with Pd—C(53 mg, 0.050 mmol) and $H_2$ under balloon pressure for 18 h. The reaction mixture was filtered and concentrated under reduced pressure to furnish 5-(3-(ethoxycarbonyl)cyclohexyl)-2-methoxybenzoic acid (142-4, 155 mg, 0.504 mmol, 100% yield). Analytical LC-MS: 1.15 min; MS (ESI) m/z 307.2 (M+H); Method A.

Example 142 was prepared as a mixture of four diastereomers from V-2 and 142-4 according to the general procedures employed in Example 1 (12.9 mg, 36% yield). 1H NMR (500 MHz, DMSO-d6) δ 10.62 (s, 1H), 9.83 (br d, J=7.6 Hz, 1H), 8.21 (br d, J=6.1 Hz, 1H), 7.81-7.71 (m, 2H), 7.49 (br t, J=9.3 Hz, 1H), 7.39-7.30 (m, 1H), 7.10 (d, J=8.5 Hz, 1H), 5.96-5.89 (m, 1H), 4.55-4.48 (m, 1H), 4.16-4.04 (m, 2H), 3.95 (s, 3H), 3.29-3.17 (m, 2H), 2.98 (br s, 1H), 2.71-2.63 (m, 1H), 2.38-2.30 (m, 1H), 2.12-1.94 (m, 3H), 1.88-1.76 (m, 2H), 1.68-1.57 (m, 1H), 1.55-1.37 (m, 6H), 1.20 (q, J=7.1 Hz, 3H). Analytical LC-MS: 2.81 min; MS (ESI) m/z 685.2 (M+H); Method C.

Example 143 (Table 2) was prepared according to the procedures outlined for Example 142 by substituting the appropriate cyclohexanone. Example 144 was prepared from Example 142 through saponification according to the procedure employed for the synthesis of 12-3. Examples 145-148 were prepared according to the procedures outlined for Example 142 starting from the appropriate norbornyl amine, and 3-benzyloxy-cyclobutanone, with the benzyl ether being cleaved during hydrogenation of the ester, and the diastereomers being separable by reverse phase HPLC.

Example 149 & 150

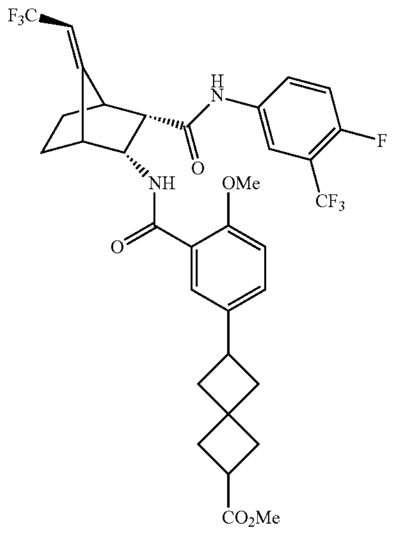

Intermediate 149-1

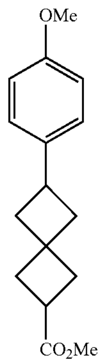

A solution of 6-oxospiro[3.3]heptane-2-carboxylic acid (500 mg, 3.24 mmol) in THF (6.5 mL) at −78° C. was treated with (4-methoxyphenyl) magnesium bromide (7.8 mL 3.89 mmol) and allowed to warm to rt over 18 h. The reaction mixture was extracted from 1 N HCl with EtOAc. The organic layer was concentrated under reduced pressure to furnish 6-hydroxy-6-(4-methoxyphenyl)spiro[3.3]heptane-2-carboxylic acid (851 mg, 3.24 mmol, 100% yield) which was used without further purification.

A solution of 6-hydroxy-6-(4-methoxyphenyl)spiro[3.3]heptane-2-carboxylic acid (0.851 g, 3.24 mmol) in EtOAc (39 mL) was treated with Pd—C(10 wt %, 0.414 g, 3.89 mmol) and $H_2$ (50 psi). The reaction mixture was filtered through celite and concentrated under reduced pressure to furnish 6-(4-methoxyphenyl)spiro[3.3]heptane-2-carboxylic acid (0.848 g, 3.24 mmol, 100% yield) which was used without further purification.

A solution of 6-(4-methoxyphenyl)spiro[3.3]heptane-2-carboxylic acid (848 mg, 3.24 mmol) in MeOH (19 mL) was treated with Ts-OH (37 mg, 0.19 mmol) and heated at 60° C. for 18 h. The reaction mixture was partitioned between EtOAc and phosphate buffer. The organic layer was concentrated under reduced pressure and the residue purified by silica gel chromatography to furnish methyl 6-(4-methoxyphenyl)spiro[3.3]heptane-2-carboxylate (149-1, 406 mg, 1.56 mmol, 40.1% yield). Analytical LC-MS: 1.06 min; MS (ESI) m/z 261.1 (M+H); Method A.

Intermediate 149-2

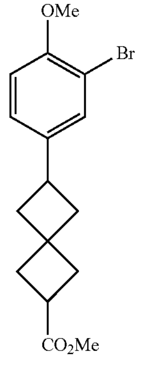 [SMILES: COC(=O)C1CC2(C1)CC(c1ccc(OC)c(Br)c1)C2]

A solution of 149-1 (574 mg, 2.20 mmol) in Acetone (22 mL) was treated with NBS (412 mg, 2.31 mmol) followed by 1 drop of HCl and the reaction mixture was allowed to stir for 18 h. The reaction mixture was concentrated under reduced pressure and the residue purified by silica gel chromatography to furnish methyl 6-(3-bromo-4-methoxyphenyl)spiro[3.3]heptane-2-carboxylate (149-2, 406 mg, 1.19 mmol, 54.3% yield). Analytical LC-MS: 1.10 min; no mol. ion detected. (M+H); Method A.

Intermediate 149-3

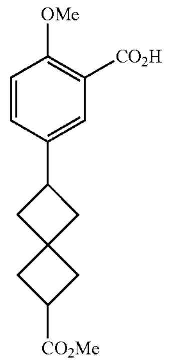 [SMILES: COC(=O)C1CC2(C1)CC(c1ccc(OC)c(C(=O)O)c1)C2]

To a slurry 149-2 (100 mg, 0.295 mmol), $Pd(OAc)_2$ (6.6 mg, 0.029 mmol), 1,3-bis(diphenylphosphino) propane (12 mg, 0.029 mmol), TEA (0.13 mL, 0.88 mmol) in DMF (2.6 mL)/water (0.3 mL) was introduced an atmosphere of CO under 100 psi pressure and the reaction mixture heated at 100° C. for 18 h. The reaction mixture was extracted from 1N HCl with EtOAc. The organic layer was concentrated under reduced pressure and the residue purified by reverse phase chromatography to furnish 2-methoxy~5-(6-(methoxycarbonyl)spiro[3.3]heptan-2-yl)benzoic acid (149-3, 41 mg, 0.15 mmol, 45% yield). Analytical LC-MS: 0.87 min; MS (ESI) m/z 305.1 (M+H); Method A.

Examples 149 & 150

Combining V-2 and 149-3 according to the general procedures employed in Example 1 led to a mixture of 2 diastereomers. The diastereomers were separated according to the following conditions. Instrument: Waters 100 Prep SFC Column: Chiral IC, 21×250 mm. 5 micron Mobile Phase: 90% $CO_2$/10% IPA/0.1% DEA Flow Conditions: 60 mL/min.

Example 149, Peak 1, RT=10.5 min (8.1 mg, 21% yield, >95% de). 1H NMR (500 MHz, DMSO-d6) δ 10.63 (s, 1H), 9.86 (d, J=7.3 Hz, 1H), 8.23 (dd, J=6.4, 2.1 Hz, 1H), 7.85-7.71 (m, 2H), 7.50 (t, J=9.8 Hz, 1H), 7.32 (dd, J=8.5, 2.1 Hz, 1H), 7.09 (d, J=8.5 Hz, 1H), 5.94 (q, J=7.8 Hz, 1H), 4.52 (br dd, J=6.9, 3.2 Hz, 1H), 3.96 (s, 3H), 3.60 (8, 3H), 3.33-3.20 (m, 3H), 3.10-2.92 (m, 2H), 2.48-2.35 (m, 2H), 2.31-2.23 (m, 2H), 2.13 (d, J=8.2 Hz, 2H), 2.07-1.92 (m, 3H), 1.90-1.83 (m, 1H), 1.49 (br d, J=6.7 Hz, 2H). Analytical LC-MS: 2.82 min; MS (ESI) m/z 683.2 (M+H); Method C.

Example 150, Peak 2, RT=13.5 min (8.4 mg, 22% yield, >95% de). $^1$H NMR (500 MHz, DMSO-d6) δ 10.63 (s, 1H), 9.86 (d, J=7.0 Hz, 1H), 8.22 (dd, J=6.3, 2.3 Hz, 1H), 7.83-7.74 (m, 2H), 7.50 (t, J=9.8 Hz, 1H), 7.32 (dd, J=8.5, 2.1 Hz, 1H), 7.09 (d, J=8.5 Hz, 1H), 5.93 (d, J=7.9 Hz, 1H), 4.57-4.46 (m, 1H), 3.96 (s, 3H), 3.60 (s, 3H), 3.36-3.20 (m, 2H), 3.13-2.93 (m, 2H), 2.56 (s, 1H), 2.38 (br d, J=9.2 Hz, 2H), 2.33-2.24 (m, 2H), 2.13 (d, J=8.5 Hz, 2H), 2.07-1.81 (m, 4H), 1.58-1.42 (m, 2H). Analytical LC-MS: 2.82 min; MS (ESI) m/z 683.1 (M+H); Method C.

Examples 151 & 152

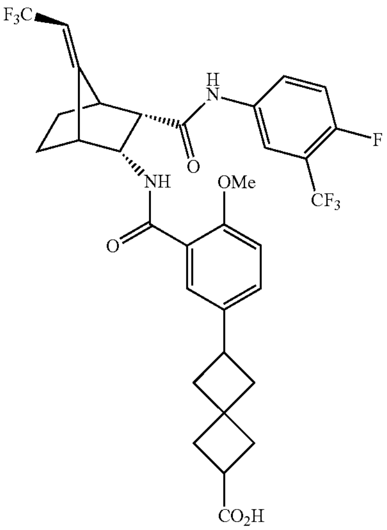

Examples 151 & 152 were prepared from the epimeric mixture of Examples 149 & 150 through saponification according to the general procedure outlined in the preparation of 12-3. The diastereomers were separated according to the following conditions. Column: XBridge C18, 200 mm×19 mm, 5-μm particles; Mobile Phase A: 5:95 acetonitrile:water with 0.05% trifluoroacetic acid; Mobile Phase B: 95:5 acetonitrile:water with 0.05% trifluoroacetic acid; Gradient: a 0-minute hold at 49% B, 49-89% B over 30 minutes, then a 0-minute hold at 100% B; Flow Rate: 20 mL/min; Column Temperature: 25° C.

Example 151, Peak 1 (5.5 mg, 14% yield, >95% de). 1H NMR (500 MHz, DMSO-d6) δ 10.45 (s, 1H), 8.40 (br d, J=6.4 Hz, 1H), 8.12 (dd, J=6.1, 2.1 Hz, 1H), 7.89-7.76 (m, 1H), 7.47 (t, J=9.6 Hz, 1H), 7.42 (d, J=2.1 Hz, 1H), 7.29 (dd, J=8.5, 1.8 Hz, 1H), 7.07 (d, J=8.5 Hz, 1H), 5.74 (q, J=8.1 Hz, 1H), 4.63-4.55 (m, 1H), 3.86 (s, 3H), 3.32 (brt, J=8.5 Hz, 1H), 3.25-3.15 (m, 1H), 2.95 (t, J=8.4 Hz, 1H), 2.78 (br d, J=3.7 Hz, 1H), 2.46-2.40 (m, 1H), 2.36 (br t, J=9.8 Hz, 1H), 2.29-2.21 (m, 2H), 2.15-2.07 (m, 2H), 2.05-1.89 (m, 4H), 1.80-1.65 (m, 2H), 1.62-1.50 (m, 1H). Analytical LC-MS: 2.82 min; MS (ESI) m/z 683.2 (M+H); Metbod C.

Example 152, Peak 2 (7.8 mg, 38% yield, >95% de). 1H NMR (500 MHz, DMSO-d6) 10.64 (s, 1H), 9.86 (br d, J=6.9 Hz, 1H), 8.29-8.17 (m, 1H), 7.83-7.70 (m, 2H), 7.49 (br t, J=9.8 Hz, 1H), 7.31 (br d, J=8.0 Hz, 1H), 7.08 (d, J=8.3 Hz, 1H), 5.92 (q, J=7.5 Hz, 1H), 4.51 (br d, J=5.1 Hz, 1H), 3.95 (s, 3H), 3.69-3.54 (m, 2H), 3.36-3.16 (m, 2H), 3.02-2.91 (m, 2H), 2.46-2.32 (m, 2H), 2.26 (q, J=9.2 Hz, 2H), 2.09 (br d, J=8.4 Hz, 2H), 2.04-1.79 (m, 4H), 1.57-1.41 (m, 2H). Analytical LC-MS: 2.82 min; MS (ESI) m/z 683.1 (M+H); Method C.

Example 153 (Table 2) was prepared as a mixture of diastereomers according to the procedures outlined for Example 149 by employing the known N-Boc spiroheptanone as the starting material. Example 154 was prepared from Example 153 through deprotection according to the procedure employed in Example 110.

Example 155

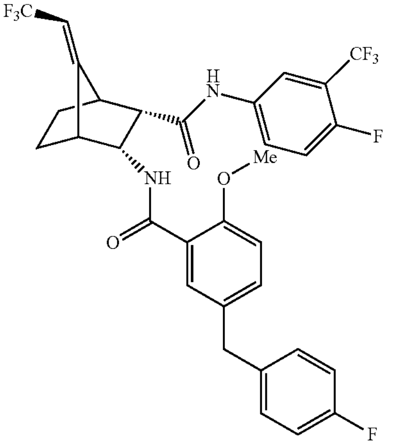

Intermediate 155-1

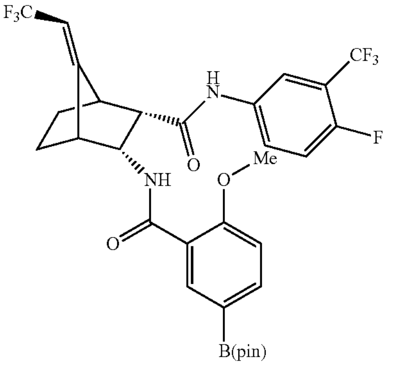

A solution of 5-borono-2-methoxybenzoic acid (0.200 g, 1.02 mmol) in EtOAc (10 ml) was treated with pinacol (0.121 g, 1.02 mmol) and the resulting solution stirred at rt for 18 h. The reaction mixture was concentrated under reduced pressure and the 2-methoxy-5-(4,4,5,5-tetramethyl-1,3,2-dioxaborolan-2-yl)benzoic acid used without further purification (0.284 g, 1.02 mmol, 100% yield), Coupling to intermediate V-2 according to the same general procedure as Example 1 to furnished intermediate 155-1. (424 mg, 58% yield). Analytical LC-MS: 1.23 min; MS (ESI) m/z 657.1 (M+H); Method A.

155-1 (50 mg, 0.076 mmol), 1-(bromomethyl)-4-fluorobenzene (14 mg, 0.076 mmol), $Pd(Ph_3P)_4$ (17 mg, 0.015 mmol) and $K_3PO_4$ (48 mg, 0.22 mmol) were combined and the reaction mixture heated at 110° C. The reaction mixture was allowed to cool to rt, and partitioned between water and EtOAc. The organic layer was concentrated under reduced pressure and the residue purified by silica gel chromatography to furnish (1R,2S,3R,4R,Z)—N-(4-fluoro-3-(trifluoromethyl)phenyl)-3-(5-(4-fluorobenzyl)-2-methoxybenzamido)-7-(2,2,2-trifluoroethylidene) bicyclo[2.2.1]heptane-2-carboxamide (24 mg, 0.039 mmol, 51% yield).

1H NMR (500 MHz, DMSO-d6) δ 10.70-10.59 (m, 1H), 9.95-9.86 (m, 1H), 8.33-8.23 (m, 1H), 7.87-7.75 (m, 2H), 7.60-7.45 (m, 1H), 7.43-7.33 (m, 1H), 7.31-7.22 (m, 2H), 7.18-7.05 (m, 3H), 6.02-5.88 (m, 1H), 4.57-4.46 (m, 1H), 4.04-3.94 (m, 3H), 3.94-3.88 (m, 2H), 3.45-3.36 (m, 1H), 3.22 (br s, 1H), 2.99 (br d, J=0.8 Hz, 1H), 2.07-1.77 (m, 2H), 1.58-1.43 (m, 2H). Analytical LC-MS: 2.80 min; MS (ESI) m/z 638.9 (M+H); Method C.

Example 157

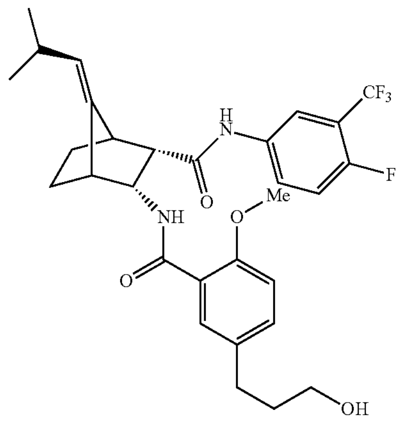

Intermediate 157-1

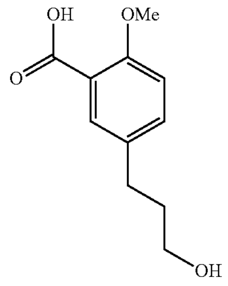 [SMILES: COc1ccc(CCCO)cc1C(=O)O]

Intermediate 157-1 was prepared from 104-1 by saponification according to the conditions described for 12-3. (quantitative yield)

Intermediate 157-2

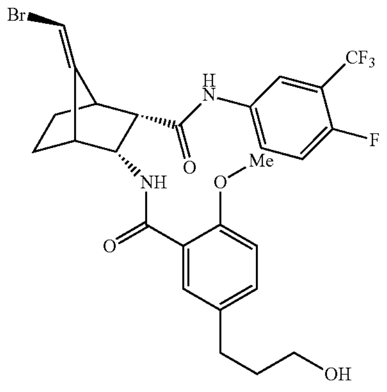

Intermediate 157-2 was prepared from II-5 and 157-1 according to the procedures outlined for Example 1 (202 mg, 63.6% yield). Analytical LC-MS: 1.07 min; MS (ESI) m/z 601.1 (M+H); Method A.

A slurry 157-2 (30 mg, 0.050 mmol), $Na_2CO_3$ (16 mg, 0.15 mmol), (4,4'-di-t-Bu-2,2'-bipyridine)bis[3,5-difluoro-2-[5-trifluoromethyl-2-pyridinyl-$\kappa_N$)phenyl-$\kappa_C$]Ir(III) $PF_6$ (0.51 mg, 0.50 μmol), NiCh-DME (0.55 mg, 2.5 μmol), 4,4'-di-t-Bu-2,2'-bipyridine (0.67 mg, 2.5 μmol), (TMS) 3SiH (0.05 mL, 0.2 mmol) and 2-bromopropane (18 mg, 0.15 mmol) in DME (2.0 mL) was degassed, and under $N_2$, irradiated with blue LED over 96 h. The reaction mixture was diluted with EtOAc, filtered through silica gel and concentrated under reduced pressure and the residue purified by reverse phase HPLC to furnish (1R,2S,3R,4R,Z)—N-(4-fluoro-3-(trifluoromethyl)phenyl)-3-(5-(3-hydroxypropyl)-2-methoxybenzamido)-7-(2-methylpropylidene) bicyclo [2.2.1]heptane-2-carboxamide (9.4 mg, 0.017 mmol, 33% yield). 1H NMR (500 MHz, DMSO-d6) δ 10.50 (s, 1H), 9.78 (d, J=7.3 Hz, 1H), 8.22 (dd, J=6.5, 2.4 Hz, 1H), 7.82-7.71 (m, 2H), 7.47 (t. J=9.8 Hz, 1H), 7.31 (dd, J=8.5, 2.4 Hz, 1H), 7.07 (d, J=8.5 Hz, 1H), 5.10 (d, J=9.0 Hz, 1H), 4.45-4.36 (m, 1H), 3.95 (s, 3H), 3.44 (br d, J=1.7 Hz, 2H), 3.13 (dd, J=10.6, 4.3 Hz, 1H), 2.96 (br s, 1H), 2.68 (br s, 1H), 2.61-2.54 (m, 3H), 2.49-2.44 (m, 1H), 1.96-1.86 (m, 1H), 1.81-1.73 (m, 1H), 1.70-1.61 (m, 2H), 1.38 (br d, J=7.7 Hz, 2H), 1.07-1.01 (m, 3H), 0.98 (d, J=6.6 Hz, 3H). Analytical LC-MS: 2.58 min; MS (ESI) m/z 563.1 (M+H); Method C.

Example 176

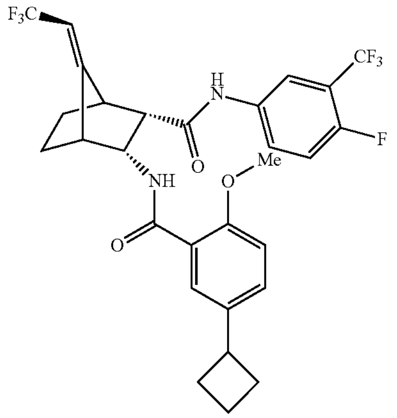

Intermediate 176-1

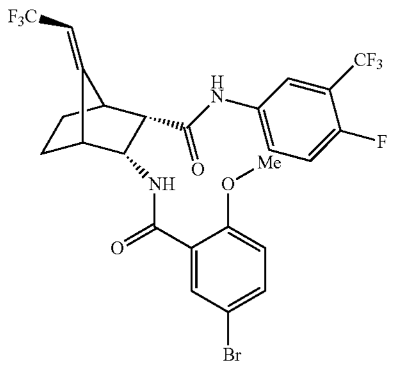

Intermediate 176-1 was prepared from V-2 and 5-bromo-2-methoxy-benzoic acid according to the general procedure described for Example 1 (1.20 g, 85% yield). Analytical LC-MS: 2.78 min; MS (ESI) m/z 609.0 (M+H); Method C.

A slurry 176-1 (25 mg, 0.041 mmol), $Na_2CO_3$ (16 mg, 0.15 mmol), (4,4'-di-t-Bu-2,2'-bipyridine)bis[3,5-difluoro-2-[5-trifluoromethyl-2-pyridinyl-$\kappa_N$)phenyl-$\kappa_C$]Ir(III) $PF_6$ (0.42 mg, 0.41 μmol), $NiCl_2$-DME (0.45 mg, 2.0 μmol), 4,4'-di-t-Bu-2,2'-bipyridine (0.55 mg, 2.0 μmol), (TMS) 3SiH (0.05 mL, 0.20 mmol) and bromocyclobutane (11 mg, 0.082 mmol) in DME (1.6 mL) was degassed, and under $N_2$, irradiated with blue LED over 96 h. The reaction mixture was diluted with EtOAc, filtered through silica gel and concentrated under reduced pressure and the residue purified by reverse phase HPLC to furnish (1R,2S,3R,4R,Z)-3-(5-cyclobutyl-2-methoxybenzamido)-N-(4-fluoro-3-(trifluoromethyl)phenyl)-7-(2,2,2-trifluoroethylidene) bicyclo [2.2.1]heptane-2-carboxamide (2.9 mg, 4.9 μmol, 12% yield). $^1H$ NMR (500 MHz, DMSO-d6) δ 10.63 (s, 1H), 9.86 (br d, J=6.7 Hz, 1H), 8.26-8.17 (m, 1H), 7.79 (br s, 2H), 7.50 (br t, J=9.8 Hz, 1H), 7.35 (br d, J=8.2 Hz, 1H), 7.10 (d, J=8.5 Hz, 1H), 6.00-5.88 (m, 1H), 4.51 (br d, J=5.8 Hz, 1H), 3.96 (s, 3H), 3.23 (br s, 2H), 2.98 (br s, 1H), 2.56-2.53 (m, 1H), 2.31-2.21 (m, 2H), 2.08-1.93 (m, 4H), 1.91-1.73 (m, 2H), 1.57-1.42 (m, 2H). Analytical LC-MS: 2.89 min; MS (ESI) m/z 585.2 (M+H); Method C.

Example 197

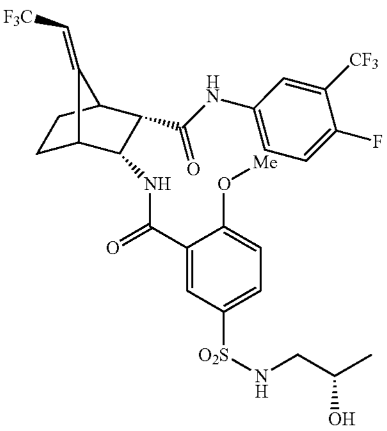

Intermediate XI-2

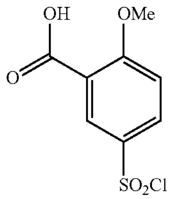 [SMILES: COc1ccc(S(=O)(=O)Cl)cc1C(=O)O]

2-methoxybenzoic acid (XI-1, 1.00 g, 6.57 mmol) was dissolved in chlorosulfonic acid (2.201 ml, 32.90 mmol) at 0° C. The resultant mixture was heated at 50° C. for 1 hour then poured into ice cold water. The precipitate was filtered and used without further purification (quantitative yield). $^1H$ NMR (500 MHz, $CDCl_3$) δ 8.82 (d, J=2.6 Hz, 1H), 8.25 (dd, J=8.9, 2.7 Hz, 1H), 7.31-7.28 (m, 1H), 4.20 (s, 3H).

Intermediate 197-1

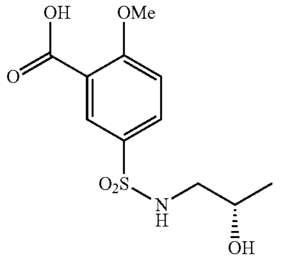 [SMILES: COc1ccc(S(=O)(=O)NC[C@H](C)O)cc1C(=O)O]

To a solution of XI-2 (50 mg, 0.199 mmol) in DCM (2.5 mL) at 0° C. was added(S)-1-aminopropan-2-ol (16.48 mg, 0.219 mmol) followed by TEA (0.11 mL, 0.79 mmol). The reaction mixture was stirred at rt for 1 h, then was extracted with EtOAc from water. The aqueous portion was by acidified and then extracted with EtOAc. The combined organic portion was concentrated under reduced pressure and the residue used without further purification (quantitative yield). MS (ESI) m/z: 290.4 (M+H).

(1R,2S,3R,4R,Z)—N-(4-fluoro-3-(trifluoromethyl)phenyl)-3-(5-(N—((S)-2-hydroxypropyl) sulfamoyl)-2-methoxybenzamido)-7-(2,2,2-trifluoroethylidene) bicyclo [2.2.1]heptane-2-carboxamide, Example 197 was prepared by the general procedures described for Example 1 by employing intermediate 197-1 (8.4 mg, 26% yield). $^1H$ NMR (500 MHz, DMSO-d6) δ 10.68 (s, 1H), 10.02 (d, J=6.8 Hz, 1H), 8.36 (d, J=2.2 Hz, 1H), 8.20 (d, J=6.0 Hz, 1H), 7.90 (dd, J=8.7, 2.4 Hz, 1H), 7.82-7.73 (m, 1H), 7.59-7.45 (m, 2H), 7.38 (d, J=8.8 Hz, 1H), 5.92 (d, J=7.9 Hz, 1H), 4.77-4.70 (m, 1H), 4.55-4.44 (m, 1H), 4.07 (s, 3H), 3.23 (br. s., 2H), 2.98 (br. s., 1H), 2.67-2.57 (m, 3H), 1.97-1.81 (m, 2H), 1.49 (d, J=5.7 Hz, 2H), 0.97 (d, J=6.1 Hz, 3H); LC-MS (M+H)=668.28; HPLC RT=2.24 min; Method B.

In Table 2, where multiple diastereomers are listed, the compounds were separated by preparative reverse phase HPLC according the general conditions previously listed unless otherwise indicated. The isomers are denoted in order of their elution order on said methods (i.e., the first compound eluting is listed as isomer one, the second as isomer 2 and so on.). Where compounds were prepared as a mixture of diastereomers, the variable stereocenter(s) are indicated with a wavy bond.

TABLE 2

| Ex # | Structure | Name | $^1H$ NMR. δ | LC RT (min) | Ion |
|---|---|---|---|---|---|
| 3 | 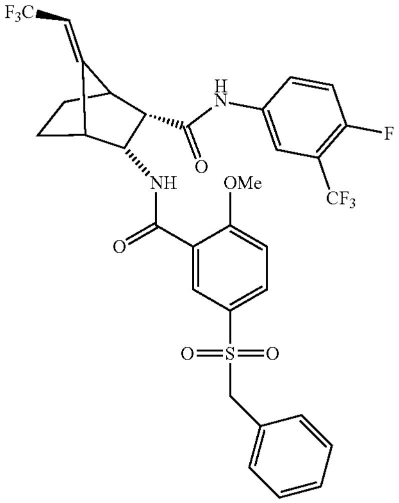 | (2S,3R,7Z)-N-[4-fluoro-3-(trifluoromethyl)phenyl]-3-(2-methoxy-5-phenylmethanesulfonylbenzamido)-7-(2,2,2-trifluoroethylidene)bicyclo[2.2.1]heptane-2-carboxamide | (500 MHz, DMSO-$d_6$) δ 10.51 (s, 1H), 9.82 (br d, J = 6.9 Hz, 1H), 8.16 (br d, J = 5.7 Hz, 1H), 7.98 (d, J = 1.9 Hz, 1H), 7.85-7.72 (m, 1H), 7.65 (dd, J = 8.8, 2.4 Hz, 1H), 7.46 (t, J = 9.7 Hz, 1H), 7.17 (d, J = 8.8 Hz, 1H), 5.89 (q, J = 7.8 Hz, 1H), 4.58-4.45 (m, 1H), 3.99 (s, 3H), 3.49-3.34 (m, 3H), 3.28-3.18 (m, 1H), 2.99 (br s, 1H), 2.57-2.54 (m, 4H), 2.08-1.95 (m, 1H), 1.95-1.83 (m, 1H), 1.50 (br d, J = 6.6 Hz, 2H) | 2.55, C | 685.0 |
| 13 | 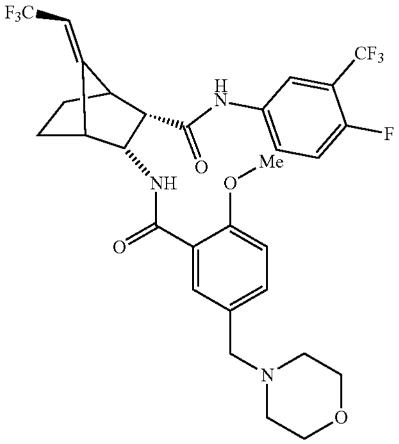 | (2S,3R,7Z)N-[4-fluoro-3-(trifluoromethyl)phenyl]-3-{2-methoxy-5-[(morpholin-4-yl)methyl]benzamido}-7-(2,2,2-trifluoroethylidene)bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 2.35 B | 630.0 |

TABLE 2-continued

| Ex # | Structure | Name | $^1$H NMR. δ | LC RT (min) | Ion |
|---|---|---|---|---|---|
| 15 | 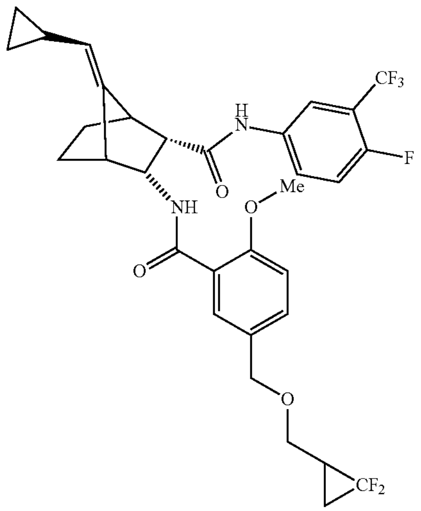 | (2S,3R,7Z)-7-(cyclopropylmethylidene)-3-(5-{[(2,2-difluorocyclopropyl) methoxy]methyl}-2-methoxybenzamido)-N-[4-fluoro-3-(trifluoromethyl)phenyl]bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 2.71 B | 623.3 |
| 16 | 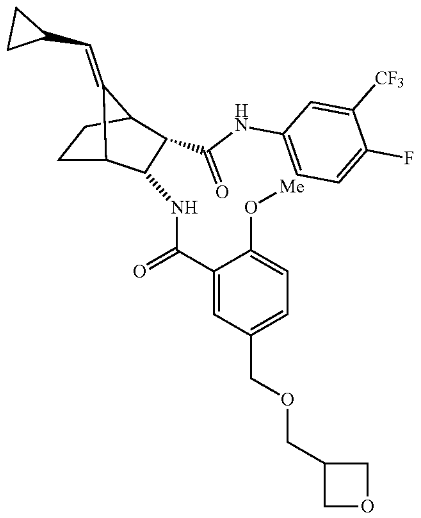 | (2S,3R,7Z)-7-(cyclopropylmethylidene)-N-[4-fluoro-3-(trifluoromethyl)phenyl]-3-(2-methoxy-5-{[(oxetan-3-yl)methoxy]methyl}benzamido)bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 2.64 B | 603.2 |

TABLE 2-continued

| Ex # | Structure | Name | $^1$H NMR. δ | LC RT (min) | Ion |
|---|---|---|---|---|---|
| 17 | 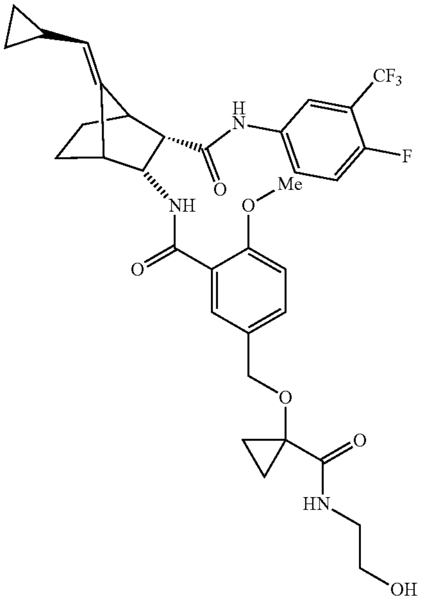 | (2S,3R,7Z)-7-(cyclopropylmethylidene)-N-[4-fluoro-3-(trifluoromethyl)phenyl]-3-[4-({1-[(2-hydroxyethyl)carbamoyl]cyclopropoxy}methyl)-2-methoxybenzamido]bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 2.36 B | 660.1 |
| 18 | 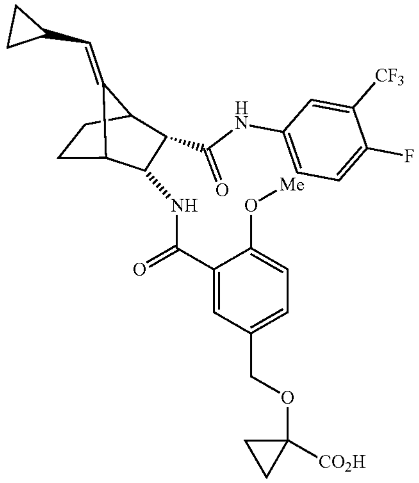 | 1-[(3-{[(2R,3S,7Z)-7-(cyclopropylmethylidene)-3-{[4-fluoro-3-(trifluoromethyl)phenyl]carbamoyl}bicyclo[2.2.1]heptan-2-yl]carbamoyl}-4-methoxyphenyl)methoxy]cyclopropane-1-carboxylic acid | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 2.03 B | 617.1 |
| 19 | 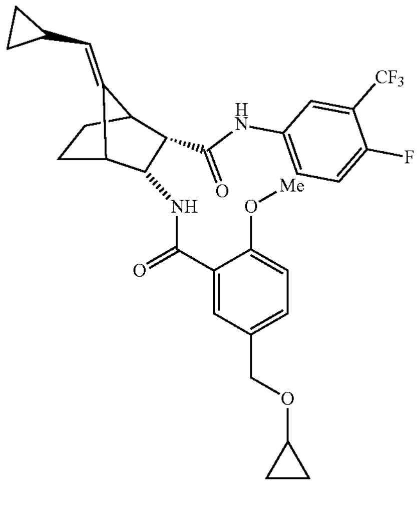 | (2S,3R,7Z)-3-[5-(cyclopropoxymethyl)-2-methoxybenzamido]-7-(cyclopropylmethylidene)-N-[4-fluoro-3-(trifluoromethyl)phenyl]bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 2.72 B | 573.3 |

TABLE 2-continued

| Ex # | Structure | Name | $^1H$ NMR. δ | LC RT (min) | Ion |
|---|---|---|---|---|---|
| 20 | 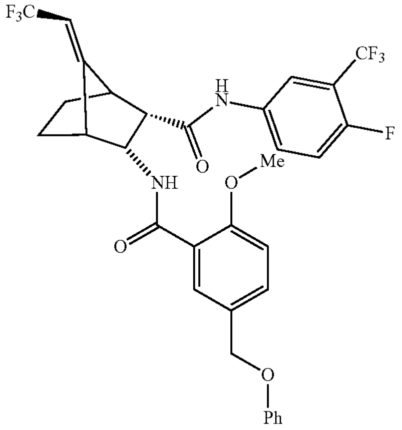 | (2S,3R,7Z)-N-[4-fluoro-3-(trifluoromethyl)phenyl]-3-[2-methoxy-5-(phenoxymethyl)benzamido]-7-(2,2,2-trifluoroethylidene)bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 2.72 B | 637.3 |
| 21 | 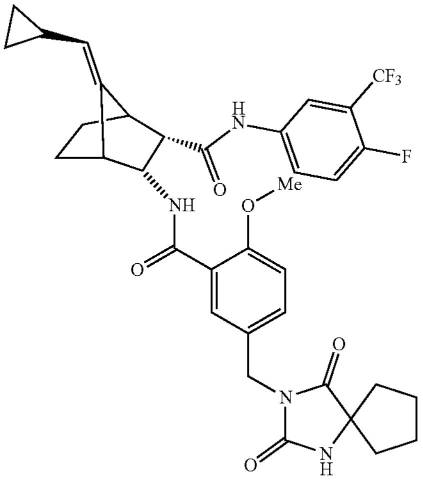 | (2S,3R,7Z)-7-(cyclopropylmethylidene)-3-[5-({2,4-dioxo-1,3-diazaspiro[4.4]nonan-3-yl}methyl)-2-methoxybenzamido]-N-[4-fluoro-3-(trifluoromethyl)phenyl]bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 2.52 B | 669.2 |
| 22 | 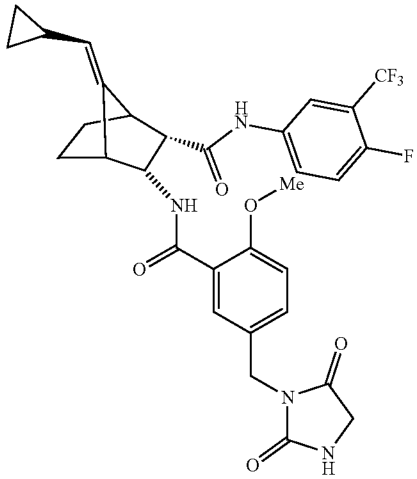 | (2S,3R,7Z)-7-(cyclopropylmethylidene)-3-{5-[(2,5-dioxoimidazolidin-1-yl)methyl]-2-methoxybenzamido}-N-[4-fluoro-3-(trifluoromethyl)phenyl]bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 2.29 B | 615.1 |

TABLE 2-continued

| Ex # | Structure | Name | $^1$H NMR. δ | LC RT (min) | Ion |
|---|---|---|---|---|---|
| 23 | 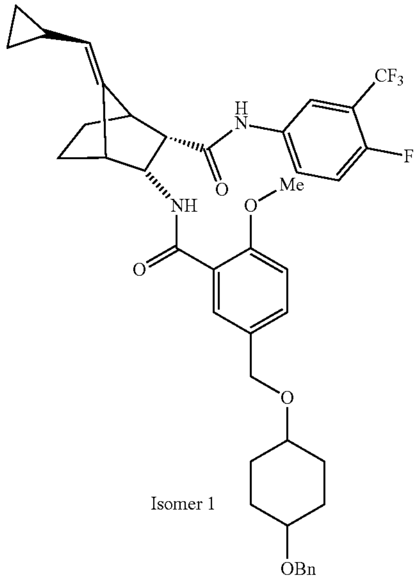 Isomer 1 | (2S,3R,7Z)-3-[5-({[4-(benzyloxy)cyclohexyl]oxy}methyl)-2-methoxybenzamido]-7-(cyclopropylmethylidene)-N-[4-fluoro-3-(trifluoromethyl)phenyl]bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 3.00 B | 721.0 |
| 24 | 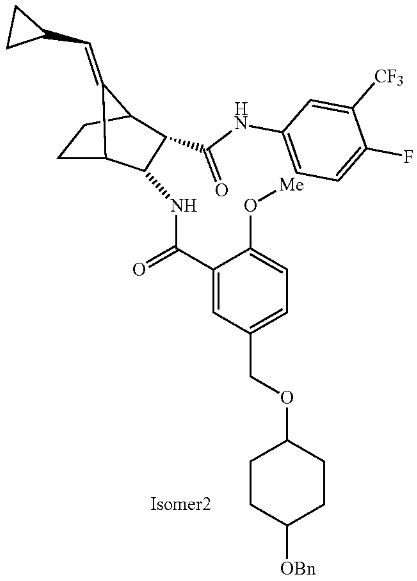 Isomer2 | (2S,3R,7Z)-3-[5-({[4-(benzyloxy)cyclohexyl]oxy}methyl)-2-methoxybenzamido]-7-(cyclopropylmethylidene)-N-[4-fluoro-3-(trifluoromethyl)phenyl]bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 3.00 B | 721.0 |
| 25 | 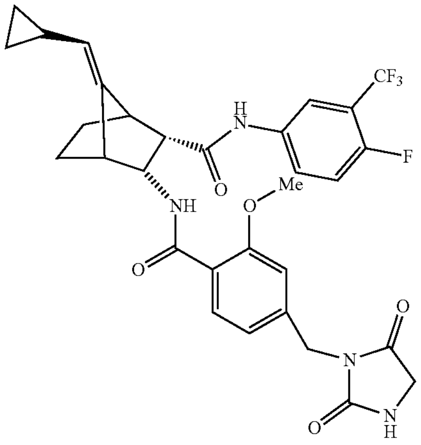 | (2S,3R,7Z)-7-(cyclopropylmethylidene)-3-{4-[(2,5-dioxoimidazolidin-1-yl)methyl]-2-methoxybenzamido}-N-[4-fluoro-3-(trifluoromethyl)phenyl]bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02- | 2.22 B | 615.0 |

TABLE 2-continued

| Ex # | Structure | Name | $^1$H NMR. δ | LC RT (min) | Ion |
| --- | --- | --- | --- | --- | --- |
| | | | 1.80 (m, 3H), 1.48 (d, J = 6.7 Hz, 2H) | | |
| 26 | 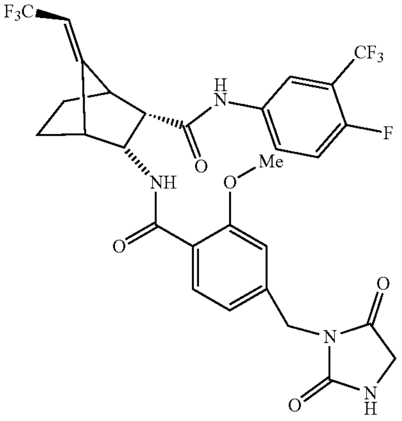 | (2S,3R,7Z)-3-{4-[(2,5-dioxoimidazolidin-1-yl)methyl]-2-methoxybenzamido}-N-[4-fluoro-3-(trifluoromethyl)phenyl]-7-(2,2,2-trifluoroethylidene)bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 2.15 B | 643.3 |
| 27 | 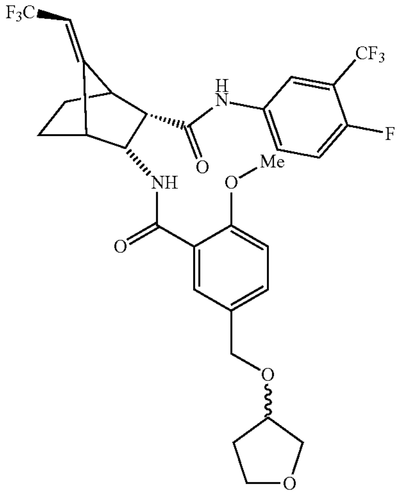 | (2S,3R,7Z)-N-[4-fluoro-3-(trifluoromethyl)phenyl]-3-{2-methoxy-5-[(oxolan-3-yloxy)methyl]benzamido}-7-(2,2,2-trifluoroethylidene)bicyclo[2.2.1]heptane-2-carboxamide | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 3.67 B | 631.2 |

TABLE 2-continued

| Ex # | Structure | Name | $^1$H NMR. δ | LC RT (min) | Ion |
|---|---|---|---|---|---|
| 28 | 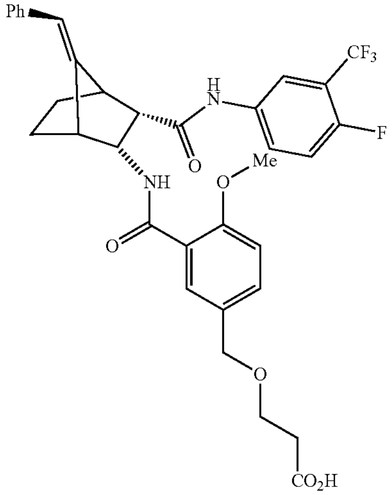 | 3-[(3-{[(2R,3S,7Z)-3-{[4-fluoro-3-(trifluoromethyl)phenyl]carbamoyl}-7-(phenylmethylidene) bicyclo[2.2.1]heptan-2-yl]carbamoyl}-4-methoxyphenyl)methoxy]propanoic acid | (500 MHz, DMSO-d6) 10.70 (s, 1H), 9.97 (d, J = 7.0 Hz, 1H), 8.23 (d, J = Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 1.19 B | 623.3 |
| 29 | 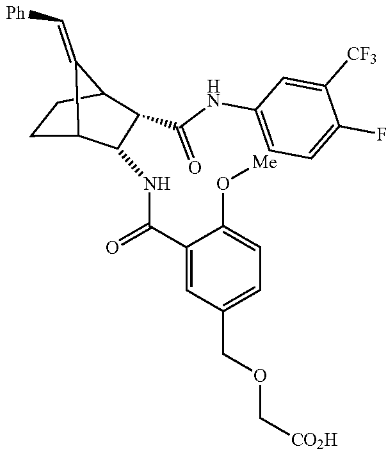 | 2-[(3-{[(2R,3S,7Z)-3-{[4-fluoro-3-(trifluoromethyl)phenyl]carbamoyl}-7-(phenylmethylidene) bicyclo[2.2.1]heptan-2-yl]carbamoyl}-4-methoxyphenyl)methoxy]acetic acid | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 1.19 A | 627.3 |
| 30 | 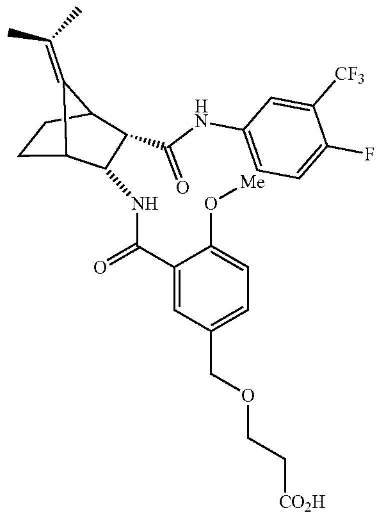 | 3-[(3-{[(2R,3S)-3-{[4-fluoro-3-(trifluoromethyl)phenyl]carbamoyl}-7-(propan-2-ylidene)bicyclo[2.2.1] heptan-2-yl]carbamoyl}-4-methoxyphenyl)methoxy]propanoic acid | (500 MHz, DMSO-d6) 10.70 (s, 1H), 9.97 (d, J = 7.0 Hz, 1H), 8.23 (d, J = 4.3 Hz, 1H), 8.11 (s, 1H), 7.78 (d, J = 8.2 Hz, 1H), 7.62 (d, J = 8.5 Hz, 1H), 7.54-7.45 (m, 1H), 7.32-7.23 (m, 2H), 7.19-7.03 (m, 1H), 5.93 (d, J = 7.9 Hz, 1H), 4.52 (br. s., 1H), 4.30 (br. s., 2H), 4.03 (s, 3H), 3.42 (br. s., 1H), 2.8-3.3 (m, 5H), 2.02-1.80 (m, 3H), 1.48 (d, J = 6.7 Hz, 2H) | 1.14 A | 593.3 |

TABLE 2-continued

| Ex # | Structure | Name | $^1$H NMR. δ | LC RT (min) | Ion |
|---|---|---|---|---|---|
| 47 | 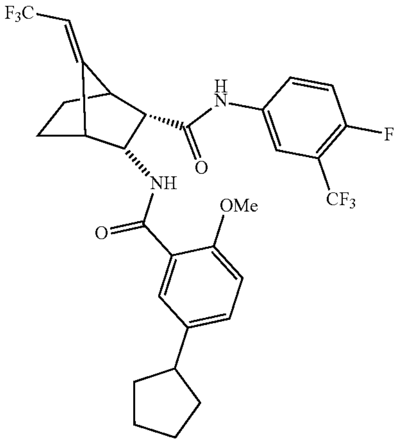 [SMILES: COc1ccc(C2CCCC2)cc1C(=O)N[C@@H]1C2CCC(/C2=C/C(F)(F)F)[C@@H]1C(=O)Nc1ccc(F)c(C(F)(F)F)c1] | (2S,3R,7Z)-3-(5-cyclopentyl-2-methoxybenzamido)-N-[4-fluoro-3-(trifluoroemthyl)phenyl]-7-(2,2,2-trifluoroethylidene) bicyclo[2.2.1]heptane-2-carboxamide | (500 MHz, DMSO-d6) δ 10.62 (s, 1H), 9.86 (d, J = 7.0 Hz, 1H), 8.24 (dd, J = 6.4, 2.4 Hz, 1H), 7.84-7.74 (m, 2H), 7.50 (s, 1H), 7.37 (dd, J = 8.5, 2.4 Hz, 1H), 7.09 (d, J = 8.5 Hz, 1H), 5.94 (d J = 7.9 Hz, 1H), 4.61-4.46 (m, 1H), 3.97 (s, 3H), 3.23 (m, 2H), 3.03-2.92 (m, 2H), 2.06-1.95 (m, 3H), 1.93-1.84 (m, 1H), 1.80-1.72 (m, 2H), 1.64 (br dd, J = 7.3, 4.9 Hz, 2H), 1.53-1.41 (m, 4H) | 2.92 | 599.3 |
| 54 | 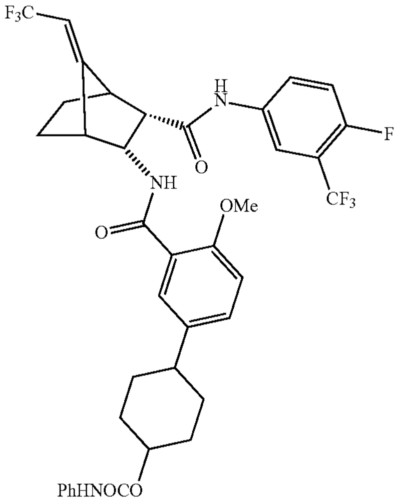 | 4-(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)cyclohexyl N-phenylcarbamate | (500 MHz, DMSO-d6) δ 10.63 (s, 1H), 9.85 (s, 1H), 9.58 (s, 1H), 8.23 (dd, J = 6.3, 2.3 Hz, 1H), 7.85-7.76 (m, 2H), 7.55-7.46 (m, 3H), 7.41 (dd, J = 8.5, 2.1 Hz, 1H), 7.27 (t, J = 7.9 Hz, 2H), 7.11 (d, J = 8.5 Hz, 1H), 7.01-6.93 (m, 1H), 5.94 (q, J = 7.9 Hz, 1H), 4.75-4.64 (m, 1H), 4.54 (br t, J = 4.0 Hz, 1H), 3.97 (s, 3H), 3.23 (br s, 1H), 2.99 (br s, 1H), 2.60-2.56 (m, 2H), 2.17-2.07 (m, 2H), 2.01 (br t, J = 9.6 Hz, 1H), 1.92-1.79 (m, 3H), 1.64-1.48 (m, 6H) | 2.78 | 748.3 |

TABLE 2-continued

| Ex # | Structure | Name | $^1$H NMR. δ | LC RT (min) | Ion |
|---|---|---|---|---|---|
| 56 | 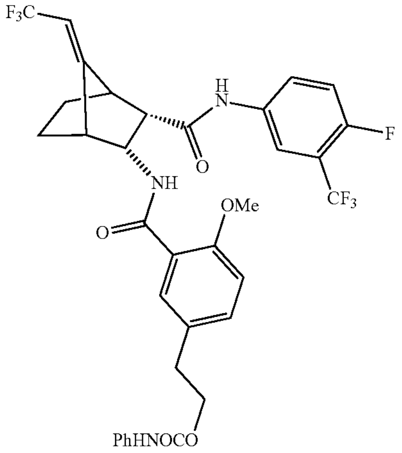 | 2-(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)ethyl N-phenylcarbamate | (500 MHz, DMSO-d6) δ 10.68-10.60 (m, 1H), 9.88 (d, J = 7.0 Hz, 1H), 9.57 (br s, 1H), 8.23 (dd, J = 6.0, 2.3 Hz, 1H), 7.86 (d, J = 2.1 Hz, 1H), 7.81-7.74 (m, 1H), 7.54-7.37 (m, 4H), 7.25 (t, J = 7.8 Hz, 2H), 7.14 (d, J = 8.5 Hz, 1H), 7.01-6.95 (m, 1H), 5.93 (d, J = 7.9 Hz, 1H), 4.58-4.48 (m, 1H), 4.27 (t, J = 6.7 Hz, 2H), 3.98 (s, 3H), 3.31-3.17 (m, 2H), 3.06-2.88 (m, 3H), 2.03-1.84 (m, 2H), 1.49 (br d, J = 7.0 Hz, 2H) | 2.67 | 694.3 |
| 60 | 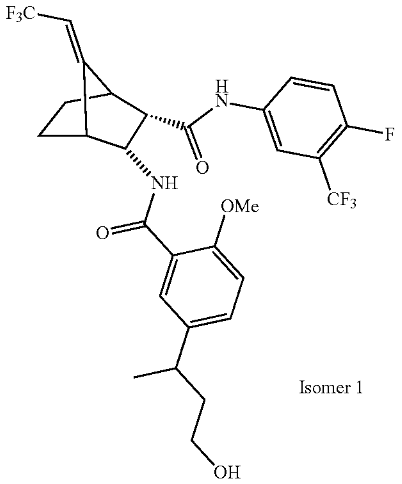 [SMILES: COc1ccc(C(C)CCO)cc1C(=O)N[C@@H]1C2CCC(/C2=C/C(F)(F)F)[C@@H]1C(=O)Nc1ccc(F)c(C(F)(F)F)c1] Isomer 1<br>Waters 100 Prep SFC Chiral IC, 21 × 250 mm. 5 micron, 90% $CO_2$/10% IPA w/0.1% DEA, 60 mL/min, Peak 1, RT = 5.4 min | (2S,3R,7Z)-N-[4-fluoro-3-(trifluoromethyl)phenyl]-3-[5-(4-hydroxybutan-2-yl)-2-methoxybenzamido]-7-(2,2,2-trifluoroethylidene)bicyclo[2.2.1]heptane-2-carboxamide | (500 MHz, DMSO-d6) δ 10.63 (s, 1H), 9.89 (br d, J = 7.0 Hz, 1H), 8.24 (dd, J = 6.4, 2.1 Hz, 1H), 7.84-7.73 (m, 2H), 7.50 (br t, J = 9.6 Hz, 1H), 7.35 (dd, J = 8.5, 2.1 Hz, 1H), 7.11 (d, J = 8.5 Hz, 1H), 5.94 (br d, J = 7.6 Hz, 1H), 4.61-4.49 (m, 1H), 4.41 (t, J = 5.0 Hz, 1H), 3.98 (s, 3H), 3.33-3.23 (m, 2H), 3.18 (d, J = 5.2 Hz, 1H), 2.99 (br s, 1H), 2.83 (br d, J = 7.0 Hz, 1H), 2.51-2.49 (m, 1H), 2.05-1.83 (m, 2H), 1.66 (br dd, J = 6.4, 4.0 Hz, 2H), 1.50 (br d, J = 6.4 Hz, 2H), 1.16 (d, J = 6.7 Hz, 3H) | 2.59 | 603.2 |

TABLE 2-continued

| Ex # | Structure | Name | $^1$H NMR. δ | LC RT (min) | Ion |
|---|---|---|---|---|---|
| 61 | 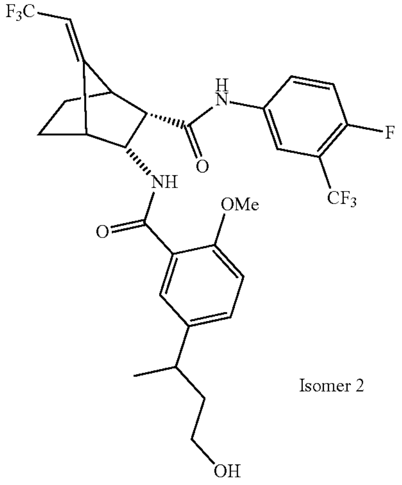 [SMILES: COc1ccc(C(C)CCO)cc1C(=O)N[C@@H]1C2CCC(/C2=C/C(F)(F)F)[C@@H]1C(=O)Nc1ccc(F)c(C(F)(F)F)c1] Isomer 2 Waters 100 Prep SFC Chiral IC, 21 × 250 mm. 5 micron, 90% $CO_2$/10% IPA w/0.1% DEA, 60 mL/min, Peak 2, RT = 7.2 min | (2S,3R,7Z)-N-[4-fluoro-3-(trifluoromethyl)phenyl]-3-[5-(4-hydroxybutan-2-yl)-2-methoxybenzamido]-7-(2,2,2-trifluoroethylidene)bicyclo[2.2.1]heptane-2-carboxamide | (500 MHz, DMSO-d6) δ 10.63 (s, 1H), 9.93-9.82 (m, 1H), 8.24 (dd, J = 6.4, 2.4 Hz, 1H), 7.85-7.72 (m, 2H), 7.51 (t, J = 9.8 Hz, 1H), 7.35 (dd, J = 8.5, 2.4 Hz, 1H), 7.11 (d, J = 8.5 Hz, 1H), 5.94 (q, J = 7.8 Hz, 1H), 4.58-4.50 (m, 1H), 4.41 (t, J = 5.0 Hz, 1H), 3.98 (s, 3H), 3.32-3.22 (m, 3H), 3.19 (d, J = 5.2 Hz, 1H), 2.99 (br s, 1H), 2.88-2.78 (m, 1H), 2.07-1.84 (m, 2H), 1.74-1.62 (m, 2H), 1.50 (br d, J = 7.0 Hz, 2H), 1.16 (d, J = 6.7 Hz, 3H) | 2.49 | 603.2 |
| 69 | 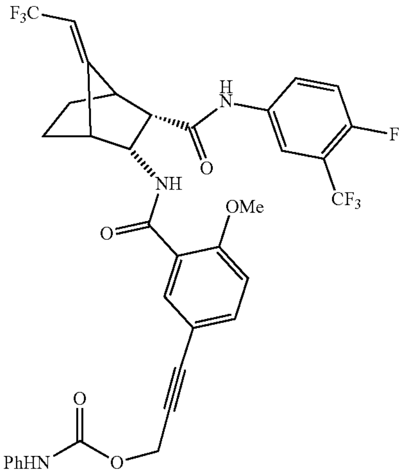 | 3-(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)prop-2-yn-1-yl N-phenylcarbamate | (500 MHz, DMSO-d6) δ 10.64 (s, 1H), 9.99-9.81 (m, 2H), 8.22 (dd, J = 6.4, 2.4 Hz, 1H), 7.99 (d, J = 2.1 Hz, 1H), 7.84-7.74 (m, 1H), 7.62 (dd, J = 8.5, 2.1 Hz, 1H), 7.53-7.44 (m, 3H), 7.37-7.19 (m, 3H), 7.02 (t, J = 7.3 Hz, 1H), 5.95 (d, J = 7.9 Hz, 1H), 5.01 (s, 2H), 4.57-4.40 (m, 1H), 4.04 (s, 3H), 3.33-3.19 (m, 2H), 2.99 (br s, 1H), 2.03-1.83 (m, 1H), 1.50 (br d, J = 6.4 Hz, 2H) | 2.67 | 704.2 |

TABLE 2-continued

| Ex # | Structure | Name | $^1$H NMR. δ | LC RT (min) | Ion |
|---|---|---|---|---|---|
| 70 | 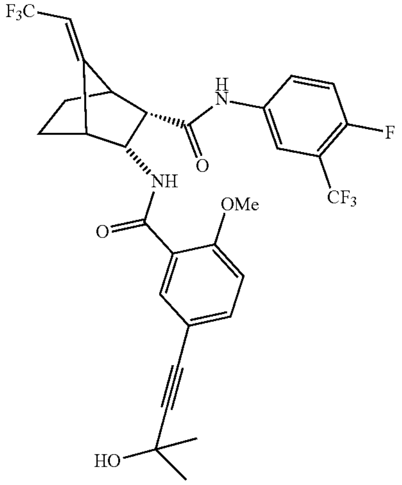 [SMILES: COc1ccc(C#CC(C)(C)O)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-[5-(3-hydroxy-3-methylbut-1-yn-1-yl)-2-methoxybenzamido]-7-(2,2,2-trifluoroethylidene)bicyclo[2.2.1]heptane-2-carboxamide | (500 MHz, DMSO-d6) 10.66 (s, 1H), 9.93 (br d, J = 7.0 Hz, 1H), 8.30-8.17 (m, 1H), 7.93 (d, J = 2.4 Hz, 1H), 7.84-7.77 (m, 1H), 7.57-7.44 (m, 2H), 7.20 (d, J = 8.5 Hz, 1H), 5.95 (q, J = 7.8 Hz, 1H), 4.60-4.47 (m, 1H), 4.03 (s, 3H), 3.42-3.34 (m, 1H), 3.30-3.18 (m, 2H), 3.00 (br d, J = 6.1 Hz, 1H), 2.05-1.80 (m, 2H), 1.61-1.40 (m, 8H) | 2.59 | 613.3 |
| 71 | 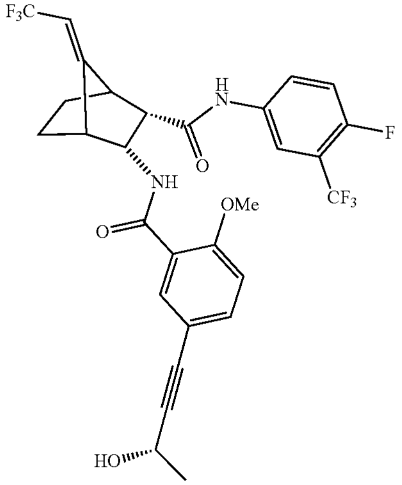 [SMILES: COc1ccc(C#C[C@H](C)O)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{5-[(3S)-3-hydroxybut-1-yn-1-yl]-2-methoxybenzamido}-7-(2,2,2-trifluoroethylidene)bicyclo[2.2.1]heptane-2-carboxamide | (500 MHz, DMSO-d6) 10.71-10.61 (m, 1H), 9.92 (d, J = 7.0 Hz, 1H), 8.22 (dd, J = 6.4, 2.4 Hz, 1H), 7.94 (d, J = 2.1 Hz, 1H), 7.85-7.75 (m, 1H), 7.59-7.46 (m, 2H), 7.20 (d, J = 8.9 Hz, 1H), 5.94 (d, J = 7.6 Hz, 1H), 4.63-4.49 (m, 2H), 4.03 (s, 3H), 3.48-3.39 (m, 1H), 3.32-3.20 (m, 1H), 2.99 (br s, 1H), 2.61-2.56 (m, 1H), 2.04-1.84 (m, 2H), 1.58-1.45 (m, 2H), 1.38 (d, J = 6.4 Hz, 3H) | 2.33 | 599.1 |
| 72 | 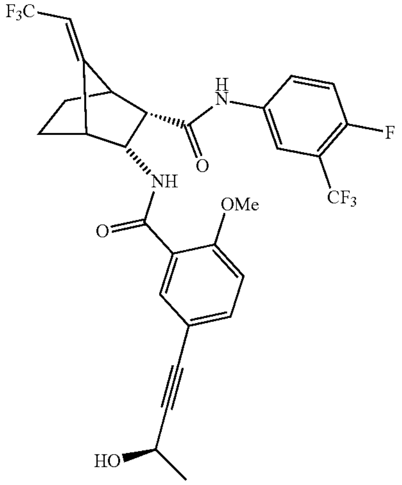 [SMILES: COc1ccc(C#C[C@@H](C)O)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{5-[(3R)-3-hydroxybut-1-yn-1-yl]-2-methoxybenzamido}-7-(2,2,2-trifluoroethylidene)bicyclo[2.2.1]heptane-2-carboxamide | (500 MHz, DMSO-d6) 10.66 (s, 1H), 10.00-9.89 (m, 1H), 8.30-8.14 (m, 1H), 7.92 (d, J = 2.1 Hz, 1H), 7.81-7.72 (m, 1H), 7.58-7.42 (m, 2H), 7.19 (d, J = 8.7 Hz, 1H), 5.93 (br d, J = 7.8 Hz, 1H), 5.50 (br d, J = 5.3 Hz, 1H), 4.62-4.55 (m, 1H), 4.53-4.44 (m, 1H), 4.01 (s, 3H), 3.31-3.20 (m, 2H), 2.98 (br s, 1H), 2.00-1.82 (m, 2H), 1.49 (br d, J = 6.7 Hz, 2H), 1.37 (d, J = 6.6 Hz, 3H) | 2.30 | 599.0 |

TABLE 2-continued

| Ex # | Structure | Name | $^1$H NMR. δ | LC RT (min) | Ion |
| --- | --- | --- | --- | --- | --- |
| 73 | 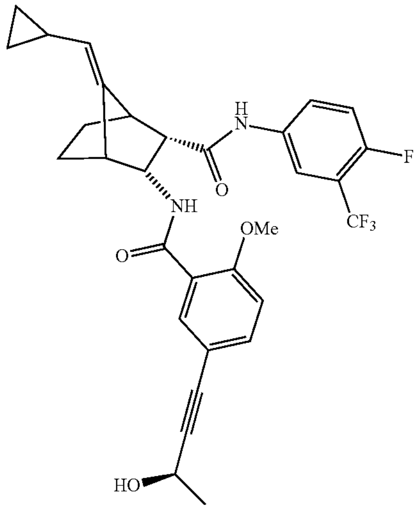 [SMILES: COc1ccc(C#C[C@@H](C)O)cc1C(=O)N[C@@H]1C2CCC(/C2=C/C2CC2)[C@@H]1C(=O)Nc1ccc(F)c(C(F)(F)F)c1] | (2S,3R,7Z)-7-(cyclopropylmethylidene)-N-[4-fluoro-3-(trifluoromethyl)phenyl]-3-{5-[(3R)-3-hydroxybut-1-yn-1-yl]-2-methoxybenzamido}bicyclo[2.2.1]heptane-2-carboxamide | (500 MHz, DMSO-d6) 10.53 (s, 1H), 9.89 (d, J = 7.3 Hz, 1H), 8.21 (dd, J = 6.4, 2.1 Hz, 1H), 7.94 (d, J = 2.1 Hz, 1H), 7.83-7.75 (m, 1H), 7.59-7.46 (m, 2H), 7.20 (d, J = 8.5 Hz, 1H), 5.47 (d, J = 5.2 Hz, 1H), 4.69 (d, J = 9.8 Hz, 1H), 4.65-4.53 (m, 1H), 4.44 (br t, J = 10.5 Hz, 1H), 4.02 (s, 3H), 3.15 (br dd, J = 10.5, 4.1 Hz, 1H), 3.09 (br s, 1H), 2.76-2.70 (m, 1H), 1.90-1.75 (m, 2H), 1.56-1.47 (m, 1H), 1.44-1.35 (m, 5H), 0.81-0.67 (m, 2H), 0.35 (br d, J = 3.1 Hz, 2H) | 2.51 | 571.1 |
| 74 | 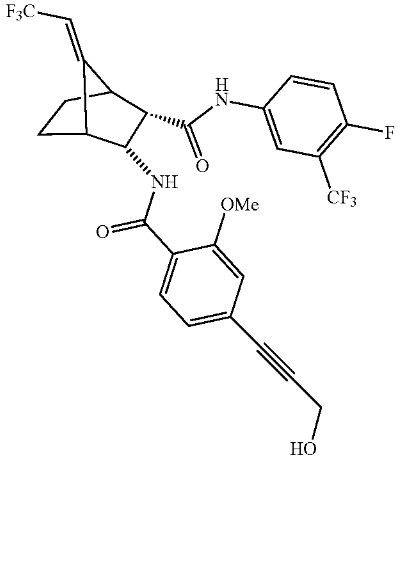 [SMILES: COc1cc(C#CCO)ccc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-[4-(3-hydroxyprop-1-yn-1-yl)-2-methoxybenzamido]-7-(2,2,2-trifluoroethylidene)bicyclo[2.2.1]heptane-2-carboxamide | (500 MHz, DMSO-d6) 10.67 (s, 1H), 9.95 (d, J = 6.9 Hz, 1H), 8.22 (dd, J = 6.3, 2.2 Hz, 1H), 7.93 (d, J = 8.0 Hz, 1H), 7.85-7.73 (m, 1H), 7.51 (t, J = 9.7 Hz, 1H), 7.20 (s, 1H), 7.11 (d, J = 8.1 Hz, 1H), 5.95 (q, J = 7.8 Hz, 1H), 4.50 (ddd, J = 10.2, 6.6, 3.9 Hz, 1H), 4.34 (d, J = 5.8 Hz, 2H), 4.02 (s, 3H), 3.60-3.40 (m, 2H), 3.33-3.19 (m, 1H), 2.99 (br s, 1H), 2.00-1.77 (m, 2H), 1.60-1.41 (m, 2H) | 2.40 | 585.0 |

TABLE 2-continued

| Ex # | Structure | Name | $^1H$ NMR. δ | LC RT (min) | Ion |
|---|---|---|---|---|---|
| 75 | 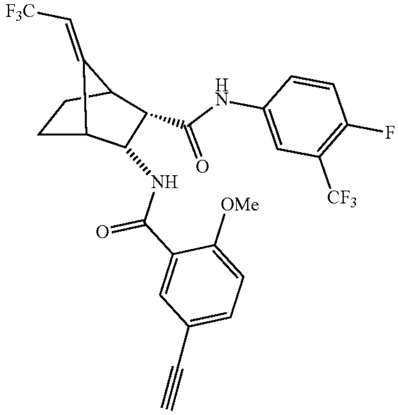 [SMILES: C#Cc1ccc(OC)c(C(=O)N[C@@H]2C3CCC(/C3=C/C(F)(F)F)[C@@H]2C(=O)Nc2ccc(F)c(C(F)(F)F)c2)c1] | (2S,3R,7Z)-3-(5-ethynyl-2-methoxybenzamido)-N-[4-fluoro-3-(trifluoromethyl)phenyl]-7-(2,2,2-trifluoroethylidene)bicyclo[2.2.1]heptane-2-carboxamide | (500 MHz, DMSO-d6) 10.66 (s, 1H), 9.92 (br d, J = 6.9 Hz, 1H), 8.27-8.18 (m, 1H), 7.97 (d, J = 2.0 Hz, 1H), 7.85-7.74 (m, 1H), 7.62 (dd, J = 8.6, 1.9 Hz, 1H), 7.50 (br t, J = 9.6 Hz, 1H), 7.21 (d, J = 8.7 Hz, 1H), 5.93 (br d, J = 7.8 Hz, 1H), 4.55-4.46 (m, 1H), 4.07 (s, 1H), 4.02 (s, 3H), 3.30-3.19 (m, 2H), 2.98 (br s, 1H), 2.01-1.82 (m, 2H), 1.49 (br d, J = 6.8 Hz, 2H) | 2.64 | 544.9 |
| 76 | 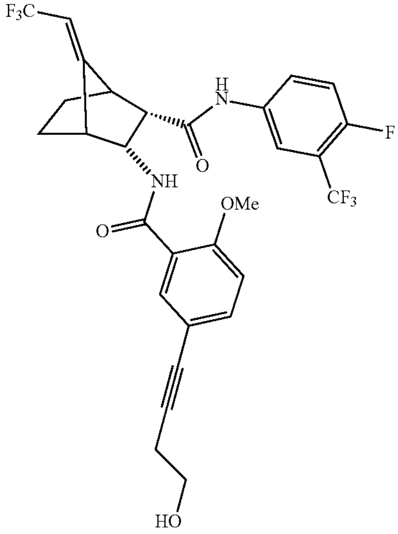 [SMILES: COc1ccc(C#CCCO)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-[5-(4-hydroxybut-1-yn-1-yl)-2-methoxybenzamido]-7-(2,2,2-trifluoroethylidene)bicyclo[2.2.1]heptane-2-carboxamide | (500 MHz, DMSO-d6) δ 9.90 (d, J = 6.7 Hz, 1H), 8.29-8.17 (m, 1H), 7.91 (d, J = 2.1 Hz, 1H), 7.84-7.73 (m, 1H), 7.59-7.45 (m, 2H), 7.17 (d, J = 8.9 Hz, 1H), 6.01-5.84 (m, 1H), 4.61-4.45 (m, 1H), 4.01 (s, 3H), 3.58 (br t, J = 6.4 Hz, 1H), 3.32-3.15 (m, 2H), 2.99 (br s, 1H), 1.97 (br t, J = 9.5 Hz, 1H), 1.93-1.79 (m, 1H), 1.58-1.38 (m, 2H) | 2.45 | 599.0 |
| 77 | 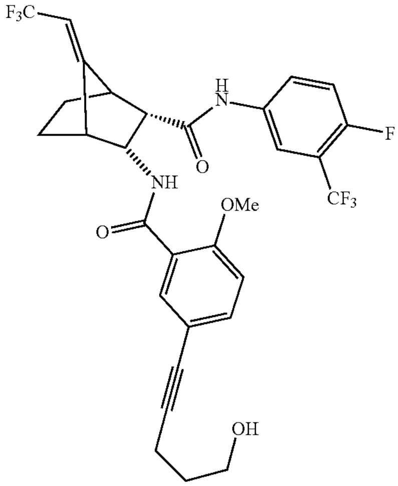 [SMILES: COc1ccc(C#CCCCO)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-[5-(5-hydroxypent-1-yn-1-yl)-2-methoxybenzamido]-7-(2,2,2-trifluoroethylidene)bicyclo[2.2.1]heptane-2-carboxamide | (500 MHz, DMSO-d6) δ 10.65 (s, 1H), 9.91 (br d, J = 6.7 Hz, 1H), 8.27-8.16 (m, 1H), 7.90 (d, J = 1.8 Hz, 1H), 7.83-7.73 (m, 1H), 7.60-7.45 (m, 2H), 7.17 (d, J = 8.5 Hz, 1H), 5.94 (q, J = 7.7 Hz, 1H), 4.58 (t, J = 5.2 Hz, 1H), 4.55-4.46 (m, 1H), 4.01 (s, 3H), 3.59-3.48 (m, 1H), 3.44-3.34 (m, 1H), 3.27 (br dd, J = 10.5, 4.1 Hz, 1H), 3.23 (br s, 1H), 2.99 (br s, 1H), 2.45 (t, J = 7.0 Hz, 2H), | 2.49 | 613.1 |

TABLE 2-continued

| Ex # | Structure | Name | $^1$H NMR. δ | LC RT (min) | Ion |
|---|---|---|---|---|---|
| | | | 2.06-1.93 (m, 1H), 1.91-1.82 (m, 1H), 1.68 (quin, J = 6.6 Hz, 2H), 1.50 (br d, J = 6.4 Hz, 2H) | | |
| 78 | 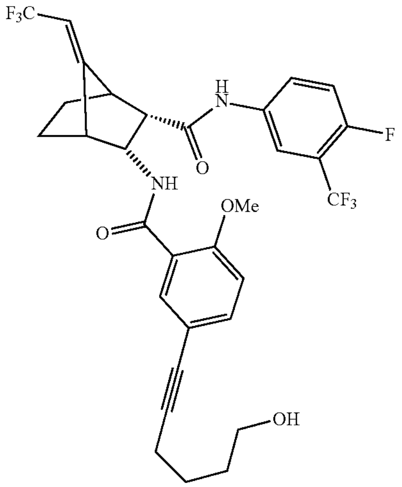 [SMILES: COc1ccc(C#CCCCCO)cc1C(=O)N[C@@H]1C2CCC(/C2=C/C(F)(F)F)[C@@H]1C(=O)Nc1ccc(F)c(C(F)(F)F)c1] | (2S,4R,7Z)-N-[4-fluoro-3-(trifluoromethyl)phenyl]-3-[5-(6-hydroxyhex-1-yn-1-yl)-2-methoxybenzamido]-7-(2,2,2-trifluoroethylidene)bicyclo[2.2.1]heptane-2-carboxamide | (500 MHz, DMSO-d6) δ 10.65 (s, 1H), 9.91 (d, J = 6.7 Hz, 1H), 8.23 (dd, J = 6.4, 2.4 Hz, 1H), 7.90 (d, J = 2.4 Hz, 1H), 7.84-7.75 (m, 1H), 7.57-7.46 (m, 2H), 7.17 (d, J = 8.5 Hz, 1H), 5.95 (q, J = 8.0 Hz, 1H), 4.58-4.48 (m, 1H), 4.44 (t, J = 5.2 Hz, 1H), 4.02 (s, 3H), 3.45 (br d, J = 4.9 Hz, 1H), 3.28 (br dd, J = 10.8, 3.2 Hz, 1H), 3.23 (br s, 1H), 2.42 (br s, 2H), 2.03-1.94 (m, 1H), 1.91-1.82 (m, 1H), 1.58 (br t, J = 2.7 Hz, 4H), 1.50 (br d, J = 6.7 Hz, 2H) | 2.54 | 627.3 |
| 79 | 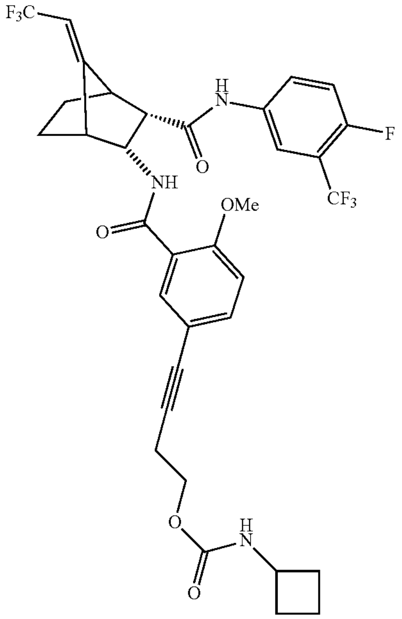 [SMILES: COc1ccc(C#CCCOC(=O)NC2CCC2)cc1C(=O)N[C@@H]1C2CCC(/C2=C/C(F)(F)F)[C@@H]1C(=O)Nc1ccc(F)c(C(F)(F)F)c1] | 4-(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)but-3-yn-1-yl N-cyclobutylcarbamate | (500 MHz, DMSO-d6) δ 10.65 (s, 1H), 9.90 (br d, J = 6.7 Hz, 1H), 8.22 (dd, J = 6.6, 2.3 Hz, 1H), 7.91 (d, J = 2.4 Hz, 1H), 7.83-7.75 (m, 1H), 7.58-7.44 (m, 3H), 7.18 (d, J = 8.9 Hz, 1H), 5.94 (q, J = 7.8 Hz, 1H), 4.60-4.45 (m, 1H), 4.09 (br t, J = 6.4 Hz, 2H), 4.01 (s, 3H), 3.97 (br dd, J = 16.2, 8.2 Hz, 1H), 3.27 (dd, J = 10.8, 4.1 Hz, 1H), 3.23 (br s, 1H), 2.99 (br s, 1H), 2.70 (br t, J = 6.4 Hz, 2H), 2.18-2.07 (m, 2H), 2.02-1.83 (m, 4H), 1.61-1.42 (m, 4H) | 2.72 | 696.3 |

TABLE 2-continued

| Ex # | Structure | Name | $^1$H NMR. δ | LC RT (min) | Ion |
|---|---|---|---|---|---|
| 80 | 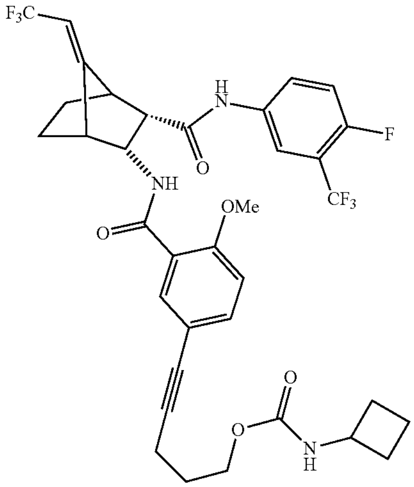 [SMILES: COc1ccc(C#CCCCOC(=O)NC2CCC2)cc1C(=O)N[C@@H]1C2CCC(/C2=C/C(F)(F)F)[C@@H]1C(=O)Nc1ccc(F)c(C(F)(F)F)c1] | 5-(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)pent-4-yn-1-yl N-cyclobutylcarbamate | (500 MHz, DMSO-d6) δ 9.91 (br d, J = 6.7 Hz, 1H), 8.29-8.19 (m, 1H), 7.91 (d, J = 2.1 Hz, 1H), 7.84-7.74 (m, 1H), 7.56-7.47 (m, 2H), 7.43 (br d, J = 7.9 Hz, 1H), 7.18 (d, J = 8.9 Hz, 1H), 5.94 (q, J = 7.8 Hz, 1H), 4.57-4.47 (m, 1H), 4.12-3.89 (m, 5H), 3.29 (br dd, J = 11.1, 4.1 Hz, 1H), 3.23 (br s, 1H), 3.00 (br s, 1H), 2.47 (br t, J = 6.9 Hz, 2H), 2.19-2.07 (m, 2H), 2.03-1.95 (m, 1H), 1.94-1.74 (m, 5H), 1.62-1.44 (m, 4H) | 2.75 | 710.3 |
| 81 | 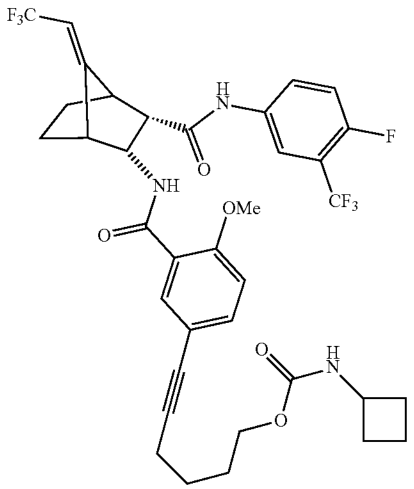 [SMILES: COc1ccc(C#CCCCCOC(=O)NC2CCC2)cc1C(=O)N[C@@H]1C2CCC(/C2=C/C(F)(F)F)[C@@H]1C(=O)Nc1ccc(F)c(C(F)(F)F)c1] | 6-(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)hex-5-yn-1-yl N-cyclobutylcarbamate | (500 MHz, DMSO-d6) δ 10.65 (s, 1H), 9.90 (br d, J = 6.7 Hz, 1H), 8.22 (dd, J = 6.3, 2.3 Hz, 1H), 7.90 (d, J = 2.1 Hz, 1H), 7.79 (br dd, J = 8.7, 3.2 Hz, 1H), 7.56-7.45 (m, 2H), 7.38 (br d, J = 7.6 Hz, 1H), 7.17 (d, J = 8.5 Hz, 1H), 5.94 (q, J = 7.8 Hz, 1H), 4.57-4.43 (m, 1H), 3.34-3.26 (m, 1H), 3.23 (br s, 1H), 2.99 (br s, 1H), 2.44 (br t, J = 6.9 Hz, 2H), 2.18-2.05 (m, 2H), 1.97 (br t, J = 9.2 Hz, 1H), 1.93-1.79 (m, 3H), 1.76-1.64 (m, 2H), 1.63-1.41 (m, 6H). | 2.78 | 723.9 |

TABLE 2-continued

| Ex # | Structure | Name | $^1$H NMR. δ | LC RT (min) | Ion |
|---|---|---|---|---|---|
| 84 | 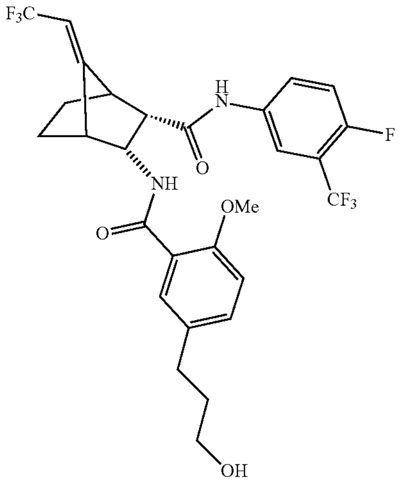 [SMILES: COc1ccc(CCCO)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-[5-(3-hydroxypropyl)-2-methoxybenzamido]-7-(2,2,2-trifluoroethylidene)bicyclo[2.2.1]heptane-2-carboxamide | (500 MHz, DMSO-d6) 10.64 (br d, J = 8.5 Hz, 1H), 9.86 (br d, J = 7.3 Hz, 1H), 8.23-8.19 (m, 1H), 7.85-7.73 (m, 2H), 7.49 (br t, J = 9.8 Hz, 1H), 7.42-7.28 (m, 1H), 7.20-7.06 (m, 1H), 6.40 (br d, J = 11.6 Hz, 1H), 5.99-5.86 (m, 1H), 4.59-4.47 (m, 1H), 4.28-4.17 (m, 1H), 3.95 (m, 3H), 3.56-3.45 (m, 2H), 3.43-3.35 (m, 1H), 3.32-3.19 (m, 2H), 2.98 (br d, J = 1.5 Hz, 1H), 2.59-2.56 (m, 1H), 2.04-1.84 (m, 2H), 1.72-1.61 (m, 1H), 1.49 (br d, J = 6.7 Hz, 2H) | 2.32 | 589.0 |
| 85 | 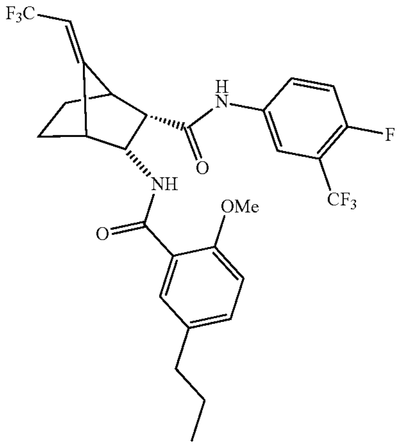 [SMILES: CCCc1ccc(OC)c(C(=O)N[C@@H]2C3CCC(/C3=C/C(F)(F)F)[C@@H]2C(=O)Nc2ccc(F)c(C(F)(F)F)c2)c1] | (2S,3R,7Z)-N-[4-fluoro-3-(trifluoromethyl)phenyl]-3-(2-methoxy-5-propylbenzamido)-7-(2,2,2-trifluoroethylidene)bicyclo[2.2.1]heptane-2 -carboxamide | (500 MHz, DMSO-d6) 10.64 (s, 1H), 9.85 (br d, J = 6.9 Hz, 1H), 8.21 (br d, J = 6.0 Hz, 1H), 7.85-7.68 (m, 2H), 7.49 (br t, J = 9.6 Hz, 1H), 7.31 (br d, J = 8.2 Hz, 1H), 7.08 (d, J = 8.5 Hz, 1H), 5.92 (br d, J = 7.6 Hz, 1H), 4.56-4.46 (m, 1H), 3.95 (s, 3H), 3.62-3.56 (m, 2H), 3.28-3.15 (m, 2H), 2.99 (br d, J = 1.3 Hz, 1H), 2.00 (s, 2H), 1.61-1.44 (m, 4H), 0.85 (t, J = 7.2 Hz, 3H) | 2.93 | 573.0 |

TABLE 2-continued

| Ex # | Structure | Name | $^1$H NMR. δ | LC RT (min) | Ion |
|---|---|---|---|---|---|
| 86 | 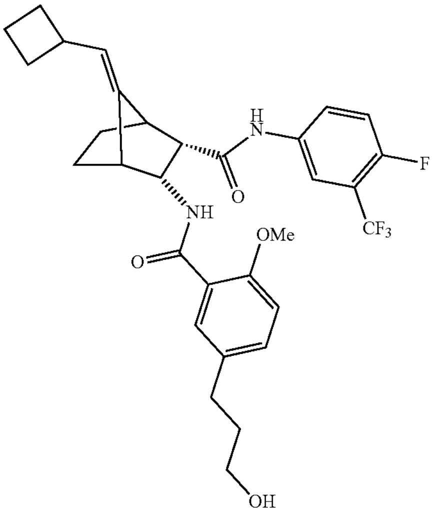 [SMILES: COc1ccc(CCCO)cc1C(=O)N[C@@H]1C2CCC(/C2=C/C2CCC2)[C@@H]1C(=O)Nc1ccc(F)c(C(F)(F)F)c1] | (2S,3R,7Z)-7-(cyclobutylmethylidene)-N-[4-fluoro-3-(trifluoromethyl)phenyl]-3-[5-(3-hydroxypropyl)-2-methoxybenzamido]bicyclo[2.2.1]heptane-2-carboxamide | (500 MHz, DMSO-d6) δ 10.52 (s, 1H), 9.79 (br d, J = 7.3 Hz, 1H), 8.22 (br d, J = 6.1 Hz, 1H), 7.80-7.72 (m, 1H), 7.48 (br t, J = 9.9 Hz, 1H), 7.31 (br d, J = 8.3 Hz, 1H), 7.25 (s, 1H), 7.15 (d, J = 2.8 Hz, 1H), 7.12-7.02 (m, 1H), 5.36 (d, J = 8.5 Hz, 1H), 4.36 (br s, 1H), 3.96 (s, 3H), 3.51 (br d, J = 12.3 Hz, 3H), 3.11 (br dd, J = 15.9, 8.0 Hz, 2H), 2.93 (br s, 1H), 2.69 (br s, 1H), 2.59-2.53 (m, 2H), 2.22-2.04 (m, 2H), 1.90-1.74 (m, 5H), 1.72-1.65 (m, 2H), 1.35 (br s, 2H). | 2.62 | 575.1 |
| 87 | 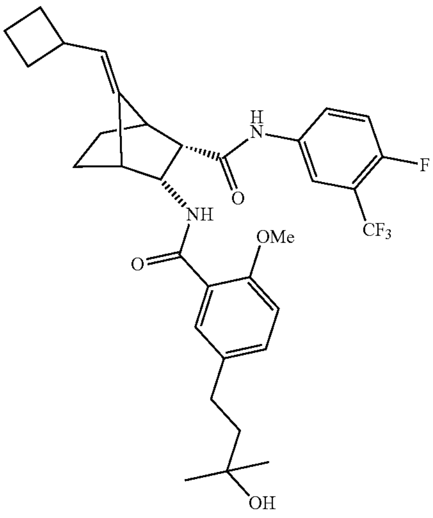 [SMILES: COc1ccc(CCC(C)(C)O)cc1C(=O)N[C@@H]1C2CCC(/C2=C/C2CCC2)[C@@H]1C(=O)Nc1ccc(F)c(C(F)(F)F)c1] | (2S,3R,7Z)-7-(cyclobutylmethylidene)-N-[4-fluoro-3-(trifluoromethyl)phenyl]-3-[5-(3-hydroxy-3-methylbutyl)-2-methoxybenzamido]bicyclo[2.2.1]heptane-2-carboxamide | (500 MHz, DMSO-d6) δ 10.52 (s, 1H), 9.78 (br d, J = 7.3 Hz, 1H), 8.19 (br d, J = 6.4 Hz, 1H), 7.77-7.72 (m, 2H), 7.46 (br t, J = 9.8 Hz, 1H), 7.30 (br d, J = 8.3 Hz, 1H), 7.06 (d, J = 8.5 Hz, 1H), 5.35 (br d, J = 8.5 Hz, 1H), 4.34 (br s, 1H), 3.94 (s, 3H), 3.09 (br dd, J = 15.4, 8.0 Hz, 1H), 2.92 (br s, 1H), 2.67 (br s, 1H), , 2.15 (br s, 1H), 2.10 (br s, 1H), 1.89-1.69 (m, 7H), 1.60-1.56 (m, 2H), 1.34 (br s, 1H), 1.12 (s, 6H). | 2.73 | 603.0 |

TABLE 2-continued

| Ex # | Structure | Name | $^1$H NMR. δ | LC RT (min) | Ion |
|---|---|---|---|---|---|
| 88 | 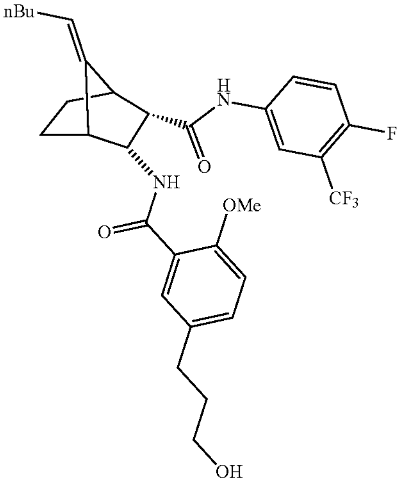 | (2S,3R,7Z)-7-butylidene-N-[4-fluoro-3-(trifluoromethyl)phenyl]-3-[5-(3-hydroxy-3-methylbutyl)-2-methoxybenzamido]bicyclo[2.2.1]heptane-2-carboxamide | (500 MHz, DMSO-d6) δ 10.55 (s, 1H), 9.81 (d, J = 7.3 Hz, 1H), 8.24 (br d, J = 4.1 Hz, 1H), 7.82-7.73 (m, 2H), 7.49 (t, J = 9.8 Hz, 1H), 7.31 (dd, J = 8.5, 2.3 Hz, 1H), 7.07 (d, J = 8.5 Hz, 1H), 5.23 (t, J = 7.5 Hz, 1H), 4.40 (br s, 1H), 3.96 (s, 3H), 3.16 (dd, J = 10.5, 4.2 Hz, 1H), 2.95 (br s, 1H), 2.72 (br s, 2H), 2.04 (dquin, J = 13.5, 6.7 Hz, 2H), 1.94-1.83 (m, 1H), 1.81-1.69 (m, 1H), 1.66-1.53 (m, 2H), 1.46-1.32 (m, 4H), 1.13 (s, 6H), 0.91 (t, J = 7.4 Hz, 3H). | 2.76 | 591.4 |
| 89 | 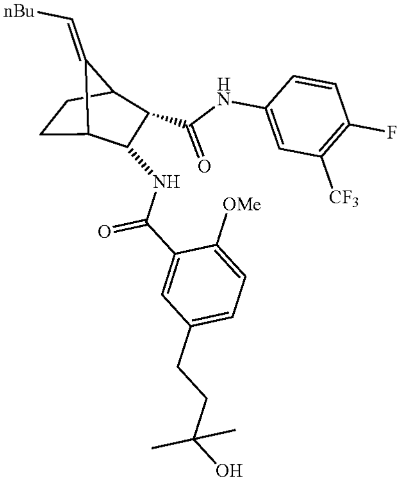 | (2S,3R,7Z)-N-[4-fluoro-3-(trifluoromethyl)phenyl]-3-[5-(3-hydroxy-3-methylbutyl)-2-methoxybenzamido]-7-pentylidenebicyclo[2.2.1]heptane-2-carboxamide | (500 MHz, DMSO-d6) δ 10.53 (s, 1H), 9.81 (d, J = 7.2 Hz, 1H), 8.27-8.21 (m, 1H), 7.80-7.74 (m, 2H), 7.49 (t, J = 9.7 Hz, 1H), 7.31 (dd, J = 8.4, 2.3 Hz, 1H), 7.07 (d, J = 8.5 Hz, 1H), 5.22 (t, J = 7.4 Hz, 1H), 4.46-4.29 (m, 1H), 3.96 (s, 3H), 3.50 (br s, 1H), 3.46-3.38 (m, 1H), 3.15 (dd, J = 11.0, 4.2 Hz, 1H), 2.95 (br s, 1H), 2.72 (br s, 1H), 2.14-2.00 (m, 2H), 1.94-1.82 (m, 1H), 1.81-1.68 (m, 1H), 1.64-1.53 (m, 2H), 1.43-1.25 (m, 6H), 1.20-1.07 (m, 6H), 0.91 (t, J = 7.0 Hz, 3H). | 2.86 | 605.2 |

TABLE 2-continued

| Ex # | Structure | Name | $^1H$ NMR. δ | LC RT (min) | Ion |
|---|---|---|---|---|---|
| 90 | 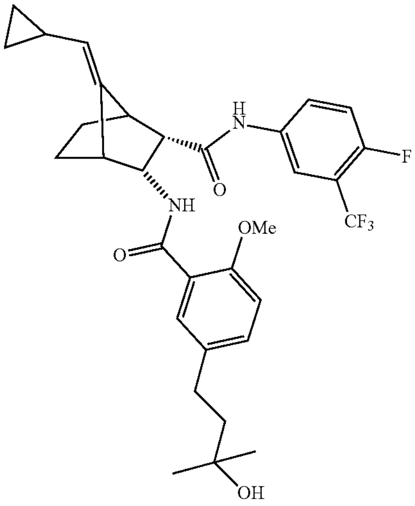 [SMILES: COc1ccc(CCC(C)(C)O)cc1C(=O)N[C@@H]1C2CCC(/C2=C/C2CC2)[C@@H]1C(=O)Nc1ccc(F)c(C(F)(F)F)c1] | (2S,3R,7Z)-7-(cyclopropylmethylidene)-N-[4-fluoro-3-(trifluoromethyl)phenyl]-3-[5-(3-hydroxy-3-methylbutyl)-2-methoxybenzamido]bicyclo[2.2.1]heptane-2-carboxamide | (500 MHz, DMSO-d6) 10.51 (s, 1H), 9.81 (br d, J = 7.0 Hz, 1H), 8.20 (br d, J = 4.3 Hz, 1H), 7.81-7.72 (m, 2H), 7.47 (br t, J = 9.5 Hz, 1H), 7.37-7.25 (m, 1H), 7.08 (d, J = 8.5 Hz, 1H), 4.68 (d, J = 9.5 Hz, 1H), 4.51-4.40 (m, 1H), 3.95 (s, 3H), 3.55 (br d, J = 10.1 Hz, 1H), 3.14 (br dd, J = 10.7, 4.0 Hz, 1H), 3.07 (br s, 1H), 2.70 (br s, 1H), 2.59 (br d, J = 8.2 Hz, 2H), 1.94-1.71 (m, 2H), 1.67-1.55 (m, 2H), 1.55-1.45 (m, 1H), 1.41 (br s, 2H), 1.13 (s, 6H), 0.81-0.65 (m, 2H), 0.35 (br d, J = 2.7 Hz, 2H) | 2.58 | 589.1 |
| 91 | 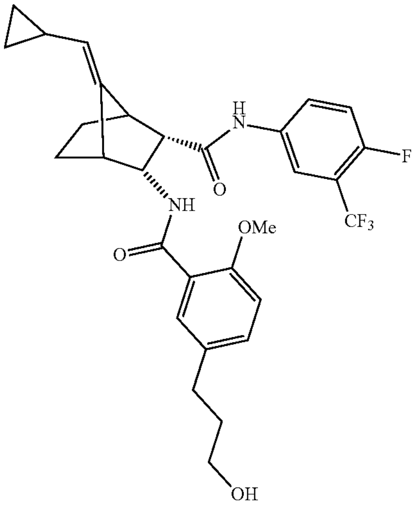 [SMILES: COc1ccc(CCCO)cc1C(=O)N[C@@H]1C2CCC(/C2=C/C2CC2)[C@@H]1C(=O)Nc1ccc(F)c(C(F)(F)F)c1] | (2S,3R,7Z)-7-(cyclopropylmethylidene)-N-[4-fluoro-3-(trifluoromethyl)phenyl]-3-[5-(3-hydroxypropyl)-2-methoxybenzamido]bicyclo[2.2.1]heptane-2-carboxamide | (500 MHz, DMSO-d6) 10.50 (s, 1H), 9.82 (br d, J = 7.3 Hz, 1H), 8.23 (dd, J = 6.3, 1.7 Hz, 1H), 7.84-7.74 (m, 2H), 7.49 (t, J = 9.8 Hz, 1H), 7.32 (dd, J = 8.5, 2.1 Hz, 1H), 7.09 (d, J = 8.5 Hz, 1H), 4.70 (d, J = 9.8 Hz, 1H), 4.50-4.40 (m, 2H), 3.97 (s, 3H), 3.09 (br s, 2H), 2.72 (br s, 1H), 2.59 (t, J = 7.6 Hz, 2H), 1.97-1.77 (m, 2H), 1.75-1.63 (m, 3H), 1.59-1.34 (m, 4H), 10.75 (br dd, J = 12.2, 9.5 Hz, 2H), 0.36 (br s, 2H) | 2.43 | 561.2 |

TABLE 2-continued

| Ex # | Structure | Name | $^1$H NMR. δ | LC RT (min) | Ion |
|---|---|---|---|---|---|
| 92 | 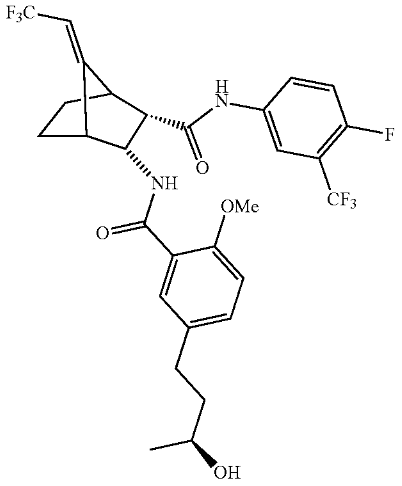 [SMILES: COc1ccc(CC[C@H](C)O)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{5-[(3S)-3-hydroxybutyl]-2-methoxybenzamido}-7-(2,2,2-trifluoroethylidene)bicyclo[2.2.1]heptane-2-carboxamide | (500 MHz, DMSO-d6) 10.70-10.60 (m, 1H), 9.87 (br d, J = 7.0 Hz, 1H), 8.22 (dd, J = 6.5, 2.5 Hz, 1H), 7.82-7.69 (m, 2H), 7.50 (s, 1H), 7.32 (dd, J = 8.5, 2.1 Hz, 1H), 7.08 (d, J = 8.4 Hz, 1H), 5.93 (br d, J = 7.8 Hz, 1H), 4.57-4.48 (m, 2H), 3.96 (s, 3H), 3.55 (br dd, J = 12.3, 5.6 Hz, 2H), 3.31-3.19 (m, 2H), 3.07-2.96 (m, 1H), 2.61 (br dd, J = 9.6, 5.6 Hz, 1H), 2.04-1.82 (m, 2H), 1.63-1.52 (m, 2H), 1.53-1.43 (m, 2H), 1.07 (d, J = 6.1 Hz, 3H) | 2.46 | 603.1 |
| 93 | 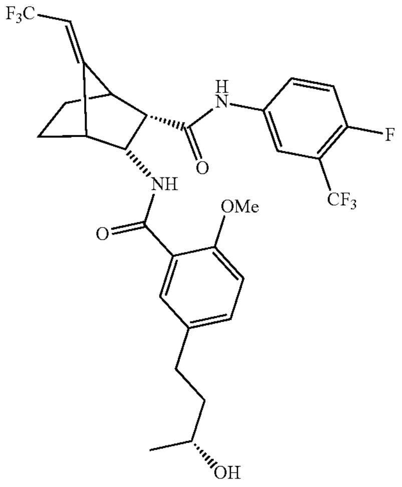 [SMILES: COc1ccc(CC[C@@H](C)O)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{5-[(3R)-3-hydroxybutyl]-2-methoxybenzamido}-7-(2,2,2-trifluoroethylidene)bicyclo[2.2.1]heptane-2-carboxamide | (500 MHz, DMSO-d6) 10.69-10.62 (m, 1H), 9.87 (d, J = 7.0 Hz, 1H), 8.27-8.18 (m, 1H), 7.84-7.73 (m, 2H), 7.51 (t, J = 9.8 Hz, 1H), 7.33 (dd, J = 8.4, 2.3 Hz, 1H), 7.09 (d, J = 8.5 Hz, 1H), 5.94 (d, J = 7.6 Hz, 1H), 4.58-4.48 (m, 2H), 3.97 (s, 3H), 3.66-3.52 (m, 1H), 3.32-3.18 (m, 2H), 2.99 (br s, 1H), 2.70-2.61 (m, 1H), 2.58-2.56 (m, 1H), 2.07-1.82 (m, 2H), 1.65-1.45 (m, 4H), 1.08 (d, J = 6.1 Hz, 3H) | 2.31 | 603.3 |

TABLE 2-continued

| Ex # | Structure | Name | $^1$H NMR. δ | LC RT (min) | Ion |
|---|---|---|---|---|---|
| 94 | 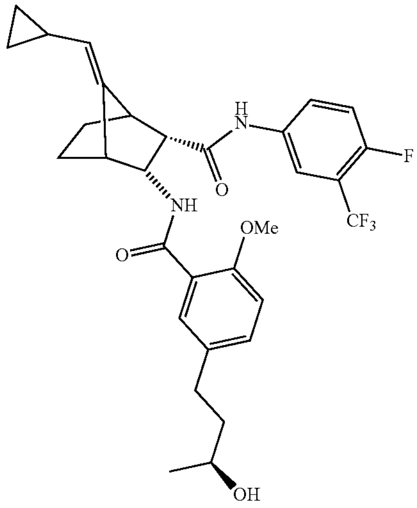 [SMILES: COc1ccc(CC[C@H](C)O)cc1C(=O)N[C@@H]1C2CCC(/C2=C/C2CC2)[C@@H]1C(=O)Nc1ccc(F)c(C(F)(F)F)c1] | (2S,3R,7Z)-7-(cyclopropylmethylidene)-N-[4-fluoro-3-(trifluoromethyl)phenyl]-3-{5-[(3S)-3-hydroxybutyl]-2-methoxybenzamido}bicyclo[2.2.1]heptane-2-carboxamide | (500 MHz, DMSO-d6) 10.50 (s, 1H), 9.82 (d, J = 7.5 Hz, 1H), 8.23 (dd, J = 6.2, 2.1 Hz, 1H), 7.82-7.73 (m, 2H), 7.49 (t, J = 9.8 Hz, 1H), 7.32 (dd, J = 8.5, 2.3 Hz, 1H), 7.08 (d, J = 8.5 Hz, 1H), 4.69 (d, J = 9.7 Hz, 1H), 4.47 (br d, J = 4.7 Hz, 2H), 3.96 (s, 3H), 3.62-3.54 (m, 1H), 3.42 (br s, 1H), 3.15 (br dd, J = 10.6, 4.2 Hz, 1H), 3.08 (br s, 1H), 2.76-2.68 (m, 1H), 2.67-2.59 (m, 1H), 1.92-1.75 (m, 2H), 1.62-1.47 (m, 3H), 1.41 (br t, J = 9.5 Hz, 2H), 1.07 (d, J = 6.1 Hz, 3H), 0.83-0.68 (m, 2H), 0.36 (br d, J = 1.6 Hz, 2H) | 2.53 | 575.1 |
| 95 | 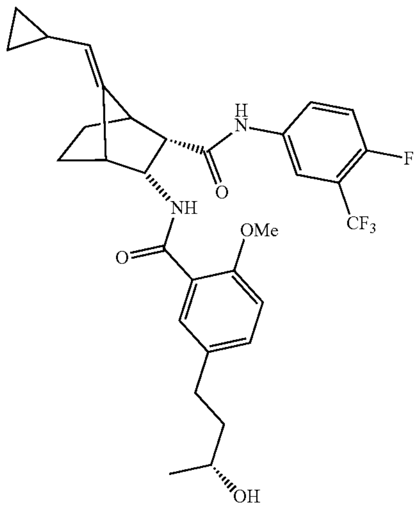 [SMILES: COc1ccc(CC[C@@H](C)O)cc1C(=O)N[C@@H]1C2CCC(/C2=C/C2CC2)[C@@H]1C(=O)Nc1ccc(F)c(C(F)(F)F)c1] | (2S,3R,7Z)-7-(cyclopropylmethylidene)-N-[4-fluoro-3-(trifluoromethyl)phenyl]-3-{5-[(3R)-3-hydroxybutyl]-2-methoxybenzamido}bicyclo[2.2.1]heptane-2-carboxamide | (500 MHz, DMSO-d6) 10.26 (s, 1H), 9.57 (d, J = 7.3 Hz, 1H), 7.97 (br d, J = 4.0 Hz, 1H), 7.57-7.49 (m, 2H), 7.23 (t, J = 9.8 Hz, 1H), 7.07 (dd, J = 8.4, 2.3 Hz, 1H), 6.83 (d, J = 8.2 Hz, 1H), 4.44 (d, J = 9.5 Hz, 1H), 4.33-4.26 (m, 1H), 4.20 (br t, J = 10.7 Hz, 1H), 3.71 (s, 3H), 3.33 (br d, J = 7.0 Hz, 1H), 3.29-3.20 (m, 1H), 2.97-2.88 (m, 1H), 2.83 (br s, 1H), 2.46 (br s, 1H), 2.40-2.33 (m, 1H), 1.69-1.50 (m, 2H), 1.40-1.22 (m, 3H), 1.19-1.08 (m, 2H), 0.82 (d, J = 6.1 Hz, 3H), 0.50 (br dd, J = 11.3, 9.2 Hz, 2H), 0.11 (br d, J = 2.7 Hz, 2H) | 2.52 | 575.3 |

TABLE 2-continued

| Ex # | Structure | Name | $^1$H NMR. δ | LC RT (min) | Ion |
|---|---|---|---|---|---|
| 96 | 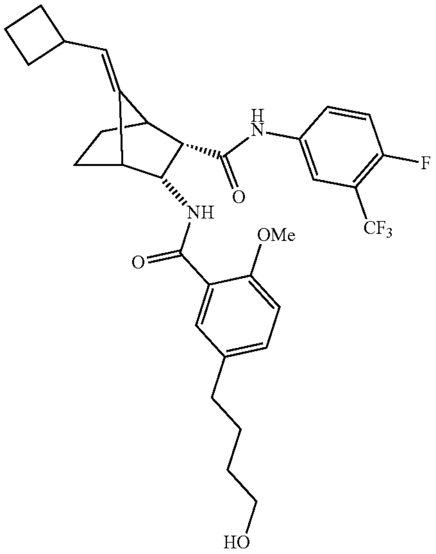 [SMILES: COc1ccc(CCCCO)cc1C(=O)N[C@@H]1C2CCC(/C2=C/C2CCC2)[C@@H]1C(=O)Nc1ccc(F)c(C(F)(F)F)c1] | (2S,3R,7Z)-7-(cyclobutylmethylidene)-N-[4-fluoro-3-(trifluoromethyl)phenyl]-3-[5-(4-hydroxybutyl)-2-methoxybenzamido]bicyclo[2.2.1]heptane-2-carboxamide | (500 MHz, DMSO-d6) δ 10.50 (s, 1H), 9.79 (d, J = 7.3 Hz, 1H), 8.22 (dd, J = 6.4, 2.1 Hz, 1H), 7.82-7.71 (m, 2H), 7.48 (t, J = 9.8 Hz, 1H), 7.31 (dd, J = 8.2, 2.1 Hz, 1H), 7.08 (d, J = 8.2 Hz, 1H), 5.37 (d, J = 8.2 Hz, 1H), 4.43 (t, J = 5.0 Hz, 1H), 4.39-4.31 (m, 1H), 3.96 (s, 3H), 3.42-3.34 (m, 1H), 3.15-3.01 (m, 2H), 2.94 (br s, 1H), 2.69 (br s, 1H), 2.23-2.04 (m, 2H), 1.95-1.68 (m, 6H), 1.56 (quin, J = 7.6 Hz, 2H), 1.46-1.28 (m, 4H) | 2.66 | 589.2 |
| 97 | 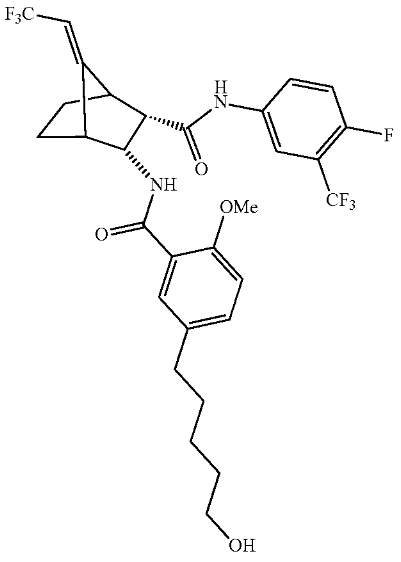 [SMILES: COc1ccc(CCCCCO)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-[5-(5-hydroxypentyl)-2-methoxybenzamido]-7-(2,2,2-trifluoroethylidene)bicyclo[2.2.1]heptane-2-carboxamide | (500 MHz, DMSO-d6) δ 10.64 (s, 1H), 9.87 (d, J = 7.0 Hz, 1H), 8.24 (dd, J = 6.4, 2.4 Hz, 1H), 7.84-7.78 (m, 1H), 7.75 (d, J = 2.1 Hz, 1H), 7.51 (t, J = 9.8 Hz, 1H), 7.33 (dd, J = 8.4, 2.3 Hz, 1H), 7.10 (d, J = 8.5 Hz, 1H), 5.94 (q, J = 8.0 Hz, 1H), 4.62-4.48 (m, 1H), 4.37 (t, J = 5.3 Hz, 1H), 3.97 (s, 3H), 3.50-3.34 (m, 1H), 3.27 (br dd, J = 10.8, 4.4 Hz, 1H), 3.23 (br s, 1H), 2.99 (br s, 1H), 2.06-1.98 (m, 1H), 1.93-1.83 (m, 1H), 1.61-1.47 (m, 3H), 1.47-1.38 (m, 2H), 1.28 (quin, J = 7.4 Hz, 2H) | 2.62 | 617.4 |

TABLE 2-continued

| Ex # | Structure | Name | $^1$H NMR. δ | LC RT (min) | Ion |
|---|---|---|---|---|---|
| 98 | 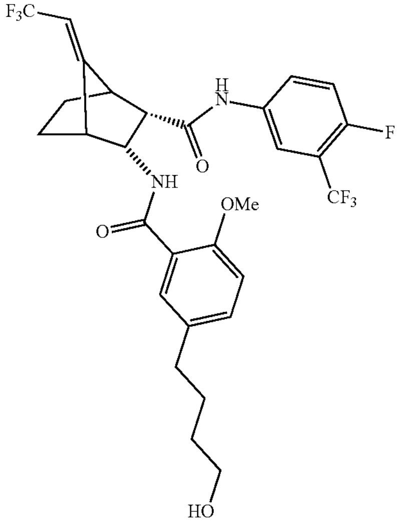 [SMILES: COc1ccc(CCCCO)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-[5-(4-hydroxybutyl)-2-methoxybenzamido]-7-(2,2,2-trifluoroethylidene)bicyclo[2.2.1]heptane-2-carboxamide | (500 MHz, DMSO-d6) δ 9.87 (d, J = 7.0 Hz, 1H), 8.23 (dd, J = 6.3, 2.3 Hz, 1H), 7.85-7.73 (m, 2H), 7.50 (t, J = 9.8 Hz, 1H), 7.32 (dd, J = 8.5, 2.1 Hz, 1H), 7.09 (d, J = 8.5 Hz, 1H), 5.93 (q, J = 7.9 Hz, 1H), 4.53 (ddd, J = 10.5, 6.5, 4.1 Hz, 1H), 3.97 (s, 3H), 3.34-3.18 (m, 1H), 2.99 (br s, 1H), 2.00 (br t, J = 9.5 Hz, 1H), 1.93-1.80 (m, 1H), 1.61-1.51 (m, 2H), 1.49 (br d, J = 6.1 Hz, 2H), 1.44-1.34 (m, 2H) | 2.49 | 603.3 |
| 99 | 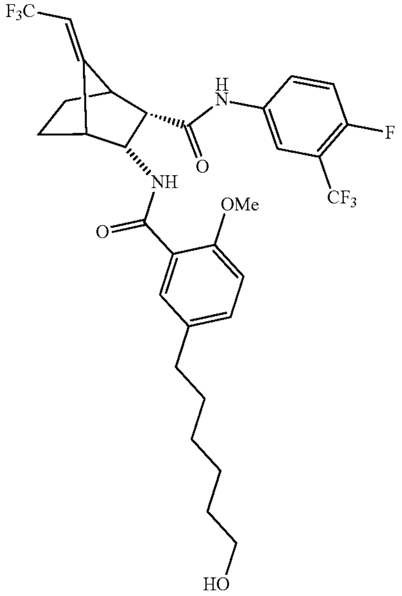 [SMILES: COc1ccc(CCCCCCO)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-[5-(6-hydroxyhexyl)-2-methoxybenzamido]-7-(2,2,2-trifluoroethylidene)bicyclo[2.2.1]heptane-2-carboxamide | (500 MHz, DMSO-d6) δ 10.63 (s, 1H), 9.86 (d, J = 7.0 Hz, 1H), 8.27-8.14 (m, 1H), 7.83-7.76 (m, 1H), 7.74 (d, J = 2.1 Hz, 1H), 7.50 (t, J = 9.8 Hz, 1H), 7.32 (dd, J = 8.4, 2.3 Hz, 1H), 7.09 (d, J = 8.5 Hz, 1H), 5.93 (q, J = 7.9 Hz, 1H), 4.61-4.46 (m, 1H), 3.96 (s, 3H), 3.37 (q, J = 6.1 Hz, 1H), 3.26 (dd, J = 10.8, 4.1 Hz, 1H), 3.22 (br s, 1H), 2.98 (br s, 1H), 2.01 (br t, J = 9.0 Hz, 1H), 1.92-1.83 (m, 1H), 1.58-1.44 (m, 4H), 1.43-1.34 (m, 2H), 1.33-1.19 (m, 4H) | 2.7 | 631.4 |

TABLE 2-continued

| Ex # | Structure | Name | $^1$H NMR. δ | LC RT (min) | Ion |
|---|---|---|---|---|---|
| 100 | 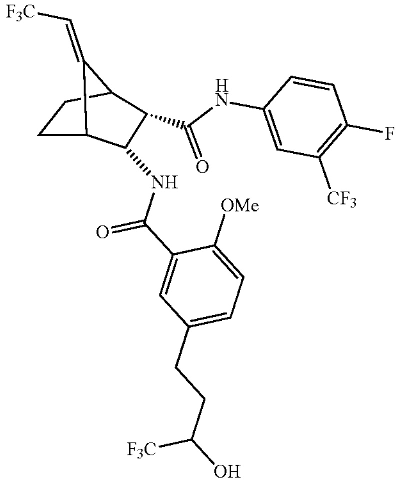 [SMILES: COc1ccc(CCC(O)C(F)(F)F)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-[2-methoxy-5-(4,4,4-trifluoro-3-hydroxybutyl)benzamido]-7-(2,2,2-trifluoroethylidene)bicyclo[2.2.1]heptane-2-carboxamide | (500 MHz, DMSO-d6) 10.63 (s, 1H), 9.88 d, J = 7.0 Hz, 1H), 8.22 (dd, J = 6.3, 2.3 Hz, 1H), 7.82-7.74 (m, 2H), 7.49 (t, J = 9.8 Hz, 1H), 7.37 (dd, J = 8.5, 2.1 Hz, 1H), 7.12 (d, J = 8.5 Hz, 1H), 6.28 (d, J = 6.7 Hz, 1H), 5.93 (d, J = 7.9 Hz, 1H), 4.58-4.44 (m, 1H), 3.97 (s, 3H), 3.83 (br d, J = 7.3 Hz, 1H), 3.32-3.19 (m, 2H), 2.98 (br s, 1H), 2.84-2.75 (m, 1H), 2.70-2.60 (m, 1H), 2.06-1.86 (m, 2H), 1.83-1.66 (m, 2H), 1.49 (br d, J = 6.7 Hz, 2H) | 2.63 | 656.9 |
| 101 | 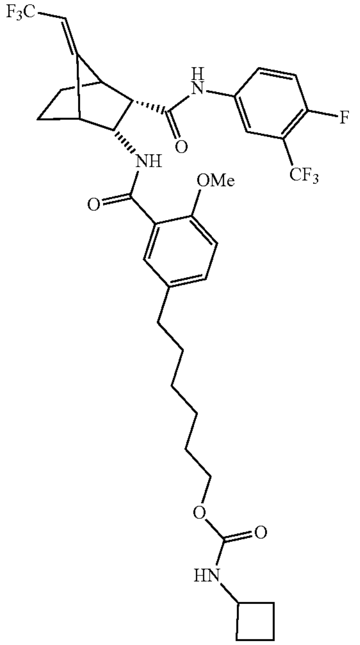 [SMILES: COc1ccc(CCCCCCOC(=O)NC2CCC2)cc1C(=O)N[C@@H]1C2CCC(/C2=C/C(F)(F)F)[C@@H]1C(=O)Nc1ccc(F)c(C(F)(F)F)c1] | 6-(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)hexyl N-cyclobutylcarbamate | (500 MHz, DMSO-d6) δ 10.64 (s ,1H), 9.87 (br d, J = 7.0 Hz, 1H), 8.23 (br d, J = 6.3 Hz, 1H), 7.82-7.70 (m, 2H), 7.49 (br t, J = 9.9 Hz, 1H), 7.33 (br dd, J = 16.0, 8.2 Hz, 2H), 7.08 (d, J = 8.5 Hz, 1H), 6.01-5.81 (m, 1H), 4.61-4.44 (m, 1H), 3.96 (s, 3H), 3.95-3.79 (m, 3H), 3.26 (br dd, J = 10.9, 3.2 Hz, 1H), 3.22 (br s, 1H), 2.98 (br s, 1H), 2.15-2.05 (m, 2H), 2.00 (br t, J = 9.0 Hz, 1H), 1.90-1.78 (m, 3H), 1.64-1.42 (m, 9H), 1.35-1.17 (m, 4H) | 2.88 | 728.2 |

TABLE 2-continued

| Ex # | Structure | Name | $^1$H NMR. δ | LC RT (min) | Ion |
|---|---|---|---|---|---|
| 102 | 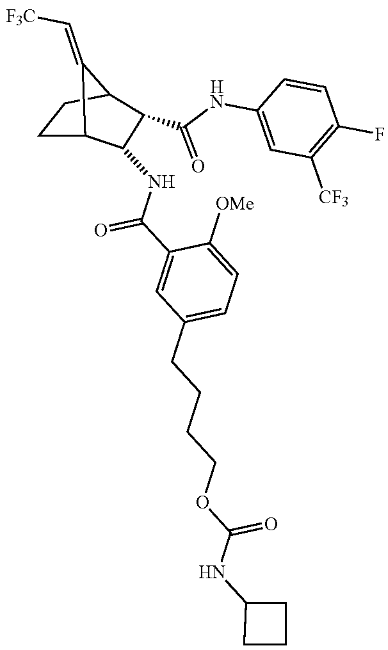 [SMILES: COc1ccc(CCCCOC(=O)NC2CCC2)cc1C(=O)N[C@@H]1C2CCC(/C2=C/C(F)(F)F)[C@@H]1C(=O)Nc1ccc(F)c(C(F)(F)F)c1] | 4-(3-{[(2R,3S,7Z)-3-{[4-fluoro-3-(trifluoromethyl)phe-nyl]carbamoyl}-7-(2,2,2-trifluoroethylidene)bi-cyclo[2.2.1]heptan-2-yl]carbamoyl}-4-methoxyphenyl)butyl N-cyclobutylcarbamate | (500 MHz, DMSO-d6) δ 10.63 (s, 1H), 9.88 (br d, J = 7.0 Hz, 1H), 8.23 (dd, J = 6.3, 2.3 Hz, 1H), 7.84-7.72 (m, 2H), 7.50 (t, J = 9.8 Hz, 1H), 7.39-7.26 (m, 2H), 7.10 (d, J = 8.5 Hz, 1H), 6.03-5.88 (m, 1H), 4.52 (ddd, J = 10.5, 6.6, 4.3 Hz, 1H), 3.97 (s, 3H), 3.94-3.84 (m, 2H), 3.27 (dd, J = 10.8, 4.1 Hz, 1H), 3.23 (br s, 1H), 2.99 (br s, 1H), 2.17-2.05 (m, 2H), 2.02-1.94 (m, 1H), 1.92-1.77 (m, 3H), 1.65-1.42 (m, 8H) | 2.78 | 700.1 |
| 103 | 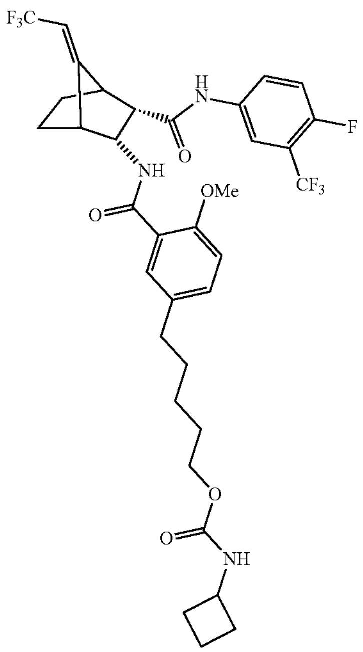 [SMILES: COc1ccc(CCCCCOC(=O)NC2CCC2)cc1C(=O)N[C@@H]1C2CCC(/C2=C/C(F)(F)F)[C@@H]1C(=O)Nc1ccc(F)c(C(F)(F)F)c1] | 5-(3-{[(2R,3S,7Z)-3-{[4-fluoro-3-(trifluoromethyl)phe-nyl]carbamoyl}-7-(2,2,2-trifluoroethylidene)bi-cyclo[2.2.1]heptan-2-yl]carbamoyl}-4-methoxyphenyl)pent-yl N-cyclobutylcarbamate | (500 MHz, DMSO-d6) δ 10.63 (s, 1H), 9.88 (br d, J = 7.3 Hz, 1H), 8.24 (dd, J = 6.4, 2.1 Hz, 1H), 7.83-7.70 (m, 2H), 7.51 (t, J = 9.8 Hz, 1H), 7.39-7.27 (m, 2H), 7.10 (d, J = 8.5 Hz, 1H), 5.95 (q, J = 7.6 Hz, 1H), 4.59-4.47 (m, 1H), 3.98 (s, 3H), 3.95-3.82 (m, 3H), 3.27 (br dd, J = 10.5, 4.4 Hz, 1H), 3.23 (br s, 1H), 3.05-2.91 (m, 1H), 2.10 (br d, J = 8.2 Hz, 2H), 2.01 (br t, J = 9.5 Hz, 1H), 1.93-1.80 (m, 3H), 1.64-1.42 (m, 8H), 1.36-1.21 (m, 2H) | 2.99 | 714.1 |

TABLE 2-continued

| Ex # | Structure | Name | $^1$H NMR. δ | LC RT (min) | Ion |
|---|---|---|---|---|---|
| 105 | 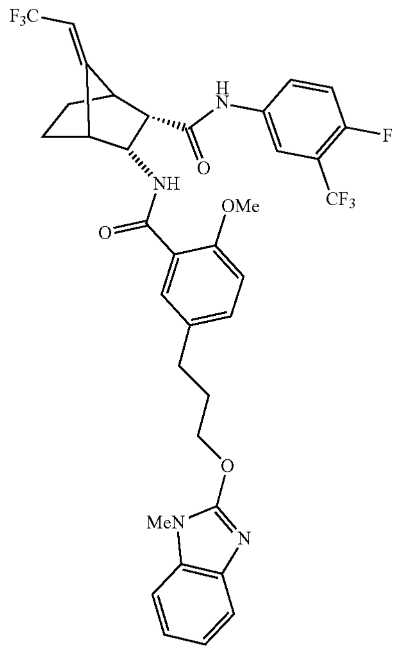 [SMILES: COc1ccc(CCCOc2nc3ccccc3n2C)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-(2-methoxy-5-{3-[(1-methyl-1H-1,3-benzodiazol-2-yl)oxy]propyl}benzamido)-7-(2,2,2-trifluoroethylidene)bicyclo[2.2.1]heptane-2-carboxamide | (500 MHz, DMSO-d6) 10.64 (s, 1H), 9.87 (br d, J = 7.0 Hz, 1H), 8.23 (dd, J = 6.4, 2.4 Hz, 1H), 7.89-7.74 (m, 2H), 7.50 (t, J = 9.9 Hz, 1H), 7.44-7.36 (m, 2H), 7.30 (dd, J = 6.0, 2.6 Hz, 1H), 7.16-7.04 (m, 3H), 5.93 (br d, J = 7.6 Hz, 1H), 4.57-4.38 (m, 3H), 3.97 (s, 3H), 3.30-3.17 (m, 2H), 2.99 (br s, 1H), 2.76 (br t, J = 7.3 Hz, 2H), 2.56 (s, 3H), 2.09 (quin, J = 7.0 Hz, 2H), 2.04-1.82 (m, 2H), 1.49 (br d, J = 7.3 Hz, 2H) | 2.77 | 719.0 |
| 107 | 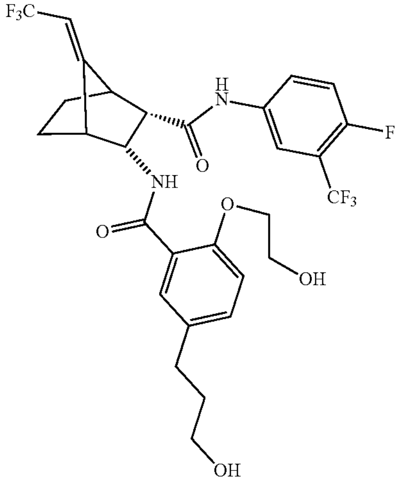 [SMILES: O=C(N[C@@H]1C2CCC(/C2=C/C(F)(F)F)[C@@H]1C(=O)Nc1ccc(F)c(C(F)(F)F)c1)c1cc(CCCO)ccc1OCCO] | (2S,3R,7Z)-N-[4-fluoro-3-(trifluoromethyl)phenyl]-3-[2-(2-hydroxyethoxy)-5-(3-hydroxypropyl)benzamido]-7-(2,2,2-trifluoroethylidene)bicyclo[2.2.1]heptane-2-carboxamide | (500 MHz, DMSO-d6) δ 10.57 (s, 1H), 9.52 (d, J = 7.9 Hz, 1H), 8.07 (dd, J = 6.7, 2.1 Hz, 1H), 7.79-7.72 (m, 1H), 7.70 (d, J = 2.1 Hz, 1H), 7.47 (t, J = 9.8 Hz, 1H), 7.29 (dd, J = 8.4, 2.0 Hz, 1H), 7.13 (d, J = 8.2 Hz, 1H), 5.93 (q, J = 7.9 Hz, 1H), 4.66-4.54 (m, 1H), 4.31-4.17 (m, 2H), 3.97-3.83 (m, 2H), 3.25 (dd, J = 11.0, 4.3 Hz, 1H), 3.18 (br s, 1H), 2.98 (br s, 1H), 2.06 (br d, J = 12.8 Hz, 2H), 1.66 (quin, J = 7.0 Hz, 2H), 1.51 (br d, J = 8.2 Hz, 2H) | 2.11 | 619.4 |

TABLE 2-continued

| Ex # | Structure | Name | $^1$H NMR. δ | LC RT (min) | Ion |
|---|---|---|---|---|---|
| 108 | 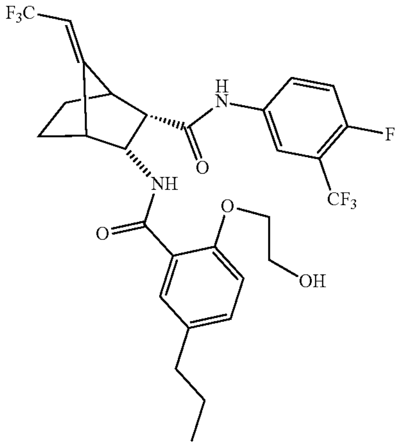 [SMILES: CCCc1ccc(OCCO)c(C(=O)N[C@@H]2C3CCC(/C3=C/C(F)(F)F)[C@@H]2C(=O)Nc2ccc(F)c(C(F)(F)F)c2)c1] | (2S,3R,7Z)-N-[4-fluoro-3-(trifluoromethyl)phenyl]-3-[2-(2-hydroxyethoxy)-5-propylbenzamido]-7-(2,2,2-trifluoroethylidene)bicyclo[2.2.1]heptane-2-carboxamide | (500 MHz, DMSO-d6) δ 10.57 (s, 1H), 9.50 (d, J = 7.6 Hz, 1H), 8.07 (dd, J = 6.1, 1.8 Hz, 1H), 7.82-7.71 (m, 1H), 7.67 (d, J = 2.1 Hz, 1H), 7.46 (t, J = 9.8 Hz, 1H), 7.28 (dd, J = 8.4, 2.0 Hz, 1H), 7.12 (d, J = 8.5 Hz, 1H), 5.93 (q, J = 7.8 Hz, 1H), 4.86 (t, J = 5.6 Hz, 1H), 4.67-4.56 (m, 1H), 4.30-.15 (m, 2H), 4.02-3.81 (m, 2H), 3.25 (br dd, J = 10.7, 4.0 Hz, 1H), 3.18 (br s, 1H), 2.98 (br s, 1H), 2.17-1.97 (m, 2H), 1.59-1.43 (m, 4H), 0.85 (t, J = 7.3 Hz, 3H) | 2.57 | 603.4 |
| 112 | 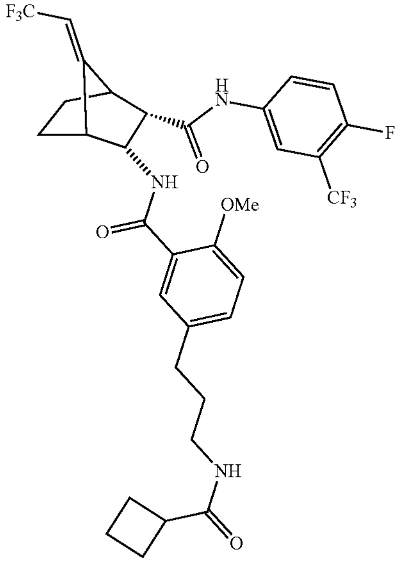 [SMILES: COc1ccc(CCCNC(=O)C2CCC2)cc1C(=O)N[C@@H]1C2CCC(/C2=C/C(F)(F)F)[C@@H]1C(=O)Nc1ccc(F)c(C(F)(F)F)c1] | (2S,3R,7Z)-3-{5-[3-(cyclobutylformamido)propyl]-2-methoxybenzamido}-N-[4-fluoro-3-(trifluoromethyl)phenyl]-7-(2,2,2-trifluoroethylidene)bicyclo[2.2.1]heptane-2-carboxamide | (500 MHz, DMSO-d6) δ 10.63 (s, 1H), 9.88 (br d, J = 7.0 Hz, 1H), 8.24 (dd, J = 6.4, 2.1 Hz, 1H), 7.84-7.73 (m, 2H), 7.64 (br t, J = 4.7 Hz, 1H), 7.51 (t, J = 9.8 Hz, 1H), 7.34 (dd, J = 8.2, 2.1 Hz, 1H), 7.10 (d, J = 8.5 Hz, 1H), 5.95 (q, J = 7.7 Hz, 1H), 4.62-4.44 (m, 1H), 3.98 (s, 3H), 3.27 (br dd, J = 11.0, 4.0 Hz, 1H), 3.23 (br s, 1H), 3.10-2.92 (m, 4H), 2.19-2.05 (m, 2H), 2.00 (q, J = 9.2 Hz, 3H), 1.93-1.80 (m, 2H), 1.80-1.70 (m, 1H), 1.65 (quin, J =7.3 Hz, 2H), 1.50 (br d, J = 6.7 Hz, 2H) | 2.52 | 670.1 |

TABLE 2-continued

| Ex # | Structure | Name | $^{1}$H NMR. δ | LC RT (min) | Ion |
|---|---|---|---|---|---|
| 113 | 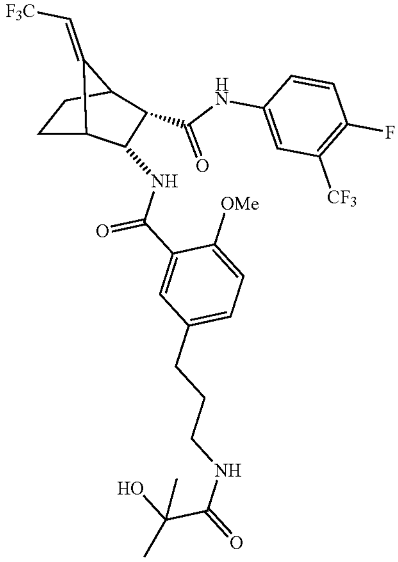 [SMILES: COc1ccc(CCCNC(=O)C(C)(C)O)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{5-[3-(2-hydroxy-2-methylpropanamido)propyl]-2-methoxybenzamido}-7-(2,2,2-trifluoroethylidene)bicyclo[2.2.1]heptane-2-carboxamide | (500 MHz, DMSO-d6) δ 10.64 (s, 1H), 9.88 (d, J = 7.0 Hz, 1H), 8.24 (dd, J = 6.4, 2.1 Hz, 1H), 7.85-7.75 (m, 2H), 7.68 (br t, J = 5.8 Hz, 1H), 7.51 (t, J = 9.8 Hz, 1H), 7.34 (dd, J = 8.4, 2.3 Hz, 1H), 7.10 (d, J = 8.5 Hz, 1H), 5.94 (q, J = 7.7 Hz, 1H), 5.32 (s, 1H), 4.59-4.47 (m, 1H), 3.98 (s, 3H), 3.28 (br dd, J = 10.5, 4.1 Hz, 1H), 3.23 (br s, 1H), 3.07 (q, J = 6.6 Hz, 2H), 2.99 (br s, 1H), 2.06-1.96 (m, 1H), 1.94-1.84 (m, 1H), 1.69 (quin, J = 7.4 Hz, 2H), 1.56-1.44 (m, 2H), 1.24 (s, 6H) | 2.23 | 674.1 |
| 114 | 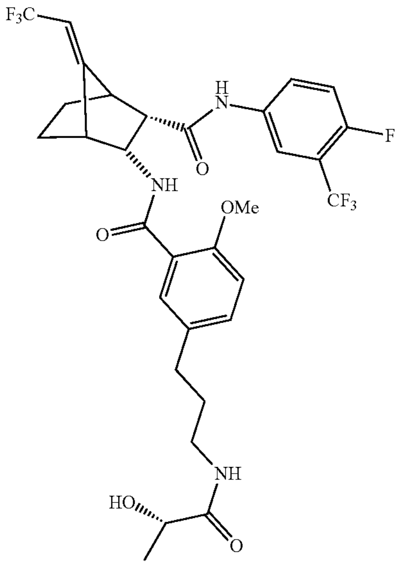 [SMILES: COc1ccc(CCCNC(=O)[C@H](C)O)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-(5-{3-[(2S)-2-hydroxypropanamido]propyl}-2-methoxybenzamido)-7-(2,2,2-trifluoroethyl)idene)bicyclo[2.2.1]heptane-2-carboxamide | (500 MHz, DMSO-d6) δ 10.64 (s, 1H), 9.88 (d, J = 7.0 Hz, 1H), 8.23 (dd, J = 6.4, 2.4 Hz, 1H), 7.84-7.68 (m, 3H), 7.50 (t, J = 9.8 Hz, 1H), 7.34 (dd, J = 8.4, 2.3 Hz, 1H), 7.10 (d, J = 8.2 Hz, 1H), 5.93 (q, J = 7.7 Hz, 1H), 4.60-4.45 (m, 1H), 3.97 (s, 4H), 3.27 (br dd, J = 10.8, 3.8 Hz, 1H), 3.23 (br s, 1H), 3.08 (q, J = 6.4 Hz, 2H), 2.99 (br s, 1H), 2.00 (br t, J = 9.3 Hz, 1H), 1.92-1.83 (m, 1H), 1.69 (dt, J = 14.8, 7.2 Hz, 2H), 1.55-1.40 (m, 2H), 1.21 (d, J = 6.7 Hz, 3H) | 2.18 | 660.2 |

TABLE 2-continued

| Ex # | Structure | Name | $^1$H NMR. δ | LC RT (min) | Ion |
| --- | --- | --- | --- | --- | --- |
| 115 | 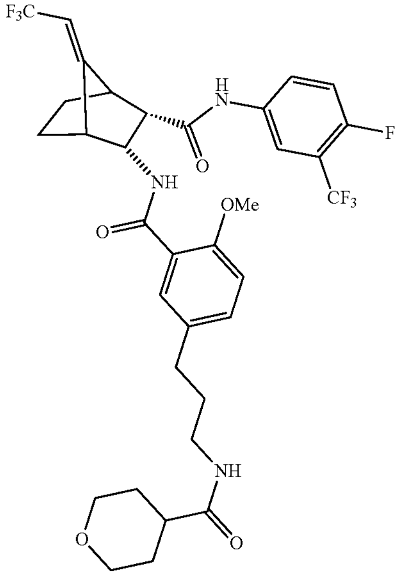 [SMILES: COc1ccc(CCCNC(=O)C2CCOCC2)cc1C(=O)N[C@@H]1C2CCC(/C2=C/C(F)(F)F)[C@@H]1C(=O)Nc1ccc(F)c(C(F)(F)F)c1] | N-[3-(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)propyl]oxane-4-carboxamide | (500 MHz, DMSO-d6) δ 10.65 (s, 1H), 9.86 (d, J = 7.0 Hz, 1H), 8.20 (dd, J = 6.1, 2.1 Hz, 1H), 7.83 (br t, J = 5.2 Hz, 1H), 7.80-7.70 (m, 2H), 7.48 (t, J = 9.6 Hz, 1H), 7.33 (dd, J = 8.4, 2.3 Hz, 1H), 7.09 (d, J = 8.5 Hz, 1H), 5.91 (q, J = 7.8 Hz, 1H), 4.57-4.44 (m, 1H), 3.95 (s, 3H), 3.88-3.77 (m, 2H), 3.35-3.16 (m, 4H), 3.03 (q, J = 6.6 Hz, 2H), 2.98 (br s, 1H), 2.33 (br t, J = 7.5 Hz, 1H), 2.04-1.94 (m, 1H), 1.90-1.80 (m, 1H), 1.65 (quin, J = 7.3 Hz, 2H), 1.60-1.52 (m, 4H), 1.51-1.40 (m, 2H) | 2.39 | 700.4 |
| 116 | 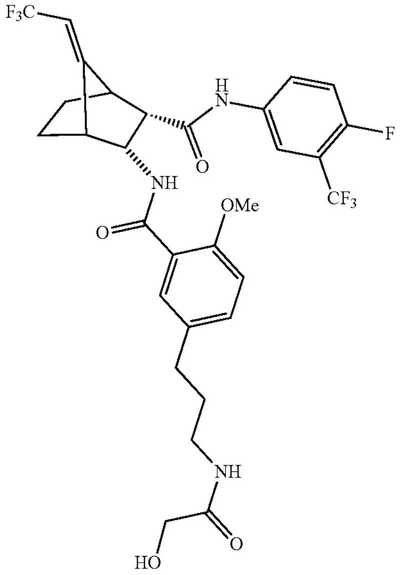 [SMILES: COc1ccc(CCCNC(=O)CO)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{5-[3-(2-hydroxyacetamido)propyl]-2-methoxybenzamido}-7-(2,2,2-trifluoroethylidene)bicyclo[2.2.1]heptane-2-carboxamide | (500 MHz, DMSO-d6) δ 10.64 (s, 1H), 9.88 (d, J = 7.0 Hz, 1H), 8.22 (dd, J = 6.6, 2.3 Hz, 1H), 7.85-7.73 (m, 3H), 7.50 (t, J = 9.8 Hz, 1H), 7.34 (dd, J = 8.2, 2.1 Hz, 1H), 7.10 (d, J = 8.5 Hz, 1H), 5.93 (q, J = 7.7 Hz, 1H), 4.58-4.50 (m, 1H), 3.97 (s, 3H), 3.80 (d, J = 5.8 Hz, 1H), 3.27 (dd, J = 10.8, 4.1 Hz, 1H), 3.22 (br s, 1H), 3.11 (q, J = 6.4 Hz, 2H), 2.99 (br s, 1H), 2.00 (br t, J = 9.2 Hz, 1H), 1.88 (br t, J = 8.7 Hz, 1H), 1.70 (quin, J = 7.5 Hz, 2H), 1.56-1.41 (m, 2H) protons obscured. | 2.26 | 646.1 |

TABLE 2-continued

| Ex # | Structure | Name | $^1$H NMR. δ | LC RT (min) | Ion |
|---|---|---|---|---|---|
| 118 | 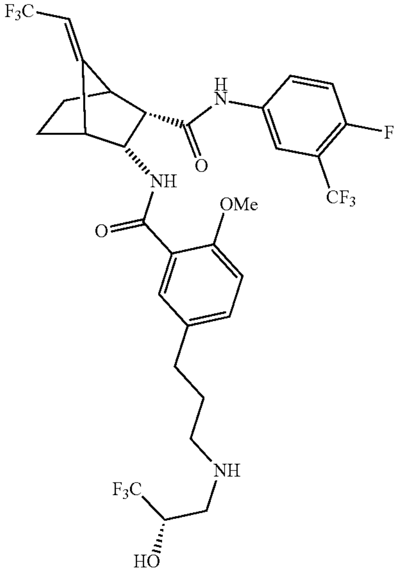 [SMILES: COc1ccc(CCCNC[C@H](O)C(F)(F)F)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-[2-methoxy-5-(3-{[(2S)-3,3,3-trifluoro-2-hydroxypropyl]amino}propyl)benzamido]-7-(2,2,2-trifluoroethylidene)bicyclo[2.2.1]heptane-2-carboxamide | (500 MHz, DSO-d6) δ 10.64 (s, 1H), 9.87 (br d, J = 7.0 Hz, 1H), 8.23 (dd, J = 6.4, 2.1 Hz, 1H), 7.84-7.71 (m, 2H), 7.50 (t, J = 9.8 Hz, 1H), 7.34 (dd, J = 8.5, 2.1 Hz, 1H), 7.10 (d, J = 8.5 Hz, 1H), 5.94 (q, J = 7.6 Hz, 1H), 4.53 (br t, J = 10.4 Hz, 1H), 4.08-3.78 (m, 4H), 3.27 (br dd, J = 10.8, 4.1 Hz, 1H), 3.23 (br s, 1H), 2.99 (br s, 1H), 2.76-2.60 (m, 2H), 2.01 (br t, J = 9.0 Hz, 1H), 1.93-1.82 (m, 3H), 1.73-1.63 (m, 2H), 1.50 (br d, J = 6.7 Hz, 2H). DMSO and water obscure some peaks. | 2.24 | 700.4 |
| 119 | 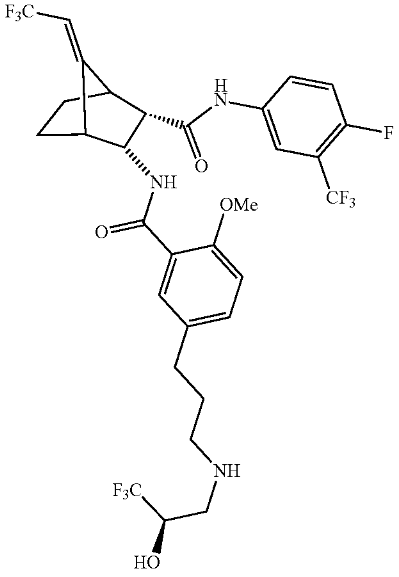 [SMILES: COc1ccc(CCCNC[C@@H](O)C(F)(F)F)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-[2-methoxy-5-(3-{[(2R)-3,3,3-trifluoro-2-hydroxypropyl]amino}propyl)benzamido]-7-(2,2,2-trifluoroethylidene)bicyclo[2.2.1]heptane-2-carboxamide | (500 MHz, DMSO-d6) δ 10.65 (s, 1H), 9.85 (d, J = 7.0 Hz, 1H), 8.19 (dd, J = 6.3, 2.0 Hz, 1H) 7.83-7.70 (m, 2H), 7.48 (t, J = 9.8 Hz, 1H), 7.33 (dd, J = 8.4, 2.0 Hz, 1H), 7.09 (d, J = 8.5 Hz, 1H), 5.90 (q, J = 8.0 Hz, 1H), 4.57-4.45 (m, 1H), 4.02 (td, J = 7.9, 2.6 Hz, 1H), 3.95 (s, 2H), 3.75-3.58 (m, 1H), 3.24 (br dd, J = 11.0, 4.3 Hz, 1H), 3.22-3.16 (m, 1H), 2.97 (br s, 1H), 2.79-2.68 (m, 1H), 2.67-2.58 (m, 1H), 2.04-1.95 (m, 1H), 1.93-1.80 (m, 3H), 1.67 (quin, J = 7.2 Hz, 2H), 1.55-1.41 (m, 2H) proton obscured | 2.28 | 700.2 |

TABLE 2-continued

| Ex # | Structure | Name | $^1$H NMR. δ | LC RT (min) | Ion |
|---|---|---|---|---|---|
| 121 | 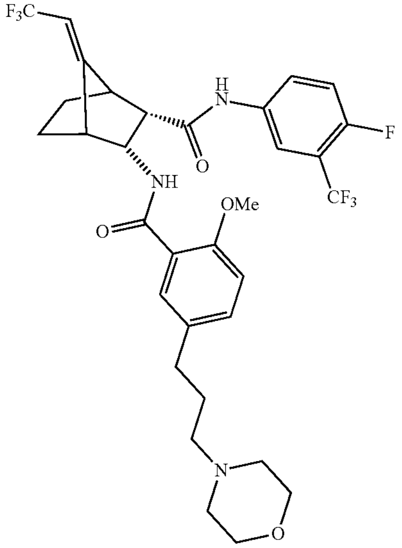 [SMILES: COc1ccc(CCCN2CCOCC2)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{2-methoxy-5-[3-(morpholin-4-yl)propyl]benzamido}-7-(2,2,2-trifluoroethylidene)bicyclo[2.2.1]heptane-2-carboxamide | (500 MHz, DMSO-d6) δ 9.85 (d, J = 7.0 Hz, 1H), 8.29-8.17 (m, 1H), 7.83-7.72 (m, 2H), 7.50 (t, J = 9.8 Hz, 1H), 7.34 (dd, J = 8.4, 2.3 Hz, 1H), 7.09 (d, J = 8.5 Hz, 1H), 5.93 (q, J = 8.2 Hz, 1H), 4.58-4.45 (m, 1H), 3.96 (s, 3H), 3.56 (br t, J = 4.4 Hz, 1H), 3.27 (dd, J = 11.1, 4.1 Hz, 1H), 3.22 (br s, 1H), 2.99 (br s, 1H), 2.31 (br s, 3H), 2.23 (t, J = 7.2 Hz, 2H), 2.05-1.96 (m, 1H), 1.93-1.79 (m, 2H), 1.74-1.62 (m, 2H), 1.49 (br d, J = 7.0 Hz, 2H) | 2.15 | 658.3 |
| 122 | 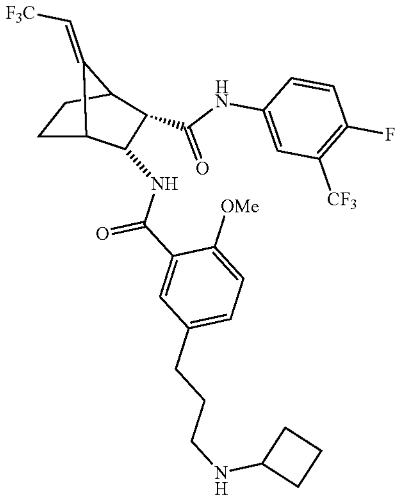 [SMILES: COc1ccc(CCCNC2CCC2)cc1C(=O)N[C@@H]1C2CCC(/C2=C/C(F)(F)F)[C@@H]1C(=O)Nc1ccc(F)c(C(F)(F)F)c1] | (2S,3R,7Z)-3-{5-[3-(cyclobutylamino)propyl]-2-methoxybenzamido}-N-[4-fluoro-3-(trifluoromethyl)phenyl]-7-(2,2,2-trifluoroethylidene)bicyclo[2.2.1]heptane-2-carboxamide | (500 MHz, DMSO-d6) δ 10.69 (s, 1H), 9.91 (d, J = 7.0 Hz, 1H), 8.81-8.59 (m, 1H), 8.25 (dd, J = 6.3, 2.3 Hz, 1H), 7.86-7.75 (m, 2H), 7.51 (t, J = 9.6 Hz, 1H), 7.36 (dd, J = 8.2, 2.1 Hz, 1H), 7.14 (d, J = 8.5 Hz, 1H), 5.94 (q, J = 7.8 Hz, 1H), 4.57-4.45 (m, 1H), 3.99 (s, 3H), 3.68 (br d, J = 5.2 Hz, 1H), 3.28 (br dd, J = 10.8, 4.1 Hz, 1H), 3.23 (br s, 1H), 3.00 (br d, J = 3.4 Hz, 1H), 2.77 (br d, J = 6.7 Hz, 2H), 2.63 (br t, J = 7.5 Hz, 2H), 2.25-2.05 (m, 4H), 1.99 (br t, J = 9.5 Hz, 1H), 1.92-1.69 (m, 5H), 1.50 (br d, J = 7.3 Hz, 2H) | 2.19 | 614.9 |

TABLE 2-continued

| Ex # | Structure | Name | $^1$H NMR. δ | LC RT (min) | Ion |
|---|---|---|---|---|---|
| 125 | 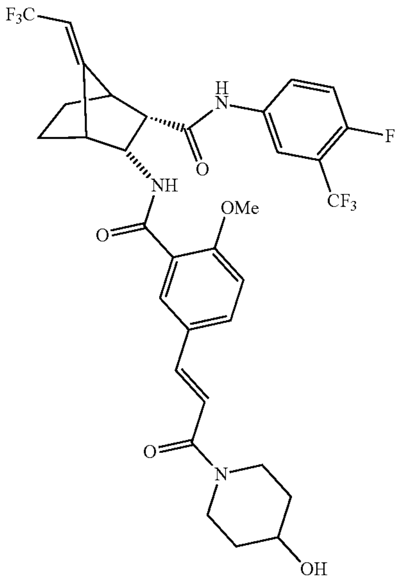 [SMILES: COc1ccc(/C=C/C(=O)N2CCC(O)CC2)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{5-[(1E)-3-(4-hydroxypiperidin-1-yl)-3-oxoprop-1-en-1-yl]-2-methoxybenzamido}-7-(2,2,2-trifluoroethylidene)bicyclo[2.2.1]heptane-2-carboxamide | (500 MHz, DMSO-d6) δ 10.68 (s, 1H), 9.92 (br d, J = 6.7 Hz, 1H), 8.26-8.13 (m, 2H), 7.87 (dd, J = 8.5, 1.8 Hz, 1H), 7.79 (br dd, J = 5.5, 2.7 Hz, 1H), 7.50 (br t, J = 9.6 Hz, 1H), 7.44 (d, J = 15.6 Hz, 1H), 7.23 (d, J = 8.5 Hz, 1H), 7.15 (d, J = 15.3 Hz, 1H), 5.93 (q, J = 7.9 Hz, 1H), 4.94 (br d, J = 4.3 Hz, 1H), 4.59-4.45 (m, 1H), 4.07-3.96 (m, 4H), 3.78-3.53 (m, 2H), 3.38-3.17 (m, 3H), 3.16-3.05 (m, 1H), 3.00 (br s, 1H), 2.05-1.85 (m, 2H), 1.83-1.67 (m, 2H), 1.50 (br d, J = 6.7 Hz, 2H), 1.41-1.22 (m, 2H) | 2.27 | 684.0 |
| 126 | 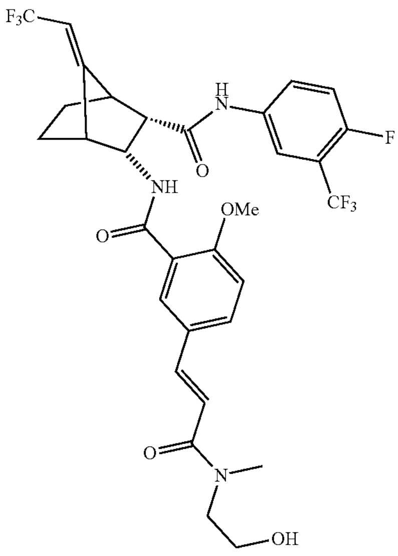 [SMILES: COc1ccc(/C=C/C(=O)N(C)CCO)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{5-[(1E)-2-[(2-hydroxyethyl)(methyl)carbamoyl]eth-1-en-1-yl]-2-methoxybenzamido}-7-(2,2,2-trifluoroethylidene)bicyclo[2.2.1]heptane-2-carboxamide | (500 MHz, DMSO-d6) δ 10.65 (s, 1H), 9.90 (br d, J = 6.7 Hz, 1H), 8.22 (dd, J = 6.6, 2.3 Hz, 1H), 7.91 (d, J = 2.4 Hz, 1H), 7.83-7.75 (m, 1H), 7.58-7.44 (m, 3H), 7.18 (d, J = 8.9 Hz, 1H), 5.94 (q, J = 7.8 Hz, 1H), 4.60-4.45 (m, 1H), 4.09 (br t, J = 6.4 Hz, 2H), 4.01 (s, 3H), 3.97 (br dd, J = 16.2, 8.2 Hz, 1H), 3.27 (dd, J = 10.8, 4.1 Hz, 1H), 3.23 (br s, 1H), 2.99 (br s, 1H), 2.70 (br t, J = 6.4 Hz, 2H), 2.18-2.07 (m, 2H), 2.02-1.83 (m, 4H), 1.61-1.42 (m, 4H) | 2.72 | 696.3 |

TABLE 2-continued

| Ex # | Structure | Name | $^1H$ NMR. δ | LC RT (min) | Ion |
|---|---|---|---|---|---|
| 127 | 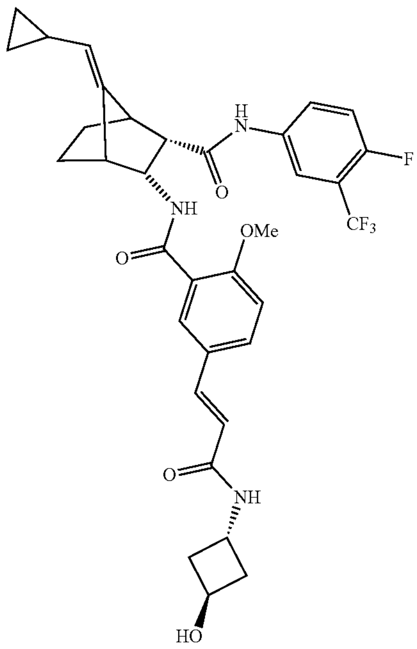 [SMILES: COc1ccc(/C=C/C(=O)N[C@H]2C[C@H](O)C2)cc1C(=O)N[C@@H]1C2CCC(/C2=C/C2CC2)[C@@H]1C(=O)Nc1ccc(F)c(C(F)(F)F)c1] | (2S,3R,7Z)-7-(cyclopropylmethylidene)-N-[4-fluoro-3-(trifluoromethyl)phenyl]-3-{2-methoxy-5-[(1E)-2-{[(1r,3r)-3-hydroxycyclobutyl]carbamoyl}eth-1-en-1-yl]benzamido}bicyclo[2.2.1]heptane-2-carboxamide | (500 MHz, DMSO-d6) δ 10.53 (s, 1H), 9.88 (br d, J = 7.2 Hz, 1H), 8.44 (br d, J = 6.3 Hz, 1H), 8.18 (br d, J = 4.6 Hz, 1H), 8.11 (s, 1H), 7.84-7.73 (m, 1H), 7.69 (dd, J = 8.5, 2.0 Hz, 1H), 7.45 (br t, J = 9.6 Hz, 1H), 7.35 (d, J = 15.6 Hz, 1H), 7.22 (d, J = 8.7 Hz, 1H), 6.51 (d, J = 15.8 Hz, 1H), 4.68 (d, J = 9.7 Hz, 1H), 4.49-4.35 (m, 1H), 4.34-4.20 (m, 2H), 4.01 (s, 3H), 3.21-3.05 (m, 2H), 2.98 (s, 1H), 2.70 (br s, 1H), 2.14 (t, J = 6.3 Hz, 4H), 1.92-1.67 (m, 3H), 1.57-1.29 (m, 3H), 0.80-0.62 (m, 2H), 0.40-0.22 (m, 2H) | 2.29 | 641.9 |
| 128 | 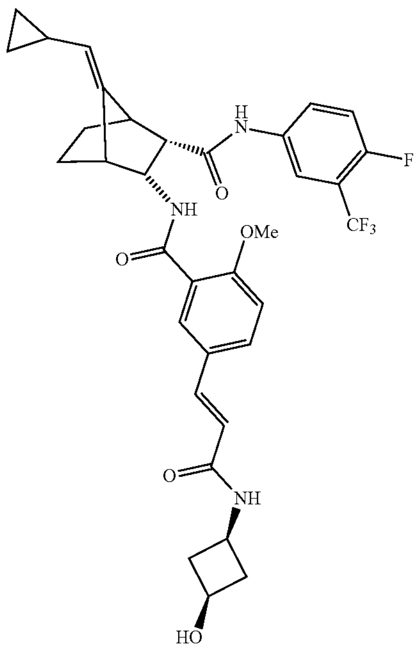 [SMILES: COc1ccc(/C=C/C(=O)N[C@H]2C[C@@H](O)C2)cc1C(=O)N[C@@H]1C2CCC(/C2=C/C2CC2)[C@@H]1C(=O)Nc1ccc(F)c(C(F)(F)F)c1] | (2S,3R,7Z)-7-(cyclopropylmethylidene)-N-[4-fluoro-3-(trifluoromethyl)phenyl]-3-{2-methoxy-5-[(1E)-2-{[(1s,3s)-3-hydroxycyclobutyl]carbamoyl}eth-1-en-1-yl]benzamido}bicyclo[2.2.1]heptane-2-carboxamide | (500 MHz, DMSO-d6) 10.28 (s, 1H), 9.63 (br d, J = 7.1 Hz, 1H), 8.09 (br d, J = 7.5 Hz, 1H), 7.93 (br d, J = 6.2 Hz, 1H), 7.87 (s, 1H), 7.58-7.48 (m, 1H), 7.43 (dd, J = 8.6, 2.2 Hz, 1H), 7.21 (br t, J = 9.7 Hz, 1H), 7.11 (d, J = 15.7 Hz, 1H), 6.97 (d, J = 8.7 Hz, 1H), 6.25 (d, J = 15.7 Hz, 1H), 4.43 (d, J = 9.6 Hz, 1H), 4.18 (br t, J = 10.2 Hz, 1H), 3.76 (s, 3H), 3.67-3.47 (m, 3H), 2.89 (br dd, J = 10.8, 3.6 Hz, 1H), 2.84 (br s, 1H), 2.73 (s, 1H), 2.45 (br s, 1H), 1.68-1.44 (m, 5H), 1.33-1.03 (m, 4H), 0.55-0.39 (m, 2H), 0.15--0.02 (m, 2H) | 2.25 | 641.9 |

TABLE 2-continued

| Ex # | Structure | Name | $^1$H NMR. δ | LC RT (min) | Ion |
|---|---|---|---|---|---|
| 129 | 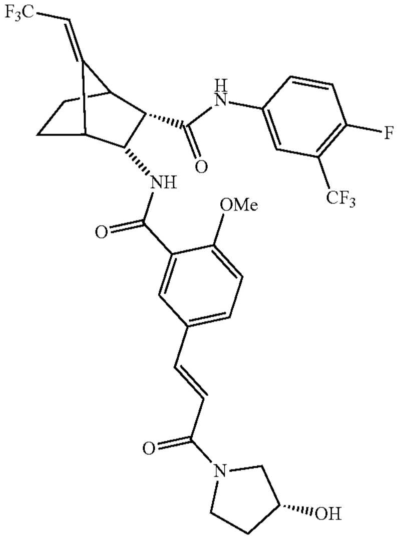 [SMILES: COc1ccc(/C=C/C(=O)N2CC[C@@H](O)C2)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{5-[(1E)-3-[(3R)-3-hydroxypyrrolidin-1-yl]-3-oxoprop-1-en-1-yl]-2-methoxybenzamido}-7-(2,2,2-trifluoroethylidene)bicyclo[2.2.1]heptane-2-carboxamide | (500 MHz, DMSO-d6) δ 10.68 (s, 1H), 9.94 (br d, J = 6.7 Hz, 1H), 8.34-8.15 (m, 2H), 7.90-7.74 (m, 2H), 7.59-7.36 (m, 2H), 7.25 (d, J = 8.5 Hz, 1H), 6.97-6.75 (m, 1H), 5.96 (q, J = 7.7 Hz, 1H), 5.14-4.91 (m, 1H), 4.63-4.48 (m, 1H), 4.44-4.25 (m, 1H), 4.05 (s, 3H), 3.84-3.65 (m, 1H), 3.58-3.38 (m, 1H), 3.34-3.19 (m, 1H), 3.01 (br s, 1H), 2.08-1.83 (m, 3H), 1.81 (br d, J = 3.1 Hz, 1H), 1.58-1.39 (m, 2H) | 2.30 | 670.1 |
| 130 | 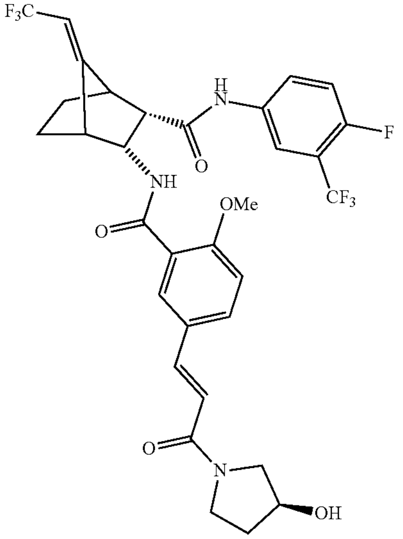 [SMILES: COc1ccc(/C=C/C(=O)N2CC[C@H](O)C2)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{5-[(1E)-3-[(3S)-3-hydroxypyrrolidin-1-yl]-3-oxoprop-1-en-1-yl]-2-methoxybenzamido}-7-(2,2,2-trifluoroethylidene)bicyclo[2.2.1]heptane-2-carboxamide | (500 MHz, DMSO-d6) δ 10.67 (s, 1H), 9.93 (br dd, J = 6.4, 3.1 Hz, 1H), 8.28-8.12 (m, 2H), 7.90-7.71 (m, 2H), 7.57-7.35 (m, 2H), 7.23 (br d, J = 8.5 Hz, 1H), 6.95-6.73 (m, 1H), 5.93 (q, J = 7.7 Hz, 1H), 5.21-4.98 (m, 1H), 4.62-4.46 (m, 1H), 4.44-4.21 (m, 1H), 4.03 (s, 3H), 3.84-3.67 (m, 1H), 3.63-3.34 (m, 2H), 3.33-3.20 (m, 1H), 3.00 (br s, 1H), 2.10-1.70 (m, 4H), 1.60-1.35 (m, 2H) | 2.30 | 669.9 |

TABLE 2-continued

| Ex # | Structure | Name | $^1H$ NMR. δ | LC RT (min) | Ion |
|---|---|---|---|---|---|
| 131 | 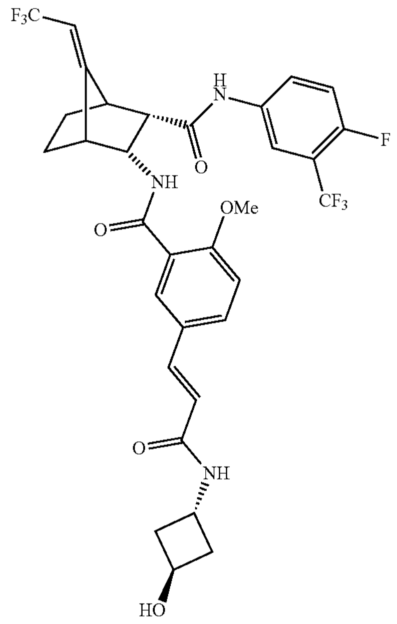 | (2S,3R,7Z)-N-[4-fluoro-3-(trifluoromethyl)phenyl]-3-{2-methoxy-5-[(1E)-2-{[(1r,3r)-3-hydroxycyclobutyl]carbamoyl}eth-1-en-1-yl]benzamido}-7-(2,2,2-trifluoroethylidene)bicyclo[2.2.1]heptane-2-carboxamide | (500 MHz, DMSO-d6) δ 10.65 (s, 1H), 9.92 (d, J = 6.9 Hz, 1H), 8.36 (br d, J = 6.8 Hz, 1H), 8.22 (dd, J = 6.4, 2.2 Hz, 1H), 8.15 (d, J = 2.2 Hz, 1H), 7.79 (dt, J = 7.9, 4.1 Hz, 1H), 7.69 (dd, J = 8.6, 2.4 Hz, 1H), 7.49 (t, J = 9.7 Hz, 1H), 7.35 (d, J = 15.8 Hz, 1H), 7.23 (d, J = 8.8 Hz, 1H), 6.54 (d, J = 15.8 Hz, 1H), 5.93 (q, J = 7.7 Hz, 1H), 4.61-4.47 (m, 1H), 4.37-4.22 (m, 2H), 4.03 (s, 3H), 3.33-3.16 (m, 2H), 2.99 (s, 1H), 2.13 (t, J = 6.3 Hz, 4H), 2.02-1.79 (m, 2H), 1.49 (br d, J = 7.0 Hz, 2H) | 2.25 | 670.2 |
| 132 | 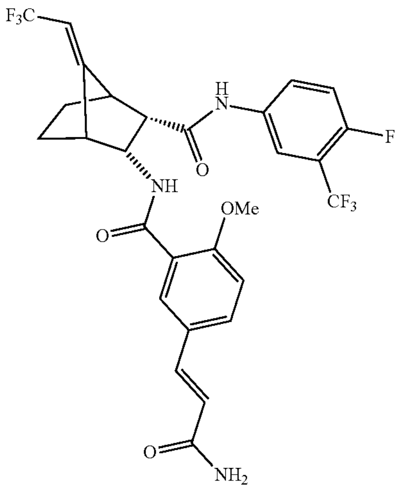 [SMILES: COc1ccc(/C=C/C(N)=O)cc1C(=O)N[C@@H]1C2CCC(/C2=C/C(F)(F)F)[C@@H]1C(=O)Nc1ccc(F)c(C(F)(F)F)c1] | (2S,3R,7Z)-3-{5-[(1E)-2-carbamoyleth-1-en-1-yl]-2-methoxybenzamido}-N-[4-fluoro-3-(trifluoromethyl)phenyl]-7-(2,2,2-trifluoroethylidene)bicyclo[2.2.1]heptane-2-carboxamide | (500 MHz, DMSO-d6) δ 10.68 (s, 1H), 9.94 (d, J = 7.0 Hz, 1H), 8.24 (dd, J = 6.6, 2.3 Hz, 1H), 8.16 (d, J = 2.1 Hz, 1H), 7.85-7.77 (m, 1H), 7.71 (dd, J = 8.5, 2.1 Hz, 1H), 7.57-7.46 (m, 2H), 7.39 (d, J = 15.9 Hz, 1H), 7.25 (d, J = 8.5 Hz, 1H), 7.07 (br s, 1H), 6.56 (d, J = 15.9 Hz, 1H), 5.95 (q, J = 7.8 Hz, 1H), 4.54 (ddd, J = 10.8, 6.3, 4.3 Hz, 1H), 4.04 (s, 3H), 3.29 (br dd, J = 10.1, 4.3 Hz, 1H), 3.26 (br s, 1H), 3.00 (br s, 1H), 1.97 (br t, J = 9.0 Hz, 1H), 1.93-1.83 (m, 1H), 1.50 (br d, J = 5.8 Hz, 2H) | 2.21 | 600.1 |

TABLE 2-continued

| Ex # | Structure | Name | $^1$H NMR. δ | LC RT (min) | Ion |
|---|---|---|---|---|---|
| 133 | 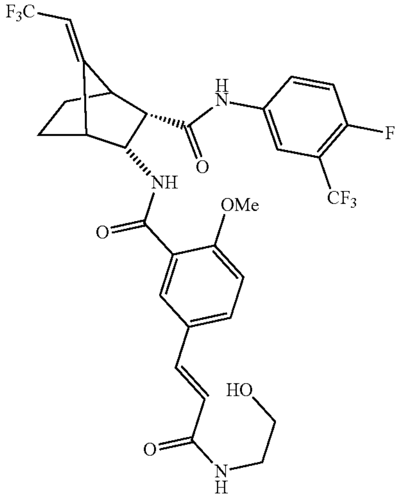 [SMILES: COc1ccc(/C=C/C(=O)NCCO)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{5-[(1E)-2-[(2-hydroxyethyl)carbamoyl]eth-1-en-1-yl]-2-methoxybenzamido}-7-(2,2,2-trifluoroethylidene)bicyclo[2.2.1]heptane-2-carboxamide | (500 MHz, DMSO-d6) δ 10.67 (s, 1H), 9.94 (d, J = 7.0 Hz, 1H), 8.23 (dd, J = 6.3, 2.3 Hz, 1H), 8.15 (d, J = 2.1 Hz, 1H), 8.11 (br t, J = 5.5 Hz, 1H), 7.80 (br dd, J = 8.2, 3.4 Hz, 1H), 7.71 (dd, J = 8.5, 2.1 Hz, 1H), 7.51 (t, J = 9.8 Hz, 1H), 7.39 (d, J = 15.9 Hz, 1H), 7.25 (d, J = 8.9 Hz, 1H), 6.62 (d, J = 15.9 Hz, 1H), 5.94 (q, J = 7.6 Hz, 1H), 4.79 (t, J = 5.3 Hz, 1H), 4.59-4.49 (m, 1H), 4.04 (s, 3H), 3.34-3.21 (m, 3H), 3.00 (br s, 1H), 2.04-1.83 (m, 2H), 1.58-1.43 (m, 2H) | 2.19 | 644.1 |
| 134 | 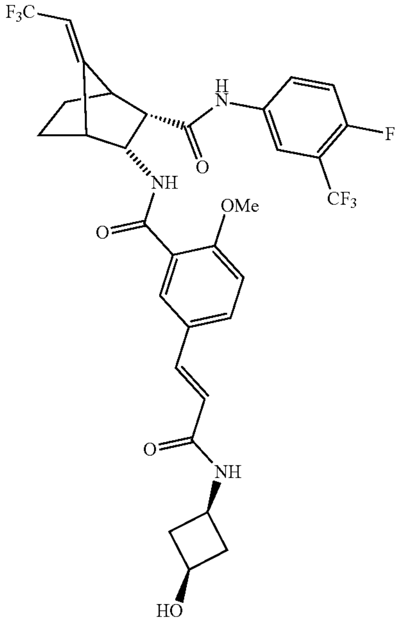 [SMILES: COc1ccc(/C=C/C(=O)N[C@H]2C[C@@H](O)C2)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-{2-methoxy-5-[(1E)-2-{[(1s,3s)-3-hydroxycyclobutyl]carbamoyl}eth-1-en-1-yl]benzamido}-7-(2,2,2-trifluoroethylidene)bicyclo[2.2.1]heptane-2-carboxamide | (500 MHz, DMSO-d6) δ 10.67 (s, 1H), 9.93 (br d, J = 7.0 Hz, 1H), 8.33 (br d, J = 7.3 Hz, 1H), 8.25-8.19 (m, 1H), 8.14 (d, J = 1.8 Hz, 1H), 7.86-7.76 (m, 1H), 7.70 (dd, J = 8.4, 1.7 Hz, 1H), 7.50 (br t, J = 9.8 Hz, 1H), 7.37 (d, J = 15.9 Hz, 1H), 7.24 (d, J = 8.5 Hz, 1H), 6.53 (d, J = 15.6 Hz, 1H), 5.93 (q, J = 7.5 Hz, 1H), 4.60-4.46 (m, 1H), 4.03 (s, 3H), 3.91-.372 (m, 2H), 3.65-3.50 (m, 2H), 3.34-3.18 (m, 2H), 2.99 (br s, 1H), 2.04-1.83 (m, 2H), 1.80-1.69 (m, 2H), 1.57-1.41 (m, 2H) | 2.17 | 670.2 |

TABLE 2-continued

| Ex # | Structure | Name | $^1H$ NMR. δ | LC RT (min) | Ion |
|---|---|---|---|---|---|
| 135 | 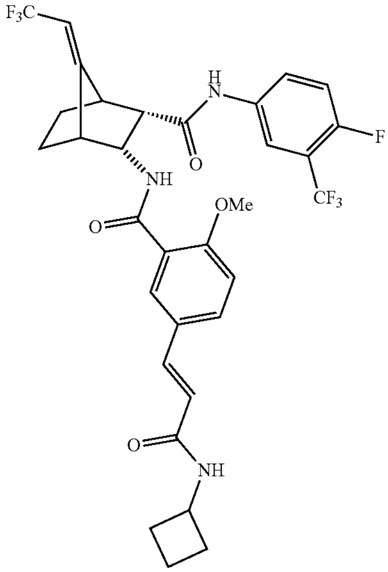 | (2S,3R,7Z)-3-{5-[(1E)-2-(cyclobutylcarbamoyl)eth-1-en-1-yl]-2-methoxybenzamido}-N-[4-fluoro-3-(trifluoromethyl)phenyl]-7-(2,2,2-trifluoroethylidene)bicyclo[2.2.1]heptane-2-carboxamide | (500 MHz, DMSO-d6) δ 10.66 (s, 1H), 9.93 (d, J = 7.0 Hz, 1H), 8.36 (d, J = 7.6 Hz, 1H), 8.22 (dd, J = 6.6, 2.3 Hz, 1H), 8.15 (d, J = 2.1 Hz, 1H), 7.85-7.76 (m, 1H), 7.70 (dd, J = 8.7, 2.3 Hz, 1H), 7.51 (t, J = 9.8 Hz, 1H), 7.37 (d, J = 15.6 Hz, 1H), 7.24 (d, J = 8.5 Hz, 1H), 6.52 (d, J = 15.6 Hz, 1H), 5.94 (q, J = 7.9 Hz, 1H), 4.61-4.46 (m, 1H), 4.38-4.23 (m, 1H), 3.35-3.18 (m, 2H), 3.00 (br s, 1H), 2.30-2.15 (m, 2H), 2.07-1.84 (m, 4H), 1.76-1.60 (m, 2H), 1.50 (br d, J = 6.4 Hz, 2H) | 2.44 | 654.4 |
| 136 | 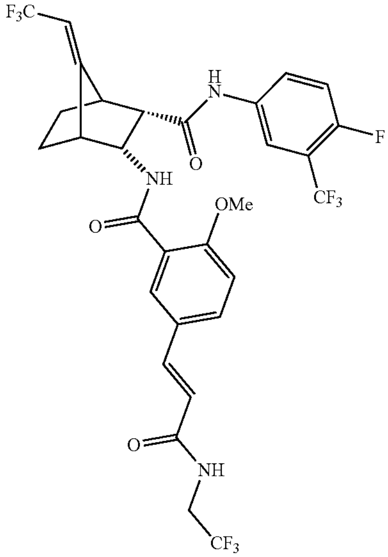 | (2S,3R,7Z)-N-[4-fluoro-3-(trifluoromethyl)phenyl]-3-{2-methoxy-5-[(1E)-2-[(2,2,2-trifluoroethyl)carbamoyl]eth-1-en-1-yl]benzamido}-7-(2,2,2-trifluoroethylidene)bicyclo[2.2.1]heptane-2-carboxamide | (500 MHz, DMSO-d6) δ 10.66 (s, 1H), 9.94 (d, J = 6.7 Hz, 1H), 8.72 (t, J = 6.4 Hz, 1H), 8.28-8.14 (m, 2H), 7.86-7.69 (m, 2H), 7.56-7.45 (m, 2H), 7.26 (d, J = 8.5 Hz, 1H), 6.65 (d, J = 15.9 Hz, 1H), 5.94 (q, J = 7.8 Hz, 1H), 4.54 (ddd, J = 10.7, 6.7, 4.0 Hz, 1H), 4.04 (s, 4H), 3.39-3.11 (m, 2H), 3.00 (br s, 1H), 2.08-1.83 (m, 2H), 1.50 (br d, J = 7.3 Hz, 2H) | 2.49 | 682.1 |

TABLE 2-continued

| Ex # | Structure | Name | $^1$H NMR. δ | LC RT (min) | Ion |
|---|---|---|---|---|---|
| 137 | 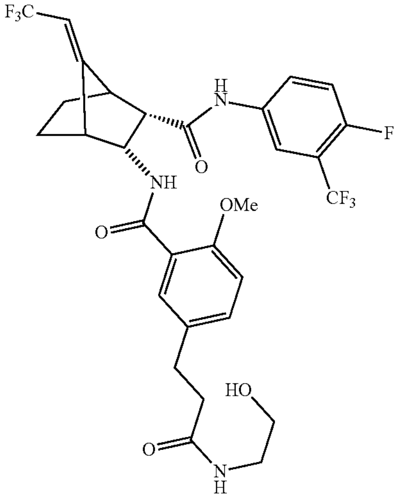 [SMILES: COc1ccc(CCC(=O)NCCO)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-(5-{2-[(2-hydroxyethyl)carbamoyl]ethyl}-2-methoxybenzamido)-7-(2,2,2-trifluoroethylidene)bicyclo[2.2.1]heptane-2-carboxamide | (500 MHz, DMSO-d6) δ 10.65 (s, 1H), 9.87 (d, J = 7.0 Hz, 1H), 8.22 (dd, J = 6.1, 2.1 Hz, 1H), 7.84 (br t, J = 5.0 Hz, 1H), 7.82-7.73 (m, 2H), 7.50 (t, J = 9.8 Hz, 1H), 7.33 (dd, J = 8.5, 2.1 Hz, 1H), 7.09 (d, J = 8.5 Hz, 1H), 5.93 (q, J = 7.8 Hz, 1H), 4.69 (t, J = 5.5 Hz, 1H), 4.57-4.45 (m, 1H), 3.96 (s, 3H), 3.51-3.43 (m, 1H), 3.36 (q, J = 5.9 Hz, 1H), 3.27 (dd, J = 10.7, 4.3 Hz, 1H), 3.23 (br s, 1H), 3.10 (q, J = 6.1 Hz, 2H), 2.99 (br s, 1H), 2.82-2.71 (m, 3H), 2.40-2.29 (m, 2H), 2.03-1.95 (m, 1H), 1.90-1.83 (m, 1H), 1.49 (br d, J = 7.0 Hz, 2H) | 2.15 | 645.9 |
| 138 | 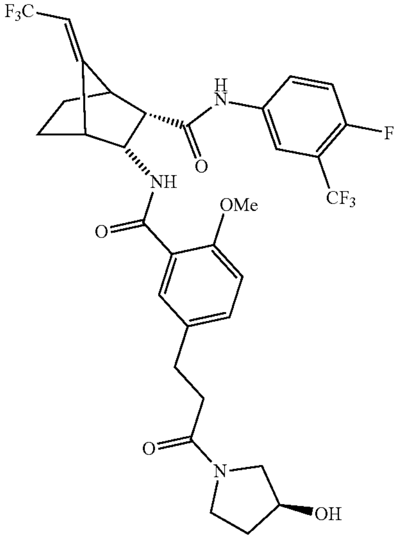 [SMILES: COc1ccc(CCC(=O)N2CC[C@H](O)C2)cc1C(=O)N[C@@H]1C2CCC(/C2=C/C(F)(F)F)[C@@H]1C(=O)Nc1ccc(F)c(C(F)(F)F)c1] | (2S,3R,7Z)-N-[4-fluoro-3-(trifluoromethyl)phenyl]-3-(5-{3-[(3S)-3-hydroxypyrrolidin-1-yl]-3-oxopropyl}-2-methoxybenzamido)-7-(2,2,2-trifluoroethylidene)bicyclo[2.2.1]heptane-2-carboxamide | (500 MHz, DMSO-d6) δ 10.63 (s, 1H), 9.84 (dd, J = 6.8, 2.1 Hz, 1H), 8.27-8.14 (m, 1H), 7.76 (br d, J = 1.7 Hz, 2H), 7.47 (br t, J = 9.6 Hz, 1H), 7.36 (br d, J = 8.4 Hz, 1H), 7.07 (d, J = 8.5 Hz, 1H), 5.97-5.85 (m, 1H), 4.55-4.44 (m, 1H), 4.28-4.15 (m, 1H), 3.94 (s, 3H), 3.45-3.37 (m, 1H), 3.30-3.16 (m, 4H), 3.03-2.95 (m, 2H), 2.92-2.82 (m, 1H), 2.77 (br t, J = 7.2 Hz, 2H), 2.07-1.65 (m, 5H), 1.54-1.40 (m, 3H) | 2.18 | 672.3 |

TABLE 2-continued

| Ex # | Structure | Name | $^1$H NMR. δ | LC RT (min) | Ion |
|---|---|---|---|---|---|
| 139 | 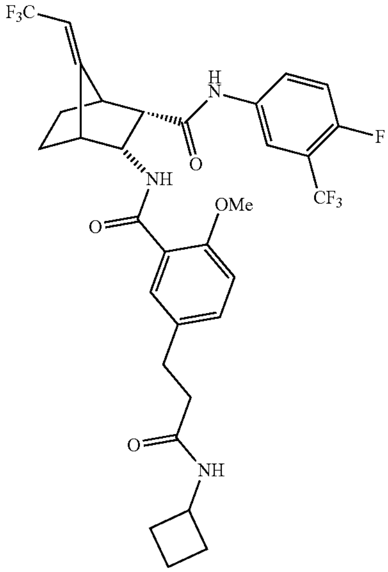 | (2S,3R,7Z)-3-{5-[2-(cyclobutylcarbamoyl)ethyl]-2-methoxybenzamido}-N-[4-fluoro-3-(trifluoromethyl)phenyl]-7-(2,2,2-trifluoroethylidene)bicyclo[2.2.1]heptane-2-carboxamide | (500 MHz, DMSO-d6) δ 10.64 (s, 1H), 9.84 (d, J = 7.0 Hz, 1H), 8.22 (dd, J = 6.4, 2.1 Hz, 1H), 8.05 (br d, J = 7.6 Hz, 1H), 7.84-7.70 (m, 2H), 7.50 (t, J = 9.8 Hz, 1H), 7.32 (dd, J = 8.4, 2.0 Hz, 1H), 7.08 (d, J = 8.5 Hz, 1H), 5.93 (q, J = 8.0 Hz, 1H), 4.61-4.46 (m, 1H), 4.22-4.05 (m, 1H), 3.96 (s, 3H), 3.26 (br dd, J = 10.8, 4.1 Hz, 1H), 3.22 (br d, J = 1.5 Hz, 1H), 2.98 (br s, 1H), 2.80-2.70 (m, 2H), 2.29 (t, J = 7.6 Hz, 2H), 2.10 (qd, J = 7.6, 3.7 Hz, 2H), 2.03-1.96 (m, 1H), 1.93-1.70 (m, 3H), 1.65-1.54 (m, 2H), 1.49 (br d, J = 6.1 Hz, 1H) | 2.47 | 656.3 |
| 140 | 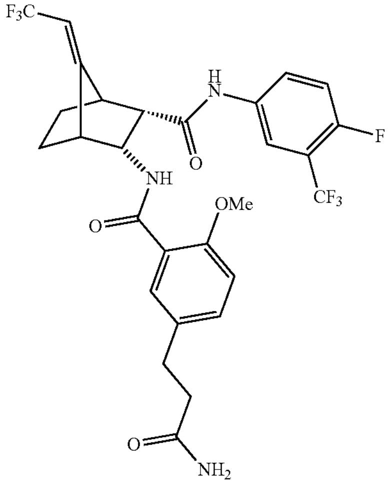 | (2S,3R,7Z)-3-[5-(2-carbamoylethyl)-2-methoxybenzamido]-N-[4-fluoro-3-(trifluoromethyl)phenyl]-7-(2,2,2-trifluoroethylidene)bicyclo[2.2.1]heptane-2-carboxamide | (500 MHz, DMSO-d6) δ 10.43 (s, 1H), 9.87 (d, J = 7.3 Hz, 1H), 8.21 (br dd, J = 6.3, 2.3 Hz, 1H), 7.77 (br d, J = 2.1 Hz, 2H), 7.49 (br t, J = 9.3 Hz, 1H), 7.35 (dd, J = 8.5, 2.1 Hz, 2H), 7.09 (d, J = 8.5 Hz, 1H), 6.75 (br s, 1H), 5.92 (q, J = 7.8 Hz, 1H), 4.56-4.43 (m, 1H), 3.96 (s, 2H), 3.30-3.19 (m, 2H), 3.04-2.94 (m, 1H), 2.77 (br t, J = 7.5 Hz, 2H), 2.34 (t, J = 7.6 Hz, 2H), 2.06-1.94 (m, 1H), 1.57-1.40 (m, 3H) | 2.18, | 602.3 |

TABLE 2-continued

| Ex # | Structure | Name | $^1$H NMR. δ | LC RT (min) | Ion |
|---|---|---|---|---|---|
| 141 | 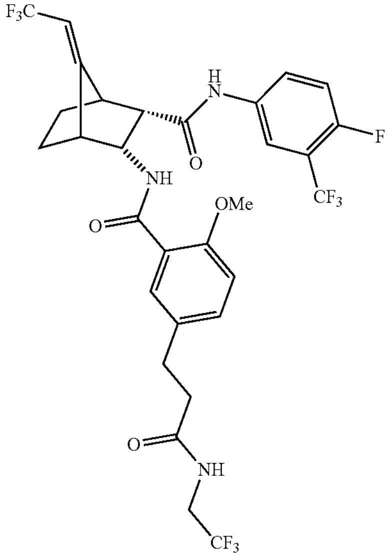 | (2S,3R,7Z)-N-[4-fluoro-3-(trifluoromethyl)phenyl]-3-(2-methoxy-5-{2-[(2,2,2-trifluoroethyl)carbamoyl]ethyl}benzamido)-7-(2,2,2-trifluoroethylidene)bicyclo[2.2.1]heptane-2-carboxamide | (500 MHz, DMSO-d6) δ 10.64 (s, 1H), 9.86 (d, J = 7.0 Hz, 1H), 8.51 (br t, J = 6.6 Hz, 1H), 8.23 (dd, J = 6.3, 2.3 Hz, 1H), 7.84-7.75 (m, 2H), 7.50 (t, J = 9.6 Hz, 1H), 7.34 (dd, J = 8.5, 2.1 Hz, 1H), 7.09 (d, J = 8.5 Hz, 1H), 5.94 (q, J = 7.8 Hz, 1H), 4.60-4.44 (m, 1H), 3.97 (s, 3H), 3.91-3.78 (m, 2H), 3.27 (dd, J = 10.5, 3.8 Hz, 1H), 3.23 (br s, 1H), 2.99 (br s, 1H), 2.56 (s, 2H), 2.52 (s, 4H), 2.45 (t, J = 7.6 Hz, 2H), 2.03-1.95 (m, 1H), 1.91-1.82 (m, 1H), 1.49 (br d, J = 6.7 Hz, 2H) | 2.42 | 684.1 |
| 143 | 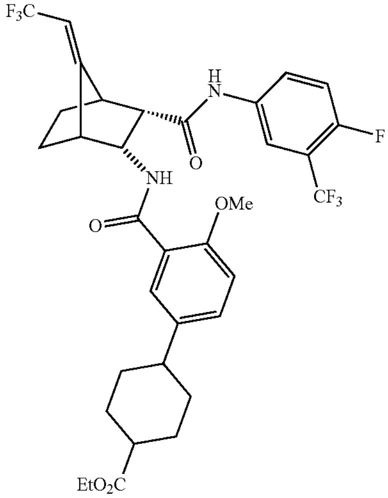 | ethyl 4-(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)cyclohexane-1-carboxylate | (500 MHz, DMSO-d6) 10.67-10.58 (m, 1H), 9.85 (br d, J = 6.1 Hz, 1H), 8.21 (br d, J = 3.4 Hz, 1H), 7.78 (br s, 2H), 7.49 (br t, J = 9.8 Hz, 1H), 7.39-7.30 (m, 1H), 7.11 (dd, J = 8.5, 3.4 Hz, 1H), 5.92 (q, J = 7.5 Hz, 1H), 4.59-4.44 (m, 1H), 4.17-4.09 (m, 1H), 4.05-4.00 (m, 1H), 3.96 (s, 3H), 3.29-3.14 (m, 2H), 2.98 (br s, 1H), 2.68-2.54 (m, 2H), 2.09-1.86 (m, 4H), 1.75-1.59 (m, 2H), 1.52-1.38 (m, 4H), 1.37-1.29 (m, 1H), 1.22-1.13 (m, 3H) | 2.82 | 685.2 |

TABLE 2-continued

| Ex # | Structure | Name | $^1$H NMR. δ | LC RT (min) | Ion |
|---|---|---|---|---|---|
| 144 | 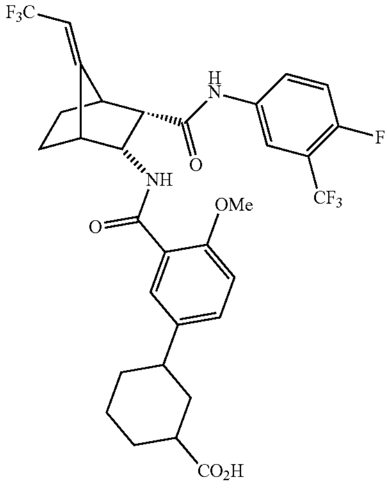 | 3-(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)cyclohexane-1-carboxylic acid | (500 MHz, DMSO-d6) δ 10.65 (s, 1H), 9.85 (d, J = 7.1 Hz, 1H), 8.28-8.17 (m, 1H), 7.77 (br d, J = 1.9 Hz, 2H), 7.49 (t, J = 9.6 Hz, 1H), 7.36 (dd, J = 8.5, 2.1 Hz, 1H), 7.09 (d, J = 8.8 Hz, 1H), 5.92 (q, J = 8.1 Hz, 1H), 4.57-4.45 (m, 1H), 3.95 (s, 3H), 3.21 (br s, 2H), 2.97 (br s, 1H), 2.50-2.42 (m, 1H), 2.31-2.18 (m, 1H), 2.03-1.73 (m, 7H), 1.56-1.34 (m, 6H) | 2.45 | 657.1 |
| 145 | 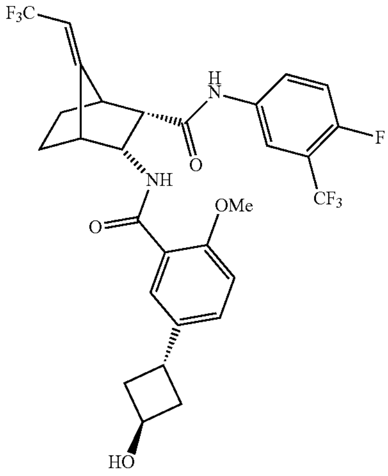 | (2S,3R,7Z)-N-[4-fluoro-3-(trifluoromethyl)phenyl]-3-{2-methoxy-5-[(1r,3r)-3-hydroxycyclobutyl] benzamido}-7-(2,2,2-trifluoroethylidene)bicyclo[2.2.1]heptane-2-carboxamide | (500 MHz, DMSO-d6) 10.64 (s, 1H), 9.87 (br d, J = 7.0 Hz, 1H), 8.18 (br d, J = 4.0 Hz, 1H), 7.80 (d, J = 2.1 Hz, 3H), 7.46 (br t, J = 9.8 Hz, 1H), 7.37 (dd, J = 8.5, 1.8 Hz, 1H), 7.10 (d, J = 8.5 Hz, 1H), 5.89 (q, J = 7.8 Hz, 1H), 4.56-4.46 (m, 1H), 4.33-4.23 (m, 1H), 3.95 (s, 3H), 3.51-3.39 (m, 1H), 3.29-3.20 (m, 2H), 2.97 (br s, 1H), 2.30-2.24 (m, 4H), 2.01-1.85 (m, 2H), 1.54-1.46 (m, 2H) | 2.43 | 601.1 |
| 146 | 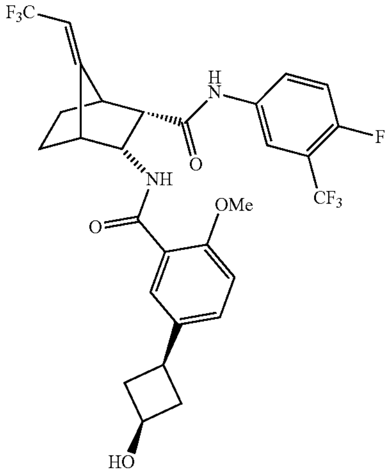 | (2S,7Z)-N-[4-fluoro-3-(trifluoromethyl)phenyl]-3-{2-methoxy-5-[(1s,3s)-3-hydroxycyclobutyl]benzamido}-7-(2,2,2-trifluoroethylidene)bicyclo[2.2.1]heptane-2-carboxamide | (500 MHz, DMSO-d6) 10.66 (s, 1H), 9.87 (br d, J = 7.0 Hz, 1H), 8.25-8.17 (m, 1H), 7.80 (br d, J = 1.8 Hz, 2H), 7.54-7.47 (m, 1H), 7.36 (dd, J = 8.5, 1.8 Hz, 1H), 7.11 (d, J = 8.5 Hz, 1H), 5.91 (q, J = 7.5 Hz, 1H), 4.51 (br s, 1H), 4.09-4.00 (m, 1H), 3.96 (s, 2H), 3.69 (br s, 2H), 3.31-3.18 (m, 2H), 2.98 (br s, 1H), 2.91-2.77 (m, 1H), 2.60 (br s, 2H), | 2.45 | 600.9 |

TABLE 2-continued

| Ex # | Structure | Name | $^1$H NMR. δ | LC RT (min) | Ion |
|---|---|---|---|---|---|
| | | | 2.06-1.95 (m, 1H), 1.92-1.76 (m, 3H), 1.49 (br d, J = 7.3 Hz, 2H) | | |
| 147 | 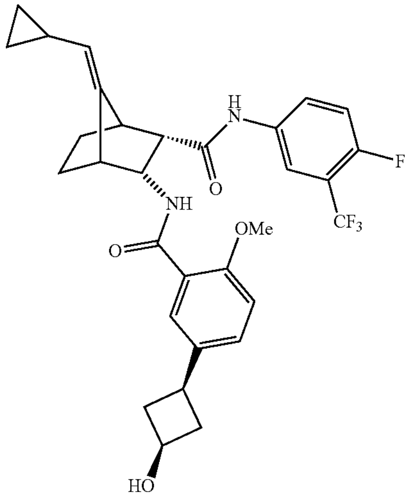 | (2S,3R,7Z)-7-(cyclopropylmethylidene)-N-[4-fluoro-3-(trifluoromethyl)phenyl]-3-{2-methoxy-5-[(1r,3r)-3-hydroxycyclobutyl]benzamido}bicyclo[2.2.1]heptane-2-carboxamide | (500 MHz, DMSO-d6) 10.53 (s, 1H), 9.84 (br d, J = 7.3 Hz, 1H), 8.23 (br d, J = 4.0 Hz, 1H), 7.90-7.75 (m, 2H), 7.49 (br t, J = 9.8 Hz, 1H), 7.36 (dd, J = 8.4, 1.7 Hz, 1H), 7.12 (d, J = 8.5 Hz, 1H), 4.71 (d, J = 9.8 Hz, 1H), 4.49-4.42 (m, 1H), 4.11-4.00 (m, 1H), 3.98 (s, 3H), 3.56-3.43 (m, 2H), 3.16 (br dd, J = 10.5, 3.8 Hz, 1H), 3.10 (br s, 1H), 2.90-2.82 (m, 1H), 2.73 (br s, 1H), 2.63-2.58 (m, 1H), 1.94-1.76 (m, 4H), 1.58-1.47 (m, 1H), 1.46-1.33 (m, 2H), 0.88-0.69 (m, 2H), 0.37 (br d, J = 2.7 Hz, 2H) | 2.57 | 573.1 |
| 148 | 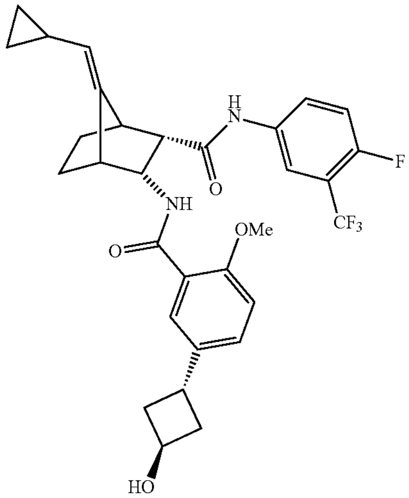 | (2S,3R,7Z)-7-(cyclopropylmethylidene)-N-[4-fluoro-3-(trifluoromethyl)phenyl]-3-{2-methoxy-5-[(1r,3r)-3-hydroxycyclobutyl]benzamido}bicyclo[2.2.1]heptane-2-carboxamide | (500 MHz, DMSO-d6) 10.51 (s, 1H), 9.83 (d, J = 7.3 Hz, 1H), 8.18 (dd, J = 6.3, 2.3 Hz, 1H), 7.82-7.71 (m, 2H), 7.44 (t, J = 9.7 Hz, 1H), 7.36 (dd, J = 8.5, 2.4 Hz, 1H), 7.09 (d, J = 8.6 Hz, 1H), 4.67 (d, J = 9.6 Hz, 1H), 4.47-4.38 (m, 1H), 4.30-4.22 (m, 1H), 3.94 (s, 3H), 3.75-3.72 (m, 1H), 3.48-3.38 (m, 1H), 3.15-3.02 (m, 2H), 2.69 (br s, 1H), 2.32-2.20 (m, 4H), 1.88-1.70 (m, 2H), 1.54-1.33 (m, 3H), 0.72 (br t, J = 8.6 Hz, 2H), 0.33 (br d, J = 4.4 Hz, 2H) | 2.56 | 573.1 |

TABLE 2-continued

| Ex # | Structure | Name | $^1$H NMR. δ | LC RT (min) | Ion |
|---|---|---|---|---|---|
| 153 | 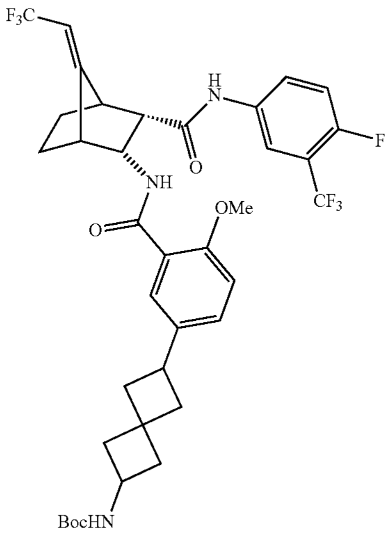 | tert-butyl N-[6-(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)spiro[3.3]heptan-2-yl]carbamate | (500 MHz, DMSO-d6) 10.64 (s, 1H), 9.85 (br d, J = 6.7 Hz, 1H), 8.22 (dd, J = 6.6, 2.3 Hz, 1H), 7.86-7.71 (m, 2H), 7.49 (t, J = 9.9 Hz, 1H), 7.31 (dd, J = 8.5, 2.1 Hz, 1H), 7.16-6.99 (m, 2H), 5.93 (d, J = 7.6 Hz, 1H), 4.51 (br s, 1H), 3.95 (s, 3H), 3.88-3.76 (m, 1H), 3.52-3.43 (m, 1H), 3.38-3.17 (m, 2H), 3.04-2.92 (m, 1H), 2.45-2.36 (m, 2H), 2.29-2.17 (m, 1H), 2.16-2.08 (m, 1H), 2.04-1.93 (m, 4H), 1.90-1.78 (m, 2H), 1.49 (br d, J = 6.7 Hz, 2H), 1.37 (s, 9H) | 2.95 | 740.3 |
| 154 | 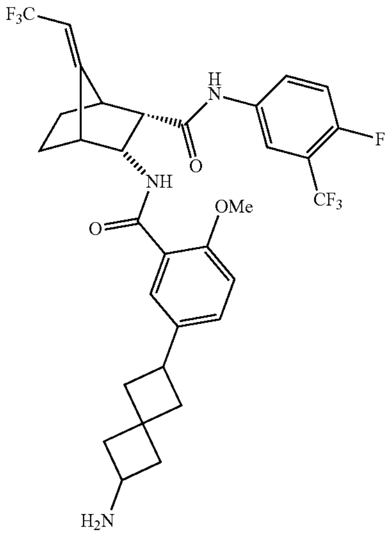 | (2S,3R,7Z)-3-(5-{6-aminospiro[3.3]heptan-2-yl}-2-methoxybenzamido)-N-[4-fluoro-3-(trifluoromethyl)phenyl]-7-(2,2,2-trifluoroethylidene)bicyclo[2.2.1]heptane-2-carboxamide | (500 MHz, DMSO-d6) 9.87 (br d, J = 6.6 Hz, 1H), 8.22 (br d, J = 4.0 Hz, 1H), 7.77 (br d, J = 4.8 Hz, 1H), 7.58-7.43 (m, 1H), 7.31 (br d, J = 8.2 Hz, 1H), 7.08 (d, J = 8.6 Hz, 1H), 5.98-5.84 (m, 1H), 4.54-4.43 (m, 1H), 3.95 (s, 3H), 3.63 (m, 2H), 3.39-3.14 (m, 3H), 3.02-2.95 (m, 1H), 2.47-2.35 (m, 2H), 2.30-2.10 (m, 2H), 2.07-1.92 (m, 4H), 1.90-1.73 (m, 4H), 1.48 (br d, J = 7.2 Hz, 2H) | 2.18 | 640.3 |

TABLE 2-continued

| Ex # | Structure | Name | $^1$H NMR. δ | LC RT (min) | Ion |
| --- | --- | --- | --- | --- | --- |
| 156 | 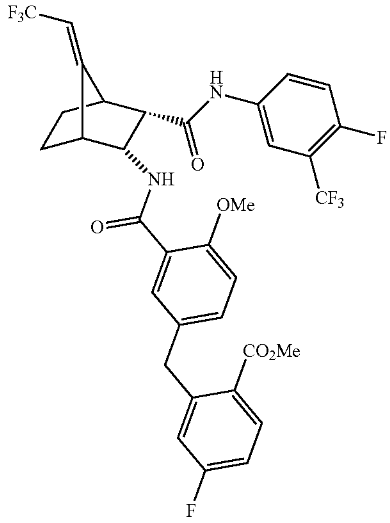 | methyl 4-fluoro-2-[(3-{[(2R,3S,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)methyl]benzoate | (500 MHz, DMSO-d6) 10.61 (s, 1H), 9.86 (br d, J = 7.0 Hz, 1H), 8.21 (br d, J = 4.6 Hz, 1H), 7.77 (br dd, J = 4.7, 3.5 Hz, 1H), 7.68 (s, 1H), 7.58-7.45 (m, 2H), 7.39 (br d, J = 6.4 Hz, 2H), 7.27 (br d, J = 8.2 Hz, 1H), 7.08 (d, J = 8.5 Hz, 1H), 5.92 (q, J = 7.7 Hz, 1H), 4.52-4.42 (m, 1H), 4.22 (s, 2H), 3.95 (s, 3H), 3.77 (s, 3H), 3.26-3.13 (m, 2H), 2.97 (br s, 1H), 2.03-1.80 (m, 2H), 1.47 (br d, J = 6.1 Hz, 2H) | 2.65 | 697.0 |
| 158 | 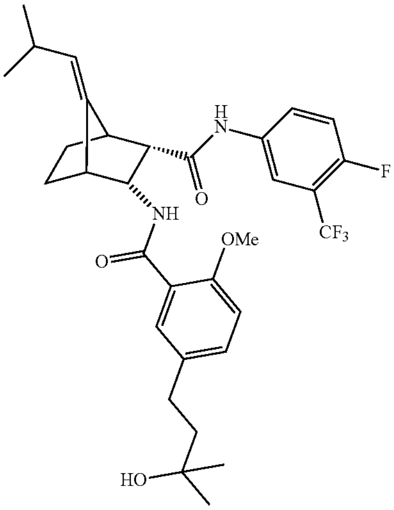 | (7Z)-N-[4-fluoro-3-(trifluoromethyl)phenyl]-3-[5-(3-hydroxy-3-methylbutyl)-2-methoxybenzamido]-7-(2-methylpropylidene)bicyclo[2.2.1]heptane-2-carboxamide | (500 MHz, DMSO-d6) 10.37 (s, 1H), 9.64 (d, J = 7.3 Hz, 1H), 8.05 (br d, J = 5.8 Hz, 1H), 7.66-7.56 (m, 2H), 7.31 (br t, J = 9.7 Hz, 1H), 7.17 (dd, J = 8.5, 2.2 Hz, 1H), 6.92 (d, J = 8.5 Hz, 1H), 4.95 (d, J = 9.0 Hz, 1H), 4.28-4.19 (m, 1H), 3.80 (s, 3H), 2.98 (br dd, J = 10.6, 4.1 Hz, 1H), 2.53 (br s, 1H), 2.46-2.40 (m, 4H), 2.32 (br d, J = 8.5 Hz, 1H), 1.73 (s, 1H), 1.63-1.53 (m, 1H), 1.51-1.37 (m, 2H), 1.23 (br d, J = 6.6 Hz, 2H), 0.98 (s, 6H), 0.93-0.79 (m, 6H) | 2.72 | 590.9 |

TABLE 2-continued

| Ex # | Structure | Name | $^1H$ NMR. δ | LC RT (min) | Ion |
|---|---|---|---|---|---|
| 159 | 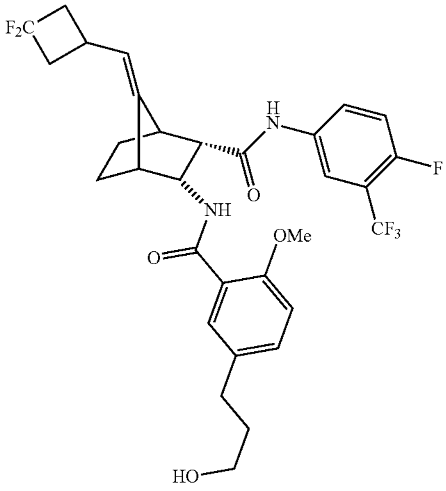 | (2S,3R,7Z)-7-[(3,3-difluorocyclobutyl) methylidene]-N-[4-fluoro-3-(trifluoromethyl)phe-yl]-3-[5-(3-hydroxypropyl)-2-methoxybenzamideo] bicyclo[2.2.1]heptane-2-carboxamide | (500 MHz, $CD_3OD$) 10.17-10.10 (m, 1H), 8.21-8.13 (m, 1H), 7.91-7.84 (m, 1H), 7.75 (br dd, J = 5.6, 3.4 Hz, 1H), 7.39-7.34 (m, 1H), 7.29 (t, J = 9.5 Hz, 1H), 7.15-7.03 (m, 1H), 5.43-5.37 (m, 1H), 4.55-4.47 (m, 1H), 4.42-4.35 (m, 1H), 4.09-4.00 (m, 3H), 3.58 (t, J = 6.5 Hz, 1H), 3.38-3.34 (m, 2H), 3.20-3.13 (m, 1H), 3.12-3.02 (m, 2H), 2.89-2.67 (m, 5H), 2.54-2.32 (m, 2H), 2.12-2.03 (m, 2H), 1.94-1.79 (m, 2H), 1.50 (br s, 2H) | 1.11 | 611.2 |
| 160 | 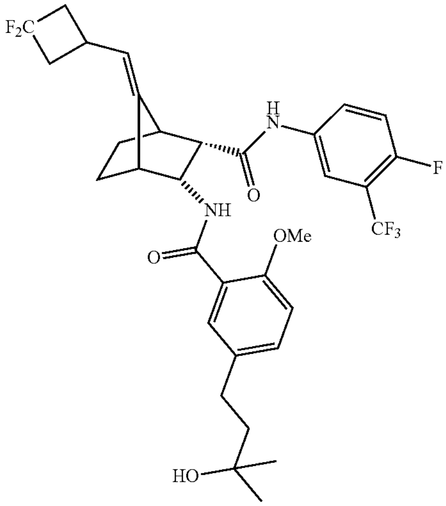 | (2S,3R,7Z)-7-[(3,3-difluorocyclobutyl) methylidene]-N-[4-fluoro-3-(trifluoromethyl)phe-nyl]-3-[5-(3-hydroxy-3-methylbutyl)-2-methoxybenzamido] bicyclo[2.2.1]heptane-2-carboxamide | (500 MHz, $CD_3OD$) 10.33-10.09 (m, 1H), 8.20-8.12 (m, 1H), 7.88 (d, J = 2.3 Hz, 1H), 7.75 (s, 1H), 7.40-7.35 (m, 1H), 7.32-7.26 (m, 1H), 7.14-7.02 (m, 1H), 5.42 (d, J = 9.0 Hz, 1H), 4.51 (br d, J = 4.6 Hz, 1H), 4.05 (s, 3H), 3.47 (t, J = 1.6 Hz, 1H), 3.37-3.35 (m, 4H), 3.22-3.09 (m, 1H), 3.10-3.00 (m, 1H), 2.96-2.65 (m, 4H), 2.51-2.36 (m, 2H), 2.14-1.88 (m, 2H), 1.80-1.72 (m, 2H), 1.57-1.45 (m, 1H), 1.35-1.13 (m, 6H) | 1.11 | 611.3 |

TABLE 2-continued

| Ex # | Structure | Name | $^1$H NMR. δ | LC RT (min) | Ion |
|---|---|---|---|---|---|
| 161 | 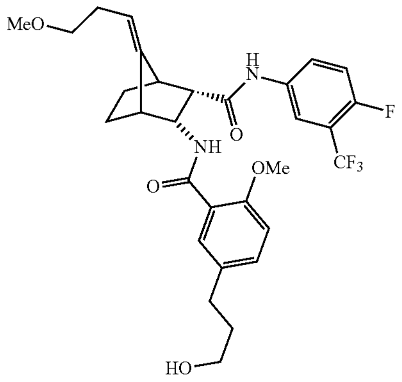 | (7Z)-N-[4-fluoro-3-(trifluoromethyl)phenyl]-3-[5-(3-hydroxypropyl)-2-methoxybenzamido]-7-(3-methoxypropylidene)bicyclo[2.2.1]heptane-2-carboxamide | (500 MHz, DMSO-d6) 10.47 (br d, J = 7.0 Hz, 1H), 9.79-9.70 (m, 1H), 8.16 (br d, J = 5.2 Hz, 1H), 7.69 (br s, 2H), 7.43 (td, J = 9.5, 5.0 Hz, 1H), 7.26 (br d, J = 7.9 Hz, 1H), 7.02 (br dd, J = 8.5, 1.5 Hz, 1H), 5.25-5.11 (m, 1H), 4.46-4.31 (m, 2H), 3.90 (s, 3H), 3.40-3.31 (m, 3H), 3.22 (s, 3H), 3.08 (br d, J = 4.0 Hz, 1H), 3.01-2.87 (m, 1H), 2.67 (br s, 1H), 2.55-2.49 (m, 2H), 2.32-2.15 (m, 2H), 1.91-1.82 (m, 1H), 1.75-1.55 (m, 4H), 1.33 (br d, J = 4.9 Hz, 2H) | 2.28 | 578.9 |
| 162 | 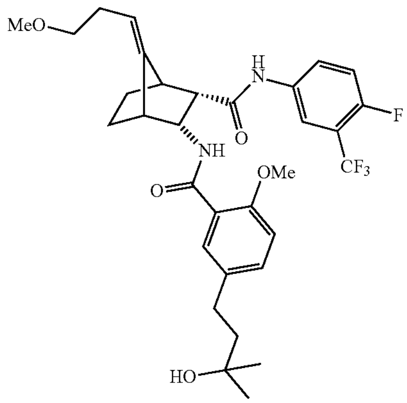 | (7Z)-N-[4-fluoro-3-(trifluoromethyl)phenyl]-3-[5-(3-hydroxy-3-methylbutyl)-2-methoxybenzamido]-7-(3-methoxypropylidene)bicyclo[2.2.1]heptane-2-carboxamide | (500 MHz, DMSO-d6) 10.43 (br d, J = 7.3 Hz, 1H), 9.68 (br t, J = 7.2 Hz, 1H), 8.13 (br d, J = 5.8 Hz, 1H), 7.77-7.61 (m, 2H), 7.39 (td, J = 9.4, 4.4 Hz, 1H), 7.21 (br d, J = 8.5 Hz, 1H), 6.98 (br d, J = 8.2 Hz, 1H), 5.22-5.05 (m, 1H), 4.31 (br d, J = 6.1 Hz, 1H), 3.86 (s, 3H), 3.32-3.25 (m, 1H), 3.18 (s, 3H), 3.12-2.95 (m, 2H), 2.88-2.83 (m, 1H), 2.69-2.44 (m, 4H), 2.33-2.14 (m, 2H), 1.85-1.78 (m, 1H), 1.70-1.61 (m, 1H), 1.55-1.44 (m, 2H), 1.29 (br d, J = 5.2 Hz, 2H), 1.10-0.98 (m, 6H) | 2.55 | 606.9 |

TABLE 2-continued

| Ex # | Structure | Name | $^1$H NMR. δ | LC RT (min) | Ion |
|---|---|---|---|---|---|
| 163 | 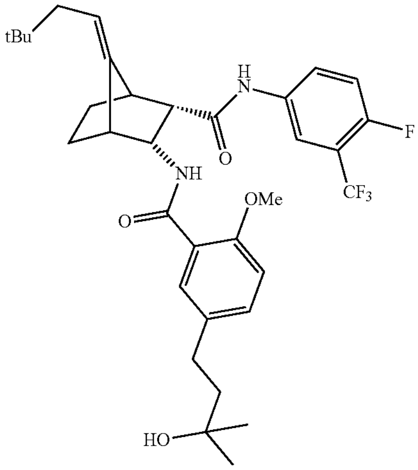 | (7Z)-7-(3,3-dimethylbutylidene)-N-[4-fluoro-3-(trifluoromethyl)phenyl]-3-[5-(3-hydroxy-3-methylbutyl)-2-methoxybenzamido] bicyclo[2.2.1]heptane-2-carboxamide | (500 MHz, DMSO-d6) 10.55-10.30 (m, 1H), 9.72 (br d, J = 7.0 Hz, 1H), 8.22-8.01 (m, 1H), 7.78-7.63 (m, 2H), 7.39 (br t, J = 9.8 Hz, 1H), 7.27-7.17 (m, 1H), 6.99 (d, J = 8.5 Hz, 1H), 5.31-5.14 (m, 1H), 4.34 (br d, J = 10.7 Hz, 1H), 3.87 (s, 3H), 3.14-2.95 (m, 1H), 2.85 (br s, 1H), 2.66 (br s, 1H), 1.98-1.76 (m, 4H), 1.74-1.56 (m, 1H), 1.58-1.41 (m, 3H), 1.34-1.22 (m, 2H), 1.05 (s, 7H), 0.83 (s, 9H) | 2.87 | 619.3 |
| 164 | 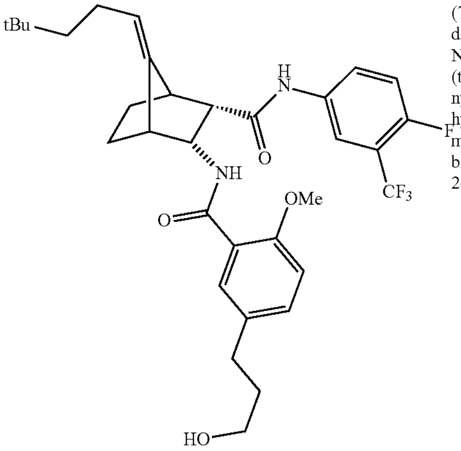 | (7Z)-7-(4,4-dimethylpentylidene)-N-[4-fluoro-3-(trifluoromethyl)phenyl]-3-[5-(3-hydroxypropyl)-2-methoxybenzamido] bicyclo[2.2.1]heptane-2-carboxamide | (500 MHz, DMSO-d6) 10.44 (s, 1H), 9.74 (d, J =7.2 Hz, 1H), 8.14 (dd, J = 6.3, 2.4 Hz, 1H), 7.73-7.65 (m, 2H), 7.39 (t, J = 9.8 Hz, 1H), 7.24 (dd, J = 8.4, 2.3 Hz, 1H), 7.00 (d, J = 8.5 Hz, 1H), 5.16 (t, J = 7.3 Hz, 1H), 4.32 (br d, J = 3.0 Hz, 1H), 3.87 (s, 3H), 3.51-3.45 (m, 2H), 3.31 (br d, J = 5.3 Hz, 1H), 3.10-3.04 (m, 1H), 2.88 (br s, 1H), 2.62 (br s, 1H), 2.54-2.49 (m, 2H), 1.95 (br dd, J = 6.4, 3.4 Hz, 2H), 1.83-1.66 (m, 2H), 1.64-1.54 (m, 2H), 1.29 (br s, 2H), 1.22-1.12 (m, 2H), 0.83 (s, 9H) | 2.86 | 605.3 |

TABLE 2-continued

| Ex # | Structure | Name | $^1$H NMR. δ | LC RT (min) | Ion |
|---|---|---|---|---|---|
| 165 | 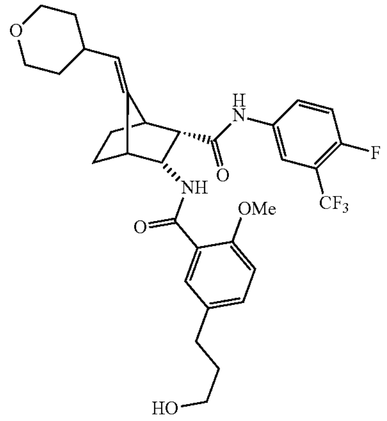 | (7Z)-N-[4-fluoro-3-(trifluoromethyl)phenyl]-3-[5-(3-hydroxypropyl)-2-methoxybenzamido]-7-[(oxan-4-yl)methylidene]bicyclo[2.2.1]heptane-2-carboxamide | (500 MHz, DMSO-d6) 10.51 (s, 1H), 9.79 (d, J = 7.0 Hz, 1H), 8.25-8.16 (m, 1H), 7.85-7.72 (m, 2H), 7.47 (br t, J = 9.6 Hz, 1H), 7.31 (dd, J = 8.3, 2.4 Hz, 1H), 7.07 (d, J = 8.5 Hz, 1H), 5.12 (d, J = 8.6 Hz, 1H), 4.56-4.36 (m, 2H), 3.95 (s, 3H), 3.89-3.81 (m, 2H), 3.62-3.49 (m, 1H), 3.38 (br s, 1H), 3.14 (br dd, J = 10.7, 4.1 Hz, 1H), 2.99 (br s, 1H), 2.70 (br s, 1H), 2.62-2.56 (m, 2H), 2.41 (br dd, J = 8.5, 3.6 Hz, 1H), 1.96-1.85 (m, 1H), 1.80-1.73 (m, 1H), 1.71-1.62 (m, 3H), 1.61-1.47 (m, 2H), 1.46-1.30 (m, 5H) | 2.37 | 605.1 |
| 166 | 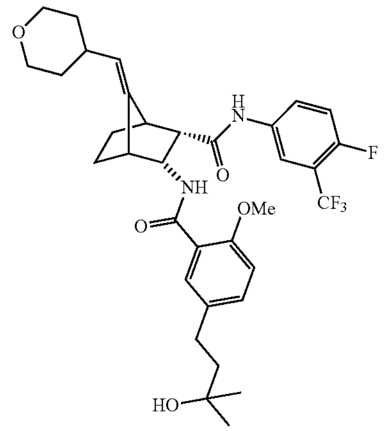 | (7Z)-N-[4-fluoro-3-(trifluoromethyl)phenyl]-3-[5-(3-hydroxy-3-methylbutyl)-2-methoxybenzamido]-7-[(oxan-4-yl)methylidene]bicyclo[2.2.1]heptane-2-carboxamide | (500 MHz, DMSO-d6) 10.57-10.46 (m, 1H), 9.79 (br d, J = 7.1 Hz, 1H), 8.20 (br d, J = 4.3 Hz, 1H), 7.80-7.71 (m, 2H), 7.46 (br t, J = 9.6 Hz, 1H), 7.30 (dd, J = 8.4, 2.3 Hz, 1H), 7.06 (d, J = 8.5 Hz, 1H), 5.12 (d, J = 8.6 Hz, 1H), 4.43-4.36 (m, 2H), 3.94 (s, 3H), 3.88-3.79 (m, 2H), 3.57-3.54 (m, 1H), 3.44-3.30 (m, 1H), 3.13 (br dd, J = 10.7, 3.8 Hz, 1H), 2.98 (br s, 1H), 2.69 (br s, 1H), 2.58 (br s, 2H), 2.41 (br s, 1H), 1.94-1.71 (m, 2H), 1.64-1.55 (m, 3H), 1.51-1.30 (m, 5H), 1.12 (s, 6H) | 2.60 | 633.1 |

TABLE 2-continued

| Ex # | Structure | Name | $^{1}$H NMR. δ | LC RT (min) | Ion |
|---|---|---|---|---|---|
| 167 | 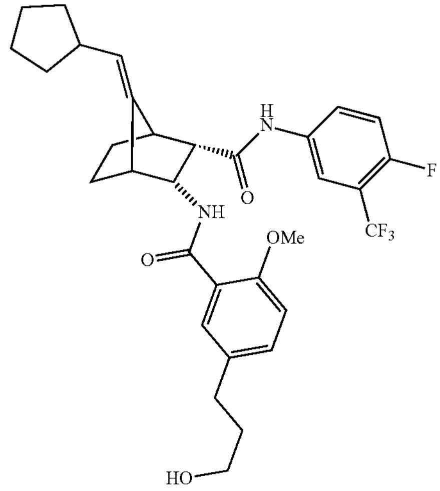 | (7Z)-7-(cyclopentylmethylidene)-N-[4-fluoro-3-(trifluoromethyl)phenyl]-3-[5-(3-hydroxypropyl)-2-methoxybenzamido]bicyclo[2.2.1]heptane-2-carboxamide | (500 MHz, DMSO-d6) 10.54-10.47 (m, 1H), 9.78 (br d, J = 7.3 Hz, 1H), 8.26-8.17 (m, 1H), 7.84-7.71 (m, 2H), 7.46 (br t, J = 9.7 Hz, 1H), 7.31 (dd, J = 8.4, 2.3 Hz, 1H), 7.07 (d, J = 8.5 Hz, 1H), 5.17 (d, J = 9.0 Hz, 1H), 4.45-4.34 (m, 1H), 3.94 (s, 3H), 3.38 (br s, 1H), 3.12 (br dd, J = 10.7, 4.2 Hz, 1H), 2.96 (br s, 1H), 2.63-2.53 (m, 5H), 1.96-1.50 (m, 11H), 1.43-1.32 (m, 2H), 1.32-1.16 (m, 2H) | 2.81 | 589.1 |
| 168 | 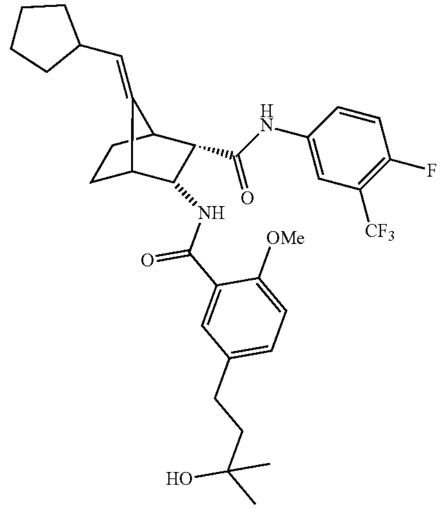 | (7Z)-7-(cyclopentylmethylidene)-N-[4-fluoro-3-(trifluoromethyl)phenyl]-3-[5-(3-hydroxy-3-methylbutyl)-2-methoxybenzamido]bicyclo[2.2.1]heptane-2-carboxamide | (500 MHz, DMSO-d6) 10.38 (s, 1H), 9.66 (br d, J = 7.3 Hz, 1H), 8.14-8.07 (m, 1H), 7.63 (br d, J = 1.8 Hz, 2H), 7.35 (br t, J = 9.6 Hz, 1H), 7.19 (dd, J = 8.4, 2.0 Hz, 1H), 6.95 (d, J = 8.5 Hz, 1H), 5.06 (d, J = 8.9 Hz, 1H), 4.27 (br s, 1H), 3.83 (s, 3H), 3.01 (br dd, J = 10.7, 4.0 Hz, 1H), 2.59 (br s, 1H), 2.39 (br s, 4H), 1.87-1.39 (m, 11H), 1.33-1.09 (m, 4H), 1.01 (s, 6H) | 2.73 | 617.1 |
| 169 | 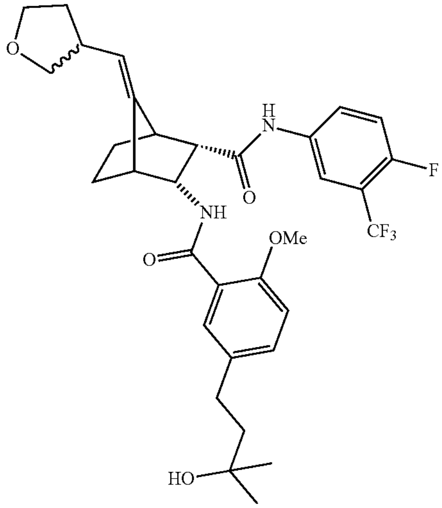 | (7Z)-N-[4-fluoro-3-(trifluoromethyl)phenyl]-3-[5-(3-hydroxy-3-methylbutyl)-2-methoxybenzamido]-7-[(oxolan-3-yl)methylidene]bicyclo[2.2.1]heptane-2-carboxamide | (500 MHz, DMSO-d6) 10.52 (s, 1H), 9.79 (d, J = 7.3 Hz, 1H), 8.22-8.15 (m, 1H), 7.79-7.67 (m, 2H), 7.45 (br t, J = 9.5 Hz, 1H), 7.30 (dd, J = 8.4, 2.3 Hz, 1H), 7.06 (d, J = 8.5 Hz, 1H), 5.19 (d, J = 9.0 Hz, 1H), 4.44-4.35 (m, 1H), 3.93 (s, 3H), 3.82-3.78 (m, 2H), 3.64-3.62 (m, 2H), 3.27 (t, J = 7.8 Hz, 1H), 3.13 (br dd, J = 10.9, 4.0 Hz, 1H), 2.98 (br t, J = 7.9 Hz, 2H), 2.72 (br s, 1H), | 2.41 | 619.1 |

TABLE 2-continued

| Ex # | Structure | Name | $^1$H NMR. δ | LC RT (min) | Ion |
|---|---|---|---|---|---|
| | | | 2.57 (br s, 2H), 2.16-2.07 (m, 1H), 1.92-1.70 (m, 2H), 1.67-1.54 (m, 3H), 1.37 (br d, J = 5.9 Hz, 2H), 1.17-1.09 (m, 6H) | | |
| 170 | 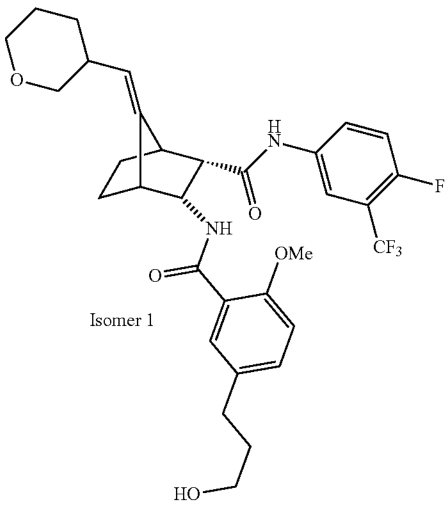 Isomer 1 | (7Z)-N-[4-fluoro-3-(trifluoromethyl)phenyl]-3-[5-(3-hydroxypropyl)-2-methoxybenzamido]-7-[(oxan-3-yl)methylidene]bicyclo[2.2.1]heptane-2-carboxamide | (500 MHz, DMSO-d6) 10.53 (s, 1H), 9.81 (br d, J = 7.0 Hz, 1H), 8.23 (br d, J = 4.6 Hz, 1H), 7.77 (br s, 2H), 7.49 (br t, J = 9.5 Hz, 1H), 7.33 (dd, J = 8.2, 1.8 Hz, 1H), 7.09 (d, J = 8.5 Hz, 1H), 5.07 (br d, J = 8.5 Hz, 1H), 4.56-4.36 (m, 2H), 3.97 (s, 3H), 3.79 (br d, J = 10.7 Hz, 1H), 3.66 (br dd, J = 10.2, 3.5 Hz, 1H), 3.46-3.35 (m, 1H), 3.22-3.11 (m, 2H), 3.01 (s, 1H), 2.97 (br s, 1H), 2.72 (br s, 1H), 2.62-2.57 (m, 3H), 2.41 (br dd, J = 9.6, 5.0 Hz, 1H), 1.96-1.83 (m, 2H), 1.81-1.64 (m, 3H), 1.61 (br s, 2H), 1.48-1.32 (m, 3H) | 2.32 | 603.1 |
| 171 | 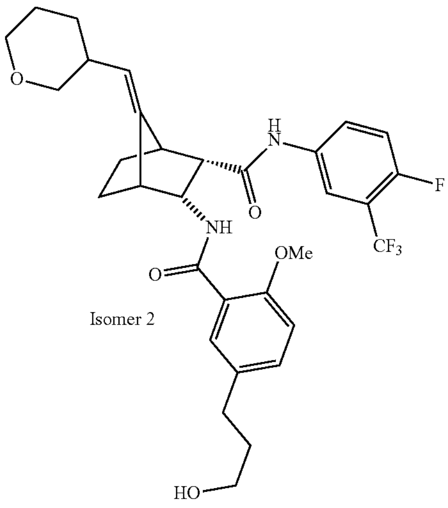 Isomer 2 | (7Z)-N-[4-fluoro-3-(trifluoromethyl)phenyl]-3-[5-(3-hydroxypropyl)-2-methoxybenzamido]-7-[(oxan-3-yl)methylidene]bicyclo[2.2.1]heptane-2-carboxamide | (500 MHz, DMSO-d6) 10.51 (s, 1H), 9.80 (d, J = 7.4 Hz, 1H), 8.19 (br d, J = 4.9 Hz, 1H), 7.73 (br d, J = 2.2 Hz, 2H), 7.45 (s, 1H), 7.34-7.27 (m, 1H), 7.07 (d, J = 8.5 Hz, 1H), 5.02 (d, J = 8.9 Hz, 1H), 4.37 (br s, 1H), 3.94 (s, 3H), 3.81-3.67 (m, 2H), 3.41-3.35 (m, 2H), 3.32-3.24 (m, 1H), 3.17-3.07 (m, 2H), 2.95 (br s, 1H), 2.69 (br s, 1H), 2.57 (br s, 2H), 2.44-2.34 (m, 1H), 1.87 (s, 1H), 1.82-1.72 (m, 2H), 1.71-1.60 (m, 2H), 1.55 (br d, J = 2.6 Hz, 2H), 1.46-1.31 (m, 4H) | 2.42 | 605.3 |

TABLE 2-continued

| Ex # | Structure | Name | $^1$H NMR. δ | LC RT (min) | Ion |
|---|---|---|---|---|---|
| 172 | 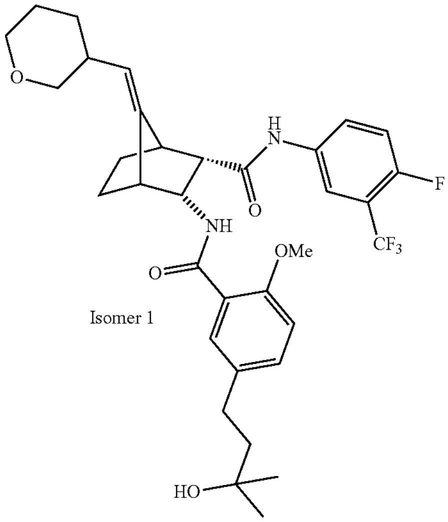 Isomer 1 | (7Z)-N-[4-fluoro-3-(trifluoromethyl)phenyl]-3-[5-(3-hydroxy-3-methylbutyl)-2-methoxybenzamido]-7-[(oxan-3-yl)methylidene]bicyclo[2.2.1]heptane-2-carboxamide | (500 MHz, DMSO-d6) 10.51 (s, 1H), 9.80 (s, 1H), 8.19 (dd, J = 6.4, 2.1 Hz, 1H), 7.74 (br d, J = 2.2 Hz, 2H), 7.45 (s, 1H), 7.30 (dd, J = 8.5, 2.3 Hz, 1H), 7.06 (d, J = 8.5 Hz, 1H), 5.04 (d, J = 8.8 Hz, 1H), 4.39 (br d, J = 6.4 Hz, 1H), 3.94 (s, 3H), 3.63-3.57 (m, 4H), 3.30 (br d, J = 1.7 Hz, 1H), 3.16-3.09 (m, 2H), 2.94 (br s, 1H), 2.69 (br s, 1H), 2.58 (br s, 1H), 2.43-2.33 (m, 1H), 1.91-1.71 (m, 3H), 1.63-1.53 (m, 4H), 1.37 (br d, J = 5.6 Hz, 3H), 1.12 (s, 6H) | 2.59 | 633.0 |
| 173 | 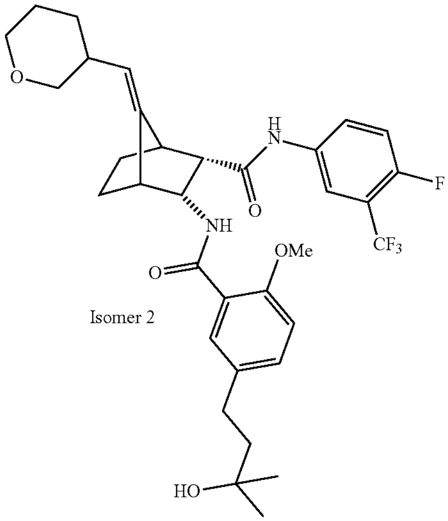 Isomer 2 | (7Z)-N-[4-fluoro-3-(trifluoromethyl)phenyl]-3-[5-(3-hydroxy-3-methylbutyl)-2-methoxybenzamido]-7-[(oxan-3-yl)methylidene]bicyclo[2.2.1]heptane-2-carboxamide | (500 MHz, DMSO-d6) 10.47 (s, 1H), 9.75 (d, J = 7.2 Hz, 1H), 8.20-8.13 (m, 1H), 7.70 (br d, J = 2.1 Hz, 2H), 7.42 (t, J = 9.7 Hz, 1H), 7.26 (dd, J = 8.4, 2.3 Hz, 1H), 7.02 (d, J = 8.5 Hz, 1H), 4.98 (d, J = 9.0 Hz, 1H), 4.34 (br s, 1H), 3.90 (s, 3H), 3.76-3.64 (m, 3H), 3.33-3.20 (m, 1H), 3.13-3.05 (m, 2H), 2.91 (br s, 1H), 2.65 (br s, 1H), 2.56-2.52 (m, 2H), 2.41-2.32 (m, 1H), 1.83 (br t, J = 9.1 Hz, 1H), 1.75-1.65 (m, 2H), 1.62-1.45 (m, 4H), 1.39-1.25 (m, 3H), 1.08 (s, 6H) | 2.69 | 632.9 |

TABLE 2-continued

| Ex # | Structure | Name | $^1H$ NMR. δ | LC RT (min) | Ion |
|---|---|---|---|---|---|
| 174 | 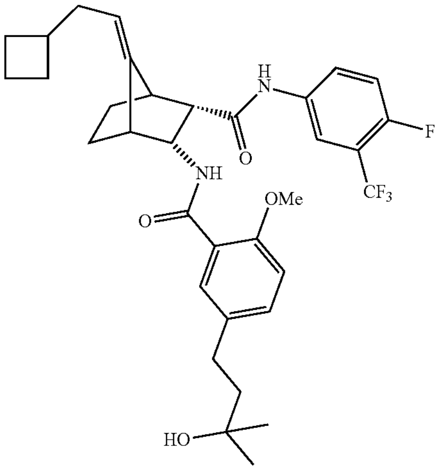 | (7Z)-7-(2-cyclobutylethylidene)-N-[4-fluoro-3-(trifluoromethyl)phenyl]-3-[5-(3-hydroxy-3-methylbutyl)-2-methoxybenzamido]bicyclo[2.2.1]heptane-2-carboxamide | (500 MHz, DMSO-d6) 10.41 (s ,1H), 9.68 (d, J = 7.1 Hz, 1H), 8.09 (br d, J = 4.1 Hz, 1H), 7.70-7.57 (m, 2H), 7.35 (t, J = 9.8 Hz, 1H), 7.20 (dd, J = 8.5, 2.3 Hz, 1H), 6.95 (d, J = 8.5 Hz, 1H), 5.05 (t, J = 7.6 Hz, 1H), 4.31-4.25 (m, 1H), 3.83 (s, 3H), 3.52-3.48 (m, 2H), 3.01 (br dd, J = 10.7, 4.0 Hz, 1H), 2.84 (br s, 1H), 2.58 (br s, 1H), 2.47 (br d, J = 5.5 Hz, 1H), 2.26-2.14 (m, 1H), 2.07-1.99 (m, 2H), 1.89 (td, J = 7.7, 4.3 Hz, 2H), 1.78-1.42 (m, 8H), 1.25 (br d, J = 3.2 Hz, 2H), 1.02 (s, 6H) | 2.87 | 617.3 |
| 175 | 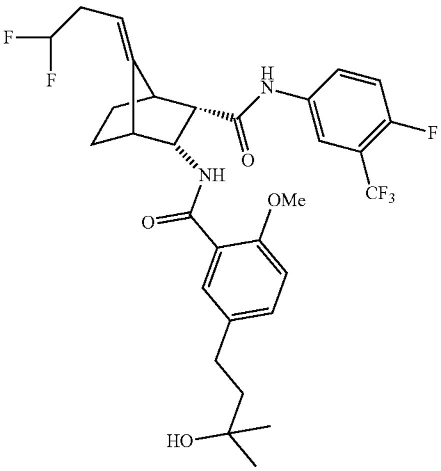 | (7Z)-7-(3,3-difluoropropylidene)-N-[4-fluoro-3-(trifluoromethyl)phenyl]-3-[5-(3-hydroxy-3-methylbutyl)-2-methoxybenzamido]bicyclo[2.2.1]heptane-2-carboxamide | (500 MHz, DMSO-d6) 10.47 (s, 1H), 9.70 (br d, J = 6.9 Hz, 1H), 8.21-8.10 (m, 1H), 7.79-7.64 (m, 2H), 7.42 (br t, J = 9.8 Hz, 1H), 7.25 (dd, J = 8.3, 1.9 Hz, 1H), 7.02 (d, J = 8.5 Hz, 1H), 6.22-5.89 (m, 1H), 5.19 (t, J = 7.5 Hz, 1H), 4.38 (dt, J = 10.8, 5.3 Hz, 1H), 4.28-4.17 (m, 1H), 3.90 (s, 3H), 3.11 (br dd, J = 10.2, 3.1 Hz, 1H), 2.93 (br s, 1H), 2.77-2.73 (m, 1H), 2.67-2.49 (m, 4H), 1.96-1.85 (m, 1H), 1.79-1.69 (m, 1H), 1.61-1.50 (m, 2H), 1.43-1.30 (m, 2H), 1.15-1.04 (m, 6H) | 2.55 | 613.1 |

TABLE 2-continued

| Ex # | Structure | Name | $^1$H NMR. δ | LC RT (min) | Ion |
|---|---|---|---|---|---|
| 177 | 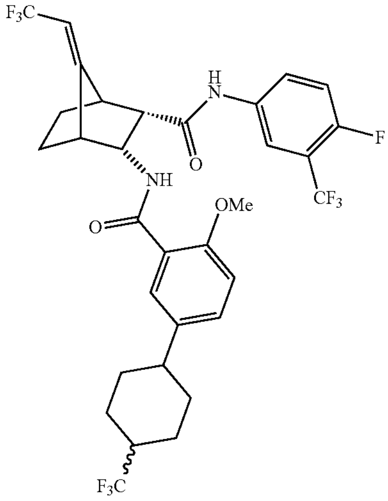 | (7Z)-N-[4-fluoro-3-(trifluoromethyl)phenyl]-3-{2-methoxy-5-[4-(trifluoromethyl)cyclohexyl]benzamido}-7-(2,2,2-trifluoroethylidene)bicyclo[2.2.1]heptane-2-carboxamide | (500 MHz, DMSO-d6) 10.54 (s, 1H), 9.77 (br d, J = 6.8 Hz, 1H), 8.16-8.09 (m, 1H), 7.76-7.63 (m, 2H), 7.37 (br t, J = 9.5 Hz, 1H), 7.29-7.21 (m, 1H), 7.00 (d, J = 8.4 Hz, 1H), 5.85-5.76 (m, 1H), 4.39 (br d, J = 3.4 Hz, 1H), 3.92-3.80 (m, 3H), 3.36-3.30 (m, 2H), 3.20-3.07 (m, 1H), 2.86 (br s, 1H), 2.68-2.55 (m, 1H), 1.95-1.55 (m, 9H), 1.36 (br d, J = 6.4 Hz, 3H) | 2.92 | 681.1 |
| 178 | 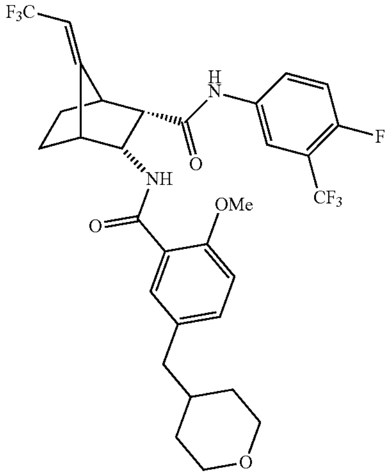 | (7Z)-N-[4-fluoro-3-(trifluoromethyl)phenyl]-3-{2-methoxy-5-[(oxan-4-yl)methyl]benzamido}-7-(2,2,2-trifluoroethylidene)bicyclo[2.2.1]heptane-2-carboxamide | (500 MHz, DMSO-d6) 10.66 (s, 1H), 9.86 (br d, J = 6.9 Hz, 1H), 8.25-8.16 (m, 1H), 7.81-7.67 (m, 2H), 7.47 (br t, J = 9.7 Hz, 1H), 7.29 (dd, J = 8.6, 1.9 Hz, 1H), 7.08 (d, J = 8.5 Hz, 1H), 5.90 (br d, J = 7.8 Hz, 1H), 4.56-4.44 (m, 1H), 3.95 (s, 3H), 3.28-3.11 (m, 5H), 2.96 (br s, 1H), 2.45 (br d, J = 7.0 Hz, 2H), 2.04-1.81 (m, 2H), 1.68-1.58 (m, 1H), 1.52-1.37 (m, 5H), 1.22-1.06 (m, 2H) | 2.63 | 629.3 |

TABLE 2-continued

| Ex # | Structure | Name | $^1$H NMR. δ | LC RT (min) | Ion |
|---|---|---|---|---|---|
| 179 | 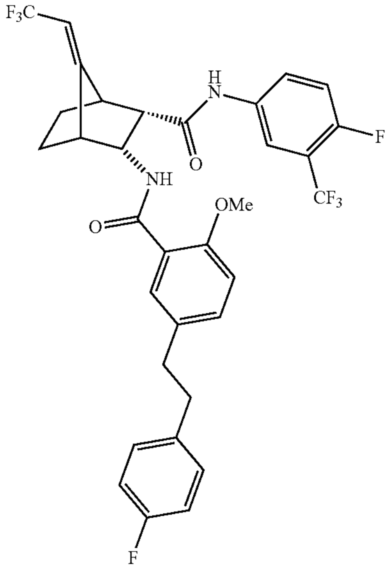 | (7Z)-N-[4-fluoro-3-(trifluoromethyl)phenyl]-3-{5-[2-(4-fluorophenyl)ethyl]-2-methoxybenzamido}-7-(2,2,2-trifluoroethylidene)bicyclo[2.2.1]heptane-2-carboxamide | (500 MHz, DMSO-d6) 10.66 (s, 1H), 9.87 (br d, J = 7.0 Hz, 1H), 8.22 (dd, J = 6.3, 1.9 Hz, 1H), 7.81-7.74 (m, 2H), 7.49 (t, J = 9.6 Hz, 1H), 7.32 (dd, J = 8.3, 2.2 Hz, 1H), 7.22 (dd, J = 8.4, 5.8 Hz, 2H), 7.12-7.01 (m, 3H), 5.97-5.88 (m, 1H), 4.55-4.46 (m, 1H), 3.95 (s, 3H), 3.30-3.16 (m, 2H), 2.98 (br s, 1H), 2.82 (s, 4H), 2.02-1.82 (m, 2H), 1.48 (br d, J = 6.5 Hz, 2H) | 2.79 | 653.0 |
| 180 | 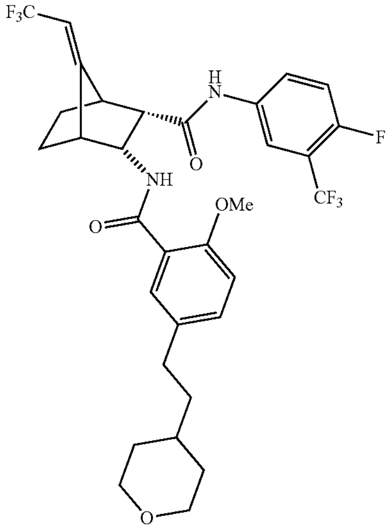 | (7Z)-N-[4-fluoro-3-(trifluoromethyl)phenyl]-3-{2-methoxy-5-[2-(oxan-4-yl)ethyl]benzamido}-7-(2,2,2-trifluoroethylidene)bicyclo[2.2.1]heptane-2-carboxamide | (500 MHz, DMSO-d6) 10.65 (s, 1H), 9.86 (br d, J = 7.0 Hz, 1H), 8.27-8.18 (m, 1H), 7.82-7.71 (m, 2H), 7.49 (br t, J = 9.7 Hz, 1H), 7.34-7.28 (m, 1H), 7.08 (d, J = 8.4 Hz, 1H), 5.96-5.87 (m, 1H), 4.57-4.45 (m, 1H), 3.95 (s, 3H), 3.81 (br d, J = 10.0 Hz, 2H), 3.31-3.20 (m, 3H), 2.97 (br s, 1H), 2.57 (br s, 1H), 2.05-1.82 (m, 2H), 1.59 (br d, J = 12.5 Hz, 2H), 1.52-1.38 (m, 5H), 1.31-1.09 (m, 3H), 0.86 (br d, J = 7.2 Hz, 1H) | 2.75 | 643.4 |

TABLE 2-continued

| Ex # | Structure | Name | $^1$H NMR. δ | LC RT (min) | Ion |
|---|---|---|---|---|---|
| 181 | 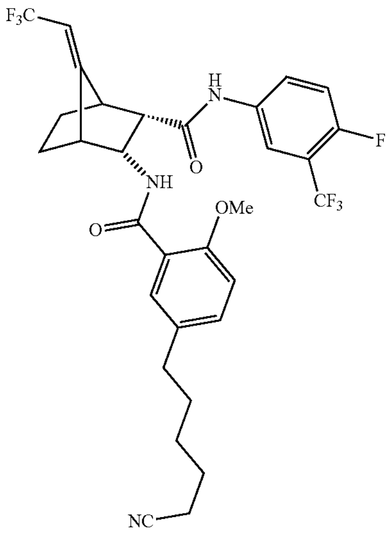 | (7Z)-3-[5-(5-cyanopentyl)-2-methoxybenzamido]-N-[4-fluoro-3-(trifluoromethyl)phenyl]-7-(2,2,2-trifluoroethylidene)bicyclo[2.2.1]heptane-2-carboxamide | (500 MHz, DMSO-d6) 10.68-10.57 (m, 1H), 9.84 (br d, J = 7.0 Hz, 1H), 8.22-8.14 (m, 1H), 7.79-7.69 (m, 2H), 7.54-7.45 (m, 1H), 7.31 (br dd, J = 8.2, 1.8 Hz, 1H), 7.07 (d, J = 8.5 Hz, 1H), 5.89 (q, J = 7.9 Hz, 1H), 4.55-4.45 (m, 1H), 3.94 (s, 3H), 3.63-3.59 (m, 1H), 3.31-3.14 (m, 2H), 2.96 (br s, 1H), 2.55 (s, 1H), 2.43 (br t, J = 7.0 Hz, 2H), 2.06-1.80 (m, 2H), 1.56-1.42 (m, 6H), 1.36-1.28 (m, 2H) | 2.64 | 626.0 |
| 182 | 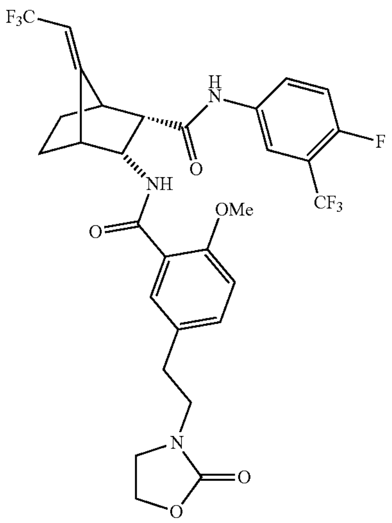 | (7Z)-N-[4-fluoro-3-(trifluoromethyl)phenyl]-3-{2-methoxy-5-[2-(2-oxo-1,3-oxazolidin-3-yl)ethyl]benzamido}-7-(2,2,2-trifluoroethylidene)bicyclo[2.2.1]heptane-2-carboxamide | (500 MHz, DMSO-d6) 10.66 (s, 1H), 9.92 (br s, 1H), 8.29-8.20 (m, 1H), 7.81 (br d, J = 2.3 Hz, 2H), 7.50 (br s, 1H), 7.39 (br dd, J = 8.4, 2.3 Hz, 1H), 7.16-7.07 (m, 1H), 5.94 (br d, J = 7.8 Hz, 1H), 4.52 (br d, J = Hz, 1H), 4.25-4.15 (m, 2H), 4.02-3.95 (m, 3H), 3.38-3.20 (m, 6H), 3.05-2.94 (m, 1H), 2.77 (br t, J = 6.9 Hz, 2H), 2.03-1.83 (m, 2H), 1.49 (br d, J = 6.7 Hz, 2H) | 2.33 | 643.9 |

TABLE 2-continued

| Ex # | Structure | Name | $^1$H NMR. δ | LC RT (min) | Ion |
|---|---|---|---|---|---|
| 183 | 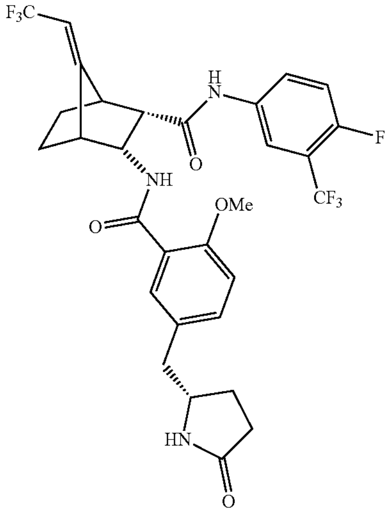 | (7Z)-N-[4-fluoro-3-(trifluoromethyl)phenyl]-3-(2-methoxy-5-{[(2S)-5-oxopyrrolidin-2-yl]methyl}benzamido)-7-(2,2,2-trifluoroethylidene)bicyclo[2.2.1]heptane-2-carboxamide | (500 MHz, DMSO-d6) 10.67 (s, 1H), 9.89 (br d, J = 6.8 Hz, 1H), 8.31-8.14 (m, 1H), 7.86-7.67 (m, 3H), 7.49 (br s, 1H), 7.35 (s, 1H), 7.11 (d, J = 8.4 Hz, 1H), 5.98-5.85 (m, 1H), 4.58-4.46 (m, 1H), 3.97 (s, 3H), 3.78-3.71 (m, 1H), 3.30-3.15 (m, 2H), 2.98 (br s, 1H), 2.82-2.72 (m, 1H), 2.61 (br dd, J = 13.3, 7.7 Hz, 1H), 2.03-1.84 (m, 5H), 1.70-1.58 (m, 1H), 1.49 (br d, J = 7.2 Hz, 2H) | 2.18 | 628.0 |
| 184 | 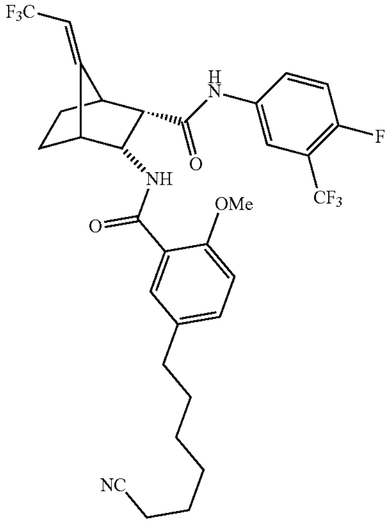 | (7Z)-3-[5-(6-cyanohexyl)-2-methoxybenzamido]-N-[4-fluoro-3-(trifluoromethyl)phenyl]-7-(2,2,2-trifluoroethylidene)bicyclo[2.2.1]heptane-2-carboxamide | (500 MHz, DMSO-d6) 10.62-10.48 (m, 1H), 9.82 (br d, J = 7.0 Hz, 1H), 8.08 (br d, J = 4.3 Hz, 1H), 7.87 (d, J = 2.4 Hz, 1H), 7.70-7.63 (m, 1H), 7.56 (dd, J = 8.9, 2.4 Hz, 1H), 7.37 (br t, J = 9.6 Hz, 1H), 7.06 (d, J = 8.9 Hz, 1H), 5.86-5.75 (m, 1H), 4.46-4.32 (m, 1H), 3.92-3.82 (m, 3H), 3.48-3.36 (m, 6H), 3.19-3.04 (m, 2H), 2.87 (br s, 1H), 2.44 (s, 2H), 2.33 (br t, J = 7.0 Hz, 1H), 1.98-1.68 (m, 2H), 1.48-1.34 (m, 3H), 1.27-1.09 (m, 1H) | 2.77 | 640.1 |

TABLE 2-continued

| Ex # | Structure | Name | $^1$H NMR. δ | LC RT (min) | Ion |
|---|---|---|---|---|---|
| 185 | 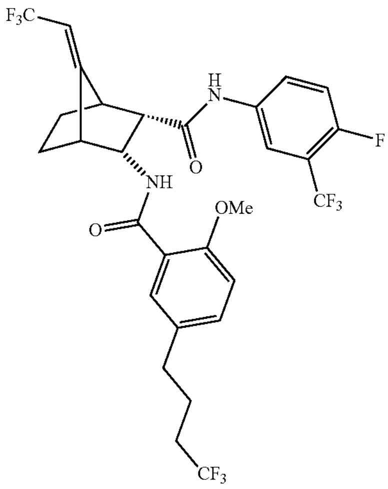 | (7Z)-N-[4-fluoro-3-(trifluoromethyl)phenyl]-3-[2-methoxy-5-(4,4,4-trifluorobutyl)benzamido]-7-(2,2,2-trifluoroethylidene)bicyclo[2.2.1]heptane-2-carboxamide | (500 MHz, DMSO-d6) 10.69-10.55 (m, 1H), 9.85 (br d, J = 6.7 Hz, 1H), 8.20 (br d, J = 4.9 Hz, 1H), 7.76 (br s, 2H), 7.48 (br t, J = 9.6 Hz, 1H), 7.35 (br d, J = 7.0 Hz, 1H), 7.11 (d, J = 8.5 Hz, 1H), 5.91 (br d, J = 7.9 Hz, 1H), 4.51 (br d, J = 3.4 Hz, 1H), 3.96 (s, 3H), 3.31-3.19 (m, 2H), 2.97 (br s, 1H), 2.62 (br t, J = 7.5 Hz, 2H), 2.28-2.13 (m, 2H), 2.06-1.82 (m, 2H), 1.73 (quin, J = 7.6 Hz, 2H), 1.52-1.40 (m, 2H) | 2.67 | 641.0 |
| 186 | 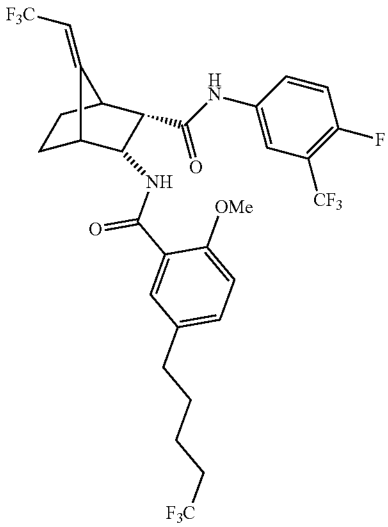 | (7Z)-N-[4-fluoro-3-(trifluoromethyl)phenyl]-3-[2-methoxy-5-(5,5,5-trifluoropentyl)benzamido]-7-(2,2,2-trifluoroethylidene)bicyclo[2.2.1]heptane-2-carboxamide | (500 MHz, DMSO-d6) 10.67-10.57 (m, 1H), 9.85 (br d, J = 7.0 Hz, 1H), 8.21 (br d, J = 4.0 Hz, 1H), 7.83-7.72 (m, 2H), 7.49 (br t, J = 9.9 Hz, 1H), 7.38-7.29 (m, 1H), 7.09 (d, J = 8.5 Hz, 1H), 5.92 (q, J = 7.8 Hz, 1H), 4.52 (br d, J = 4.0 Hz, 1H), 3.96 (s, 3H), 3.31-3.16 (m, 2H), 2.97 (br s, 1H), 2.57 (br t, J = 7.3 Hz, 2H), 2.33-2.19 (m, 2H), 2.05-1.81 (m, 2H), 1.64-1.44 (m, 6H) | 2.73 | 655.1 |
| 187 | 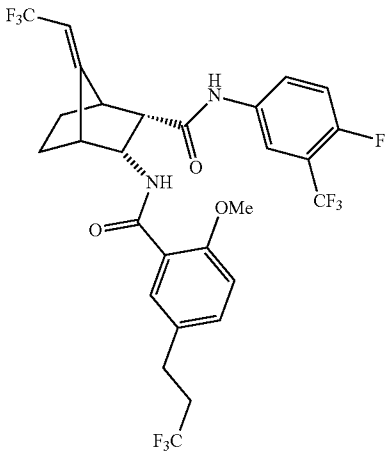 | (7Z)-N-[4-fluoro-3-(trifluoromethyl)phenyl]-3-[2-methoxy-5-(3,3,3-trifluoropropyl)benzamido]-7-(2,2,2-trifluoroethylidene)bicyclo[2.2.1]heptane-2-carboxamide | (500 MHz, DMSO-d6) 10.72-10.58 (m, 1H), 9.92 (br d, J = 7.0 Hz, 1H), 8.19 (br d, J = 4.9 Hz, 1H), 7.97 (d, J = 2.1 Hz, 1H), 7.28-7.72 (m, 1H), 7.66 (dd, J = 8.7, 2.3 Hz, 1H), 7.48 (br t, J = 9.6 Hz, 1H), 7.16 (d, J = 8.9 Hz, 1H), 5.91 (q, J = 7.8 Hz, 1H), 4.54-4.41 (m, 1H), 4.06-3.93 (m, 3H), 3.70-3.58 (m, 3H), 3.30-3.16 (m, 2H), 2.97 (br s, 1H), 2.82-2.75 (m, 1H), 2.01- | 2.58 | 627.0 |

TABLE 2-continued

| Ex # | Structure | Name | $^{1}$H NMR. δ | LC RT (min) | Ion |
|---|---|---|---|---|---|
| | | | 1.73 (m, 2H), 1.48 (br d, J = 7.0 Hz, 2H) | | |
| 188 | 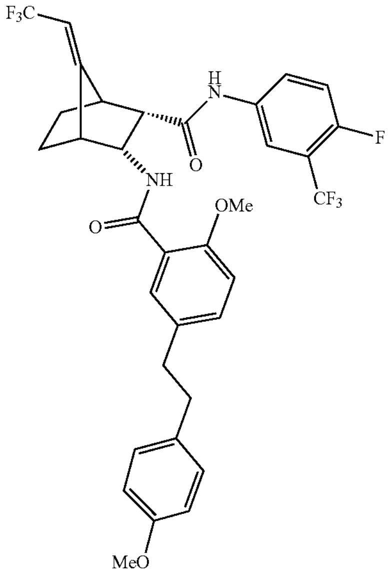 | (7Z)-N-[4-fluoro-3-(trifluoromethyl)phenyl]-3-{2-methoxy-5-[2-(4-methoxyphenyl)ethyl]benzamido}-7-(2,2,2-trifluoroethylidene)bicyclo[2.2.1]heptane-2-carboxamide | (500 MHz, DMSO-d6) 10.57 (s, 1H), 9.77 (d, J = 7.0 Hz, 1H), 8.13 (dd, J = 6.7, 2.4 Hz, 1H), 7.75-7.64 (m, 2H), 7.41 (t, J = 9.8 Hz, 1H), 7.24 (dd, J = 8.5, 2.4 Hz, 1H), 7.09-6.94 (m, 3H), 6.73 (d, J = 8.5 Hz, 2H), 5.84 (q, J = 8.0 Hz, 1H), 4.43 (br dd, J = 7.2, 3.8 Hz, 1H), 3.87 (s, 3H), 3.62 (s, 1H), 3.25-3.08 (m, 2H), 2.90 (br s, 1H), 2.77-2.66 (m, 4H), 2.48 (s, 1H), 2.00-1.87 (m, 1H), 1.82-1.75 (m, 1H), 1.41 (br d, J = 6.7 Hz, 2H), 1.15 (br s, 1H) | 2.81 | 665.3 |
| 189 | 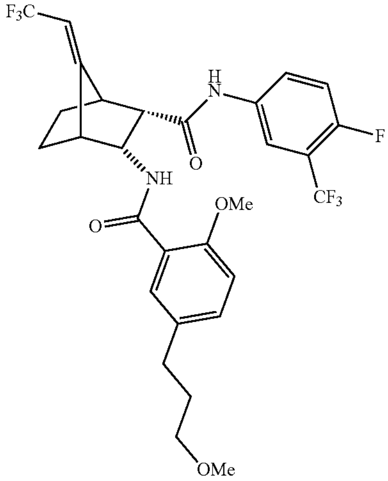 | (2S,3R,7Z)-N-[4-fluoro-3-(trifluoromethyl)phenyl]-3-[2-methoxy-5-(3-methoxypropyl)benzamido]-7-(2,2,2-trifluoroethylidene)bicyclo[2.2.1]heptane-2-carboxamide | (500 MHz, DMSO-d6) 10.68-10.54 (m, 1H), 9.85 (d, J = 7.0 Hz, 1H), 8.19 (dd, J = 6.1, 2.1 Hz, 1H), 7.83-7.70 (m, 3H), 7.47 (t, J = 9.6 Hz, 1H), 7.32 (dd, J = 8.4, 2.0 Hz, 1H), 7.09 (d, J = 8.5 Hz, 1H), 5.90 (q, J = 7.9 Hz, 1H), 4.60-4.39 (m, 1H), 3.95 (s, 3H), 3.30-3.24 (m, 3H), 3.21 (s, 4H), 2.97 (br s, 1H), 2.07-1.80 (m, 3H), 1.75-1.64 (m, 2H), 1.48 (br d, J = 6.1 Hz, 1H) | 2.71 | 603.0 |

TABLE 2-continued

| Ex # | Structure | Name | $^1$H NMR. δ | LC RT (min) | Ion |
|---|---|---|---|---|---|
| 190 | 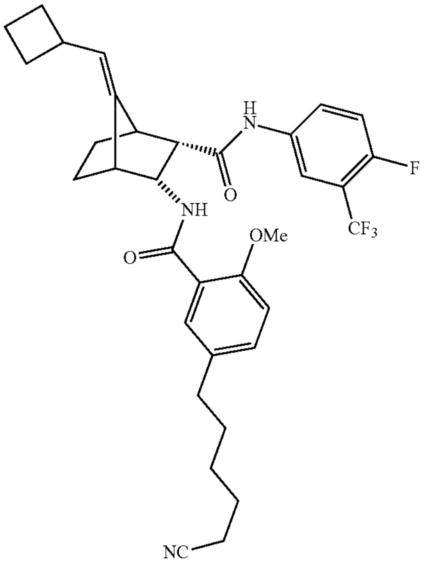 | (7Z)-3-[5-(5-cyanopentyl)-2-methoxybenzamido]-7-(cyclobutylmethylidene)-N-[4-fluoro-3-(trifluoromethyl)phenyl]bicyclo[2.2.1]heptane-2-carboxamide | (500 MHz, DMSO-d6) 10.52 (s, 1H), 9.79 (br d, J = 7.3 Hz, 1H), 8.19 (br d, J = 4.6 Hz, 1H), 7.83-7.69 (m, 2H), 7.46 (br t, J = 9.8 Hz, 1H), 7.35-7.23 (m, 1H), 7.08 (br d, J = 8.5 Hz, 1H), 5.36 (d, J = 8.5 Hz, 1H), 4.40-4.31 (m, 1H), 3.95 (s, 3H), 3.76-3.51 (m, 2H), 3.11 (br dd, J = 10.8, 4.7 Hz, 1H), 2.92 (br s, 1H), 2.68 (br s, 1H), 2.45 (br t, J = 6.9 Hz, 2H), 2.24-2.04 (m, 2H), 1.96-1.69 (m, 6H), 1.61-1.47 (m, 5H), 1.40-1.25 (m, 4H) | 2.91 | 612.3 |
| 191 | 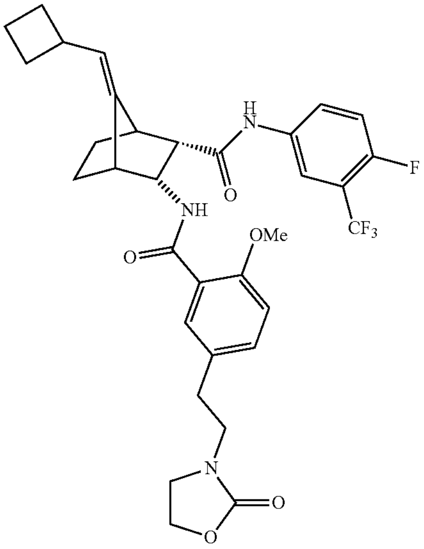 | (7Z)-7-(cyclobutylmethylidene)-N-[4-fluoro-3-(trifluoromethyl)phenyl]-3-{2-methoxy-5-[2-(2-oxo-1,3-oxazolidin-3-yl)ethyl]benzamido}bicyclo[2.2.1]heptane-2-carboxamide | (500 MHz, DMSO-d6) 10.42 (s, 1H), 9.71 (br d, J = 7.0 Hz, 1H), 8.18-8.10 (m, 1H), 7.78-7.64 (m, 2H), 7.44-7.36 (m, 1H), 7.32-7.23 (m, 1H), 7.02 (br d, J = 8.5 Hz, 1H), 5.28 (br d, J = 8.5 Hz, 1H), 4.31-4.23 (m, 1H), 4.11 (br t, J = 7.9 Hz, 2H), 3.88 (s, 3H), 3.46-3.39 (m, 1H), 3.36-3.24 (m, 3H), 3.11-2.95 (m, 2H), 2.85 (br s, 1H), 2.68 (br t, J = 6.9 Hz, 2H), 2.60 (br s, 1H), 2.17-1.97 (m, 2H), 1.85-1.59 (m, 6H), 1.34-1.21 (m, 2H) | 2.53 | 630.2 |

TABLE 2-continued

| Ex # | Structure | Name | $^1$H NMR. δ | LC RT (min) | Ion |
|---|---|---|---|---|---|
| 192 | 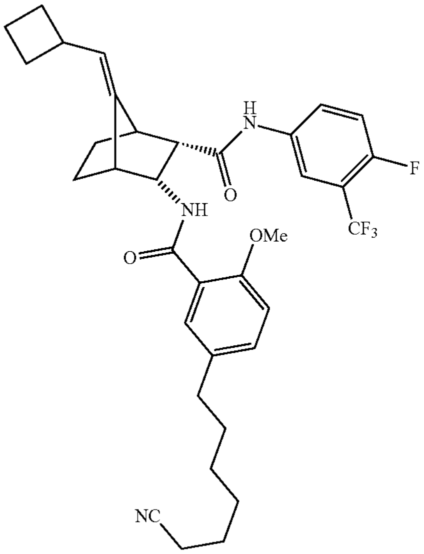 | (7Z)-3-[5-(6-cyanohexyl)-2-methoxybenzamido]-7-(cyclobutylmethylidene)-N-[4-fluoro-3-(trifluoromethyl)phenyl]bicyclo[2.2.1]heptane-2-carboxamide | (500 MHz, DMSO-d6) 10.50-10.36 (m, 1H), 9.70 (br d, J = 7.1 Hz, 1H), 8.12 (br d, J = 6.1 Hz, 1H), 7.73-7.61 (m, 2H), 7.38 (br t, J = 9.6 Hz, 1H), 7.23 (dd, J = 8.4, 2.2 Hz, 1H), 6.99 (d, J = 8.5 Hz, 1H), 5.27 (d, J = 8.4 Hz, 1H), 4.28 (br d, J = 5.6 Hz, 1H), 3.86 (s, 3H), 3.53 (br s, 2H), 3.08-2.96 (m, 2H), 2.84 (br s, 1H), 2.60 (br s, 1H), 2.36 (br t, J = 7.0 Hz, 2H), 2.16-1.99 (m, 2H), 1.87-1.59 (m, 6H), 1.44 (quin, J = 7.3 Hz, 4H), 1.35-1.24 (m, 4H), 1.24-1.11 (m, 2H) | 3.06 | 625.9 |
| 193 | 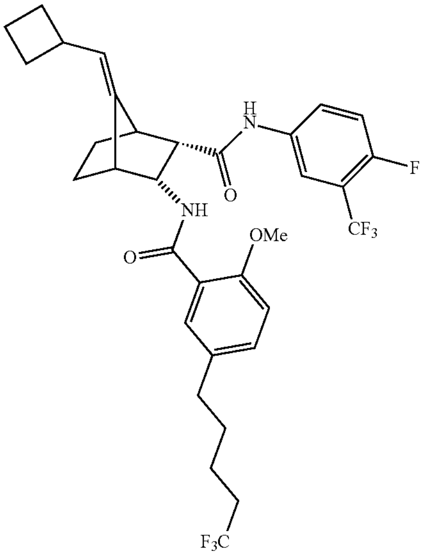 | (7Z)-7-(cyclobutylmethylidene)-N-[4-fluoro-3-(trifluoromethyl)phenyl]-3-[2-methoxy-5-(5,5,5-trifluoropentyl)benzamido]bicyclo[2.2.1]heptane-2-carboxamide | (500 MHz, DMSO-d6) 10.50 (s, 1H), 9.77 (d, J = 7.3 Hz, 1H), 8.18 (br d, J = 6.4 Hz, 1H), 7.82-7.69 (m, 2H), 7.45 (br t, J = 9.5 Hz, 1H), 7.31 (dd, J = 8.4, 2.3 Hz, 1H), 7.07 (d, J = 8.5 Hz, 1H), 5.35 (d, J = 8.4 Hz, 1H), 4.41-4.30 (m, 1H), 3.93 (s, 3H), 3.11-3.05 (m, 1H), 2.91 (br s, 1H), 2.67 (br s, 1H), 2.61-2.53 (m, 3H), 2.29-2.03 (m, 4H), 1.93-1.66 (m, 6H), 1.58 (quin, J = 7.3 Hz, 2H), 1.49-1.41 (m, 2H), 1.39-1.28 (m, 2H) | 3.18 | 641.1 |

TABLE 2-continued

| Ex # | Structure | Name | $^1$H NMR. δ | LC RT (min) | Ion |
|---|---|---|---|---|---|
| 194 | 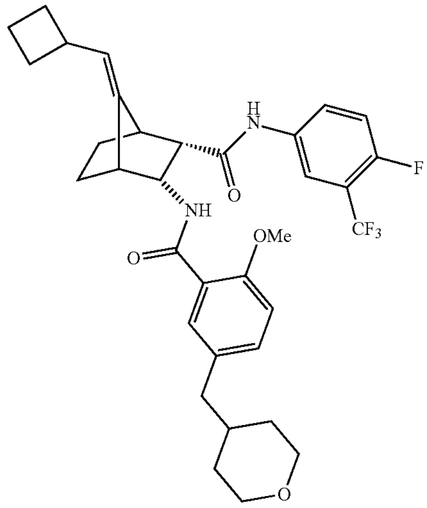 | (7Z)-7-(cyclobutylmethylidene)-N-[4-fluoro-3-(trifluoromethyl)phenyl]-3-{2-methoxy-5-[(oxan-4-yl)methyl]benzamido}bicyclo[2.2.1]heptane-2-carboxamide | (500 MHz, DMSO-d6) 10.55-10.49 (m, 1H), 9.80 (br d, J = 7.3 Hz, 1H), 8.24 (br d, J = 4.9 Hz, 1H), 7.84-7.71 (m, 2H), 7.50 (br t, J = 9.6 Hz, 1H), 7.31 (br d, J = 8.5 Hz, 1H), 7.10 (br d, J = 8.5 Hz, 1H), 5.42-5.37 (m, 1H), 4.43-4.35 (m, 1H), 3.98 (s, 3H), 3.84-3.76 (m, 2H), 3.27-3.18 (m, 2H), 3.18-3.06 (m, 2H), 2.95 (br s, 1H), 2.71 (br s, 1H), 2.49 (br s, 1H), 2.28-2.11 (m, 2H), 2.00-1.62 (m, 8H), 1.50-1.32 (m, 4H), 1.25-1.13 (m, 2H) | 2.79 | 615.1 |
| 195 | 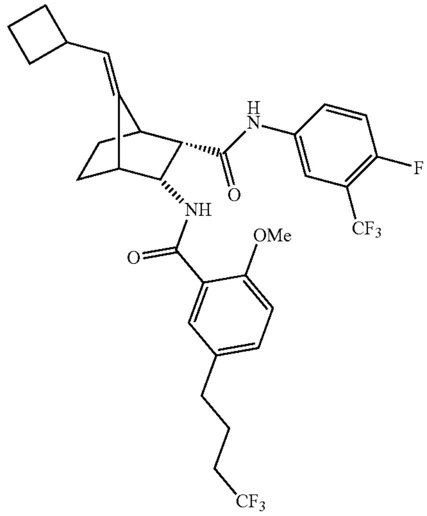 | (7Z)-7-(cyclobutylmethylidene)-N-[4-fluoro-3-(trifluoromethyl)phenyl]-3-[2-methoxy-5-(4,4,4-trifluorobutyl)benzamido]bicyclo[2.2.1]heptane-2-carboxamide | (500 MHz, DMSO-d6) 10.60-10.50 (m, 1H), 9.81 (br d, J = 6.7 Hz, 1H), 8.21 (br d, J = 5.5 Hz, 1H), 7.77 (br s, 2H), 7.55-7.44 (m, 1H), 7.37 (br d, J = 8.9 Hz, 1H), 7.12 (br d, J = 8.9 Hz, 1H), 5.38 (br d, J = 8.2 Hz, 1H), 4.45-4.33 (m, 1H), 3.97 (s, 3H), 3.60 (br s, 1H), 3.19-3.05 (m, 2H), 2.95 (br s, 1H), 2.70 (br s, 1H), 2.69-2.60 (m, 2H), 2.29-2.09 (m, 5H), 1.94-1.84 (m, 3H), 1.75 (br s, 3H), 1.37 (br s, 2H) | 3.05 | 627.0 |

TABLE 2-continued

| Ex # | Structure | Name | $^1$H NMR. δ | LC RT (min) | Ion |
|---|---|---|---|---|---|
| 196 | 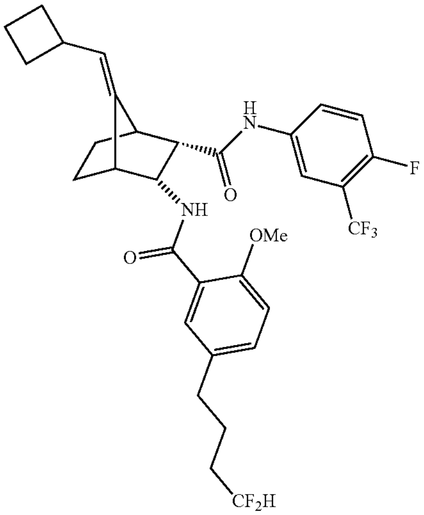 | (7Z)-7-(cyclobutylmethylidene)-3-[5-(4,4-difluorobutyl)-2-methoxybenzamido]-N-[4-fluoro-3-(trifluoromethyl)phenyl]bicyclo[2.2.1]heptane-2-carboxamide | (500 MHz, DMSO-d6) 10.51 (s, 1H), 9.80 (br d, J = 7.0 Hz, 1H), 8.21 (br d, J = 4.3 Hz, 1H), 7.82-7.73 (m, 2H), 7.47 (s, 1H), 7.38-7.29 (m, 1H), 7.10 (d, J = 8.5 Hz, 1H), 6.26-5.92 (m, 1H), 5.37 (d, J = 8.2 Hz, 1H), 4.37 (br d, J = 6.4 Hz, 1H), 3.96 (s, 3H), 3.18-3.05 (m, 2H), 2.94 (br s, 1H), 2.69 (br s, 1H), 2.61 (br t, J = 7.2 Hz, 2H), 2.24-2.09 (m, 2H), 1.95-1.72 (m, 8H), 1.70-1.60 (m, 2H), 1.42-1.31 (m, 2H) | 3.04 | 609.1 |
| 198 | 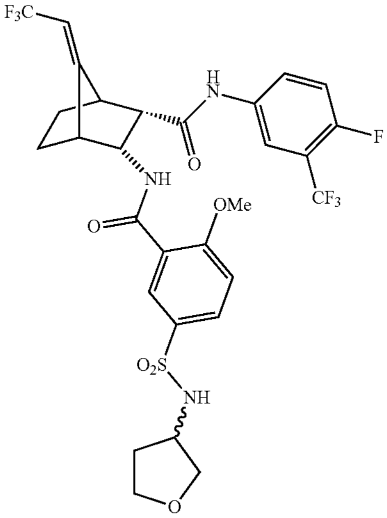 | (2S,3R,7Z)-N-[4-fluoro-3-(trifluoromethyl)phenyl]-3-{2-methoxy-5-[(oxolan-3-yl)sulfamoyl]benzamido}-7-(2,2,2-trifluoroethylidene)bicyclo[2.2.1]heptane-2-carboxamide | 1HNMR (500 MHz, DMSO-d6) 10.67 (s, 1H), 10.02 (d, J = 7.0 Hz, 1H), 8.38 (d, J = 2.4 Hz, 1H), 8.19 (d, J = 4.0 Hz, 1H), 7.95-7.86 (m, 2H), 7.28-7.74 (m, 1H), 7.54-7.44 (m, 1H), 7.39 (d, J = 8.9 Hz, 1H), 5.98-5.86 (m, 1H), 4.50 (br. s., 1H), 4.08 (s, 3H), 3.75-3.48 (m, 2H), 3.32 (dd, J = 8.9, 4.3 Hz, 1H), 3.29-3.20 (m, 2H), 2.98 (s, 2H), 2.00-1.78 (m, 4H), 1.63-1.52 (m, 1H), 1.49 (d, J = 7.3 Hz, 2H) | 2.32 B | 680.0 |

TABLE 2-continued

| Ex # | Structure | Name | $^1$H NMR. δ | LC RT (min) | Ion |
|---|---|---|---|---|---|
| 199 | 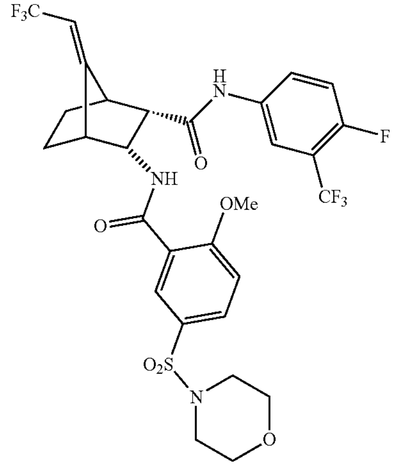 | (2S,3R,7Z)-N-[4-fluoro-3-(trifluoromethyl)phenyl]-3-[2-methoxy-5-(morpholine-4-sulfonyl)benzamido]-7-(2,2,2-triflurooethylidene)bicyclo[2.2.1]heptane-2-carboxamide | 1HNMR (500 MHz, DMSO-d6) 10.67 (s, 1H), 10.06 (d, J = 6.7 Hz, 1H), 8.25 (d, J = 2.4 Hz, 1H), 8.21 (d, J = 4.0 Hz, 1H), 7.86 (dd, J = 8.9, 2.4 Hz, 1H), 7.78 (d, J = 8.9 Hz, 1H), 7.52-7.39 (m, 2H), 5.93 (q, J = 7.9 Hz, 1H), 4.50 (br. s., 1H), 4.11 (s, 3H), 3.61 (br. s., 2H), 3.33-3.20 (m, 2H), 2.99 (br. s., 1H), 2.82 (br. s., 4H), 1.99-1.80 (m, 2H), 1.49 (d, J = 4.6 Hz, 2H) | 2.32 B | 680.1 |
| 200 | 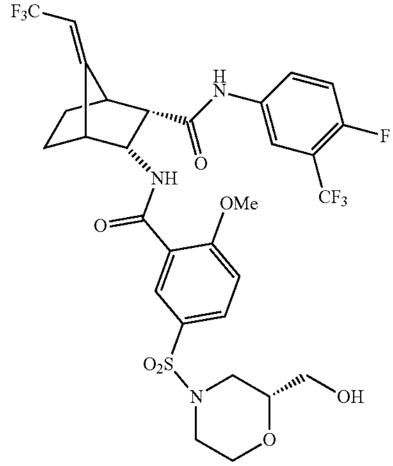 | (2S,3R,7Z)-N-[4-fluoro-3-(trifluoromethyl)phenyl]-3-(5-{[(2R)-2-(hydroxymethyl)morpholin-4-yl]sulfonyl}-2-methoxybenzamido)-7-(2,2,2-trifluoroethylidene)bicyclo[2.2.1]heptane-2-carboxamide | (500 MHz, DMSO-d6) 10.68 (s, 1H), 10.07 (d, J = 7.0 Hz, 1H), 8.25 (d, J = 2.4 Hz, 1H), 8.21 (d, J = 4.0 Hz, 1H), 7.85 (dd, J = 8.7, 2.6 Hz, 1H), 7.81-7.72 (m, 1H), 7.53-7.40 (m, 2H), 5.93 (d, J = 7.9 Hz, 1H), 4.84 (t, J = 5.8 Hz, 1H), 4.50 (br. s., 1H), 4.11 (s, 3H), 3.91-3.78 (m, 1H), 3.54-3.33 (m, 2H), 3.32-3.19 (m, 3H), 2.99 (br. s., 1H), 2.28-2.16 (m, 1H), 2.03-1.81 (m, 4H), 1.49 (d, J = 5.2 Hz, 2H) | 2.31 B | 709.9 |
| 201 | 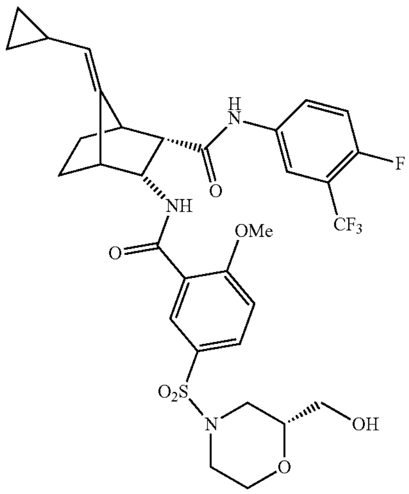 | (2S,3R,7Z)-7-(cyclopropylmethylidene)-N-[4-fluoro-3-(trifluoromethyl)phenyl]-3-(5-{[(2R)-2-(hydroxymethyl)morpholin-4-yl]sulfonyl}-2-methoxybenzamido) bicyclo[2.2.1]heptane-2-carboxamide | (500 MHz, DMSO-d6) 10.55 (s, 1H), 10.03 (d, J = 7.0 Hz, 1H), 8.26 (d, J = 2.1 Hz, 1H), 8.19 (d, J = 4.6 Hz, 1H), 7.85 (dd, J = 8.5, 2.1 Hz, 1H), 7.76 (br. s., 1H), 7.51-7.41 (m, 2H), 4.85 (t, J = 5.3 Hz, 1H), 4.69 (d, J = 9.5 Hz, 1H), 4.42 (br. s., 1H), 4.11 (s, 3H), 3.90-3.80 (m, 1H), 3.57-3.49 (m, 1H), 3.45-3.33 (m, 1H), 3.27 (dt, J = 11.4, 5.8 Hz, 1H), 3.19-3.12 (m, 1H), | 2.43 B | 682.3 |

TABLE 2-continued

| Ex # | Structure | Name | $^1$H NMR. δ | LC RT (min) | Ion |
|---|---|---|---|---|---|
| | | | 3.10 (br. s., 1H), 2.72 (br. s., 1H), 2.28-2.17 (m, 1H), 1.98 (t, J = 10.7 Hz, 1H), 1.78 (dd, J = 13.3, 8.7 Hz, 2H), 1.54-1.35 (m, 3H), 0.80-0.67 (m, 2H), 0.33 (br. s., 2H) | | |
| 202 | 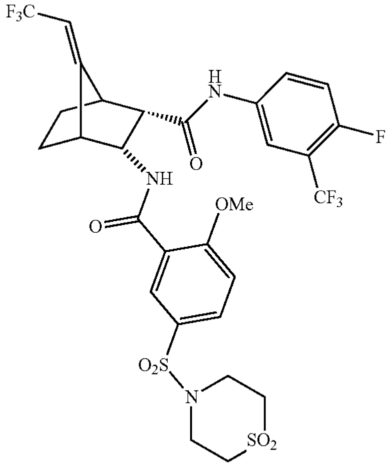 | (2S,3R,7Z)-3-{5-[(1,1-dioxo-1λ$^6$-thiomorpholin-4-yl)sulfonyl]-2-methoxybenzamido}-N-[4-fluoro-3-(trifluoromethyl)phenyl]-7-(2,2,2-trifluoroethylidene)bicyclo[2.2.1]heptane-2-carboxamide | 1HNMR (500 MHz, DMSO-d6) 10.68 (s, 1H), 10.08 (d, J = 6.8 Hz, 1H), 8.30 (d, J = 2.5 Hz, 1H), 8.21 (d, J = 4.1 Hz, 1H), 7.94 (dd, J = 8.7, 2.5 Hz, 1H), 7.83-7.74 (m, 1H), 7.54-7.42 (m, 2H), 5.93 (d, J = 7.8 Hz, 1H), 4.49 (br. s., 1H), 4.11 (s, 3H), 3.52-3.81 (m, 3H), 3.32-3.21 (m, 4H), 2.99 (br. s., 1H), 1.98-1.81 (m, 2H), 1.49 (br. s., 2H) | 2.34 B | 728.2 |
| 203 | 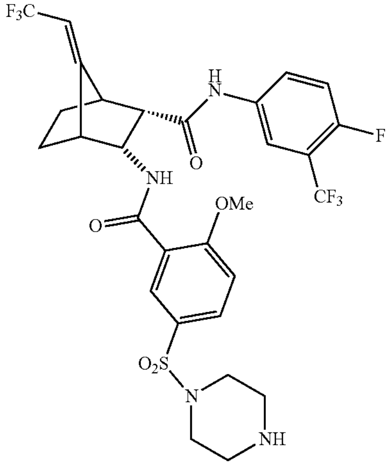 | (2S,3R,7Z)-N-[4-fluoro-3-(trifluoromethyl)phenyl]-3-[2-methoxy-5-(piperazine-1-sulfonyl)benzamido]-7-(2,2,2-trifluoroethylidene)bicyclo[2.2.1]heptane-2-carboxamide | 1HNMR (500 MHz, DMSO-d6) 10.72 (s, 1H), 10.10 (d, J = 6.8 Hz, 1H), 8.27 (d, J = 2.2 Hz, 1H), 8.20 (d, J = 2.4 Hz, 1H), 7.91 (dd, J = 8.7, 2.4 Hz, 1H), 7.80-7.74 (m, 1H), 7.53-7.43 (m, 2H), 5.97-5.87 (m, 1H), 4.53-4.42 (m, 1H), 4.11 (s, 3H), 3.32-2.93 (m, 11H), 2.01-1.78 (m, 3H), 1.49 (d, J = 6.6 Hz, 2H) | 2.22 B | 679.0 |

TABLE 2-continued

| Ex # | Structure | Name | $^1$H NMR. δ | LC RT (min) | Ion |
|---|---|---|---|---|---|
| 204 | 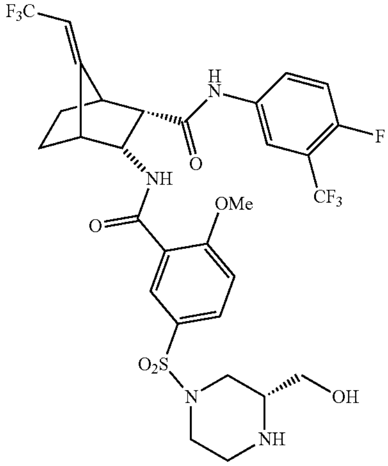 | (2S,3R,7Z)-N-[4-fluoro-3-(trifluoromethyl)phenyl]-3-(5-{[(3R)-3-(hydroxymethyl)piperazin-1-yl]sulfonyl}-2-methoxybenzamido)-7-(2,2,2-trifluoroethylidene)bicyclo[2.2.1]heptane-2-carboxamide | (500 MHz, DMSO-d6) 10.68 (s, 1H), 10.07 (s, 1H), 8.24 (d, J = 2.2 Hz, 1H), 8.21-8.17 (m, 1H), 7.87-7.81 (m, 1H), 7.80-7.71 (m, 1H), 7.44 (d, J = 9.0 Hz, 2H), 5.98-5.85 (m, 1H), 4.55-4.44 (m, 1H), 4.10 (s, 3H), 3.33-3.14 (m, 3H), 2.98 (br. s., 1H), 2.90 (d, J = 12.2 Hz, 1H), 2.72-2.59 (m, 2H), 2.19-2.08 (m, 1H), 1.96-1.77 (m, 4H), 1.49 (d, J = 5.6 Hz, 2H) | 2.18 B | 709.2 |
| 205 | 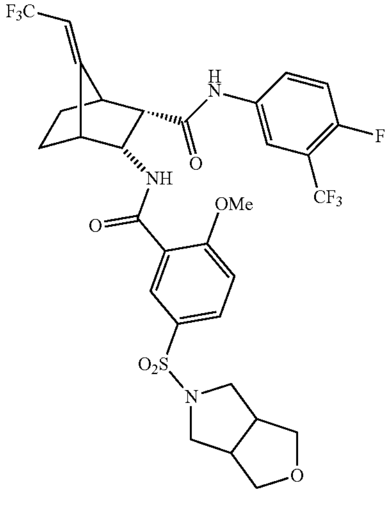 | (2S,3R,7Z)-N-[4-fluoro-3-(trifluoromethyl)phenyl]-3-(5-{hexahydro-1H-furo[3,4-c]pyrrole-5-sulfonyl}-2-methoxybenzamido)-7-(2,2,2-trifluoroethylidene)bicyclo[2.2.1]heptane-2-carboxamide | (500 MHz, DMSO-d6) 10.66 (s, 1H), 10.05 (d, J = 6.8 Hz, 1H), 8.28 (d, J = 2.4 Hz, 1H), 8.24-8.17 (m, 1H), 7.88 (dd, J = 8.7, 2.5 Hz, 1H), 7.83-7.74 (m, 1H), 7.53-7.40 (m, 2H), 5.98-5.88 (m, 1H), 4.56-4.46 (m, 1H), 4.14-4.08 (m, 3H), 3.66-3.58 (m, 2H), 3.56-3.37 (m, 3H), 3.32-3.20 (m, 2H), 3.09 (dt, J = 9.1, 6.8 Hz, 2H), 2.99 (br. s., 1H), 2.86-2.71 (m, 3H), 1.99-1.82 (m, 2H), 1.49 (d, J = 4.8 Hz, 2H) | 2.36 B | 706.2 |

TABLE 2-continued

| Ex # | Structure | Name | $^1$H NMR. δ | LC RT (min) | Ion |
|---|---|---|---|---|---|
| 206 | 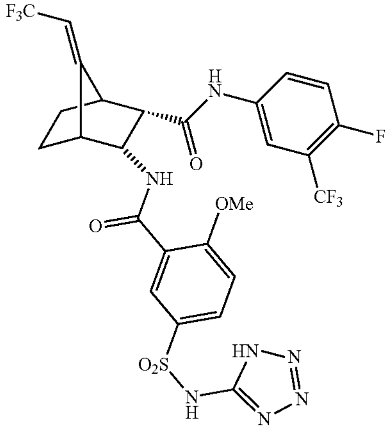 | (2S,3R,7Z)-N-[4-fluoro-3-(trifluoromethyl)phenyl]-3-{2-methoxy-5-[(1H-1,2,3,4-tetrazol-5-yl)sulfamoyl]benzamido}-7-(2,2,2-trifluoroethylidene)bicyclo[2.2.1]heptane-2-carboxamide | 1HNMR (500 MHz, DMSO-d6) 10.64 (s, 1H), 9.92 (d, J = 6.7 Hz, 1H), 8.35 (s, 1H), 8.22-8.15 (m, 2H), 7.93 (d, J = 7.0 Hz, 1H), 7.77 (br. s., 1H), 7.47 (t, J = 9.9 Hz, 1H), 7.20 (d, J = 8.5 Hz, 1H), 5.96-5.86 (m, 1H), 4.49 (br. s., 1H), 4.01 (s, 3H), 3.30-3.20 (m, 2H), 2.96 (br. s., 1H), 2.01-1.81 (m, 3H), 1.47 (d, J = 4.9 Hz, 2H) | 1.88 B | 678.1 |
| 207 | 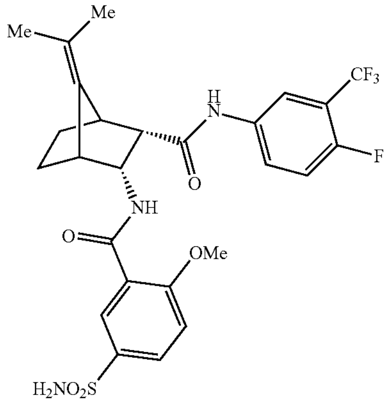 [SMILES: COc1ccc(S(N)(=O)=O)cc1C(=O)N[C@@H]1C2CCC(C2=C(C)C)[C@@H]1C(=O)Nc1ccc(F)c(C(F)(F)F)c1] | (2S,3R)-N-[4-fluoro-3-(trifluoromethyl)phenyl]-3-(2-methoxy-5-sulfamoylbenzamido)-7-(propan-2-ylidene)bicyclo[2.2.1] heptane-2-carboxamide | (500 MHz, DMSO-d6) δ 10.59 (s, 1H), 9.97 (d, J = 6.1 Hz, 1H), 8.40 (d, J = 2.1 Hz, 1H), 8.21 (d, J = 4.9 Hz, 1H), 7.90 (dd, J = 8.8, 2.4 Hz, 1H), 7.80 (d, J = 8.3 Hz, 1H), 7.48 (t, J = 9.7 Hz, 1H), 7.38-7.30 (m, 3H), 4.38-4.30 (m, 1H), 4.06 (s, 3H), 3.11 (dd, J = 10.6, 4.0 Hz, 1H), 3.06-3.01 (m, 1H), 2.97-2.91 (m, 1H), 1.81-1.74 (m, 1H), 1.74-1.65 (m, 7H), 1.40-1.28 (m, 2H) | 222, B | 570.3 |
| 208 | 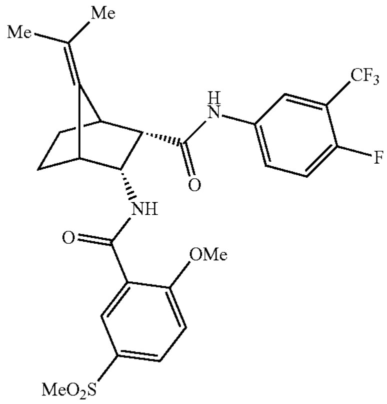 [SMILES: COc1ccc(S(C)(=O)=O)cc1C(=O)N[C@@H]1C2CCC(C2=C(C)C)[C@@H]1C(=O)Nc1ccc(F)c(C(F)(F)F)c1] | (2S,3R)-N-[4-fluoro-3-(trifluoromethyl)phenyl]-3-(5-methanesulfonyl-2-methoxybenzamido)-7-(propan-2-ylidene)bicyclo[2.2.1] heptane-2-carboxamide | 500 MHz, DMSO-d6) δ 10.57 (s, 1H), 9.98 (br d, J = 7.0 Hz, 1H), 8.40 (d, J = 2.1 Hz, 1H), 8.18 (d, J = 4.3 Hz, 1H), 8.01 (dd, J = 8.7, 2.0 Hz, 1H), 7.82-7.75 (m, 1H), 7.46 (t, J = 9.8 Hz, 1H), 7.42 (d, J = 8.9 Hz, 1H), 4.36-4.29 (m, 1H), 4.08 (s, 3H), 3.14 (s, 3H), 3.10 (dd, J = 10.5, 3.8 Hz, 1H), 3.04-3.00 (m, 1H), 2.95-2.91 (m, 1H), 1.81-1.74 (m, 1H), 1.73-1.65 (m, 7H), 1.40-1.28 (m, 2H) | 2.29, B | 569.3 |

All LC RT are method C unless otherwise denoted.

Example 209 to Example 226 were prepared as described by the general procedure given for Example 197

Example 227

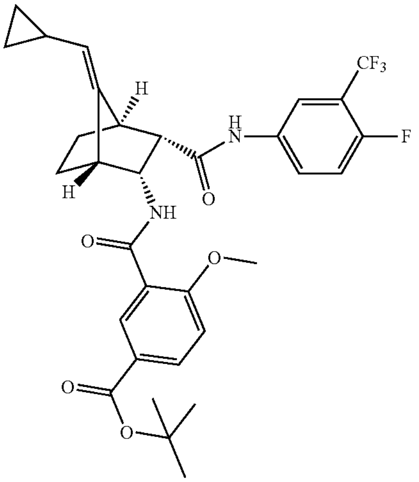 [SMILES: COc1ccc(C(=O)OC(C)(C)C)cc1C(=O)N[C@H]1[C@@H](C(=O)Nc2ccc(F)c(C(F)(F)F)c2)[C@H]2CC[C@@H]1/C2=C\C1CC1]

Intermediate 227-1

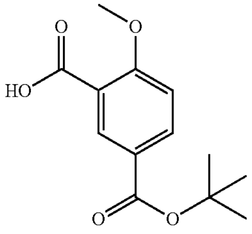 [SMILES: COc1ccc(C(=O)OC(C)(C)C)cc1C(=O)O]

Intermediate 227-1 was prepared from methyl 5-formyl-2-methoxybenzoate as described in US patent U.S. Pat. No. 5,665,719. (320 mg, 68%). LC-MS RT: 2.5 min, m/z=251.1 (M−H); Method B.

Example 227: Prepared from intermediate 227-1 and IV-2a according to the general procedure for Example 1 to afford (1R,2S,3R,4R,Z)-3-amino-7-(cyclopropylmethylene)-N-(4-fluoro-3-(trifluoromethyl)phenyl) bicyclo[2.2.1]heptane-2-carboxamide (310 mg, 94% yield). 1H-NMR (500 MHZ, DMSO-d6) δ 1H NMR (400 MHZ, DMSO-d6) δ=10.53 (s, 1H), 9.90 (d, J=7.1 Hz, 1H), 8.49 (d, J=2.4 Hz, 1H), 8.22 (dd, J=2.7, 6.6 Hz, 1H), 8.01 (dd, J=2.3, 8.7 Hz, 1H), 7.77 (br s, 1H), 7.48 (t, J=9.8 Hz, 1H), 7.28 (d, J=8.8 Hz, 1H), 4.68 (d, J=9.8 Hz, 1H), 4.47-4.36 (m, 1H), 4.06 (s, 3H), 3.20-3.06 (m, 2H), 2.72 (t, J=3.7 Hz, 1H), 1.85-1.72 (m, 2H), 1.58-1.32 (m, 14H), 0.82-0.67 (m, 2H), 0.35 (dd, J=2.0, 4.6 Hz, 2H). LC-MS RT: 2.83 min; MS (ESI) m/z 603.3 $(M-H)^+$; Method B.

Example 228

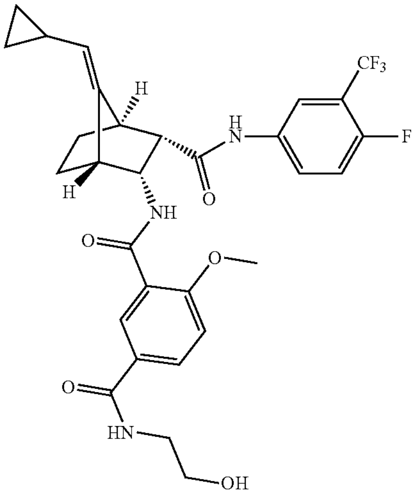 [SMILES: COc1ccc(C(=O)NCCO)cc1C(=O)N[C@H]1[C@@H](C(=O)Nc2ccc(F)c(C(F)(F)F)c2)[C@H]2CC[C@@H]1/C2=C\C1CC1]

Intermediate 238-1

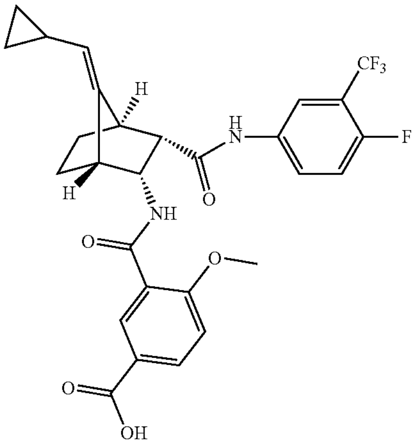 [SMILES: COc1ccc(C(=O)O)cc1C(=O)N[C@H]1[C@@H](C(=O)Nc2ccc(F)c(C(F)(F)F)c2)[C@H]2CC[C@@H]1/C2=C\C1CC1]

Example 227 (150 mg, 0.25 mmol) was dissolved DCM (3.0 mL) at 0° C. and treated with TFA (0.3 mL, 4 mmol). The cooling bath was removed and the reaction mixture stirred at rt for 3 h. The reaction mixture was concentrated under reduced pressure to afford Intermediate 236-1 (130 mg, 96% yield) as an off-white solid which was used without further purification. LC-MS RT: 0.56 min, m/z=547.3 $(M+H)^+$; Method B.

Example 228: Prepared from intermediate 238-1 and IV-2a according to the general procedure for Example 1 to afford (1R,2S,3R,4R,Z)-3-amino-7-(cyclopropylmethylene)-N-(4-fluoro-3-(trifluoromethyl)phenyl) bicyclo[2.2.1]heptane-2-carboxamide (310 mg, 94% yield). $^1$H NMR (400 MHZ, DMSO-d6) δ 10.53 (s, 1H), 9.88 (d, J=7.0 Hz, 1H), 8.51-8.39 (m, 2H), 8.23 (dd, J=2.5, 6.5 Hz, 1H), 7.98 (dd, J=2.5, 9.0 Hz, 1H), 7.85-7.74 (m, 1H), 7.49 (t, J=9.8 Hz, 1H), 7.25 (d, J=8.5 Hz, 1H), 4.70 (d, J=9.5 Hz, 1H), 4.51-4.41 (m, 2H), 4.05 (s, 3H), 3.46 (q, J=6.0 Hz, 2H), 3.17 (br dd, J=4.3, 10.8 Hz, 1H), 3.13-3.09 (m, 1H), 2.73 (br s, 1H), 1.88-1.77 (m, 2H), 1.67 (quin, J=6.7 Hz, 2H), 1.51 (br d, J=5.0 Hz, 1H), 1.45-1.33 (m, 2H), 1.24 (s, 1H), 0.80-0.67 (m, 2H), 0.36 (dd, J=2.3, 4.8 Hz, 2H). LC-MS RT: 2.12 min; MS (ESI) m/z 646.3 $(M+H)^+$; Method B.

Examples 229 to Example 259 were prepared as described by the general procedure given for Example 228

Examples 260 to Example 279 were prepared as described by the general procedure given for Example 157

Example 280 and 281

Example 280

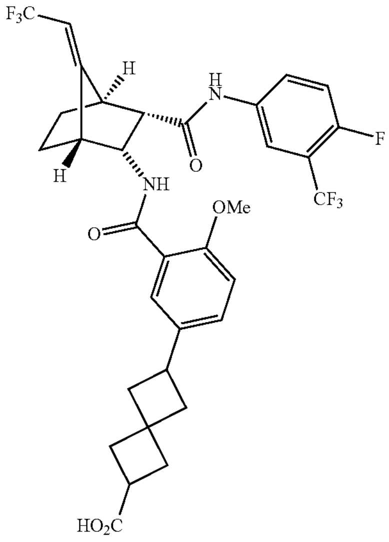

Example 281

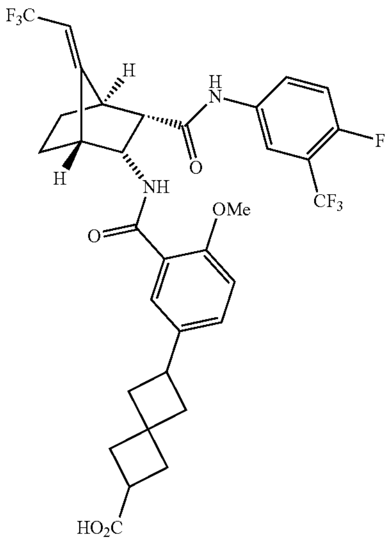

Examples 280 and 281 were prepared by the general procedures described for Example 149 to afford a mixture of 2 diastereomers. The diastereomers were separated according to the following conditions: Preparative Chromatographic Conditions: Instrument: Berger SFC Column: AS 25×3 cm ID, 5 micron Temperature: 40° C. Flow rate: 85 mL/min Mobile Phase: 88 $CO_2$/12% MeOH Analytical Conditions: Analytical Chromatographic Conditions: Instrument: Agilent SFC (LVL-L4021 Lab) Column: AS 250×4.6 mm ID, 5 micron. Flow rate: 2.0 mL/min Mobile Phase: 85 $CO_2$/15% MeOH.

Example 280, Peak 1, RT=15.8 min (5.1 mg, 7%). 1H NMR (500 MHz, DMSO-d6) δ 10.62 (s, 1H), 9.84 (d, J=7.1 Hz, 1H), 8.28-8.16 (m, 1H), 7.84-7.73 (m, 2H), 7.48 (t, J=9.8 Hz, 1H), 7.30 (dd, J=8.5, 2.2 Hz, 1H), 7.07 (d, J=8.6 Hz, 1H), 5.92 (q, J=7.8 Hz, 1H), 4.57-4.44 (m, 1H), 3.94 (s, 3H), 3.52 (br d, J=3.0 Hz, 2H), 3.35-3.14 (m, 4H), 2.97 (br s, 1H), 2.38 (ddd, J=10.4, 7.7, 4.9 Hz, 1H), 2.29-2.21 (m, 2H), 2.17-2.08 (m, 1H), 2.02-1.79 (m, 6H), 1.65 (dd, J=11.4, 7.7 Hz, 1H), 1.48 (br d, J=7.2 Hz, 2H). LC-MS: 2.67 min; MS (ESI) m/z 655.3 $(M+H)^+$; Method C.

Example 281, Peak 2, RT=18.1 min (854 mg, 6% yield). 1H NMR (500 MHz, DMSO-d6) δ 9.84 (d, J=7.0 Hz, 1H), 8.26-8.16 (m, 1H), 7.81-7.71 (m, 2H), 7.48 (t, J=9.6 Hz, 1H), 7.30 (dd, J=8.5, 2.2 Hz, 1H), 7.07 (d, J=8.5 Hz, 1H), 5.92 (q, J=7.8 Hz, 1H), 4.54-4.45 (m, 1H), 3.94 (s, 3H), 3.54-3.50 (m, 2H), 3.38-3.15 (m, 4H), 2.97 (br s, 1H), 2.39 (ddd, J=10.5, 7.8, 4.6 Hz, 1H), 2.29-2.20 (m, 2H), 2.18-2.10 (m, 1H), 2.02-1.77 (m, 6H), 1.65 (dd, J=11.4, 7.5 Hz, 1H), 1.47 (br d, J=7.9 Hz, 2H). LC-MS: 2.67 min; MS (ESI) m/z 655.3 $(M+H)^+$; Method C.

Example 282

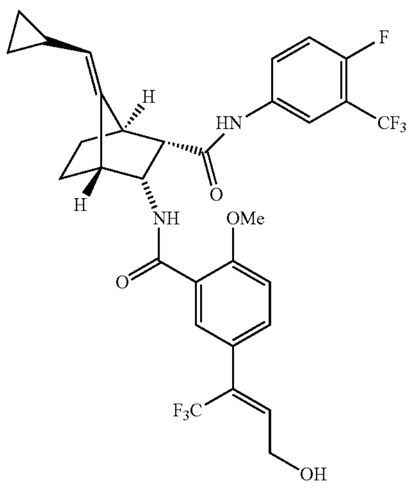

Intermediate 282-1

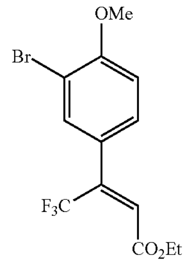 [SMILES: CCOC(=O)/C=C(/c1ccc(OC)c(Br)c1)C(F)(F)F]

A solution of triethyl phosphonoacetate (0.20 g, 0.90 mmol) in toluene (2 mL) at 0° C. was treated with NaH (60% in mineral oil) (0.036 g, 0.90 mmol) and the reaction mixture stirred for 30 min. To this solution was added 1-(3-bromo-4-methoxyphenyl)-2,2,2-trifluoroethan-1-one (0.17 g, 0.60 mmol) as a solution in toluene (2 mL) and the resulting solution was allowed to warm to rt over 14 h. The reaction mixture was diluted with EtOAc and extracted with brine (2×). The layers were separated and the organic extracts were dried over sodium sulfate, filtered and concentrated under reduced pressure. The residue was purified by silica gel chromatography to furnish ethyl (Z)-3-(3-bromo-4-methoxyphenyl)-4,4,4-trifluorobut-2-enoate (140 mg, 0.40 mmol, 66% yield). 1H NMR (500 MHz, $CDCl_3$) δ 7.52 (d, J=2.1 Hz, 1H), 7.25 (s, 1H), 6.94 (d, J=8.5 Hz, 1H), 6.64-6.59 (m, 1H), 4.12 (q, J=7.1 Hz, 2H), 3.95 (s, 3H), 1.16 (d, J=14.2 Hz, 3H). LCMS?

Example 282: A solution of 282-1 (0.039 g, 0.11 mmol) in DCM (10 mL) was treated with DIBAL-H (0.24 mL, 0.24 mmol) at 0° C. and the solution was allowed to warm to RT over 14 h. The reaction mixture was quenched with 1N HCl, diluted with EtOAc and the layers were separated. The organic layer was concentrated under reduced pressure. The residue was combined with $Pd(OAc)_2$ (2.5 mg, 11 μmol), 1,3-bis(diphenylphosphino) propane (4.5 mg, 11 μmol), TEA (0.46 mL, 0.33 mmol) in DMF (1 mL)/water (0.11 mL), blanketed under CO (100 psi) at 100° C. and stirred for 14 h. 1 N HCl (5 mL)) was added to the reaction mixture and the resulting aqueous solution extracted with EtOAc. The organic layer was concentrated under reduced pressure to afford a residue which was combined with IV-2a to afford example 282 according to the general procedure described for Example 1. (1R,2S,3R,4R,Z)-7-(cyclopropylmethylene)-N-(4-fluoro-3-(trifluoromethyl)phenyl)-3-(2-methoxy-5-((Z)-1,1,1-trifluoro-4-hydroxybut-2-en-2-yl)benzamido) bicyclo[2.2.1]heptane-2-carboxamide (5.8 mg, 9.3 μmol, 10% yield). 1H NMR (500 MHz, $CD_3OD$) δ 8.18 (dd, J=6.3, 2.7 Hz, 1H), 7.94 (d, J=2.3 Hz, 1H), 7.79-7.72 (m, 1H), 7.41 (dd, J=8.5, 2.3 Hz, 1H), 7.34-7.24 (m, 2H), 6.66-6.58 (m, 1H), 4.74 (d, J=9.5 Hz, 1H), 4.58 (ddd, J=10.6, 4.0, 1.4 Hz, 1H), 4.13 (s, 3H), 4.08 (d, J=11.4 Hz, 1H), 3.24 (t, J=4.0 Hz, 1H), 3.17 (ddd, J=10.7, 4.4, 1.1 Hz, 1H), 2.73 (t, J=3.9 Hz, 1H), 2.06-1.99 (m, 1H), 1.98-1.90 (m, 1H), 1.68 (dq, J=7.1, 2.5 Hz, 3H), 1.62-1.47 (m, 4H). LC-MS (M-OH)=611.5; HPLC RT=1.53 min; Method A.

Example 283 to Example 296 were prepared as described by the general procedure given for Example 14 Example 297

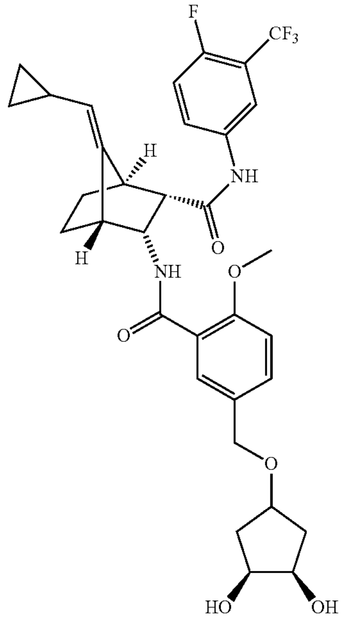 [SMILES: COc1ccc(COC2C[C@@H](O)[C@@H](O)C2)cc1C(=O)N[C@H]1[C@@H](C(=O)Nc2ccc(F)c(C(F)(F)F)c2)[C@H]2CC[C@@H]1/C2=C\C1CC1]

A solution of Example 285 (30 mg, 0.05 mmol) in acetone (2.0 mL) was treated with NMO (12 mg, 0.10 mmol) and osmium tetroxide in t-BuOH (0.039 mL, 5.0 μmol). The reaction mixture was allowed to stir at RT. After 6 h, the reaction mixture was diluted with ethyl acetate and washed with sodium thiosulfate (2×) and brine (2×). The layers were separated, and the organic layer was dried over sodium sulfate, filtered and concentrated under reduced pressure to afford a residue which was purified by preparative HPLC to afford (1R,2S,3R,4R,7Z)-7-(cyclopropylmethylidene)-3-[5-({[(3R,4S)-3,4-dihydroxycyclopentyl]oxy}methyl)-2-methoxybenzamido]-N-[4-fluoro-3-(trifluoromethyl)phenyl]bicyclo[2.2.1]heptane-2-carboxamide (2.9 mg, 9.0%). 1H NMR (400 MHz, METHANOL-d4) δ 8.21-8.08 (m, 1H), 7.99 (d, J=2.2 Hz, 1H), 7.84-7.70 (m, 1H), 7.60-7.42 (m, 1H), 7.35-7.12 (m, 2H), 5.14-5.05 (m, 1H), 4.94-4.81 (m, 10H), 4.22-4.11 (m, 1H), 4.08 (s, 2H), 3.65 (dd, J=10.5, 3.2 Hz, 1H), 2.48 (dt, J=18.0, 3.8 Hz, 2H), 2.37-2.14 (m, 1H), 2.08-1.76 (m, 5H), 1.73-1.44 (m, 2H), 1.38-1.24 (m, 1H), 0.65-0.54 (m, 2H), 0.46-0.31 (m, 2H), LC-MS RT: 2.32 min; MS (ESI) m/z 633.2 $(M+H)^+$; Method B.

Example 298
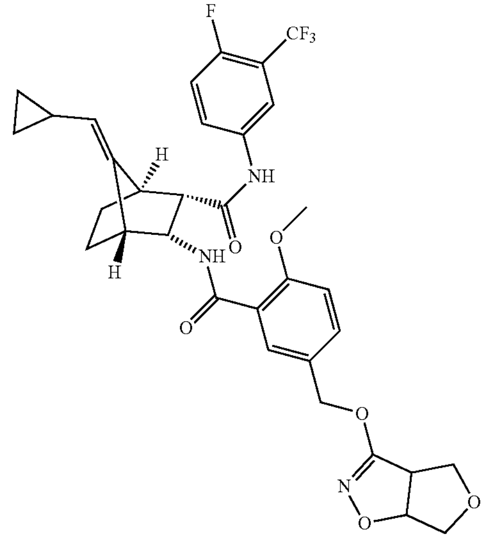
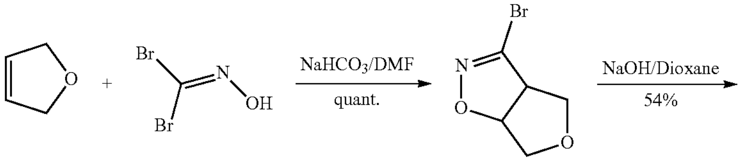
298-1
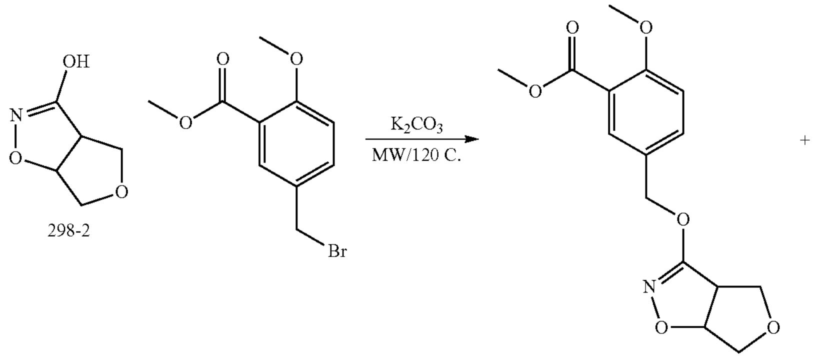
298-2
298-3
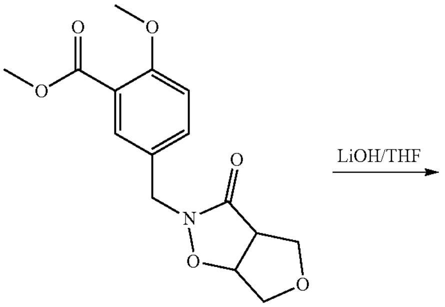
298-4

-continued

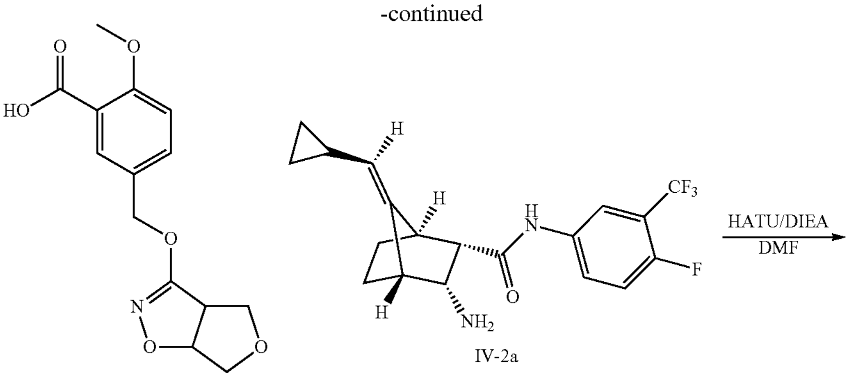

298-5

IV-2a

Example 298

Intermediate 298-1

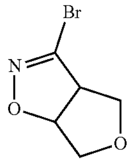

To a solution of hydroxycarbonimidic dibromide (300 mg, 1.5 mmol) in DMF (10 mL) at −15° C. were added 2,5-dihydrofuran (0.12 mL, 1.8 mmol) and then saturated aqueous sodium bicarbonate (3.0 mL, 3.0 mmol) over 1 h 45 min (internal temperature rising to 0° C.). After stirring for 75 min at 0° C., the reaction mixture was diluted with EtOAc, and the resulting solution extracted with water. The layers were separated, and the aqueous layer was further extracted with EtOAc (2×). The combined organic layers were washed successively with brine and water (10 mL each), dried and concentrated under reduced pressure. The residue was purified on ISCO (0-100% Hex/EtOAc) to afford 3-bromo-3a, 4,6,6a-tetrahydrofuro[3,4-d]isoxazole (90 mg, 32%) as a clear oil. 1H NMR (500 MHZ, CHLOROFORM-d) δ 5.39-5.19 (m, 1H), 4.38-4.22 (m, 2H), 4.02-3.94 (m, 1H), 3.75-3.64 (m, 2H)

Intermediate 298-2

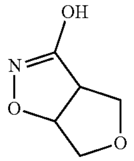

Intermediate 298-1 (90 mg, 0.47 mmol) in dioxane (10 mL) was treated with sodium hydroxide (1N, 1.9 mL, 1.9 mmol) and heated at 80° C. for 16 h. After allowing to cool to RT, the reaction mixture was acidified with 1N HCl and extracted with ethyl acetate (3×) The combined organic extracts were dried over sodium sulfate, filtered and concentrated under reduced pressure. The residue was purified on ISCO (0-100% EtOAc/Hex) to afford 3a,4,6,6a-tetrahydrofuro[3,4-d]isoxazol-3-ol (30 mg, 50%). 1H NMR (500 MHz, CHLOROFORM-d) δ 5.33-5.15 (m, 1H), 4.13 (d, J=7.2 Hz, 1H), 3.94 (br d, J=8.5 Hz, 2H), 3.61-3.37 (m, 2H).

Intermediate 298-3 and 298-4

298-3

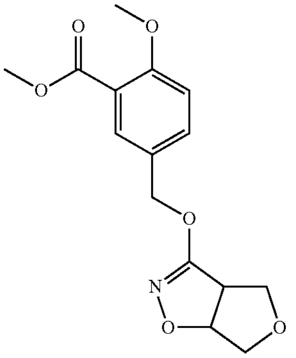

298-4

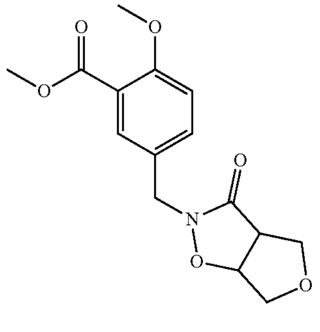

Intermediate 298-2 (30 mg, 0.23 mmol), methyl 5-(bromomethyl)-2-methoxybenzoate and potassium carbonate in acetonitrile (2 mL) were combined in a pressure vial, capped and heated via microwave irradiation at 120° C. for 30 min. After allowing to cool to RT, the reaction mixture was filtered, concentrated under reduced pressure and purified on ISCO (0-100% EtOAc/Hex) to afford methyl 2-methoxy-5-(((3a,4,6,6a-tetrahydrofuro[3,4-d]isoxazol-3-yl)oxy) methyl)benzoate, Intermediate 298-3 (8.0 mg 13%. 1H NMR (400 MHZ, CHLOROFORM-d) δ 7.90-7.84 (m, 1H), 7.53 (dd, J=8.6, 2.4 Hz, 1H), 7.01 (d, J=8.6 Hz, 1H), 5.28 (dd, J=8.8, 4.2 Hz, 1H), 5.10 (d, J=4.4 Hz, 2H), 4.32-4.26 (m, 2H), 3.94 (s, 3H), 3.92 (s, 3H), 3.85-3.78 (m, 1H), 3.70-3.63 (m, 2H) LC-MS RT: 0.71 min; MS (ESI) m/z 330.0 $(M+Na)^+$ Method D and methyl 2-methoxy-5-((3-oxotetrahydrofuro[3,4-d]isoxazol-2 (3H)-yl)methyl)benzoate, Intermediate 298-4 (15 mg, 22%). 1H NMR (600 MHz, $CDCl_3$) δ 7.75 (d, J=2.3 Hz, 1H), 7.42 (dd, J=8.6, 2.4 Hz, 1H), 6.97 (d, J=8.5 Hz, 1H), 5.08 (dd, J=8.2, 4.1 Hz, 1H), 4.65 (s, 2H), 4.44 (dd, J=9.4, 1.0 Hz, 1H), 4.13 (d, J=11.0 Hz, 1H), 3.91 (s, 3H), 3.90 (s, 3H), 3.76 (dd, J=9.4, 6.7 Hz, 1H), 3.67 (dd, J=11.1, 4.2 Hz, 1H), 3.56-3.49 (m, 1H). LC-MS RT: 0.64 min; MS (ESI) m/z 308.0 (M+H)+; Method D.

Intermediate 298-5

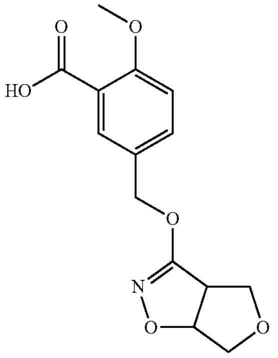 [SMILES: COc1ccc(COC2=NOC3COCC23)cc1C(=O)O]

To a suspension of 298-3 (8 mg, 0.03 mmol) in THF (1.0 mL) and water (0.3 mL) was added LiOH (1.0 M, 78 µl, 0.078 mmol). After stirring for 12 h at room temperature, the reaction mixture was diluted with water and acidified to pH 1.0 with 1N HCL. The reaction mixture was extracted with EtOAc (3×), dried over sodium sulfate, filtered and concentrated under reduced pressure to afford to afford 2-methoxy-5-(((3a,4,6,6a-tetrahydrofuro[3,4-d]isoxazol-3-yl)oxy)methyl)benzoic acid (7.0 mg, 86%) which was used without further purification.

Example 298: Prepared from intermediate 298-5 and IV-2a according to the general procedure for Example 1 to afford (1R,2S,3R,4R,7Z)-3-(5-{[(3aR,6aR)-3-oxo-hexahydrofuro[3,4-d][1,2]oxazol-2-yl]methyl}-2-methoxybenzamido)-7-(cyclopropylmethylidene)-N-[4-fluoro-3-(trifluoromethyl)phenyl]bicyclo[2.2.1]heptane-2-carboxamide (1.0 mg, 14% yield). 1H NMR (500 MHZ, DMSO-d6) δ 10.60-10.47 (m, 1H), 9.86 (t, J=6.6 Hz, 1H), 8.22 (br d, J=6.3 Hz, 1H), 7.87 (s, 1H), 7.82-7.73 (m, 1H), 7.48 (brt, J=9.9 Hz, 1H), 7.38 (dd, J=8.6, 2.4 Hz, 1H), 7.17 (d, J=8.5 Hz, 1H), 5.16 (dd, J=7.3, 4.4 Hz, 1H), 4.69 (d, J=9.5 Hz, 1H), 4.61 (s, 2H), 4.51-4.37 (m, 1H), 4.12 (br d, J=8.0 Hz, 1H), 4.05-3.91 (m, 4H), 3.72-3.56 (m, 2H), 3.21-3.02 (m, 2H), 2.72 (br s, 1H), 1.95-1.72 (m, 2H), 1.57-1.33 (m, 3H), 0.83-0.66 (m, 2H), 0.35 (br s, 2H). LC-MS RT: 2.36 min; MS (ESI) m/z 644.05 (M+H)+; Method B.

Example 299: Prepared from intermediate 298-4 according to the general procedure for Example 298 to afford (1R,2S,3R,4R,7Z)-3-(5-{[(3aR,6aR)-3-oxo-hexahydrofuro[3,4-d][1,2]oxazol-2-yl]methyl}-2-methoxybenzamido)-7-(cyclopropylmethylidene)-N-[4-fluoro-3-(trifluoromethyl)phenyl]bicyclo[2.2.1]heptane-2-carboxamide (20 mg, 47% yield). 1H NMR (500 MHz, DMSO-d6) δ 10.29 (br s, 1H), 9.63 (br s, 1H), 7.97 (br s, 1H), 7.62 (br s, 1H), 7.53 (br d, J=1.2 Hz, 1H), 7.30-7.11 (m, 2H), 6.93 (br d, J=8.2 Hz, 1H), 4.92 (br d, J=3.7 Hz, 1H), 4.45 (br d, J=9.5 Hz, 1H), 4.37 (br s, 2H), 4.19 (br d, J=5.2 Hz, 1H), 3.88 (br d, J=7.9 Hz, 1H), 3.80-3.68 (m, 3H), 3.47-3.24 (m, 4H), 2.97-2.80 (m, 2H), 2.48 (br s, 1H), 1.65-1.47 (m, 2H), 1.33-1.07 (m, 3H), 0.58-0.43 (m, 2H), 0.11 (br s, 2H). LC-MS RT: 2.37 min; MS (ESI) m/z 644.05 $(M+H)^+$; Method B.

Examples 300 to Example 301 were prepared as described by the general procedure given for Example 298

Examples 302 to Example 320 were prepared as described by the general procedure given for Example 124

Examples 321 to Example 326 were prepared as described by the general procedure given for Example 62

Examples 327 to Example 333 were prepared as described by the general procedure given for Example 48

Example 340

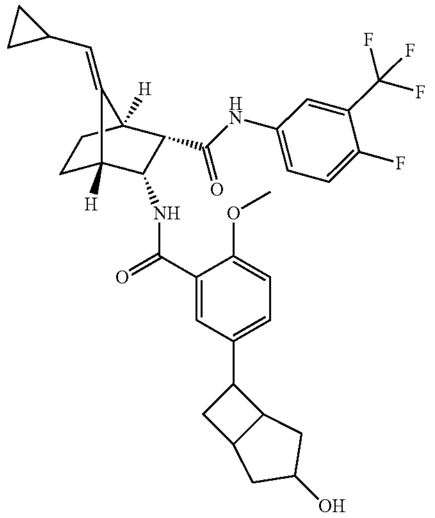 [SMILES: COc1ccc(C2CC3CC(O)CC32)cc1C(=O)N[C@H]1[C@@H](C(=O)Nc2ccc(F)c(C(F)(F)F)c2)[C@H]2CC[C@@H]1/C2=C\C1CC1]

Intermediate 340-1

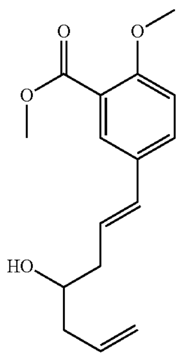 [SMILES: C=CCC(O)C/C=C/c1ccc(OC)c(C(=O)OC)c1]

A solution of hepta-1,6-dien-4-ol (4.9 g, 44 mmol) in acetonitrile (53 mL) was treated with methyl 5-bromo-2-methoxybenzoate (2.2 g, 8.8 mmol), $Et_3N$ (2.4 mL, 18 mmol), tri-o-tolylphosphine (0.27 g, 0.88 mmol) and $Pd(OAc)_2$ (0.1 g, 0.4 mmol). The reaction mixture was heated at reflux for 16 h. The reaction mixture was allowed to cool to rt and the reaction mixture was concentrated under reduced pressure to afford a residue, which was purified by silica gel chromatography to afford methyl (E)-5-(4-hydroxyhepta-1,6-dien-1-yl)-2-methoxybenzoate (2.3 g, 8.3 mmol, 95% yield). MS (ESI) m/z 277.0 $(M+H)^+$.

Intermediate 340-2a, 34-2b, 340-2c and 340-2d 340-2a

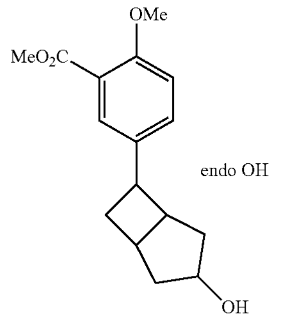

340-2b

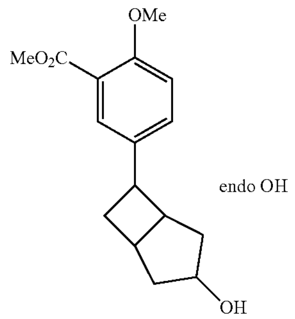

340-2c

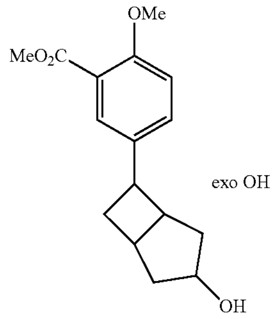

340-2d

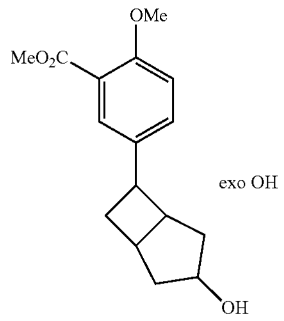

To a solution of Intermediate 340-1 (2.3 g, 8.3 mmol) dissolved in acetonitrile (179 mL) was added $(Ir[dF(CF_3)ppy]_2(dtbpy))-PF_6$, (93 mg, 83 μmol) and the solution irradiated with purple LED for 24 h. The reaction mixture was concentrated under reduced pressure and the isomers were separated on silica gel chromatography to afford: Isomer mixture peak 1 as methyl 5-(3-hydroxybicyclo[3.2.0]heptan-6-yl)-2-methoxybenzoate (425 mg, 1.5 mmol, 18% yield): $^1H$ NMR (500 MHz, $CDCl_3$) δ 7.71 (d, J=2.4 Hz, 1H), 7.38 (dd, J=8.5, 2.3 Hz, 1H), 6.95 (d, J=8.5 Hz, 1H), 4.62 (tt, J=5.3, 2.5 Hz, 1H), 3.92 (s, 3H), 3.91 (s, 3H), 3.59-3.49 (m, 1H), 2.90-2.76 (m, 2H), 2.43-2.34 (m, 1H), 2.33-2.23 (m, 1H), 2.12-2.04 (m, 1H), 2.03-1.97 (m, 1H), 1.95-1.83 (m, 2H) and isomer mixture peak 2 as methyl 5-(3-hydroxybicyclo[3.2.0]heptan-6-yl)-2-methoxybenzoate (264 mg, 0.96 mmol, 11% yield): $^1H$ NMR (500 MHz, $CDCl_3$) δ 7.66 (d, J=2.3 Hz, 1H), 7.35 (dd, J=8.6, 2.4 Hz, 1H), 6.95 (d, J=8.5 Hz, 1H), 4.82 (tt, J=8.4, 6.0 Hz, 1H), 3.92 (s, 3H), 3.91 (s, 3H), 3.03 (ddd, J=9.2, 7.2, 5.3 Hz, 1H), 2.94-2.80 (m, 2H), 2.35-2.24 (m, 1H), 2.11-1.98 (m, 3H), 1.76-1.65 (m, 2H).

Isomer mixture peak 1 was further purified by SFC Chiralpak IA (4.6×100 mm), 3 micron, Mobile Phase: 20% IPA-ACN/80% $CO_2$, Flow Conditions: 2.0 mL/min, 150 Bar, 40° C. to afford 340-2a (Peak 1), RT: 3.7 min; and 340-2b (Peak 2, 264 mg, 11%)), RT: 7.0 min.

Isomer mixture peak 2 was further purified by SFC Chiralpak IA (4.6×100 mm), 3 micron, Mobile Phase: 20% IPA-ACN/80% $CO_2$, Flow Conditions: 2.0 mL/min, 150 Bar, 40° C. to afford 340-2c (Peak 1), RT: 3.2 min; and 340-2d (Peak 2): RT: 5.5 min. Example 340 was prepared from intermediate 340-2a according to the general procedure for Example 298 to afford (1R,2S,3R,4R,7Z)-7-(cyclopropylmethylidene)-N-[4-fluoro-3-(trifluoromethyl)phenyl]-3-(5-{3-hydroxybicyclo[3.2.0]heptan-6-yl}-2-methoxybenzamido) bicyclo[2.2.1]heptane-2-carboxamide (35 mg, 89% yield). 1H NMR (500 MHZ, $CD_3CN$) δ 9.81-9.70 (m, 1H), 8.73 (s, 1H), 8.11 (dd, J=6.6, 2.9 Hz, 1H), 7.94 (d, J=2.4 Hz, 1H), 7.76-7.69 (m, 1H), 7.39 (dd, J=8.5, 2.1 Hz, 1H), 7.28 (t, J=9.7 Hz, 1H), 7.06 (d, J=8.4 Hz, 1H), 4.73 (d, J=9.5 Hz, 1H), 4.61-4.53 (m, 1H), 4.46 (tt, J=5.6, 2.7 Hz, 1H), 4.01 (s, 3H), 3.58-3.50 (m, 1H), 3.15 (t, J=4.0 Hz, 1H), 3.11 (dd, J=10.7, 4.3 Hz, 1H), 2.80 (d, J=3.1 Hz, 2H), 2.74-2.67 (m, 2H), 2.38-2.28 (m, 1H), 2.25-2.19 (m, 1H), 2.13-2.12 (m, 1H), 1.85 (tdd, J=2.4, 1.2, 0.6 Hz, 1H), 1.84-1.82 (m, 1H), 1.81-1.76 (m, 1H), 1.61-1.53 (m, 1H), 1.52-1.43 (m, 2H), 0.83-0.69 (m, 2H), 0.47-0.33 (m, 2H). LC-MS RT: 2.66 min; MS (ESI) m/z 613.4 $(M+H)^+$; Method A Examples 341 to Example 343 were prepared from intermediate 340-2b to 340-2d according to the procedure for Example 340

Example 348

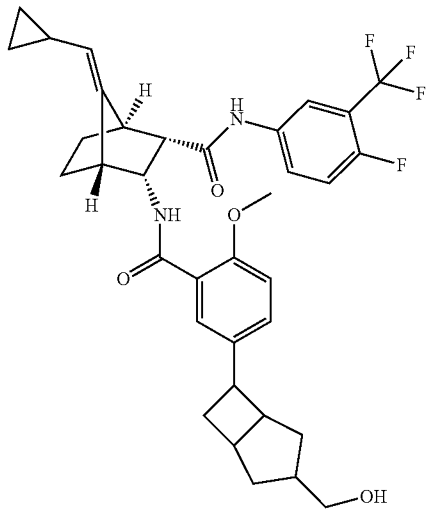 [SMILES: COc1ccc(C2CC3CC(CO)CC32)cc1C(=O)N[C@H]1[C@@H](C(=O)Nc2ccc(F)c(C(F)(F)F)c2)[C@H]2CC[C@@H]1/C2=C\C1CC1]

Intermediate 348-1

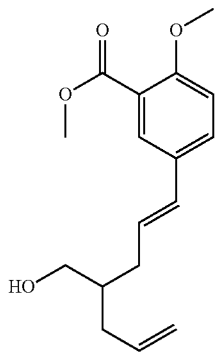 [SMILES: C=CCC(CO)C/C=C/c1ccc(OC)c(C(=O)OC)c1]

2-allylpent-4-en-1-ol (0.98 g, 7.8 mmol) was combined with methyl 5-bromo-2-methoxybenzoate (0.50 g, 2.0 mmol), EtsN (0.57 mL, 4.1 mmol), tri-o-tolylphosphine (0.062 g, 0.20 mmol) and $Pd(OAc)_2$ (0.023 g, 0.10 mmol) in acetonitrile (12 mL) and the reaction mixture heated at reflux for 16 hours. The reaction mixture was allwed to cool to rt. The reaction mixture was concentrated under reduced pressure, then purified on silica gel chromatography to afford a mixture of regioisomers methyl (E)-5-(4-(hydroxymethyl) hepta-1,6-dien-1-yl)-2-methoxybenzoate and methyl 5-(4-(hydroxymethyl) hepta-1,6-dien-2-yl)-2-methoxybenzoate (180 mg, 0.63 mmol, 31% yield). MS (ESI) m/z 291.1 (M+H) $^1$H NMR (500 MHz, $CDCl_3$) δ 7.81 (d, J=2.3 Hz, 1H), 7.45 (dd, J=8.6, 2.4 Hz, 1H), 6.94 (d, J=8.7 Hz, 1H), 6.38 (d, J=15.9 Hz, 1H), 6.15 (dt, J=15.7, 7.3 Hz, 1H), 5.97-5.64 (m, 1H), 5.19-4.96 (m, 2H), 3.96-3.88 (m, 6H), 3.64 (d, J=5.5 Hz, 2H), 2.32-2.25 (m, 2H), 2.22-2.12 (m, 2H), 1.81 (dt, J=12.7, 6.1 Hz, 1H)

Intermediate 348-2a1 to 348-2a7 and 348-2b1 to 348-2b2

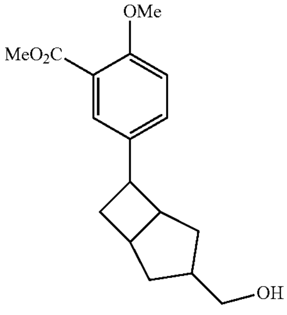

348-2a1 to 348-2a7

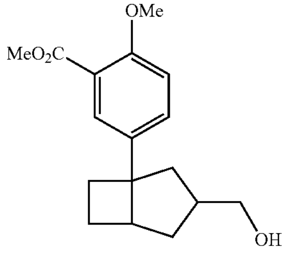

348-2b1 to 348-2b2

Intermediate 348-2a1 to 348-2a7 and 348-2b1 to 348-2b2 were prepared from 350-1 and methyl 5-(4-(hydroxymethyl) hepta-1,6-dien-2-yl)-2-methoxybenzoate according to the general procedure used for intermediate 340-2. The stereoisomers were separated by SFC IG 250×4.6 mm ID, 5 mm, 85/15 $CO_2$/MeOH, 2 mL/min to afford: 348-2a1 (Peak 1): methyl 5-(3-(hydroxymethyl) bicyclo[3.2.0]heptan-6-yl)-2-methoxybenzoate (2.0 mg, 0.0069 mmol, 1.1% yield) RT: 16.1 min. H NMR (500 MHz, $CDCl_3$) δ 7.51 (d, J=2.0 Hz, 1H), 7.21 (dd, J=8.3, 2.0 Hz, 1H), 6.94 (d, J=8.6 Hz, 1H), 3.90 (s, 6H), 3.73 (q, J=9.5 Hz, 1H), 3.58-3.45 (m, 2H), 3.12 (q, J=8.5 Hz, 1H), 2.97-2.85 (m, 1H), 2.49-2.38 (m, 1H), 2.29-2.16 (m, 1H), 1.94 (ddd, J=12.2, 9.7, 6.7 Hz, 1H), 1.70 (dd, J=12.6, 6.0 Hz, 1H), 1.44 (dd, J=13.6, 6.7 Hz, 1H), 1.25-1.22 (m, 1H), 1.17-1.10 (m, 1H).

348-2a2 (Peak 2): regioisomeric mixture of methyl 5-(3-(hydroxymethyl) bicyclo[3.2.0]heptan-6-yl)-2-methoxybenzoate and methyl 5-((1R,3S,5R)-3-(hydroxymethyl) bicyclo [3.2.0]heptan-1-yl)-2-methoxybenzoate (5.5 mg mixture) RT: 17.6 min. LC-MS RT: 0.65 min; MS (ESI) m/z=291.0 (M+H)+; Method A 348-2a3 (Peak 3): methyl 5-(3-(hydroxymethyl) bicyclo[3.2.0]heptan-6-yl)-2-methoxybenzoate (3.1 mg, 0.010 mmol, 1.7% yield) RT=18.8 min, 1H NMR (500 MHZ, $CDCl_3$) δ 7.49 (dd, J=2.4, 0.9 Hz, 1H), 7.18 (ddd, J=8.5, 2.4, 0.9 Hz, 1H), 6.91 (d, J=8.6 Hz, 1H), 3.90 (s, 3H), 3.89 (s, 3H), 3.67-3.54 (m, 3H), 3.10-2.99 (m, 1H), 2.77-2.63 (m, 2H), 2.18-2.03 (m, 2H), 1.94 (td, J=10.4, 7.4 Hz, 1H), 1.80-1.72 (m, 1H), 1.25 (br s, 1H), 1.16-1.04 (m, 2H).

348-2a4 (Peak 6): methyl 5-(3-(hydroxymethyl) bicyclo [3.2.0]heptan-6-yl)-2-methoxybenzoate (4.6 mg, 0.016 mmol, 2.5% yield) RT=31.8 min. 1H NMR (500 MHz, $CDCl_3$) δ 7.67 (d, J=2.3 Hz, 1H), 7.35 (dd, J=8.6, 2.3 Hz, 1H), 6.93 (d, J=8.6 Hz, 1H), 3.90 (s, 3H), 3.89 (s, 3H), 3.73 (d, J=6.3 Hz, 2H), 3.02-2.94 (m, 1H), 2.88-2.83 (m, 1H), 2.83-2.79 (m, 1H), 2.67 (tt, J=11.8, 6.0 Hz, 1H), 2.31-2.23

(m, 1H), 2.05-1.98 (m, 1H), 1.84 (dd, J=12.7, 5.9 Hz, 1H), 1.77 (dd, J=12.8, 6.3 Hz, 1H), 1.41-1.32 (m, 2H).

348-2a5 (Peak 7): methyl 5-(3-(hydroxymethyl) bicyclo [3.2.0]heptan-6-yl)-2-methoxybenzoate (23 mg, 0.079 mmol, 12% yield) RT=32.8 min. $^1$H NMR (500 MHz. $CDCl_3$) δ 7.75-7.57 (m, 1H), 7.33 (dd, J=8.5, 2.0 Hz, 1H), 6.99-6.88 (m, 1H), 3.90 (d, J=6.1 Hz, 6H), 3.76 (d, J=6.4 Hz, 2H), 3.23-3.08 (m, 1H), 2.83-2.63 (m, 2H), 2.34-2.06 (m, 5H), 1.52-1.40 (m, 2H)

348-2a6 (Peak 8): methyl 5-(3-(hydroxymethyl) bicyclo [3.2.0]heptan-6-yl)-2-methoxybenzoate (6.4 mg, 0.022 mmol, 3.5% yield) RT=44.7 min. $^1$H NMR (500 MHz, $CDCl_3$) δ 7.67 (d, J=2.3 Hz, 1H), 7.35 (dd, J=8.6, 2.3 Hz, 1H), 6.93 (d, J=8.6 Hz, 1H), 3.90 (s, 3H), 3.89 (s, 3H), 3.73 (d, J=6.3 Hz, 2H), 3.02-2.94 (m, 1H), 2.88-2.83 (m, 1H), 2.83-2.79 (m, 1H), 2.67 (tt, J=11.8, 6.0 Hz, 1H), 2.31-2.23 (m, 1H), 2.05-1.98 (m, 1H), 1.84 (dd, J=12.7, 5.9 Hz, 1H), 1.77 (dd, J=12.8, 6.3 Hz, 1H), 1.41-1.32 (m, 2H).

348-2a7 (Peak 9): methyl 5-(3-(hydroxymethyl) bicyclo [3.2.0]heptan-6-yl)-2-methoxybenzoate (36 mg, 0.12 mmol, 19% yield) RT=46.4 min. 1H NMR (500 MHZ, $CDCl_3$) δ 7.66 (d, J=2.4 Hz, 1H), 7.34 (dd, J=8.5, 2.4 Hz, 1H), 6.94 (d, J=8.5 Hz, 1H), 3.91 (d, J=6.0 Hz, 6H), 3.77 (br d, J=6.4 Hz, 2H), 3.27-3.13 (m, 1H), 2.82-2.65 (m, 2H), 2.34-2.08 (m, 5H), 1.52-1.38 (m, 3H)

348-2b1 (Peak 4): methyl 5-((1R,3S,5R)-3-(hydroxymethyl) bicyclo[3.2.0]heptan-1-yl)-2-methoxybenzoate (5.6 mg, 0.019 mmol, 3.0% yield) RT=20.5 min. 1H NMR (500 MHZ, CDCl3) δ 7.58 (d, J=2.4 Hz, 1H), 7.27 (dd, J=8.0, 2.5 Hz, 1H), 6.92 (d, J=8.6 Hz, 1H), 3.90 (s, 3H), 3.89 (s, 3H), 3.72 (br s, 2H), 3.00-2.89 (m, 1H), 2.40-2.31 (m, 1H), 2.31-2.17 (m, 4H), 2.06-2.01 (m, 1H), 2.00-1.93 (m, 1H), 1.74-1.66 (m, 1H), 1.46 (ddd, J=13.2, 9.2, 4.0 Hz, 1H), 1.33 (br s, 1H).

348-2b2 (Peak 5): methyl 5-((1R,3S,5R)-3-(hydroxymethyl) bicyclo[3.2.0]heptan-1-yl)-2-methoxybenzoate (1.6 mg, 0.0055 mmol, 1.0% yield) RT=22.1 min. 1H NMR (500 MHz, $CDCl_3$) δ 7.64 (d, J=2.4 Hz, 1H), 7.35 (dd, J=8.6, 2.4 Hz, 1H), 6.94 (d, J=8.6 Hz, 1H), 3.91 (s, 3H), 3.90 (s, 3H), 3.73 (br t, J=5.1 Hz, 2H), 3.02-2.94 (m, 1H), 2.83-2.73 (m, 1H), 2.31 (dd, J=11.7, 6.1 Hz, 1H), 2.25-2.20 (m, 1H), 2.11 (td, J=10.9, 6.5 Hz, 1H), 2.04-2.01 (m, 1H), 1.81 (dd, J=12.3, 5.7 Hz, 1H), 1.60-1.57 (m, 2H), 1.35-1.32 (m, 1H).

Examples 348 was prepared from intermediate 348-2a1 according to the general procedure for Example 340 to afford (1R,2S,3R,4R,7Z)-7-(cyclopropylmethylidene)-N-[4-fluoro-3-(trifluoromethyl)phenyl]-3-{5-[3-(hydroxymethyl) bicyclo[3.2.0]heptan-6-yl]-2-methoxybenzamido}bicyclo[2.2.1]heptane-2-carboxamide (26 mg, 57% yield). 1H NMR (500 MHz, DMSO-d6) δ 10.25 (s, 1H), 9.56 (d, J=7.1 Hz, 1H), 7.98 (dd, J=6.4, 2.3 Hz, 1H), 7.61-7.48 (m, 2H), 7.23 (t, J=9.7 Hz, 1H), 7.10 (dd, J=8.5, 2.3 Hz, 1H), 6.85 (d, J=8.5 Hz, 1H), 4.44 (d, J=9.6 Hz, 1H), 4.37-4.26 (m, 1H), 4.24-4.15 (m, 1H), 3.72 (s, 3H), 3.27 (br t, J=5.8 Hz, 1H), 3.16 (s, 1H), 2.98-2.87 (m, 1H), 2.84 (brt, J=3.6 Hz, 1H), 2.46 (br s, 1H), 2.39-2.32 (m, 3H), 1.98-1.68 (m, 6H), 1.63 (br t, J=8.7 Hz, 1H), 1.58-1.49 (m, 1H), 1.31-1.06 (m, 5H), 0.61-0.42 (m, 2H), 0.11 (br dd, J=4.3, 1.9 Hz, 2H) LC-MS RT: 2.79 min; MS (ESI) m/z 627.1 (M+H)+; Method A Examples 349 to 352 were prepared according to the general procedure for Example 348

Example 353 was prepared from intermediate 348-2b2 according to the procedure for Example 348

Example 354

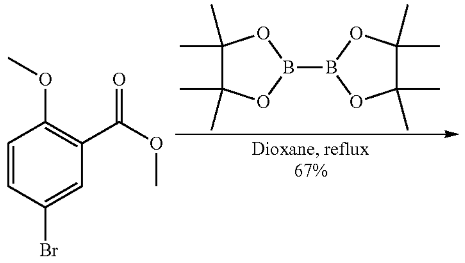

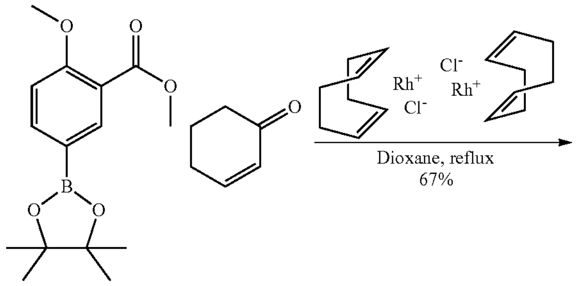

354-1

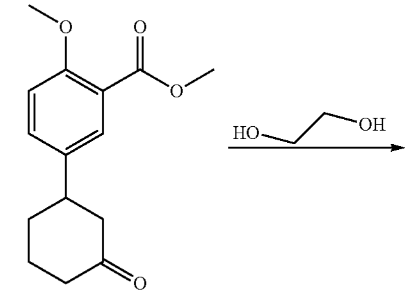

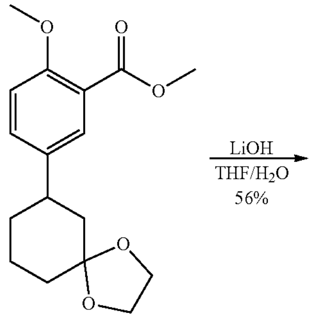

354-2

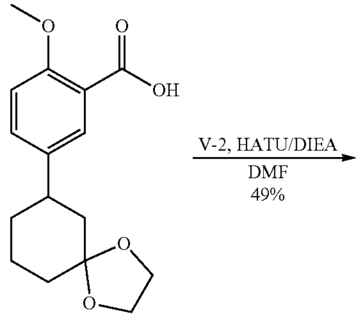

354-4

-continued

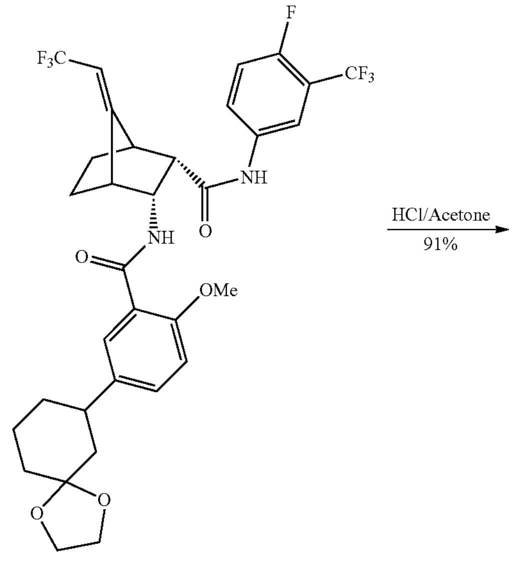

354-5

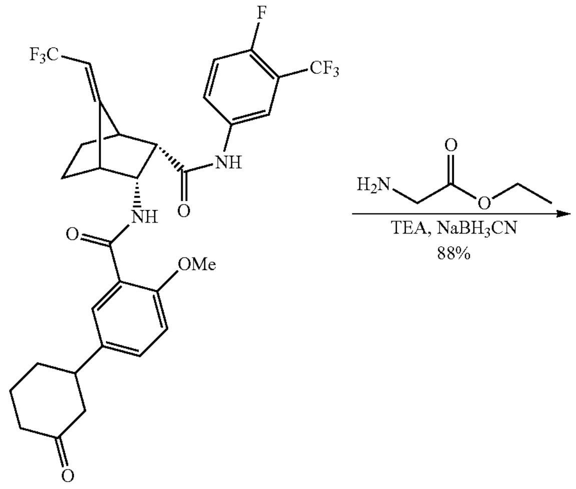

354-6

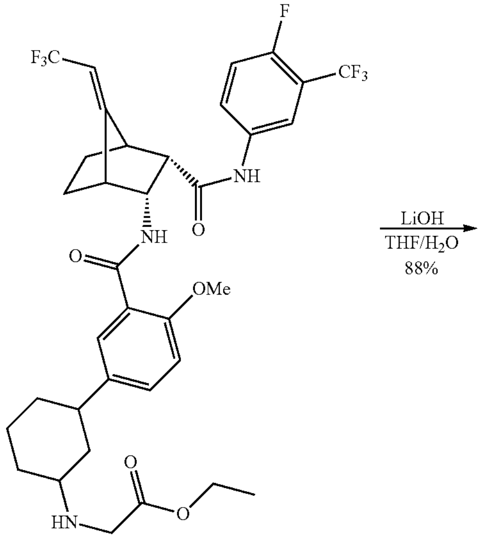

354-6

-continued

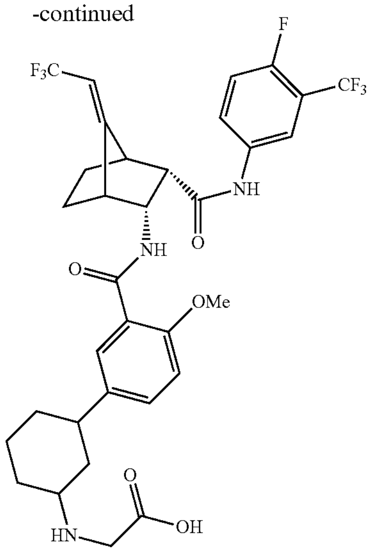

Example 354

Intermediate 354-1

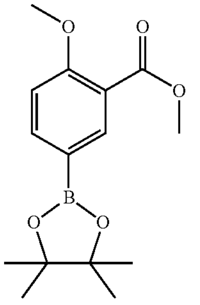

Methyl 5-bromo-2-methoxybenzoate (10 g, 41 mmol), bis(pinacolato)diboron (12 g, 47 mmol), potassium acetate (12 g, 12 mmol) and [1,1'-bis(diphenylphosphino) ferrocene]dichloropalladium (II) (2.7 g, 3.3 mmol) were combined in 1,4-dioxane (100 mL) and heated at reflux for 2 h. After cooling to rt, the reaction mixture was concentrated under reduced pressure. The resulting residue was diluted with EtOAc and filtered through a pad of celite. The filtrate was concentrated under reduced pressure and purified via silica gel column chromatography to afford methyl 2-methoxy-5-(4,4,5,5-tetramethyl-1,3,2-dioxaborolan-2-yl) benzoate (8.0 g, 27 mmol, 67% yield). MS (ESI) m/z 293.1 (M+H)$^+$.

Intermediate 354-2

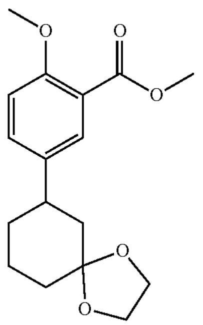 [SMILES: COC(=O)c1cc(C2CCCC3(C2)OCCO3)ccc1OC]

Potassium hydroxide (0.15 g, 2.7 mmol) was combined with $H_2O$ (2.5 mL) and the solution degassed with nitrogen for 5 minutes. The solution was added to chloro (1,5-cyclooctadiene)rhodium(I) dimer (6.6 mg, 0.013 mmol) in 1,4-dioxane (10 mL) and the reaction mixture allowed to stir at rt. After 10 minutes, the reaction mixture was sequentially treated with intermediate 354-1 (1.8 g, 5.4 mmol) and cyclohex-2-en-1-one (0.52 mL, 5.4 mmol) and stirred at room temperature. After 10 h, the reaction mixture was diluted with ethyl acetate and washed with a 10% aqueous sodium hydroxide solution (2×). The layers were separated and the organic layer washed with brine (2×), dried over sodium sulfate and concentrated under reduced pressure. The residue was purified on silica gel column chromatography afford methyl 2-methoxy-5-(3-oxocyclohexyl)benzoate (1.0 g, 3.3 mmol, 61% yield).

To a stirred solution of methyl 2-methoxy-5-(3-oxocyclohexyl)benzoate (2 g, 8 mmol) and ethylene glycol (4.3 mL, 76 mmol) in toluene (15 mL) was added p-toluene sulfonic acid (0.15 g, 0.76 mmol) and the reaction mixture heated at reflux with a Dean-Stark trap for 4 h. On cooling to rt, the reaction mixture was diluted with EtOAc and washed with sodium bicarbonate (2×). The layers were separated and the combined organic portions were concentrated under reduced pressure and purified on silica gel chromatography to afford methyl 2-methoxy-5-(1,4-dioxaspiro[4.5]decan-7-yl)benzoate (1.3 g, 4.2 mmol, 56% yield). 1H NMR (400 MHz, DMSO-$d_6$) δ=7.47 (d, J=2.4 Hz, 1H), 7.40 (dd, J=2.4, 8.8 Hz, 1H), 7.06 (d, J=8.6 Hz, 1H), 3.93-3.84 (m, 4H), 3.78 (s, 3H), 3.77 (s, 3H), 2.72 (tt, J=3.3, 12.6 Hz, 1H), 1.80-1.66 (m, 4H), 1.60 (t, J=12.7 Hz, 1H), 1.57-1.41 (m, 2H), 1.39-1.27 (m, 1H).

Intermediate 354-4

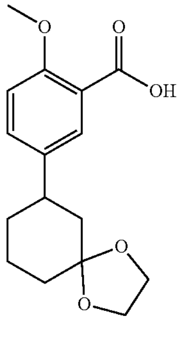 [SMILES: COc1ccc(C2CCCC3(C2)OCCO3)cc1C(=O)O]

To a solution of Intermediate 354-2 (1.5 g, 4.9 mmol) in THF (15 mL) and water (3.0 mL) was added LiOH (0.59 g, 24 mmol). The resulting solution was stirred at room temperature for 1 h, acidified by the addition of 1N HCl and the solution extracted with ethyl acetate. The combined organic portions were concentrated under reduced pressure to yield 2-methoxy-5-(1,4-dioxaspiro[4.5]decan-7-yl)benzoic acid which was used without further purification (1.3 g, 91% yield). MS (ESI) m/z: 293.1 $(M+H)^+$, RT=0.59 min, Method B.

Intermediate 354-5

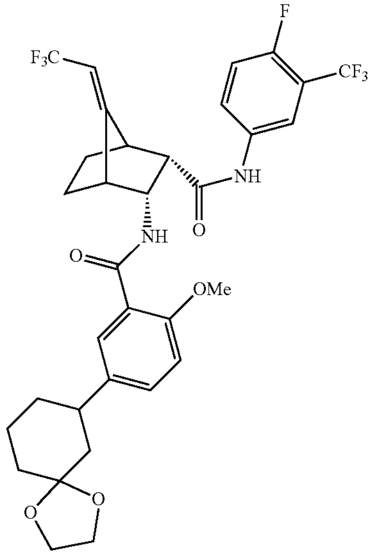 [SMILES: COc1ccc(C2CCCC3(C2)OCCO3)cc1C(=O)N[C@@H]1C2CCC(/C2=C/C(F)(F)F)[C@@H]1C(=O)Nc1ccc(F)c(C(F)(F)F)c1]

Intermediate 354-5 was prepared from intermediate 354-4 and V-2 according to the general procedure for Example 1 to afford (1R,2S,3R,4R,Z)—N-(4-fluoro-3-(trifluoromethyl)phenyl)-3-(2-methoxy-5-(1,4-dioxaspiro[4.5]decan-7-yl)benzamido)-7-(2,2,2-trifluoroethylidene) bicyclo[2.2.1]heptane-2-carboxamide (10 mg, 49%). MS (ESI) m/z: 671.4 $(M+H)^+$, RT=1.40 min, Method B.

Intermediate 354-6

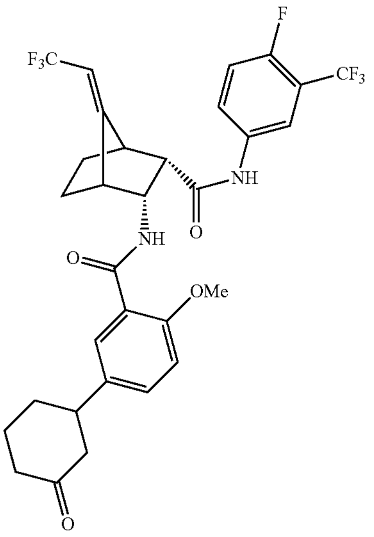 [SMILES: COc1ccc(C2CCCC(=O)C2)cc1C(=O)N[C@@H]1C2CCC(/C2=C/C(F)(F)F)[C@@H]1C(=O)Nc1ccc(F)c(C(F)(F)F)c1]

To a stirred solution of 354-5 (130 mg, 0.19 mmol) in DCM (5 mL) was added TFA (75 μL, 0.97 mmol) and the reaction mixture was allowed to stir at rt for 12 h. The reaction mixture was diluted with DCM, washed with saturated sodium bicarbonate solution (2×) and the layers separated. The organic layer was dried over sodium sulfate, concentrated under reduced pressure and purified on silica gel chromatography to afford (1R,2S,3R,4R,Z)—N-(4-fluoro-3-(trifluoromethyl)phenyl)-3-(2-methoxy-5-(3-oxocyclohexyl)benzamido)-7-(2,2,2-trifluoroethylidene) bicyclo[2.2.1]heptane-2-carboxamide (110 mg, 0.18 mmol, 91% yield). MS (ESI) m/z: 627.3 $(M+H)^+$, RT=1.21 min, Method B.

Intermediate 354-7

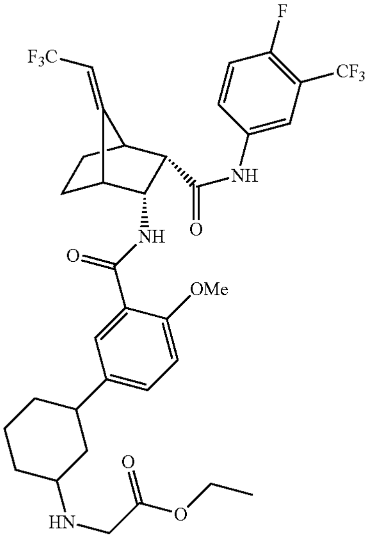 [SMILES: CCOC(=O)CNC1CCCC(c2ccc(OC)c(C(=O)N[C@@H]3C4CCC(/C4=C/C(F)(F)F)[C@@H]3C(=O)Nc3ccc(F)c(C(F)(F)F)c3)c2)C1]

To a stirred solution of 354-6 (100 mg, 0.16 mmol) and glycine ethyl ester hydrochloride (67 mg, 0.48 mmol) in a DMF (2 mL) and THF (2 mL) mixture, was added triethylamine (67 μL, 0.48 mmol). The reaction mixture was allowed to stir at rt for 14 h. Sodium cyanoborohydride (30.1 mg, 0.479 mmol) was added and the solution allowed to stir for an additional 1 h at RT. The reaction mixture was diluted with ethyl acetate, washed with brine, concentrated under reduced pressure and purified on silica gel column chromatography to afford ethyl (3-(3-(((1R,2R,3S,4R,Z)-3-((4-fluoro-3-(trifluoromethyl)phenyl) carbamoyl)-7-(2,2,2-trifluoroethylidene) bicyclo[2.2.1]heptan-2-yl) carbamoyl)-4-methoxyphenyl)cyclohexyl)glycinate (100 mg, 0.14 mmol, 88% yield). MS (ESI) m/z: 714.4 $(M+H)^+$, RT=1.29 min, Method B.

Example 354

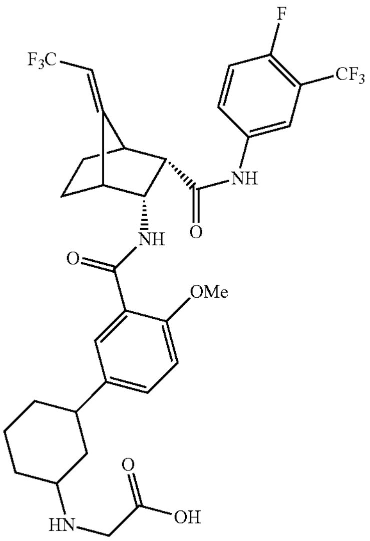 [SMILES: COc1ccc(C2CCCC(NCC(=O)O)C2)cc1C(=O)N[C@@H]1C2CCC(/C2=C/C(F)(F)F)[C@@H]1C(=O)Nc1ccc(F)c(C(F)(F)F)c1]

Example 354: To a solution of Intermediate 354-7 (100 mg, 0.14 mmol) in THF (3.0 mL) and water (2.0 mL) was added LiOH (3.4 mg, 0.14 mmol). The resulting solution was stirred at room temperature for 16 h, acidified by the addition of 1N HCl and the solution extracted with ethyl acetate. The combined organic portions were concentrated under reduced pressure and purified on HPLC to yield (1R,2S,3R,4R,7Z)-3-{5-[3-(3,3-difluoroazetidin-1-yl)cyclohexyl]-2-methoxybenzamido}-N-[4-fluoro-3-(trifluoromethyl)phenyl]-7-(2,2,2-trifluoroethylidene) bicyclo [2.2.1]heptane-2-carboxamide (1.0 mg, 1%). 1H NMR (400 MHZ, DMSO-d6) δ=10.64 (br s, 1H), 9.88 (d, J=7.0 Hz, 1H), 9.00-8.59 (m, 7H), 8.23 (dd, J=2.8, 6.3 Hz, 1H), 7.85-7.73 (m, 2H), 7.67-7.45 (m, 2H), 7.38 (dd, J=2.3, 8.3 Hz, 1H), 7.12 (d, J=8.5 Hz, 1H), 5.94 (q, J=8.2 Hz, 1H), 4.53 (br s, 1H), 3.97 (s, 3H), 2.98 (br d, J=4.0 Hz, 3H), 2.10 (s, 7H), 2.03-1.83 (m, 5H), 1.79-1.65 (m, 5H), 1.61-1.44 (m, 6H), 1.24 (s, 3H) MS (ESI) m/z: 686.3 $(M+H)^+$, RT=2.0 min, Method A.

Example 355 was prepared from 354-6 and 3,3-difluoroazetidine according to the procedure for Example 354

Example 356
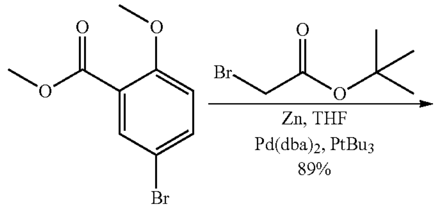
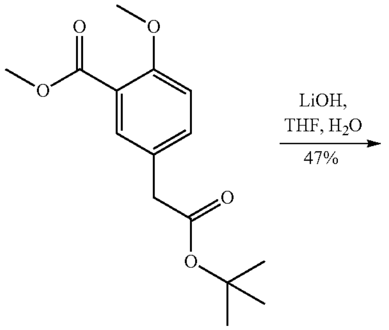
356-1
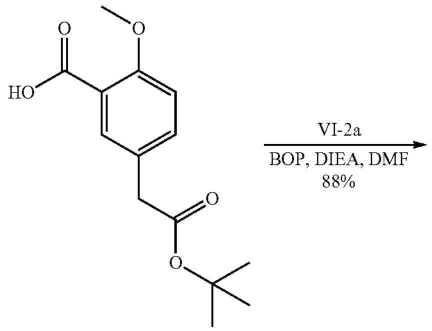
356-2
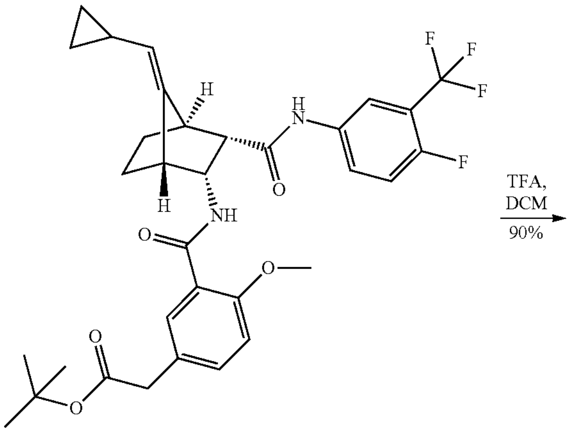
356-3
-continued
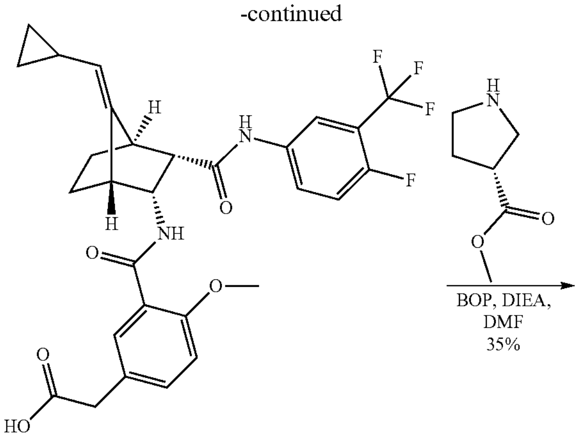
356-4
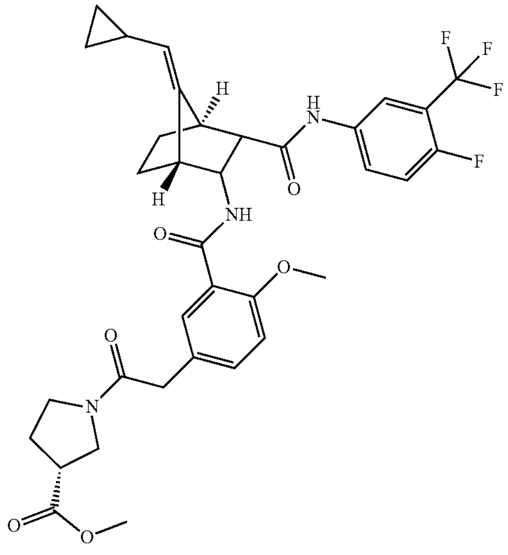
356
Intermediate 356-1
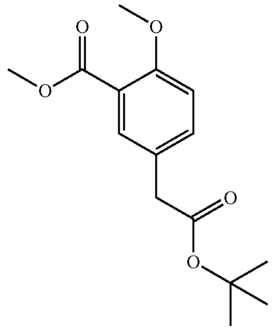 [SMILES: COC(=O)c1cc(CC(=O)OC(C)(C)C)ccc1OC]
To an oven dried 2-dram vial flushed with $N_2$ atmosphere, was added zinc (100 mg, 1.5 mmol), tert-butyl 2-bromoacetate (170 μl, 1.1 mmol) and THF (2.0 mL). Separately, in an oven dried 1-dram vial flushed with $N_2$ atmosphere, was added methyl 5-bromo-2-methoxybenzoate (250 mg, 1.0 mmol), bis(dibenzylideneacetone) palladium (0) (29 mg, 0.051 mmol) and tri-tertbutylphosphine, (1M in THF, 51 μl, 0.051 mmol), and THF (2.0 mL). Both solutions were stirred at room temperature for 15 minutes, upon which time the 1-dram contents were transferred to the 2-dram vial via syringe. The resulting suspension was stirred at room temperature for 16 h. The reaction mixture was filtered, concentrated under reduced pressure and purified by column chromatography (0-100% EtOAc/Hex) to give methyl 5-(2-(tert-butoxy)-2-oxoethyl)-2-methoxybenzoate (255 mg, 0.91 mmol, 89% yield). $^{1}$H NMR (500 MHz, CHLOROFORM-d) δ 7.79 (d, J=7.7 Hz, 1H), 6.97-6.88 (m, 2H), 3.94 (s, 3H), 3.91 (s, 3H), 3.57 (s, 2H), 1.46 (s, 9H). LC-MS RT: 0.98 min; MS (ESI) m/z 281.3 $(M+H)^+$; Method A.

Intermediate 356-2

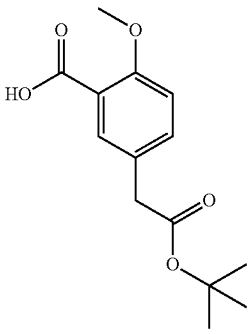 [SMILES: COc1ccc(CC(=O)OC(C)(C)C)cc1C(=O)O]

Intermediate 356-1 (255 mg, 0.91 mmol) in THF (3.6 mL), water (0.91 mL) and MeOH (0.10 mL) was treated with lithium hydroxide monohydrate (57 mg, 1.4 mmol). The reaction mixture was allowed to stir at room temperature for 18 h. The reaction mixture was diluted with ethyl acetate (10 mL) and 1N HCl (5 mL). The layers were separated and the aqueous solution was extracted with ethyl acetate (3×). The combined organic extracts were washed with brine, dried over $Na_2SO_4$ and concentrated under reduced pressure. The residue was purified by column chromatography (0-100% EtOAc/Hex) to give 5-(2-(tert-butoxy)-2-oxoethyl)-2-methoxybenzoic acid (114 mg, 0.43 mmol, 47% yield). 1H NMR (500 MHz, CHLOROFORM-d) δ 8.16 (d, J=8.0 Hz, 1H), 7.07 (d, J=8.0 Hz, 1H), 7.04 (s, 1H), 4.11 (s, 3H), 3.61 (s, 2H), 1.48 (s, 9H). LC-MS RT: 0.88 min; MS (ESI) m/z 267.2 $(M+H)^+$; Method A.

Intermediate 356-3

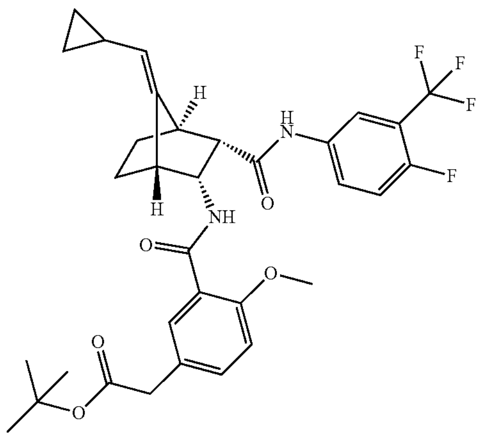 [SMILES: COc1ccc(CC(=O)OC(C)(C)C)cc1C(=O)N[C@H]1[C@@H](C(=O)Nc2ccc(F)c(C(F)(F)F)c2)[C@H]2CC[C@@H]1/C2=C\C1CC1]

Intermediate 356-3 was prepared from intermediate 356-2 and VI-2a according to the general procedure for Example 1 to afford tert-butyl 2-(3-(((1R,2R,3S,4R,Z)-7-(cyclopropylmethylene)-3-((4-fluoro-3-(trifluoromethyl)phenyl) carbamoyl) bicyclo[2.2.1]heptan-2-yl)carbamoyl)-4-methoxyphenyl)acetate (257 mg, 0.42 mmol, 88% yield). 1H NMR (500 MHZ, CHLOROFORM-d) δ 9.26 (br d, J=8.0 Hz, 1H), 8.16 (d, J=8.0 Hz, 1H), 8.05 (br s, 1H), 7.88 (dd, J=6.2, 2.3 Hz, 1H), 7.58 (dt, J=8.3, 3.5 Hz, 1H), 7.07 (t, J=9.5 Hz, 1H), 6.98 (d, J=8.0 Hz, 1H), 6.92 (s, 1H), 4.91-4.81 (m, 1H), 4.65 (d, J=9.6 Hz, 1H), 4.01 (s, 3H), 3.56 (s, 2H), 3.18 (t, J=3.7 Hz, 1H), 3.11 (dd, J=10.7, 3.0 Hz, 1H), 2.79-2.69 (m, 1H), 2.27-2.16 (m, 1H), 1.91-1.82 (m, 1H), 1.77-1.62 (m, 2H), 1.53-1.46 (m, 2H), 1.45 (s, 9H), 0.79-0.70 (m, 2H), 0.36 (br d, J=2.8 Hz, 2H). LC-MS RT: 2.82 min; MS (ESI) m/z 617.33 $(M+H)^+$; Method B.

Intermediate 356-4

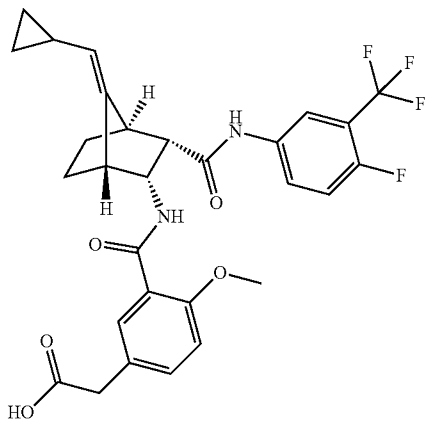 [SMILES: COc1ccc(CC(=O)O)cc1C(=O)N[C@H]1[C@@H](C(=O)Nc2ccc(F)c(C(F)(F)F)c2)[C@H]2CC[C@@H]1/C2=C\C1CC1]

To a solution of 356-3 (257 mg, 0.42 mmol) in DCM (2.0 mL) was added TFA (0.3 mL). The reaction mixture was allowed to stir at rt for 18 h, concentrated under reduced pressure and the residue was dissolved in EtOAc and washed with brine. The organic layer was dried over $Na_2SO_4$, filtered and concentrated under reduced pressure. The residue was purified via column chromatography (0-100% EtOAc/Hex) to give 2-(3-(((1R,2R,3S,4R,Z)-7-(cyclopropylmethylene)-3-((4-fluoro-3-(trifluoromethyl) phenyl) carbamoyl) bicyclo[2.2.1]heptan-2-yl) carbamoyl)-4-methoxyphenyl) acetic acid (210 mg, 0.38 mmol, 90% yield) 1H NMR (500 MHZ, DMSO-$d_6$) δ 10.54 (s, 1H), 9.81 (d, J=7.3 Hz, 1H), 8.21 (dd, J=6.5, 2.5 Hz, 1H), 7.86 (d, J=8.0 Hz, 1H), 7.80 (dt, J=8.4, 3.5 Hz, 1H), 7.48 (t, J=9.8 Hz, 1H), 7.08 (s, 1H), 6.93 (d, J=7.9 Hz, 1H), 4.68 (d, J=9.5 Hz, 1H), 4.49-4.38 (m, 1H), 3.98 (s, 3H), 3.57 (s, 2H), 3.20-3.11 (m, 1H), 3.10-3.02 (m, 1H), 2.74-2.67 (m, 1H), 1.94-1.82 (m, 1H), 1.82-1.70 (m, 1H), 1.50 (td, J=8.7, 4.7 Hz, 1H), 1.44-1.31 (m, 2H), 0.81-0.66 (m, 2H), 0.35 (dd, J=4.3, 2.4 Hz, 2H). LC-MS RT: 1.95 min; MS (ESI) m/z 561.08 $(M+H)^+$; Method B.

Example 356

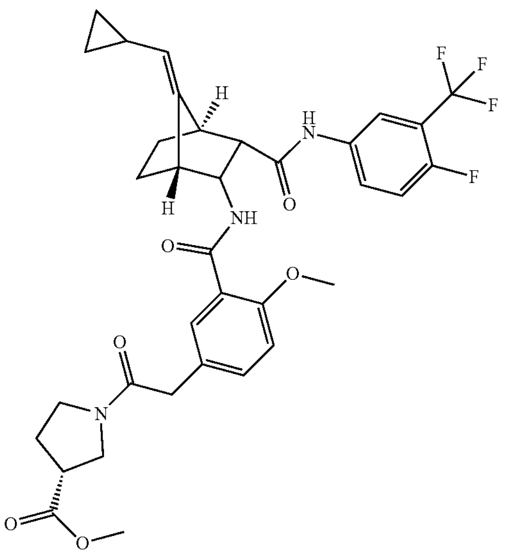 [SMILES: COC(=O)[C@@H]1CCN(C(=O)Cc2ccc(OC)c(C(=O)NC3C(C(=O)Nc4ccc(F)c(C(F)(F)F)c4)[C@H]4CC[C@@H]3/C4=C\C3CC3)c2)C1]

To a solution of 356-4 (20 mg, 0.036 mmol) and methyl (R)-pyrrolidine-3-carboxylate. HCl (5.9 mg, 0.036 mmol) in DMF (0.5 mL) was added DIEA (0.019 mL, 0.11 mmol) and BOP (17 mg, 0.039 mmol). The reaction mixture was stirred at rt for 18 h, concentrated under vacuum and purified via preparative HPLC to give methyl (R)-1-(2-(3-(1R,2R,3S,4R,Z)-7-(cyclopropylmethylene)-3-(4-fluoro-3-(trifluoromethyl)phenyl) carbamoyl) bicyclo[2.2.1]heptan-2-yl) carbamoyl)-4-methoxyphenyl) acetyl) pyrrolidine-3-carboxylate (8.5 mg, 0.013 mmol, 35% yield). $^1$H NMR (500 MHz, DMSO-$d_6$) δ 10.50 (s, 1H), 9.80 (d, J=7.2 Hz, 1H), 8.22 (dd, J=6.5, 2.4 Hz, 1H), 7.86 (d, J=8.0 Hz, 1H), 7.81-7.74 (m, 1H), 7.48 (t, J=9.7 Hz, 1H), 7.04 (d, J=5.9 Hz, 1H), 6.90 (br d, J=8.0 Hz, 1H), 4.69 (d, J=9.5 Hz, 1H), 4.49-4.38 (m, 1H), 3.98 (s, 3H), 3.75 (dd, J=10.3, 8.0 Hz, 1H), 3.69 (br d, J=5.8 Hz, 2H), 3.66-3.60 (m, 3H), 3.60-3.33 (m, 2H), 3.29-3.11 (m, 2H), 3.10-3.02 (m, 1H), 2.75-2.66 (m, 1H), 2.23-2.14 (m, 1H), 2.14-2.03 (m, 1H), 2.03-1.93 (m, 1H), 1.91-1.82 (m, 1H), 1.83-1.73 (m, 1H), 1.51 (ddd, J=12.6, 8.1, 4.6 Hz, 1H), 1.46-1.31 (m, 2H), 0.84-0.67 (m, 2H), 0.35 (dd, J=4.1, 2.6 Hz, 2H). LC-MS RT: 2.39 min; MS (ESI) m/z 672.32 (M+H)$^+$; Method A.

Example 357 was prepared from 356-4 and 3-methylpyrrolidin-3-ol according to the general procedure for Example 356

Example 358 to Example 361 were prepared as described by the general procedure given for Example 197

TABLE 3

| Ex # | Structure | Name |
|---|---|---|
| 209 | 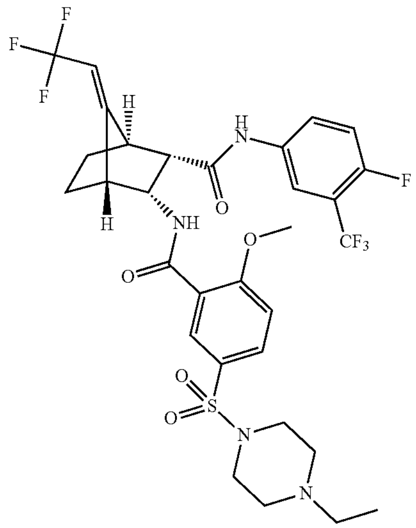 [SMILES: CCN1CCN(S(=O)(=O)c2ccc(OC)c(C(=O)N[C@H]3[C@@H](C(=O)Nc4ccc(F)c(C(F)(F)F)c4)[C@H]4CC[C@@H]3/C4=C\C(F)(F)F)c2)CC1] | (1R,2S,3R,4R,7Z)-3-[5-1(4-ethylpiperazin-1-yl)sulfonyl]-2-methoxybenzamido}-N-[4-fluoro-3-(trifluoromethyl) phenyl]-7-(2,2,2-trifluoroethylidene) bicyclo[2.2.1]heptane-2-carboxamide |

TABLE 3-continued

| | | |
|---|---|---|
| 210 | 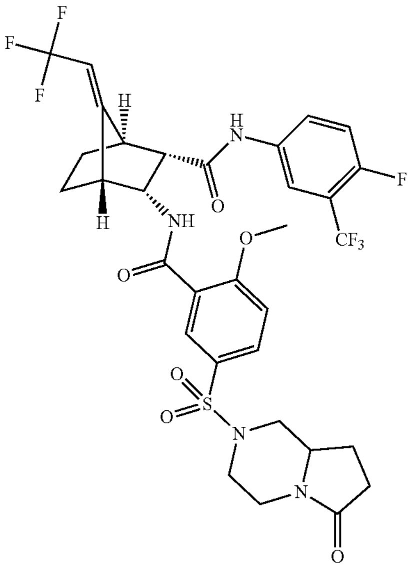 [SMILES: COc1ccc(S(=O)(=O)N2CCN3C(=O)CCC3C2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-[2-methoxy-5-({6-oxo-octabydropyrrolo[1,2-a]piperazin-2-yl}sulfonyl)benzamido]-7-(2,2,2-trifluoroethylidene)bicyclo[2.2.1]heptane-2-carboxamide |
| 211 | 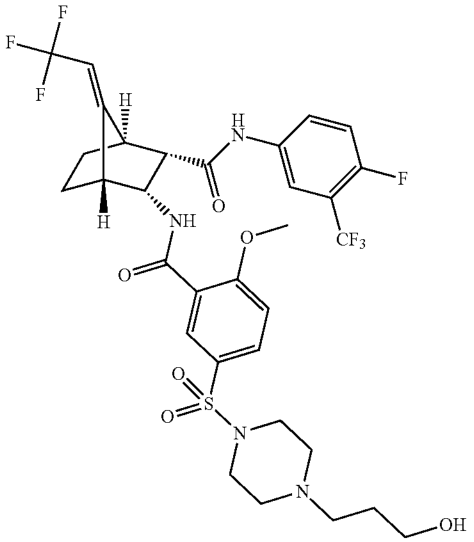 [SMILES: COc1ccc(S(=O)(=O)N2CCN(CCCO)CC2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3(trifluoromethyl)phenyl]-3-(5-{[4-(3-hydroxypropyl)piperazin-1-yl]sulfonyl}-2-methoxybenzamido)-7-(2,2,2-trifluoroethylidene)bicyclo[2.2.1]heptane-2-carboxamide |
| 212 | 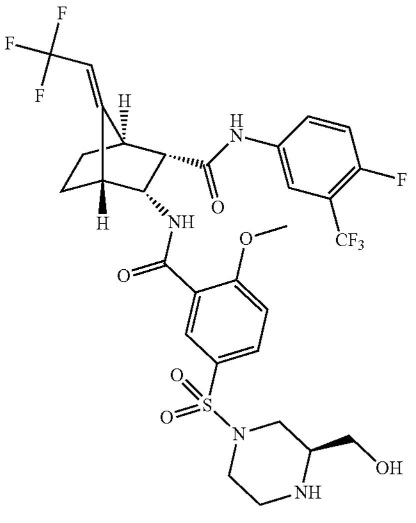 [SMILES: COc1ccc(S(=O)(=O)N2CCN[C@H](CO)C2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-(5-{[(3S)-3-(hydroxymethyl)piperazin-1-yl]sulfonyl}-2-methoxybenzamido)-7-(2,2,2-trifluoroethylidene)bicyclo[2.2.1]heptane-2-carboxamide |

TABLE 3-continued
| | | |
|---|---|---|
| 213 | 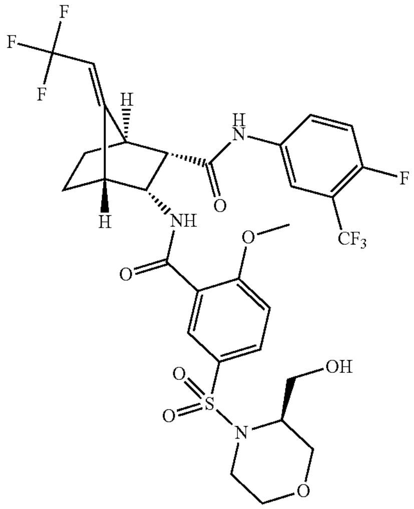 [SMILES: COc1ccc(S(=O)(=O)N2CCOC[C@@H]2CO)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-(5-{[(3S)-3-(hydroxymethyl)morpholin-4-yl]sulfonyl}-2-methoxybenzamido)-7-(2,2,2-trifluoroethylidene)bicyclo[2.2.1]heptane-2-carboxamide |
| 214 | 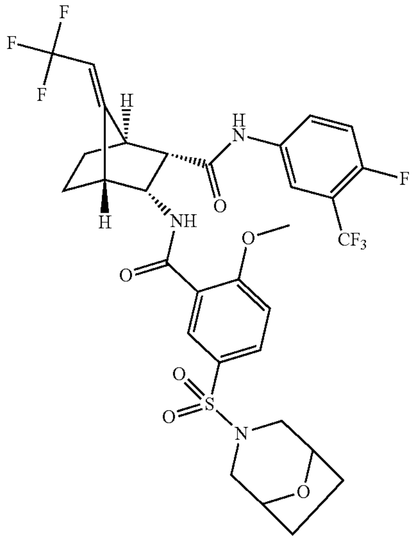 [SMILES: COc1ccc(S(=O)(=O)N2CC3CCC(C2)O3)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-(2-methoxy-5-{8-oxa-3-azabicyclo[3.2.1]octane-3-sulfonyl}benzamido)-7-(2,2,2-trifluoroethylidene)bicyclo[2.2.1]heptane-2-carboxamide |

TABLE 3-continued

| | | |
|---|---|---|
| 215 | 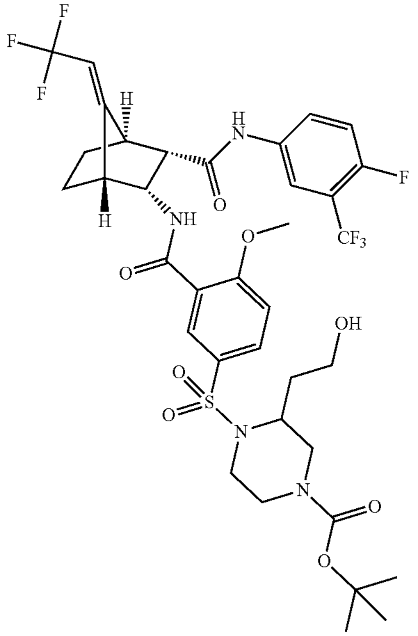 [SMILES: COc1ccc(S(=O)(=O)N2CCN(C(=O)OC(C)(C)C)CC2CCO)cc1C(=O)N[C@H]1[C@@H](C(=O)Nc2ccc(F)c(C(F)(F)F)c2)[C@H]2CC[C@@H]1/C2=C\C(F)(F)F] | tert-butyl 4-(3-{[(1R,2R,3S,4R,7Z)-3-{[4-fluoro-3-(trifluoromethyl) phenyl]carbamoyl}-7-(2,2,2-trifluoroethylidene) bicyclo[2.2.1]heptan-2-yl]carbamoyl}-4-methoxy-benzenesulfonyl)-3-(2-hydroxyethyl) piperazine-1-carboxylate |
| 216 | 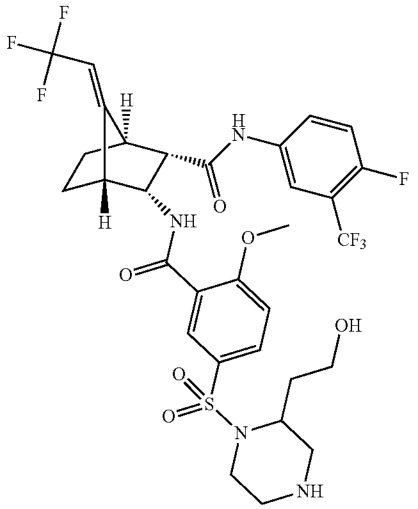 [SMILES: COc1ccc(S(=O)(=O)N2CCNCC2CCO)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl) phenyl]-3-(5-{[2-(2-hydroxyethyl) piperazin-1-yl]sulfonyl}-2-methoxybenzamido)-7-(2,2,2-trifluoroethylidene) bicyclo[2.2.1]heptane-2-carboxamide |
| 217 | 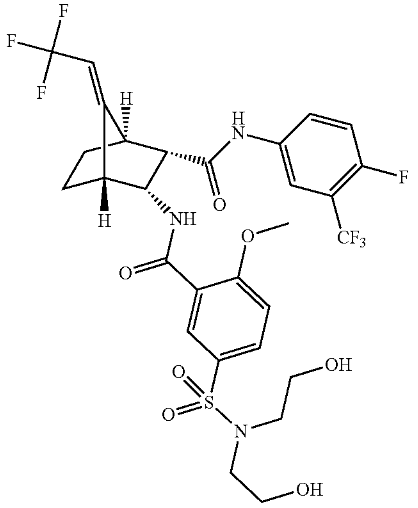 [SMILES: COc1ccc(S(=O)(=O)N(CCO)CCO)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-3-{5-[bis(2-hydroxyethyl) sulfamoyl]-2-methoxybenzamido}-N-[4-fluoro-3-(trifluoromethyl) phenyl]-7-(2,2,2-trifluoroethylidene) bicyclo[2.2.1] heptane-2-carboxamide |

TABLE 3-continued

| | | |
|---|---|---|
| 218 | 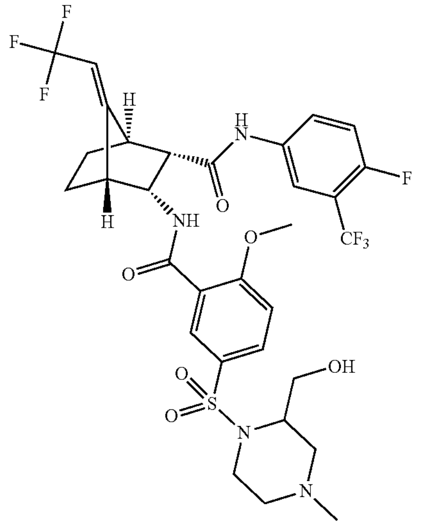 [SMILES: COc1ccc(S(=O)(=O)N2CCN(C)CC2CO)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-(5-{[2-(hydroxymethyl)-4-methylpiperazin-1-ylsulfonyl}-2-methoxybenzamido)-7-(2,2,2-trifluoroethylidene)bicyclo[2.2.1]heptane-2-carboxamide |
| 219 | 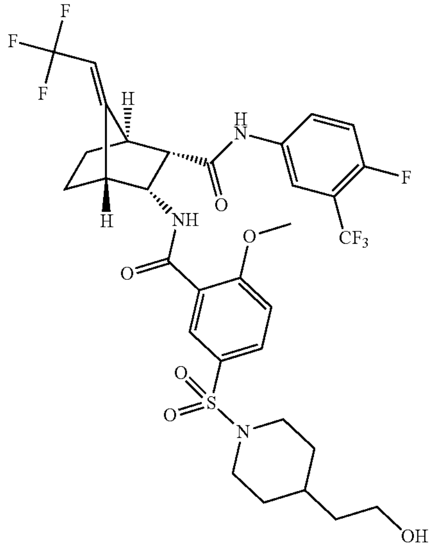 [SMILES: COc1ccc(S(=O)(=O)N2CCC(CCO)CC2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-(5-{[4-(2-hydroxyethyl)piperidin-1-yl]sulfonyl}-2-methoxybenzamido)-7-(2,2,2-trifluoroethylidene)bicyclo[2.2.1]heptane-2-carboxamide |
| 220 | 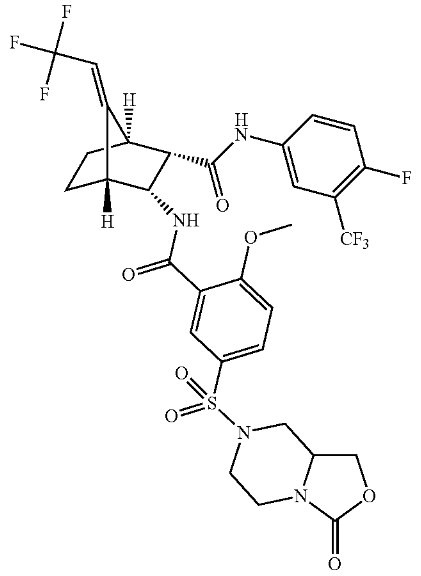 [SMILES: COc1ccc(S(=O)(=O)N2CCN3C(=O)OCC3C2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-[2-methoxy-5-({3-oxo-hexahydro-1H-[1,3]oxazolo[3,4-a]piperazin-7-yl}sulfonyl)benzamido]-7-(2,2,2-trifluoroethylidene)bicyclo[2.2.1]heptane-2-carboxamide |

TABLE 3-continued

| | | |
|---|---|---|
| 221 | 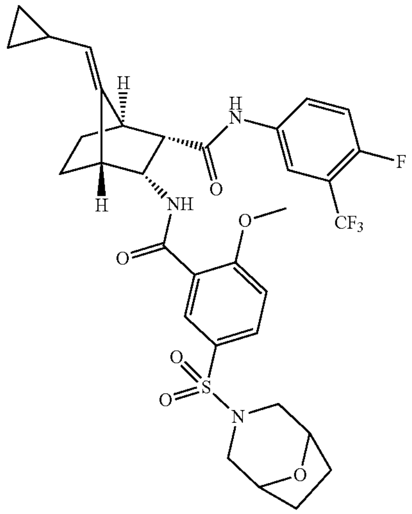 [SMILES: COc1ccc(S(=O)(=O)N2CC3CCC(C2)O3)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl-idene)-N-[4-fluoro-3-(trifluoromethyl)phenyl]-3-(2-methoxy-5-{8-oxa-3-azabicyclo[3.2.1]octane-3-sulfonyl}benzamido)bicyclo[2.2.1]heptane-2-carboxamide |
| 222 | 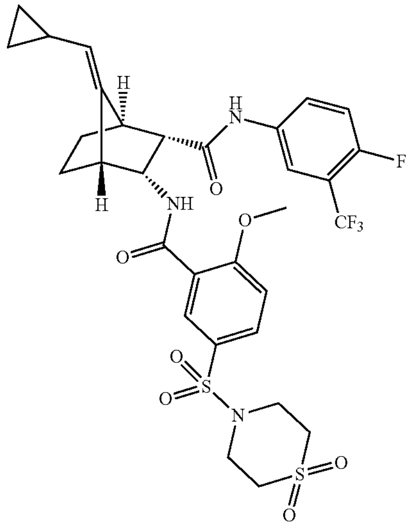 [SMILES: COc1ccc(S(=O)(=O)N2CCS(=O)(=O)CC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl idene)-3-{5-[(1,1-dioxo-1λ$^6$-thiomorpholin-4-yl)sulfonyl]-2-methoxybenzamido}-N-[4-fluoro-3-(trifluoromethyl)phenyl]bicyclo[2.2.1]heptane-2-carboxamide |
| 223 | 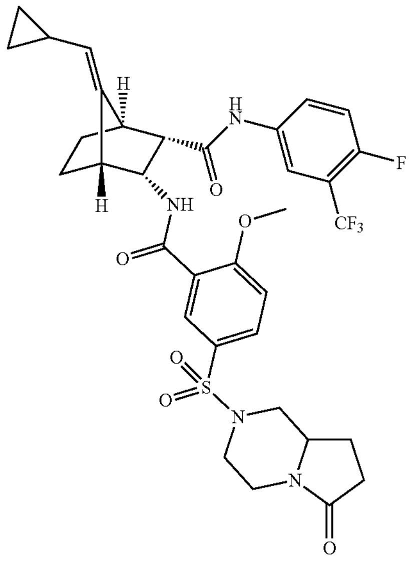 [SMILES: COc1ccc(S(=O)(=O)N2CCN3C(=O)CCC3C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-[2-methoxy-5-({6-oxo-octahydropyrrolo[1,2-a]piperazin-2-yl}sulfonyl)benzamido]bicyclo[2.2.1]heptane-2-carboxamide |

TABLE 3-continued
| | | |
|---|---|---|
| 224 | 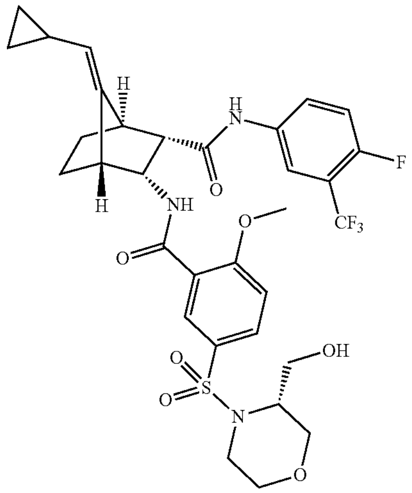 [SMILES: COc1ccc(S(=O)(=O)N2CCOC[C@H]2CO)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl-idene)-N-[4-fluoro-3-(trifluoromethyl)phenyl]-3-(5-{[(3R)-3-(hydroxymethyl)morpholin-4-yl]sulfonyl}-2-methoxybenzamido)bicyclo[2.2.1]heptane-2-carboxamide |
| 225 | 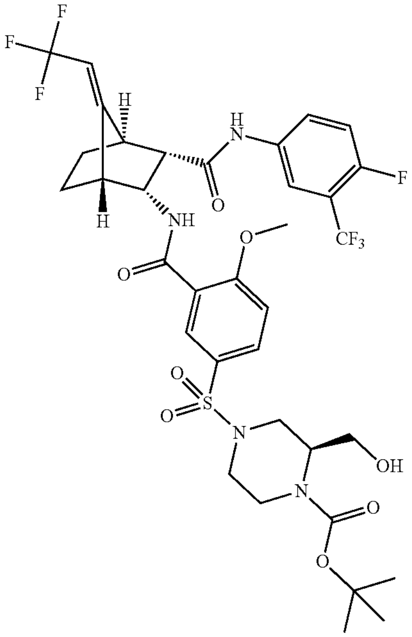 [SMILES: COc1ccc(S(=O)(=O)N2CCN(C(=O)OC(C)(C)C)[C@H](CO)C2)cc1C(=O)N[C@H]1[C@@H](C(=O)Nc2ccc(F)c(C(F)(F)F)c2)[C@H]2CC[C@@H]1/C2=C\C(F)(F)F] | tert-butyl (2S)-4-(3-{[(1R,2R,3S,4R,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxy-benzenesulfonyl-2-(hydroxymethyl)piperazine-1-carboxylate |

TABLE 3-continued
| | | |
|---|---|---|
| 226 | 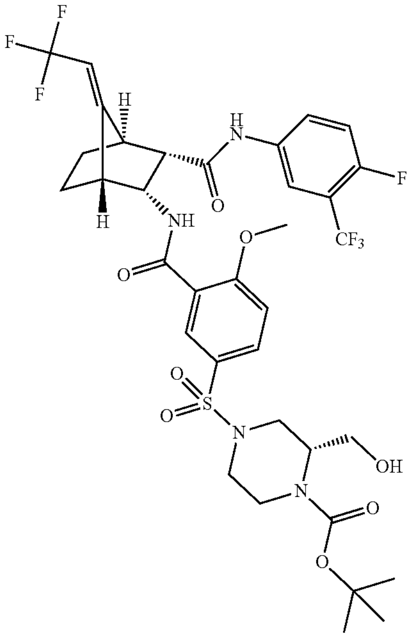 [SMILES: COc1ccc(S(=O)(=O)N2CCN(C(=O)OC(C)(C)C)[C@@H](CO)C2)cc1C(=O)N[C@H]1[C@@H](C(=O)Nc2ccc(F)c(C(F)(F)F)c2)[C@H]2CC[C@@H]1/C2=C\C(F)(F)F] | tert-butyl (2R)-4-(3-{[(1R,2R,3S,4R,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxy-benzenesulfonyl)-2-(hydroxymethyl)piperazine-1-carboxylate |
| 229 | 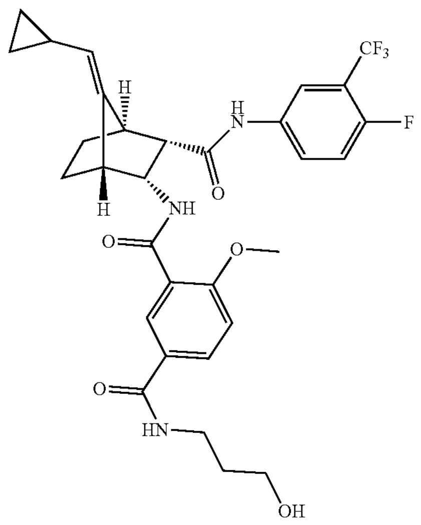 [SMILES: COc1ccc(C(=O)NCCCO)cc1C(=O)N[C@H]1[C@@H](C(=O)Nc2ccc(F)c(C(F)(F)F)c2)[C@H]2CC[C@@H]1/C2=C\C1CC1] | N3-[(1R,2R,3S,4R,7Z)-7-(cyclopropyl-methylidene)-3-{[4-fluoro-3-(trifluoromethyl)phenyl]carbamoyl}bicyclo[2.2.1]heptan-2-yl]-N1-(3-hydroxypropyl)-4-methoxybenzene-1,3-dicarboxamide |

TABLE 3-continued

| | | |
|---|---|---|
| 230 | 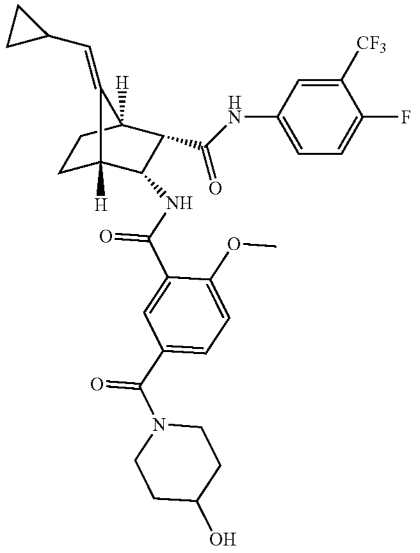 [SMILES: COc1ccc(C(=O)N2CCC(O)CC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-[5-(4-hydroxypiperidine-1-carbonyl)-2-methoxybenzamido]bicyclo[2.2.1]heptane-2-carboxamide |
| 231 | 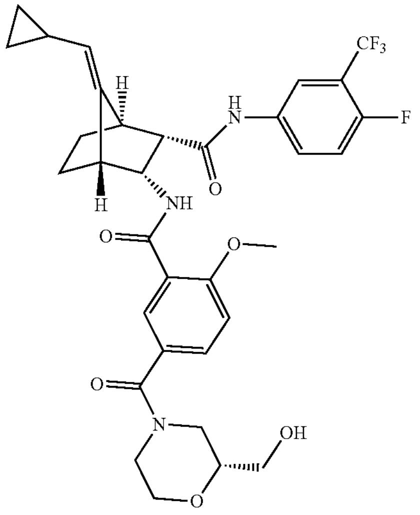 [SMILES: COc1ccc(C(=O)N2CCO[C@@H](CO)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl-idene)-N-[4-fluoro-3-(trifluoromethyl)phenyl]-3-{5-[(2R)-2-(hydroxymethyl)morpholine-4-carbonyl]-2-methoxybenzamido}bicyclo[2.2.1]heptane-2-carboxamide |
| 232 | 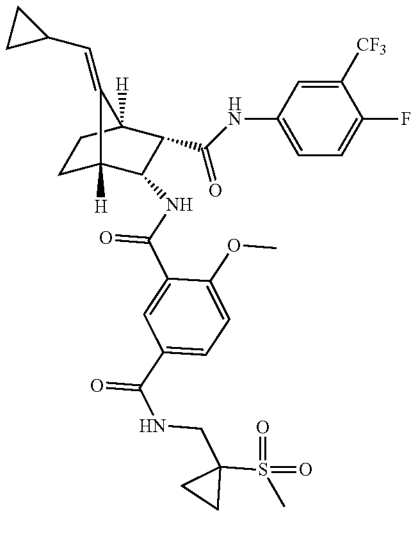 [SMILES: COc1ccc(C(=O)NCC2(S(C)(=O)=O)CC2)cc1C(=O)N[C@H]1[C@@H](C(=O)Nc2ccc(F)c(C(F)(F)F)c2)[C@H]2CC[C@@H]1/C2=C\C1CC1] | N3-[(1R,2R,3S,4R,7Z)-7-(cyclopropyl-methylidene)-3-{[4-fluoro-3-(trifluoromethyl)phenyl]carbamoyl}bicyclo[2.2.1]heptan-2-yl]-NI-[(1-methanesulfonyl-cyclopropyl)methyl]-4-methoxybenzene-1,3-dicarboxamide |

TABLE 3-continued

| | | |
|---|---|---|
| 233 | 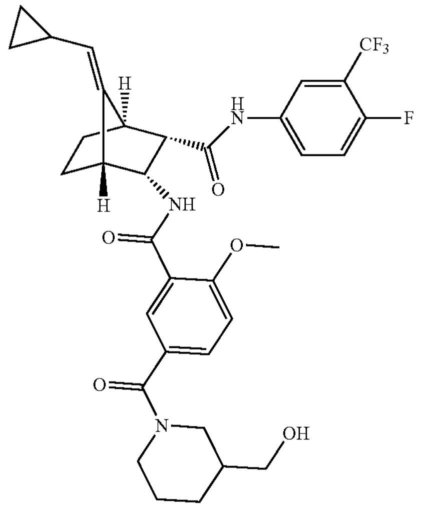 [SMILES: COc1ccc(C(=O)N2CCCC(CO)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-[5-[3-(hydroxymethyl)piperidine-1-carbonyl]-2-methoxybenzamido}bicyclo[2.2.1]heptane-2-carboxamide |
| 234 | 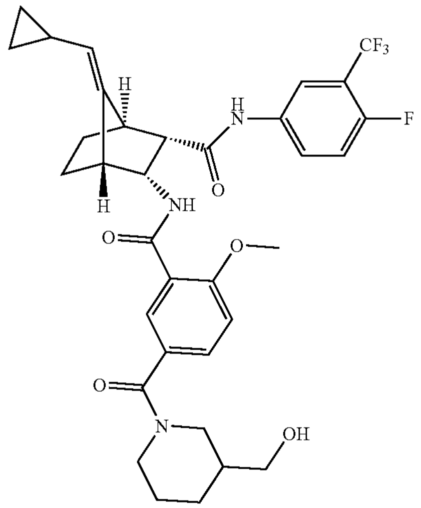 [SMILES: COc1ccc(C(=O)N2CCCC(CO)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-{5-[3-(hydroxymethyl)piperidine-1-carbonyl]-2-methoxybenzamido}bicyclo[2.2.1]heptane-2-carboxamide |
| 235 | 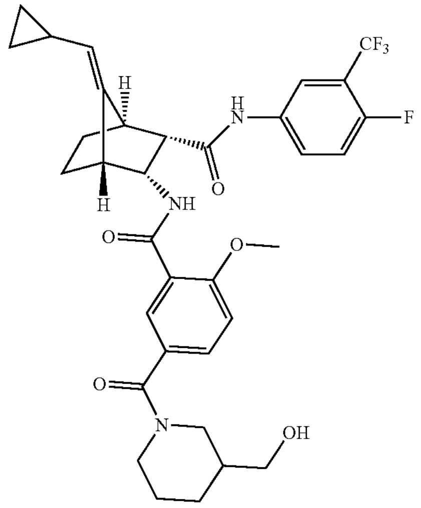 [SMILES: COc1ccc(C(=O)N2CCCC(CO)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl-idene)-N-[4-fluoro-3-(trifluoromethyl)phenyl]-3-{5-[3-(hydroxymethyl)piperidine-1-carbonyl]-2-methoxybenzamido}bicyclo[2.2.1]heptane-2-carboxamide |

TABLE 3-continued

| | | |
|---|---|---|
| 236 | 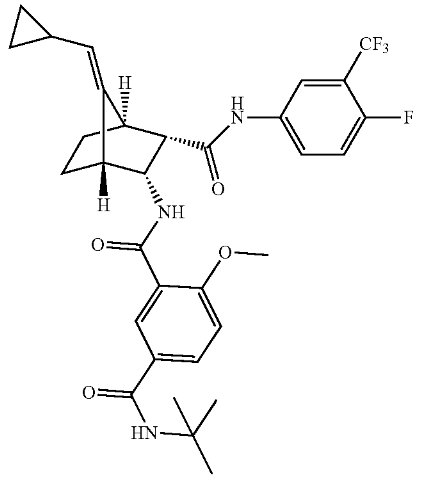 [SMILES: COc1ccc(C(=O)NC(C)(C)C)cc1C(=O)N[C@H]1[C@@H](C(=O)Nc2ccc(F)c(C(F)(F)F)c2)[C@H]2CC[C@@H]1/C2=C\C1CC1] | N1-tert-butyl-N3-[(1R,2R,3S,4R,7Z)-7-(cyclopropyl-methylidene)-3-{[4-fluoro-3-(trifluoromethyl)phenyl]carbamoyl}bicyclo[2.2.1]heptan-2-yl]-4-methoxybenzene-1,3-dicarboxamide |
| 237 | 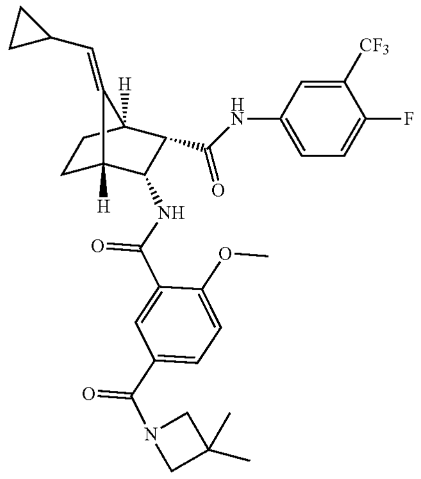 [SMILES: COc1ccc(C(=O)N2CC(C)(C)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-3-[5-(3,3-dimethylazetidine-1-carbonyl)-2-methoxybenzamido 1-N-[4-fluoro-3(trifluoromethyl)phenyl]bicyclo[2.2.1]heptane-2-carboxamide |
| 238 | 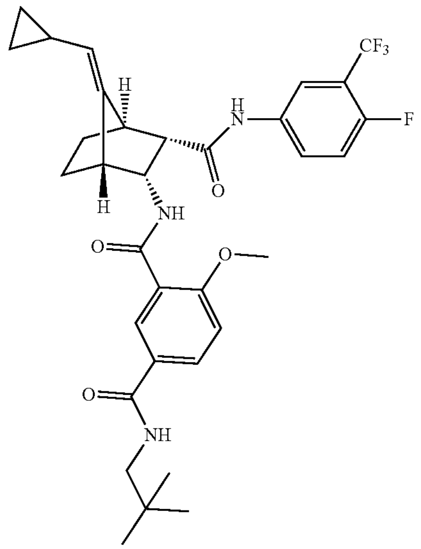 [SMILES: COc1ccc(C(=O)NCC(C)(C)C)cc1C(=O)N[C@H]1[C@@H](C(=O)Nc2ccc(F)c(C(F)(F)F)c2)[C@H]2CC[C@@H]1/C2=C\C1CC1] | N3-[(1R,2R,3S,4R,7Z)-7-(cyclopropyl-methylidene)-3-{[4-fluoro-3-(trifluoromethyl)phenyl]carbamoyl}bicyclo[2.2.1]heptan-2-yl]-N1-(2,2-dimethylpropyl)-4-methoxybenzene-1,3-dicarboxamide |

TABLE 3-continued

| | | |
|---|---|---|
| 239 | 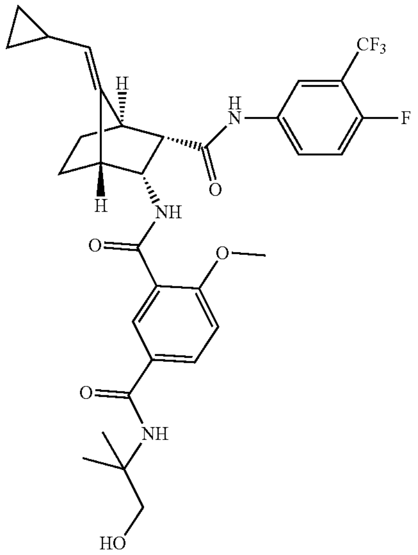 [SMILES: COc1ccc(C(=O)NC(C)(C)CO)cc1C(=O)N[C@H]1[C@@H](C(=O)Nc2ccc(F)c(C(F)(F)F)c2)[C@H]2CC[C@@H]1/C2=C\C1CC1] | N3-[(1R,2R,3S,4R,7Z)-7-(cyclopropyl-methylidene)-3-{[4-fluoro-3-(trifluoromethyl)phenyl]carbamoyl}bicyclo[2.2.1]heptan-2-yl]-N1-(1-hydroxy-2-methylpropan-2-yl)-4-methoxybenzene-1,3-dicarboxamide |
| 240 | 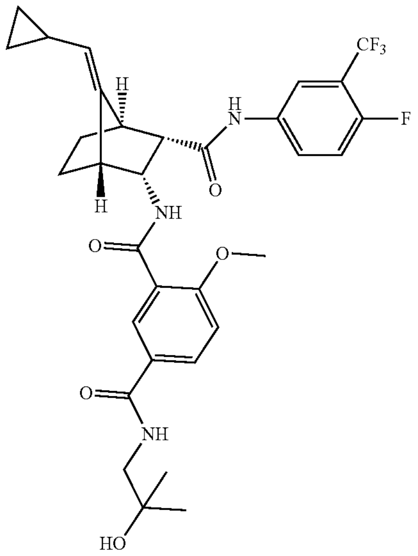 [SMILES: COc1ccc(C(=O)NCC(C)(C)O)cc1C(=O)N[C@H]1[C@@H](C(=O)Nc2ccc(F)c(C(F)(F)F)c2)[C@H]2CC[C@@H]1/C2=C\C1CC1] | N3-[(1R,2R,3S,4R,7Z)-7-(cyclopropyl-methylidene)-3-{[4-fluoro-3-(trifluoromethyl)phenyl]carbamoyl}bicyclo[2.2.1]heptan-2-yl]-N1-(2-hydroxy-2-methylpropyl)-4-methoxybenzene-1,3-dicarboxamide |
| 241 | 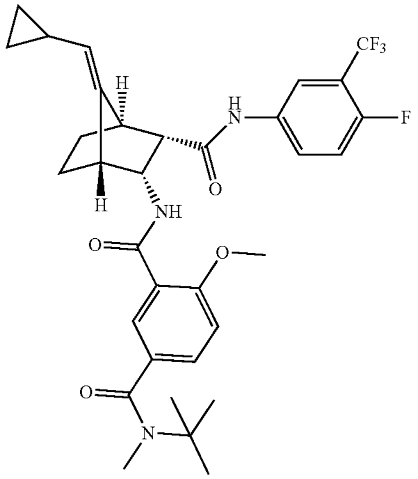 [SMILES: COc1ccc(C(=O)N(C)C(C)(C)C)cc1C(=O)N[C@H]1[C@@H](C(=O)Nc2ccc(F)c(C(F)(F)F)c2)[C@H]2CC[C@@H]1/C2=C\C1CC1] | N1-tert-butyl-N3-[(1R,2R,3S,4R,7Z)-7-(cyclopropyl-methylidene)-3-{[4-fluoro-3-(trifluoromethyl)phenyl]carbamoyl}bicyclo[2.2.1]heptan-2-yl]-4-methoxy-N1-methylbenzene-1,3-dicarboxamide |

TABLE 3-continued

| | | |
|---|---|---|
| 242 | 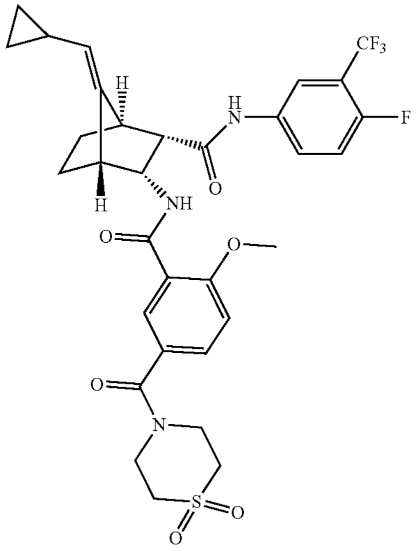 [SMILES: COc1ccc(C(=O)N2CCS(=O)(=O)CC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-3-[5-(1,1-dioxo-1λ.⁶-thiomorpholine-4-carbonyl)-2-methoxybenzamido]-N-[4-fluoro-3-(trifluoromethyl)phenyl]bicyclo[2.2.1]heptane-2-carboxamide |
| 243 | 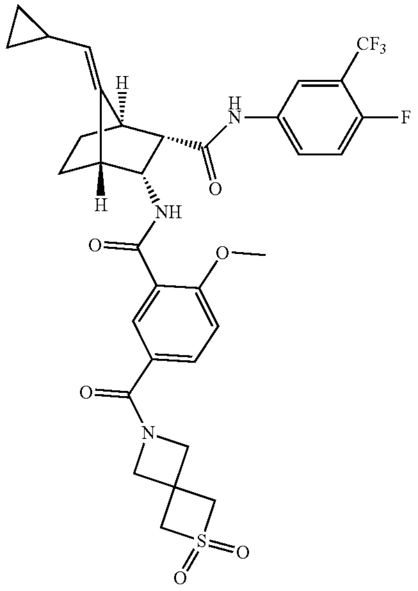 [SMILES: COc1ccc(C(=O)N2CC3(C2)CS(=O)(=O)C3)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-3-(5-{2,2-dioxo-2λ⁶-thia-6-azaspiro[3.3]heptane-6-carbonyl}-2-methoxybenzamido)-N-[4-fluoro-3-(trifluoromethyl)phenyl]bicyclo[2.2.1]heptane-2-carboxamide |
| 244 | 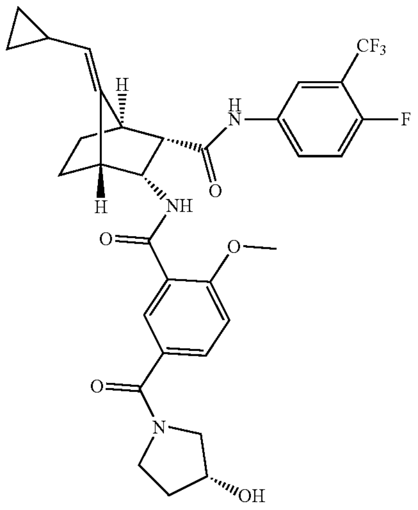 [SMILES: COc1ccc(C(=O)N2CC[C@@H](O)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-{5-[(3R)-3-hydroxypyrrolidine-1-carbonyl]-2-methoxybenzamido}bicyclo[2.2.1]heptane-2-carboxamide |

TABLE 3-continued

| | | |
|---|---|---|
| 245 | 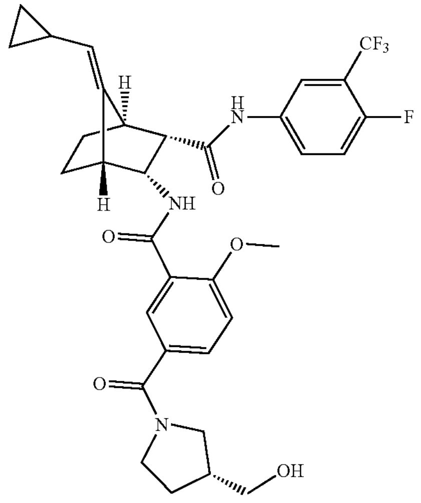 [SMILES: COc1ccc(C(=O)N2CC[C@@H](CO)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl) phenyl]-3-{5-[(3R)-3-(hydroxymethyl) pyrrolidine-1-carbonyl]-2-methoxybenzamido} bicyclo[2.2.1]heptane-2-carboxamide |
| 246 | 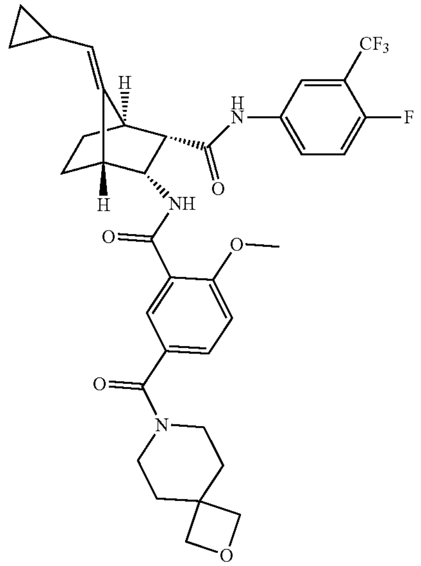 [SMILES: COc1ccc(C(=O)N2CCC3(CC2)COC3)cc1C(=O)N[C@H]1[C@@H](C(=O)Nc2ccc(F)c(C(F)(F)F)c2)[C@H]2CC[C@@H]1/C2=C\C1CC1] | (1R,2S,3R, 4R,7Z)-7-(cyclopropyl-methylidene)-N-[4-fluoro-3-(trifluoromethyl) phenyl]-3-(2-methoxy-5-{2-oxa-7-azaspiro[3.5] nonane-7-carbonyl} benzamido) bicyclo[2.2.1] heptane-2-carboxamide |
| 247 | 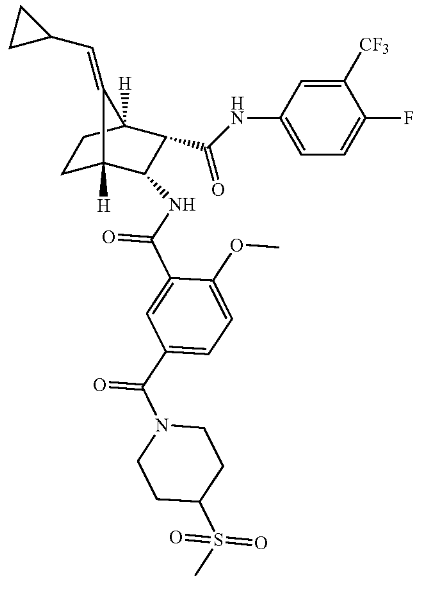 [SMILES: COc1ccc(C(=O)N2CCC(S(C)(=O)=O)CC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl-idene)-N-[4-fluoro-3-(trifluoromethyl) phenyl]-3-[5-(4-methanesulfonyl-piperidine-1-carbonyl)-2-methoxybenzamido] bicyclo[2.2.1] heptane-2-carboxamide |

TABLE 3-continued

| | | |
|---|---|---|
| 248 | 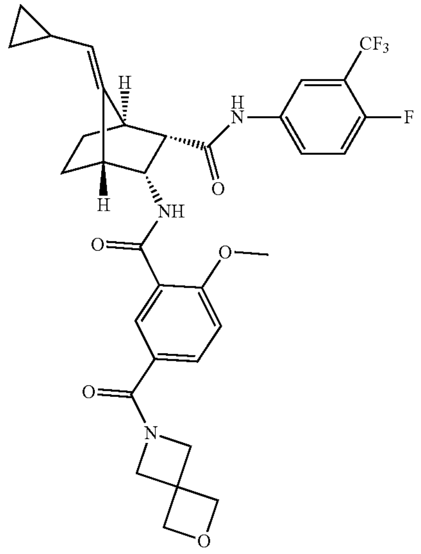 [SMILES: COc1ccc(C(=O)N2CC3(COC3)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl-idene)-N-[4-fluoro-3-(trifluoromethyl) phenyl]-3-(2-methoxy-5-{2-oxa-6-azaspiro[3.3]heptane-6-carbonyl}benzamido) bicyclo[2.2.1]heptane-2-carboxamide |
| 249 | 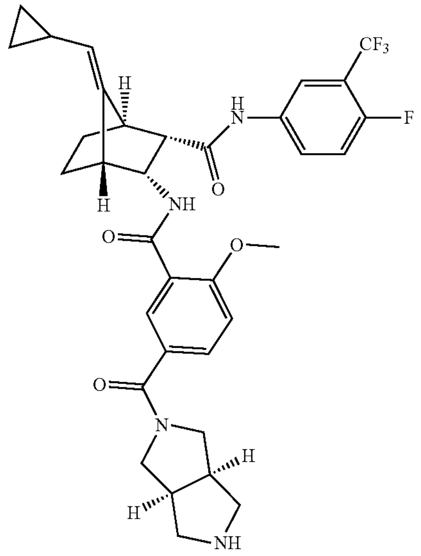 [SMILES: COc1ccc(C(=O)N2C[C@H]3CNC[C@H]3C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-3-{5-[(3aR,6aS)-octahydropyrrolo[3,4-c]pyrrole-2-carbonyl]-2-methoxybenzamido 3-7-(cyclopropylmethyl-idene)-N-[4-fluoro-3-(trifluoromethyl) phenyl]bicyclo[2.2.1] heptane-2-carboxamide |
| 250 | 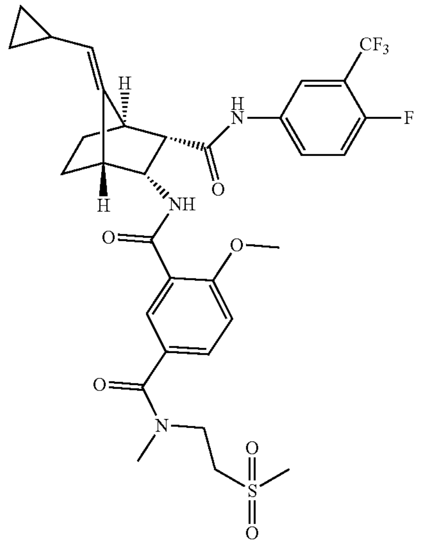 [SMILES: COc1ccc(C(=O)N(C)CCS(C)(=O)=O)cc1C(=O)N[C@H]1[C@@H](C(=O)Nc2ccc(F)c(C(F)(F)F)c2)[C@H]2CC[C@@H]1/C2=C\C1CC1] | N3-[(1R,2R,3S,4R,7Z)-7-(cyclopropyl-methylidene)-3-{[4-fluoro-3-(trifluoromethyl) phenyl]carbamoyl} bicyclo[2.2.1]heptan-2-yl]-N1-(2-methane-sulfonylethyl)-4-methoxy-N1-methylbenzene-1,3-dicarboxamide |

TABLE 3-continued

| | | |
|---|---|---|
| 251 | 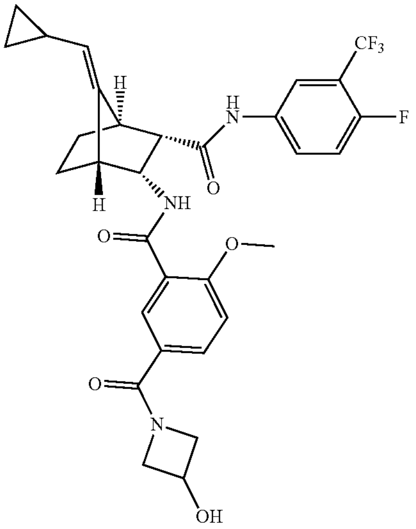 [SMILES: COc1ccc(C(=O)N2CC(O)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl-idene)-N-[4-fluoro-3-(trifluoromethyl) phenyl]-3-[5-(3-hydroxyazetidine-1-carbonyl)-2-methoxybenzamido] bicyclo[2.2.1]heptane-2-carboxamide |
| 252 | 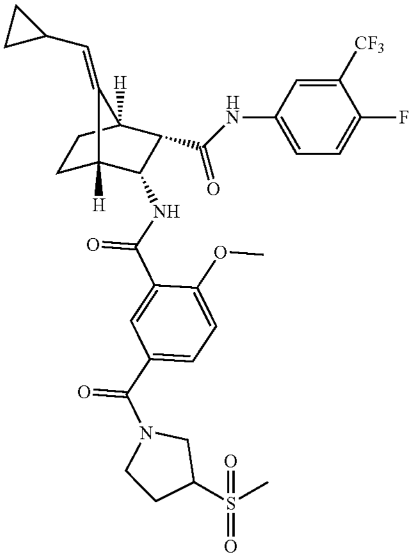 [SMILES: COc1ccc(C(=O)N2CCC(S(C)(=O)=O)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-(trifluoromethyl) phenyl]-3-[5-(3-methanesulfonyl-pyrrolidine-1-carbonyl)-2-methoxybenzamido] bicyclo[2.2.1] heptane-2-carboxamide |
| 253 | 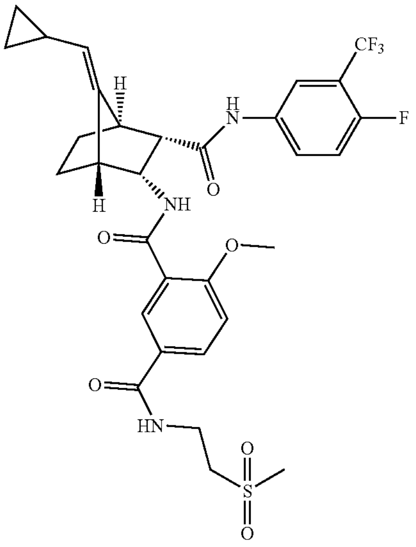 [SMILES: COc1ccc(C(=O)NCCS(C)(=O)=O)cc1C(=O)N[C@H]1[C@@H](C(=O)Nc2ccc(F)c(C(F)(F)F)c2)[C@H]2CC[C@@H]1/C2=C\C1CC1] | N3-[(1R,2R,3S,4R,7Z)-7-(cyclopropylmethyl-idene)-3-{[4-fluoro-3-(trifluoromethyl) phenyl]carbamoyl} bicyclo[2.2.1] heptan-2-yl]-N1-(2-methanesulfonyl ethyl)-4-methoxybenzene-1,3-dicarboxamide |

TABLE 3-continued
| | | |
|---|---|---|
| 254 | 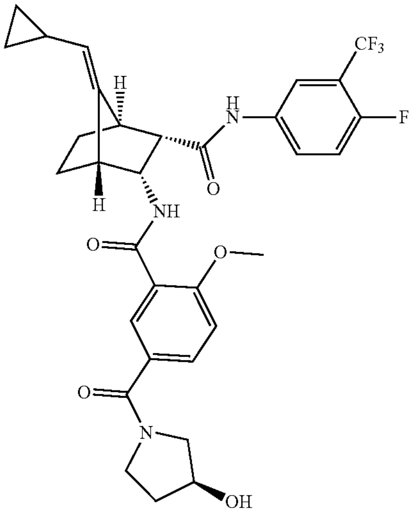 [SMILES: COc1ccc(C(=O)N2CC[C@H](O)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-{5-[(3S)-3-hydroxypyrrolidine-1-carbonyl]-2-methoxybenzamido}bicyclo[2.2.1]heptane-2-carboxamide |
| 255 | 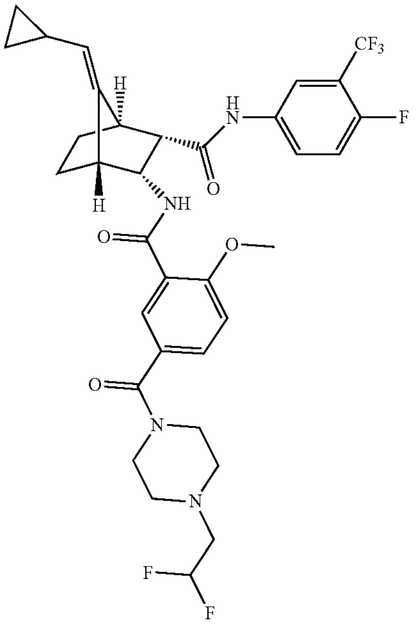 [SMILES: COc1ccc(C(=O)N2CCN(CC(F)F)CC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-3-{5-[4-(2,2-difluoroethyl)piperazine-1-carbonyl]-2-methoxybenzamido}-N-[4-fluoro-3-heptane-2-(trifluoromethyl)phenyl]bicyclo[2.2.1]carboxamide |

TABLE 3-continued

| | | |
|---|---|---|
| 256 | 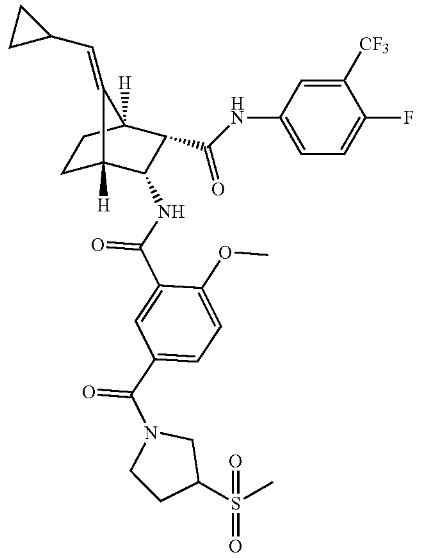 [SMILES: COc1ccc(C(=O)N2CCC(S(C)(=O)=O)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl-idene)-N-[4-fluoro-3-(trifluoromethyl)phenyl]-3-(trifluoromethyl)phenyl]-3-[5-(3-methanesulfonyl-pyrrolidine-1-carbonyl)-2-methoxybenzamido]bicyclo[2.2.1]heptane-2-carboxamide |
| 257 | 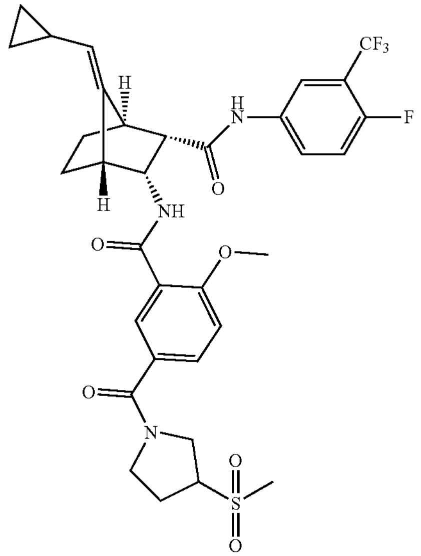 [SMILES: COc1ccc(C(=O)N2CCC(S(C)(=O)=O)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl-idene)-N-[4-fluoro-3-(trifluoromethyl)phenyl]-3-[5-(3-methanesulfonyl-pyrrolidine-1-carbonyl)-2-methoxybenzamido]bicyclo[2.2.1]heptane-2-carboxamide |
| 258 | 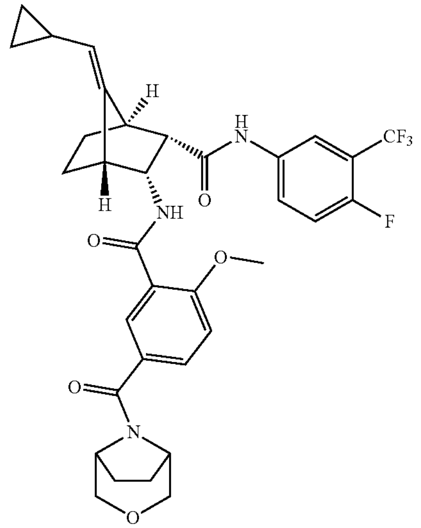 [SMILES: COc1ccc(C(=O)N2C3CCC2COC3)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-(2-methoxy-5-{3-oxa-8-azabicyclo[3.2.1]octane-8-carbonyl}benzamido)bicyclo[2.2.1]heptane-2-carboxamide |

TABLE 3-continued

| | | |
|---|---|---|
| 259 | 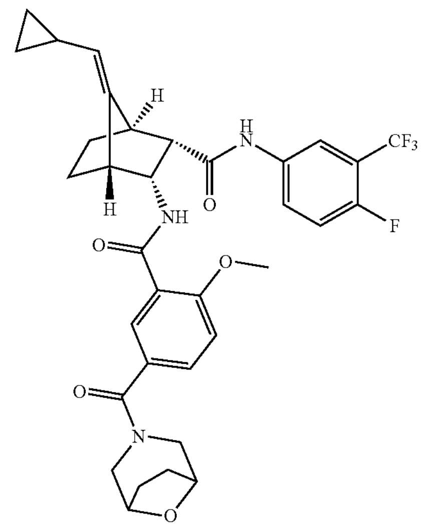 [SMILES: COc1ccc(C(=O)N2CC3CCC(C2)O3)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethylidene)-N-[4-fluoro-3-(trifluoromethyl)phenyl]-3-(2-methoxy-5-{8-oxa-3-azabicyclo[3.2.1]octane-3-carbonyl}benzamido)bicyclo[2.2.1]heptane-2-carboxamide |
| 260 | 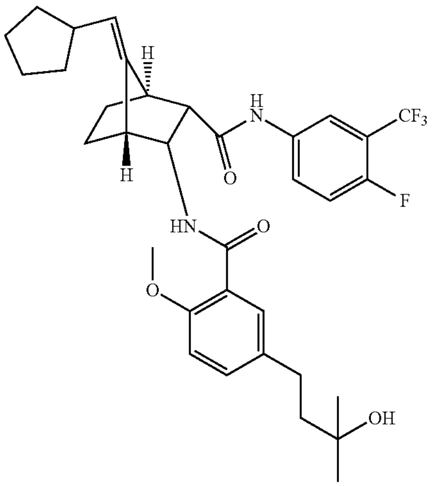 [SMILES: COc1ccc(CCC(C)(C)O)cc1C(=O)NCC1C(C(=O)Nc2ccc(F)c(C(F)(F)F)c2)[C@H]2CC[C@@H]1/C2=C\C1CCCC1] | (1R,4R,7Z)-7-(cyclopentyl-methylidene)-N-[4-fluoro-3-(trifluoromethyl)phenyl]-3-[5-(3-hydroxy-3-methylbutyl)-2-methoxybenzamido]bicyclo[2.2.1]heptane-2-carboxamide |
| 261 | 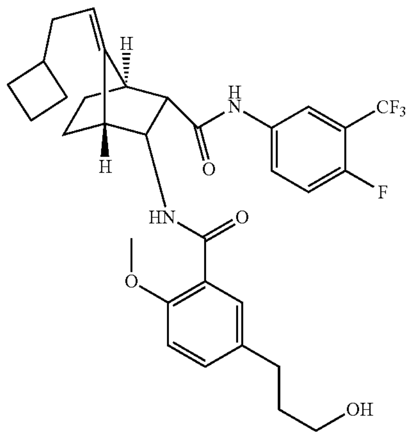 [SMILES: COc1ccc(CCCO)cc1C(=O)NCC1C(C(=O)Nc2ccc(F)c(C(F)(F)F)c2)[C@H]2CC[C@@H]1/C2=C\CC1CCC1] | (1R,4R,7Z)-7-(2-cyclobutylethylidene)-N-[4-fluoro-3-(trifluoromethyl)phenyl]-3-[5-(3-hydroxypropyl)-2-methoxybenzamido]bicyclo[2.2.1]heptane-2-carboxamide |

TABLE 3-continued

262

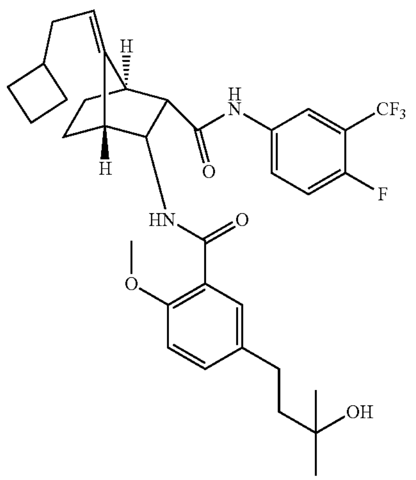 [SMILES: COc1ccc(CCC(C)(C)O)cc1C(=O)NCC1C(C(=O)Nc2ccc(F)c(C(F)(F)F)c2)[C@H]2CC[C@@H]1/C2=C\CC1CCC1]

(1R,4R,7Z)-7-(2-cyclobutylethylidene)-N-[4-fluoro-3-(trifluoromethyl)phenyl]-3-[5-(3-hydroxy-3-methylbutyl)-2-methoxybenzamido]bicyclo[2.2.1]heptane-2-carboxamide

263

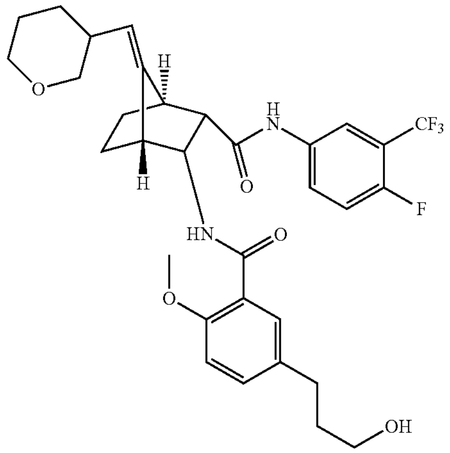 [SMILES: COc1ccc(CCCO)cc1C(=O)NCC1C(C(=O)Nc2ccc(F)c(C(F)(F)F)c2)[C@H]2CC[C@@H]1/C2=C\C1CCCOC1]

(1R,4R,7Z)-N-[4-fluoro-3-(trifluoromethyl)phenyl]-3-[5-(3-hydroxypropyl)-2-methoxybenzamido]-7-[(oxan-3-yl)methylidene]bicyclo[2.2.1]heptane-2-carboxamide

264

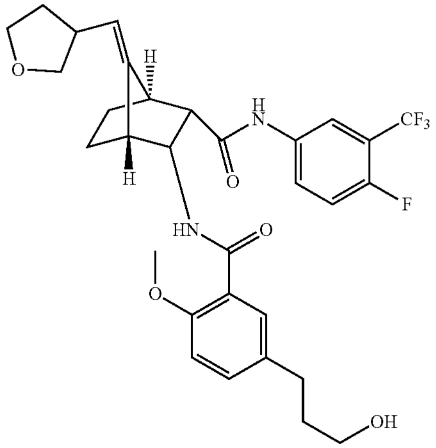 [SMILES: COc1ccc(CCCO)cc1C(=O)NCC1C(C(=O)Nc2ccc(F)c(C(F)(F)F)c2)[C@H]2CC[C@@H]1/C2=C\C1CCOC1]

(1R,4R,7Z)-N-[4-fluoro-3-(trifluoromethyl)phenyl]-3-[5-(3-hydroxypropyl)-2-methoxybenzamido]-7-[(oxolan-3-yl)methylidene]bicyclo[2.2.1]heptane-2-carboxamide TABLE 3-continued

| | | |
|---|---|---|
| 265 | 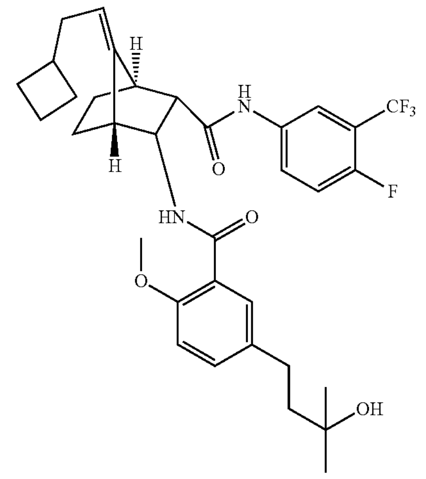 [SMILES: COc1ccc(CCC(C)(C)O)cc1C(=O)NCC1C(C(=O)Nc2ccc(F)c(C(F)(F)F)c2)[C@H]2CC[C@@H]1/C2=C\CC1CCC1] | (1R,4R,7Z)-7-(2-cyclobutylethylidene)-N-[4-fluoro-3-(trifluoromethyl)phenyl]-3-[5-(3-hydroxy-3-methylbutyl)-2-methoxybenzamido]bicyclo[2.2.1]heptane-2-carboxamide |
| 266 | 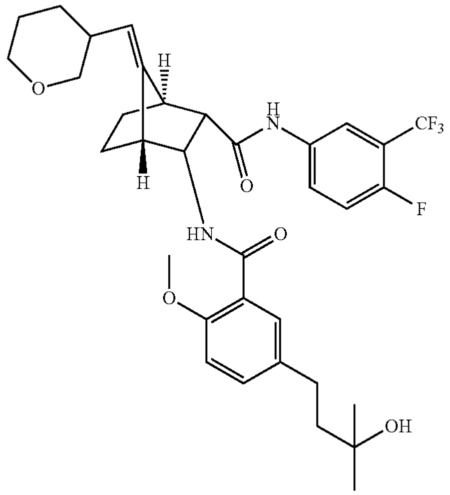 [SMILES: COc1ccc(CCC(C)(C)O)cc1C(=O)NCC1C(C(=O)Nc2ccc(F)c(C(F)(F)F)c2)[C@H]2CC[C@@H]1/C2=C\C1CCCOC1] | (1R,4R,7Z)-N-14-fluoro-3-(trifluoromethyl)phenyl]-3-[5-(3-hydroxy-3-methylbutyl)-2-methoxybenzamido1-7-[(oxan-3-yl)methylidene]bicyclo[2.2.1]heptane-2-carboxamide |
| 267 | 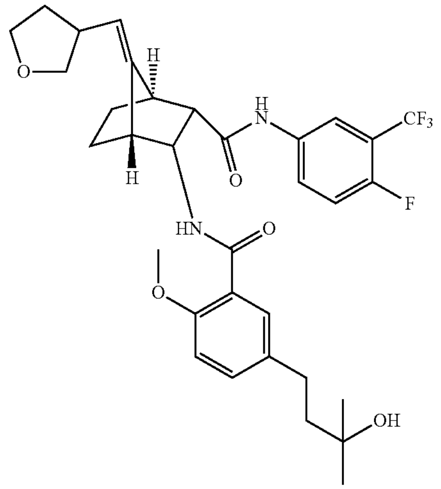 [SMILES: COc1ccc(CCC(C)(C)O)cc1C(=O)NCC1C(C(=O)Nc2ccc(F)c(C(F)(F)F)c2)[C@H]2CC[C@@H]1/C2=C\C1CCOC1] | (1R,4R,7Z)-N-[4-fluoro-3-(trifluoromethyl)phenyl]-3-[5-(3-hydroxy-3-methylbutyl)-2-methoxybenzamido1-7-[(oxolan-3-yl)methylidene]bicyclo[2.2.1]heptane-2-carboxamide |

TABLE 3-continued

| | | |
|---|---|---|
| 268 | 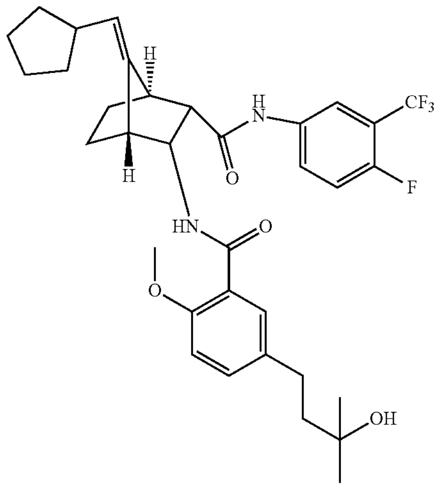 [SMILES: COc1ccc(CCC(C)(C)O)cc1C(=O)NCC1C(C(=O)Nc2ccc(F)c(C(F)(F)F)c2)[C@H]2CC[C@@H]1/C2=C\C1CCCC1] | (1R,4R,7Z)-7-(cyclopentyl-methylidene)-N-[4-fluoro-3-(trifluoromethyl)phenyl]-3-[5-(3-hydroxy-3-methylbutyl)-2-methoxybenzamido]bicyclo[2.2.1]heptane-2-carboxamide |
| 269 | 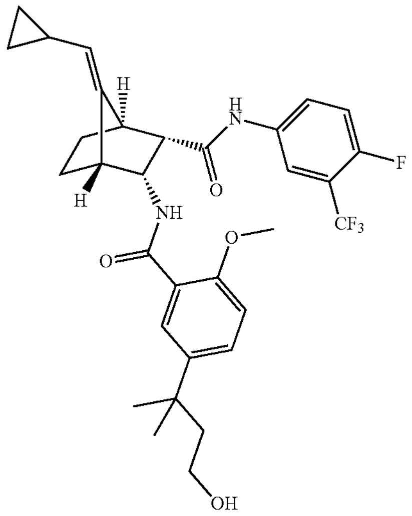 [SMILES: COc1ccc(C(C)(C)CCO)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-[5-(4-hydroxy-2-methylbutan-2-yl)-2-methoxybenzamido]bicyclo[2.2.1]heptane-2-carboxamide |
| 270 | 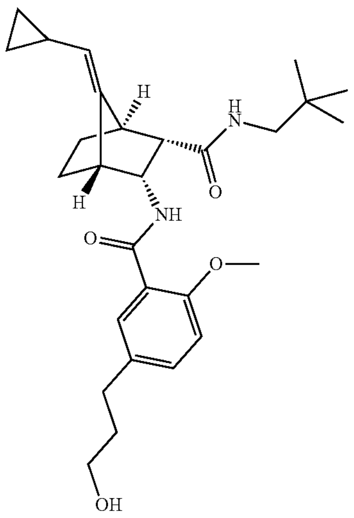 [SMILES: COc1ccc(CCCO)cc1C(=O)N[C@H]1[C@@H](C(=O)NCC(C)(C)C)[C@H]2CC[C@@H]1/C2=C\C1CC1] | (1R,2S,3R,4R,7Z)-7-(cyclopropylmethyl-idene)-N-(2,2-dimethylpropyl)-3-[5-(3-hydroxypropyl)-2-methoxybenzamido]bicyclo[2.2.1]heptane-2-carboxamide |

TABLE 3-continued

| | | |
|---|---|---|
| 271 | 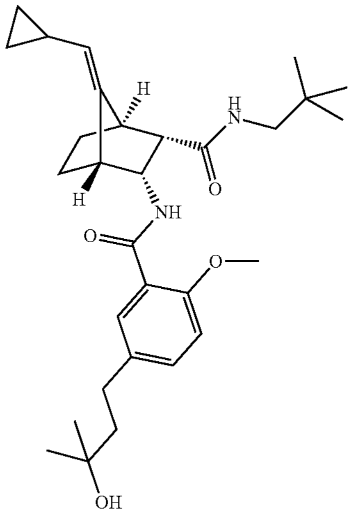 [SMILES: COc1ccc(CCC(C)(C)O)cc1C(=O)N[C@H]1[C@@H](C(=O)NCC(C)(C)C)[C@H]2CC[C@@H]1/C2=C\C1CC1] | (1R,2S,3R,4R,7Z)-7-(cyclopropylmethyl-idene)-N-(2,2-dimethylpropyl)-3-[5-(3-hydroxy-3-methylbutyl)-2-methoxybenzamido] bicyclo[2.2.1]heptane-2-carboxamide |
| 272 | 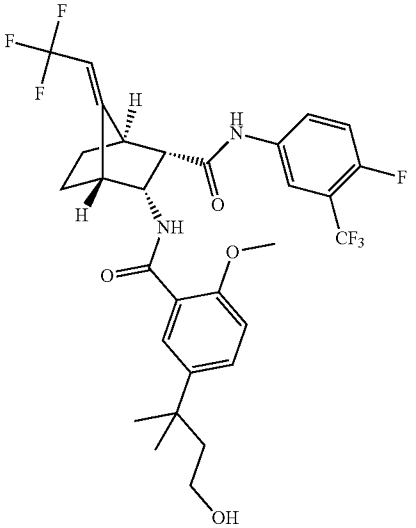 [SMILES: COc1ccc(C(C)(C)CCO)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl) phenyl]-3-[5-(4-hydroxy-2-methylbutan-2-yl)-2-methoxybenzamido]-7-(2,2,2-trifluoroethylidene) bicyclo[2.2.1]heptane-2-carboxamide |
| 273 | 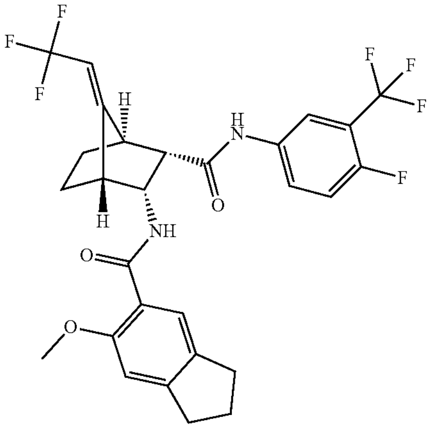 [SMILES: COc1cc2c(cc1C(=O)N[C@H]1[C@@H](C(=O)Nc3ccc(F)c(C(F)(F)F)c3)[C@H]3CC[C@@H]1/C3=C\C(F)(F)F)CCC2] | [(1R,2R,3S,4R,7Z)-3-{[4-fluoro~3-(trifluoromethyl) phenyl]carbamoyl}-7-(2,2,2-trifluoroethylidene) bicyclo[2.2.1]heptan-2-yl]-6-methoxy-2,3-dihydro-IH-indene-5-carboxamide |

TABLE 3-continued

274

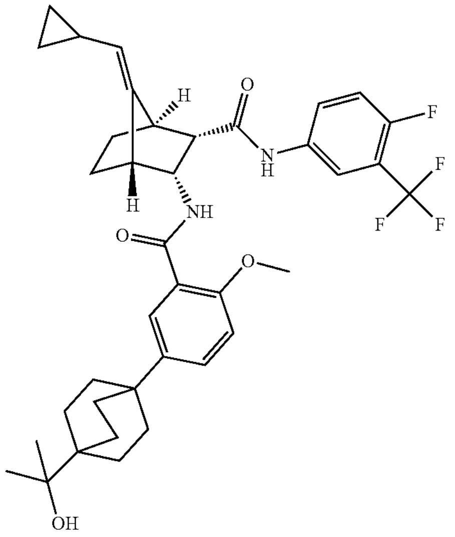 [SMILES: COc1ccc(C23CCC(C(C)(C)O)(CC2)CC3)cc1C(=O)N[C@H]1[C@@H](C(=O)Nc2ccc(F)c(C(F)(F)F)c2)[C@H]2CC[C@@H]1/C2=C\C1CC1]

(1R,2S,3R,4R,7Z)-7-(cyclopropylmethylidene)-N-[4-fluoro-3-(trifluoromethyl)phenyl]-3-{5-[4-(2-hydroxypropan-2-yl)bicyclo[2.2.2]octan-1-yl]-2-methoxybenzamido}bicyclo[2.2.1]heptane-2-carboxamide

275

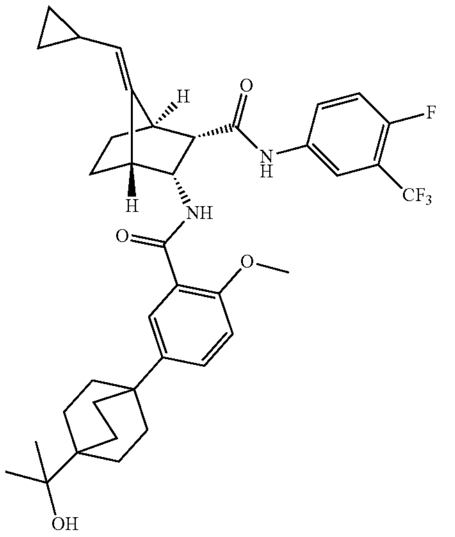 [SMILES: COc1ccc(C23CCC(C(C)(C)O)(CC2)CC3)cc1C(=O)N[C@H]1[C@@H](C(=O)Nc2ccc(F)c(C(F)(F)F)c2)[C@H]2CC[C@@H]1/C2=C\C1CC1]

(1R,2S,3R,4R,7Z)-7-(cyclopropylmethylidene)-N-[4-fluoro-3-(trifluoromethyl)phenyl]-3-{5-[4-(2-hydroxypropan-2-yl)bicyclo[2.2.2]octan-1-yl]-2-methoxybenzamido}bicyclo[2.2.1]heptane-2-carboxamide

276

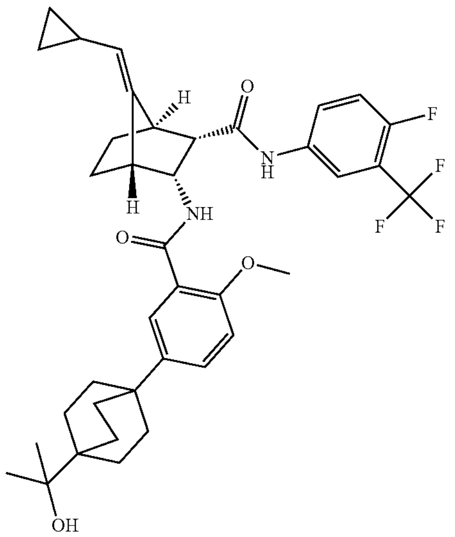 [SMILES: COc1ccc(C23CCC(C(C)(C)O)(CC2)CC3)cc1C(=O)N[C@H]1[C@@H](C(=O)Nc2ccc(F)c(C(F)(F)F)c2)[C@H]2CC[C@@H]1/C2=C\C1CC1]

(1R,2S,3R,4R,7Z)-7-(cyclopropylmethylidene)-N-[4-fluoro-3-(trifluoromethyl)phenyl]-3-{5-[4-(2-hydroxypropan-2-yl)bicyclo[2.2.2]octan-1-yl]-2-methoxybenzamido}bicyclo[2.2.1]heptane-2-carboxamide TABLE 3-continued

| | | |
|---|---|---|
| 277 | 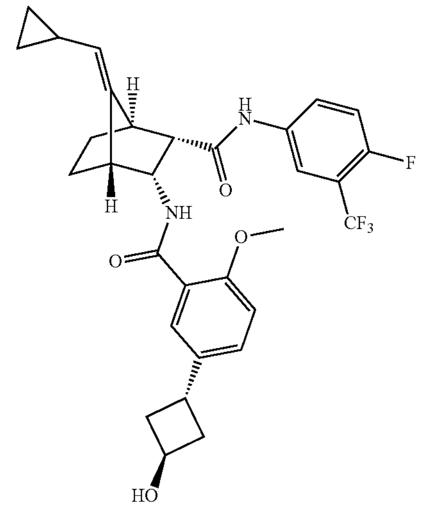 [SMILES: COc1ccc([C@H]2C[C@H](O)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl-idene)-N-[4-fluoro-3-(trifluoromethyl) phenyl]-3-{2-methoxy-5-[(1r,3r)-3-hydroxycyclobutyl] benzamido} bicyclo [2.2.1]heptane-2-carboxamide |
| 278 | 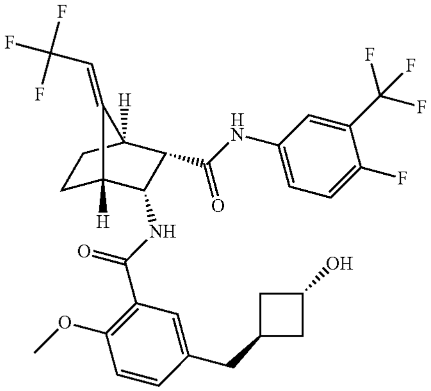 [SMILES: COc1ccc(C[C@H]2C[C@H](O)C2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl) phenyl]-3-(2-methoxy-5-{[(1r,3s)-3-hydroxycyclobutyl] methyl}benzamido)-7-(2,2,2-trifluoroethylidene) bicyclo[2.2.1]heptane-2-carboxamide |
| 279 | 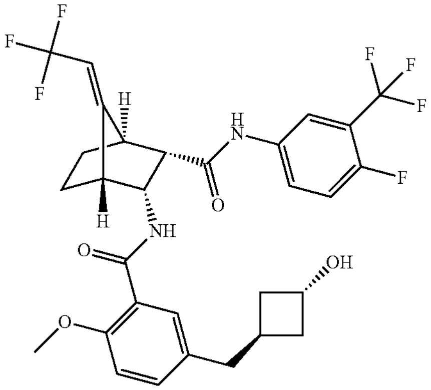 [SMILES: COc1ccc(C[C@H]2C[C@H](O)C2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl) phenyl]-3-(2-methoxy-5-{[(1r,3s)-3-hydroxycyclobutyl] methyl}benzamido)-7-(2,2,2-trifluoroethylidene) bicyclo[2.2.1]heptane-2-carboxamide |

TABLE 3-continued
| | | |
|---|---|---|
| 283 | 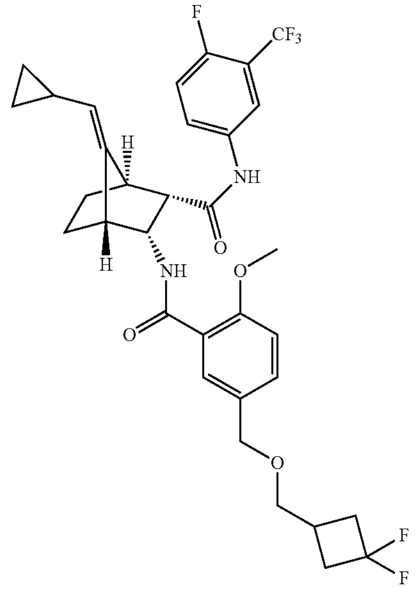 [SMILES: COc1ccc(COCC2CC(F)(F)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-3-(5-{[(3,3-difluorocyclobutyl)methoxy]methyl}-2-methoxybenzamido)-N-[4-fluoro-3-(trifluoromethyl)phenyl]bicyclo[2.2.1]heptane-2-carboxamide |
| 284 | 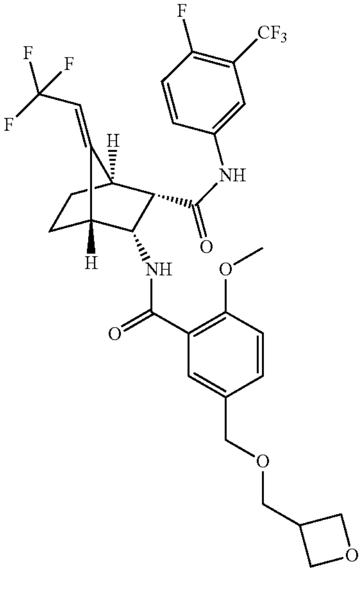 [SMILES: COc1ccc(COCC2COC2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-(2-methoxy-5-{[(oxetan-3-yl)methoxy]methyl}benzamido)-7-(2,2,2-trifluoroethylidene)bicyclo[2.2.1]heptane-2-carboxamide |

TABLE 3-continued
| | | |
|---|---|---|
| 285 | 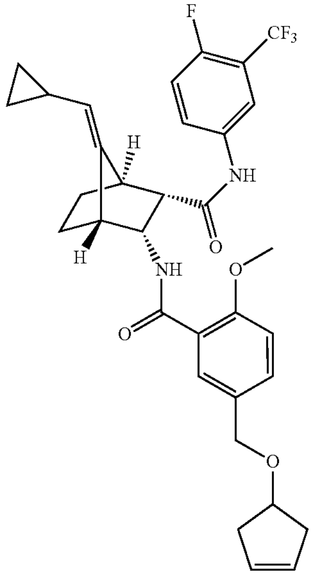 [SMILES: COc1ccc(COC2CC=CC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-3-{5-[(cyclopent-3-en-1-yloxy)methyl]-2-methoxybenzamido}-(cyclopropylmethylidene)-N-[4-fluoro-3-(trifluoromethyl)phenyl]bicyclo[2.2.1]heptane-2-carboxamide |
| 286 | 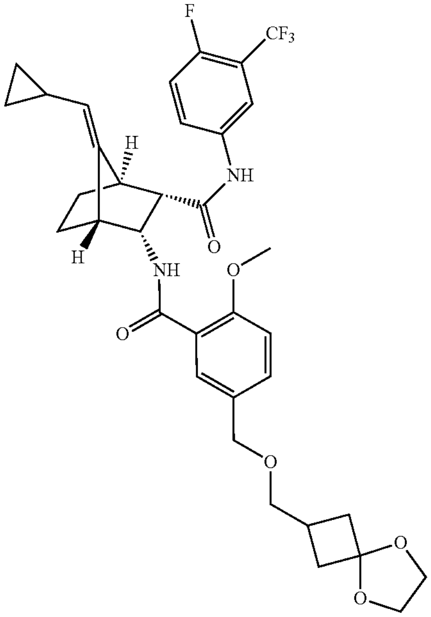 [SMILES: COc1ccc(COCC2CC3(C2)OCCO3)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethylidene)-3-{5-[({5,8-dioxaspiro[3.4]octan-2-yl}methoxy)methyl1-2-methoxybenzamido}-N-[4-fluoro-3-(trifluoromethyl)phenyl]bicyclo[2.2.1]heptane-2-carboxamide |

TABLE 3-continued
| | | |
|---|---|---|
| 287 | 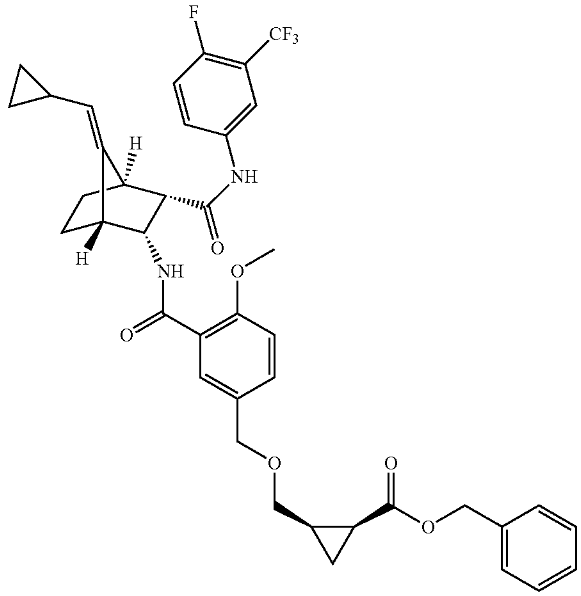 [SMILES: COc1ccc(COC[C@@H]2C[C@@H]2C(=O)OCc2ccccc2)cc1C(=O)N[C@H]1[C@@H](C(=O)Nc2ccc(F)c(C(F)(F)F)c2)[C@H]2CC[C@@H]1/C2=C\C1CC1] | benzyl (1S, 2R)-2-{[(3-{[(1R,3S,4R,7Z)-7-(cyclopropylmethyl idene)-3-{[4-fluoro-3-(trifluoromethyl) phenyl]carbamoyl} bicyclo[2.2.1]heptan-2-yl]carbamoyl}-4-methoxyphenyl) methoxy]methyl} cyclopropane-1-carboxylate |
| 288 | 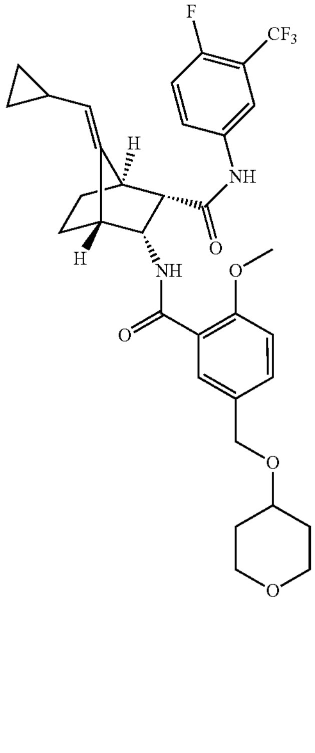 [SMILES: COc1ccc(COC2CCOCC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl) phenyl]-3-{2-methoxy-5-[(oxan-4-yloxy)methyl] benzamido} bicyclo[2.2.1] heptane-2-carboxamide |

TABLE 3-continued
289
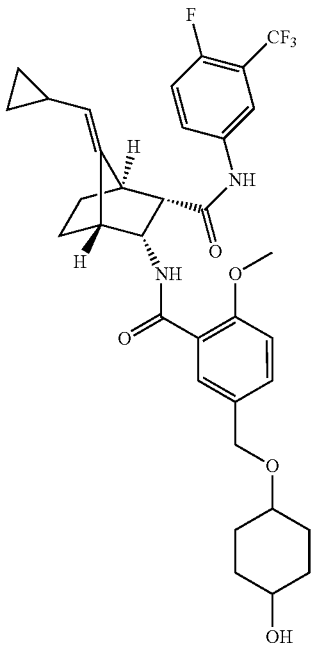 [SMILES: COc1ccc(COC2CCC(O)CC2)cc1C(=O)N[C@H]1[C@@H](C(=O)Nc2ccc(F)c(C(F)(F)F)c2)[C@H]2CC[C@@H]1/C2=C\C1CC1]
(1R,2S,3R,4R,7Z)-7-(cyclopropyl-methylidene)-N-[4-fluoro-3-(trifluoromethyl)phenyl]-3-(5-{[(4-hydroxycyclohexyl)oxy]methyl}-2-methoxybenzamido)bicyclo[2.2.1]heptane-2-carboxamide
290
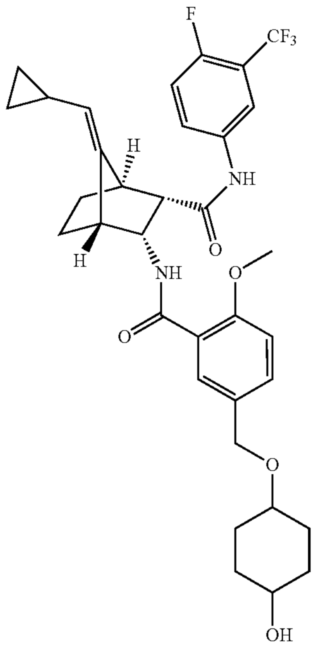 [SMILES: COc1ccc(COC2CCC(O)CC2)cc1C(=O)N[C@H]1[C@@H](C(=O)Nc2ccc(F)c(C(F)(F)F)c2)[C@H]2CC[C@@H]1/C2=C\C1CC1]
(1R,2S,3R,4R,7Z)-7-(cyclopropyl-methylidene)-N-[4-fluoro-3-(trifluoromethyl)phenyl]-3-(5-{[(4-hydroxycyclohexyl)oxy]methyl}-2-methoxybenzamido)bicyclo[2.2.1]heptane-2-carboxamide TABLE 3-continued
| | | |
|---|---|---|
| 291 | 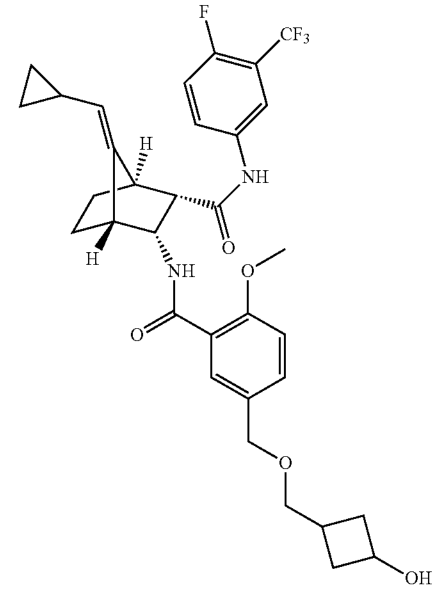 [SMILES: COc1ccc(COCC2CC(O)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-(5-{[(3-hydroxycyclobutyl)methoxy]methyl}-2-methoxybenzamido)bicyclo[2.2.1]heptane-2-carboxamide |
| 292 | 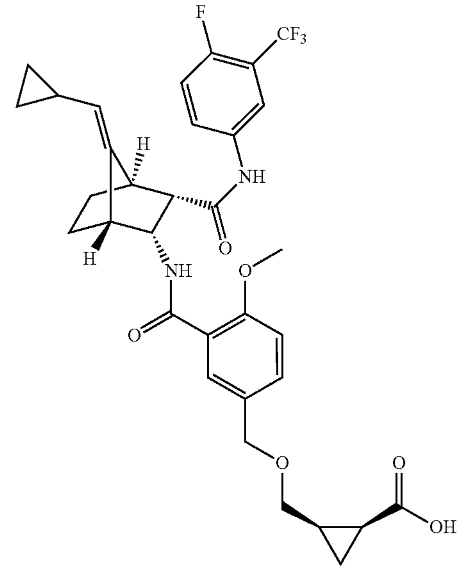 [SMILES: COc1ccc(COC[C@@H]2C[C@@H]2C(=O)O)cc1C(=O)N[C@H]1[C@@H](C(=O)Nc2ccc(F)c(C(F)(F)F)c2)[C@H]2CC[C@@H]1/C2=C\C1CC1] | (1S,2R)-2-{[(3-{[(1R.2R,3S,4R,7Z)-7-(cyclopropyl-methylidene)-3-{[4-fluoro-3-(trifluoromethyl)phenyl]carbamoyl}bicyclo[2.2.1]heptan-2-yl]carbamoyl}-4-methoxyphenyl)methoxy]methyl}cyclopropane-1-carboxylic acid |

TABLE 3-continued
| | | |
|---|---|---|
| 293 | 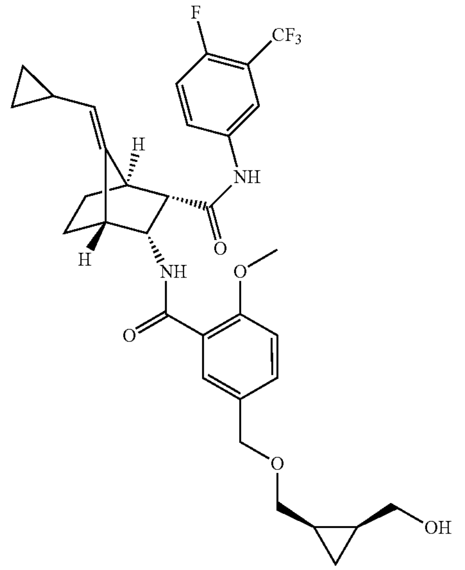 [SMILES: COc1ccc(COC[C@@H]2C[C@@H]2CO)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phonyl]-3-[5-({[(1R,2S)-2-(hydroxymethyl)cyclopropyl]methoxy}methyl)-2-methoxybenzamido]bicyclo[2.2.1]heptane-2-carboxamide |
| 294 | 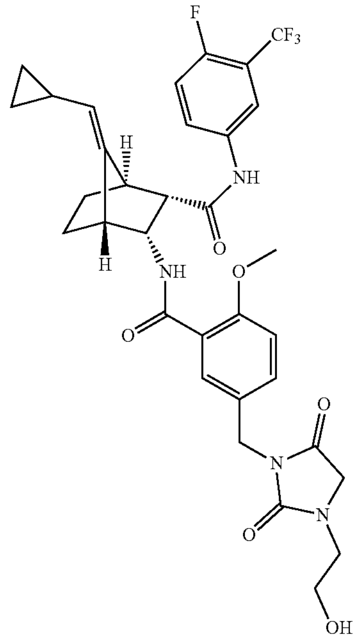 [SMILES: COc1ccc(CN2C(=O)CN(CCO)C2=O)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-(5-{[3-(2-hydroxyethyl)-2,5-dioxoimidazolidin-1-yl]methyl}-2-methoxybenzamido)bicyclo[2.2.1]heptane-2-carboxamide |

TABLE 3-continued
| | | |
|---|---|---|
| 295 | 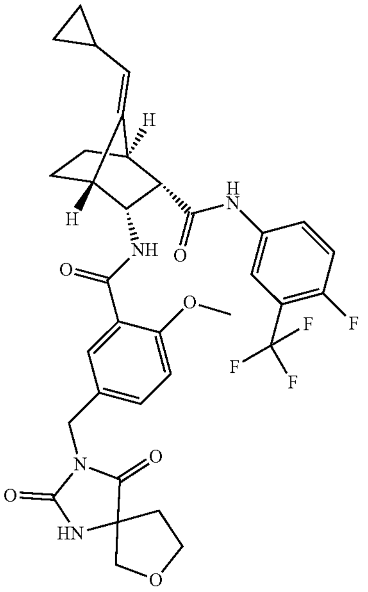 [SMILES: COc1ccc(CN2C(=O)NC3(CCOC3)C2=O)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-3-[5-({2,4-dioxo-7-oxa-1,3-diazaspiro[4.4]nonan-3-yl}methyl)-2-methoxybenzamido]-N-[4-fluoro-3-(trifluoromethyl)phenyl]bicyclo[2.2.1]heptane-2-carboxamide |
| 296 | 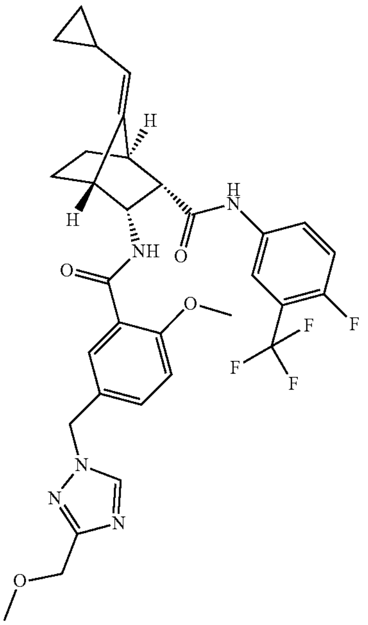 [SMILES: COCc1ncn(Cc2ccc(OC)c(C(=O)N[C@H]3[C@@H](C(=O)Nc4ccc(F)c(C(F)(F)F)c4)[C@H]4CC[C@@H]3/C4=C\C3CC3)c2)n1] | (1R,2S,3R,4R,7Z)-7-(cyclopropyl-methylidene)-N-[4-fluoro-3-(trifluoromethyl)phenyl]-3-(2-methoxy-5-{[3-(methoxymethyl)-1H-1,2,4-triazol-1-yl]methyl}benzamido)bicyclo[2.2.1]heptane-2-carboxamide |

TABLE 3-continued
| | | |
|---|---|---|
| 299 | 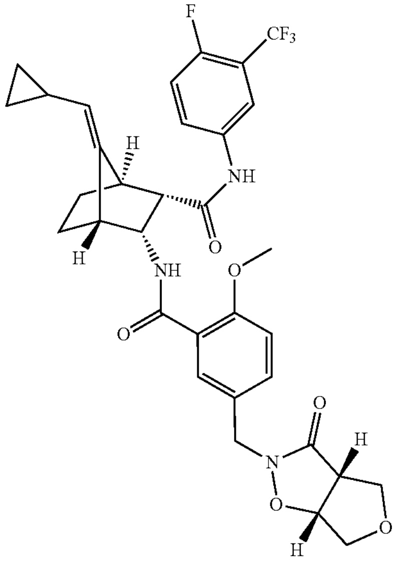 [SMILES: COc1ccc(CN2O[C@H]3COC[C@H]3C2=O)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-3-(5-{[(3aR,6aR)-3-oxo-hexahydrofuro[3,4-d][1,2]oxazol-2-yl]methyl}-2-methoxy-benzamido)-7-(cyclopropyl-methylidene)-N-[4-fluoro-(trifluoromethyl)phenyl]bicyclo[2.2.1]heptane-2-carboxamide |
| 300 | 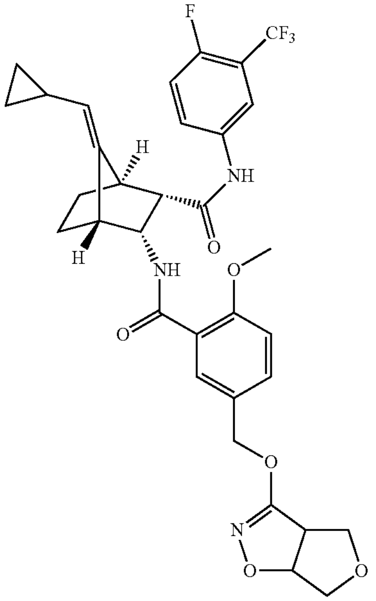 [SMILES: COc1ccc(COC2=NOC3COCC23)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-3-[5-({3aH,4H,6H,6aH-furo[3,4-d][1,2]oxazol-3-yloxy}methyl)-2-methoxybenzamido]-7-(cyclopropylmethylidene)-N-[4-fluoro-3-(trifluoromethyl)phenyl]bicyclo[2.2.1]heptane-2-carboxamide |

TABLE 3-continued

| | | |
|---|---|---|
| 301 | 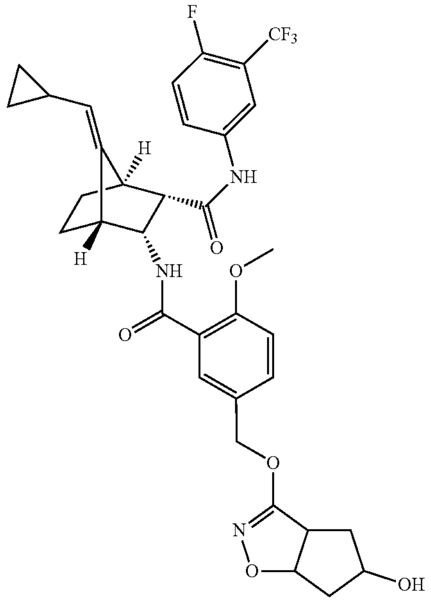 [SMILES: COc1ccc(COC2=NOC3CC(O)CC23)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethylidene)-N-[4-fluoro-3-(trifluoromethyl)phenyl]-3-{5-[({5-hydroxy-3aH,4H,5H,6H,6aH cyclopenta[d][1,2]oxazol-3-yl}oxy)methyl]-2-methoxybenzamido}bicyclo[2.2.1]heptane-2-carboxamide |
| 302 | 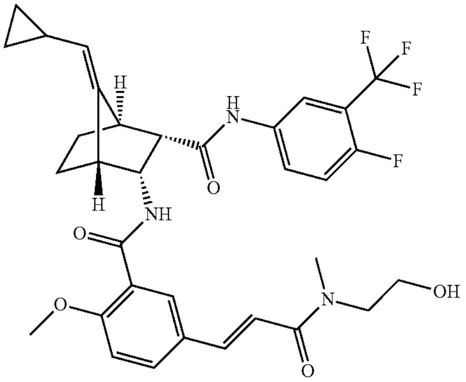 [SMILES: COc1ccc(/C=C/C(=O)N(C)CCO)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-{5-[(1E)-2-[(2-hydroxyethyl)(methyl)carbamoyl]eth-1-en-1-yl]-2-methoxybenzamido}bicyclo[2.2.1]heptane-2-carboxamide |
| 303 | 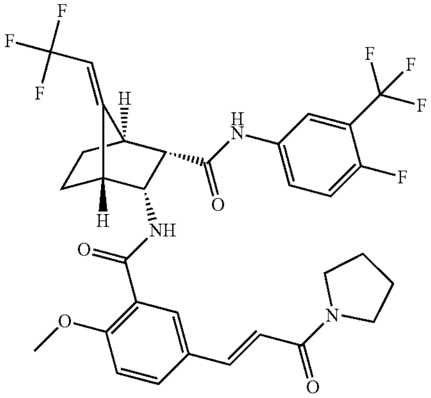 [SMILES: COc1ccc(/C=C/C(=O)N2CCCC2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-{2-methoxy-5-[(1E)-3-oxo-3-(pyrrolidin-1-yl)prop-1-en-1-yl]benzamido}-7-(2,2,2-trifluoroethylidene)bicyclo[2.2.1]heptane-2-carboxamide |

TABLE 3-continued

| | | |
|---|---|---|
| 304 | 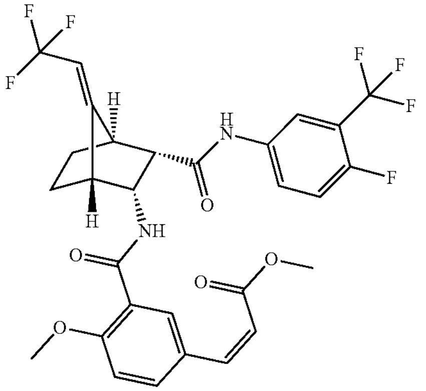 [SMILES: COC(=O)/C=C\c1ccc(OC)c(C(=O)N[C@H]2[C@@H](C(=O)Nc3ccc(F)c(C(F)(F)F)c3)[C@H]3CC[C@@H]2/C3=C\C(F)(F)F)c1] | methyl (2Z)-3-(3-{[(1R,2R,3S,4R,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)prop-2-enoate |
| 305 | 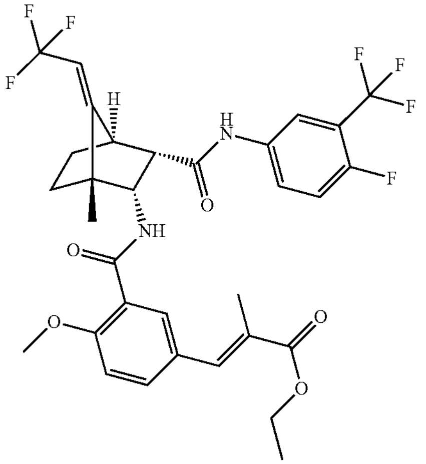 [SMILES: CCOC(=O)/C(C)=C/c1ccc(OC)c(C(=O)N[C@H]2[C@@H](C(=O)Nc3ccc(F)c(C(F)(F)F)c3)[C@H]3CC[C@]2(C)/C3=C\C(F)(F)F)c1] | ethyl (2E)-3-(3-{[(1R,2R,3S,4R,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)-2-methylprop-2-enoate |
| 306 | 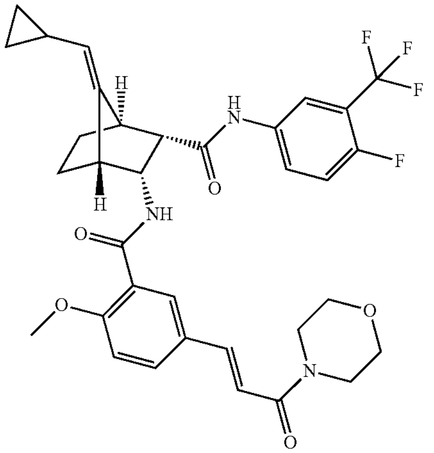 [SMILES: COc1ccc(/C=C/C(=O)N2CCOCC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-{2-methoxy-5-[(1E)-3-(morpholin-4-yl)-3-oxoprop-1-en-1-yl]benzamido}bicyclo[2.2.1]heptane-2-carboxamide |

TABLE 3-continued

| | | |
|---|---|---|
| 307 | 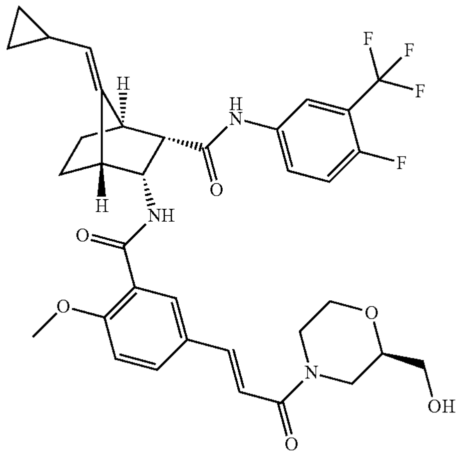 [SMILES: COc1ccc(/C=C/C(=O)N2CCO[C@@H](CO)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-{5-[(1E)-3-[(2R)-2-(hydroxymethyl)morpholin-4-yl]-3-oxoprop-1-en-1-yl]-2-methoxybenzamido}bicyclo[2.2.1]heptane-2-carboxamide |
| 308 | 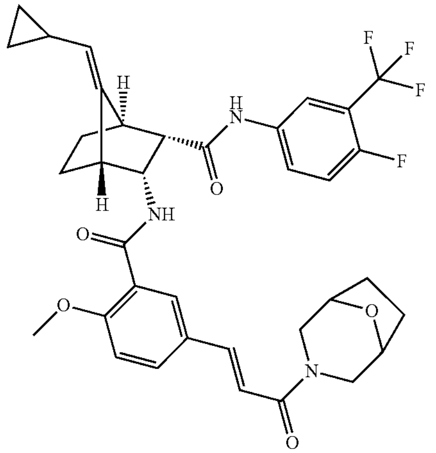 [SMILES: COc1ccc(/C=C/C(=O)N2CC3CCC(C2)O3)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethylidene)-N-[4-fluoro-3-(trifluoromethyl)phenyl]-3-{2-methoxy-5-[(1E)-3-{8-oxa-3-azabicyclo[3.2.1]octan-3-yl}-3-oxoprop-1-en-1-yl]benzamido}bicyclo[2.2.1]heptane-2-carboxamide |
| 309 | 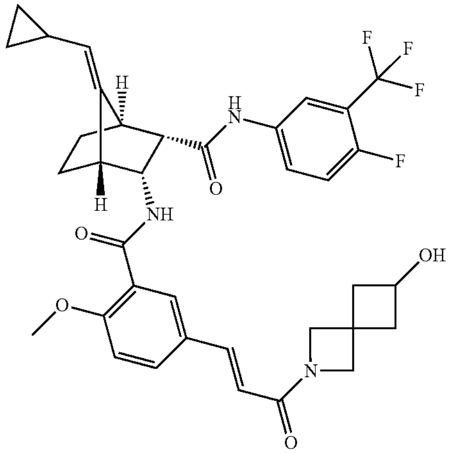 [SMILES: COc1ccc(/C=C/C(=O)N2CC3(CC(O)C3)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethylidene)-N-[4-fluoro-3-(trifluoromethyl)phenyl]-3-{5-[(1E)-3-{6-hydroxy-2-azaspiro[3.3]heptan-2-yl}-3-oxoprop-1-en-1-yl]-2-methoxybenzamido}bicyclo[2.2.1]heptane-2-carboxamide |

TABLE 3-continued

| | | |
|---|---|---|
| 310 | 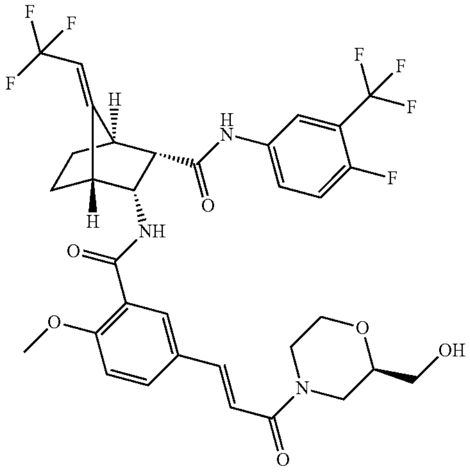 [SMILES: COc1ccc(/C=C/C(=O)N2CCO[C@@H](CO)C2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl) phenyl]-3-{5-[(1E)-3-[(2R)-2-(hydroxymethyl) morpholin-4-yl]-3-oxoprop-1-en-1-yl]-2-methoxybenzamido 3-7-(2,2,2-trifluoroethylidene) bicyclo[2.2.1] heptane-2-carboxamide |
| 311 | 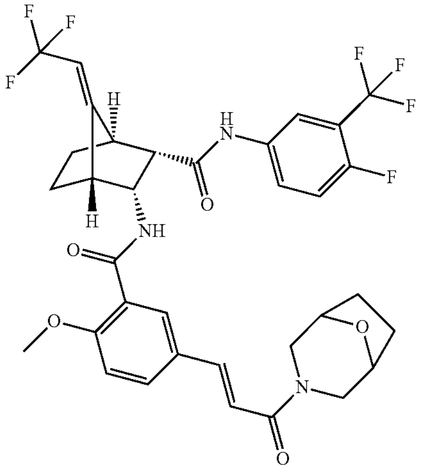 [SMILES: COc1ccc(/C=C/C(=O)N2CC3CCC(C2)O3)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl) phenyl]-3-{2-methoxy-5-[(1E)-3-{8-oxa-3-azabicyclo[3.2.1] octan-3-yl}-3-oxoprop-1-en-1-yl]benzamido}-7-(2,2,2-trifluoroethylidene) bicyclo[2.2.1]heptane-2-carboxamide |
| 312 | 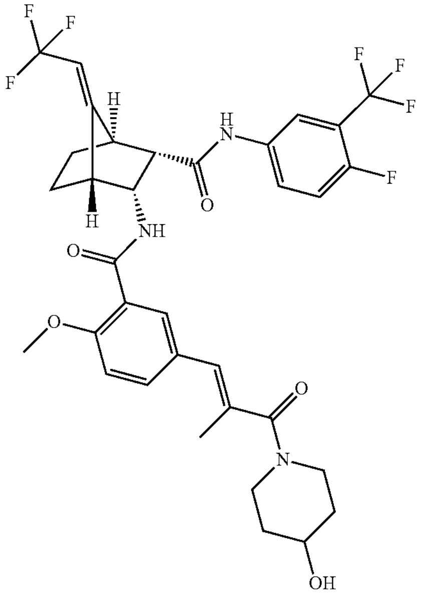 [SMILES: COc1ccc(/C=C(\C)C(=O)N2CCC(O)CC2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl) phenyl]-3-{5-[(1E)-3-(4-hydroxypiperidin-1-yl)-2-methyl-3-oxoprop-1-en-1-yl]-2-methoxybenzamido}-7-(2,2,2-trifluoroethylidene) bicyclo[2.2.1]heptane-2-carboxamide |

TABLE 3-continued

| | | |
|---|---|---|
| 313 | 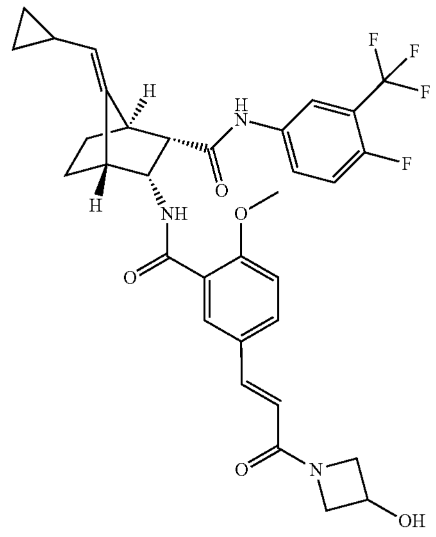 [SMILES: COc1ccc(/C=C/C(=O)N2CC(O)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl) phenyl]-3-{5-[(1E)-3-(3-hydroxyazetidin-1-yl)-3-oxoprop-1-en-1-yl]-2-methoxybenzamido} bicyclo[2.2.1]heptane-2-carboxamide |
| 314 | 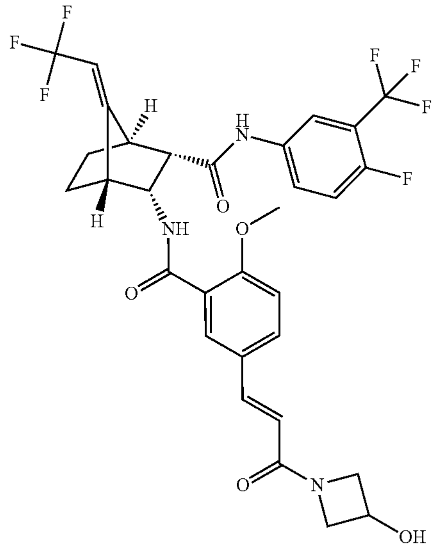 [SMILES: COc1ccc(/C=C/C(=O)N2CC(O)C2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl) phenyl]-3-{5-[(1E)-3-(3-hydroxyazetidin-1-yl)-3-oxoprop-1-en-1-yl]-2-methoxybenzamido 3-7-(2,2,2-trifluoroethylidene) bicyclo[2.2.1]heptane-2-carboxamide |
| 315 | 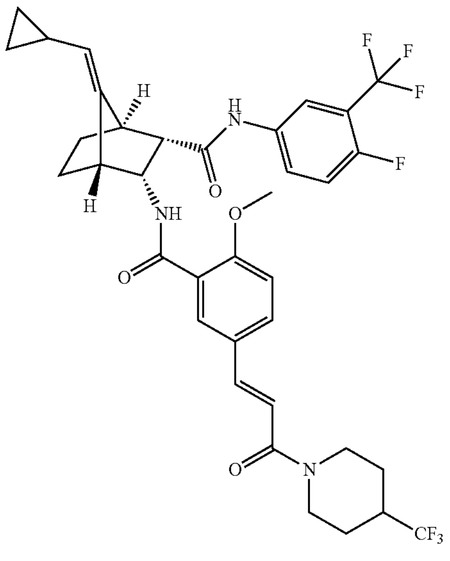 [SMILES: COc1ccc(/C=C/C(=O)N2CCC(C(F)(F)F)CC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl-idene)-N-[4-fluoro-3-(trifluoromethyl) phenyl]-3-{2-methoxy-5-[(1E)-3-oxo-3-14-(trifluoromethyl) piperidin-1-yl]prop-1-en-1-yl]benzamido} bicyclo[2.2.1] heptane-2-carboxamide |

TABLE 3-continued

| | | |
|---|---|---|
| 316 | 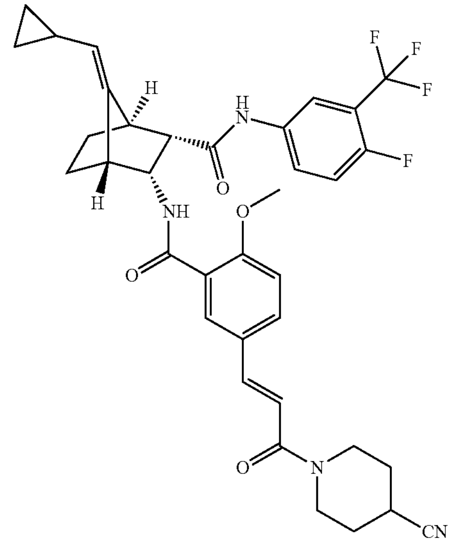 [SMILES: COc1ccc(/C=C/C(=O)N2CCC(C#N)CC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-3-{5-[(1E)-3-(4-cyanopiperidin-1-yl)-3-oxoprop-1-en-1-yl]-2-methoxybenzamido}-7-(cyclopropyl methylidene)-N-[4-fluoro-3-(trifluoromethyl) phenyl]bicyclo[2.2.1] heptane-2-carboxamide |
| 317 | 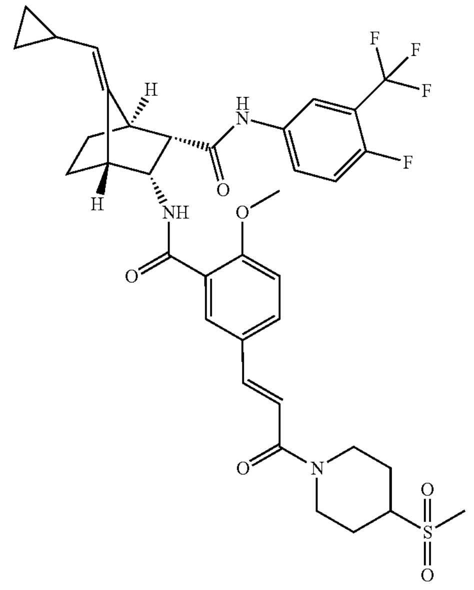 [SMILES: COc1ccc(/C=C/C(=O)N2CCC(S(C)(=O)=O)CC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl) phenyl]-3-{5-[(1E)-3-(4-methanesulfonyl-piperidin-1-yl)-3-oxoprop-1-en-1-yl]-2-methoxybenzamido} bicyclo[2.2.1]heptane-2-carboxamide |
| 318 | 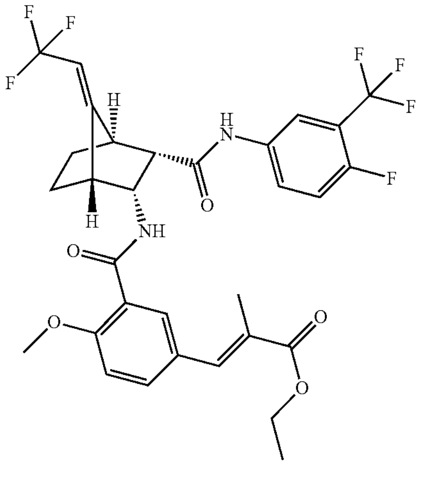 [SMILES: CCOC(=O)/C(C)=C/c1ccc(OC)c(C(=O)N[C@H]2[C@@H](C(=O)Nc3ccc(F)c(C(F)(F)F)c3)[C@H]3CC[C@@H]2/C3=C\C(F)(F)F)c1] | ethyl (2E)-3-(3-{[(1R,2R,3S,4R,7Z)-3-{[4-fluoro-3-(trifluoromethyl) phenyl]carbamoyl}-7-(2,2,2-trifluoroethylidene) bicyclo[2.2.1]heptan-2-yl]carbamoyl}-4-methoxyphenyl)-2-methylprop-2-enoate |

TABLE 3-continued

| | | |
|---|---|---|
| 319 | 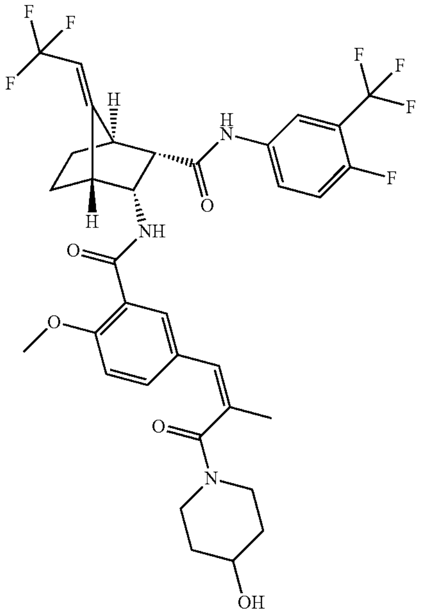 [SMILES: COc1ccc(/C=C(/C)C(=O)N2CCC(O)CC2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-{5-[(1Z)-3-(4-hydroxypiperidin-1-yl)-2-methyl-3-oxoprop-1-en-1-yl]-2-methoxybenzamido3-7-(2,2,2-trifluoroethylidene)bicyclo[2.2.1]heptane-2-carboxamide |
| 320 | 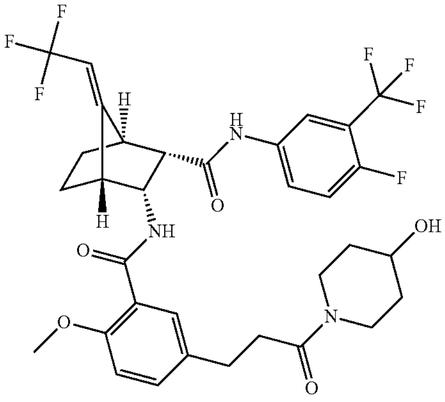 [SMILES: COc1ccc(CCC(=O)N2CCC(O)CC2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-{5-[3-(4-hydroxypiperidin-1-yl)-3-oxopropyl]-2-methoxybenzamido3-7-(2,2,2-trifluoroethylidene)bicyclo[2.2.1]heptane-2-carboxamide |
| 321 | 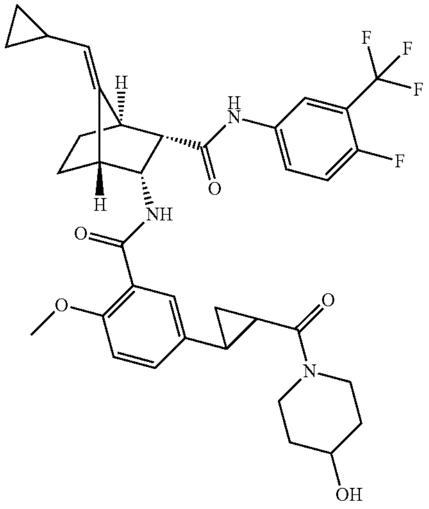 [SMILES: COc1ccc(C2CC2C(=O)N2CCC(O)CC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethylidene)-N-[4-fluoro-3-(trifluoromethyl)phenyl]-3-{5-[2-(4-hydroxypiperidine-1-carbonyl)cyclopropyl]-2-methoxybenzamido}bicyclo[2.2.1]heptane-2-carboxamide |

TABLE 3-continued

| | | |
|---|---|---|
| 322 | 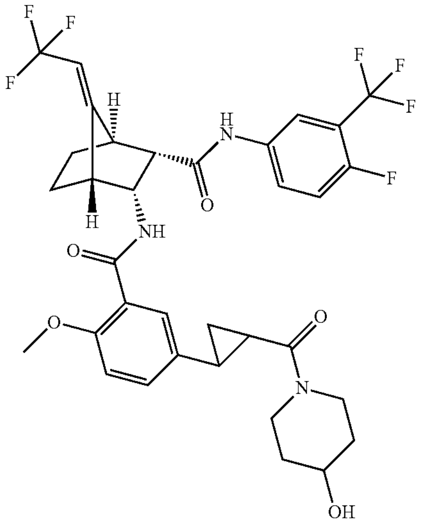 [SMILES: COc1ccc(C2CC2C(=O)N2CCC(O)CC2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl) phenyl]-3-{5-[2-(4-hydroxypiperidine-1-carbonyl) cyclopropyl]-2-methoxybenzamido 3-7-(2,2,2-trifluoroethylidene) bicyclo[2.2.1] heptane-2-carboxamide |
| 323 | 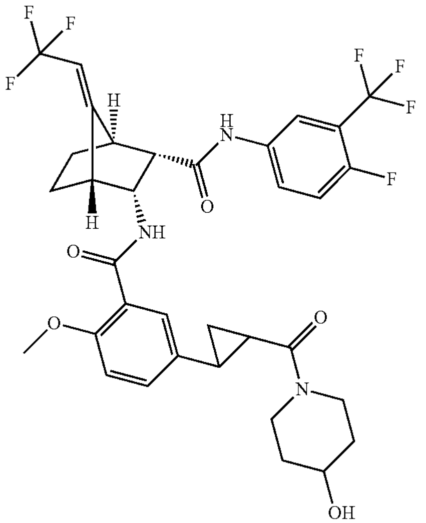 [SMILES: COc1ccc(C2CC2C(=O)N2CCC(O)CC2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl) phenyl]-3-{5-[2-(4-hydroxypiperidine-1-carbonyl) cyclopropyl]-2-methoxybenzamido}-7-(2,2,2-trifluoroethylidene) bicyclo[2.2.1] heptane-2-carboxamide |
| 324 | 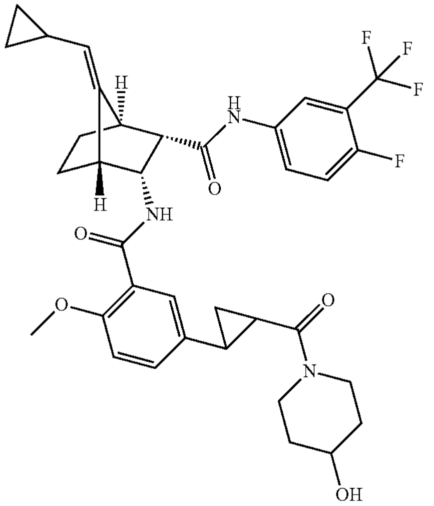 [SMILES: COc1ccc(C2CC2C(=O)N2CCC(O)CC2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl) phenyl]-3-{5-[2-(4-hydroxypiperidine-1-carbonyl)cycloprop yl]-2-methoxybenzamido} bicyclo [2.2.1]heptane-2-carboxamide |

TABLE 3-continued

| | | |
|---|---|---|
| 325 | 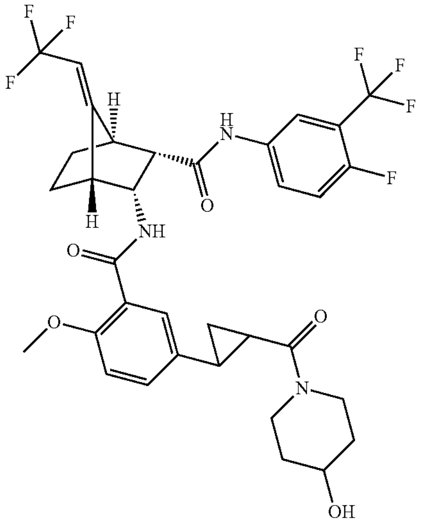 [SMILES: COc1ccc(C2CC2C(=O)N2CCC(O)CC2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-{5-[2-(4-hydroxypiperidine-1-carbonyl)cyclopropyl]-2-methoxybenzamido}-7-(2,2,2-trifluoroethylidene)bicyclo[2.2.1]heptane-2-carboxamide |
| 326 | 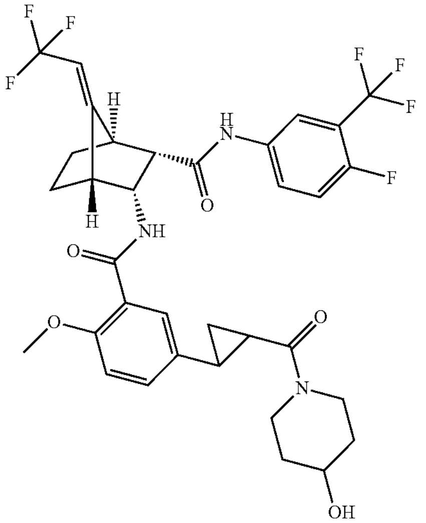 [SMILES: COc1ccc(C2CC2C(=O)N2CCC(O)CC2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-N-[4-fluoro-3-(trifluoromethyl)phenyl]-3-{5-[2-(4-hydroxypiperidine-1-carbonyl)cyclopropyl]-2-methoxybenzamido 3-7-(2,2,2-trifluoroethylidene)bicyclo[2.2.1]heptane-2-carboxamide |
| 327 | 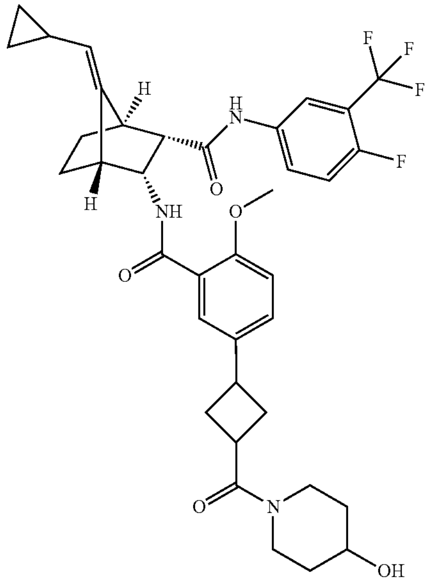 [SMILES: COc1ccc(C2CC(C(=O)N3CCC(O)CC3)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-{5-[3-(4-hydroxypiperidine-1-carbonyl)cyclobutyl 1-2-methoxybenzamido}bicyclo[2.2.1]heptane-2-carboxamide |

TABLE 3-continued

| | | |
|---|---|---|
| 328 | 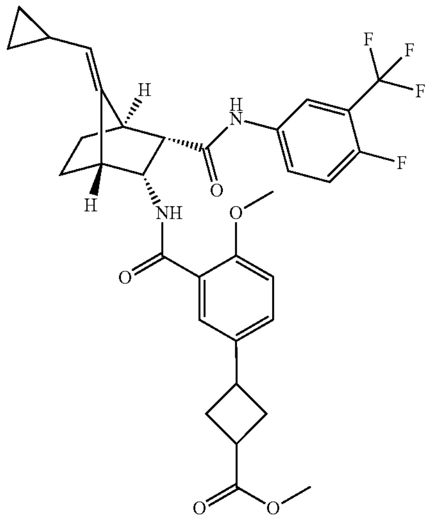 [SMILES: COC(=O)C1CC(c2ccc(OC)c(C(=O)N[C@H]3[C@@H](C(=O)Nc4ccc(F)c(C(F)(F)F)c4)[C@H]4CC[C@@H]3/C4=C\C3CC3)c2)C1] | methyl 3-(3-{[(1R,2R,3S,4R,7Z)-7-(cyclopropyl-methylidene)-3-{[4-fluoro-3-(trifluoromethyl)phenyl]carbamoyl}bicyclo[2.2.1]heptan-2-yl]carbamoyl}-4-methoxyphenyl)cyclobutane-1-carboxylate |
| 329 | 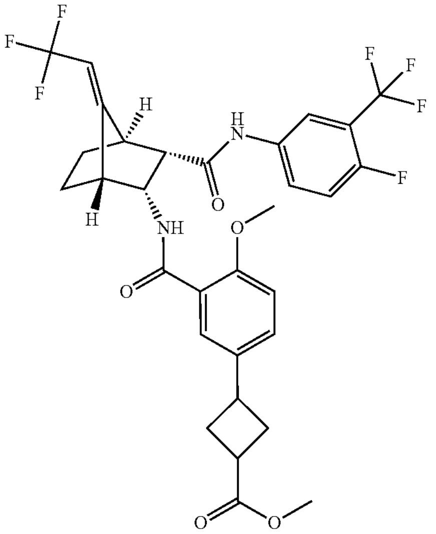 [SMILES: COC(=O)C1CC(c2ccc(OC)c(C(=O)N[C@H]3[C@@H](C(=O)Nc4ccc(F)c(C(F)(F)F)c4)[C@H]4CC[C@@H]3/C4=C\C(F)(F)F)c2)C1] | methyl 3-(3-{[(1R,2R,3S,4R,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)cyclobutane-1-carboxylate |
| 330 | 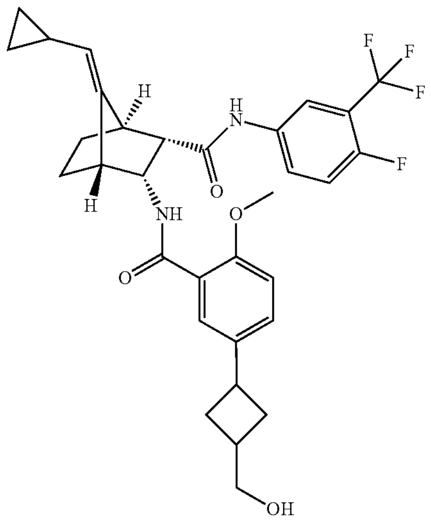 [SMILES: COc1ccc(C2CC(CO)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethylidene)-N-[4-fluoro-3-(trifluoromethyl)phenyl]-3-{5-[3-(hydroxymethyl)cyclobutyl]-2-methoxybenzamido}bicyclo[2.2.1]heptane-2-carboxamide |

TABLE 3-continued

| | | |
|---|---|---|
| 331 | 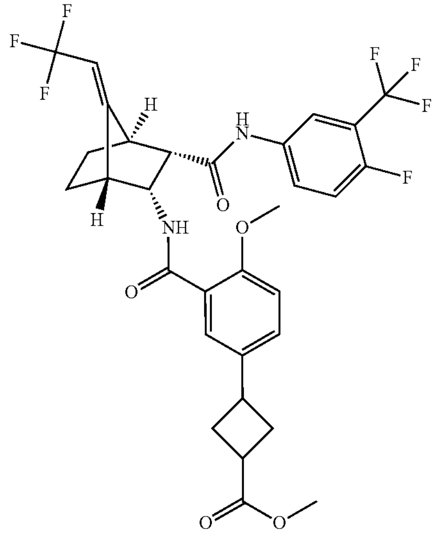 [SMILES: COC(=O)C1CC(c2ccc(OC)c(C(=O)N[C@H]3[C@@H](C(=O)Nc4ccc(F)c(C(F)(F)F)c4)[C@H]4CC[C@@H]3/C4=C\C(F)(F)F)c2)C1] | methyl 3-(3-{(1R.2R,3S,4R,7Z)-3-{[4-fluoro-3-(trifluoromethyl)phenyl]carbamoyl}-7-(2,2,2-trifluoroethylidene)bicyclo[2.2.1]heptan-2-yl]carbamoyl}-4-methoxyphenyl)cyclobutane-1-carboxylate |
| 332 | 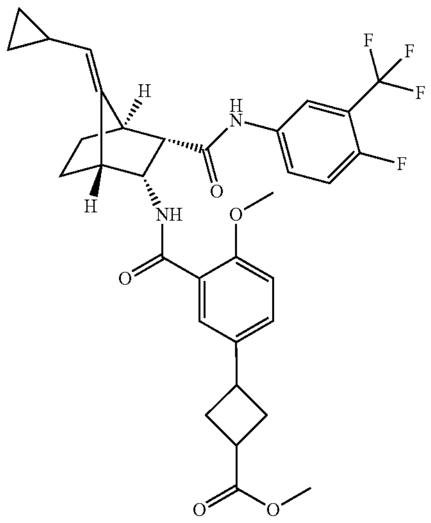 [SMILES: COC(=O)C1CC(c2ccc(OC)c(C(=O)N[C@H]3[C@@H](C(=O)Nc4ccc(F)c(C(F)(F)F)c4)[C@H]4CC[C@@H]3/C4=C\C3CC3)c2)C1] | methyl 3-(3-{[(1R,2R,3S,4R,7Z)-7-(cyclopropylmethylidene)-3-{[4-fluoro-3-(trifluoromethyl)phenyl]carbamoyl}bicyclo[2.2.1]heptan-2-yl]carbamoyl}-4-methoxyphenyl)cyclobutane-1-carboxylate |
| 333 | 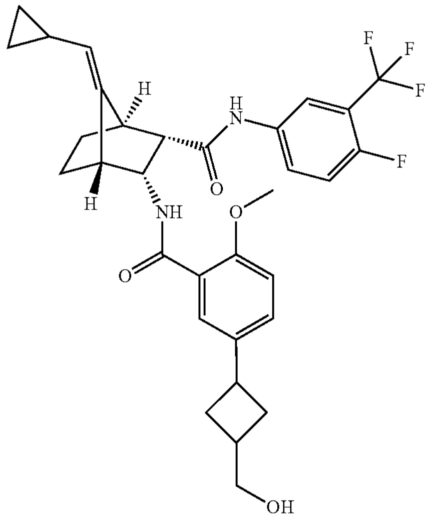 [SMILES: COc1ccc(C2CC(CO)C2)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-[5-[3-(hydroxymethyl)cyclobutyl]-2-methoxybenzamido}bicyclo[2.2.1]heptane-2-carboxamide |

TABLE 3-continued

| | | |
|---|---|---|
| 341 | 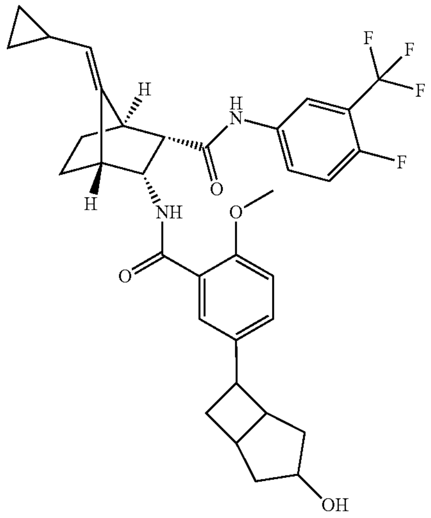 [SMILES: COc1ccc(C2CC3CC(O)CC32)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylme-thylidene)-N-[4-fluoro-3-(trifluoromethyl)phenyl]-3-(5-{3-hydroxybicyclo[3.2.0]heptan-6-yl}-2-methoxybenzamido)bicyclo[2.2.1]heptane-2-carboxamide |
| 342 | 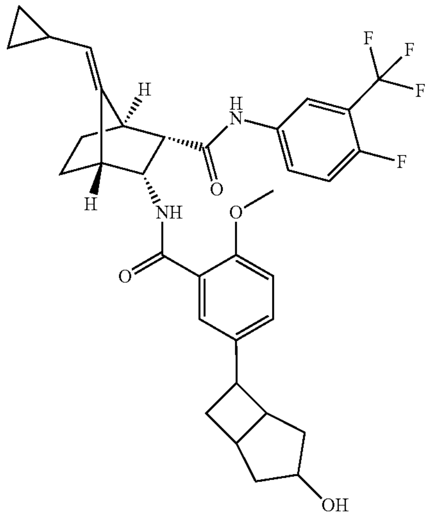 [SMILES: COc1ccc(C2CC3CC(O)CC32)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethyl-idene)-N-[4-fluoro-3-(trifluoromethyl)phenyl]-3-(5-{3-hydroxybicyclo[3.2.0]heptan-6-yl}-2-methoxybenzamido)bicyclo[2.2.1]heptane-2-carboxamide |
| 343 | 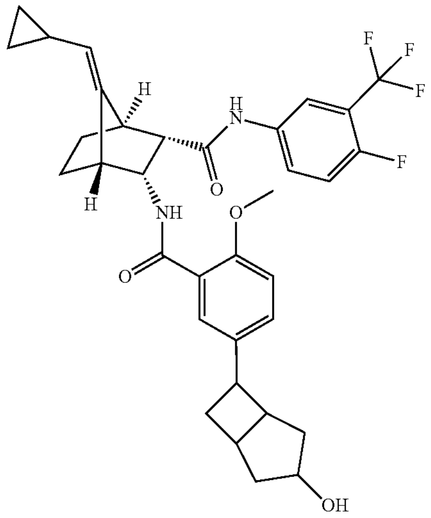 [SMILES: COc1ccc(C2CC3CC(O)CC32)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropylmethylidene)-N-[4-fluoro-3-(trifluoromethyl)phenyl]-3-(5~{3-hydroxybicyclo[3.2.0]heptan-6-yl}-2-methoxybenzamido)bicyclo[2.2.1]heptane-2-carboxamide |

TABLE 3-continued

| | | |
|---|---|---|
| 349 | 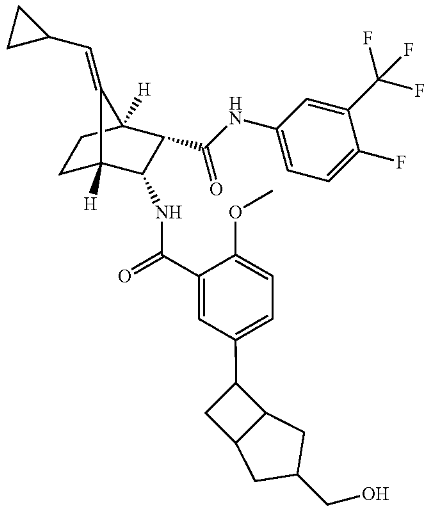 [SMILES: COc1ccc(C2CC3CC(CO)CC32)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-{5-[3-(hydroxymethyl)bicyclo[3.2.0]heptan-6-yl]-2-methoxybenzamido}bicyclo[2.2.1]heptane-2-carboxamide |
| 350 | 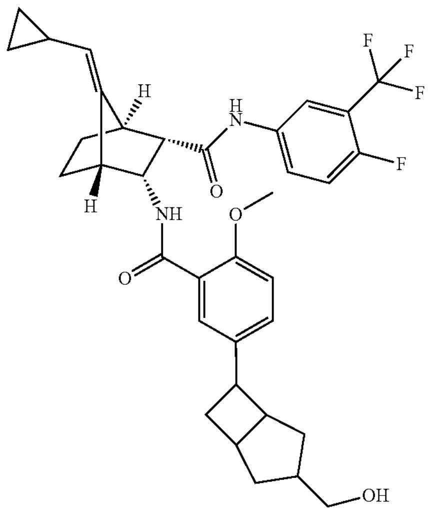 [SMILES: COc1ccc(C2CC3CC(CO)CC32)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-[5-[3-(hydroxymethyl)bicyclo[3.2.0]heptan-6-yl]-2-methoxybenzamido}bicyclo[2.2.1]heptane-2-carboxamide |
| 351 | 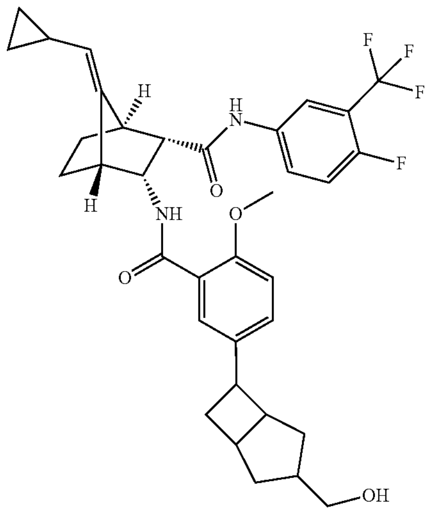 [SMILES: COc1ccc(C2CC3CC(CO)CC32)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl)phenyl]-3-{5-[3-(hydroxymethyl)bicyclo[3.2.0]heptan-6-yl]-2-methoxybenzamido}bicyclo[2.2.1]heptane-2-carboxamide |

TABLE 3-continued

| | | |
|---|---|---|
| 352 | 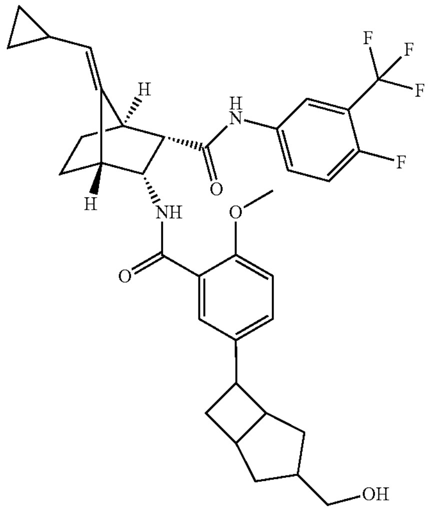 [SMILES: COc1ccc(C2CC3CC(CO)CC32)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl) phenyl]-3-[5-[3-(hydroxymethyl) bicyclo[3.2.0]heptan-6-yl]-2-methoxybenzamido} bicyclo[2.2.1]heptane-2-carboxamide |
| 353 | 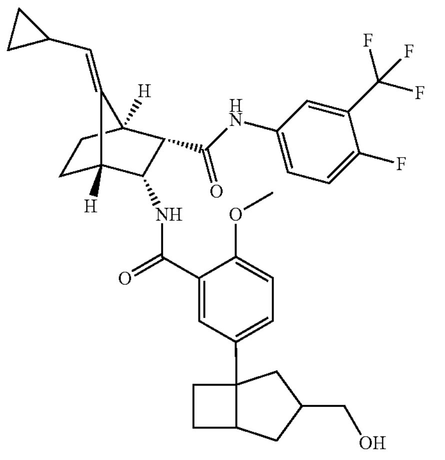 [SMILES: COc1ccc(C23CCC2CC(CO)C3)cc1C(=O)N[C@H]1[C@@H](C(=O)Nc2ccc(F)c(C(F)(F)F)c2)[C@H]2CC[C@@H]1/C2=C\C1CC1] | (1R,2S,3R,4R,7Z)-7-(cyclopropyl-methylidene)-N-[4-fluoro-3-(trifluoromethyl) phenyl]-3-{5-[3-(hydroxymethyl) bicyclo[3.2.0] heptan-1-yl]-2-methoxybenzamido} bicyclo[2.2.1]heptane-2-carboxamide |
| 355 | 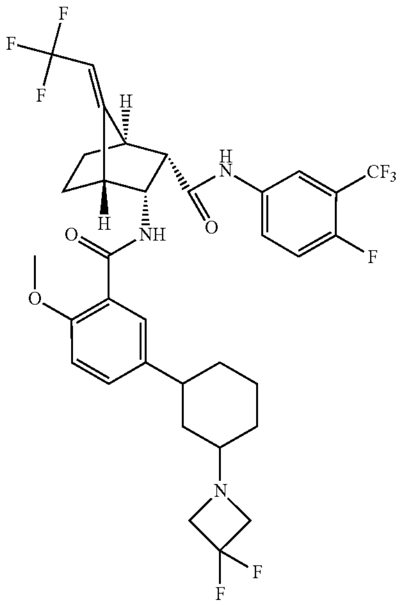 [SMILES: COc1ccc(C2CCCC(N3CC(F)(F)C3)C2)cc1C(=O)N[C@H]1[C@@H](C(=O)Nc2ccc(F)c(C(F)(F)F)c2)[C@H]2CC[C@@H]1/C2=C\C(F)(F)F] | (1R,2S,3R,4R,7Z)-3-[5-13-(3,3-difluoroazetidin-1-yl)cyclohexyl]-2-methoxybenzamido 3-N-[4-fluoro-3-(trifluoromethyl) phenyl]-7-(2,2,2-trifluoroethylidene) bicyclo[2.2.1] heptane-2-carboxamide |

TABLE 3-continued

| | | |
|---|---|---|
| 357 | 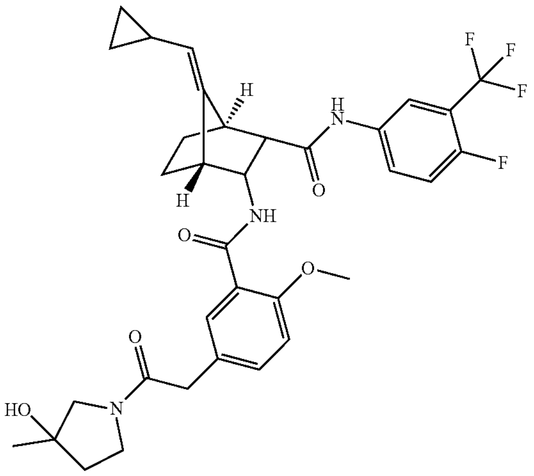 [SMILES: COc1ccc(CC(=O)N2CCC(C)(O)C2)cc1C(=O)NC1C(C(=O)Nc2ccc(F)c(C(F)(F)F)c2)[C@H]2CC[C@@H]1/C2=C\C1CC1] | (1R,4R,7Z)-7-(cyclopropyl-methylidene)-N-[4-fluoro-3-(trifluoromethyl)phenyl]-3-{5-[2-(3-hydroxy-3-methylpyrrolidin-1-yl)-2-oxoethyl]-2-methoxybenzamido}bicyclo[2.2.1]heptane-2-carboxamide |
| 358 | 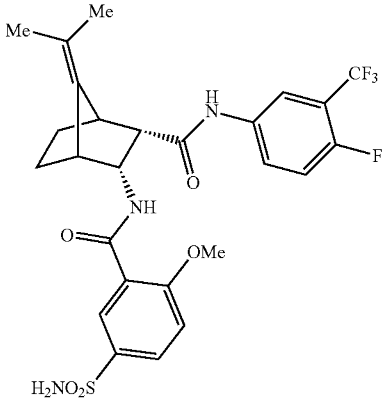 | (2S,3R)-N-[4-fluoro-3-(trifluoromethyl)phenyl]-3-(2-methoxy-5-sulfamoylbenzamido)-7-(propan-2-ylidene)bicyclo[2.2.1]heptane-2-carboxamide |
| 359 | 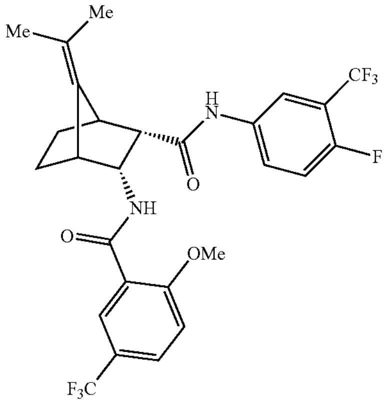 [SMILES: COc1ccc(C(F)(F)F)cc1C(=O)N[C@@H]1C2CCC(C2=C(C)C)[C@@H]1C(=O)Nc1ccc(F)c(C(F)(F)F)c1] | (2S,3R)-N-[4-fluoro-3-(trifluoromethyl)phenyl]-3-[2-methoxy-5-(trifluoromethyl)benzamidol-7-(propan-2-ylidene)bicyclo[2.2.1]heptane-2-carboxamide |

TABLE 3-continued

| | | |
|---|---|---|
| 360 | 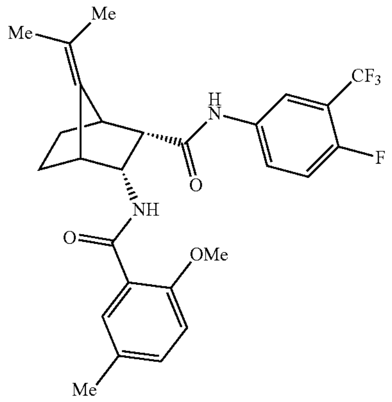 [SMILES: COc1ccc(C)cc1C(=O)N[C@@H]1C2CCC(C2=C(C)C)[C@@H]1C(=O)Nc1ccc(F)c(C(F)(F)F)c1] | (2S,3R)-N-[4-fluoro-3-(trifluoromethyl)phenyl]-3-(2-methoxy-5-methylbenzamido)-7-(propan-2-ylidene)bicyclo[2.2.1]heptane-2-carboxamide |
| 361 | 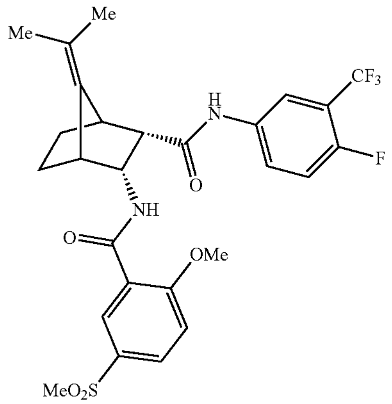 | (2S,3R)-N-[4-fluoro-3-(trifluoromethyl)phenyl]-3-(5-methanesulfonyl-2-methoxybenzamido)-7-(propan-2-ylidene)bicyclo[2.2.1]heptane-2-carboxamide |

| Ex # | $^1$H NMR | LC/MS Rt (min) Method | M + H/ M − H |
|---|---|---|---|
| 209 | (500 MHz, DMSO-d6) δ 10.67 (s, 1H), 10.05 (d, J = 7.0 Hz, 1H), 8.24 (s, 1H), 8.20 (d, J = 6.7 Hz, 1H), 7.85 (dd, J = 8.7, 2.4 Hz, 1H), 7.81 − 7.71 (m, 1H), 7.49 (t, J = 9.1 Hz, 1H), 7.44 (d, J = 8.6 Hz, 1H), 5.93 (q, J = 7.8 Hz, 1H), 4.50 (br s, 1H), 4.10 (s, 3H), 3.55 − 3.48 (m, 1H), 3.31 − 3.11 (m, 2H), 2.99 (br s, 1H), 2.84 (br s, 3H), 2.49 − 2.36 (m, 4H), 2.29 (brd, J = 7.0 Hz, 2H), 1.97 − 1.81 (m, 2H), 1.49 (br d, J = 5.3 Hz, 2H), 0.90 (t, J = 7.1 Hz, 3H) | 2.5 B | 707 |
| 210 | (500 MHz, DMSO-d6) δ 10.69 (s, 1H), 10.03 (br d, J = 7.0 Hz, 1H), 8.24 (d, J = 2.2 Hz, 1H), 8.20 (br d, J = 4.0 Hz, 1H), 7.87 (dd, J = 8.7, 2.1 Hz, 1H), 7.76 (br s, 1H), 7.51 − 7.45 (m, 1H), 7.43 (d, J = 8.6 Hz, 1H), 7.25 − 7.05 (br s, 1H), 5,92 (q, J = 7.9 Hz, 1H), 4.55 − 4.42 (m, 1H), 4.09 (s, 3H), 3.84 (br d, J = 13.2 Hz, 1H), 3.72 (brd, J = 10.8 Hz, 1H), 3.67 − 3.51 (m, 2H), 3.30 − 3.20 (m, 2H), 2.98 (br s, 1H), 2.81 (brt, J = 12.4 Hz, 1H), 2.24 − 2.04 (m, 4H), 2.00 − 1.88 (m, 2H), 1.88 − 1.76 (m, 1H), 1.49 (br d, J = 5.2 Hz, 3H) (Minor impurity seen on NMR) | 2.29 B | 732.9 8 |
| 211 | (500 MHz, DMSO-d6) δ 10.67 (s, 1H), 10.04 (d, J = 6.8 Hz, 1H), 8.22 (d, J = 2.4 Hz, 1H), 8.18 (br d, J = 4.6 Hz, 1H), 7.84 (dd, J = 8.7, 2.4 Hz, 1H), 7.80 − 7.72 (m, 1H), 7.46 (t, J-9.2 Hz, 1H), 7.43 (d, J = 8.9 Hz, 1H), 5.90 (q, J = 7.7 Hz, 1H), 4.48 (br t, J = 10.4 Hz, 1H), 4.09 (s, 3H), 3.85 (br s, 1H), 3.79 − 3.65 (m, 4H), 3.33 (t, J = 6.3 Hz, 2H), 3.29 − 3.15 (m, 2H), 2.97 (br s, 1H), 2.83 (br s, 3H), 2.39 − 2.24 (m, 3H), 1.97 − 1.80 (m, 2H), 1.54 − 1.42 (m, 4H) | 2.27 B | 737 |

TABLE 3-continued

| | | | |
|---|---|---|---|
| 212 | (500 MHz, DMSO-d6) δ 10.73 (s, 1H), 10.17 – 10.04 (m, 1H), 8.27 (d, J = 2.2 Hz, 1H), 8.20 (br s, 1H), 7.91 (dd, J = 8.7, 2.4 Hz, 1H), 7.78 (br d, J = 8.2 Hz, 1H), 7.58 – 7.45 (m, 2H), 5,99 – 5.88 (m, 1H), 4.48 (br s, 1H), 4.11 (s, 3H), 3.86 (br d, J = 12.8 Hz, 2H), 3.75 – 3.52 (m, 6H), 3.34 – 3.21 (m, 3H), 3.09 (br t, J = 12.3 Hz, 1H), 2.99 (br s, 1H), 2.49 – 2.34 (m, 1H), 1.96 – 1.76 (m, 2H), 1.50 (br d, J = 6.5 Hz, 2H) | 2.17 B | 709.2 |
| 213 | (500 MHz, DMSO-d6) δ 10.68 (s, 1H), 10.05 (br d, J = 6.7 Hz, 1H), 8.35 (d, J = 2.1 Hz, 1H), 8.22 (br d, J = 4.3 Hz, 1H), 8.08 – 7.89 (m, 1H), 7.79 (brd, J = 8.5 Hz, 1H), 7.50 (br t, J = 9.8 Hz, 1H), 7.40 (d, J = 8.9 Hz, 1H), 5.94 (q, J = 7.9 Hz, 1H), 4.50 (br s, 1H), 4.10 (s, 3H), 3.84 (br d, J = 11.6 Hz, 1H), 3.73 – 3.54 (m, 1H), 3.48 – 3.31 (m, 1H), 3.31 – 3.22 (m, 1H), 3.20 – 3.03 (m, 2H), 2.79 (s, 1H), 2.56 – 2.52 (m, 5H), 1.98 – 1.80 (m, 2H), 1.49 (br d, J = 5.2 Hz, 2H), 1.22 (br s, 1H) | 2.38 B | 710 |
| 214 | (500 MHz, DMSO-d6) δ 10.72 – 10.65 (m, 1H), 10.03 – 10.01 (m, 1H), 8.24 – 8.17 (m, 2H), 7.86 – 7.76 (m, 2H), 7.54 – 7.40 (m, 2H), 5.93 (q, J = 7.9 Hz, 1H), 4.54 – 4.44 (m, 1H), 4.31 (br s, 2H), 4.10 (s, 3H), 3.31 – 3.20 (m, 3H), 3.16 – 3.04 (m, 1H), 3.02 – 2.95 (m, 1H), 2.53 – 2.51 (m, 1H), 2.45 – 2.36 (m, 2H), 1.96 – 1.83 (m, 2H), 1.83 – 1.73 (m, 1H), 1.52 – 1.44 (m, 2H), 1.29 – 1.13 (m, 4H) | 2.6 B | 706.3 |
| 215 | (500 MHz, DMSO-d6) δ 10.15 – 10.01 (m, 1H), 8.45 – 8.29 (m, 1H), 8.22 (br s, 1H), 7.94 (brd, J = 8.7 Hz, 1H), 7.79 (br d, J = 3.6 Hz, 1H), 7.49 (br t, J = 10.0 Hz, 1H), 7.39 (d, J = 9.0 Hz, 1H), 5.94 (q, J = 7.7 Hz, 1H), 4.50 (br s, 1H), 4.10 (s, 3H), 4.00 (br s, 1H). 3.94 – 3.83 (m, 1H), 3.75 (br d, J = 14.3 Hz, 2H), 3.67 – 3.52 (m, 1H), 3.44 (s, 2H), 3.36 (br s, 1H), 3.31 – 3.14 (m, 1H), 3.12 – 2.95 (m, 2H), 2.65 (br d, J = 18.6 Hz, 2H), 2.54 (br s, 1H), 1.99 – 1.82 (m, 2H), 1.78 (br s, 1H), 1.55 (br s, 1H), 1.52 – 1.40 (m, 1H), 1.33 (s, 9H), 1.22 (br s, 1H) | 2.6 B | 823.2 |
| 216 | (500 MHz, DMSO-d6) δ 10.68 (s, 1H), 10.06 (br t, J = 6.9 Hz, 1H), 8.38 – 8.27 (m, 1H), 8.20 (br s, 1H), 7.92 (dd, J = 8.7, 2.2 Hz, 1H), 7.78 (br s, 1H), 7.49 (brt, J = 9.8 Hz, 1H), 7.39 (d, J = 9.0 Hz, 1H), 5.93 (q, J = 7.7 Hz, 1H), 4,49 (br s, 1H), 4.09 (s, 3H), 3.97 – 3.82 (m, 1H), 3.54 (br s, 2H), 3.43 – 3.31 (m, 1H), 3.30 – 3.21 (m, 1H), 3.08 – 2.92 (m, 2H), 2.74 – 2.59 (m, 2H), 2.54 (s, 2H), 2.49 – 2.35 (m, 1H), 2.32 – 2.13 (m, 1H), 1.95 – 1.77 (m, 4H), 1.64 (dt, J = 14.1, 7.0 Hz, 1H), 1.49 (br d, J = 5.7 Hz, 2H) | 2.1 B | 723.3 |
| 217 | (500 MHz, DMSO-d6) δ 10.67 (s, 1H), 10.05 (br d, J = 7.0 Hz, 1H), 8.32 (d, J = 2.4 Hz, 1H), 8.20 (br d, J = 4.3 Hz, 1H), 7.92 (dd, J = 8.7, 2.3 Hz, 1H), 7.78 (brd, J = 8.2 Hz, 1H), 7.48 (br t, J = 9.8 Hz, 1H), 7.39 (d, J = 8.9 Hz, 1H), 5.92 (q, J = 8.0 Hz, 1H), 4.89 (t, J = 5.5 Hz, 1H), 4.49 (br s, 1H), 4.09 (s, 3H), 3.63 – 3.44 (m, 2H), 3.37 – 3.19 (m, 2H), 3.11 (br t, J = 6.3 Hz, 4H), 2.52 – 2.54 (m, 2 H), 2.98 (br s, 1H), 2.02 – 1.81 (m, 3H), 1.49 (br d, J = 5.5 Hz, 2H) | 2.2 B | 698.2 |
| 218 | (500 MHz, DMSO-d6) δ 10.68 (s, 1H), 10.02 (br d, J = 6.8 Hz, 1H), 8.31 (d, J = 1.7 Hz, 1H), 8.21 – 8.15 (m, 1H), 7.93 (dd, J = 8.7, 2.4 Hz, 1H), 7.76 (br d, J = 8.0 Hz, 1H), 7.47 (t, J = 9.6 Hz, 1H), 7.38 (d, J = 9.0 Hz, 1H), 5,90 (q, J = 7.7 Hz, 1H), 4.55 – 4.44 (m, 1H), 4.07 (s, 3H), 3.87 (s, 1H), 3.76 – 3.64 (m, 4H), 3.33 (dd, J = 10.1, 5.6 Hz, 1H), 3.27 – 3.15 (m, 2H), 3.05 (br t. J = 11.5 Hz, 1H), 2.97 (br s, 1H), 2.78 (br d, J = 11.5 Hz, 1H), 2.00 (s, 3H), 1.96 – 1.80 (m, 2H), 1.69 – 1.52 (m, 2H), 1.48 (br d, J = 6.3 Hz, 2H) | 2.3 B | 723.3 |
| 219 | (500 MHz, DMSO-d6) δ 10.67 (s, 1H), 10.04 (br d, J = 6.4 Hz, 1H), 8.23 (s, 1H), 8.21 – 8.18 (m, 1H), 7.87 – 7.74 (m, 2H), 7.51 – 7.46 (m, 1H), 7.42 (d, J = 8.5 Hz, 1H), 5.92 (q, J = 7.7 Hz, 1H), 4.49 (br s, 1H), 4.09 (s, 3H), 3.50 (br s, 1H), 3.42 – 3.32 (m, 1H), 3.30 – 3.12 (m, 2H), 2.98 (br s, 2H), 2.22 – 2.04 (m, 2H), 2.00 – 1.80 (m, 3H), 1.67 (br d, J = 13.1 Hz, 2H), 1.49 (br d, J = 5.8 Hz, 2H), 1.28 (m, 4H), 1.11 (br d, J = 9.8 Hz, 2H) | 2.3 B | 722.3 |
| 220 | (500 MHz, DMSO-d6) δ 10.68 (s, 1H), 10.05 (br d, J = 7.0 Hz, 1H), 8.25 (s, 1H), 8.20 (br d, J = 4.0 Hz, 1H), 7.86 (br d, J = 8.2 Hz, 1H), 7.81 – 7.74 (m, 1H), 7.48 (t, J = 9.0 Hz, 1H), 7.43 (d, J = 8.4 Hz, 1H), 5.92 | 2.8 B | 734.9 |

TABLE 3-continued

| | | | |
|---|---|---|---|
| | (q, J = 7.8 Hz, 1H), 4.49 (br s, 1H), 4.35 – 4.28 (m, 1H), 4.09 (s, 3H), 3.94 – 3.85 (m, 1H), 3.76 (br d, J = 10.1 Hz, 1H), 3.63 – 3.46 (m, 2H), 3.29 – 3.20 (m, 2H), 3.06 (br t, J = 11.4 Hz, 1H), 2.98 (s, 2H), 2.22 – 2.10 (m, 2H), 1.95 – 1.83 (m, 2H), 1.49 (br d, J = 7.0 Hz, 2H) | | |
| 221 | (500 MHz, METHANOL-d4) δ 10.15 (s, 1H), 8.39 (d, J = 2.6 Hz, 1H), 8.17 – 8.13 (m, 1H), 7.87 (dd, J = 8.7, 2.4 Hz, 1H), 7.78 – 7.72 (m, 1H), 7.39 (d, J = 8.9 Hz, 1H), 7.28 (t, J = 9.6 Hz, 1H), 4.73 (d, J = 9.5 Hz, 1H), 4.58 – 4.52 (m, 1H), 4.36 – 4.30 (m, 2H), 4.18 (s, 3H), 3.37 – 3.32 (m, 2H), 3.30 – 3.21 (m, 1H), 3.15 (dd, J = 10.6, 4.2 Hz, 1H), 2.72 (t, J = 3.8 Hz, 1H), 2.56 (ddd, J = 11.3, 5.3, 2.2 Hz, 2H), 2.01 – 1.86 (m, 7H), 1.60 – 1.46 (m, 3H), 0.79 – 0.70 (m, 2H), 0.39 – 0.30 (m, 2H) | 1.4<br>A | 678.5 |
| 222 | (500 MHz, DMSO-d6) δ 10.55 (s, 1H), 10.05 (d, J = 7.0 Hz, 1H), 8.31 (d, J = 2.5 Hz, 1H), 8.21 (d, J = 6.8 Hz, 1H), 7.94 (dd, J = 8.8, 2.5 Hz, 1H), 7.83 – 7.75 (m, 1H), 7.52 – 7.43 (m, 2H), 4.70 (d, J = 9.6 Hz, 1H), 4.48 – 4.38 (m, 1H), 4.12 (s, 3H), 3.52 – 3.44 (m, 6H), 3.26 (br t, J = 4.5 Hz, 2H), 3,20 – 3.07 (m, 2H), 2.73 (br s, 1H), 1.86 – 1.74 (m, 2H), 1.55 – 1.35 (m, 3H), 0.82 – 0.67 (m, 2H), 0.38 – 0.28 (m, 2H) | 2.4<br>B | 699.9 |
| 223 | (500 MHz, DMSO-d6) δ 10.55 (s, 1H), 10.00 (d, J = 7.0 Hz, 1H), 8.25 (d, J = 2.1 Hz, 1H), 8.20 (br d, J = 4.2 Hz, 1H), 7.86 (br d, J = 8.5 Hz, 1H), 7.76 (br s, 1H), 7.49 – 7.40 (m, 2H), 4.69 (d, J = 9.5 Hz, 1H), 4.42 (br s, 1H), 4.10 (s, 3H), 3.85 (br d, J = 12.9 Hz, 1H), 3.73 (br s, 1H), 3.68 – 3.59 (m, 1H), 3.55 – 3.48 (m, 1H), 3.26 – 3.11 (m, 1H), 3.09 (br s, 1H), 2.81 (br t, J = 12.6 Hz, 1H), 2.72 (br s, 1H), 2.23 – 2.04 (m, 4H), 2.03 – 1.90 (m, 1H), 1.78 (br dd, J = 15.8, 9.6 Hz, 2H), 1.54 – 1.44 (m, 2H), 1.40 (br s, 2H), 0.88 – 0.68 (m, 2H), 0.34 (br s, 2H) | 2.35<br>B | 705.2 |
| 224 | (500 MHz, DMSO-d6) δ 10.55 (s, 1H), 10.01 (br d, J = 7.1 Hz, 1H), 8.35 (s, 1H), 8.24 – 8.15 (m, 1H), 8.03 – 7.88 (m, 1H), 7.76 (br s, 1H), 7.47 (brt, J = 9.9 Hz, 1H), 7.39 (d, J = 9.0 Hz, 1H), 4.69 (d, J = 9.5 Hz, 1H), 4.42 (br s, 1H), 4.10 (s, 3H), 3.84 (br d, J = 11.6 Hz, 1H), 3.73 – 3.60 (m, 2H), 3.55 – 3.49 (m, 4H), 3.41 – 3.26 (m, 1H), 3.19 – 3.07 (m, 4H), 2.72 (br s. 1H), 1.78 (br dd, J = 14.0, 9.7 Hz, 2H), 1.48 (br d, J = 4.7 Hz, 1H), 1.41 (br s, 2H), 0.81 – 0.65 (m, 2H), 0.34 (br s, 2H) | 2.37<br>B | 681.8 |
| 225 | (500 MHz, DMSO-d6) δ 10.67 (s, 1H), 10.04 (br d, J = 7.0 Hz, 1H), 8.24 (s, 1H), 8.20 (d, J = 6.7 Hz, 1H), 7.85 (dd, J = 8.7, 2.4 Hz, 1H), 7.81 – 7.75 (m, 1H), 7.52 – 7.46 (m, 1H), 7.43 (d, J = 8.6 Hz, 1H), 5.93 (q, J = 7.7 Hz, 1H), 4.98 – 4.91 (m, 1H), 4.50 (m, 1H), 4.10 (s, 3H), 4.00 (br s, 1H), 3.80 (br d, J = 11.4 Hz, 1H), 3.72 – 3.60 (m, 1H), 3.51 – 3.44 (m, 2H), 3.30 – 3.20 (m, 1H), 2.99 (br s, 1H), 2.95 (br s, 1H), 2.16 (brd, J = 7.6 Hz, 1H), 2.11 – 2.00 (m, 1H), 1.99 – 1,82 (m, 3H), 1.49 (br d, J = 6.1 Hz, 2H), 1.32 (s, 9H), 1.21 (br s, 1H) | 2.6<br>B | 807 |
| 226 | (500 MHz, DMSO-d6) δ 10.67 (s, 1H), 10.04 (brd, J = 7.0 Hz, 1H), 8.24 (s, 1H), 8.20 (d, J = 6.7 Hz, 1H), 7.85 (dd, J = 8.7, 2.4 Hz, 1H), 7.81 – 7.75 (m, 1H), 7.52 – 7.46 (m, 1H), 7.43 (d, J = 8.6 Hz, 1H), 5.93 (q, J = 7.7 Hz, 1H), 4.98 – 4.91 (m, 1H), 4.50 (m, 1H), 4.10 (s, 3H), 4.00 (br s, 1H), 3.80 (br d, J = 11.4 Hz, 1H), 3.72 – 3,60 (m, 1H), 3.51 – 3.44 (m, 2H), 3.30 – 3.20 (m, 1H), 2.99 (br s, 1H), 2.95 (br s, 1H), 2.16 (brd, J = 7.6 Hz, 1H), 2.11 – 2.00 (m, 1H), 1.99 – 1.82 (m, 3H), 1.49 (br d, J = 6.1 Hz, 2H), 1.32 (s, 9H), 1.21 (br s, 1H) | 2.6<br>B | 807 |
| 229 | (400 MHz, DMSO-d6) δ = 10.53 (s, 1H), 9.88 (d, J = 7.0 Hz, 1H), 8.51 – 8.39 (m, 2H), 8.23 (dd, J = 2.5, 6.5 Hz, 1H), 7.98 (dd, J = 2.5, 9.0 Hz, 1H), 7.85 – 7.74 (m, 1H), 7.49 (t, J = 9.8 Hz, 1H), 7.25 (d, J = 8.5 Hz, 1H), 4.70 (d, J = 9.5 Hz, 1H), 4.51 – 4,41 (m, 2H), 4,05 (s, 3H), 3.46 (q, J = 6.0 Hz, 2H), 3.17 (br dd, J = 4.3, 10.8 Hz, 1H), 3,13 – 3.09 (m, 1H), 2.73 (br s, 1H), 1.88 – 1.77 (m, 2H), 1.67 (quin, J = 6.7 Hz, 2H), 1.51 (br d, J = 5.0 Hz, 1H), 1.45 – 1.33 (m, 2H), 1.24 (s, 1H), 0.80 – 0.67 (m, 2H), 0.36 (dd, J = 2.3, 4.8 Hz, 2H) | 2.14<br>B | 604.3 |

TABLE 3-continued

| | | | |
|---|---|---|---|
| 230 | (400 MHz, DMSO-d6) δ ppm 10.52 (s, 1H), 9.92 (d, J = 7.1 Hz, 1H), 8.22 (dd, J = 2.7, 6.6 Hz, 1H), 7.96 (d, J = 2.4 Hz, 1H), 7.83 – 7.71 (m, 1H), 7.54 (dd, J = 2.3, 8.4 Hz, 1H), 7.48 (t, J = 9.8 Hz, 1H), 7.23 (d, J = 8.8 Hz, 1H), 4.78 (d, J = 4.2 Hz, 1H), 4.68 (d, J = 9.5 Hz. 1H), 4.44 (dt, J = 3.9, 7.2 Hz, 1H), 4.04 (s, 3H), 3.72 (br dd, J = 3.9, 8.1 Hz, 1H), 3.15 (br dd, J = 4.6, 10.8 Hz, 3H), 3.09 (br s, 1H), 2.71 (t, J = 3.8 Hz, 1H), 1.90 – 1.65 (m, 4H), 1.56 – 1.46 (m, 1H), 1.46 – 1.25 (m, 4H), 0.81 – 0.68 (m, 2H), 0.34 (dd, J = 2.0, 4.6 Hz, 2H). | 2.142 B | 630.3 |
| 231 | (400 MHz, DMSO-d6) δ ppm 10.52 (s, 1H), 9.93 (d, J = 7.3 Hz, 1H), 8.23 (dd, J = 2.8, 6.5 Hz, 1H), 7.99 (d, J = 2.4 Hz, 1H), 7.82 – 7.72 (m, 1H), 7.58 (dd, J = 2.3, 8.4 Hz, 1H), 7.48 (t, J = 9.8 Hz, 1H), 7.24 (d, J = 8.6 Hz, 1H), 4.83 – 4.72 (m, 1H), 4.68 (d, J = 9.8 Hz, 1H), 4.49 – 4.34 (m, 1H), 4.05 (s, 3H), 3.92 – 3.75 (m, 1H), 3.53 – 3.36 (m, 4H), 3.15 (dd, J = 4.4, 10.5 Hz, 1H), 3.09 (t, J = 3.9 Hz, 1H), 2.72 (t, J = 3,4 Hz, 1H), 1.88 – 1,74 (m, 2H), 1.56 – 1.46 (m, 1H), 1.46 – 1.31 (m, 2H), 0.80 – 0.63 (m, 2H), 0.35 (dd, J = 2.0, 4.6 Hz, 2H) 1.56 – 1.46 (m, 1H), 1.46 – 1.31 (m, 2H), 0.80 – 0.63 (m, 2H), 0.35 (dd, J = 2.0, 4.6 Hz, 2H). | 2.12 B | 646.3 |
| 232 | (400 MHz, DMSO-d6) δ ppm 10.63 – 10.46 (m, 1H), 9.97 – 9.82 (m, 1H), 8.75 – 8.63 (m, 1H), 8.53 – 8.45 (m, 1H), 8.30 – 8.18 (m, 1H), 8.04 – 7.92 (m, 1H), 7.88 – 7.73 (m, 1H), 7.57 – 7.44 (m, 1H), 7.36 – 7.19 (m, 1H), 4.79 – 4.62 (m, 1H), 4.54 – 4.33 (m, 1H), 4.15 – 3.96 (m, 3H), 3.89 – 3.74 (m, 2H), 3.21 – 3.13 (m, 1H), 3.14 – 3.08 (m, 1H), 2.77 – 2.70 (m, 1H), 1.91 – 1.73 (m, 2H), 1.57 – 1.36 (m, 3H), 1.27 – 1.20 (m, 2H), 1.17 – 1.08 (m, 2H), 0.83 – 0.68 (m, 2H), 0.42 – 0.31 (m, 2H). | 0.996 D | 678.2 |
| 233 | (400 MHz, METHANOL-d4) δ ppm 8.17 – 8.12 (m, 1H), 8.10 – 8.06 (m, 1H), 7.76 – 7.70 (m, 1H), 7.60 – 7.55 (m, 1H), 7.31 – 7.22 (m, 2H), 4.75 – 4.67 (m, 1H), 4.58 – 4.50 (m, 2H), 4.16 – 4.09 (m, 3H), 3.50 – 3.45 (m, 1H), 3.24 – 3.09 (m, 2H), 2.73 – 2.67 (m, 1H), 2.03 – 1.80 (m, 4H), 1.69 – 1.47 (m, 4H), 0.77 – 0.69 (m, 2H), 0.39 – 0.30 (m, 2H). | 3.327 D | 644.2 |
| 234 | (400 MHz, METHANOL-d4) δ ppm 8.17 – 8.12 (m, 1H), 8.10 – 8.06 (m, 1H), 7.76 – 7.70 (m, 1H), 7.60 – 7.55 (m, 1H), 7.31 – 7.22 (m, 2H), 4.75 – 4.67 (m, 1H), 4.58 – 4.50 (m, 2H), 4.16 – 4.09 (m, 3H), 3.50 – 3.45 (m, 1H), 3,24 – 3.09 (m, 2H), 2.73 – 2.67 (m, 1H), 2.03 – 1.80 (m, 4H), 1.69 – 1.47 (m, 4H), 0.77 – 0.69 (m, 2H), 0.39 – 0.30 (m, 2H). | 3.336 D | 644.2 |
| 235 | (400 MHz, METHANOL-d4) δ ppm 8.17 – 8.12 (m, 1H), 8.10 – 8.06 (m, 1H), 7.76 – 7.70 (m, 1H), 7.60 – 7.55 (m, 1H), 7.31 – 7.22 (m, 2H), 4.75 – 4.67 (m, 1H), 4.58 – 4.50 (m, 2H), 4.16 – 4.09 (m, 3H), 3.50 – 3.45 (m, 1H), 3.24 – 3.09 (m, 2H), 2.73 – 2.67 (m, 1H), 2.03 – 1,80 (m, 4H), 1.69 – 1.47 (m, 4H), 0.77 – 0.69 (m, 2H), 0.39 – 0.30 (m, 2H). | 3.336 D | 644.2 |
| 236 | (400 MHz, DMSO-d6) δ ppm 10.57 – 10.49 (m, 1H), 9.85 (d, J = 7.1 Hz, 1H), 8.39 – 8.34 (m. 1H), 8.27 – 8.19 (m, 1H), 7.98 – 7.88 (m, 1H), 7.83 – 7.74 (m, 2H), 7.53 – 7.42 (m, 1H), 7.23 – 7.17 (m, 1H), 4.76 – 4.62 (m, 1H), 4,55 – 4.34 (m, 1H), 4.11 – 3.95 (m, 3H), 3.23 – 3.02 (m, 3H), 2.79 – 2.61 (m, 1H), 2.50 (td, J = 1.7, 3.6 Hz, 17H), 1.91 – 1.68 (m, 2H), 1.59 – 1.39 (m, 3H), 1.36 (s, 12H), 0.89 – 0.61 (m, 2H), 0.46 – 0.25 (m, 2H) | 2.497 B | 602.3 |
| 237 | (400 MHz, DMSO-d6) δ = 10.52 (s, 1H), 9.90 (d, J = 7.1 Hz, 1H), 8.34 – 8.08 (m, 2H), 7.78 (dd, J = 2.2, 8.6 Hz, 2H), 7.48 (t, J = 9.7 Hz, 1H), 7.23 (d, J = 8.6 Hz, 1H), 4.68 (d, J = 9.5 Hz, 1H), 4.43 (br s, 1H), 4.05 (s, 3H), 3.97 (br s, 2H), 3.72 (br s, 2H), 3.56 (s, 1H), 3.15 (dd, J = 4.3, 11.1 Hz, 1H), 3.10 (t, J = 3.8 Hz, 1H), 2.72 (t, J = 3.8 Hz, 1H), 1.87 – 1.69 (m, 2H), 1.51 (br dd, J = 4,0, 8.2 Hz, 1H), 1.46 – 1.32 (m, 2H), 1.23 (s, 6H), 0.80 – 0.65 (m, 2H), 0.35 (dd, J = 2.0, 4.6 Hz, 2H) | 2.49 B | 614.4 |
| 238 | (400 MHz, DMSO-d6) δ ppm 10.5 – 10.49 (m, 1H), 9.85 (d, J = 7.1 Hz, 1H), 8.47 – 8.39 (m, 1H), 8.37 – 8.35 (m, 1H), 8.25 – 8.22 (m, 1H), 8.00 – 7.98 (m, 1H) 7.81 – 7.77 (m, 1H), 7.53 – 7.42 (m, 1H), 7.23 – 7.17 (m, 1H), 4.71 – 4.68 (m, 1H), 4.50 – 4.41 (m, 1H), 4.04 (s, 3H), 3.13 – 3.02 (m, 3H), 2.72 – 2.68 | 3.389 B | 616.3 |

TABLE 3-continued

| | | | |
|---|---|---|---|
| | (m, 1H), 1.86 − 1.70 (m, 2H), 1.59 − 1.39 (m, 3H), 0.901.36 (s, 9H), 0.79 − 0.64 (m, 2H), 0.38 − 0.31 (m, 2H) | | |
| 239 | (400 MHz, DMSO-d6) δ = 10.53 (s, 1H), 9.87 (d, J = 7.1 Hz, 1H), 8.37 (d, J = 2.4 Hz, 1H), 8.23 (dd, J = 2.4, 6.6 Hz, 1H), 7.93 (dd, J = 2.4, 8.8 Hz, 1H), 7.78 (td, J = 3.7, 8.8 Hz, 1H), 7.56 (s, 1H), 7.48 (t, J = 9.8 Hz, 1H), 7.21 (d, J = 8.8 Hz, 1H), 4.94 (t, J = 6.0 Hz, 1H), 4.69 (d, J = 9.8 Hz, 1H), 4.44 (dt, J = 3.7, 7.1 Hz, 1H), 4.03 (s, 3H), 3.56 (s, 1H), 3.49 (d, J = 5.9 Hz, 2H), 3.16 (dd, J = 4.3, 10.9 Hz, 1H), 3.10 (t, J = 3.8 Hz, 1H), 2.72 (t, J = 3.7 Hz, 1H), 1.88 −1.66 (m, 2H), 1.57 − 1.43 (m, 1H), 1.43 − 1.34 (m, 2H), 1.30 (s, 6H), 0.82 − 0.65 (m, 2H), 0.35 (dd, J = 2.3, 4.8 Hz, 2H) | 2.2 B | 618.3 |
| 240 | (400 MHz, DMSO-d6) δ = 10.53 (s, 1H), 9.89 (d, J = 7.1 Hz, 1H), 8.47 (d, J = 2.4 Hz, 1H), 8.27 (t, J = 6.2 Hz, 1H), 8.22 (dd, J = 2.6, 6.5 Hz, 1H), 8.01 (dd, J = 2.4, 8.6 Hz, 1H), 7.78 (td, J = 3.6, 8.9 Hz, 1H), 7.48 (t, J = 9.7 Hz, 1H), 7.25 (d, J = 8.8 Hz, 1H), 4.69 (d, J = 9.8 Hz, 1H), 4.58 (s, 1H), 4.51 − 4.40 (m, 1H), 4.04 (s, 3H), 3.56 (s, 1H), 3.24 (d, J = 6.1 Hz, 2H), 3.16 (dd, J = 3.9, 11.0 Hz, 1H), 3.10 (t, J = 3.7 Hz, 1H), 2.72 (br s, 1H), 1.85 − 1.71 (m, 2H), 1.55 − 1.44 (m, 1H), 1.44 − 1.32 (m, 2H), 1.09 (s, 6H), 0.74 (br t, J = 9.3 Hz, 2H), 0.35 (dd, J = 2.1, 4.8 Hz, 2H) | 2.2 B | 618.4 |
| 241 | (400 MHz, DMSO-d6) δ = 10.51 (s, 1H), 9,90 (d, J = 7.3 Hz, 1H), 8.22 (dd, J = 2.8, 6.5 Hz, 1H), 7.97 (d, J = 2.2 Hz, 1H), 7.83 − 7.73 (m, 1H), 7.56(dd, J = 2.4, 8.6 Hz, 1H), 7.48 (t, J = 9.7 Hz, 1H), 7.21 (d, J = 8.6 Hz, 1H), 4.69 (d, J = 9.5 Hz, 1H), 4.50 − 4.35 (m, 1H), 4.03 (s, 3H), 3.15 (dd, J = 4.6, 11.0 Hz, 1H), 3.09 (t, J = 3.2 Hz, 1H), 2.80 (s, 3H), 2.72 (br s, 1H), 1.87 − 1.72 (m, 2H), 1.55 − 1.33 (m, 14H), 0.80 − 0.66 (m, 2H), 0.35 (dd, J = 2.1, 4.5 Hz, 2H) | 2.6 B | 616.4 |
| 242 | (400 MHz, DMSO-d6) δ = 10.53 (s, 1H), 9.92 (d, J = 7.3 Hz, 1H), 8.23 (dd, J = 2.6, 6.5 Hz, 1H), 8.08 (d, J = 2.4 Hz, 1H), 7.82 − 7.72 (m, 1H), 7.66 (dd, J = 2.2, 8.6 Hz, 1H), 7.49 (t, J = 9.9 Hz, 1H), 7.26 (d, J = 8.6 Hz, 1H), 4.69 (d, J = 9.5 Hz, 1H), 4.49 − 4.39 (m, 1H), 4.05 (s, 3H), 3.97 − 3.66 (m, 4H), 3.24 (br s, 4H), 3.15 (dd, J = 3.7, 11.2 Hz, 1H), 3.12 − 3.05 (m, 1H), 2.75 − 2.69 (m, 1H), 1.87 − 1.72 (m, 2H), 1.56 − 1.45 (m, 1H), 1.45 − 1.31 (m, 2H), 0.83 − 0.64 (m,2H), 0.41 − 0.26 (m, 2H) | 2.21 B | 664.3 |
| 243 | (400 MHz, DMSO-d6) δ = 10.53 (s, 1H), 9.89 (d, J = 7.1 Hz, 1H), 8.47 (d, J = 2.4 Hz, 1H), 8.27 (t, J = 6.2 Hz, 1H), 8.22 (dd, J = 2.6, 6.5 Hz, 1H), 8.01 (dd, J = 2.4, 8.6 Hz, 1H), 7.78 (td, J = 3.6, 8.9 Hz, 1H), 7.48 (t, J = 9,7 Hz, 1H), 7.25 (d, J = 8.8 Hz, 1H), 4.69 (d, J = 9.8 Hz, 1H), 4.58 (s, 1H), 4.51 − 4.40 (m, 1H), 4.04 (s, 3H), 3.56 (s, 1H), 3.24 (d, J = 6.1 Hz, 2H), 3.16 (dd, J = 3.9, 11.0 Hz, 1H), 3.10 (t, J = 3.7 Hz, 1H), 2.72 (br s, 1H), 1.85 − 1.71 (m, 2H), 1.55 − 1.44 (m, 1H), 1.44 − 1.32 (m, 2H), 1.09 (s, 6H), 0.74 (br t, J = 9.3 Hz, 2H), 0.35 (dd, J = 2.1, 4.8 Hz, 2H) | 3.292 D | 676.3 |
| 244 | (400 MHz, DMSO-d6) δ = 10.51 (s, 1H), 9.90 (d, J = 7.3 Hz, 1H), 8.22 (dd, J = 2.8, 6.5 Hz, 1H), 7.97 (d, J = 2.2 Hz, 1H), 7.83 − 7.73 (m, 1H), 7.56(dd, J = 2.4, 8.6 Hz, 1H), 7.48 (t, J = 9.7 Hz, 1H), 7.21 (d, J = 8.6 Hz, 1H), 4,69 (d, J = 9.5 Hz, 1H), 4.50 − 4.35 (m, 1H), 4.03 (s, 3H), 3.15 (dd, J = 4.6, 11.0 Hz, 1H), 3.09 (t, J = 3.2 Hz, 1H), 2.80 (s, 3H), 2.72 (br s, 1H), 1.87 − 1.72 (m, 2H), 1.55 − 1.33 (m, 14H), 0.80 − 0.66 (m, 2H), 0.35 (dd, J = 2.1, 4.5 Hz, 2H) | 2.10 B | 616.3 |
| 245 | (400 MHz, DMSO-d6) δ = 10.53 (s, 1H), 9.92 (d, J = 7.3 Hz, 1H), 8.23 (dd, J = 2.6, 6.5 Hz, 1H), 8.08 (d, J = 2.4 Hz, 1H), 7.82 − 7.72 (m, 1H), 7.66 (dd, J = 2.2, 8.6 Hz, 1H), 7.49 (t, J = 9.9 Hz, 1H), 7.26 (d, J = 8.6 Hz, 1H), 4.69 (d, J = 9.5 Hz, 1H), 4.49 − 4.39 (m, 1H), 4.05 (s, 3H), 3.97 − 3.66 (m, 4H), 3.24 (br s, 4H), 3.15 (dd, J = 3.7, 11.2 Hz, 1H), 3.12 − 3.05 (m, 1H), 2.75 − 2.69 (m, 1H), 1.87 − 1.72 (m, 2H), 1.56 − 1.45 (m, 1H), 1.45 − 1.31 (m, 2H), 0.83 − 0.64 (m,2H), 0.41 − 0.26 (m, 2H) | 2.14 B | 630.3 |

TABLE 3-continued

| | | | |
|---|---|---|---|
| 246 | (400 MHz, DMSO-d6) δ ppm 10.53 (s, 1H), 9.93 (d, J = 7.0 Hz, 1H), 8.27 − 8.22 (m, 2H), 7.80 (dd, J = 2.3, 8.8 Hz, 2H), 7.49 (t, J = 9.5 Hz, 1H), 7.27 (d, J = 9.0 Hz, 1H), 4,70 (d, J = 9.5 Hz, 1H), 4.59 (br s, 2H), 4,53 − 4.41 (m, 6H), 4.28 (br s, 2H), 4.06 (s, 3H), 3.43 (s. 2H), 3.40 − 3.36 (m, 2H), 3.30 − 3.26 (m, 1H), 3.19 − 3.08 (m, 2H), 2.75 − 2.69 (m, 1H), 2.61 − 2.53 (m, 3H), 1.88 − 1.70 (m, 2H), 1.42 (br s, 3H), 0.75 (br t, J = 9.0 Hz, 2H), 0.39 − 0.33 (m, 2H). | 2.28<br>B | 628.4 |
| 247 | (400 MHz, DMSO-d6) δ = 10.52 (s, 1H), 9.97 − 9.84 (m, 1H), 8.22 (dd, J = 1.6, 6.7 Hz, 1H), 8.15 − 8.06 (m, 1H), 7.78 (td, J = 4.0, 8.1 Hz, 1H), 7.72 − 7.61 (m, 1H), 7.48 (t, J = 9.7 Hz, 1H), 7.23 (d, J = 8.6 Hz, 1H), 5.08 − 4.81 (m, 1H), 4.68 (d, J = 9.8 Hz, 1H), 4.48 − 4.40 (m, 1H), 4.33 − 4.17 (m, 1H), 4.05 (s, 3H), 3.62 − 3.47 (m, 3H), 3.24 − 3.19 (m, 1H), 3.19 − 3.12 (m, 1H), 3.09 (br s, 1H), 2.78 − 2.69 (m, 1H), 1.99 − 1.66 (m, 4H), 1.57 − 1.31 (m, 3H), 0.81 − 0.62 (m, 2H), 0.35 (dd, J = 2.0, 4.4 Hz, 2H) | 2.20<br>B | 714.3<br>(m + H) |
| 248 | (400 MHz, DMSO-d6) δ = 10.52 (s, 1H), 9.98 − 9.83 (m, 1H), 8.22 (dd, J = 2.1, 6.5 Hz, 1H), 8.12 (d, J = 2.2 Hz, 1H), 7.78 (td, J = 3.3, 8.6 Hz, 1H), 7.69 (dd, J = 2.4, 8.6 Hz, 1H), 7.48 (t, J = 9.9 Hz, 1H), 7.27 − 7.15 (m, 1H), 4.68 (d, J = 9.5 Hz, 1H), 4.48 − 4.41 (m, 1H), 4.04 (s, 3H), 3.57 − 3.40 (m, 5H), 3.28 − 3.18 (m, 2H), 3.18 − 3.12 (m, 1H), 3.10 (br s, 1H), 2.74 − 2.69 (m, 1H), 2.34 − 2.20 (m, 1H), 1.95 − 1.73 (m, 3H), 1.67 − 1.56 (m, 1H), 1.54 − 1.37 (m, 3H), 0.81 −0.64 (m, 2H), 0.41 − 0.25 (m, 2H) | 3.23<br>D | 628.2 |
| 249 | (400 MHz, DMSO-d6) δ = 10.52 (s, 1H), 9.92 (d, J = 7.3 Hz, 1H), 8.23 (dd, J = 2.7, 6.6 Hz, 1H), 7.95 (d, J = 2.2 Hz, 1H), 7.83 − 7.72 (m, 1H), 7.59 −7.43 (m, 2H), 7.24 (d, J = 8.8 Hz, 1H), 4.68 (d, J = 9.5 Hz, 1H), 4.49 − 4.39 (m, 1H), 4.32 (s, 4H), 4.04 (s, 3H), 3.19 − 3.12 (m, 2H), 3.09 (t, J = 3.4 Hz, 1H), 2.72(t, J = 3.2 Hz, 1H), 1.89 − 1.70 (m, 6H), 1.54 − 1.33 (m, 3H), 0.82 − 0.62 (m, 2H), 0.35 (dd, J = 1.7, 4.4 Hz, 2H) | 1.97<br>D | 641.4 |
| 250 | (400 MHz, DMSO-d6) δ = 10.52 (s, 1H), 9.92 (br d, J = 6.8 Hz, 1H), 8.22 (dd, J = 2.4, 6.6 Hz, 1H), 8.01 (d, J = 2.0 Hz, 1H), 7.82 − 7.72 (m, 1H), 7.58 (dd, J = 2.3, 8.4 Hz, 1H), 7.48 (t, J = 9.8 Hz, 1H), 7.24 (d, J = 8.8 Hz, 1H), 4.68 (d, J = 9.5 Hz, 1H), 4.49 − 4.37 (m, 1H), 4.04 (s, 3H), 3.88 − 3.72 (m, 2H), 3.48 (br t, J = 7.0 Hz, 2H), 3.15 (dd, J = 4.2, 10.5 Hz, 1H), 3.11 − 3.07 (m, 1H), 3.07 − 2.98 (m, 2H), 2.96 (s, 3H), 2.74 − 2.69 (m, 1H), 1.88 − 1.74 (m, 2H), 1.56 − 1.30 (m, 3H), 0.82 − 0.62 (m, 2H), 0.41 − 0.26 (m, 2H) | 0.91<br>B | 666.4 |
| 251 | (400 MHz, DMSO-d6) δ ppm 10.64 − 10.47 (m, 1H), 10.62 − 10.47 (m, 1H), 9.96 − 9.86 (m, 1H), 8.31 − 8.16 (m, 2H), 7.90 − 7.67 (m, 2H), 7.58 − 7.42 (m, 1H), 7.31 − 7.14 (m, 1H), 5.84 − 5.62 (m, 1H), 4.77 − 4.64 (m, 1H), 4.56 − 4.36 (m, 3H), 4.34 − 4.16 (m, 1H), 3.88 − 3.70 (m, 1H), 3.21 − 3.06 (m, 2H), 2.80 − 2.67 (m, 2H), 2.80 − 2.62 (m, 2H), 1.92 − 1.72 (m, 2H), 1.64 − 1.33 (m, 4H), 1.59 − 1.30 (m, 3H), 0.84 − 0.65 (m, 2H), 0.45 − 0.27 (m, 2H). | 3.03<br>D | 602.3 |
| 252 | (400 MHz, METHANOL-$d_4$) δ ppm 8.28 − 8.23 (m, 1H), 8.18 − 8.11 (m, 1H), 7.79 − 7.70 (m, 2H), 7.34 − 7.23 (m, 2H), 4.61 − 4.49 (m, 1H), 4.63 − 4.48 (m, 2H), 4.20 − 4.07 (m, 4H), 4.07 − 3.85 (m, 3H), 3.85 − 3.63 (m, 2H), 3.29 − 3.10 (m, 3H), 3.09 − 2.86 (m, 3H), 2.76 − 2.65 (m, 1H), 2.54 − 2.30 (m, 2H), 2.12 1.81 (m, 2H), 1.65 − 1.39 (m, 3H), 0.83 − 0.69 (m, 2H), 0.45 − 0.26 (m, 2H). | 3.25<br>D | 678.3 |
| 253 | (400 MHz, DMSO-d6) δ ppm 10.62 − 10.47 (m, 1H), 9.98 − 9.82 (m, 1H), 8.84 − 8.68 (m, 1H), 8.53 − 8.40 (m, 1H), 8.31 − 8.16 (m, 1H), 8.05 − 7.88 (m, 1H), 7.86 − 7.74 (m, 1H), 7.59 − 7.41 (m, 1H), 7.32 − 7.17 (m, 1H), 4.80 − 4.59 (m, 1H), 4.52 − 4.34 (m, 1H), 4.09 − 3.98 (m, 3H), 3.71 − 3.61 (m, 2H), 3.40 − 3.15 (m, 4H), 3.28 − 3.13 (m, 1H), 3.07 − 2.96 (m, 3H), 1.91 − 1.67 (m, 3H), 1.59 − 1.33 (m, 4H), 0.82 − 0.68 (m, 2H), 0.41 − 0.31 (m, 2H) | 3.24<br>D | 652.3 |
| 254 | (400 MHz, DMSO-d6) δ = 10.50 (s, 1H), 9.90 (br d, J = 6.6 Hz, 1H), 8.22 (dd, J = 2.4, 6.4 Hz, 1H), 8.17 − 8.04 (m, 1H), 7.82 − 7.74 (m, 1H), 7.69 | 0.97<br>B | 616.4 |

TABLE 3-continued

| | | | |
|---|---|---|---|
| | (ddd, J = 1.1, 3.2, 6.7 Hz, 1H), 7.48 (t, J = 9.5 Hz, 1H), 7.23 (d, J = 8.8 Hz, 1H), 5.03 − 4.88 (m, 1H), 4.69 (d, J = 9.5 Hz, 1H), 4.49 − 4.38 (m, 1H), 4.35 − 4.15 (m, 1H), 4.05 (s, 3H), 3.65 − 3.37 (m, 3H), 3.24 − 3.12 (m, 2H), 3.10 (t, J = 3.4 Hz, 1H), 2.75 − 2.69 (m, 1H), 1.99 − 1.71 (m, 4H), 1.55 − 1.34 (m, 3H), 0.82 − 0.63 (m, 2H), 0.35 (dd, J = 1.8, 4.8 Hz, 2H) | | |
| 255 | (400 MHz, DMSO-d6) δ = 10.50 (s, 1H), 9.90 (d, J = 6.8 Hz, 1H), 8.22 (dd, J = 2.7, 6.4 Hz, 1H), 7.97 (d, J = 2.4 Hz, 1H), 7.83 − 7.72 (m, 1H), 7.55 (dd, J = 2.3, 8.4 Hz, 1H), 7.48 (t, J = 9.8 Hz, 1H), 7.24 (d, J = 8.8 Hz, 1H), 6.30 − 5.95 (m, 1H), 4.69 (d, J = 9.8 Hz, 1H), 4.49 − 4.37 (m, 1H), 4.04 (s, 3H), 3.63 − 3.37 (m, 4H), 3.20 − 3.12 (m, 2H), 3.09 (t, J = 3.4 Hz, 1H), 2.85 − 2.68 (m, 3H), 2.61 − 2.52 (m, 4H), 1.91 − 1.70 (m, 2H), 1.56 − 1.33 (m, 3H), 0.81 − 0.66 (m, 2H), 0.35 (dd, J = 2.2, 4.4 Hz. 2H) | 2.40<br>B | 679.4 |
| 256 | (400 MHz, METHANOL-d4) δ ppm 8.27 (d, J = 2.5 Hz, 1H), 8.18 (dd, J = 2.5, 6.5 Hz, 1H), 7.75 (br d, J = 9.0 Hz, 2H), 7.33 − 7.27 (m, 2H), 4.98 (s, 1H), 4.93 (s, 1H), 4.85 − 4.80 (m, 1H), 4.74 (d, J = 9.5 Hz, 1H), 4.57 (br dd, J = 4.3, 11.3 Hz, 2H), 4.16 (s, 4H), 4.01 (s, 1H), 3.96 (br s, 2H), 3.70 (br d, J = 4.0 Hz, 2H), 3.61 (s, 1H), 3.55 − 3.43 (m, 1H), 3.43 − 3.35 (m, 1H), 3.26 − 3.14 (m, 2H), 3.09 − 3.00 (m, 2H), 2.97 (br s, 1H), 2.80 − 2.67 (m, 1H), 2.45 (br s, 2H), 2.04 − 1.87 (m, 3H), 1.63 − 1.47 (m, 3H), 1.31 (s, 1H), 0.96 − 0.72 (m, 3H), 0.41 − 0.33 (m, 2H). | 2.28<br>D | 676.2 |
| 257 | (400 MHz, METHANOL-d4) δ ppm 8.27 (d, J = 2.5 Hz, 1H), 8.18 (dd, J = 2.8, 6.3 Hz, 1H), 7.76 (br d, J = 7.0 Hz, 2H), 7.34 − 7.27 (m, 2H), 5.01 − 4.91 (m, 3H), 4.85 − 4.80 (m, 1H), 4.74 (d, J = 9.0 Hz, 2H), 4.56 (br d, J = 3.0 Hz, 1H), 4.16 (s, 4H), 3.99 (br d, J = 18.1 Hz, 3H), 3.83 − 3.66 (m, 2H), 3.61 (s, 2H), 3.54 − 3.43 (m, 1H), 3.42 − 3.35 (m, 1H), 3.31 − 3.15 (m, 3H), 3.05 (br d, J = 14.1 Hz, 2H), 2.97 (br s, 2H), 2.73 (br s, 1H), 2.68 (s, 1H), 2.00 (br d, J = 9.0 Hz, 2H), 1.91 (s, 4H), 1.75 − 1.48 (m, 4H), 1.42 (s, 1H), 1.31 (s, 4H), 0.92 (s, 1H), 0.85 − 0.72 (m, 2H), 0.37 (dd, J = 2.5, 4.5 Hz, 2H). | 2.28<br>D | 676.2 |
| 258 | (400 MHz, DMSO-d6) δ = 10.50 (s, 1H), 9.90 (d, J = 6.8 Hz, 1H), 8.22 (s, 1H), 8.09 (d, J = 2.2 Hz, 1H), 7.83 − 7.73 (m, 1H), 7.66 (dd, J = 2.2, 8.6 Hz, 1H), 7.49 (d, J = 9.8 Hz, 1H), 7.25 (d, J = 8.6 Hz, 1H), 4.69 (d, J = 9.5 Hz, 1H), 4.44 (br d, J = 0.7 Hz, 1H), 4.05 (s, 3H), 3.71 − 3.49 (m, 4H), 3.19 − 3.12 (m, 2H), 3.09 (t, J = 3.3 Hz, 1H), 2.72 (t, J = 3.9 Hz, 1H), 1.95 − 1.68 (m, 6H), 1.57 − 1.31 (m, 3H), 0.81 − 0.60 (m, 2H), 0.35 (dd, J = 2.2, 4.9 Hz, 2H) | 2.40<br>B | 642.4 |
| 259 | (400 MHz, DMSO-d6) δ = 10.53 (s, 1H), 9.92 (d, J = 7.3 Hz, 1H), 8.23 (dd, J = 2.6, 6.5 Hz, 1H), 7.97 (d, J = 2.4 Hz, 1H), 7.85 − 7.72 (m, 1H), 7.56 (dd, J = 2.3, 8.4 Hz, 1H), 7.49 (t, J = 9.7 Hz, 1H), 7.25 (d, J = 8.6 Hz, 1H), 4.69 (d, J = 9.5 Hz, 1H), 4.45 (br s, 1H), 4.36 − 4.10 (m, 2H), 4.05 (s, 3H), 3.16 (dd, J = 4.6, 11.1 Hz, 1H), 3.10 (br t, J = 3.8 Hz, 1H), 2.72 (t, J = 3.8 Hz, 1H), 1.91 − 1.69 (m, 5H), 1.66 − 1.58 (m, 1H), 1.55 − 1.46 (m, 1H), 1.46 − 1.33 (m, 2H), 0.82 − 0.66 (m, 2H), 0.41 − 0.27 (m, 2H) | 2.38<br>B | 642.3 |
| 260 | (500 MHz, DMSO-d6) Shift 10.38 (s, 1H), 9.66 (br d, J = 7.3 Hz, 1H), 8.15 − 8.01 (m, 1H), 7.71 − 7.59 (m, 2H), 7.35 (br t, J = 9.6 Hz, 1H), 7.19 (dd, J = 8.4, 2.0 Hz, 1H), 6.95 (d, J = 8.5 Hz, 1H), 5.06 (d, J = 8.9 Hz, 1H), 4.32 − 4.21 (m, 1H), 3.83 (s, 3H), 3.01 (br dd, J = 10.7, 4.0 Hz, 1H), 2.86 (br d, J = 15.3 Hz, 2H), 2.47 (br s, 1H), 1.81 − 1.57 (m, 4H), 1.55 − 1.38 (m. 6H), 1.25 (br s, 2H), 1.14 (td, J = 8.3, 3.2 Hz, 2H), 1.01 (s, 6H) some protons obscured by solvent suppression | 2.69<br>C | 617.3 |
| 261 | (500 MHz, DMSO-d6) Shift 10.51 (s, 1H), 9.80 (d, J = 7.3 Hz, 1H), 8.19 (br d, J = 5.1 Hz, 1H), 7.81 − 7.71 (m, 2H), 7.45 (t, J = 9.8 Hz, 1H), 7.31 (dd, J = 8.5, 2.2 Hz, 1H), 7.07 (d, J = 8.5 Hz, 1H), 5.15 (t, J = 7.5 Hz, 1H), 4.63 (br dd, J = 4.6, 2.9 Hz, 1H), 4.43 − 4.32 (m, 1H), 3.94 (s, 3H), 3.63 (s, 1H), 3.45 − 3.34 (m, 2H), 3.20 − 3.08 (m, 2H), 2.57 (br | 2.63<br>C | 589.2 |

TABLE 3-continued

| | | | |
|---|---|---|---|
| | s, 1H), 2.37 – 2.27 (m, 1H), 2.12 (brt, J = 7.0 Hz, 2H), 2.04 – 1.93 (m, 2H), 1.91 – 1.59 (m, 8H), 1.36 (br d, J = 3.2 Hz, 2H) | | |
| 262 | (500 MHz, DMSO-d6) Shift 10.49 – 10.35 (m, 1H), 9.69 – 9.64 (m, 1H), 8.15 – 8.08 (m, 1H), 7.71 – 7.61 (m, 2H), 7.40 – 7.32 (m, 1H), 7.18 (br dd, J = 8.5, 2.4 Hz, 1H), 6.98 – 6.90 (m, 1H), 5.76 – 5.66 (m, 1H), 5.11 (brt, J = 7.4 Hz, 1H), 4.95 – 4.79 (m, 1H), 4.33 – 4.23 (m, 1H), 3.83 (s, 3H), 3.09 – 2.97 (m, 1H), 2.48 – 2.43 (m, 2H), 2.04 – 1.88 (m, 3H), 1.84 – 1,61 (m, 3H), 1.58 – 1.41 (m, 4H), 1.36 – 1.18 (m, 4H), 1.01 (s, 6H) some protons obscured by solvent suppression | 2.82 C | 617.4 |
| 263 | (500 MHz, DMSO-d6) Shift 10.51 (s, 1H), 9.80 (d, J = 7.4 Hz, 1H), 8.19 (br d, J = 4.9 Hz, 1H), 7.81 – 7.68 (m, 2H), 7.45 (t, J = 9.7 Hz, 1H), 7.31 (dd, J = 8.5, 2.3 Hz, 1H), 7.07 (d, J = 8.5 Hz, 1H), 5.02 (d, J = 8.9 Hz, 1H), 4.69 – 4.55 (m, 1H), 4.44 – 4.33 (m, 1H), 3.82 – 3.68 (m, 2H), 3.63 – 3.60 (m, 2H), 3.42 – 3.37 (m, 1H), 3.32 – 3.24 (m, 1H), 3.16 – 3.04 (m, 2H), 2.59 – 2.55 (m, 2H), 2.45 – 2.31 (m, 1H), 1.93 – 1.82 (m, 1H), 1.80 – 1.72 (m, 2H), 1.70 – 1.61 (m, 2H), 1.58 – 1.47 (m, 2H), 1.44 – 1.27 (m, 3H) some protons obscured by solvent suppression | 2.42 C | 605.4 |
| 264 | (500 MHz, DMSO-d6) Shift 10.55 (s, 1H), 9.82 (brd, J = 7.3 Hz, 1H), 8.22 (br d, J = 4.3 Hz, 1H), 7.86 – 7.72 (m, 2H), 7.54 – 7.44 (m, 1H), 7.34 (br d, J = 7.9 Hz, 1H), 7.10 (br d, J = 8.5 Hz, 1H), 5.22 (br d, J = 9.2 Hz, 1H), 4.46 – 4.31 (m, 1H), 3.97 (s. 3H), 3.89 (br t, J = 8.1 Hz, 1H), 3.84 – 3.76 (m, 1H), 3.72 (br d, J = 7.6 Hz, 1H), 3.62 – 3.50 (m, 2H), 3.46 – 3.37 (m, 1H), 3.35 – 3.30 (m, 1H), 3.15 (br dd, J = 10.8, 3.8 Hz, 1H), 3.05 – 2.93 (m, 2H), 2.65 – 2.58 (m, 2H), 2.14 – 2.04 (m, 1H), 1.96 – 1.88 (m, 1H), 1.82 – 1.74 (m, 1H), 1.72 – 1.56 (m, 3H), 1.49 – 1.36 (m, 2H) | 2.30 C | 591.2 |
| 265 | (500 MHz, DMSO-d6) Shift 10.41 (s, 1H), 9.68 (d, J = 7.1 Hz, 1H), 8.09 (br d, J = 4.1 Hz, 1H), 7.75 – 7.59 (m, 2H), 7.35 (t, J = 9.8 Hz, 1H), 7.20 (dd, J = 8.5, 2.3 Hz, 1H), 6.95 (d, J = 8.5 Hz, 1H), 5.05 (t, J = 7.6 Hz, 1H), 4.34 – 4.21 (m, 1H), 3.83 (s, 3H), 3.52 – 3.46 (m, 2H), 3.01 (br dd, J = 10.7, 4.0 Hz, 1H), 2.52 – 2.45 (m, 2H), 2.19 (dt, J = 15.3, 7.5 Hz, 1H), 2.10 – 1.99 (m, 2H), 1.89 (td, J = 7.7, 4.3 Hz, 2H), 1.81 – 1.63 (m, 4H), 1.59 – 1.41 (m, 4H), 1.25 (br d, J = 3.2 Hz, 2H), 1.02 (s, 6H) | 2.82 C | 617.4 |
| 266 | (500 MHz, DMSO-d6) Shift 10.47 (s, 1H), 9.75 (d, J = 7.2 Hz, 1H), 8.21 – 8.12 (m, 1H), 7.79 – 7.65 (m, 2H), 7.42 (t, J = 9.7 Hz, 1H), 7.26 (dd, J = 8.4, 2.3 Hz, 1H), 7.02 (d, J = 8.5 Hz, 1H), 4.98 (d, J = 9.0 Hz, 1H), 4.40 – 4.29 (m, 1H), 3.90 (s, 3H), 3.79 – 3.65 (m, 3H), 3.25 (br d, J = 2.7 Hz, 1H), 3.13 – 3.04 (m, 2H), 2.91 (br s, 1H), 2.65 (br s, 1H), 2.58 – 2.52 (m, 1H), 2.33 (br s, 1H), 1.89 – 1.79 (m, 1H), 1.76 – 1.62 (m, 2H), 1.59 – 1.45 (m, 4H), 1.39 – 1.23 (m, 3H), 1.14 – 1.05 (m. 6H) | 2.69 C | 633 |
| 267 | (500 MHz, DMSO-d6) Shift 10.47 – 10.35 (m, 1H), 9.76 – 9.64 (m, 1H), 8.18 – 8.08 (m, 1H), 7.74 – 7.64 (m, 2H), 7.46 – 7.35 (m, 1H), 7.22 (br dd, J = 8.3, 2.1 Hz, 1H), 6.99 (br d, J = 8.5 Hz, 1H), 5.12 (br d, J = 9.0 Hz, 1H), 4.30 (br d, J = 3.6 Hz, 1H), 3.87 (s, 3H), 3.84 – 3.77 (m, 1H), 3.72 (td, J = 7.9, 4.6 Hz, 1H), 3.68 – 3.58 (m, 1H), 3.33 (br s, 2H), 3.10 – 2.98 (m, 1H), 2.94 – 2.83 (m, 1H), 2.65 (br s, 1H), 2.52 – 2.47 (m, 2H), 2.04 – 1.95 (m, 1H), 1.89 – 1.81 (m, 1H), 1.71 – 1.61 (m, 1H), 1.59 – 1.47 (m, 3H), 1.37 – 1.27 (m, 2H), 1.04 (s, 6H) | 2.47 C | 619.4 |
| 268 | (500 MHz, DMSO-d6) Shift 10.38 (s, 1H), 9.66 (br d, J = 7.3 Hz, 1H), 8.16 – 8.03 (m, 1H), 7.73 – 7.59 (m, 2H), 7.35 (brt, J = 9.6 Hz, 1H), 7.19 (dd, J = 8.4, 2.0 Hz, 1H), 6.95 (d, J = 8.5 Hz, 1H), 5.06 (d, J = 8.9 Hz, 1H), 4.27 (br s, 1H), 3.83 (s, 3H), 3.31 (br s, 1H), 3.01 (br dd, J = 10.7, 4.0 Hz, 1H), 2.85 (br s, 1H), 2.57 (br s, 1H), 2.49 – 2.45 (m, 2H), 1.83 – 1.59 (m, 4H), 1.56 – 1.38 (m, 6H), 1.32 – 1.21 (m, 2H), 1.19 – 1.08 (m, 2H), 1.01 (s, 6H) | 2.73 C | 617.1 |
| 269 | (500 MHz, DMSO-d6) Shift 10.50 (s, 1H), 9.85 (d, J = 7.3 Hz, 1H), 8.23 (dd, J = 6.1, 1.8 Hz, 1H), 7.93 (d, J = 2.7 Hz, 1H), 7.84 – 7.74 (m, 1H), 7.55 – 7.39 (m, 2H), 7.10 (d, J = 8.7 Hz, 1H), 4.69 (d, J = 9.5 Hz, | 2.56 C | 588.9 |

TABLE 3-continued

| | | | |
|---|---|---|---|
| | 1H), 4.52 – 4.42 (m, 1H), 3.97 (s, 3H), 3.22 – 3.13 (m, 2H), 3.10 – 3.04 (m, 1H), 2.71 (br s, 1H), 1.91 – 1.71 (m, 4H), 1.54 – 1.34 (m, 3H), 1.32 – 1.17 (m, 7H), 0,80 – 0.64 (m, 2H), 0.42 – 0.30 (m, 2H) | | |
| 270 | (500 MHz, DMSO-d6) δ 9.87 – 9.82 (m, 1H), 7.93 (brt, J = 6.1 Hz, 1H), 7.68 (d, J = 1.8 Hz, 1H), 7.29 (dd, J = 8.2, 2.1 Hz, 1H), 7.03 (d, J = 8.2 Hz, 1H), 4.61 (d, J = 9.8 Hz, 1H), 4.51 (t, J = 5.0 Hz, 1H), 4.33 – 4.24 (m, 1H), 3.94 – 3.86 (m, 3H), 3.05 – 2.96 (m, 3H), 2.81 – 2.75 (m, 1H), 2.59 – 2.55 (m, 2H), 1.91 – 1.84 (m, 1H), 1.80 – 1.71 (m, 1H), 1.71 – 1.62 (m, 2H), 1.51 – 1.40 (m, 1H), 1.37 – 1.24 (m, 2H), 0.80 (s, 9H), 0.75 – 0.63 (m, 2H), 0.31 (br d, J = 1.8 Hz, 2H). | 2.21<br>B | 469.4 |
| 271 | (500 MHz, DMSO-d6) δ 9.84 (br d, J = 7.3 Hz, 1H), 7.95 – 7.89 (m, 1H), 7.69 (d, J = 1.8 Hz, 1H), 7.28 (dd, J = 8.4, 2.0 Hz, 1H), 7.05 – 6.99 (m, 1H), 6.51 (s, 1H), 4.62 (d, J = 9.5 Hz, 1H), 4.33 – 4.26 (m, 1H), 4.24 (s, 1H), 3.94 – 3.88 (m, 3H), 3,05 – 2.96 (m, 2H), 2.82 – 2.75 (m, 1H), 2.61 – 2.55 (m, 2H), 2.53 – 2.52 (m, 1H), 1.89 (br t, J = 8.2 Hz, 1H). 1.79 – 1.70 (m, 1H), 1.63 – 1.56 (m, 2H), 1.50 – 1.40 (m, 1H), 1.38 – 1.26 (m, 2H), 1.13 (s, 5H), 0.81 (s, 7H), 0.77 – 0.64 (m, 2H), 0.32 (br d, J = 1.8 Hz, 2H). | 2.36<br>C | 497.5 |
| 272 | (500 MHz, DMSO-d6) Shift 10.63 (s, 1H), 9.91 (d, J = 6.9 Hz, 1H), 8.24 (dd, J = 6.4, 2.4 Hz, 1H), 7.93 (d, J = 2.6 Hz, 1H), 7.79 (br dd, J = 8.6, 3.8 Hz, 1H), 7.56 – 7.46 (m, 2H), 7.11 (d, J = 8.7 Hz, 1H), 5.94 (d, J = 8.0 Hz, 1H), 4.60 – 4.44 (m, 1H), 3.98 (s, 3H), 3,32 – 3.23 (m, 1H), 3.20 – 3.10 (m, 1H), 2.99 (br s, 1H), 2.55 (s, 1H), 2.07 – 1.95 (m, 1H), 1.92 – 1.84 (m, 1H), 1.80 – 1.72 (m, 2H), 1.49 (br d, J = 6.7 Hz, 2H), 1.25 (s, 6H) some protons obscured by solvent suppression | 2.50<br>C | 617.1 |
| 273 | (500 MHz, DMSO-d6) δ 10.63 (s, 1H), 9.81 (br d, J = 7.3 Hz, 1H), 8.21 (br d, J = 4.0 Hz, 1H), 7.85 – 7.71 (m, 2H), 7.50 (br t, J = 9.9 Hz, 1H), 7.07 (s, 1H), 5.93 (q, J = 8.1 Hz, 1H), 4.60 – 4.40 (m, 1H), 3.96 (s, 3H), 3.26 (br dd, J = 11.0, 3.7 Hz, 1H), 3.22 (br s, 1H), 2.98 (br s, 1H), 2.90 (br t, J = 7.2 Hz, 2H), 2.81 (br t, J = 7.5 Hz, 2H), 2.09 – 1.97 (m, 3H), 1.93 – 1.80 (m, 1H), 1.59 – 1.36 (m, 2H) | 2.79<br>A | 570.9 |
| 274 | $^{1}$H NMR (400 MHz, DMSO-$d_6$) δ = 10.49 – 10.45 (m, 1H), 9.79 – 9.74 (m, 1H), 8.23 – 8.18 (m, 1H), 7.88 – 7.86 (m, 1H), 7.80 – 7.73 (m, 1H), 7.51 – 7.40 (m, 2H), 7.08 – 7.04 (m, 1H), 4.70 – 4.65 (m, 1H), 4.48 – 4.40 (m, 1H), 3.96 – 3.93 (m, 3H), 3.86 – 3.83 (m, 1H), 3.17 – 3.10 (m, 1H), 3.09 – 3.05 (m, 1H), 2.72 – 2.64 (m, 1H), 1.91 – 1.82 (m, 1H), 1.81 – 1.73 (m, 1H), 1.72 – 1.64 (m, 6H), 1.59 – 1.52 (m, 6H), 1.42 – 1.34 (m, 2H), 1.24 – 1.21 (m, 1H), 1.02 – 0.97 (m, 6H), 0.78 – 0.70 (m, 2H), 0.37 – 0.31 (m, 2H) | 2.82<br>C | 694.4 |
| 275 | (400 MHz, DMSO-d6) δ 10.47 (s, 1H), 9.77 (d, J = 7.3 Hz, 1H), 8.25 – 8.17 (m, 1H), 7.88 (d, J = 2.4 Hz, 1H), 7.80 – 7.73 (m, 1H), 7.52 – 7.39 (m, 2H), 7.07 (d, J = 8.8 Hz, 1H), 4.68 (d, J = 9.5 Hz, 1H), 4.47 – 4.39 (m, 1H), 3.94 (s, 3H), 3.84 (s, 1H), 3.16 – 3.11 (m, 1H), 3.09 – 3.04 (m, 1H), 2.70 (t, J = 3.7 Hz, 1H), 1.90 – 1.83 (m, 1H), 1.81 – 1.74 (m, 1H), 1.72 – 1.64 (m, 7H), 1.59 – 1.45 (m, 8H), 1.43 – 1.34 (m, 2H), 1.01 (s, 7H), 0.79 – 0.69 (m, 2H), 0.41 – 0.30 (m, 2H) | 2.82<br>B | 669.5 |
| 276 | $^{1}$H NMR (400 MHz, DMSO-$d_6$) δ = 10.35 (s, 1H), 8.31 – 8.27 (m, 1H), 8.14 – 8.10 (m, 1H), 7.85 – 7.79 (m, 1H), 7.60 – 7.58 (m, 1H), 7.48 – 7.38 (m, 2H), 7.07 – 7.03 (m, 1H), 4.58 – 4.53 (m, 1H), 4.51 – 4.46 (m, 1H), 3.87 – 3.85 (m, 3H), 3.85 – 3.83 (m, 1H), 3.09 – 3.05 (m, 1H), 2.69 – 2.65 (m, 1H), 2.55 – 2.52 (m, 1H), 2.38 – 2.35 (m, 1H), 2.34 – 2.30 (m, 1H), 1.72 – 1.65 (m, 6H), 1.59 – 1.51 (m, 6H), 1.43 – 1.35 (m, 2H), 1.25 – 1.21 (m, 1H), 1.03 – 0.98 (m, 6H), 0.73 – 0.63 (m, 2H), 0.31 – 0.22 (m, 2H) | 2.84<br>C | 669.4 |
| 277 | (500 MHz, DMSO-d6) Shift 10.51 (s, 1H), 9.83 (d, J = 7.3 Hz, 1H), 8.18 (dd, J = 6.3, 2.3 Hz, 1H), 7.80 – 7.71 (m, 2H), 7.44 (t, J = 9.7 Hz, 1H), 7.36 (dd, J = 8.5, 2.4 Hz, 1H), 7.09 (d, J = 8.6 Hz, 1H), 4.67 (d, J = 9.6 Hz, 1H), 4.49 – 4.37 (m, 1H), 4.30 – 4.21 (m, | 2.56<br>C | 573.2 |

TABLE 3-continued

| | | | |
|---|---|---|---|
| | 1H), 3.94 (s, 3H), 3.49 – 3.38 (m, 1H), 3.19 – 3.02 (m, 2H), 2.69 (br s, 1H), 2.57 – 2.55 (m, 2H), 2.36 – 2.20 (m, 4H), 1.93 – 1.70 (m, 2H), 1.55 – 1.34 (m, 3H), 0.72 (br t, J = 8.6 Hz, 2H) | | |
| 278 | (500 MHz, DMSO-d6) δ 10.64 (s, 1H), 9.84 (d, J = 7.0 Hz, 1H), 8.25 – 8.13 (m, 1H), 7.81 – 7.70 (m, 1H), 7.66 (d, J = 1,7 Hz, 1H), 7.45 (br t, J = 9.8 Hz, 1H), 7.25 (dd, J = 8.5, 2.2 Hz, 1H), 7.05 (d, J = 8.5 Hz, 1H), 5.97 – 5.77 (m, 1H), 4.55 – 4.41 (m, 1H), 3.93 (s, 3H), 3.29 – 3.13 (m, 2H), 2.95 (br s, 1H), 2.57 (br d, J = 7.5 Hz, 2H), 2.27 – 2.13 (m, 2H), 1.98 (br t, J = 9.3 Hz, 1H), 1,87 – 1.69 (m, 2H), 1.54 – 1.36 (m, 4H) | 2.56 A | 615.4 |
| 279 | (500 MHz, DMSO-d6) δ 9.88 (br d, J = 7.0 Hz, 1H), 8.24 (br d, J = 4.6 Hz, 1H), 7.87 – 7.78 (m, 1H), 7.74 (d, J = 1.5 Hz, 1H), 7.51 (br t, J = 9.9 Hz, 1H). 7.32 (dd, J = 8.2, 1.8 Hz, 1H), 7.10 (d, J = 8.5 Hz, 1H), 5.95 (q, J = 7.8 Hz, 1H), 4.60 – 4.47 (m, 1H), 4.24 (br d, J = 2.4 Hz, 1H), 3.98 (s, 3H), 3.28 (br dd, J = 10.8, 4.1 Hz, 1H), 3.24 (br s, 1H), 3.06 – 2.93 (m, 1H), 2.65 (br d, J = 7.9 Hz, 2H), 2.33 (dt, J = 8.0, 4.1 Hz, 1H), 2.02 (brt, J = 8.9 Hz, 1H), 1.97 – 1.82 (m, 4H), 1.58 – 1.41 (m, 2H) | 2.56 A | 615.4 |
| 283 | (500 MHz, DMSO-d6) δ 10.53 (s, 1H), 9.86 (br d, J = 7.3 Hz, 1H), 8.30 – 8.19 (m, 1H), 7.92 (d, J = 1.8 Hz, 1H), 7.84 – 7.77 (m, 1H), 7.56 – 7.42 (m, 2H), 7.18 (d, J = 8.5 Hz, 1H), 4.70 (br d, J = 9.5 Hz, 1H), 4.01 (s, 3H), 3.17 (br dd, J = 10.8, 3.8 Hz, 1H), 3.10 (m, 1H), 2.73 (m, 1H), 2.68 – 2.47 (m, 7H), 2.45 – 2.22 (m, 3H), 1.96 – 1.71 (m, 2H), 1.59 – 1.33 (m, 3H), 0.84 – 0.66 (m, 2H), 0.37 (m, 2H) | 2.76 B | 637.0 8 |
| 284 | (500 MHz, DMSO-d6) δ 10.66 (s, 1H), 9.92 (br d, J = 7.0 Hz, 1H), 8.25 (br d, J = 6.4 Hz, 1H), 7.92 (s, 1H), 7.85 – 7.74 (m, 1H), 7.59 – 7.43 (m, 2H), 7.19 (d, J = 8.5 Hz, 1H), 5.96 (g, J = 7.4 Hz, 1H), 4.63 (t, J = 6.9 Hz, 2H), 4.54 (br s, 1H), 4.48 (s, 2H), 4.30 (t, J = 6.0 Hz, 2H), 4.02 (s, 3H), 3.63 (m, 2H), 3.35 – 3.12 (m, 2H), 3.01 (br d, J = 5.8 Hz, 2H), 2.09 – 1.82 (m, 2H), 1.51 (br d, J = 6.4 Hz, 2H) | 2.47 B | 631.3 |
| 285 | (500 MHz, DMSO-d6) δ 10.52 (s, 1H), 9.85 (br d, J = 7.3 Hz, 1H), 8.34 – 8.16 (m, 1H), 7.89 (d, J = 2.1 Hz, 1H), 7.83 – 7.74 (m, 1H), 7.54 – 7.40 (m, 2H), 7.15 (d, J = 8.5 Hz, 1H), 5,69 (s, 2H), 4.70 (d, J = 9.5 Hz, 1H), 4.51 – 4.36 (m, 3H), 4.25 (tt, J = 6.8, 3.2 Hz, 1H), 3.99 (s, 2H), 3.47 – 3.34 (m, 1H), 3.22 – 3.06 (m, 2H), 2.72 (br s, 1H), 2.33 (br d, J = 18.6 Hz, 2H), 1.93 – 1.74 (m, 2H), 1.59 – 1.32 (m, 3H), 0.84 – 0.66 (m, 2H), 0.36 (br s, 2H) | 2.89 B | 599.3 |
| 286 | (500 MHz, DMSO-d6) δ 10.53 (s, 1H), 9.86 (br d, J = 7.0 Hz, 1H), 8.23 (br d, J = 4.0 Hz, 1H), 7.90 (d, J = 1.8 Hz, 1H), 7.83 – 7.75 (m, 1H), 7.55 – 7.39 (m, 2H), 7.17 (d, J = 8.5 Hz, 1H), 4.70 (d, J = 9.5 Hz, 1H), 4.51 – 4.36 (m, 3H), 4.00 (s, 3H), 3.78 (dq, J = 9.9, 4.9 Hz, 4H), 3.22 – 3.05 (m, 2H), 2.72 (br s, 1H), 2.34 – 2.16 (m, 3H), 1.97 (br dd, J = 11.9, 5.5 Hz, 2H), 1.91 – 1.75 (m, 2H), 1.59 – 1.32 (m, 4H), 0.87 – 0.67 (m, 3H), 0.36 (br s, 2H) | 2.66 B | 658.9 8 |
| 287 | (500 MHz, DMSO-d6) δ 10.53 (br d, J = 2.4 Hz, 1H), 9.87 (br d, J = 6.1 Hz, 1H), 8.29 – 8.21 (m, 1H), 7.91 (s, 1H), 7.84 – 7.76 (m, 1H), 7.50 (br t, J = 9.9 Hz, 1H), 7.40 (br d, J = 8.2 Hz, 1H), 7.36 – 7.27 (m, 4H), 7.14 (br d, J = 8.2 Hz, 1H), 5.08 (d, J = 7.0 Hz, 2H), 4.70 (br dd, J = 9.8, 3.7 Hz, 1H), 4.51 – 4.36 (m, 2H), 4.35 – 4.28 (m, 1H), 4.01 (s, 3H), 3.79 – 3.68 (m, 1H), 3.22 – 3.12 (m, 1H), 3.08 (br dd, J = 6.0, 2.0 Hz, 1H), 2.73 (br s, 1H), 1.91 – 1.77 (m, 3H), 1.73 – 1.63 (m, 1H), 1.54 – 1,35 (m, 3H), 1,17 – 1.08 (m, 1H), 0.93 (dt, J = 10.5, 5.4 Hz, 1H), 0.82 – 0.67 (m, 2H), 0.36 (br s, 2H) | 2.86 B | 721.1 6 |
| 288 | (500 MHz, DMSO-d6) δ 10.52 (s, 1H), 9.85 (br d, J = 7.0 Hz, 1H), 8.29 – 8.18 (m, 1H), 7.92 (d, J = 1.5 Hz, 1H), 7.84 – 7.74 (m, 1H), 7.55 – 7.37 (m, 2H), 7.16 (d, J = 8.5 Hz, 1H), 4.70 (d, J = 9.8 Hz, 1H), 4.54 – 4.37 (m, 3H), 4.00 (s, 3H), 3.81 (dt, J = 11.4, 4.2 Hz. 2H), 3.63 – 3.48 (m, 1H), 3.46 – 3.25 (m, 1H), 3.22 – 3.06 (m, 2H), 2.72 (br s, 1H), 1.95 – 1.70 (m, 4H), 1.59 – 1.34 (m, 5H), 0.75 (br dd, J = 11.0, 9.2 Hz, 2H), 0.36 (br s, 2H) | 2.73 B | 617.3 5 |
| 289 | (500 MHz, DMSO-d6) δ 10.53 (s, 1H), 9.85 (br d, J = 7.3 Hz, 1H), 8.33 – 8.18 (m, 1H), 7.90 (d, J = 1.8 | 2.62 B | 631.3 5 |

TABLE 3-continued

| | | | |
|---|---|---|---|
| | Hz, 1H), 7.84 – 7.73 (m, 1H), 7.57 – 7.35 (m, 2H), 7.15 (d, J = 8.5 Hz. 1H), 4.70 (d, J = 9.8 Hz, 1H), 4.51 (d, J = 4.3 Hz, 1H), 4.48 – 4.41 (m, 3H), 4.00 (s, 3H), 3.49 – 3.25 (m, 1H), 3.20 – 3.06 (m, 1H), 3.01 (s, 1H), 2.73 (br s, 1H), 2.00 – 1.73 (m, 6H), 1.58 – 1.35 (m, 3H), 1.32 – 1.11 (m, 4H), 0.83 – 0.68 (m. 2H), 0.36 (br s, 2H) | | |
| 290 | (500 MHz, DMSO-d6) δ 10.52 (s, 1H), 9.85 (br d, J = 7.0 Hz, 1H), 8.24 (dd, J = 6.3, 2.0 Hz, 1H), 7.92 (d, J = 1.8 Hz, 1H), 7.84 – 7.74 (m, 1H), 7.57 – 7.33 (m, 2H), 7.16 (d, J = 8.5 Hz, 1H), 4.70 (d, J = 9.8 Hz, 1H), 4.53 – 4.34 (m, 4H), 4.00 (s, 3H), 3.59 – 3.30 (m, 1H), 3.22 – 3.05 (m, 2H), 2.72 (br s, 1H), 1.93 – 1,67 (m, 4H), 1.62 – 1.33 (m, 9H), 0.81 – 0.68 (m, 2H), 0.36 (br s, 2H) | 2.53 A | 631.2 4 |
| 291 | (500 MHz, DMSO-d6) δ 10.52 (s, 1H), 9.85 (d, J = 7.1 Hz, 1H), 8.23 (dd, J = 6.5, 2.4 Hz, 1H), 7.89 (d, J = 2.3 Hz, 1H), 7.83 – 7.71 (m, 1H), 7.55 – 7.39 (m, 2H), 7.16 (d, J = 8.5 Hz, 1H), 4.69 (d, J = 9.6 Hz, 1H), 4.54 – 4.28 (m, 3H), 4.00 (s, 3H), 3.94 – 3.88 (m, 1H), 3.22 – 3.13 (m, 1H), 3.09 (br t, J = 3.5 Hz, 1H), 2.75 – 2.68 (m, 1H), 2.28 – 2.15 (m, 2H), 2.04 – 1.70 (m, 4H), 1.58 – 1.34 (m, 5H), 0.82 – 0.67 (m, 2H), 0.36 (br dd, J = 4.4, 2.4 Hz, 2H) | 2.64 B | 617.1 5 |
| 292 | (500 MHz, DMSO-d6) δ 10.52 (s, 1H), 9.86 (br d, J = 7.2 Hz, 1H), 8.23 (dd, J = 6.5, 2.6 Hz, 1H), 7.88 (d, J = 2.1 Hz, 1H), 7.79 (br dd, J = 8.5, 3.3 Hz, 1H), 7.55 – 7.36 (m, 2H), 7.15 (d, J = 8.5 Hz, 1H), 4.69 (d, J = 9.6 Hz, 1H), 4.50 – 4.42 (m, 1H), 4.39 (s, 2H), 3,99 (s, 3H), 3.66 (dd, J = 10.3, 5.9 Hz, 1H), 3.21 – 3.04 (m, 2H), 2.76 – 2.68 (m, 1H), 1.91 – 1.75 (m, 2H), 1.68 (td, J = 8.0, 5.7 Hz, 1H), 1.63 – 1.35 (m, 5H), 1.03 (td, J = 8.1, 4.2 Hz, 1H), 0.87 – 0.66 (m, 3H), 0.39 – 0.32 (m, 2H) | 2.49 B | 631.2 2 |
| 293 | (500 MHz, DMSO-d6) δ 10.35 (s, 1H), 9.70 (br d, J = 7.0 Hz. 1H), 8.06 (dd, J = 6.1, 2.2 Hz, 1H), 7.75 (d, J = 2.2 Hz, 1H), 7.63 (br dd, J = 8.4, 3.6 Hz, 1H), 7.40 – 7.22 (m, 2H), 7.00 (d, J = 8.5 Hz, 1H), 4.53 (br d, J = 9.5 Hz, 1H), 4.37 – 4.21 (m, 3H), 4.18 – 4.06 (m, 1H), 3.83 (s, 3H), 3.39 – 3.18 (m, 2H), 3.07 – 2.91 (m, 2H), 2.56 (br s, 1H), 1.77 – 1.57 (m, 2H), 1.41 – 1.16 (m, 3H), 1.02 – 0.82 (m, 2H), 0.67 – 0.46 (m, 3H), 0.20 (br s, 2H), 0.08 – – 0.07 (m, 1H) | 2.54 B | 617.2 2 |
| 294 | (500 MHz, DMSO-d6) δ 10.55 (s, 1H), 9.87 (br d, J = 7.0 Hz, 1H), 8.26 – 8.16 (m, 1H), 7.87 (s, 1H), 7.82 – 7.72 (m, 1H), 7.50 – 7.35 (m, 2H), 7.15 (br d, J = 8.5 Hz, 1H), 4.69 (br d, J = 9.8 Hz, 1H), 4.51 (s, 2H), 4.45 – 4.36 (m, 1H), 3.97 (s, 2H), 3.75 – 3.62 (m, 3H), 3.53 (br d, J = 5.2 Hz, 1H), 3.35 (brt, J = 5.3 Hz, 2H), 3.21 – 3.04 (m, 2H), 2.92 (br d, J = 7.3 Hz, 1H), 2.71 (br s, 1H), 1.91 – 1.70 (m, 2H), 1.59 – 1.34 (m, 3H), 1.17 (br t, J = 7.3 Hz, 1H), 0.82 – 0.67 (m, 2H), 0.35 (br d, J = 4.0 Hz, 2H) | 2.26 B | 658.9 6 |
| 295 | (500 MHz, DMSO-d6) δ 10.63 – 10.44 (m, 1H), 9.87 (br d, J = 7.3 Hz, 1H), 8.84 (s, 1H), 8.31 – 8.14 (m, 1H), 7.91 – 7.69 (m, 2H), 7.56 – 7.35 (m, 2H), 7.16 (d, J = 8.9 Hz, 1H), 4.69 (d, J = 9.8 Hz, 1H), 4.52 (s, 2H), 4.43 (br d, J = 2.7 Hz, 1H), 3.99 (s, 3H), 3.90 (br t, J = 6.9 Hz, 2H), 3.72 (br d, J = 9.8 Hz, 1H), 3.58 – 3.45 (m, 2H), 3.19 – 3.06 (m, 2H), 2.72 (br s, 1H), 2.34 – 2.21 (m, 1H), 2.09 – 1.98 (m, 1H), 1.91 – 1.72 (m, 2H), 1.58 – 1.37 (m, 3H), 1.29 – 1.13 (m, 1H), 0.75 (br dd, J = 12.4, 9.0 Hz. 2H) | 2.39 B | 671.1 8 |
| 296 | (500 MHz, DMSO-d6) δ 10.27 (s, 1H), 9.62 (d, J = 7.0 Hz, 1H), 7.96 (br d, J = 3.7 Hz, 1H), 7.63 (s, 1H), 7.58 – 7.47 (m, 1H), 7.29 – 7.15 (m, 2H), 6.93 (d, J = 8.6 Hz, 1H), 5.10 (s, 2H), 4.43 (d, J = 9.5 Hz, 1H), 4.16 (br d, J = 5.8 Hz, 1H), 4.08 (s, 2H), 3.73 (s, 3H), 3.32 (s, 3H), 3.00 (s, 2H), 2.94 – 2.79 (m, 2H), 1.65 – 1.43 (m, 2H), 1.33 – 1.09 (m, 3H), 0.57 – 0.39 (m, 2H), 0.10 (br s, 2H) | 2.35 B | 628.3 6 |
| 299 | (500 MHz, DMSO-d6) δ 10.29 (br s, 1H), 9.63 (br s, 1H), 7.97 (br s, 1H), 7.62 (br s, 1H), 7.53 (br d, J = 1.2 Hz, 1H), 7.30 – 7.11 (m, 2H), 6.93 (br d, J = 8.2 Hz, 1H), 4.92 (br d, J = 3.7 Hz, 1H), 4.45 (br d, J = 9.5 Hz, 1H), 4.37 (br s, 2H), 4.19 (br d, J = 5.2 Hz, 1H), 3.88 (br d, J = 7.9 Hz, 1H), 3.80 – 3.68 (m, 3H), 3.47 – 3.24 (m, 4H), 2.97 – 2.80 (m, 2H), 2.48 | 2.36 B | 644.0 5 |

TABLE 3-continued

| | | | |
|---|---|---|---|
| | (br s, 1H), 1.65 − 1.47 (m, 2H), 1.33 − 1.07 (m, 3H), 0.58 − 0.43 (m. 2H), 0.11 (br s, 2H) | | |
| 300 | (500 MHz, DMSO-d6) δ 10.55 (br s, 1H), 10.02 − 9.74 (m, 1H), 8.23 (br d, J = 5.8 Hz, 1H), 7.99 (s, 1H), 7.88 − 7.75 (m, 1H), 7.64 − 7.41 (m, 2H), 7.20 (d, J = 8.5 Hz, 1H), 5.22 (dd, J = 8.8, 3.7 Hz, 1H), 5.11 − 4.99 (m, 2H), 4.69 (d, J = 9.5 Hz, 1H), 4.53 − 4.35 (m, 1H), 4.08 − 3.98 (m, 5H), 3.97 − 3.89 (m, 1H), 3.59 − 3.50 (m, 1H), 3.20 − 3.08 (m, 2H), 2.72 (br s, 1H), 1.92 − 1.73 (m, 3H), 1.55 − 1.36 (m, 3H), 0.84 − 0.66 (m. 2H), 0.36 (br s, 2H) | 2.47 B | 644.1 3 |
| 301 | (500 MHz, DMSO-d6) δ 10.54 (s, 1H), 9.89 (br d, J = 7.0 Hz, 1H), 8.24 (br d, J = 4.6 Hz, 1H), 8.00 (d, J = 1.8 Hz, 1H), 7.86 − 7.76 (m, 1H), 7.63 − 7.43 (m, 2H), 7.21 (br d, J = 8.5 Hz, 2H), 5.10 − 4.96 (m, 3H), 4.70 (d, J = 9.5 Hz, 1H), 4.46 (br s, 1H), 4.11 (br d, J = 3.1 Hz, 1H), 4.02 (s, 2H), 3.70 − 3.57 (m, 1H), 3.22 − 3.08 (m, 1H), 2.73 (br s, 1H), 2.02 − 1.91 (m, 2H), 1.90 − 1.61 (m, 4H), 1.58 − 1.35 (m, 3H), 0.85 − 0.64 (m, 2H), 0.37 (br s, 2H) | 2.37 B | 658.2 9 |
| 302 | (500 MHz, DMSO-d6) δ 10.56 (s, 1H), 9.89 (br d, J = 6.4 Hz, 1H), 8.23 (br d, J = 4.9 Hz, 1H), 8.17 (br s, 1H), 7.93 − 7.75 (m, 2H), 7.55 − 7.40 (m, 2H), 7.24 (br d, J = 8.2 Hz, 1H), 7.14 − 6.99 (m, 1H). 4.71 (br d, J = 9.8 Hz, 1H), 4.51 − 4.37 (m, 1H), 4.04 (s, 3H), 3.57 (br s, 1H), 3.46 (br s, 2H), 3.24 − 3.19 (m, 1H), 3.19 − 3.15 (m, 1H), 3.12 (br s, 1H), 2.96 (s, 1H), 2.74 (br s, 1H), 1.90 − 1.70 (m, 2H), 1.59 − 1,48 (m, 1H), 1.47 − 1.34 (m, 2H), 0.85 − 0.68 (m, 2H), 0.37 (br s, 2H) | 2.30 A | 630 |
| 303 | (500 MHz, DMSO-d6) δ 10.68 (s, 1H), 9.93 (br d, J = 6.7 Hz, 1H), 8.23 (br d, J = 4.3 Hz, 1H), 8.19 (d, J = 1.8 Hz, 1H), 7.85 (dd, J = 8.5, 1.8 Hz, 1H), 7.82 − 7.74 (m, 1H), 7.51 (brt, J = 9.6 Hz, 1H), 7.45 (d, J = 15.6 Hz, 1H), 7.24 (d, J = 8.9 Hz, 1H), 6.87 (d, J = 15.6 Hz, 1H), 5.94 (q, J = 7.6 Hz, 1H), 4.60 − 4.43 (m, 1H), 4.04 (s, 3H), 3.64 (br t, J = 6.7 Hz, 1H), 3.43 − 3.35 (m, 1H), 3.32 − 3.28 (m, 1H), 3.26 (br s, 1H), 3.01 (br s, 1H), 2.00 − 1.86 (m, 4H), 1.82 (quin, J = 6.6 Hz, 2H), 1.59 − 1.40 (m, 2H) | 2.45 A | 654.3 |
| 304 | (500 MHz, DMSO-d6) δ 10.66 (br s, 1H), 9.91 (br d, J = 5.5 Hz, 1H), 8.25 (br s, 2H), 7.88 (br d, J = 8.5 Hz, 1H), 7.81 (br d, J = 4.0 Hz, 1H), 7.51 (brt, J = 9.3 Hz, 1H), 7.25 − 7.19 (m, 1H), 7.01 (br d, J = 12.2 Hz, 1H), 6.02 − 5.88 (m, 2H), 4.53 (br s, 1H), 4.05 (br s, 3H), 3.70 − 3.60 (m, 3H), 3.32 − 3.27 (m, 1H), 3.25 (br s, 1H), 3.01 (br s, 1H), 2.08 − 1.82 (m, 2H), 1.60 − 1.43 (m, 2H) | 2.61 A | 615.3 |
| 305 | (500 MHz, DMSO-d6) δ 10.65 (s, 1H), 9.91 (d, J = 7.0 Hz, 1H), 8.21 (dd, J = 6.3, 1.9 Hz, 1H), 8.05 (d, J = 2.2 Hz, 1H), 7.83 − 7.72 (m, 1H), 7.64 (dd, J = 8.7, 2.3 Hz, 1H), 7.56 (s, 1H), 7.48 (t, J = 9.9 Hz, 1H), 7.25 (d, J = 8,7 Hz, 1H), 5.92 (g, J = 7.8 Hz, 1H), 4.58 − 4.44 (m, 1H), 4.19 (q, J = 7.1 Hz, 2H), 4.03 (s, 3H), 3.27 (br d, J = 4.3 Hz, 1H), 3.24 (br d, J = 7.9 Hz. 1H), 2.98 (br s, 1H), 2.04 (d, J = 0.9 Hz, 3H), 1.97 (br t, J = 9.5 Hz, 1H), 1.92 − 1.80 (m, 1H), 1.59 − 1.42 (m, 2H), 1.26 (t, J = 7.1 Hz, 3H) | 2.78 A | 643 |
| 306 | (500 MHz, DMSO-d6) δ 10.55 (s, 1H), 9.87 (br d, J = 7.0 Hz, 1H), 8.26 − 8.11 (m, 2H), 7.87 (dd, J = 8.5, 1.5 Hz, 1H), 7.81 − 7.72 (m, 1H), 7.54 − 7.41 (m, 2H), 7.23 (d, J = 8.9 Hz, 1H), 7.12 (d, J = 15.6 Hz, 1H), 4.70 (d, J = 9.5 Hz, 1H), 4.54 − 4.38 (m, 1H), 4.02 (s, 3H), 3.23 − 3.12 (m, 1H), 3.10 (br s, 1H), 2.72 (br s, 1H), 1.92 − 1.72 (m, 2H), 1.58 − 1.33 (m, 3H), 0.74 (quin, J = 9.7 Hz, 2H), 0.46 − 0.28 (m, 2H) | 2.46 A | 642.2 |
| 307 | (500 MHz, DMSO-d6) δ 10.56 (s, 1H), 9.88 (br d, J = 7.0 Hz, 1H), 8.25 − 8.12 (m, 2H), 7.87 (br d, J = 8.2 Hz, 1H), 7.80 − 7.71 (m, 1H), 7.52 − 7.41 (m, 2H), 7.23 (d, J = 8.9 Hz, 1H), 7.16 − 7.01 (m, 1H), 4.70 (br d, J = 9.5 Hz, 1H), 4.52 − 4.22 (m, 2H), 4.20 − 4.08 (m, 1H), 4.02 (s, 2H), 3.94 − 3.82 (m, 1H), 3,75 − 3.59 (m, 2H), 3.54 − 3.31 (m, 3H), 3.26 − 3.11 (m, 2H), 3.10 (br s, 1H), 2.72 (br s, 1H), 1.90 − 1.71 (m, 2H), 1.54 − 1.32 (m, 3H), 0.81 − 0.64 (m, 2H), 0.44 − 0.28 (m, 2H) | 2.33 A | 672.2 |
| 308 | (500 MHz, DMSO-d6) Shift 10.59 (s, 1H), 9.90 (br d, J = 7.3 Hz, 1H), 8.28 (br d, J = 5.8 Hz, 1H), 8.24 (s, 1H), 7.93 (br d, J = 8.9 Hz, 1H), 7.84 (br d, | 2.49 A | 668.4 |

TABLE 3-continued

| | | | |
|---|---|---|---|
| | J = 8.5 Hz, 1H), 7.60 − 7.46 (m, 2H), 7.28 (br d, J = 8.5 Hz, 1H), 7.13 (br d, J = 15.3 Hz, 1H), 4.76 (br d, J = 9.5 Hz, 1H), 4.50 (br d, J = 5.2 Hz, 1H), 4.40 (br d, J = 1.8 Hz, 2H), 4.23 − 3.93 (m, 5H), 3.36 (br d, J = 11.6 Hz, 1H), 3.22 (br dd, J = 10.4, 4.3 Hz, 1H), 3.16 (br s, 1H), 2.96 − 2.86 (m, 1H), 2.78 (br s, 1H), 1.94 − 1.79 (m, 4H), 1.78 − 1.70 (m, 1H), 1.68 − 1.61 (m, 1H), 1.60 − 1.52 (m, 1H), 1.47 (br s, 2H), 0.87 − 0.71 (m, 2H), 0.41 (br s, 2H) | | |
| 309 | (500 MHz, DMSO-d6) Shift 10.55 (s, 1H), 9.87 (br d, J = 7.0 Hz, 1H), 8.24 (br d, J = 4.0 Hz, 1H), 8.16 (d, J = 1.5 Hz, 1H), 7.81 (br t, J = 9.5 Hz, 2H), 7.50 (br t, J = 9.8 Hz, 1H), 7.40 (d, J = 15.9 Hz, 1H), 7.24 (d, J = 8.9 Hz, 1H), 6.57 (d, J = 15.6 Hz, 1H), 5.16 − 5.06 (m, 1H), 4.71 (d, J = 9.2 Hz, 1H), 4.51 − 4.42 (m, 1H), 4.31 − 4.19 (m, 2H), 4.04 (s, 3H), 4.02 − 3.94 (m, 1H), 3.94 − 3.82 (m, 2H), 3.18 (br dd, J = 11.0, 3.7 Hz, 1H), 3.12 (br s, 1H), 2.74 (br s, 1H), 2.46 (br d, J = 2.1 Hz, 2H), 2.05 − 1.95 (m, 2H), 1.90 − 1.75 (m, 2H), 1.58 − 1.47 (m, 1H), 1.43 (br s, 2H), 0.84 − 0.69 (m, 2H), 0.37 (br s, 2H) | 2.34 A | 668.1 |
| 310 | (500 MHz, DMSO-d6) δ 10.70 (s, 1H), 9.93 (br d, J = 7.0 Hz, 1H), 8.26 − 8.15 (m, 2H), 7.86 (br d, J = 8.9 Hz, 1H), 7.83 − 7.73 (m, 1H), 7.55 − 7.41 (m, 2H), 7.24 (d, J = 8.5 Hz, 1H), 7.12 (br d, J = 14.6 Hz, 1H), 5.92 (q, J = 7.5 Hz, 1H), 4.60 − 4.47 (m, 1H), 4.46 − 4.24 (m, 1H), 4.22 − 4.07 (m, 1H), 4.03 (s, 3H), 3.95 − 3.85 (m, 1H), 3.56 − 3.32 (m, 3H), 3.30 − 3.14 (m, 2H), 3.00 (br s, 1H), 2.03 − 1.81 (m, 2H), 1.50 (br d, J = 7.3 Hz, 2H). | 2.26 A | 700.2 |
| 311 | (500 MHz, DMSO-d6) Shift 10.68 (s, 1H), 9.92 (br d, J = 6.4 Hz, 1H), 8.33 − 8.14 (m, 2H), 7.87 (br d, J = 7.9 Hz, 1H), 7.83 − 7.74 (m, 1H), 7.57 − 7.40 (m, 2H), 7.24 (br d, J = 8.5 Hz, 1H), 7.09 (br d, J = 15.6 Hz, 1H), 6.01 − 5.88 (m, 1H), 4.52 (br d, J = 4.3 Hz, 1H), 4.36 (br s, 2H), 4.10 (br d, J = 12.8 Hz, 1H), 4.04 (s, 3H), 4.00 − 3.92 (m, 1H), 3.36 − 3.22 (m, 2H), 3.01 (br s, 1H), 2.93 − 2.80 (m, 1H), 2.04 − 1.86 (m, 2H), 1.85 − 1.75 (m, 2H), 1.74 − 1.65 (m, 1H), 1.65 − 1.56 (m, 1H), 1.55 − 1.42 (m, 2H) | 2.43 A | 696.4 |
| 312 | (500 MHz, DMSO-d6) δ 10.67 (s, 1H), 9.92 (br d, J = 7.0 Hz, 1H), 8.25 − 8.17 (m, 1H), 7.95 (d, J = 1.8 Hz, 1H), 7.83 − 7.75 (m, 1H), 7.57 − 7.44 (m, 2H), 7.22 (d, J = 8.5 Hz, 1H), 6.43 (s, 1H), 5.93 (q, J = 7.7 Hz, 1H), 4.57 − 4.47 (m, 1H), 4.02 (s, 3H), 3.78 − 3.53 (m, 2H), 3.33 − 3.11 (m, 3H), 2.99 (br s, 1H), 2.03 − 1.83 (m, 5H), 1.81 − 1.70 (m, 2H), 1.50 (br d, J = 6.1 Hz, 2H), 1.40 − 1,27 (m, 2H) | 2.30 A | 698.2 |
| 313 | (500 MHz, CHLOROFORM-d) δ 9.54 (br d, J = 7.6 Hz, 1H), 8.46 (d, J = 2.3 Hz, 1H), 8.00 − 7.92 (m, 1H), 7.76 (s, 1H), 7.62 (d, J = 15.6 Hz, 1H), 7.59 − 7.54 (m, 1H), 7.52 (dd, J = 8.4, 2.1 Hz, 1H), 7.12 (t, J = 9.2 Hz, 1H), 6.97 (d, J = 8.5 Hz, 1H), 6.47 (d, J = 15.6 Hz, 1H), 4.85 − 4.71 (m, 2H), 4,66 (d, J = 9.3 Hz, 1H), 4.57 − 4.49 (m, 1H), 4.44 − 4.36 (m, 1H), 4.21 − 4.13 (m, 1H), 4.07 − 4.03 (m, 3H), 4.03 − 3.97 (m, 1H), 3.22 (t, J = 3.8 Hz, 1H), 3.09 (dd, J = 10.1, 4.3 Hz, 1H), 2.72 (t, J = 3.7 Hz, 1H), 2.19 − 2.09 (m, 1H), 1.93 − 1.83 (m, 1H), 0.93 − 0.81 (m, 2H), 0.79 − 0.71 (m, 2H), 0.40 − 0.27 (m, 2H) | 2.25 A | 628.4 |
| 314 | (500 MHz, CHLOROFORM-d) δ 9.45 − 9.32 (m, 1H), 8.44 (d, J = 2.3 Hz, 1H), 8.05 − 7.89 (m, 2H), 7.67 − 7.49 (m, 3H), 7.15 − 7.09 (m, 1H), 6,96 (br d, J = 8.4 Hz, 1H), 6.47 (d, J = 15.6 Hz, 1H), 5.60 (q, J = 7.4 Hz, 1H), 4.94 − 4.82 (m, 1H), 4.80 − 4.72 (m, 1H), 4.62 − 4.49 (m, 1H), 4.46 − 4.34 (m, 1H), 4.25 − 4.15 (m, 1H), 4.08 − 3.95 (m, 4H), 3.43 (br s, 1H), 3.16 (dd, J = 10.7, 4.0 Hz, 1H), 2.92 (t, J = 3.9 Hz, 1H), 2.46 − 2.31 (m, 1H), 2.02 − 1.92 (m, 1H), 1.77 − 1.69 (m, 2H) | 2.18 A | 656.3 |
| 315 | (500 MHz, DMSO-d6) δ 10.55 (s, 1H), 9.86 (br d, J = 7.0 Hz, 1H), 8.26 (br d, J = 4.3 Hz, 1H), 8.21 (d, J = 1.8 Hz, 1H), 7.90 (dd, J = 8.5, 1.8 Hz, 1H), 7.85 − 7.75 (m, 1H), 7.55 − 7.44 (m, 2H), 7.25 (d, J = 8.5 Hz, 1H), 7.19 (d, J = 15.3 Hz, 1H), 4.72 (d, J = 9.5 Hz, 1H), 4,65 − 4.53 (m, 1H), 4.51 − 4.36 (m, 2H), 4.05 (s, 3H), 3.19 (br dd, J = 11.0, 4.3 Hz, 1H), 3.13 | 2.66 A | 708.2 |

TABLE 3-continued

| | | | |
|---|---|---|---|
| | (br s, 1H), 2.75 (br s, 1H), 2.69 − 2.59 (m, 1H), 1.97 − 1.74 (m, 4H), 1.58 − 1.25 (m, 5H), 0.87 − 0.69 (m, 2H), 0.38 (br s, 2H) | | |
| 316 | (500 MHz, DMSO-d6) δ 10.53 (s, 1H), 9.84 (d, J = 7.0 Hz, 1H), 8.23 (dd, J = 6.6, 2.1 Hz, 1H), 8.18 (d, J = 2.2 Hz, 1H), 7.88 (dd, J = 8.6, 2.2 Hz, 1H), 7.83 − 7.73 (m, 1H), 7.54 − 7.42 (m, 2H), 7.22 (d, J = 8.7 Hz, 1H), 7.15 (d, J = 15.3 Hz, 1H), 4.70 (d, J = 9.6 Hz. 1H), 4.53 − 4.40 (m, 1H), 4.03 (s, 3H), 3.89 (br dd, J = 7.3, 3.9 Hz, 2H), 3.23 − 3.07 (m, 2H), 2.72 (br s, 1H), 1.91 (br s, 2H), 1.86 − 1.74 (m, 2H), 1.74 − 1.60 (m, 2H), 1.56 − 1.47 (m, 1H), 1.46 − 1.31 (m, 2H), 0.82 − 0.67 (m, 2H), 0.46 − 0.30 (m. 2H) | 2.49 A | 665.2 |
| 317 | (500 MHz, DMSO-d6) δ 10.55 (s, 1H), 9.87 (br d, J = 6.7 Hz, 1H), 8.35 − 8.18 (m, 2H), 7.91 (dd, J = 8.5, 1.8 Hz, 1H), 7.85 − 7.77 (m, 1H), 7.59 − 7.44 (m, 2H), 7.30 − 7.11 (m, 2H), 4.72 (d, J = 9.5 Hz, 1H), 4.68 − 4.54 (m, 1H), 4.52 − 4.39 (m, 2H), 4.05 (s, 3H), 3.19 (br dd, J = 10.4, 4.0 Hz, 1H), 3.13 (br s, 1H), 2.97 (s, 3H), 2.75 (br s, 1H), 2.11 (br d, J = 11.9 Hz, 2H), 1.90 − 1.75 (m, 2H), 1.65 − 1.36 (m, 5H), 0.87 − 0.68 (m, 2H), 0.38 (br s, 2H) | 2.40 A | 718 |
| 318 | (500 MHz, DMSO-d6) δ 10.65 (s, 1H), 9.85 (d, J = 7.0 Hz, 1H), 8.21 (dd, J = 6.3, 2.0 Hz, 1H), 7.84 (d, J = 2.2 Hz, 1H), 7.78 (br dd, J = 8.3, 3.6 Hz, 1H), 7.49 (t, J = 9.8 Hz, 1H), 7.38 (dd, J = 8.7, 2.3 Hz, 1H), 7.14 (d, J = 8,6 Hz, 1H), 6.69 (s, 1H), 5,92 (q, J = 8.0 Hz, 1H), 4.57 − 4.45 (m, 1H), 4.14 − 4.04 (m, 2H), 3.98 (s, 2H), 3.25 (dd, J = 10.9, 4.3 Hz, 1H), 3.20 (br s, 1H), 2.97 (br s, 1H), 2.00 (d, J = 1.2 Hz, 3H), 1.98 − 1.92 (m, 1H), 1.89 − 1.80 (m, 1H), 1.56 − 1.40 (m, 2H), 1.05 (t, J = 7.1 Hz, 3H) | 2.71 A | 643 |
| 319 | (500 MHz, DMSO-d6) δ 10.45 (s, 1H), 8.45 (br d, J = 6.4 Hz, 1H), 8.11 (br d, J = 4.3 Hz, 1H), 7.89 − 7.75 (m, 1H), 7.58 (s, 1H), 7.53 − 7.42 (m, 2H), 7.18 (d, J = 8.9 Hz, 1H), 6.43 (s, 1H), 5.73 (q, J = 7.8 Hz, 1H), 4.69 − 4.55 (m, 1H), 3.90 (s, 3H), 3.77 − 3.48 (m, 2H), 3.30 − 3.07 (m, 2H), 2.79 (br d, J = 2.4 Hz, 1H), 2.59 (br d, J = 4.9 Hz, 1H), 2.04 − 1.89 (m, 4H), 1.83 − 1.66 (m, 4H), 1.57 (br t, J = 10.8 Hz, 1H), 1.41 − 1.27 (m, 2H) | 2.24 A | 698.2 |
| 320 | (500 MHz, DMSO-d6) δ 10.65 (s, 1H), 9.87 (br d, J = 7.0 Hz. 1H), 8.24 (br d, J = 4.6 Hz, 1H), 7.79 (br s, 2H), 7.51 (br t, J = 9.8 Hz, 1H), 7.38 (br d, J = 6.4 Hz, 1H), 7.10 (d, J = 8.5 Hz, 1H), 5.95 (q, J = 7.7 Hz, 1H), 4,60 − 4.46 (m, 1H), 3.97 (s, 3H), 3.93 − 3,82 (m, 1H), 3.67 (br d, J = 1.2 Hz, 2H), 3.47 − 3.34 (m, 1H), 3.28 (br dd, J = 10.7, 3.7 Hz, 1H), 3.24 (br s. 1H), 3.17 − 3.08 (m, 1H), 3.00 (br d, J = 9.5 Hz, 2H), 2.84 − 2.73 (m, 2H), 2.59 (br s, 1H), 2.08 − 1.96 (m, 1H), 1.93 − 1.81 (m, 1H), 1.74 − 1.60 (m, 2H), 1.57 − 1.40 (m, 2H), 1.35 − 1.13 (m, 2H) | 2.23 A | 686.2 |
| 321 | (500 MHz, DMSO-d6) δ 9.84 (br d, J = 4.9 Hz, 1H), 8.21 (br d, J = 4.0 Hz, 1H), 7.82 − 7.73 (m, 1H), 7.70 (br s, 1H), 7.47 (br t, J = 9.5 Hz, 1H), 7.32 (br d, J = 7.9 Hz, 1H), 7.10 (br d, J = 7.6 Hz, 1H), 4.69 (d, J = 9.5 Hz, 1H), 4.50 − 4.36 (m, 1H), 4.02 − 3.83 (m, 4H), 3.33 − 3.19 (m, 1H), 3.14 (br dd, J = 10.2, 3.8 Hz, 1H), 3.09 − 2.94 (m, 2H), 2.71 (br s, 1H), 2.28 − 2.21 (m, 1H), 2.17 (brs, 1H), 1.91 − 1,81 (m, 1H), 1.79 − 1.63 (m, 3H), 1.56 − 1.46 (m, 1H), 1.44 − 1.20 (m, 5H), 1.16 (br s, 1H), 0.81 − 0.66 (m, 2H), 0.35 (br d, J = 3.4 Hz, 2H) | 2.38 A | 670.2 |
| 322 | (500 MHz, DMSO-d6) δ 9.90 (br d, J = 5.2 Hz, 1H), 8.23 (br d, J = 4.9 Hz, 1H), 7.83 − 7.76 (m, 1H), 7.70 (br s, 1H), 7.50 (br t, J = 9.8 Hz, 1H), 7.34 (br d, J = 7.9 Hz, 1H), 7.10 (br d, J = 8.2 Hz, 1H), 5.93 (q, J = 7.6 Hz, 1H), 4.51 (br s, 1H), 4.01 − 3.80 (m, 5H), 3.70 (br s, 1H), 3.31 − 3.17 (m, 2H), 3.09 − 2.92 (m, 2H), 2.30 − 2.14 (m, 2H), 2.04 − 1.93 (m, 1H), 1.91 − 1.83 (m, 1H), 1.73 (br d, J = 11.6 Hz, 2H), 1.49 (br d, J = 6.1 Hz, 2H), 1.42 − 1.20 (m, 3H), 1.16 (br s, 1H) | 2.31 A | 698.2 |
| 323 | (500 MHz, DMSO-d6) δ 9.87 (br d, J = 7.0 Hz, 1H), 8.20 (br d, J = 4.6 Hz, 1H), 7.82 − 7.74 (m, 1H), 7.69 (br s, 1H), 7.49 (br t, J = 9.6 Hz, 1H), 7.32 (br d, J = 8.2 Hz, 1H), 7.10 (br d, J = 7.6 Hz, 1H), 5.92 (q, J = 7.7 Hz, 1H), 4.56 − 4.42 (m, 1H), 4.04 − 3.82 (m, 4H), 3.33 − 3.18 (m, 3H), 3.09 − 2.95 (m, 2H), | 2.31 A | 698.1 |

TABLE 3-continued

| | | | |
|---|---|---|---|
| | 2.30 – 2.21 (m, 1H), 2.18 (br d, J = 2.4 Hz, 1H), 2.03 – 1.94 (m, 1H), 1.91 – 1.82 (m, 1H), 1.77 – 1.63 (m, 2H), 1.49 (br d, J = 6.4 Hz, 2H), 1.42 – 1.34 (m, 1H), 1.32 – 1.19 (m, 2H), 1.16 (br s, 1H) | | |
| 324 | (500 MHz, DMSO-d6) δ 9.58 (br d, J = 6.1 Hz, 1H), 7.96 (br d, J = 4.0 Hz, 1H), 7.59 – 7.51 (m, 1H), 7.46 (br s, 1H), 7.22 (br t, J = 9.8 Hz, 1H), 7.06 (br d, J = 8.2 Hz, 1H), 6.85 (br d, J = 8.2 Hz, 1H), 4.44 (br d, J = 9.5 Hz, 1H), 4.19 (br s, 1H), 3.77 – 3.58 (m, 4H), 3.45 (br s, 1H), 3.07 – 2.96 (m, 1H), 2.90 (br dd, J = 10.8, 3.5 Hz, 1H), 2.83 (br s, 1H), 2.80 – 2.70 (m, 1H), 2.46 (br s, 1H), 2.04 – 1.97 (m, 1H), 1.93 (br s, 1H), 1.83 (s, 1H), 1.65 – 1.57 (m, 1H), 1.56 – 1.38 (m, 4H), 1.31 – 1.08 (m, 5H), 1.07 – 0.96 (m, 2H), 0.91 (br s, 1H), 0.49 (br dd, J = 11.6, 9.2 Hz, 2H), 0.10 (br d, J = 3.4 Hz, 2H) | 2.38 A | 670.2 |
| 325 | (500 MHz, DMSO-d6) δ 10.65 (s, 1H), 9.97 – 9.77 (m, 1H), 8.23 (br d, J = 5.2 Hz, 1H), 7.78 (br d, J = 6.4 Hz, 2H), 7.50 (br t, J = 9.6 Hz, 1H), 7.20 (brt, J = 6.6 Hz, 1H), 7.04 (br t, J = 8.2 Hz, 1H), 5.93 (q, J = 8.1 Hz, 1H), 4.51 (br s, 1H), 4.04 – 3,77 (m, 4H), 3,73 – 3.65 (m, 1H), 3.33 – 3.10 (m, 3H), 2.98 (br s, 1H), 2.87 – 2.74 (m, 1H), 2.49 – 2.39 (m, 1H), 2.37 – 2.20 (m, 1H), 2.05 – 1.76 (m, 3H), 1.71 – 1.58 (m, 1H), 1.39 – 1.27 (m, 1H), 1.22 – 1.10 (m, 2H), 0.97 – 0.69 (m, 2H) | 2.29 A | 698.4 |
| 326 | (500 MHz, DMSO-d6) Shift 10.65 (br s, 1H), 9.93 – 9.74 (m, 1H), 8.20 (br d, J = 6.1 Hz, 1H), 7.81 – 7.67 (m, 2H), 7.49 (brt, J = 9.5 Hz, 1H), 7.20 (br d, J = 7.9 Hz, 1H), 7.03 (br t, J = 7.6 Hz, 1H), 6.01 – 5.84 (m, 1H), 4.50 (br d, J = 7.0 Hz, 1H), 3.94 (br s, 3H), 3,88 – 3.77 (m, 1H), 3.30 – 3.14 (m, 2H), 2.98 (br s, 1H), 2.93 – 2.74 (m, 1H), 2.49 – 2.40 (m, 1H), 2.32 – 2.21 (m, 1H), 2.06 – 1.92 (m, 1H), 1.90 – 1.79 (m, 1H), 1.72 – 1.61 (m, 1H), 1.49 (br s, 3H), 1.41 – 1.27 (m, 1H), 1.25 – 1.09 (m, 2H), 0.98 – 0.85 (m, 1H), 0.84 – 0.66 (m, 1H) | 2.27 A | 698.4 |
| 327 | (500 MHz, DMSO-d6) Shift 10.50 (s, 1H), 9.81 (d, J = 7.2 Hz, 1H), 8.20 (br s, 1H), 7.86 – 7.71 (m, 2H), 7.46 (br t, J = 9.6 Hz, 1H), 7.42 – 7.27 (m, 1H), 7.10 (t, J = 8.3 Hz, 1H), 4.86 – 4.74 (m, 1H), 4.67 (br d, J = 9.6 Hz, 1H), 4.50 – 4.36 (m, 1H), 4.01 ~ 3.93 (m, 3H), 3.92 – 3.85 (m, 1H), 3.75 – 3.57 (m, 2H), 3.34 – 2.90 (m, 4H), 2.69 (br s, 1H), 2.48 – 2.40 (m, 1H), 2.29 – 2.08 (m, 2H), 1.84 (br dd, J = 10.9, 5.0 Hz, 1H), 1.80 – 1.61 (m, 3H), 1.48 (td, J = 8.4, 4.5 Hz, 1H), 1.44 – 1.33 (m, 2H), 1.30 – 1.16 (m, 2H), 0.80 – 0.64 (m, 2H), 0.34 (br s, 2H) | 2.44 A | 684.2 |
| 328 | (500 MHz, DMSO-d6) δ 10.52 (s, 1H), 9.83 (br d, J = 7.3 Hz, 1H), 8.22 (br d, J = 3.7 Hz, 1H), 7.86 – 7.73 (m, 2H), 7.48 (brt, J = 9.8 Hz, 1H), 7.35 (dd, J = 8.4, 2.0 Hz, 1H), 7.12 (d, J = 8.5 Hz, 1H), 4.69 (d, J = 9.8 Hz, 1H), 4.44 (br d, J = 4.3 Hz, 1H), 3.97 (s, 3H), 3.62 (s, 1H), 3.44 (br dd, J = 17.1, 8.2 Hz, 1H), 3.24 – 3.06 (m, 3H), 3.00 (s, 1H), 2.71 (br s, 1H), 2.18 (q, J = 10,4 Hz, 2H), 1.94 – 1.81 (m, 1H), 1.81 – 1.71 (m, 1H), 1.58 – 1.47 (m, 1H), 1.46 – 1.32 (m, 2H), 0.87 – 0.66 (m. 2H), 0.43 – 0.29 (m, 2H) | 2.71 A | 615 |
| 329 | (500 MHz, DMSO-d6) δ 10.65 (s, 1H), 9.88 (br d, J = 7.0 Hz, 1H), 8.29 – 8.13 (m, 1H), 7.84 – 7.73 (m, 2H), 7.50 (br t, J = 9.6 Hz, 1H), 7.36 (dd, J = 8.4, 2.0 Hz, 1H), 7.13 (d, J = 8.5 Hz, 1H), 5.93 (g, J = 7.7 Hz, 1H), 4.60 – 4.43 (m, 1H), 3.97 (s, 3H), 3.62 (s, 3H), 3.54 – 3.38 (m, 2H), 3.33 – 3.20 (m, 2H), 3.19 – 3.08 (m, 1H), 3.06 – 2.91 (m, 2H), 2.18 (q, J = 10.3 Hz, 2H), 1.99 (br t, J = 9.2 Hz, 1H), 1.92 – 1.77 (m, 1H), 1.55 – 1.38 (m, 2H) | 2.67 A | 643.2 |
| 330 | (500 MHz, DMSO-d6) δ 10.54 (s, 1H), 9.82 (br d, J = 7.3 Hz, 1H), 8.24 (br d, J = 4.3 Hz, 1H), 7.80 (br d, J = 1.8 Hz, 2H), 7.49 (br t, J = 9.6 Hz, 1H), 7.34 (dd, J = 8.1, 1.7 Hz, 1H), 7.11 (d, J = 8.2 Hz, 1H), 4.70 (br d, J = 9.8 Hz, 1H), 4.52 ~ 4.40 (m, 1H), 3.97 (s, 3H), 3.17 (br dd, J = 10.4, 3.7 Hz, 1H), 3.10 (br s, 1H), 2.73 (br s, 1H), 2.43 – 2.26 (m, 3H), 1.95 – 1.84 (m, 1H), 1.83 – 1.71 (m, 3H), 1.51 (br dd, J = 9.0, 3.8 Hz, 1H), 1.47 – 1.34 (m, 2H), 0.81 – 0.66 (m, 2H), 0.37 (br s, 2H) | 2.57 A | 587.1 |
| 331 | (500 MHz, DMSO-d6) δ 10.65 (s, 1H), 9.87 (br d, J = 6.7 Hz, 1H), 8.22 (br d, J = 4.6 Hz, 1H), 7.88 – 7.75 (m, 2H), 7.49 (brt, J = 9.6 Hz, 1H), 7.44 – 7.37 | 2.67 A | 642.9 |

TABLE 3-continued

| | | | |
|---|---|---|---|
| | (m, 1H), 7.13 (d, J = 8.5 Hz, 1H), 5.93 (q, J = 8.0 Hz, 1H), 4.58 – 4.43 (m, 1H), 3.97 (s, 3H), 3.67 (s, 1H), 3.32 – 3.20 (m, 2H), 3.20 – 3.08 (m, 1H), 3.03 – 2.94 (m, 2H), 2.37 – 2.25 (m, 2H), 2.04 – 1.94 (m, 1H), 1.92 – 1.81 (m, 1H), 1.56 – 1.41 (m, 2H) | | |
| 332 | (500 MHz, DMSO-d6) δ 10.54 (s, 1H), 9.83 (br d, J = 7.3 Hz. 1H), 8.23 (br d, J = 4.3 Hz, 1H), 7.87 – 7.72 (m, 2H), 7.49 (br t, J = 9.8 Hz, 1H), 7.43 (br d, J = 8.5 Hz, 1H), 7.14 (d, J = 8.5 Hz, 1H), 4.70 (br d, J = 9.8 Hz, 1H), 4.46 (br d, J = 4.9 Hz, 1H), 3.98 (s, 3H), 3.68 (s, 1H), 3.22 – 3.06 (m, 3H), 3.01 (s, 1H), 2.72 (br s, 1H), 2.41 – 2.25 (m, 2H), 1.96 – 1.83 (m, 1H), 1.82 – 1.72 (m, 1H), 1.58 – 1.48 (m. 1H), 1.47 – 1.34 (m, 2H), 0.87 – 0.68 (m, 2H), 0.36 (br d, J = 2.1 Hz, 2H) | 2.73 A | 615 |
| 333 | (500 MHz, DMSO-d6) δ 10.53 (s, 1H), 9.81 (br d, J = 7.1 Hz, 1H), 8.28 – 8.16 (m, 1H), 7.80 (d, J = 2.1 Hz, 1H), 7.79 – 7.73 (m, 1H), 7.46 (br t, J = 9.7 Hz, 1H), 7.36 (dd, J = 8.4, 2.2 Hz, 1H), 7.10 (d, J = 8.5 Hz, 1H), 4.75 – 4.64 (m, 1H), 4.50 – 4.38 (m, 1H), 3.95 (s, 3H), 3.89 (s, 1H), 3.17 (s, 1H), 3.14 (br dd, J = 11.0, 3.8 Hz, 1H), 3.07 (br s, 1H), 2.70 (br s, 1H), 2.40 – 2.25 (m, 1H), 2.19 – 2.01 (m, 4H), 1.93 – 1.82 (m, 1H), 1.82 – 1.68 (m, 2H), 1.49 (ddt, J = 12.7, 8.5, 4.1 Hz, 1H), 1.45 – 1.30 (m, 2H), 0.73 (quin, J = 9.7 Hz, 2H), 0.34 (br d, J = 3.5 Hz, 2H) | 2.58 A | 587.2 |
| 341 | (500 MHz, ACETONITRILE-d3) δ 9.75 (br d, J = 6.7 Hz, 1H), 8.77 (s, 1H), 8.12 (dd, J = 6.4, 2.6 Hz, 1H), 7.93 (d, J = 2.4 Hz, 1H), 7.75 – 7.70 (m, 1H), 7.39 (dd, J = 8.5, 2.1 Hz, 1H), 7.28 (t, J = 9.7 Hz, 1H), 7.06 (d, J = 8.5 Hz, 1H), 4.72 (d, J = 9.6 Hz, 1H), 4.61 – 4.53 (m, 1H), 4.50 – 4.42 (m, 1H), 4.01 (s, 3H), 3.58 – 3.49 (m, 1H), 3.15 (t, J = 3.7 Hz, 1H), 3.12 (ddd, J = 10.8, 4.3, 1.1 Hz, 1H), 2.81 (d, J = 3.1 Hz, 2H), 2.73 (brt, J = 4.0 Hz, 2H), 2.37 – 2.29 (m, 1H), 2.25 – 2.19 (m, 1H), 2.14 – 2.11 (m, 1H), 1.93 – 1.87 (m, 3H), 1.86 – 1.82 (m, 2H), 1.81 1.75 (m, 1H), 1.60 – 1.53 (m, 1H), 1.52 – 1.42 (m, 2H), 0.84 – 0.73 (m, 2H), 0.46 – 0.33 (m, 2H) | 2.65 A | 613.4 |
| 342 | (500 MHz, ACETONITRILE-d3) δ 9.75 (br d, J = 7.3 Hz, 1H), 8.76 (s, 1H), 8.12 (dd, J = 6.4, 2.7 Hz, 1H), 7.91 (d, J = 2.4 Hz, 1H), 7.73 (dt, J = 8.9, 3.6 Hz, 1H), 7.38 (dd, J = 8.5, 2.5 Hz, 1H), 7.28 (t, J = 9.7 Hz, 1H), 7.06 (d, J = 8.5 Hz, 1H), 4.76 – 4.66 (m, 2H), 4.60 – 4.53 (m, 1H), 4.01 (s, 3H), 3.15 (t, J = 4.0 Hz, 1H), 3.13 – 3.09 (m, 1H), 3.06 (br dd, J = 8.3, 7.1 Hz, 1H), 2.89 – 2.79 (m, 1H), 2.75 (d, J = 5.3 Hz, 1H), 2.74 – 2.70 (m, 1H), 2.29 – 2.19 (m, 1H), 2.08 – 2.02 (m, 1H), 1.93 – 1.86 (m, 3H), 1.66 – 1.44 (m, 6H), 0.84 – 0.73 (m, 2H), 0.46 – 0.33 (m, 2H) | 2.60 A | 613.4 |
| 343 | (500 MHz, ACETONITRILE-d3) δ 9.81 – 9.68 (m, 1H), 8.76 (s, 1H), 8.12 (dd, J = 6.3, 2.7 Hz, 1H), 7.91 (d, J = 2.4 Hz, 1H), 7.76 – 7.69 (m, 1H), 7.38 (dd, J = 8.5, 2.6 Hz, 1H), 7.30 – 7.24 (m, 1H), 7.06 (d, J = 8.5 Hz, 1H), 4.75 – 4.65 (m, 2H), 4.60 – 4.52 (m, 1H), 4.01 (s, 3H), 3.15 (t, J = 3.9 Hz, 1H), 3.11 (dd, J = 10.8, 4.1 Hz, 1H), 3.07 (dd, J = 6.9, 1.2 Hz, 1H), 2.75 (d, J = 5.2 Hz, 1H), 2.74 – 2.70 (m, 1H), 2.28 – 2.19 (m, 1H), 1.93 – 1.85 (m, 3H), 1.64 – 1.44 (m, 6H), 0.84 – 0.72 (m, 2H), 0.44 – 0.34 (m, 2H) | 2.59 A | 613.4 |
| 349 | (500 MHz, DMSO-d6) δ 10.50 (s, 1H), 9.81 (br d, J = 7.0 Hz, 1H), 8.23 (br d, J = 4.3 Hz, 1H), 7.87 – 7.74 (m, 2H), 7.55 – 7.43 (m, 1H), 7.35 (br dd, J = 8.5, 2.1 Hz, 1H), 7.16 – 7.02 (m, 1H), 4.70 (d, J = 9.8 Hz, 1H), 4.61 – 4.50 (m, 1H), 4.46 (br t, J = 10.4 Hz, 1H), 3.97 (s, 3H), 3.52 (br t, J = 5.2 Hz, 1H), 3.25 – 3.12 (m, 1H), 3.09 (br s, 1H), 2.72 (br s, 1H), 2.62 (br d, J = 1.8 Hz, 2H), 2.20 – 1.93 (m, 6H), 1.92 – 1.74 (m, 2H), 1.57 – 1.33 (m, 6H), 0.83 – 0.68 (m, 2H), 0.36 (br s, 2H) | 2.68 A | 627.3 |
| 350 | (500 MHz, DMSO-d6) δ 10.51 (s, 1H), 9.82 (br d, J = 7.3 Hz, 1H), 8.28 – 8.20 (m, 1H), 7.84 (d, J = 2.1 Hz, 1H), 7.80 (br dd, J = 8.4, 3.5 Hz, 1H), 7.49 (t, J = 9.8 Hz, 1H), 7.38 (dd, J = 8.4, 2.0 Hz, 1H), 7.12 (d, J = 8.5 Hz, 1H), 4.70 (d, J = 9.8 Hz, 1H), 4.54 – 4.40 (m, 1H), 3.98 (s, 3H), 3.48 (br t, J = 5.5 Hz, 1H), 3.17 (br dd, J = 11.0, 3.7 Hz, 1H), 3.10 (br s, 1H), 3.03 – 2.92 (m, 1H), 2.83 – 2.69 (m, 2H), 2.69 – | 2.800 A | 627.4 |

TABLE 3-continued

| | | | |
|---|---|---|---|
| | 2.60 (m, 1H), 2.24 − 2.12 (m, 1H), 2.04 − 1.93 (m, 1H), 1,92 − 1.85 (m, 1H), 1.83 − 1.76 (m, 1H), 1.72 (br dd, J = 12.5, 6.1 Hz, 1H), 1.66 (br dd, J = 12.4, 6.3 Hz, 1H), 1.57 − 1.48 (m, 1H), 1.46 − 1.36 (m, 2H), 1.35 − 1.20 (m, 2H), 0.84 − 0.70 (m, 2H), 0.37 (br d, J = 1.8 Hz, 2H) | | |
| 351 | (500 MHz, DMSO-d6) δ 10.51 (s, 1H), 9.82 (br d, J = 7.3 Hz, 1H), 8.28 − 8.19 (m, 1H), 7.87 − 7.72 (m, 2H), 7.49 (br t, J = 9.8 Hz, 1H), 7.41 − 7.32 (m, 1H), 7.12 (br d, J = 8.5 Hz, 1H), 4.70 (d, J = 9.5 Hz, 1H), 4.46 (br s, 1H), 3.98 (s, 3H), 3.57 − 3.44 (m, 1H), 3.16 (br dd, J = 10.7, 4.0 Hz, 1H), 3.10 (br s, 1H), 3.01 − 2.91 (m, 1H), 2.85 − 2.70 (m, 2H), 2.69 − 2.58 (m, 2H), 2.25 − 2.03 (m, 2H), 2.00 − 1,92 (m, 1H), 1.91 − 1.85 (m, 1H), 1.83 − 1.75 (m, 1H), 1.72 (br dd, J = 13.0, 6.3 Hz, 1H), 1.65 (br dd, J = 12.7, 6.3 Hz, 1H), 1.59 − 1.37 (m, 4H), 1.35 − 1.20 (m, 2H), 0.85 − 0.68 (m, 2H), 0.37 (br s, 2H) | 2.70<br>A | 727.2 |
| 352 | (500 MHz, DMSO-d6) δ 10.60 (br s, 1H), 9.91 − 9.77 (m, 1H), 8.34 − 8.21 (m, 1H), 7.80 (br s, 1H), 7.67 (br s, 1H), 7.54 − 7.40 (m, 1H), 7.21 (br d, J = 8.5 Hz, 1H), 7.11 (br d, J = 8.5 Hz, 1H), 4.70 (br d, J = 9.2 Hz, 1H), 4.51 − 4.38 (m, 1H), 3.98 (d, J = 1.5 Hz, 3H), 3.66 − 3.54 (m, 1H), 3.24 − 3.12 (m, 1H), 3.09 (br s, 1H), 3.03 − 2.91 (m, 1H), 2.72 (br s, 1H), 2.68 − 2.60 (m, 1H), 2.07 − 1.84 (m, 4H), 1.84 − 1.74 (m, 1H), 1.68 (br s, 1H), 1.63 − 1.34 (m, 4H), 1.11 − 0.92 (m, 2H), 0.82 − 0.67 (m, 2H), 0.36 (br s, 2H) | 2.72<br>A | 627.2 |
| 353 | (500 MHz, DMSO-d6) δ 10.51 (s, 1H), 9.84 (br d, J = 7.0 Hz, 1H), 8.30 − 8.19 (m, 1H), 7.83 − 7.72 (m, 2H), 7.50 (br t, J = 9.8 Hz, 1H), 7.29 (dd, J = 8.2, 2.4 Hz, 1H), 7.12 (d, J = 8.5 Hz, 1H), 4.70 (d, J = 9.5 Hz, 1H), 4.46 (dt, J = 10.8, 5.3 Hz, 1H), 3.98 (s, 3H), 3.59 − 3.41 (m, 1H), 3.16 (br dd, J = 11.0, 4.0 Hz, 1H), 3.10 (br s, 1H), 2.81 (br d, J = 4.6 Hz, 1H), 2.73 (br s, 1H), 2.27 − 2.05 (m, 5H), 1.98 − 1.84 (m, 3H), 1.83 − 1.74 (m, 1H), 1.71 − 1.62 (m, 1H), 1.58 − 1.34 (m, 4H), 0.75 (quin, J = 9.7 Hz, 2H), 0.37 (br s, 2H) | 2.80<br>A | 627.4 |
| 355 | (400 MHz, DMSO-d6) δ = 10.59 − 10.46 (m, 1H), 8.40 (dd, J = 0.9, 6.2 Hz, 1H), 8.17 − 8.06 (m, 1H), 7.90 − 7.77 (m, 1H), 7.53 − 7.37 (m, 2H), 7.35 − 7.24 (m, 1H), 7.04 (d, J = 8.6 Hz, 1H), 5.73 (q, J = 7.8 Hz, 1H), 4.64 − 4.54 (m, 1H), 3.84 (s, 3H), 3.58 − 3.46 (m, 4H), 3.23 − 3.15 (m, 1H), 2.89 − 2.81 (m, 1H), 2.77 (br d, J = 3.4 Hz, 1H), 2.59 (br d, J = 5.1 Hz, 2H), 1.97 − 1.88 (m, 1H), 1.77 − 1.20 (m, 12H) | 2.84<br>B | 704.3 |
| 357 | (500 MHz, DMSO-d6) δ 10.56 (s, 1H), 9.81 (br d, J = 7.4 Hz, 1H), 8.22 (br d, J = 5.1 Hz, 1H), 7.86 (d, J = 8.0 Hz, 1H), 7.80 (br dd, J = 5.1, 4.1 Hz, 1H), 7.48 (t, J = 9.7 Hz, 1H), 7.04 (s, 1H), 6.91 (br d, J = 7.8 Hz, 1H), 4.68 (d, J = 9.6 Hz, 1H), 4.49 − 4.38 (m, 1H), 3.97 (s, 3H), 3.67 (s, 1H), 3.65 − 3.61 (m, 1H), 3.62 − 3.55 (m, 4H), 3.47 − 3.32 (m, 1H), 3.15 (br dd, J = 10.7, 4.1 Hz, 1H), 3.12 − 3.02 (m, 1H), 2.74 − 2.67 (m, 1H), 1.90 − 1.70 (m, 4H), 1.56 − 1.45 (m, 1H), 1.44 − 1.31 (m, 2H), 1.28 (d, J = 1.7 Hz, 3H), 0.74 (br dd, J = 11.1, 9.0 Hz, 2H), 0.39 − 0.28 (m, 2H) | 2.15<br>B | 644.1<br>1 |
| 358 | (500 MHz, DMSO-d6) δ 10.59 (s, 1H), 9.97 (d, J = 6.1 Hz, 1H), 8.40 (d, J = 2.1 Hz, 1H), 8.21 (d, J = 4.9 Hz, 1H), 7.90 (dd, J = 8.8, 2.4 Hz, 1H), 7.80 (d, J = 8.3 Hz, 1H), 7.48 (t, J = 9.7 Hz, 1H), 7.38 − 7.30 (m, 3H), 4.38 − 4.30 (m, 1H), 4.06 (s, 3H), 3.11 (dd, J = 10.6, 4.0 Hz, 1H), 3.06 − 3.01 (m, 1H), 2.97 − 2.91 (m, 1H), 1.81 − 1.74 (m, 1H), 1,74 − 1.65 (m, 7H), 1.40 − 1.28 (m, 2H) | 2.22, B | 570.3 |
| 359 | (500 MHz, DMSO-d6) δ 10.54 (s, 1H), 9.94 (br d, J = 7.0 Hz, 1H), 8.20 − 8.14 (m, 2H), 7.84 (d, J = 9.2 Hz, 1H), 7.79 − 7.74 (m, 1H), 7.45 (t, J = 9.8 Hz, 1H), 7.37 (d, J = 8.9 Hz, 1H), 4.36 − 4.28 (m, 1H), 4.05 (s, 3H), 3.09 (dd, J = 10.7, 4.0 Hz, 1H), 3.04 − 2.99 (m, 1H), 2.95 − 2.90 (m, 1H), 1.84 − 1.75 (m, 1H), 1.75 − 1.63 (m, 7H), 1.41 − 1.27 (m, 2H) | 2.62, B | 559.0 |
| 360 | (500 MHz, DMSO-d6) δ 10.50 (s, 1H), 9.77 (br d, J = 7.0 Hz, 1H), 8.17 (d, J = 5.2 Hz, 1H), 7.80 − 7.72 (m, 1H), 7.68 (s, 1H), 7.44 (t, J = 9.8 Hz, 1H), 7.27 (d, J = 7.6 Hz, 1H), 7.03 (d, J = 8.5 Hz, 1H), 4.37 − 4.27 (m, 1H), 3.91 (s, 3H), 3.07 (dd, J = 10.7, 4.0 | 2.54, B | 505.0 |

TABLE 3-continued

| | | | |
|---|---|---|---|
| | Hz, 1H), 3.02 - 2.96 (m, 1H), 2.93 - 2.85 (m, 1H), 2.23 (s, 3H), 1.88 - 1.77 (m, 1H), 1.75 - 1.61 (m, 7H), 1.40 - 1.25 (m, 2H) | | |
| 361 | (500 MHz, DMSO-d6) δ 10.57 (s, 1H), 9.98 (br d, J = 7.0 Hz, 1H), 8.40 (d, J = 2.1 Hz, 1H), 8.18 (d, J = 4.3 Hz, 1H), 8.01 (dd, J = 8.7, 2.0 Hz, 1H), 7.82 - 7.75 (m, 1H), 7.46 (t, J = 9.8 Hz, 1H), 7.42 (d, J = 8.9 Hz, 1H), 4.36 - 4.29 (m, 1H), 4.08 (s, 3H), 3.14 (s, 3H), 3.10 (dd, J = 10.5, 3.8 Hz, 1H), 3.04 - 3.00 (m, 1H), 2.95 - 2.91 (m, 1H), 1.81 - 1.74 (m, 1H), 1.73 - 1.65 (m, 7H), 1.40 - 1.28 (m, 2H) | 2.29, B | 569.3 |

TABLE 4

| Ex # | Structure | Name | $^1$H NMR | LC/MS Rt (min) Method | M + H/ M - H |
|---|---|---|---|---|---|
| 362 | 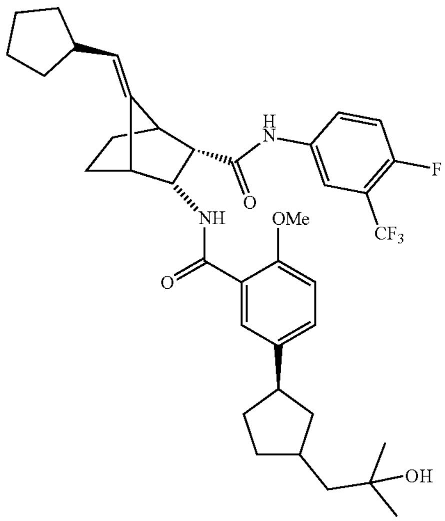 | (1R,2S,3R,4R,Z)-7-(cyclopentyl-methylene)-N-(4-fluoro-3-(trifluoromethyl) phenyl)-3-(5-((1R)-3-(2-hydroxy-2-methylpropyl) cyclopentyl)-2-methoxybenzamido) bicyclo[2.2.1] heptane-2-carboxamide | 1H NMR (400 MHz, DMSO-d6) δ = 10.50 (s, 1H), 9.78 (br d, J = 7.0 Hz, 1H), 8.23 (dd, J = 6.4, 1.8 Hz, 1H), 7.84-7.70 (m, 2H), 7.48 (t, J = 9.6 Hz, 1H), 7.34 (dd, J = 8.4, 2.0 Hz, 1H), 7.07 (d, J = 8.5 Hz, 1H), 5.19 (d, J = 8.9 Hz, 1H), 4.48-4.35 (m, 1H), 4.04 (s, 1H), 3.96 (s, 3H), 3.14 (br dd, J = 10.7, 4.0 Hz, 1H), 2.98 (br s, 1H), 2.70 (br s, 1H), 2.64-2.57 (m, 1H), 2.25-2.07 (m, 2H), 2.04-1.72 (m, 6H), 1.68-1.46 (m, 7H), 1.43-1.23 (m, 5H), 1.11 (s, 6H) | 3.10 | 671.2 |
| 363 | 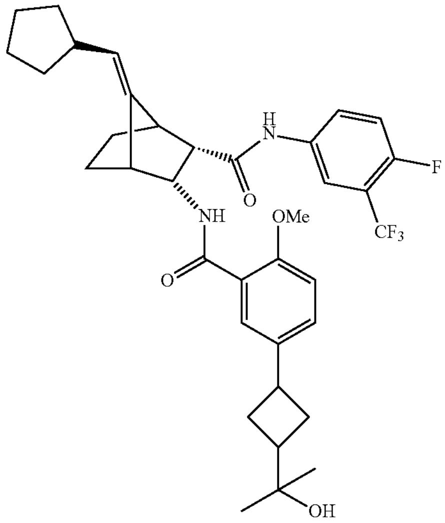 | (1R,2S,3R,4R,Z)-7-(cyclopentyl-methylene)-N-(4-fluoro-3-(trifluoromethyl) phenyl)-3-(5-(3-(2-hydroxypropan-2-yl)cyclobutyl)-2-methoxybenzamido) bicyclo[2.2.1] heptane-2-carboxamide | 1H NMR (500 MHz, DMSO-d6) δ 10.49 (s, 1H), 9.80 (br d, J = 7.0 Hz, 1H), 8.23 (br d, J = 3.7 Hz, 1H), 7.87 (s, 1H), 7.80-7.72 (m, 1H), 7.48 (br t, J = 9.7 Hz, 1H), 7.38 (dd, J = 8.3, 2.0 Hz, 1H), 7.10 (d, J = 8.5 Hz, 1H), 5.18 (br d. J = 9.0 Hz, 1H), 4.46-4.34 (m, 1H), 3.97 (s, 3H), 3.14 (br dd, J = 10.2, 3.7 Hz, 1H), 2.98 (br s, 1H), 2.70 (br s, 1H), 2.65-2.57 (m, 1H), 2.45-2.35 (m, 2H), 2.30 (dt, J = 15.3, 7.8 Hz, 1H), 1.99-1.71 (m, 6H), 1.69-1.49 (m, 4H), 1.46-1.33 (m, 2H), 1.32-1.18 (m, 2H), 1.05 (s, 6H) | 2.94 | 643.4 |

(a) All LC retention times are based on Method C unless otherwise specified.

(b) 1-3 protons were not accounted for in these samples due to overlap with solvent residue and/or artifacts of water suppression.

TABLE 5

| Ex # | Structure | Name | $^1$H NMR | LC/MS Rt (min) Method | M + H/ M − H |
|---|---|---|---|---|---|
| 364 | 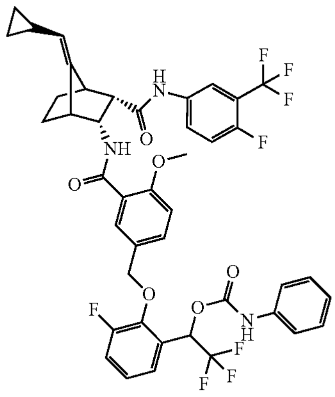 | 1-(2-((3-(((1R,2R,3S,4R,Z)-7-(cyclopropyl-methylene)-3-((4-fluoro-3-(trifluoromethyl) phenyl)carbamoyl) bicyclo[2.2.1]heptan-2-yl)carbamoyl)-4-methoxybenzyl)oxy)-3-fluorophenyl)-2,2,2-trifluoroethyl phenylcarbamate | 1H NMR (500 MHz, DMSO-d6) δ 10.51 (s, 1H), 10.27-10.24 (m, 1H), 9.87 (t, J = 6.2 Hz, 1H), 8.24-8.20 (m, 1H), 8.08 (t, J = 2.6 Hz, 1H), 7.80-7.76 (m, 1H), 7.64 (d, J = 8.1 Hz, 1H), 7.49-7.46 (m, 1H), 7.44 (br d, J = 8.1 Hz, 3H), 7.36-7.32 (m, 1H), 7.31-7.26 (m, 3H), 7.22 (dd, J = 8.5, 3.9 Hz, 1H), 7.01 (t, J = 7.5 Hz, 1H), 6.57 (br t, J = 6.6 Hz, 1H), 5.18-5.12 (m, 2H), 4.68 (d, J = 9.5 Hz, 1H), 4.46-4.41 (m, 1H), 3.99 (d, J = 4.9 Hz, 3H), 3.14 (dt, J = 10.7, 3.6 Hz, 1H), 3.09 (br d, J = 3.1 Hz, 1H), 2.71 (br s, 1H), 1.87-1.76 (m, 2H), 1.49 (dt, J = 8.4, 4.2 Hz, 1H), 1.39 (br s, 2H), 0.77-0.68 (m, 2H), 0.36-0.32 (m, 2H) | 2.98 | 844.1 |
| 365 | 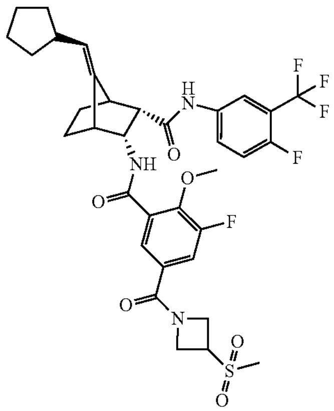 | (1R,2S,3R,4R,7Z)-7-(cyclopentyl-methylidene)-N-[4-fluoro-3-(trifluoromethyl) phenyl]-3-[3-fluoro-5-(3-methanesulfonyl-azetidine-1-carbonyl)-2-methoxybenzamido] bicyclo[2.2.1]heptane-2-carboxamide | 1H NMR (400 MHz, DMSO-d6) δ ppm 10.52 (s, 1H), 9.70 (d, J = 7.3 Hz, 1H), 8.12 (dd, J = 2.6, 6.6 Hz, 1H), 7.98 (dd, J = 1.0, 2.1 Hz, 1H), 7.88-7.76 (m, 1H), 7.71 (dd, J = 2.3, 12.1 Hz, 1H), 7.48 (t, J = 9.8 Hz, 1H), 5.20 (d, J = 8.9 Hz, 1H), 4.66 (br d, J = 7.8 Hz, 1H), 4.53-4.30 (m, 4H), 4.24 (br d, J = 4.8 Hz, 1H), 4.13 (d, J = 3.3 Hz, 3H), 3.19-3.14 (m, 1H), 3.06 (s, 3H), 3.01 (br s, 1H), 2.73 (br s, 1H), 2.64-2.55 (m, 1H), 1.92-1.72 (m, 4H), 1.70-1.52 (m, 4H), 1.41 (br dd, J = 1.8, 5.9 Hz, 2H), 1.34-1.17 (m, 2H) | 2.51 A | 710.2 |
| 366 | 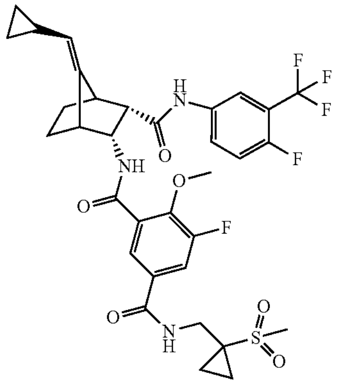 | N3-[(1R,2R,3S,4R,7Z)-7-(cyclopropyl-methylidene)-3-{[4-fluoro 3-(trifluoromethyl) phenyl]carbamoyl} bicyclo[2.2.1]heptan-2-yl]-5-fluoro-N1-[(1-methanesulfonyl-cyclopropyl)methyl]-4-methoxybenzene-1,3-dicarboxamide | 1H NMR (400 MHz, DMSO-d6) δ ppm 10.53 (s, 1H), 9.71 (d, J = 7.3 Hz, 1H), 8.81 (t, J = 6.1 Hz, 1H), 8.25 (d, J = 1.3 Hz, 1H), 8.13 (dd, J = 2.6, 6.5 Hz, 1H), 7.90 (dd, J = 2.3, 12.6 Hz, 1H), 7.82 (td, J = 3.9, 8.0 Hz, 1H), 7.48 (t, J = 9.8 Hz, 1H), 4.71 (d, J = 9.6 Hz, 1H), 4.48 (ddd, J = 3.8, 7.0, 10.7 Hz, 1H), 4.12 (d, J = 3.0 Hz, 3H), 3.82 (d, J = 6.1 Hz, 2H), 3.18 (dd, J = 4.8, 10.5 Hz, 1H), 3.12 (t, J = 3.7 Hz, 1H), 3.06 (s, 3H), 2.79-2.69 (m, 1H), 1.90-1.72 (m, 2H), 1.59-1.35 (m, 3H), 1.28-1.19 (m, 2H), 1.17-1.04 (m, 2H), 0.84-0.64 (m, 2H), 0.36 (dd, J = 2.1, 4.4 Hz, 2H) | 2.37 A | 696.2 |

TABLE 5-continued

| Ex # | Structure | Name | $^1$H NMR | LC/MS Rt (min) Method | M + H/ M − H |
|---|---|---|---|---|---|
| 367 | 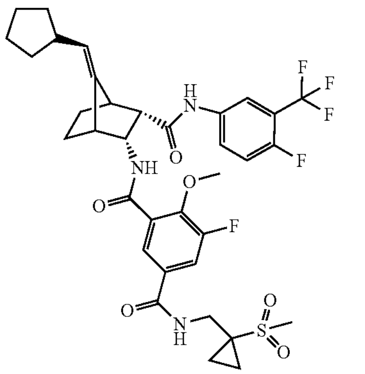 | N3-[(1R,2R,3S,4R,7Z)-7-(cyclopentyl-methylidene)-3-{[4-fluoro-3-(trifluoromethyl) phenyl]carbamoyl} bicyclo[2.2.1]heptan-2-yl]-5-fluoro-N1-[(1-methanesulfonyl-cyclopropyl)methyl]-4-methoxybenzene-1,3-dicarboxamide | 1H NMR (400 MHz, DMSO-d6) δ ppm 10.52 (s, 1H), 9.67 (d, J = 7.1 Hz, 1H), 8.80 (t, J = 5.9 Hz, 1H), 8.25 (d, J = 1.1 Hz, 1H), 8.13 (dd, J = 2.6, 6.4 Hz, 1H), 7.89 (dd, J = 2.2, 12.6 Hz, 1H), 7.85-7.70 (m, 1H), 7.48 (t, J = 9.8 Hz, 1H), 5.20 (d, J = 8.9 Hz, 1H), 4.42 (ddd, J = 3.8, 6.9, 10.6 Hz, 1H), 4.11 (d, J = 3.0 Hz, 3H), 3.82 (d, J = 6.0 Hz, 2H), 3.20-3.13 (m, 1H), 3.06 (s, 3H), 3.01 (br s, 1H), 2.73 (br s, 1H), 2.64-2.55 (m, 1H), 1.91-1.27 (m, 4H), 1.70-1.48 (m, 4H), 1.48-1.35 (m, 2H), 1.33-1.18 (m, 4H), 1.16-1.01 (m, 2H) | 2.61 A | 724.2 |
| 368 | 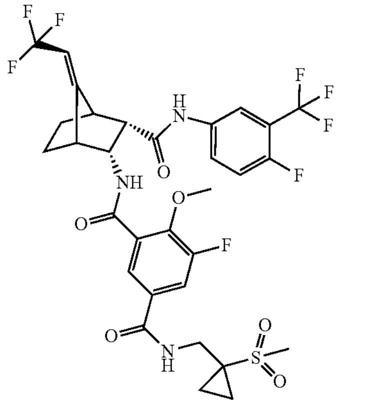 | 5-fluoro-N3-[(1R,2R,3S,4R,7Z)-3-{[4-fluoro-3-(trifluoromethyl) phenyl]carbamoyl}-7-(2,2,2-trifluoroethylidene) bicyclo[2.2.1]heptan-2-yl]-N1-[(1-methanesulfonyl-cyclopropyl)methyl]-4-methoxybenzene-1,3-dicarboxamide | 1H NMR (400 MHz, DMSO-d6) δ ppm 10.65 (s, 1H), 9.78 (d, J = 6.9 Hz, 1H), 8.82 (t, J = 6.1 Hz, 1H), 8.27 (s, 1H), 8.14 (dd, J = 2.5, 6.5 Hz, 1H), 7.91 (dd, J = 2.2, 12.6 Hz, 1H), 7.86-7.71 (m, 1H), 7.51 (t, J = 9.8 Hz, 1H), 5.96 (q, J = 8.0 Hz, 1H), 4.56 (ddd, J = 4.1, 6.8, 10.6 Hz, 1H), 4.12 (d, J = 3.1 Hz, 3H), 3.82 (d, J = 6.0 Hz, 2H), 3.30-3.19 (m, 1H), 3.06 (s, 3H), 3.01 (br s, 1H), 2.01-1.69 (m, 2H), 1.52 (br d, J = 8.0 Hz, 2H), 1.30-1.20 (m, 2H), 1.17-1.05 (m, 2H) | 2.31 A | 724.1 |
| 369 | 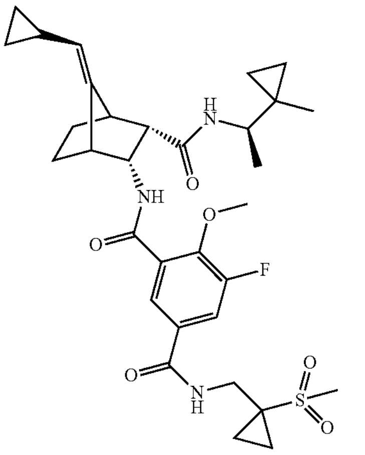 | N3-[(1R,2R,3S,4R,7Z)-7-(cyclopropyl-methylidene)-3-{[(1R)-1-(1-methylcyclopropyl) ethyl]carbamoyl} bicyclo[2.2.1]heptan-2-yl]-5-fluoro-N1-[(1-methanesulfonyl-cyclopropyl)methyl]-4-methoxybenzene-1,3-dicarboxamide | 1H NMR (400 MHz, DMSO-d6) δ ppm 10.00 (d, J = 6.8 Hz, 1H), 8.80 (t, J = 6.0 Hz, 1H), 8.24-8.12 (m, 1H), 7.99 (d, J = 8.6 Hz, 1H), 7.88 (dd, J = 2.4, 12.5 Hz, 1H), 4.65 (d, J = 9.5 Hz, 1H), 4.36-4.22 (m, 1H), 4.13-4.02 (m, 3H), 3.82 (d, J = 6.1 Hz, 2H), 3.45 (dd, J = 7.0, 8.5 Hz, 1H), 3.12-3.02 (m, 4H), 2.96 (dd, J = 4.3, 10.9 Hz, 1H), 2.55 (br d, J = 3.8 Hz, 1H), 1.91-1.69 (m, 2H), 1.53-1.30 (m, 3H), 1.28-1.19 (m, 2H), 1.17-1.10 (m, 2H), 1.05-0.93 (m, 6H), 0.79-0.65 (m, 2H), 0.58-0.48 (m, 1H), 0.42-0.26 (m, 3H), 0.25-0.08 (m, 2H) | 2.25 A | 616.2 |

TABLE 5-continued

| Ex # | Structure | Name | $^1$H NMR | LC/MS Rt (min) Method | M + H/ M − H |
|---|---|---|---|---|---|
| 370 | 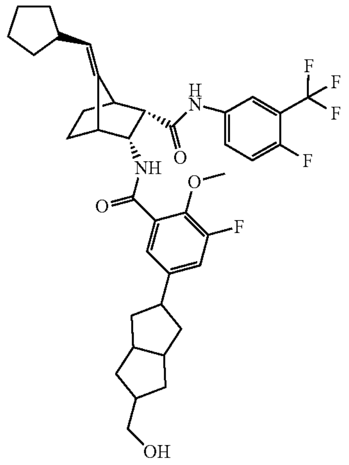 | (1R,2S,3R,4R,7Z)-7-(cyclopentyl-methylidene)-N-[4-fluoro-3-(trifluoromethyl) phenyl]-3-{3-fluoro-5-[5-(hydroxymethyl)-octahydropentalen-2-yl]-2-methoxybenzamido} bicyclo[2.2.1]heptane-2-carboxamide | 1H NMR (400 MHz, DMSO-d6) δ ppm 10.48 (s, 1H), 9.53 (d, J = 7.4 Hz, 1H), 8.12 (dd, J = 2.7, 6.6 Hz, 1H), 7.88-7.72 (m, 1H), 7.57-7.43 (m, 2H), 7.33 (dd, J = 2.1, 12.8 Hz, 1H), 5.19 (d, J = 9.0 Hz, 1H), 4.52-4.30 (m, 2H), 3.96 (d, J = 1.9 Hz, 3H), 3.38-3.36 (m, 2H), 3.18-3.12 (m, 1H), 3.06 (td, J = 6.1, 12.1 Hz, 1H), 2.98 (br s, 1H), 2.72 (br s, 1H), 2.64-2.56 (m, 1H), 2.23-2.03 (m, 3H), 1.99-1.73 (m, 6H), 1.71-1.48 (m, 4H), 1.40 (br d, J = 6.0 Hz, 2H), 1.34-1.17 (m, 4H), 1.08-0.96 (m, 2H) | 2.96 A | 687.3 |
| 371 | 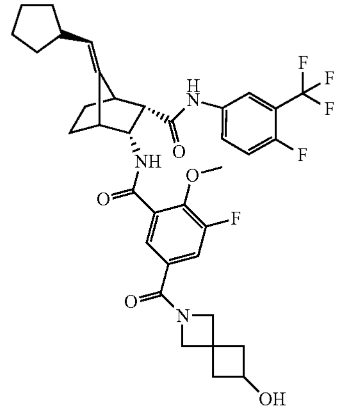 | (1R,2S,3R,4R,7Z)-7-(cyclopentyl-methylidene)-N-[4-fluoro-3-(trifluoromethyl) phenyl]-3-(3-fluoro-5-{6-hydroxy-2-azaspiro[3.3]heptane-2-carbonyl}-2-methoxybenzamido) bicyclo[2.2.1]heptane-2-carboxamide | 1H NMR (400 MHz, DMSO-d6) δ ppm 10.52 (s, 1H), 9.66 (br d, J = 5.6 Hz, 1H), 8.12 (dd, J = 2.6, 6.6 Hz, 1H), 7.94 (s, 1H), 7.86-7.75 (m, 1H), 7.72-7.62 (m, 1H), 7.48 (t, J = 9.8 Hz, 1H), 5.20 (d, J = 9.0 Hz, 1H), 5.03 (d, J = 6.1 Hz, 1H), 4.47-4.37 (m, 1H), 4.34-4.18 (m, 2H), 4.10 (d, J = 3.0 Hz, 3H), 3.99 (br d, J = 19.8 Hz, 2H), 3.16 (dd, J = 4.7, 10.8 Hz, 1H), 3.00 (br s, 1H), 2.73 (br s, 1H), 2.64-2.57 (m, 1H), 2.44 (ddd, J = 3.0, 6.8, 9.4 Hz, 1H), 2.03-1.92 (m, 2H), 1.89-1.73 (m, 4H), 1.71-1.52 (m, 4H), 1.50-1.35 (m, 2H), 1.34-1.14 (m, 2H) | 2.53 A | 688.2 |
| 372 | 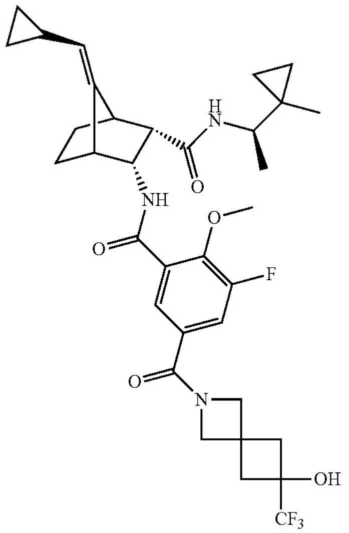 | (1R,2S,3R,4R,7Z)-7-(cyclopropyl-methylidene)-3-{3-fluoro-5-[6-hydroxy-6-(trifluoromethyl)-2-azaspiro[3.3]heptane-2-carbonyl]-2-methoxybenzamido}-N-[(1R)-1-(1-methylcyclopropyl) ethyl]bicyclo[2.2.1] heptane-2-carboxamide | 1H NMR (400 MHz, DMSO-d6) δ ppm 10.52 (s, 1H), 9.66 (br d, J = 5.6 Hz, 1H), 8.12 (dd, J = 2.6, 6.6 Hz, 1H), 7.94 (s, 1H), 7.86-7.75 (m, 1H), 7.72-7.62 (m, 1H), 7.48 (t, J = 9.8 Hz, 1H), 5.20 (d, J = 9.0 Hz, 1H), 5.03 (d, J = 6.1 Hz, 1H), 4.47-4.37 (m, 1H), 4.34-4.18 (m, 2H), 4.10 (d, J = 3.0 Hz, 3H), 3.99 (br d, J = 19.8 Hz, 2H), 3.16 (dd, J = 4.7, 10.8 Hz, 1H), 3.00 (br s, 1H), 2.73 (br s, 1H), 2.64-2.57 (m, 1H), 2.44 (ddd, J = 3.0, 6.8, 9.4 Hz, 1H), 2.03-1.92 (m, 2H), 1.89-1.73 (m, 4H), 1.71-1.52 (m, 4H), 1.50-1.35 (m, 2H), 1.34-1.14 (m, 2H) | 2.33 A | 648.3 |

TABLE 5-continued

| Ex # | Structure | Name | $^{1}$H NMR | LC/MS Rt (min) Method | M + H/ M − H |
|---|---|---|---|---|---|
| 373 | 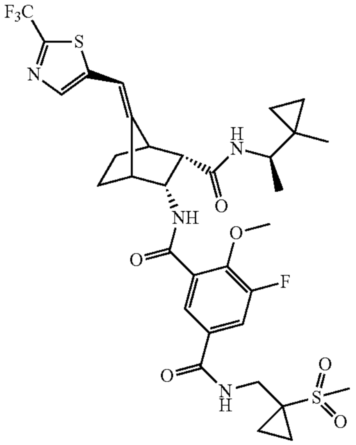 | 5-fluoro-N1-[(1-methanesulfonyl-cyclopropyl)methyl]-4-methoxy-N3-[(1R,2R,3S,4R,7Z)-3-{[(1R)-1-(1-methylcyclopropyl) ethyl]carbamoyl}-7-{[2-(trifluoromethyl)-1,3-thiazol-5-yl]methylidene} bicyclo[2.2.1]heptan-2-yl]benzene-1,3-dicarboxamide | 1H NMR (400 MHz, DMSO-d6) δ ppm 10.20 (d, J = 6.5 Hz, 1H), 8.83 (t, J = 6.0 Hz, 1H), 8.27 (d, J = 1.3 Hz, 1H), 8.13 (d, J = 8.8 Hz, 1H), 8.10 (s, 1H), 7.90 (dd, J = 2.3, 12.5 Hz, 1H), 6.68 (s, 1H), 4.47-4.28 (m, 1H), 4.10 (d, J = 3.0 Hz, 3H), 3.82 (d, J = 6.3 Hz, 2H), 3.49 (dd, J = 6.9, 8.4 Hz, 1H), 3.14 (dd, J = 4.4, 10.8 Hz, 1H), 3.06 (s, 3H), 2.86 (br s, 1H), 1.97-1.81 (m, 2H), 1.52 (br d, J = 7.0 Hz, 2H), 1.30-1.21 (m, 2H), 1.18-1.10 (m, 2H), 1.05 (d, J = 6.9 Hz, 3H), 1.01 (s, 3H), 0.60-0.50 (m, 1H), 0.40-0.33 (m, 1H), 0.28-0.13 (m, 2H) | 2.38 A | 727.2 |
| 374 | 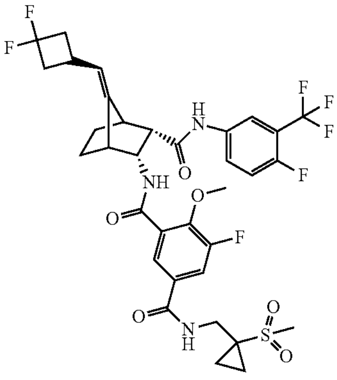 | N3-[(1R,2R,3S,4R,7Z)-7-[(3,3-difluorocyclobutyl) methylidene]-3-{[4-fluoro-3-(trifluoromethyl) phenyl]carbamoyl} bicyclo[2.2.1]heptan-2-yl]-5-fluoro-N1-[(1-methanesulfonyl-cyclopropyl)methyl]-4-methoxybenzene-1,3-dicarboxamide | 1H NMR (400 MHz, DMSO-d6) δ ppm 10.55 (s, 1H), 9.68 (d, J = 7.3 Hz, 1H), 8.80 (t, J = 6.0 Hz, 1H), 8.28-8.20 (m, 1H), 8.12 (dd, J = 2.5, 6.5 Hz, 1H), 7.90 (dd, J = 2.3, 12.6 Hz, 1H), 7.86-7.77 (m, 1H), 7.48 (t, J = 9.8 Hz, 1H), 5.41 (d, J = 8.4 Hz, 1H), 4.42 (ddd, J = 4.1, 6.9, 10.6 Hz, 1H), 4.11 (d, J = 3.1 Hz, 3H), 3.82 (d, J = 6.0 Hz, 2H), 3.21-3.14 (m, 1H), 3.05 (s, 3H), 3.01 (br s, 1H), 2.97-2.72 (m, 4H), 2.48-2.37 (m, 2H), 1.89-1.73 (m, 2H), 1.51-1.35 (m, 2H), 1.27-1.20 (m, 2H), 1.16-1.03 (m, 2H) | 2.42 A | 746.2 |
| 375 | 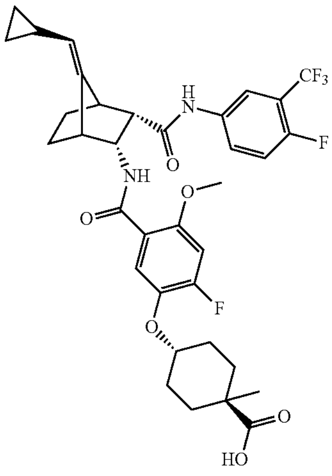 | (1R,4r)-4-(5-(((1R,2R,3S,4R,Z)-7-(cyclopropyl-methylene)-3-((4-fluoro-3-(trifluoromethyl) phenyl)carbamoyl) bicyclo[2.2.1]heptan-2-yl)carbamoyl)-2-fluoro-4-methoxyphenoxy)-1-methylcyclohexane-1-carboxylic acid | 1H NMR (500 MHz, DMSO-d6) δ 10.46 (s, 1H), 9.88 (d, J = 7.0 Hz, 1H), 8.26-8.14 (m, 1H), 7.73 (br dd, J = 5.6, 4.2 Hz, 1H), 7.67 (d, J = 9.8 Hz, 1H), 7.37 (t, J = 9.7 Hz, 1H), 7.07 (d, J = 12.7 Hz, 1H), 4.66 (d, J = 9.5 Hz, 1H), 4.46-4.38 (m, 1H), 4.29 (br s, 1H), 4.26-4.15 (m, 1H), 4.09-3.84 (m, 3H), 3.13-3.05 (m, 2H), 1.88-1.81 (m, 1H), 1.81-1.76 (m, 2H), 1.72-1.64 (m, 3H), 1.58-1.52 (m, 2H), 1.47 (br dd, J = 8.5, 4.4 Hz, 1H), 1.42-1.36 (m, 2H), 1.31-1.25 (m, 1H), 1.13 (s, 3H), 0.95-0.83 (m, 2H), 0.74-0.64 (m, 2H), 0.44-0.25 (m, 2H) | 2.70 | 677.1 |

TABLE 5-continued

| Ex # | Structure | Name | $^1$H NMR | LC/MS Rt (min) Method | M + H/ M − H |
|---|---|---|---|---|---|
| 376 | 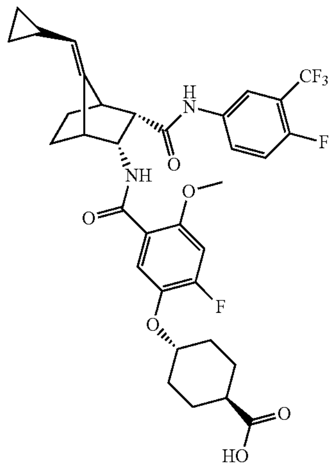 | (1R,4r)-4-(5-(((1R,2R,3S,4R,Z)-7-(cyclopropyl-methylene)-3-((4-fluoro-3-(trifluoromethyl) phenyl)carbamoyl) bicyclo[2.2.1]heptan-2-yl)carbamoyl)-2-fluoro-4-methoxyphenoxy) cyclohexane-1-carboxylic acid | 1H NMR (500 MHz, DMSO-d6) δ 10.50 (s, 1H), 9.93-9.82 (m, 1H), 8.20 (dd, J = 6.4, 2.3 Hz, 1H), 8.07 (s, 2H), 7.80-7.73 (m, 1H), 7.68 (d, J = 9.9 Hz, 1H), 7.43 (t, J = 9.6 Hz, 1H), 7.13 (d, J = 12.7 Hz, 1H), 4.67 (d, J = 9.9 Hz, 1H), 4.46-4.33 (m, 2H), 4.22 (dd, J = 5.4, 2.7 Hz, 2H), 3.96 (s, 3H), 3.16-3.04 (m, 2H), 1.81-1.76 (m, 3H), 1.70-1.62 (m, 3H), 1.43-1.36 (m, 4H), 1.31-1.27 (m, 2H), 0.93-0.88 (m, 2H), 0.76-0.65 (m, 2H) | 2.58 | 663.3 |
| 377 | 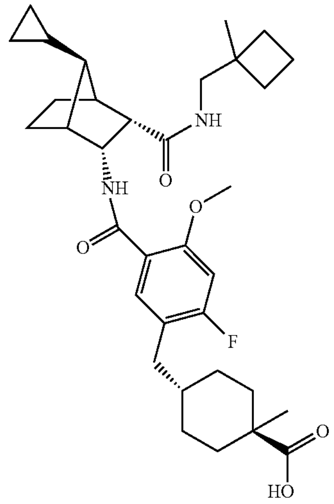 [SMILES: COc1cc(F)c(C[C@H]2CC[C@](C)(C(=O)O)CC2)cc1C(=O)N[C@@H]1C2CCC([C@@H]2C2CC2)[C@@H]1C(=O)NCC1(C)CCC1] | (1R,4r)-4-(5-(((1R,2R,3S,4R,Z)-7-(cyclopropyl-methylene)-3-(((1-methylcyclobutyl) methyl)carbamoyl) bicyclo[2.2.1]heptan-2-yl)carbamoyl)-2-fluoro-4-methoxyphenoxy)-1-methylcyclohexane-1-carboxylic acid | 1H NMR (500 MHz, DMSO-d6) δ 9.93 (br d, J = 7.1 Hz, 1H), 8.08-7.98 (m, 1H), 7.65 (d, J = 9.9 Hz, 1H), 7.17-7.01 (m, 1H), 4.63 (d, J = 9.4 Hz, 1H), 4.41-4.18 (m, 2H), 3.93 (s, 3H), 3.23-3.11 (m, 1H), 3.03-2.90 (m, 5H), 1.85-1.76 (m, 5H), 1.74-1.68 (m, 4H), 1.62-1.51 (m, 4H), 1.50-1.41 (m, 1H), 1.39-1.23 (m, 4H), 1.15 (s, 3H), 1.06-0.96 (m, 3H), 0.92-0.81 (m, 1H), 0.73-0.53 (m, 2H), 0.48--0.04 (m, 2H) | 2.57 | 597.2 |

(a) All LC retention times are based on Method C unless otherwise specified.

(b) 1-3 protons were not accounted for in these samples due to overlap with solvent residue and/or artifacts of water suppression.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

What is claimed is:

1. A compound of Formula (I):

(I)

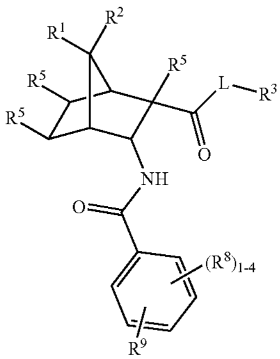

or a pharmaceutically acceptable salt thereof, wherein:

L is —O— or —NH—;

$R^1$ is $C_{1-3}$ alkyl substituted with 1 aryl or $C_{3-6}$ cycloalkyl substituent;

$R^2$ is H; or $R^1$ and $R^2$ are taken together to be $=CR^6R^7$, wherein "=" is a double bond;

or $R^1$ and $R^2$ together with the carbon atom to which they are both attached form a dioxolanyl substituted with 0-1 aryl substituent;

$R^3$ is $C_{1-8}$ alkyl substituted with 0-5 halo, CN, —OH, or $—OC_{1-3}$ alkyl substituents, $—(CR^dR^d)_n—C_{3-10}$-carbocyclyl substituted with 0-5 $R^4$ or $—(CR^dR^d)_n$-3 to 12-membered heterocyclyl comprising 1-4 heteroatoms selected from O, $S(=O)_P$, N, $NR^{4a}$, and substituted with 0-5 $R^4$;

$R^4$ is halo, CN, —OH, $—SF_5$, $—S(=O)_pR^c$, $C_{1-4}$ alkyl substituted with 0-5 halo, —OH, or $—OC_{1-4}$ alkyl substituents, or $—OC_{1-4}$ alkyl substituted with 0-5 halo substituents, —, $—(CR^dR^d)_n—C_{3-10}$ carbocyclyl substituted with 0-5 $R^e$, or $—(CR^dR^d)_n$-4- to 6-membered heterocyclyl comprising 1-4 heteroatoms selected from O, $S(=O)_p$, N, and $NR^{4a}$;

$R^{4a}$ is H, $C_{1-4}$ alkyl, or $—S(=O)_2CF_3$;

$R^5$ is H, halo, OH, $C_{1-4}$ alkyl substituted with 0-5 halo substituents, or $—OC_{1-4}$ alkyl substituted with 0-5 halo substituents;

$R^6$ is H, halo, CN, $C_{1-7}$alkyl substituted with 0-3 $R^{6a}$, $C_{2-7}$ alkenyl substituted with 0-3 $R^{6a}$, $C_{2-7}$ alkynyl substituted with 0-3 $R^{6a}$, $—C(=O)OR^{6b}$, $—CONR^{6b}R^{6b}$, $—(CH_2)_n—C_{3-6}$ carbocyclyl substituted with 0-5 $R^{14}$, or 3- to 12-membered heterocyclyl comprising 1-4 heteroatoms selected from O, $S(=O)_p$, N, or $NR^{13}$, and substituted with 0-5 $R^{14}$; $R^{6a}$ is halo, —OH, $—OC_{1-4}$ alkyl, $C_{1-4}$ alkyl, aryl, or $C_{3-6}$ cycloalkyl substituted with 0-4 halo substituents;

$R^{6b}$ is H, $C_{1-4}$ alkyl substituted with 0-1 aryl, or $C_{3-6}$ cycloalkyl substituted with 0-4 halo substituents;

$R^7$ is H or $C_{1-4}$ alkyl;

$R^8$ is H, halo, CN, $—NR^7R^7$ or $—OC_{1-4}$ alkyl substituted with 0-5 halo, OH, $—OC_{1-4}$ alkyl, $C_{3-6}$ cycloalkyl, aryl, or 4- to 9-membered heterocyclyl comprising 1-4 heteroatoms selected from O, $S(=O)_p$, and N substituents;

$R^9$ is $—C(=O)OR^{15}$, $—C(=O)NR^{15}R^{15}$, $—S(=O)_pNR^{15}R^{15}$, $—S(=O)_pR^c$, $—NR^{17}R^{17}$, $C_{1-8}$ alkyl substituted with 0-4 $R^{10}$ and 0-2 $R^{11}$, $C_{2-8}$ alkenyl substituted with 0-2 $R^{10}$ and 0-2 $R^{11}$, $C_{2-8}$ alkynyl substituted with 0-2 $R^{10}$ and 0-2 $R^{11}$, $C_{3-9}$ cycloalkyl substituted with 0-2 $R^{10}$ and 0-2 $R^{11}$, $C_{3-9}$cycloalkenyl substituted with 0-2 $R^{10}$ and 0-2 $R^{11}$, fused $C_{3-6}$ cycloalkyl substituted with 0-2 $R^{10}$ and 0-2 $R^{11}$, $C_{6-9}$ spirocycloalkyl substituted with 0-2 $R^{10}$ and 0-2 $R^{11}$, A-$C_{3-6}$ carbocyclyl substituted with 0-2 $R^{10}$ and 0-2 $R^{11}$, or A-4- to 9-membered heterocyclyl comprising 1-4 heteroatoms selected from O, $S(=O)_p$, N and $NR^{18}$, and substituted with 0-2 $R^{10}$ and 0-2 $R^{11}$;

A is —O—, —S—, $—CH_2O—$, or $—OCH_2—$;

$R^{10}$ is halo, CN, or $C_{1-6}$ alkyl substituted with 0-4 $R^{11}$;

$R^{11}$ is halo, $—OR^b$, $—NR^aR^a$, $—NR^aC(=O)R^b$, $—NR^aC(=O)OR^b$, $—NR^aC(=O)NR^aR^a$, $—NR^aS(=O)_pR^c$, $—NR^aS(=O)_pNR^aR^a$, $—C(=O)R^b$, $—C(=O)OR^b$, $—C(=O)NR^aR^a$, $—C(=O)NR^aS(=O)_pR^c$, $—OC(=O)R^b$, $—OC(=O)OR^b$, $—OC(=O)NR^aR^a$, $—OC(=O)NR^aOR^b$, $—S(=O)_pR^c$, $—S(=O)_pNR^aR^a$, $C_{3-9}$ carbocyclyl substituted with 0-5 $R^e$, 3- to 12-membered heterocyclyl comprising 1-4 heteroatoms selected from O, $S(=O)_p$, N, and $NR^{12}$, and substituted with 0-5 $R^e$;

$R^{12}$ is H, $C_{1-4}$ alkyl substituted with 0-4 halo or $OR^b$ substituents, or aryl;

$R^{13}$ is H, $C(=O)C_{1-4}$ alkyl, $C_{1-3}$ alkyl substituted with 0-3 $Si(C_{1-3}\ alkyl)_3$, or aryl substituted with 0-2 halo substituents;

$R^{14}$ is halo, CN, $C_{1-4}$ alkyl substituted with 0-3 halo substituents, $—OC_{1-4}$ alkyl substituted with 0-3 halo substituents, $—(CH_2)_nNR^aR^a$, $—(CH_2)_n$-aryl substituted with 0-3 $R^e$, —O-aryl substituted with 0-3 $R^e$, or $—(CH_2)_n$-3- to 12-membered heterocyclyl comprising 1-4 heteroatoms selected from O, $S(=O)_p$, and N, and substituted with 0-3 $R^e$;

$R^{15}$ is H, $C_{1-6}$ alkyl substituted with 0-5 $R^e$, $C_{2-6}$ alkenyl substituted with 0-5 $R^e$, $C_{2-6}$ alknyl substituted with 0-5 $R^e$, $—(CH_2)_n—C_{3-10}$ carbocyclyl substituted with 0-5 $R^e$, or $—(CH_2)_n$-3- to 12-membered heterocyclyl comprising 1-4 heteroatoms selected from O, $S(=O)_p$, N and $NR^{16}$, and substituted with 0-5 $R^e$; or $R^{15}$ and $R^{15}$ together with the nitrogen atom to which they are both attached form a 3-to 12-membered heterocyclyl comprising 1-4 heteroatoms selected from O, $S(=O)_p$, N, and $NR^{16}$, and substituted with 0-5 $R^e$;

$R^{16}$ is H, $C_{1-6}$ alkyl substituted with 0-5 $R^e$, $—C(=O)R^f$, $—C(=O)OR^f$, $—C(=O)NR^fR^f$, $—S(=O)_pR^f$, or $—S(=O)_pNR^fR^f$;

$R^{17}$ is H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, $—(CH_2)_n$-$C_{3-10}$ carbocyclyl substituted with 0-5 $R^e$, or $—(CH_2)_n$-4- to 12-membered heterocyclyl comprising 1-4 heteroatoms selected from O, $S(=O)_p$, N, and $NR^{18}$, and substituted with 0-5 $R^e$;

$R^{18}$ is H, $C_{1-4}$ alkyl substituted with 0-4 halo or —OH substituents, $—C(=O)R^b$, —C(=O)OR, $—C(=O)NR^aR^a$, $—S(=O)_pR^c$, —S(=O), $NR^aR^a$, aryl substituted with 0-5 $R^e$, $C_{3-6}$ cycloalkyl substituted with 0-5 $R^e$, or 4- to 6-membered heterocyclyl comprising 1-4 heteroatoms selected from O, $S(=O)_p$, and N, and substituted with 0-5 $R^e$;

$R^a$ is H, $C_{1-6}$ alkyl substituted with 0-8 $R^e$, $C_{2-6}$ alkenyl substituted with 0-5 $R^e$, $C_{2-6}$ alkynyl substituted with 0-5 $R^e$, —$(CH_2)_n$-$C_{3-10}$ carbocyclyl substituted with 0-5 $R^e$, or —$(CH_2)_n$-3- to 12-membered heterocyclyl comprising 1-5 heteroatoms selected from O, $S({=}O)_p$, and N, and substituted with 0-5 $R^e$; or $R^a$ and $R^a$ together with the nitrogen atom to which they are both attached form a 3- to 12-membered heterocyclyl comprising 1-4 heteroatoms selected from O, $S({=}O)_p$, and N, and substituted with 0-5 $R^e$;

$R^b$ is H, $C_{1-6}$ alkyl substituted with 0-5 $R^e$, $C_{2-6}$ alkenyl substituted with 0-5 $R^e$, $C_{2-6}$ alkynyl substituted with 0-5 $R^e$, —$(CH_2)_n$—$C_{3-10}$carbocyclyl substituted with 0-5 $R^e$, or —$(CH_2)_n$-3- to 12-membered heterocyclyl comprising 1-5 heteroatoms selected from O, $S({=}O)_p$, and N, and substituted with 0-5 $R^e$;

$R^c$ is $C_{1-6}$ alkyl substituted with 0-5 $R^e$, $C_{2-6}$alkenyl substituted with 0-5 $R^e$, $C_{2-6}$ alkynyl substituted with 0-5 $R^e$, $C_{3-6}$ carbocyclyl substituted with 0-5 $R^e$, or 3-to 12-membered heterocyclyl comprising 1-5 heteroatoms selected from O, $S({=}O)_p$, and N, and substituted with 0-5 $R^e$;

$R^d$ is H, $C\text{-}_{1-4}$ alkyl, or $C_{3-6}$ cycloalkyl;

$R^e$ is halo, CN, $NO_2$, =O, $C_{1-6}$ alkyl substituted with 0-5 $R^g$, $C_{2-6}$ alkenyl substituted with 0-5 $R^g$, $C_{2-6}$ alkynyl substituted with 0-5 $R^g$, —$(CH_2)_n$—$C_{3-6}$ carbocyclyl substituted with 0-5 $R^g$, —$(CH_2)_n$-3- to 12-membered heterocyclyl comprising 1-5 hetero atoms selected from O, $S({=}O)_p$, and N, and substituted with 0-5 $R^g$, —$(CH_2)_nOR^f$, —$C({=}O)R^f$, —$C({=}O)OR^f$, —$C({=}O)NR^fR^f$, —$NR^fC({=}O)R^f$, —$S({=}O)_pR^f$, —$S({=}O)_pNR^fR^f$, —$NR^fS({=}O)_pR^f$, —$NR^fC({=}O)OR^f$, —$OC({=}O)NR^fR^f$, or —$(CH_2)_nNR^fR^f$;

$R^f$ is H, $C_{1-6}$ alkyl, $C_{3-6}$ cycloalkyl, aryl, or 3- to 12-membered heterocyclyl comprising 1-4 heteroatoms selected from O, $S({=}O)_p$, and N; or $R^f$ and $R^f$ together with the nitrogen atom to which they arm both attached form a 3- to 12-membered heterocyclyl comprising 1-4 heteroatoms selected from O, $S({=}O)_p$, and N;

$R^g$ is halo, CN, OH, $OC_{1-6}$alkyl, $C_{1-6}$alkyl, $C_{3-6}$ cycloalkyl, or aryl;

n is zero, 1, 2, or 3; and p is zero, 1, or 2.

2. The compound of claim 1, having Formula (II):

(II)

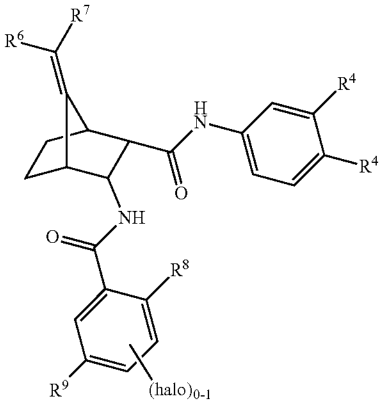

or a pharmaceutically acceptable salt thereof, wherein:

$R^4$ is halo, $C_{1-4}$ alkyl substituted with 0-3 halo substituents, or —$OC_{1-4}$ alkyl substituted with 0-3 halo substituents;

$R^6$ is halo, CN, $C_{1-6}$ alkyl substituted with 0-3 $R^{6a}$, $C_{2-6}$ alkenyl substituted with 0-3 $R^{6a}$, $C_{2-6}$ alkynyl substituted with 0-3 $R^{6a}$, $C_{3-6}$ cycloalkyl substituted with 0-3 $R^{14}$, $C_{3-6}$ cycloalkenyl substituted with 0-3 $R^{14}$, phenyl substituted with 0-3 $R^{14}$, or 5- to 6-membered heterocyclyl comprising 1-3 heteroatoms selected from O, $S({=}O)_p$, N, and $NR^{13}$, and substituted with 0-3 $R^{14}$;

$R^7$ is H or $C_{1-2}$ alkyl;

$R^{6a}$ is halo, —$OC_{1-4}$ alkyl, $C_{1-6}$ cycloalkyl, or phenyl;

$R^8$ is H, halo, CN, or —$OC_{1-4}$ alkyl substituted with 0-4 halo, OH, or —$OC_{1-4}$ alkyl;

$R^9$ is $C_{1-7}$ alkyl substituted with 0-3 $R^{10}$ and 0-2 $R^{11}$, $C_{2-7}$ alkenyl substituted with 0-2 $R^{10}$ and 0-2 $R^{11}$, $C_{2-7}$ alkynyl substituted with 0-2 $R^{10}$ and 0-2 $R^{11}$, $C_{3-9}$ cycloalkyl substituted with 0-2 $R^{10}$ and 0-2 $R^{10}$, or $C_{6-9}$ spirocycloalkyl substituted with 0-2 $R^{10}$ and 0-2 $R^{11}$, —$CH_2$—O—$C_{6-9}$ carbocyclyl substituted with 0-2 $R^{10}$ and 0-2 $R^{11}$, or —O—$C_{3-6}$ cycloalkyl substituted with 0-2 $R^{10}$ and 0-2 $R^{11}$;

$R^{10}$ is halo, CN, or $C_{1-5}$ alkyl substituted with 0-4 halo or —OH substituents;

$R^{11}$ is —$OR^b$, —$NR^aR^a$, —$NR^aC({=}O)R^b$, —$NR^aC({=}O)OR^b$, —$NR^aC({=}O)NR^aR^a$, —$NR^aS({=}O)_pR^c$, —$NR^aS({=}O)_pNR^aR^a$, —$C({=}O)R^b$, —$C({=}O)OR^b$, —$C({=}O)NR^aR^a$, —$C({=}O)NR^aS({=}O)$, $R^c$, —$OC({=}O)R^b$, —$OC({=}O)NR^aR^a$, —$S({=}O)$, $R^e$, —$S({=}O)_pNR^aR^a$, aryl substituted with 0-4 $R^e$, $C_{3-6}$ cycloalkyl substituted with 0-4 $R^c$, or 4- to 6-membered heterocyclyl comprising 1-4 heteroatoms selected from O, $S({=}O)_p$, N and $NR^{12}$, and substituted with 0-4 $R^e$;

$R^{12}$ is H, $C_{1-2}$ alkyl, or phenyl;

$R^{13}$ is H, $C({=}O)C_{1-3}$ alkyl, or $C_{1-3}$ alkyl substituted with 0-2 aryl substituted with 0-2 halo substituents;

$R^{14}$ is halo, CN, $C_{1-4}$ alkyl substituted with 0-3 halo, —$OC_{1-4}$ alkyl substituted with 0-3 halo, —$(CH_2)_{0-2}$—$NR^aR^a$, —$(CH_2)_{0-2}$-aryl substituted with 0-3 $R^c$, —O-aryl substituted with 0-3 $R^e$, or —$(CH_2)_{0-2}$-4- to 9-membered heterocyclyl comprising 1-4 heteroatoms selected from O, $S({=}O)_p$, and N, and substituted with 0-3 $R^e$;

$R^a$ is H, $C_{1-8}$ alkyl substituted with 0-4 $R^e$, $C_{2-5}$ alkenyl substituted with 0-4 $R^e$, $C_{2-5}$ alkynyl substituted with 0-4 $R^e$, —$(CH_2)_n$—$C_{3-10}$ carbocyclyl substituted with 0-4 $R^e$, or —$(CH_2)_n$-4- to 9-membered heterocyclyl comprising 1-4 heteroatoms selected from O, $S({=}O)_p$, and N, and substituted with 0-4 $R^e$; or $R^a$ and $R^a$ together with the nitrogen atom to which they are both attached form a 4- to 9-membered heterocyclyl comprising 1-4 heteroatoms selected from 0, $S({=}O)_p$, and N, and substituted with 0-4 $R^c$;

$R^b$ is H, $C_{1-5}$ alkyl substituted with 0-4 $R^e$, $C_{2-5}$ alkenyl substituted with 0-4 $R^e$, $C_{2-5}$ alkynyl substituted with 0-4 $R^e$, —$(CH_2)_n$—$C_{3-10}$ carbocyclyl substituted with 0-4 $R^c$, or —$(CH_2)_n$-4- to 9-membered heterocyclyl comprising 1-4 heteroatoms selected from O, $S({=}O)_p$, and N, and substituted with 0-4 $R^c$;

$R^c$ is $C_{1-5}$ alkyl substituted with 0-4 $R^e$, $C_{2-5}$ alkenyl substituted with 0-4 $R^e$, $C_{2-5}$ alkynyl substituted with 0-4 $R^c$, $C_{3-6}$ carbocyclyl substituted with 0-4 $R^e$, or 4-to 9-membered heterocyclyl comprising 1-4 heteroatoms selected from 0, $S({=}O)_p$, and N, and substituted with 0-4 $R^c$;

$R^e$ is halo, CN, =O, $C_{1-6}$ alkyl substituted with 0-5 $R^g$, $C_{2-6}$ alkenyl substituted with 0-5 $R^g$, $C_{2-6}$ alkynyl substituted with 0-5 $R^g$, —$(CH_2)_n$—$C_{3-6}$ carbocyclyl substituted with 0-5 $R^g$, —$(CH_2)_n$—4- to 9-membered heterocyclyl comprising 1-4 heteroatoms selected from O, $S(=O)_p$, and N, and substituted with 0-5 $R^g$, $-(CH_2)_nOR^f$, $-C(=O)OR^f$, $S(=O)_pR^f$, $C(=O)NR^fR^f$, $NR^fC(=O)R^f$, $S(=O)_pNR^fR^f$, $NR^fS(=O)_pR^f$, $NR^fC(=O)OR^f$, or $-(CH_2)NR^fR^f$;

$R^f$ is H, $C_{1-6}$ alkyl, $C_{3-6}$ cycloalkyl, or aryl; or $R^f$ and $R^f$ together with the nitrogen atom to which they are both attached form a 4- to 9-membered heterocyclyl comprising 1-4 heteroatoms selected from O, $S(=O)_p$, and N;

$R^g$ is halo, CN, OH, $C_{1-4}$ alkyl, $C_{3-6}$ cycloalkyl, or aryl, n is zero, 1, 2, or 3; and p is zero, 1, or 2.

3. The compound of claim 2, or a pharmaceutically acceptable salt thereof, wherein:

$R^4$ is halo or $C_{1-3}$ alkyl substituted with 0-3 halo substituents;

$R^6$ is $C_{1-5}$ alkyl substituted with 0-3 $R^{6a}$, $C_{3-6}$ cycloalkyl substituted with 0-3 $R^{14}$, or 5- to 6-membered heterocyclyl comprising 1-3 heteroatoms selected from 0, $S(=O)_p$, N, and $NR^{13}$, and substituted with 0-3 $R^{14}$;

$R^{6a}$ is halo, $-OC_{1-4}$ alkyl, or $C_{3-6}$ cycloalkyl $R^7$ is H;

R is $-OC_{1-3}$ alkyl substituted with 0-2 halo or OH substituents;

$R^9$ is $C_{1-7}$ alkyl substituted with 0-3 $R^{10}$ and 0-2 $R^{14}$;

$R^{10}$ is halo, CN or $C_{1-4}$ alkyl substituted with 0-4 halo substituents;

$R^{11}$ is $-OR^b$, $-NR^aR^a$, $-NR^aC(=O)R^b$, $-NR^aC(=O)OR^b$, $-C(=O)R^b$, $-C(=O)OR^b$, $-C(=O)NR^aR^a$, $-OC(=O)NR^aR^a$, aryl substituted with 0-3 Rr, $C_{3-6}$ cycloalkyl substituted with 0-3 $R^e$, or 4- to 6-membered heterocyclyl comprising 1-4 heteroatoms selected from O, $S(=O)_p$, N and $NR^{12}$, and substituted with 0-3 $R^e$;

$R^{12}$ is H, $C_{1-2}$ alkyl, or phenyl;

$R^{14}$ is halo, CN, $C_{1-4}$ alkyl substituted with 0-3 halo substituents, $-OC_{1-4}$ alkyl substituted with 0-3 halo substituents, $-(CH_2)_{0-2}-NR^aR^a$, $-(CH_2)_{0-2}$-aryl substituted with 0-3 $R^e$, —O-aryl substituted with 0-3 $R^e$, or $-(CH_2)_{0-2}$-4- to 9-membered heterocyclyl comprising 1-4 heteroatoms selected from O, $S(=O)_p$, and N, and substituted with 0-3 $R^e$;

$R^a$ is H, $C_{1-8}$ alkyl substituted with 0-4 $R^1$, $C_{2-5}$ alkenyl substituted with 0-4 $R^e$, $C_{2-5}$ alkynyl substituted with 0-4 $R^e$, $-(CH_2)_n-C_{3-10}$ carbocyclyl substituted with 0-4 $R^b$, or $-(CH_2)_n$—4- to 9-membered heterocyclyl comprising 1-4 heteroatoms selected from O, $S(=O)_p$, and N, and substituted with 0-4 $R^e$; or $R^a$ and $R^a$ together with the nitrogen atom to which they are both attached form a 4- to 9-membered heterocyclyl comprising 1-4 heteroatoms selected from 0, $S(=O)_p$, and N, and substituted with 0-4 $R^e$;

$R^b$ is H, $C_{1-4}$ alkyl substituted with 0-4 $R^e$, $C_{2-4}$ alkenyl substituted with 0-4 $R^e$, $C_{2-5}$ alkynyl substituted with 0-4 $R^e$, $-(CH_2)_n-C_{3-10}$ carbocyclyl substituted with 0-3 $R^c$, or $-(CH_2)_n$—4- to 9-membered heterocyclyl comprising 1-4 heteroatoms selected from O, $S(=O)_p$, and N, and substituted with 0-3 $R^e$;

$R^c$ is halo, CN, =O, $C_{1-5}$ alkyl substituted with 0-5 $R^g$, $C_{2-5}$ alkenyl substituted with 0-4 $R^g$, $C_{2-5}$ alkynyl substituted with 0-4 $R^g$, $-(CH_2)_n-C_{3-6}$ cycloalkyl substituted with 0-4 $R^g$, $-(CH_2)_n$—4- to 9-membered heterocyclyl comprising 1-4 heteroatoms selected from O, $S(=O)_p$, and N, and substituted with 0-4 $R^f$, $-(CH_2)_n$-aryl substituted with 0-4 $R^g$, $-(CH_2)_nOR^f$, $-C(=O)OR^f$, $S(=O)_pR^f$, $C(=O)NR^fR^f$, $NR^fC(=O)R^f$, or $-(CH_2)NR^fR^f$;

$R^f$ is H, $C_{1-5}$ alkyl substituted with 0-3 $R^g$, $C_{3-6}$ cycloalkyl, or aryl; or $R^f$ and $R^f$ together with the nitrogen atom to which they are both attached form a 4- to 6-membered heterocyclyl comprising 1-4 heteroatoms selected from O, $S(=O)_p$, and N;

$R^g$ is halo, CN, OH, $OC_{1-4}$ alkyl, $C_{1-4}$ alkyl, $C_{3-6}$ cycloalkyl, or aryl;

n is zero, 1, 2, or 3; and p is zero, 1, or 2.

4. The compound of claim 3, or a pharmaceutically acceptable salt thereof, wherein:

$R^4$ is halo or $CF_3$;

$R^6$ is $C_{1-3}$ alkyl substituted with 0-3 halo or $OC_{1-3}$ alkyl substituents, $C_{3-6}$ cycloalkyl substituted with 0-2 halo, or heterocyclyl selected from

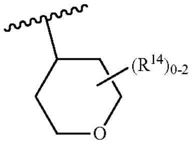 and 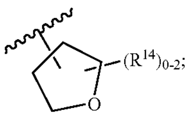;

$R^8$ is $-OC_{1-3}$ alkyl substituted with 0-1 —OH substituents;

$R^9$ is $C_{1-7}$ alkyl substituted with 0-3 halo, —OH, or CN substituents; and $R^{14}$ is halo, CN, or $C_{1-3}$ alkyl substituted with 0-3 halo substituents.

5. The compound of claim 3, or a pharmaceutically acceptable salt thereof, wherein:

$R^4$ is halo or $CF_3$;

$R^6$ is $C_{1-3}$ alkyl substituted with 0-3 halo substituents or $C_{3-6}$ cycloalkyl;

$R^9$ is $C_{1-3}$ alkyl substituted with 0-1 $R^{10}$ and 0-1 $R^{11}$;

$R^{10}$ is halo or $C_{1-4}$ alkyl substituted with 0-4 halo substituents;

$R^{11}$ is $-OR^b$;

$R^b$ is $C_{1-4}$ alkyl substituted with 0-4 $R^c$, $-(CH_2)_{0-1}-C_{3-6}$ cycloalkyl substituted with 0-4 $R^e$, $-(CH_2)_{0-1}$-phenyl substituted with 0-4 $R^e$, or $-(CH_2)_{0-1}$-heterocyclyl wherein the heterocyclyl is

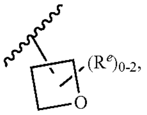, 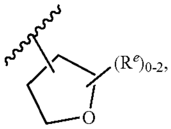, 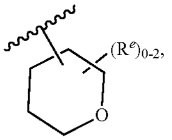,

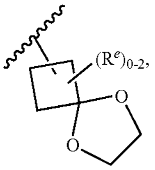, 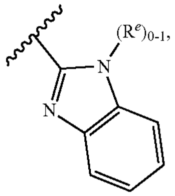,

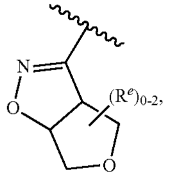 or 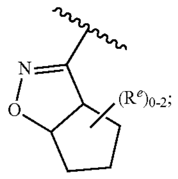;

$R^c$ is halo, CN, $C_{1-5}$ alkyl substituted with 0-5 $R^g$, $—(CH_2)_nOR^f$, $—C(=O)OR^f$, or $C(=O)NR^fR^f$;

$R^f$ is H, $C_{1-4}$ alkyl substituted with 0-3 $R^g$;

$R^g$ is halo, CN, OH, $C_{1-6}$ alkyl, $C_{3-6}$ cycloalkyl, or aryl; and n is zero or 1.

6. The compound of claim 3, or a pharmaceutically acceptable salt thereof, wherein:

$R^4$ is halo or $CF_3$;

$R^6$ is $C_{1-3}$ alkyl substituted with 0-3 halo substituents or $C_{3-6}$ cycloalkyl;

$R^9$ is $C_{1-3}$ alkyl substituted with 0-1 $R^{10}$ and 0-1 $R^{11}$;

$R^{10}$ is halo or $C_{1-4}$ alkyl substituted with 0-4 halo substituents;

$R^{11}$ is $—NR^aR^a$;

$R^a$ is H or $C_{1-4}$ alkyl substituted with 0-4 $R^e$, $C_{3-6}$ cycloalkyl substituted with 0-4 $R^e$; or $R^a$ and $R^a$ together with the nitrogen atom to which they are both attached form a heterocyclyl selected from

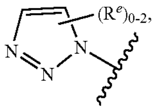,
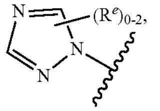,
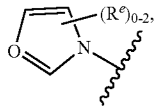,
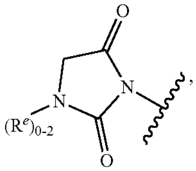,
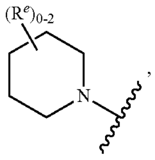,
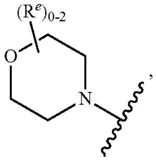,
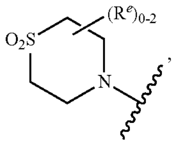,
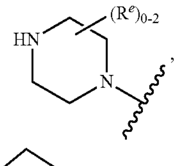,
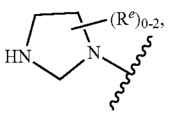,
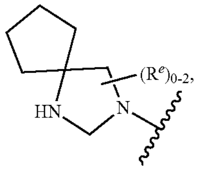,
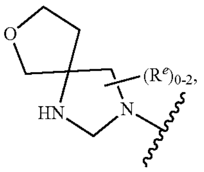,
and
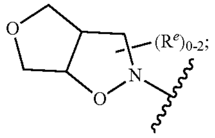;

$R^c$ is halo, CN, $=O$, $C_{1-4}$ alkyl substituted with 0-5 $R^g$, $—(CH_2)_n—C_{3-6}$ cycloalkyl, $—(CH_2)_n$-4- to 6-membered heterocyclyl comprising 1-4 heteroatoms selected from O, $S(=O)_p$, and N, $—(CH_2)_n$-aryl, $—(CH_2)_nOR^f$, $—C(=O)OR^f$, $S(=O)_pR^f$, $C(=O)NR^fR^f$, or $—(CH_2)_nNR^fR^f$;

$R^f$ is H or $C_{1-4}$ alkyl; and $R^g$ is halo, CN, OH, $OC_{1-4}$ alkyl, $C_{1-4}$ alkyl, $C_{3-6}$ cycloalkyl, or aryl.

7. The compound of claim 3, or a pharmaceutically acceptable salt thereof, wherein:

$R^4$ is halo or $CF_3$;

$R^6$ is $C_{1-3}$ alkyl substituted with 0-3 halo substituents or $C_{3-6}$ cycloalkyl;

$R^9$ is $C_{1-3}$ alkyl substituted with 0-1 $R^{10}$ and 0-1 $R^{11}$;

$R^{10}$ is halo or $C_{1-4}$ alkyl substituted with 0-4 halo;

$R^{11}$ is $—OC(=O)NR^aR^a$;

$R^a$ is H, $C_{1-4}$ alkyl substituted with 0-4 R*, $C_{3-6}$cycloalkyl substituted with 0-4 $R^e$, or phenyl substituted with 0-4 $R^e$; or $R^a$ and $R^a$ together with the nitrogen atom to which they are both attached form a heterocyclyl selected from

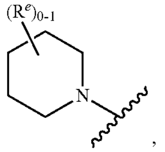,
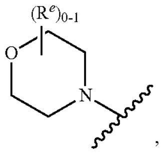,
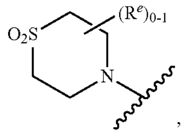,
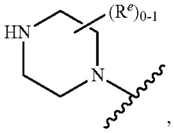,
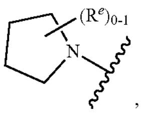,
and
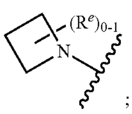;

$R^e$ is halo, CN, $=O$, $C_{1-4}$ alkyl substituted with 0-3 $R^g$, $—(CH_2)_nOR^f$, $—C(=O)OR^f$, $S(=O)_pR^f$, $C(=O)NR^fR^f$, $NR^fC(=O)R^f$, or $—(CH_2)_mNR^fR^f$, $R^f$ is H or $C_{1-4}$ alkyl;

$R^g$ is halo, CN, OH, $C_{1-4}$ alkyl, $C_{3-6}$ cycloalkyl, or aryl;

n is zero or 1; and p is 2.

8. The compound of claim 3, or a pharmaceutically acceptable salt thereof, wherein:

$R^4$ is halo or $CF_3$;

$R^6$ is $C_{1-3}$ alkyl substituted with 0-3 halo substituents or $C_{3-6}$ cycloalkyl;

$R^9$ is $C_{1-3}$ alkyl substituted with 0-1 $R^{10}$ and 0-1 $R^{11}$;

$R^{10}$ is halo or $C_{1-4}$ alkyl substituted with 0-4 halo substituents;

$R^{11}$ is $—NHC(=O)R^b$ or $—NR^aC(=O)OR^b$;

$R^a$ is H or $C_{1-3}$ alkyl;

$R^b$ is $C_{1-4}$ alkyl substituted with 0-3 $R^e$, $C_{3-6}$cycloalkyl substituted with 0-3 $R^e$, phenyl substituted with 0-3 $R^e$, heterocyclyl selected from

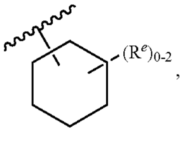,
or
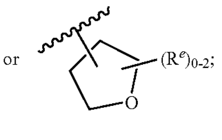;

$R^c$ is halo, CN, $C_{1-4}$ alkyl substituted with 0-4 $R^g$, —OR, $—C(=O)OR^f$, $C(=O)NR^fR^f$, $R^f$ is H or $C_{1-4}$ alkyl; and $R^g$ is halo, CN, OH, $C_{1-4}$ alkyl, $C_{3-4}$ cycloalkyl, or aryl.

9. The compound of claim 2, or a pharmaceutically acceptable salt thereof, wherein:

$R^4$ is halo or $C_{1-4}$ alkyl substituted with 0-3 halo substituents;

$R^6$ is $C_{1-3}$ alkyl substituted with 0-3 halo substituents or $C_{3-6}$ cycloalkyl;

$R^8$ is $—OC_{1-3}$ alkyl;

$R^9$ is $C_{2-4}$ alkenyl substituted with 0-2 $R^{10}$ or 0-2 $R^{11}$;

$R^{10}$ is $C_{1-2}$ alkyl substituted with 0-4 halo or OH substituents;

$R^{11}$ is $—C(=O)R^b$, $—C(=O)OR^b$, or $—C(=O)NR^aR^a$;

$R^a$ is H, $C_{1-4}$ alkyl substituted with 0-4 $R^e$, $C_{3-6}$cycloalkyl substituted with 0-4 $R^e$, or phenyl substituted with 0-4 $R^e$; or $R^a$ and $R^a$ together with the nitrogen atom to which they are both attached form a 4- to 9-membered heterocyclyl comprising 1-4 heteroatoms selected from O, S(=O)P, and N, and substituted with 0-4 $R^c$;

$R^b$ is H or $C_{1-4}$ alkyl;

$R^e$ is halo, $C_{1-6}$ alkyl substituted with 0-5 $R^g$, —$(CH_2)_{0-1}OR^f$, or —C(=O)$OR^f$;

$R^f$ H or $C_{1-4}$ alkyl; and $R^g$ is $C_{1-4}$ alkyl.

10. The compound of claim 9, or a pharmaceutically acceptable salt thereof, wherein:

$R^4$ is halo or $CF_3$;

$R^6$ is $CF_3$ or cyclopropyl;

$R^8$ is —$OC_{1-3}$ alkyl;

$R^9$ is $C_{2-3}$ alkenyl substituted with 0-1 $R^{11}$;

$R^{11}$ is —C(=O)$NR^aR^a$;

$R^a$ is H or $C_{1-4}$ alkyl substituted with 0-4 $R^e$, $C_{3-6}$ cycloalkyl substituted with 0-4 $R^e$; or $R^a$ and $R^a$ together with the nitrogen atom to which they are both attached form a heterocyclyl selected from

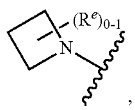, 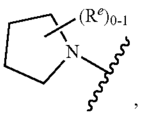, 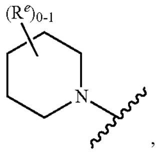,

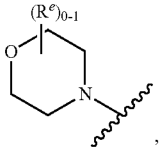, 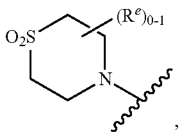, 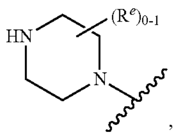,

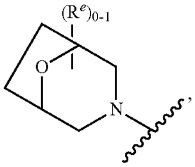, and 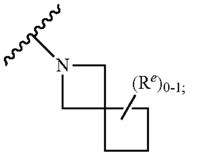

$R^e$ is halo, CN, $C_{1-4}$ alkyl substituted with 0-4 $R^g$, —$(CH_2)_{0-1}OR^f$, —C(=O)$OR^f$; and $R^f$ is H or $C_{1-4}$ alkyl; and $R^g$ is $C_{1-3}$ alkyl.

11. The compound of claim 2, or a pharmaceutically acceptable salt thereof, wherein:

$R^4$ is halo or $C_{1-4}$ alkyl substituted with 0-3 halo substituents;

$R^6$ is $C_{1-3}$ alkyl substituted with 0-3 halo or $C_{3-6}$ cycloalkyl;

$R^8$ is —$OC_{1-3}$ alkyl substituted with 0-2 halo or OH substituents;

$R^9$ is $C_{2-6}$ alkynyl substituted with 0-2 $R^{11}$;

$R^{11}$ is —$OR^b$ or —OC(=O)$NR^aR^a$;

$R^a$ is H, $C_{1-4}$ alkyl substituted with 0-4 $R^e$, $C_{3-6}$cycloalkyl substituted with 0-4 $R^e$, or phenyl substituted with 0-4 $R^e$;

$R^b$ is H or $C_{1-4}$ alkyl; and $R^c$ is halo or $C_{1-4}$ alkyl.

12. The compound of claim 2, or a pharmaceutically acceptable salt thereof, wherein:

$R^4$ is halo or $C_{1-4}$ alkyl substituted with 0-3 halo substituents;

$R^6$ is $C_{1-2}$ alkyl substituted with 0-3 F substituents or $C_{3-6}$ cycloalkyl;

$R^8$ is —$OC_{1-3}$ alkyl;

$R^9$ is $C_{3-9}$ cycloalkyl, —O—$C_{3-9}$ cycloalkyl, or fused $C_{3-6}$ cycloalkyl, each substituted with 0-2 $R^{10}$ and 0-2 $R^{11}$, $R^{10}$ is halo, CN, or $C_{1-4}$ alkyl substituted with 0-4 halo or —OH substituents;

$R^{11}$ is —OR, —$NR^aR^a$, —$NR^a$C(=O)$R^b$, —C(=O)$OR^b$, —C(=O)$NR^aR^a$, or —OC(=O)$NR^aR^a$;

$R^a$ is H, $C_{1-4}$ alkyl substituted with 0-4 $R^c$, $C_{3-6}$cycloalkyl substituted with 0-4 $R^c$, or phenyl substituted with 0-4 $R^e$; or $R^a$ and $R^a$ together with the nitrogen atom to which they are both attached form a 4- to 6-membered heterocyclyl comprising 1-4 heteroatoms selected from O, $S(=O)_p$, and N, and substituted with 0-4 $R^e$; and $R^b$ is H, $C_{1-4}$ alkyl, or 4- to 6-membered heterocyclyl comprising 1-4 heteroatoms selected from O, $S(=O)_p$, and N;

$R^c$ is halo, —$(CH_2—)_nOR^f$ or —C(=O)$OR^f$; and $R^f$ is H or $C_{1-3}$ alkyl.

13. The compound of claim 12, or a pharmaceutically acceptable salt thereof, wherein:

$R^4$ is F or $CF_3$;

$R^6$ is $CF_3$, cyclopropyl, cyclobutyl, or cyclopentyl;

$R^8$ is —$OC_{1-3}$ alkyl;

$R^9$ is cyclobutyl, cyclopentyl, or cyclohexyl, bicycle[2,2,2]octanyl, each substituted with 0-2 $R^{10}$ and 0-2 $R^{11}$;

$R^{10}$ is F, CN, $CH_2OH$, $C(CH_3)_2OH$, or $CHC(CH_3)_2OH$;

$R^{11}$ is —OH, —NHC(=O)$R^b$, —C(=O)$OR^b$, or —OC(=O)$NR^aR^a$;

$R^a$ is H, $C_{1-4}$ alkyl substituted with 0-3 $R^c$, $C_{3-6}$ cycloalkyl substituted with 0-3 $R^e$, or phenyl substituted with 0-3 $R^c$;

$R^b$ is H, $C_{1-4}$ alkyl,

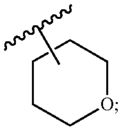;

$R^c$ is halo, —$(CH_2)_{0-1}OR^f$ or —C(=O)$OR^f$; and $R^f$ is H or $C_{1-3}$ alkyl.

14. The compound of claim 2, or a pharmaceutically acceptable salt thereof, wherein:

$R^4$ is halo or $C_{1-4}$ alkyl substituted with 0-3 halo;

$R^6$ is $C_1$-t alkyl substituted with 0-3 F substituents or $C_{3-6}$ cycloalkyl;

$R^8$ is —$OC_{1-3}$ alkyl;

$R^9$ is $C_{6-9}$ spirocycloalkyl substituted with 0-2 $R^{11}$;

$R^{11}$ is —$OR^b$, —$NR^aR^a$, or C(=O)$OR^b$;

$R^a$ is H or $C_{1-4}$ alkyl; and $R^b$ is H or $C_{1-4}$ alkyl.

15. The compound of claim 1, or a pharmaceutically acceptable salt thereof, wherein:

L is —NH;

$R^4$ is halo or $C_{1-4}$ alkyl substituted with 0-4 halosubstituents;

$R^6$ is $C_{1-4}$ alkyl substituted with 0-3 halo or $C_{3-6}$ cycloalkyl;

$R^7$ is H;

$R^8$ is halo or —$OC_{1-4}$ alkyl substituted with 0-5 halo substituents;

$R^9$ is —$S(=O)_pR^c$ or —$S(=O)_pNR^{15}R^{15}$;

$R^{15}$ is H, $C_{1-5}$ alkyl substituted with 0-5 $R^e$, $C_{3-10}$carbocyclyl substituted with 0-5 $R^e$, or 4- to 9-membered heterocyclyl comprising 1-4 heteroatoms selected from O, $S(=O)_p$, N and $NR^{16}$, and substituted with 0-5 $R^e$;

or $R^{15}$ and $R^{15}$ together with the nitrogen atom to which they are both attached form a 4- to 9-membered heterocyclyl comprising 1-4 heteroatoms selected from O, $S(=O)_p$, N and $NR^{16}$, and substituted with 0-4 $R^e$;

$R^{16}$ is H, $C_{1-4}$ alkyl substituted with 0-5 $R^e$, —C(=O)R, —C(=O)OR$^f$, —C(=O)NR$^f$R$^f$, —S(=O)$_p$R$^f$, or —S(=O)$_p$NR$^f$R$^f$, $R^c$ is $C_{1-3}$ alkyl substituted with 0-3 $R^e$;

$R^e$ is halo, —(CH$_2$)$_n$OR$^f$, C(=O)OR$^f$, or $C_{1-6}$ alkyl;

$R^f$ is H or $C_{1-3}$ alkyl; and n is zero, 1 or 2.

16. The compound of claim 15, or a pharmaceutically acceptable salt thereof, wherein:

$R^4$ is F or $CF_3$;

$R^6$ is $CF_3$ or $C_{3-6}$ cycloalkyl;

$R^a$ is F or —OC$_{1-2}$ alky;

$R^9$ is —S(=O)$_2$NR$^{15}$R$^{15}$;

$R^{15}$ is H, $C_{1-5}$ alkyl substituted with 0-5 $R^e$, phenyl substituted with 0-5 R, or heterocyclyl selected from

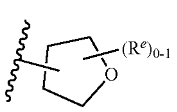 and 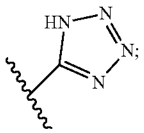

or $R^{15}$ and $R^{15}$ together with the nitrogen atom to which they are both attached form a heterocyclyl selected from

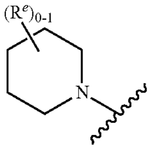, 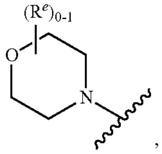, 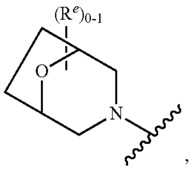,

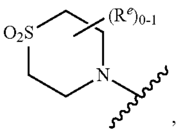, 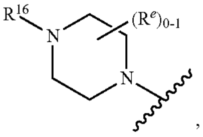, 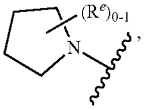,

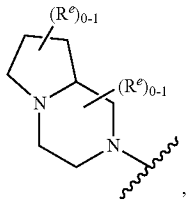, 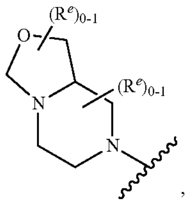,

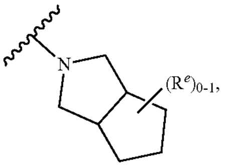 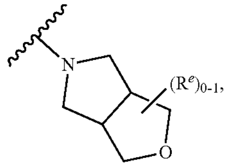

-continued

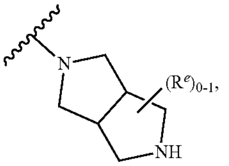 and 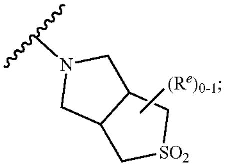

$R^{16}$ is H, $C_{1-3}$ alkyl substituted with 0-5 $R^e$, —C(=O)R$^f$, —C(=O)OR$^f$, —C(=O)NR$^f$R$^f$, —S(=O)$_p$R$^f$, or —S(=O)$_p$NR$^f$R$^f$;

$R^e$ is halo, =O, —(CH$_2$)$^{0-1}$OR$^f$, or $C_{1-5}$ alkyl; and $R^f$ is H or $C_{1-3}$ alkyl.

17. The compound of claim 1, or a pharmaceutically acceptable salt thereof, wherein:

L is —NH;

$R^3$ is phenyl substituted with 2 $R^4$;

$R^4$ is F or $CF_3$;

$R^5$ is H;

$R^6$ is $CF_3$ or $C_{3-6}$ cycloalkyl;

$R^7$ is H;

$R^8$ is —OC$_{1-2}$ alkyl;

$R^9$ is —NR$^{17}$R$^{17}$;

$R^{17}$ is H or —(CH$_2$)$_n$-phenyl substituted with 0-4 $R^e$;

$R^c$ is halo, —OH, or $C_{1-6}$ alkyl; and n is zero or 1.

18. The compound of claim 1, or a pharmaceutically acceptable salt thereof, wherein:

L is —NH;

$R^3$ is phenyl substituted with 2 $R^4$;

$R^4$ is halo or $C_{1-4}$ alkyl substituted with 0-4 halo substituents;

$R^5$ is H;

$R^6$ is $C_{1-4}$ alkyl substituted with 0-3 halo substituents or $C_{3-6}$ cycloalkyl;

$R^7$ is H;

$R^8$ is halo or —OC$_{1-4}$ alkyl substituted with 0-5 halo substituents;

$R^9$ is —C(=O)OR$^{15}$ or —C(=O)NR$^{15}$R$^{15}$;

$R^{15}$ is H, $C_{1-5}$ alkyl substituted with 0-5 $R^e$, —(CH$_2$)$_n$—C$_{3-6}$ cycloalkyl substituted with 0-5 $R^c$, phenyl substituted with 0-5 $R^e$, or 4- to 9-membered heterocyclyl comprising 1-4 heteroatoms selected from O, $S(=O)_p$, N and $NR^{16}$, and substituted with 0-5 $R^e$; or $R^{15}$ and $R^{15}$ together with the nitrogen atom to which they are both attached form a 4- to 9-membered heterocyclyl comprising 1-4 heteroatoms selected from O, $S(=O)_p$, N and $NR^{16}$, and substituted with 0-5 $R^e$;

$R^{16}$ is H, $C_{1-6}$ alkyl substituted with 0-5 $R^e$, —C(=O)R, —C(=O)OR, —C(=O)NR$^f$R$^f$, —S(=O)$_p$R$^f$, or —S(=O)$_p$NR$^f$R$^f$;

$R^c$ is $C_{1-5}$ alkyl substituted with 0-5 $R^e$;

$R^e$ is halo, =O, $C_{1-6}$ alkyl substituted with 0-2 OH substituents, —(CH$_2$)$_n$OR$^f$, —C(=O)R$^f$, —C(=O)OR$^f$, —C(=O)NR$^f$R$^f$, —NR$^f$C(=O)R$^f$, —S(=O)$_p$ R$^f$, or —S(=O)$_p$NR$^f$R$^f$;

$R^f$ is H or $C_{1-3}$ alkyl; and n is zero, 1 or 2.

19. The compound of claim 18, or a pharmaceutically acceptable salt thereof, wherein:

$R^4$ is F or $CF_3$;

$R^6$ is $CF_3$ or $C_{3-4}$ cycloalkyl;

$R^8$ is halo or —OC$_{1-2}$ alkyl;

$R^9$ is —C(=O)NR$^{15}$R$^{15}$;

$R^{15}$ is H, $C_{1-5}$ alkyl substituted with 0-5 $R^e$, $-CH_2-C_{3-6}$ cycloalkyl substituted with 0-5 $R^e$, phenyl substituted with 0-5 $R^e$, or heterocyclyl selected from

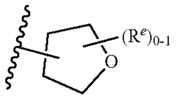 and 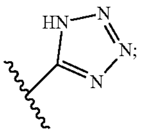

or $R^{15}$ and $R^{15}$ together with the nitrogen atom to which they are both attached form a heterocyclyl selected from

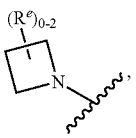, 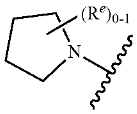, 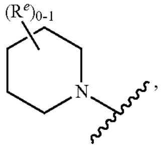,

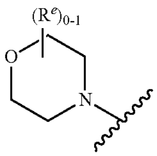, 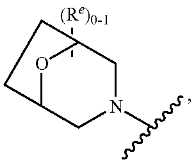,

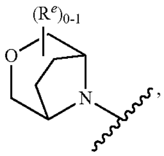, 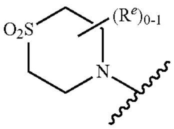,

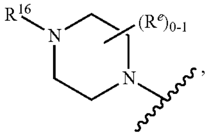, 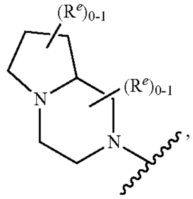,

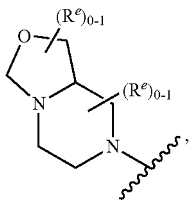, 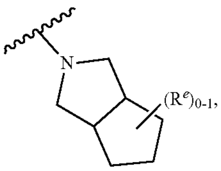,

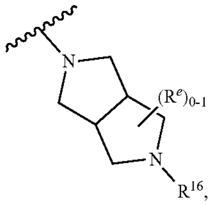, 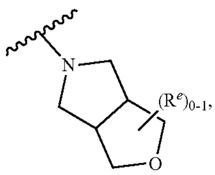,

-continued

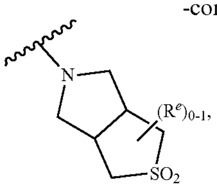, 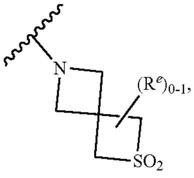, and

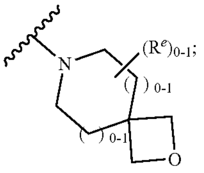;

$R^{16}$ is H or $C_{1-5}$ alkyl substituted with 0-5 $R^e$;

$R^e$ is halo, $=O$, $C_{1-6}$ alkyl substituted with 0-1 OH, $-(CH_2)_{0-1}OR^f$, $-C(=O)R^f$, $-C(=O)OR^f$, $-C(=O)NR^fR^f$, $-NR^fC(=O)R^f$, $-S(=O)_pR^f$, or $-S(=O)_pNR^fR^f$; and $R^f$ is H or $C_{1-3}$ alkyl.

20. The compound of claim 1, having Formula (III);

(III)

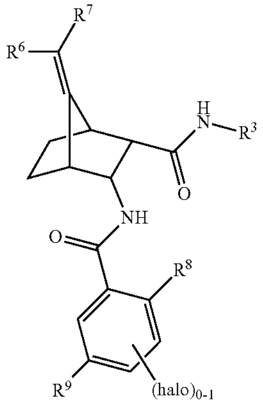

or a pharmaceutically acceptable salt thereof, wherein:

$R^3$ is $-CHR_d-C_{3-6}$-cycloalkyl substituted with 0-5 $R^4$ or phenyl substituted with 0-5 $R^4$;

$R^4$ is halo, CN, or $C_{1-4}$ alkyl substituted with 0-5 halo substituents;

$R^5$ is H;

$R^6$ is $C_{1-3}$ alkyl substituted with 0-3 $R^{6a}$, $C_{3-6}$ cycloalkyl substituted with 0-5 $R^{14}$, or 3-to 6-membered heterocyclyl comprising 1-4 heteroatoms selected from O, $S(=O)_p$, N, and substituted with 0-5 $R^{14}$;

$R^7$ is H;

$R^{6a}$ is halo;

$R^8$ is $-OC_{1-3}$ alkyl;

$R^9$ is $-C(=O)NR^{15}R^{15}$, $-CH_2-O$-phenyl substituted with 0-2 $R^{10}$ and 0-2 $R^{11}$, $C_{3-9}$ cycloalkyl substituted with 0-2 $R^{10}$ and 0-2 $R^{11}$, or $-C_{3-6}$ cycloalkyl substituted with 0-2 $R^{10}$ and 0-2 $R^{11}$;

$R^{10}$ is halo, CN, or $C_{1-4}$ alkyl substituted with 0-4 halo or $-OH$ substituents;

$R^{11}$ is $-OR^b$, $-OC(=O)NR^aR^a$, or $-C(=O)OR^b$;

$R^{14}$ is halo, CN, or $C_{1-4}$ alkyl substituted with 0-3 halo substituents;

$R^{15}$ is H, $C_{1-5}$ alkyl substituted with 0-3 $R^e$, $-(CH_2)_n-C_{3-10}$ carbocyclyl substituted with 0-3 $R^e$; or $R^{15}$ and $R^{15}$ together with the nitrogen atom to which they are both attached form a 4- to 9-membered heterocyclyl comprising 1-4 heteroatoms selected from O, $S(=O)_p$, N and $NR^{16}$, and substituted with 0-3 $R^e$;

$R^{16}$ is H or $C_{1-4}$ alkyl substituted with 0-5 $R^e$;

$R^a$ is H, $C_{1-4}$ alkyl substituted with 0-5 $R^e$, $C_{3-6}$ carbocyclyl or $-(CH_2)_n$-4- to 9-membered heterocyclyl comprising 1-4 heteroatoms selected from O, $S(=O)_p$, and N, and substituted with 0-5 $R^e$;

$R^b$ is H or $C_{1-4}$ alkyl;

$R^d$ is H or $C_{1-3}$ alkyl;

$R^e$ is halo, $C_{1-4}$ alkyl substituted with 0-3 $R^f$, $OR^f$, or $-S(=O)_2C_{1-4}$ alkyl;

$R^f$ is H or $C_{1-4}$ alkyl;

$R^g$ is halo or —OH;

n is zero or 1, 2, or 3; and p is zero, 1, or 2.

21. A pharmaceutical composition comprising a compound of claim 1 or a pharmaceutically acceptable salt thereof and a pharmaceutically acceptable carrier.

22. A method for treating a disease associated with relaxin, comprising administering a therapeutically effective amount of a pharmaceutical composition of claim 21 to a patient in need thereof.

23. The method of claim 22 wherein the disease is selected from the group consisting of angina pectoris, unstable angina, myocardial infarction, heart failure, acute coronary disease, acute heart failure, chronic heart failure, and cardiac iatrogenic damage.

24. The method of claim 23 wherein the disease is heart failure.

* * * * *